United States Patent
Bate et al.

(10) Patent No.: US 11,959,072 B2
(45) Date of Patent: Apr. 16, 2024

(54) SUPPRESSION OF SHADE AVOIDANCE RESPONSE IN PLANTS

(71) Applicant: Pairwise Plants Services, Inc., Durham, NC (US)

(72) Inventors: Nicholas Bate, Raleigh, NC (US); Yongjoo Kim, Durham, NC (US); Nathaniel Graham, Durham, NC (US); Julius Mojica, Durham, NC (US)

(73) Assignee: Pairwise Plants Services, Inc., Durham, NC (US)

( * ) Notice: Subject to any disclaimer, the term of this patent is extended or adjusted under 35 U.S.C. 154(b) by 290 days.

(21) Appl. No.: 17/162,075

(22) Filed: Jan. 29, 2021

(65) Prior Publication Data

US 2021/0238579 A1 Aug. 5, 2021

Related U.S. Application Data

(60) Provisional application No. 62/968,596, filed on Jan. 31, 2020.

(51) Int. Cl.
*C07K 14/415* (2006.01)
*C12N 15/10* (2006.01)
*C12N 15/113* (2010.01)

(52) U.S. Cl.
CPC .......... *C12N 15/102* (2013.01); *C07K 14/415* (2013.01); *C12N 15/113* (2013.01); *C12N 2310/20* (2017.05)

(58) Field of Classification Search
CPC ................ C12N 15/102; C12N 15/113; C12N 2310/20; C07K 14/415
See application file for complete search history.

(56) References Cited

U.S. PATENT DOCUMENTS

2009/0094717 A1* 4/2009 Troukhan ............. C07K 14/415
536/23.6

FOREIGN PATENT DOCUMENTS

WO 2015054000 A2 4/2015
WO WO-2015054000 A3 * 6/2015 ........... C07K 14/415

OTHER PUBLICATIONS

NCBI ONM15274.1 (NCBI Database reference, 2017, accessed Apr. 6, 2023) (Year: 2017).*
Ma X et al. Mol Plant. Jul. 6, 2016;9(7):961-74 (Year: 2016).*
Shi Q Biochem Biophys Res Commun. Aug. 13 2019;516(1):112-119 (Year: 2019).*
NCBI XP_008658438.1 (NCBI Database reference, 2014, accessed Apr. 6, 2023) (Year: 2014).*
NCBI XM_002448240.2 (NCBI Database reference, 2017, accessed Apr. 6, 2023) (Year: 2017).*
Carabelli et al. "Arabidopsis HD-Zip II proteins regulate the exit from proliferation during leaf development in canopy shade" Journal of Experimental Botany, 69(22):5419-5431 (2018).
Carabelli et al. "Twilight-zone and canopy shade induction of the Athb-2 homeobox gene in green plants" Proceedings of the National Academy of Sciences USA, 93:3530-3535 (1996).
Carriedo et al. "Molecular control of crop shade avoidance" Current Opinion in Plant Biology, 30:151-158 (2016).
Ciarbelli et al. "The *Arabidopsis homeodomain-leucine* Zipper II gene family: diversity and redundancy" Plant Molecular Biology, 68:465-478 (2008).
Elhiti et al. "Structure and function of homodomain-leucine zipper (HD-Zip) proteins" Plant Signaling and Behavior, 4(2):86-88 (2009).
Franklin et al. "Phytochromes and Shade-avoidance Responses in Plants" Annals of Botany, 96:169-175 (2005).
International Search Report and the Written Opinion of the International Searching Authority corresponding to International Patent Application No. PCT/US2021/015609 (13 pages) (dated May 10, 2021).
Kebrom et al. "The molecular analysis of the shade avoidance syndrome in the grasses has begun" Journal of Experimental Botany, 58(12):3079-3089 (2007).
Shcherban. "HD-Zip Genes and Their Role in Plant Adaption to Environmental Factors" Russian Journal of Genetics, 55(1):1-9 (2019).
Shi et al. "Molecular mechanisms governing shade responses in maize" Biochemical and Biophysical Research Communications, 516(1):112-119 (2019).
Smith, Harry "The ecological functions of the phytochrome family: Clues to a transgenic programme of crop improvement" Photochemistry and Photobiology, 56(5):815-822 (1992).
Steindler et al. "Shade avoidance responses are mediated by the ATHB-2 HD-Zip protein, a negative regulator of gene expression" Development, 126:4235-4245 (1999).

* cited by examiner

*Primary Examiner* — Neil P Hammell
*Assistant Examiner* — Douglas Charles Ryan
(74) *Attorney, Agent, or Firm* — Myers Bigel, P.A.

(57) ABSTRACT

This invention relates to compositions and methods for modifying Homeodomain-leucine zipper (HD-Zip) transcription factors in plants to suppress shade avoidance response in plants. The invention further relates to plants produced using the methods and compositions of the invention.

3 Claims, 19 Drawing Sheets

Specification includes a Sequence Listing.

```
                                 1          10         20         30
                                 |          |          |          |
Amborella trichopoda          LAKQLNLRP RQVEVW FQNRRARTKLKQ TEVDCE FL
Arabidopsis lyrate            LAKQLNLRT RQVEVW FQNRRARTKLKQ TEVDCE YL
Arabidopsis thaliana          LAKQLNLRT RQVEVW FQNRRARTKLKQ TEVDCE YL
Arabis alpina                 LAKQLNLRT RQVEVW FQNRRARTKLKQ TEVDCE YL
Brassica campestris           LAKQLNLRT RQVEVW FQNRRARTKLKQ TEVDCE YL
Brassica oleracea             LAKQLNLRT RQVEVW FQNRRARTKLKQ TEVDCE YL
Capsella rubella              LAKQLNLQT RQVEVW FQNRRARTKLKQ TEVDCE YL
Cicer arietinum               LAKQLNLMP RQVEVW FQNRRARTKLKQ TEVDCE YL
Citrus clementina             LAKQLGLRP RQVEVW FQNRRARTKLKQ TEVDCE FL
Citrus sinesis                LAKQLNLRP RQVEVW FQNRRARTKLKQ TEVDCE YL
Cucumis melo                  LAKQLNLTP RQVEVW FQNRRARTKLKQ TEVDCE YL
Cucumis sativus               LAKQLNLTP RQVEVW FQNRRARTKLKQ TEVDCE YL
Erythranthe guttata           LAKRLGLRP RQVEVW FQNRRARTKLKQ TEVDCE FL
Eucalyptus grandis            LAKQLGLRP RQVEVW FQNRRARTKLKQ TEVDCE FL
Eutrema salsugineum           LAKQLNLRT RQVEVW FQNRRARTKLKQ TEVDCE YL
Glycine max                   LAKQLGLRP RQVEVW FQNRRARTKLKQ TEVDCE VL
Gossypium raimondii           LAKQLNLKP RQVEVW FQNRRARTKLKQ TEVDCE YL
Hordeum vulgare               LARQLRLRP RQVEVW FQNRRARTKLKQ TEVDCESL
Leersia perrieri              LAQQLGLRP RQVEVW FQNRRARTKLKQ TEVDCE FL
Medicago truncatula           LAKQLGLRA RQVEVW FQNRRARTKLKQ TEVDCE FL
Morus notabilis               LAKELNLRP RQVEVW FQNRRARTKLKQ TEVDCE YL
Musa acuminata                LAKRLNLRP RQVEVW FQNRRARTKLKQ TEVDCE FL
Nelumbo nucifera              LAKQLNLRP RQVEVW FQNRRARTKLKQ TEVDCE FL
Nicotiana sylvestris          LAKRLGLRP RQVEVW FQNRRARTKLKQ TEVDCE FL
Oryza barthii                 LAKQLNLKP RQVEVW FQNRRARTKLKQ TEVDCE LL
Oryza brachyantha             LARQLGLKP RQVEVW FQNRRARTKLKQ TEVDCE LL
Oryza glaberrima              LARQLNLKP RQVEVW FQNRRARTKLKQ TEVDCE LL
Oryza glumipatula             LARQLNLKP RQVEVW FQNRRARTKLKQ TEVDCE LL
Oryza meridionalis            LARQLNLKP RQVEVW FQNRRARTKLKQ TEVDCE LL
Oryza nivara                  LAKQLNLKP RQVEVW FQNRRARTKLKQ TEVDCE YL
Oryza punctata                LARQLNLKP RQVEVW FQNRRARTKLKQ TEVDCE LL
Oryza rufipogon               LAQQLGLRP RQVEVW FQNRRARTKLKQ TEVDCE FL
Oryza sativa                  LARQLNLKP RQVEVW FQNRRARTKLKQ TEVDCE LL
Phaseolus vulgaris            LAKQLGLLP RQVEVW FQNRRARTKLKQ TEVDCE VL
Physcomitrella patens         LAKQLGLRP RQVEVW FQNRRARTKLKQ TEVDCE LL
Populus trichocarpa           LAKQLNLRP RQVEVW FQNRRARTKLKQ TEVDCE YL
Prunus persica                LAKQLGLRP RQVEVW FQNRRARTKLKQ TEVDCE FL
Ricinus communis              LAKQLNLKP RQVEVW FQNRRARTKSKQ TEVDCE YL
Setaria italica               LAKQLNLRP RQVEVW FQNRRARTKLKQ TEVDCE FL
Solanum tuberosum             LAKRLGLRP RQVEVW FQNRRARTKLKQ TEVDCE FL
Sorghum bicolor               LAKQLNLKP RQVEVW FQNRRARTKLKQ TEVDCE FL
Theobroma cacao               LAKQLNLRP RQVEVW FQNRRARTKLKQ TEVDCE YL
Triticum urartu               LAQQLGLRS RQVEVW FQNRRARTKLKQ TEVDCE FL
Vivis vinifera                LAKQLNLRP RQVEVW FQNRRARTKLKQ TEVDCE FL
Zea mays                      LAKQLNLKP RQVEVW FQNRRARTKLKQ TEVDCE FL
                                               DNA BINDING REGION
```

*FIG. 1A*

```
                                              40         50 53
                                              |          |  |
              Amborella trichopoda    KRCCENLTEENRRLQKEV  (SEQ ID NO:203)
              Arabidopsis lyrate      KRCCENLTDENRRLQKEV  (SEQ ID NO:204)
              Arabidopsis thaliana    KRCCENLTDENRRLQKEV  (SEQ ID NO:205)
              Arabis alpina           KRCCENLTEENRRLQKEV  (SEQ ID NO:206)
              Brassica campestris     KRCCENLTEENRRLQKEV  (SEQ ID NO:207)
              Brassica oleracea       KRCCENLTEENRRLQKEV  (SEQ ID NO:208)
              Capsella rubella        RRRCENLTEENRRLQKEV  (SEQ ID NO:209)
              Cicer arietinum         KRCCETLTEENRRLQKEV  (SEQ ID NO:210)
              Citrus clementina       KRCCENLTEENRRLQKEV  (SEQ ID NO:211)
              Citrus sinesis          KRCCENLTEENRRLQKEV  (SEQ ID NO:212)
              Cucumis melo            KRCCENLTEENRRLQKEV  (SEQ ID NO:213)
              Cucumis sativus         KRCCENLTEENRRLQKEV  (SEQ ID NO:214)
              Erythranthe guttata     KRCCENLTEENRRLQKEV  (SEQ ID NO:215)
              Eucalyptus grandis      KRCCENLTEENRRLQKEV  (SEQ ID NO:216)
              Eutrema salsugineum     KRCCENLTEENRRLQKEV  (SEQ ID NO:217)
              Glycine max             KRCCENLTEENRRLQKEV  (SEQ ID NO:218)
              Gossypium raimondii     KRCCENLTEENRRLHKEV  (SEQ ID NO:219)
              Hordeum vulgare         KRCCETLTEENRRLQREV  (SEQ ID NO:302)
              Leersia perrieri        KRCCETLTEENRRLQKEV  (SEQ ID NO:220)
              Medicago truncatula     KRCCENLTDENRRLQKEV  (SEQ ID NO:221)
              Morus notabilis         KRCCENLTEENRRLQKEV  (SEQ ID NO:222)
              Musa acuminata          KRCCETLTEENRRLQKEV  (SEQ ID NO:223)
              Nelumbo nucifera        KRCCENLTEENRRLQKEV  (SEQ ID NO:224)
              Nicotiana sylvestris    KRCCENLTEENRRLQKEV  (SEQ ID NO:225)
              Oryza barthii           KRCCETLTDENRRLHREL  (SEQ ID NO:226)
              Oryza brachyantha       KRCCETLTEENRRLHKEL  (SEQ ID NO:227)
              Oryza glaberrima        KRCCETLTDENRRLHREL  (SEQ ID NO:228)
              Oryza glumipatula       KRCCETLTDENRRLHREL  (SEQ ID NO:229)
              Oryza meridionalis      KRCCETLTDENRRLHREL  (SEQ ID NO:230)
              Oryza nivara            KRCCETLTEENRRLQKEL  (SEQ ID NO:231)
              Oryza punctata          KRCCETLTDENRRLHREL  (SEQ ID NO:232)
              Oryza rufipogon         KRCCETLTEENRRLQKEV  (SEQ ID NO:233)
              Oryza sativa            KRCCETLTDENRRLHREL  (SEQ ID NO:234)
              Phaseolus vulgaris      KRCCENLTEENRRLQKEV  (SEQ ID NO:235)
              Physcomitrella patens   KRCCDSLKEENRRLQKEL  (SEQ ID NO:236)
              Populus trichocarpa     KRCCENLTEENRRLQKEV  (SEQ ID NO:237)
              Prunus persica          KRCCENLTEENRRLQKEV  (SEQ ID NO:238)
              Ricinus communis        KRCCENLTQENRRLQKEV  (SEQ ID NO:239)
              Setaria italica         KRCCETLTEENRRLQREV  (SEQ ID NO:240)
              Solanum tuberosum       KRCCENLTEENRRLQKEV  (SEQ ID NO:241)
              Sorghum bicolor         KRCCETLTEENRRLQREV  (SEQ ID NO:242)
              Theobroma cacao         KRCCENLTEENRRLQKEV  (SEQ ID NO:243)
              Triticum urartu         KRCCETLTEENRRLQKEV  (SEQ ID NO:244)
              Vivis vinifera          KRCCENLTEENRRLQKEV  (SEQ ID NO:245)
              Zea mays                KRCCETLTEENRRLQREV  (SEQ ID NO:246)
```

*FIG. 1B*

```
                                  1         10        20        30
                                  |         |         |         |
Amborella trichopoda              RKKLRLSKDQSAVLEESFKEHNTLNPKQKLTLAKQ
Arabidopsis lyrate                RKKLRLSKEQALVLEETFKEHSTLNPKQKLALAKQ
Arabidopsis thaliana              RKKLRLSKDQALVLEETFKEHSTLNPKQKLALAKQ
Arabis alpina                     RKKLRLSKEQALVLEETFKEHSTLNPKQKMALAKQ
Brachypodium distachyon           RKKLRLSKDQSAVLEDSFREHPTLNPRQKAALAQQ
Brassica campestris               RKKLRLSKEQALVLEDTFKEHSTLNPKQKLALAKQ
Brassica oleracea                 RKKLRLSKEQALVLEETFKEHSTLNPKQKLALAKQ
Capsella rubella                  RKKLRLSKEQALVLEETFKVHSTLNPKQKLVLAKQ
Cicer arietinum                   RKKLRLSKEQSVLLEETFKEHNTLNPKQKQALAKQ
Citrus clementina                 RKKLRLSKEQSLLLEETFKEHSTLNPKQKLALAKQ
Citrus sinesis                    RKKLRLSKEQSLLLEETFKEHSTLNPKQKLALAKQ
Cucumis melo                      RKKLRLSKEQSMVLEETFKEHNTLNPKQKLALAKQ
Cucumis sativus                   RKKLRLSKEQSMVLEETFKEHNTLNPKQKLALAKQ
Erythranthe guttata               RKKLRLSKDQSATLEESFKEHNTLNPKQKMALAKR
Eucalyptus grandis                RKKLRLSKDQSAVLEESFREHNTLNPKQKLALAKQ
Eutrema salsugineum               RKKLRLSKEQAVVLEETFKEHTTLNPKQKLALARQ
Glycine max                       RKKLRLSKEQALVLEETFKEHNTLNPKQKQALAKQ
Gossypium raimondii               RKKLRLSKDQSAILEESFKEHNTLNPKQKMALAKQ
Hordeum vulgare                   RKKLRLSKDQSAVLEDSFREHPTLNPRQKAALAQQ
Leersia perrieri                  RKKLRLSKDQSAVLEDSFREHPTLNPRQKATLAQQ
Medicago truncatula               RKKLRLTKDQSIILEESFKEHNTLNPKQKLALAKQ
Morus notabilis                   RKKLRLTKDQSLILEETFKEHNTLNPKQKLALAKE
Musa acuminata                    RKKLRLSKDQSAVLEESFKEHTTLSPKQKLALAKQ
Nelumbo nucifera                  RKKLRLSKDQSAVLEESFKEHNTLNPKQKLALAKQ
Nicotiana sylvestris              RKKLRLSKEQAAVLEETFKEHNTLNPKQKLALSKQ
Oryza barthii                     RKKLRLSKDQSAVLEDSFREHPTLNPRQKATLAQQ
Oryza brachyantha                 RKKLRLSKDQSAVLEDSFREHPTLNPRQKAALAQQ
Oryza glaberrima                  RKKLRLSKDQSAVLEDSFREHPTLNPRQKATLAQQ
Oryza glumipatula                 RKKLRLSKDQSAVLEDSFREHPTLNPRQKATLAQQ
Oryza meridionalis                RKKLRLSKDQSAVLEDSFREHPTLNPRQKATLAQQ
Oryza nivara                      RKKLRLSKDQSAVLEDSFREHPTLNPRQKATLAQQ
Oryza punctata                    RKKLRLSKDQSAVLEDSFREHPTLNPRQKATLAQQ
Oryza rufipogon                   RKKLRLSKDQSAVLEDSFREHPTLNPRQKATLAQQ
Oryza sativa                      RKKLRLSKDQSAVLEDSFREHPTLNPRQKATLAQQ
Phaseolus vulgaris                RKKLRLSKEQALVLEETFKEHNTLNPKQKQALAKQ
Populus trichocarpa               RKKLRLSKEQSLVLEETFKEHNTLNPKEKLALAKQ
Prunus persica                    RKKLRLSKDQSAILEESFKEHNTLNPKQKLALAKQ
Ricinus communis                  RKKLRLSKEQSLLLEETFKEHNTLNPKQKLALAKQ
Setaria italica                   RKKLRLSKDQSAVLEDSFREHPTLNPRQKAALAQQ
Solanum tuberosum                 RKKLRLSKDQSAILEESFKEHNTLNPKQKLALAKR
Sorghum bicolor                   RKKLRLSKDQSAVLEDSFREHPTLNPRQKAALAQQ
Theobroma cacao                   RKKLRLSKEQSLLLEETFKEHSTLNPKQKLALAKQ
Triticum urartu                   RKKLRLSKDQSAVLEDSFREHPTLNPRQKAALAQQ
Vivis vinifera                    RKKLRLSKEQSAILEETFKEHNTLNPKQKLALAKQ
Zea mays                          RKKLRLSKDQSAVLEDSFREHPTLNPRQKAALAQQ
```

FIG. 2A

```
                              40        50        60        70
                              |         |         |         |
Amborella trichopoda          LNLRPRQVEVWFQNRRARTKLKQTEVDCEFLKRCC
Arabidopsis lyrate            LNLRARQVEVWFQNRRARTKLKQTEVDCEYLKRCC
Arabidopsis thaliana          LNLRARQVEVWFQNRRARTKLKQTEVDCEYLKRCC
Arabis alpina                 LNLRTRQVEVWFQNRRARTKLKQTEVDCEYLKRCC
Brachypodium distachyon       LGLRSRQVEVWFQNRRARTKLKQTEVDCEFLKRCC
Brassica campestris           LNLRTRQVEVWFQNRRARTKLKQTEVDCEYLKRCC
Brassica oleracea             LNLWTRQVEVWFQNRRARTKLKQTEVDCEYLKRCC
Capsella rubella              LNLRARQVEVWFQNRRARTKLKQTEVDCEYLKRCC
Cicer arietinum               LNLMPRQVEVWFQNRRARTKLKQTEVDCEYLKRCC
Citrus clementina             LNLRPRQVEVWFQNRRARTKLKQTEVDCEYLKRCC
Citrus sinesis                LNLRPRQVEVWFQNRRARTKLKQTEVDCEYLKRCC
Cucumis melo                  LNLTPRQVEVWFQNRRARTKLKQTEVDCEYLKRCC
Cucumis sativus               LNLTPRQVEVWFQNRRARTKLKQTEVDCEYLKRCC
Erythranthe guttata           LGLRPRQVEVWFQNRRARTKLKQTEVDCEFLKRCC
Eucalyptus grandis            LGLRPRQVEVWFQNRRARTKLKQTEIDCEFLKRCC
Eutrema salsugineum           LNLRTRQVEVWFQNRRARTKLKQTEVDCEYLKRCC
Glycine max                   LNLMPRQVEVWFQNRRARTKLKQTEVDCEYLKRCC
Gossypium raimondii           LGLRPRQVEVWFQNRRARTKLKQTEVDCEFLKRCC
Hordeum vulgare               LGLRSRQVEVWFQNRRARTKLKQTEVDCEFLKRCC
Leersia perrieri              LGLRPRQVEVWFQNRRARTKLKQTEVDCEFLKRCC
Medicago truncatula           LGLRARQVEVWFQNRRARTKLKQTEVDCEFLKRCC
Morus notabilis               LNLRPRQVEVWFQNRRARTKLKQTEVDCEYLKRCC
Musa acuminata                LNLRPRQVEVWFQNRRARTKLKQTEVDCEFLKRCC
Nelumbo nucifera              LNLRPRQVEVWFQNRRARTKLKQTEVDCEYLKRCC
Nicotiana sylvestris          LNLRPRQVEVWFQNRRARTKLKQTEVDCEYLRRCC
Oryza barthii                 LGLRPRQVEVWFQNRRARTKLKQTEVDCEFLKRCC
Oryza brachyantha             LGLRPRQVEVWFQNRRARTKLKQTEVDCEFLKRCC
Oryza glaberrima              LGLRPRQVEVWFQNRRARTKLKQTEVDCEFLKRCC
Oryza glumipatula             LGLRPRQVEVWFQNRRARTKLKQTEVDCEFLKRCC
Oryza meridionalis            LGLRPRQVEVWFQNRRARTKLKQTEVDCEFLKRCC
Oryza nivara                  LGLRPRQVEVWFQNRRARTKLKQTEVDCEFLKRCC
Oryza punctata                LGLRPRQVEVWFQNRRARTKLKQTEVDCEFLKRCC
Oryza rufipogon               LGLRPRQVEVWFQNRRARTKLKQTEVDCEFLKRCC
Oryza sativa                  LGLRPRQVEVWFQNRRARTKLKQTEVDCEFLKRCC
Phaseolus vulgaris            LNLSPRQVEVWFQNRRARTKLKQTEVDCEYLKRCC
Populus trichocarpa           LNLRPRQVEVWFQNRRARTKLKQTEVDCEYLKRCC
Prunus persica                LGLRPRQVEVWFQNRRARTKLKQTEVDCEFLKRCC
Ricinus communis              LNLKPRQVEVWFQNRRARTKSKQTEVDCEYLKRCC
Setaria italica               LGLRPRQVEVWFQNRRARTKLKQTEVDCEFLKRCC
Solanum tuberosum             LGLRPRQVEVWFQNRRARTKLKQTEVDCEFLKRCC
Sorghum bicolor               LGLRPRQVEVWFQNRRARTKLKQTEVDCEYLKRCC
Theobroma cacao               LNLRPRQVEVWFQNRRARTKLKQTEVDCEFLKRCC
Triticum urartu               LGLRSRQVEVWFQNRRARTKLKQTEVDCEFLKRCC
Vivis vinifera                LNLRPRQVEVWFQNRRARTKLKQTEVDCEYLKRCC
Zea mays                      LGLRPRQVEVWFQNRRARTKLKQTEVDCEYLKRCC
                                              ▬▬▬▬▬▬▬
                                          DNA BINDING REGION
```

*FIG. 2B*

```
                                    80          90          100
                                     |           |           |
Amborella trichopoda        ENLTEENRRLQKEVMELRSLKQ-TPHFYMHV-PPA
Arabidopsis lyrate          DSLTEENRRLQKEVSELRALKL-SPHLYMHMTPPT
Arabidopsis thaliana        DNLTEENRRLQKEVSELRALKL-SPHLYMHMTPPT
Arabis alpina               ENLTEENRRLQKEVSELRALKL-SPHLYMHMKPPT
Brachypodium distachyon     ETLTEENRRLQKEVQELRALKLVSPRHYMHMSPPT
Brassica campestris         DTLTEENRRLHKEVAELRALKL-SPHLYMHMTPPT
Brassica oleracea           DTLTEENRRLHKEVSELRALKL-SPHLYMHMTPPT
Capsella rubella            DNLTEENRRLQKEVSELRALKL-SPHLYMHMTPPT
Cicer arietinum             ETLTEENRRLQKEVQELRALKL-SPQLYMHMNPPT
Citrus clementina           ENLTEENRRLQKEVQELRSLKL-SPQLYMNMNPPT
Citrus sinesis              ENLTEENRRLQKEVQELRSLKL-SPQLYMNMNPPT
Cucumis melo                ENLTEENRRLQKEVQELRALKL-SPQLYMHMNPPT
Cucumis sativus             ENLTEENRRLQKEVQELRALKL-SPQLYMHMNPPT
Erythranthe guttata         ENLTEENRRLQKEVQELRALKL-SPQFYMQMTPPT
Eucalyptus grandis          ENLTEENRRLQKEVQELRALKL-SPQFYMHMPPPT
Eutrema salsugineum         DNLTEENRRLHKEVSELRALKL-SPHLYMHMTPPT
Glycine max                 ENLTEENRRLQKEVQELRALKL-SPHLYMQMNPPT
Gossypium raimondii         ENLTEENRRLQKEVQELRALKL-SPQFYMQMTPPT
Hordeum vulgare             ETLTEENRRLQKEVQELRALKLVSPHQYMHMSPPT
Leersia perrieri            ETLTEENRRLQKEVQELRALKLVSPHLYMNMSPPT
Medicago truncatula         ENLTDENRRLQKEVQELRALKL-SPQFYMQMTPPT
Morus notabilis             ENLTEENRRLQKEVQELRALKL-SPQLYMHMSPPT
Musa acuminata              ENLTEENRRLQKEVQELRALKL-SPQLYMQMTPPT
Nelumbo nucifera            ENLTEENRRLQKEVQELRALKL-SPQFYMHMTPPT
Nicotiana sylvestris        ENLTEENRRLQKEVTELRALKL-SPQMYMNMTPPT
Oryza barthii               ETLTEENRRLQKEVQELRALKLVSPHLYMNMSPPT
Oryza brachyantha           ETLTEENRRLQKEVQELRALKLVSPHLYMNMSPPT
Oryza glaberrima            ETLTEENRRLQKEVQELRALKLVSPHLYMNMSPPT
Oryza glumipatula           ETLTEENRRLQKEVQELRALKLVSPHLYMNMSPPT
Oryza meridionalis          ETLTEENRRLQKEVQELRALKLVSPHLYMNMSPPT
Oryza nivara                ETLTEENRRLQKEVQELRALKLVSPHLYMNMSPPT
Oryza punctata              ETLTEENRRLQKEVQELRALKLVSPHLYMNMSPPT
Oryza rufipogon             ETLTEENRRLQKEVQELRALKLVSPHLYMNMSPPT
Oryza sativa                ETLTEENRRLQKEVQELRALKLVSPHLYMNMSPPT
Phaseolus vulgaris          ENLTEENRRLQKEVQELRALKF-SPQLYMHMNPPT
Populus trichocarpa         ENLTEENRRLQKEVQELRALKL-SPQLYMHMNPPT
Prunus persica              ENLTEENRRLQKEVQELRALKL-SPQFYMQMTPPT
Ricinus communis            ENLTQENRRLQKEVQELRALKL-SPQLYMHMNPPT
Setaria italica             ETLTEENRRLQKEVQELRALKLVSPHLYMHMSPPT
Solanum tuberosum           ENLTEENRRLQKEVQELRALKL-SPQFYMQMTPPT
Sorghum bicolor             ETLTEENRRLHKEVQELRALKLVSPHLYMHMPPPT
Theobroma cacao             ENLTEENRRLQKEVQELRALKL-SPQLYMHMNPPT
Triticum urartu             ETLTEENRRLQKEVQELRALKLVSPHHYMHMSPPT
Vivis vinifera              ENLTEENRRLQKEVQELRTLKL-SPQLYMHMNPPT
Zea mays                    ETLTEENRRLQKEVQELRALKLVSPHLYMHMSPPT
```

FIG. 2C

```
                               110       116
                                |         |
Amborella trichopoda        ALTMCPSCERV   (SEQ ID NO:247)
Arabidopsis lyrate          TLTMCPSCERV   (SEQ ID NO:248)
Arabidopsis thaliana        TLTMCPSCERV   (SEQ ID NO:249)
Arabis alpina               TLTMCPSCERV   (SEQ ID NO:250)
Brachypodium distachyon     TLTMCPSCERV   (SEQ ID NO:251)
Brassica campestris         TLTMCPSCERV   (SEQ ID NO:252)
Brassica oleracea           TLTMCPSCERV   (SEQ ID NO:253)
Capsella rubella            TLTMCPSCERV   (SEQ ID NO:254)
Cicer arietinum             TLTMCPSCERV   (SEQ ID NO:255)
Citrus clementina           TLTMCPSCERV   (SEQ ID NO:256)
Citrus sinesis              TLTMCPSCERV   (SEQ ID NO:257)
Cucumis melo                TLTMCPQCERV   (SEQ ID NO:258)
Cucumis sativus             TLTMCPQCERV   (SEQ ID NO:259)
Erythranthe guttata         TLTMCPSCERV   (SEQ ID NO:260)
Eucalyptus grandis          TLTVCPNCERV   (SEQ ID NO:261)
Eutrema salsugineum         TLTMCPSCERV   (SEQ ID NO:262)
Glycine max                 TLTMCPSCERV   (SEQ ID NO:263)
Gossypium raimondii         TLTMCPSCERV   (SEQ ID NO:264)
Hordeum vulgare             TLTMCPSCERV   (SEQ ID NO:265)
Leersia perrieri            TLTMCPSCERV   (SEQ ID NO:266)
Medicago truncatula         TLTMCPSCERV   (SEQ ID NO:267)
Morus notabilis             TLTMCPSCERV   (SEQ ID NO:268)
Musa acuminata              TLTMCPSCERV   (SEQ ID NO:269)
Nelumbo nucifera            TLTMCPSCERV   (SEQ ID NO:270)
Nicotiana sylvestris        TLTMCPQCERV   (SEQ ID NO:271)
Oryza barthii               TLTMCPSCERV   (SEQ ID NO:272)
Oryza brachyantha           TLTMCPSCERV   (SEQ ID NO:273)
Oryza glaberrima            TLTMCPSCERV   (SEQ ID NO:274)
Oryza glumipatula           TLTMCPSCERV   (SEQ ID NO:275)
Oryza meridionalis          TLTMCPSCERV   (SEQ ID NO:276)
Oryza nivara                TLTMCPSCERV   (SEQ ID NO:277)
Oryza punctata              TLTMCPSCERV   (SEQ ID NO:278)
Oryza rufipogon             TLTMCPSCERV   (SEQ ID NO:279)
Oryza sativa                TLTMCPSCERV   (SEQ ID NO:280)
Phaseolus vulgaris          TLTMCPSCERV   (SEQ ID NO:281)
Populus trichocarpa         TLTMCPSCERV   (SEQ ID NO:282)
Prunus persica              TLTMCPSCERV   (SEQ ID NO:283)
Ricinus communis            TLTMCPSCERV   (SEQ ID NO:284)
Setaria italica             TLTMCPSCERV   (SEQ ID NO:285)
Solanum tuberosum           TLTMCPSCERV   (SEQ ID NO:286)
Sorghum bicolor             TLTMCPSCERV   (SEQ ID NO:287)
Theobroma cacao             TLTMCPSCERV   (SEQ ID NO:288)
Triticum urartu             TLTMCPSCERV   (SEQ ID NO:289)
Vivis vinifera              TLTMCPSCERV   (SEQ ID NO:290)
Zea mays                    TLTMCPSCERV   (SEQ ID NO:291)
```

FIG. 2D

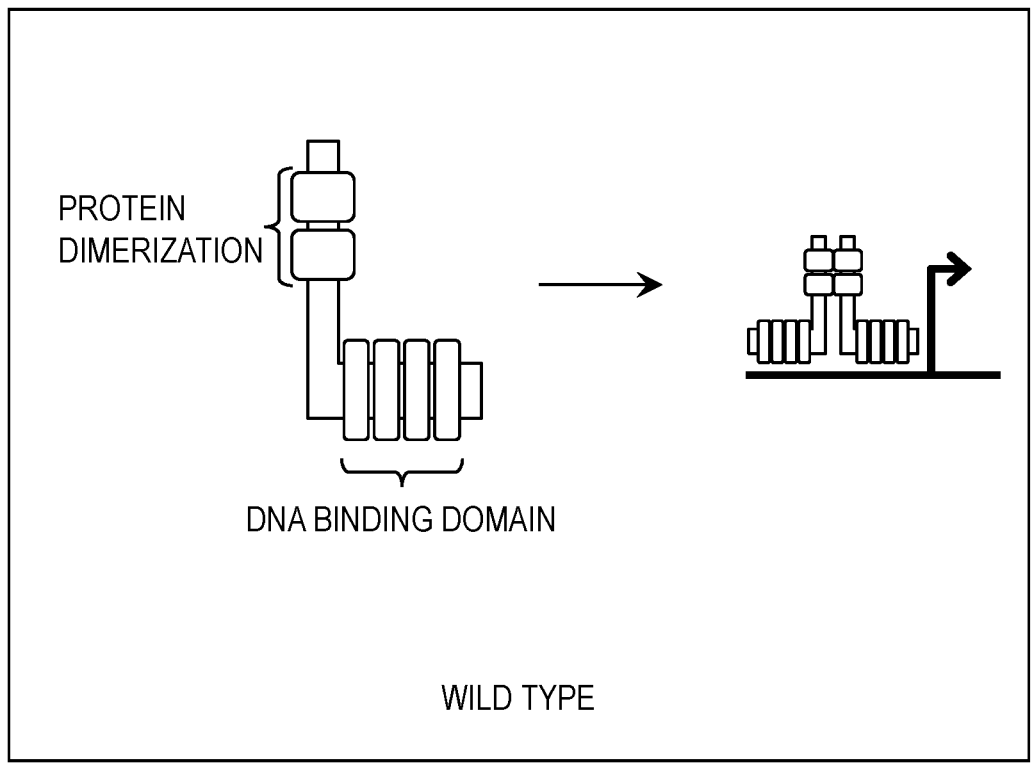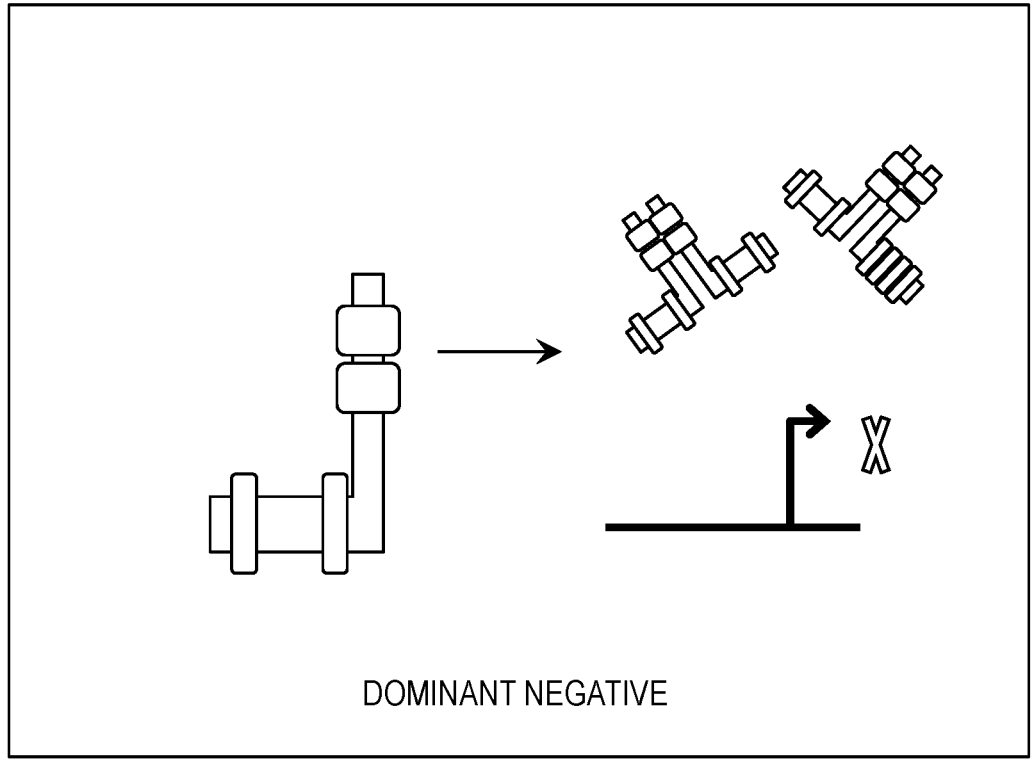
FIG. 4

SEQUENCE LISTING

```
<160> NUMBER OF SEQ ID NOS: 329

<210> SEQ ID NO 1
<211> LENGTH: 116
<212> TYPE: PRT
<213> ORGANISM: Zea mays

<400> SEQUENCE: 1

Arg Lys Lys Leu Arg Leu Ser Lys Asp Gln Ser Ala Val Leu Glu Asp
1               5                   10                  15

Ser Phe Arg Glu His Pro Thr Leu Asn Pro Arg Gln Lys Ala Ala Leu
            20                  25                  30

Ala Gln Gln Leu Gly Leu Arg Pro Arg Gln Val Glu Val Trp Phe Gln
        35                  40                  45

Asn Arg Arg Ala Arg Thr Lys Leu Lys Gln Thr Glu Val Asp Cys Glu
    50                  55                  60

Tyr Leu Lys Arg Cys Cys Glu Thr Leu Thr Glu Glu Asn Arg Arg Leu
65                  70                  75                  80

Gln Lys Glu Val Gln Glu Leu Arg Ala Leu Lys Leu Val Ser Pro His
                85                  90                  95

Leu Tyr Met His Met Ser Pro Pro Thr Thr Leu Thr Met Cys Pro Ser
            100                 105                 110

Cys Glu Arg Val
        115

<210> SEQ ID NO 2
<211> LENGTH: 116
<212> TYPE: PRT
<213> ORGANISM: Zea mays

<400> SEQUENCE: 2

Arg Lys Lys Leu Arg Leu Ser Lys Asp Gln Ala Ala Val Leu Glu Glu
1               5                   10                  15

Ser Phe Lys Glu His Asn Thr Leu Asn Pro Lys Gln Lys Ala Ala Leu
            20                  25                  30

Ala Lys Gln Leu Asn Leu Lys Pro Arg Gln Val Glu Val Trp Phe Gln
        35                  40                  45

Asn Arg Arg Ala Arg Thr Lys Leu Lys Gln Thr Glu Val Asp Cys Glu
    50                  55                  60

Phe Leu Lys Arg Cys Cys Glu Thr Leu Thr Glu Glu Asn Arg Arg Leu
65                  70                  75                  80

Gln Arg Glu Val Ala Glu Leu Arg Val Leu Lys Leu Val Ala Pro His
                85                  90                  95

His Tyr Ala Arg Met Pro Pro Thr Thr Leu Thr Met Cys Pro Ser
            100                 105                 110

Cys Glu Arg Leu
```

<210> SEQ ID NO 3
<211> LENGTH: 53
<212> TYPE: PRT
<213> ORGANISM: Artificial Sequence
<220> FEATURE:
<223> OTHER INFORMATION: Synthetic HD-zip transcription factor peptide

<400> SEQUENCE: 3

Leu Ala Lys Gln Leu Asn Leu Lys Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Phe Leu Lys Arg Cys Cys Glu Thr Leu Thr Glu Glu Asn Arg Arg
        35                  40                  45

Leu Gln Arg Glu Val
    50

<210> SEQ ID NO 4
<211> LENGTH: 24
<212> TYPE: PRT
<213> ORGANISM: Artificial Sequence
<220> FEATURE:
<223> OTHER INFORMATION: Synthetic HD-zip transcription factor peptide

<400> SEQUENCE: 4

Arg Gln Val Glu Val Trp Phe Gln Asn Arg Arg Ala Arg Thr Lys Leu
1               5                   10                  15

Lys Gln Thr Glu Val Asp Cys Glu
            20

<210> SEQ ID NO 5
<211> LENGTH: 24
<212> TYPE: PRT
<213> ORGANISM: Artificial Sequence
<220> FEATURE:
<223> OTHER INFORMATION: Synthetic HD-zip transcription factor peptide
<220> FEATURE:
<221> NAME/KEY: MISC_FEATURE
<222> LOCATION: (16)..(16)
<223> OTHER INFORMATION: Xaa denotes Leu or Ser

<400> SEQUENCE: 5

Arg Gln Val Glu Val Trp Phe Gln Asn Arg Arg Ala Arg Thr Lys Xaa
1               5                   10                  15

Lys Gln Thr Glu Val Asp Cys Glu
            20

<210> SEQ ID NO 6
<211> LENGTH: 11
<212> TYPE: PRT
<213> ORGANISM: Artificial sequence
<220> FEATURE:
<223> OTHER INFORMATION: Synthetic HD-zip transcription factor peptide
<220> FEATURE:
<221> NAME/KEY: MISC_FEATURE
<222> LOCATION: (7)..(7)
<223> OTHER INFORMATION: Xaa denotes Ser or Thr
<220> FEATURE:
<221> NAME/KEY: MISC_FEATURE
<222> LOCATION: (9)..(9)
<223> OTHER INFORMATION: Xaa denotes Asp or Glu
<220> FEATURE:
<221> NAME/KEY: MISC_FEATURE
<222> LOCATION: (11)..(11)
<223> OTHER INFORMATION: Xaa denotes Ser or Ala

```
<400> SEQUENCE: 6

Arg Lys Lys Leu Arg Leu Xaa Lys Xaa Gln Xaa
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Synthetic HD-zip transcription factor peptide
<220> FEATURE:
<221> NAME/KEY: MISC_FEATURE
<222> LOCATION: (6)..(6)
<223> OTHER INFORMATION: Xaa denotes Gln or His
<220> FEATURE:
<221> NAME/KEY: MISC_FEATURE
<222> LOCATION: (7)..(7)
<223> OTHER INFORMATION: Xaa denotes Arg or Lys
<220> FEATURE:
<221> NAME/KEY: MISC_FEATURE
<222> LOCATION: (9)..(9)
<223> OTHER INFORMATION: Xaa denotes Val or Leu

<400> SEQUENCE: 7

Glu Asn Arg Arg Leu Xaa Xaa Glu Xaa
1               5

<210> SEQ ID NO 8
<211> LENGTH: 13
<212> TYPE: PRT
<213> ORGANISM: Artificial Sequence
<220> FEATURE:
<223> OTHER INFORMATION: Synthetic HD-zip transcription factor peptide
<220> FEATURE:
<221> NAME/KEY: MISC_FEATURE
<222> LOCATION: (2)..(2)
<223> OTHER INFORMATION: Xaa denotes Pro or Ala
<220> FEATURE:
<221> NAME/KEY: MISC_FEATURE
<222> LOCATION: (3)..(4)
<223> OTHER INFORMATION: Xaa denotes Thr or Ala
<220> FEATURE:
<221> NAME/KEY: MISC_FEATURE
<222> LOCATION: (7)..(7)
<223> OTHER INFORMATION: Xaa denotes Val or Met
<220> FEATURE:
<221> NAME/KEY: MISC_FEATURE
<222> LOCATION: (10)..(10)
<223> OTHER INFORMATION: Xaa denotes Gln, Ser or Asn

<400> SEQUENCE: 8

Pro Xaa Xaa Xaa Leu Thr Xaa Cys Pro Xaa Cys Glu Arg
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Synthetic DNA binding domain peptide

<400> SEQUENCE: 9

Val Trp Phe Gln Asn Arg Arg Ala
1               5

<210> SEQ ID NO 10
<211> LENGTH: 287
<212> TYPE: PRT
<213> ORGANISM: Citrus sinensis
```

<400> SEQUENCE: 10

```
Met Gly Glu Lys Asp Asp Gly Leu Gly Leu Ser Leu Ser Leu Gly Cys
1               5                   10                  15

Ala Ala Arg Asn Glu Pro Ser Leu Arg Leu Asn His Met Pro Leu Ser
            20                  25                  30

Ser Ser Gln Ser Met Gln Asn His Lys Arg Ser Pro Trp Thr Glu
        35                  40                  45

Leu Phe His Ser Ser Asp Arg Asn Ser Asp Thr Arg Ser Phe Leu Arg
    50                  55                  60

Gly Ile Asp Val Asn Gln Ala Pro Thr Val Ala Asp Cys Glu Glu Glu
65                  70                  75                  80

Asn Gly Val Ser Ser Pro Asn Ser Thr Val Ser Ser Ile Ser Gly Lys
                85                  90                  95

Arg Ser Glu Arg Glu Pro Ile Gly Asp Glu Thr Glu Ala Glu Arg Ala
            100                 105                 110

Ser Cys Ser Arg Gly Ser Asp Asp Glu Asp Gly Gly Ala Gly Asp Ala
        115                 120                 125

Ser Arg Lys Lys Leu Arg Leu Ser Lys Glu Gln Ser Leu Leu Leu Glu
    130                 135                 140

Glu Thr Phe Lys Glu His Ser Thr Leu Asn Pro Lys Gln Lys Leu Ala
145                 150                 155                 160

Leu Ala Lys Gln Leu Asn Leu Arg Pro Arg Gln Val Glu Val Trp Phe
                165                 170                 175

Gln Asn Arg Arg Ala Arg Thr Lys Leu Lys Gln Thr Glu Val Asp Cys
            180                 185                 190

Glu Tyr Leu Lys Arg Cys Cys Glu Asn Leu Thr Glu Glu Asn Arg Arg
        195                 200                 205

Leu Gln Lys Glu Val Gln Glu Leu Arg Ser Leu Lys Leu Ser Pro Gln
    210                 215                 220

Leu Tyr Met Asn Met Asn Pro Pro Thr Thr Leu Thr Met Cys Pro Ser
225                 230                 235                 240

Cys Glu Arg Val Ala Val Ser Ser Ser Ser Ser Ser Ser Ala Ala
                245                 250                 255

Ala Asn Gly Thr Thr Arg Leu Pro Ile Gly Pro Asn His Gln Arg Leu
            260                 265                 270

Thr Pro Val Ser Pro Trp Ala Ala Leu Pro Ile His His Arg Ser
        275                 280                 285
```

<210> SEQ ID NO 11
<211> LENGTH: 294
<212> TYPE: PRT
<213> ORGANISM: Theobroma cacao

<400> SEQUENCE: 11

```
Met Gly Ala Glu Lys Asp Asp Gly Leu Gly Leu Ser Leu Ser Leu Gly
1               5                   10                  15

Cys Ala Gln Asn His Pro Ser Leu Lys Leu Asn Leu Met Pro Leu Ala
            20                  25                  30

Ser Pro Arg Met Gln Asn Leu Gln Gln Lys Asn Thr Trp Asn Glu Leu
        35                  40                  45

Phe Gln Ser Ser Asp Arg Asn Leu Asp Thr Arg Ser Phe Leu Arg Gly
    50                  55                  60

Ile Asp Val Asn Arg Ala Pro Ala Thr Val Asp Cys Glu Glu Glu Gly
65                  70                  75                  80
```

```
Gly Val Ser Ser Pro Asn Ser Thr Ile Ser Ile Ser Gly Lys Arg
                85                  90                  95

Asn Glu Arg Asp Pro Val Gly Asp Thr Glu Ala Glu Arg Ala Ser
            100                 105                 110

Cys Ser Arg Ala Ser Asp Asp Glu Asp Gly Gly Ala Gly Gly Asp Ala
        115                 120                 125

Ser Arg Lys Lys Leu Arg Leu Ser Lys Glu Gln Ser Leu Leu Glu
    130                 135                 140

Glu Thr Phe Lys Glu His Ser Thr Leu Asn Pro Lys Gln Lys Leu Ala
145                 150                 155                 160

Leu Ala Lys Gln Leu Asn Leu Arg Pro Arg Gln Val Glu Val Trp Phe
                165                 170                 175

Gln Asn Arg Arg Ala Arg Thr Lys Leu Lys Gln Thr Glu Val Asp Cys
            180                 185                 190

Glu Tyr Leu Lys Arg Cys Cys Glu Asn Leu Thr Glu Glu Asn Arg Arg
        195                 200                 205

Leu Gln Lys Glu Val Gln Glu Leu Arg Ala Leu Lys Leu Ser Pro Gln
    210                 215                 220

Leu Tyr Met His Met Asn Pro Pro Thr Thr Leu Thr Met Cys Pro Ser
225                 230                 235                 240

Cys Glu Arg Val Ala Val Ser Ser Ser Ser Ser Ala Ala Ala Thr
                245                 250                 255

Ala Ser Ser Thr Pro Thr Ser Thr Val Pro Asn Arg His His Arg Thr
                260                 265                 270

Ser Ser Val Ser Pro Trp Ala Ala Met Pro Ile Gly His Arg Pro Phe
            275                 280                 285

His Ala Pro Ala Ser Arg
    290

<210> SEQ ID NO 12
<211> LENGTH: 292
<212> TYPE: PRT
<213> ORGANISM: Cucumis melo

<400> SEQUENCE: 12

Met Gly Gly Arg Asp Asp Asp Leu Gly Leu Thr Leu Ser Leu Gly Phe
1               5                   10                  15

Gly Val Thr Thr Gln Pro Thr His Met Gln Arg Pro Ser Met His Asn
                20                  25                  30

His Leu Arg Lys Thr Ser Trp Asn Glu Leu Phe Gln Phe Ser Asp Arg
            35                  40                  45

Asn Ala Asp Ser Arg Ser Phe Leu Arg Gly Ile Asp Val Asn Arg Leu
    50                  55                  60

Pro Thr Gly Val Asp Gly Glu Glu Asn Gly Val Ser Ser Pro Asn
65                  70                  75                  80

Ser Thr Ile Ser Ser Ile Ser Gly Lys Arg Ser Glu Arg Glu Ala Ala
                85                  90                  95

Gly Asp Glu Ala Glu Ala Glu Ala Glu Ala Glu Ala Glu Ala
            100                 105                 110

Glu Ala Glu Ala Glu Arg Ala Ser Cys Ser Arg Gly Ser Asp Asp Glu
        115                 120                 125

Asp Gly Gly Gly Asp Gly Asp Ala Ser Arg Lys Lys Leu Arg Leu
    130                 135                 140

Ser Lys Glu Gln Ser Met Val Leu Glu Glu Thr Phe Lys Glu His Asn
145                 150                 155                 160
```

Thr Leu Asn Pro Lys Gln Lys Leu Ala Leu Ala Lys Gln Leu Asn Leu
            165                 170                 175

Thr Pro Arg Gln Val Glu Val Trp Phe Gln Asn Arg Arg Ala Arg Thr
        180                 185                 190

Lys Leu Lys Gln Thr Glu Val Asp Cys Glu Tyr Leu Lys Arg Cys Cys
            195                 200                 205

Glu Asn Leu Thr Glu Glu Asn Arg Arg Leu Gln Lys Glu Val Gln Glu
        210                 215                 220

Leu Arg Ala Leu Lys Leu Ser Pro Gln Leu Tyr Met His Met Asn Pro
225                 230                 235                 240

Pro Thr Thr Leu Thr Met Cys Pro Gln Cys Glu Arg Val Ala Val Ser
                245                 250                 255

Ser Ser Ser Ser Thr Ser Ala Ala Thr Thr Thr Arg His Pro Ala Ala
            260                 265                 270

Ala Gly Val Gln Arg Thr Ser Met Ala Ile Asn Pro Trp Ala Val Leu
        275                 280                 285

Pro Ile Gln Arg
    290

<210> SEQ ID NO 13
<211> LENGTH: 294
<212> TYPE: PRT
<213> ORGANISM: Cucumis sativus

<400> SEQUENCE: 13

Met Gly Gly Arg Asp Asp Val Gly Leu Thr Leu Ser Leu Gly Phe
1               5                   10                  15

Gly Val Thr Thr Gln Ser Thr His Met Gln Arg Pro Ser Ser Met His
            20                  25                  30

Asn His His Leu Arg Lys Thr His Trp Asn Glu Leu Phe Gln Phe Ser
        35                  40                  45

Asp Arg Asn Ala Asp Ser Arg Ser Phe Leu Arg Gly Ile Asp Val Asn
    50                  55                  60

Arg Leu Pro Thr Gly Val Asp Gly Glu Glu Asn Gly Val Ser Ser
65                  70                  75                  80

Pro Asn Ser Thr Ile Ser Ser Ile Ser Gly Lys Arg Ser Glu Arg Glu
                85                  90                  95

Ala Ala Gly Asp Glu Ala Glu Ala Glu Ala Glu Ala Glu Ala
            100                 105                 110

Glu Ala Glu Ala Glu Ala Glu Arg Ala Ser Cys Ser Arg Gly Ser Asp
        115                 120                 125

Asp Glu Asp Gly Gly Gly Gly Asp Gly Asp Ala Ser Arg Lys Lys Leu
    130                 135                 140

Arg Leu Ser Lys Glu Gln Ser Met Val Leu Glu Glu Thr Phe Lys Glu
145                 150                 155                 160

His Asn Thr Leu Asn Pro Lys Gln Lys Leu Ala Leu Ala Lys Gln Leu
                165                 170                 175

Asn Leu Thr Pro Arg Gln Val Glu Val Trp Phe Gln Asn Arg Arg Ala
            180                 185                 190

Arg Thr Lys Leu Lys Gln Thr Glu Val Asp Cys Glu Tyr Leu Lys Arg
        195                 200                 205

Cys Cys Glu Asn Leu Thr Glu Glu Asn Arg Arg Leu Gln Lys Glu Val
    210                 215                 220

Gln Glu Leu Arg Ala Leu Lys Leu Ser Pro Gln Leu Tyr Met His Met

```
                225                 230                 235                 240
Asn Pro Pro Thr Thr Leu Thr Met Cys Pro Gln Cys Glu Arg Val Ala
                    245                 250                 255

Val Ser Ser Ser Ser Thr Ser Ala Ala Thr Thr Thr Arg His Gln
            260                 265                 270

Ala Ala Ala Gly Val Gln Arg Pro Ser Met Ala Ile Asn Pro Trp Ala
            275                 280                 285

Val Leu Pro Ile Gln Arg
        290

<210> SEQ ID NO 14
<211> LENGTH: 298
<212> TYPE: PRT
<213> ORGANISM: Populus trichocarpa

<400> SEQUENCE: 14

Met Gly Asp Lys Asn Asp Gly Leu Gly Leu Ser Leu Ser Leu Gly Phe
1               5                   10                  15

Asp Ala Thr Gln Gln Asn His Gln Gln Gln Pro Ser Leu Lys Leu Asn
                20                  25                  30

Leu Met Pro Val Pro Ser Gln Asn Asn His Arg Lys Thr Ser Leu Thr
            35                  40                  45

Asp Leu Phe Gln Ser Ser Asp Arg Ala Cys Gly Thr Arg Phe Phe Gln
        50                  55                  60

Arg Gly Ile Asp Met Asn Arg Val Pro Ala Ala Val Thr Asp Cys Asp
65                  70                  75                  80

Asp Glu Thr Gly Val Ser Ser Pro Asn Ser Thr Leu Ser Ser Leu Ser
                85                  90                  95

Gly Lys Arg Ser Glu Arg Glu Gln Ile Gly Glu Glu Thr Glu Ala Glu
                100                 105                 110

Arg Ala Ser Cys Ser Arg Asp Ser Asp Glu Asp Gly Ala Gly Gly
            115                 120                 125

Asp Ala Ser Arg Lys Lys Leu Arg Leu Ser Lys Glu Gln Ser Leu Val
        130                 135                 140

Leu Glu Glu Thr Phe Lys Glu His Asn Thr Leu Asn Pro Lys Glu Lys
145                 150                 155                 160

Leu Ala Leu Ala Lys Gln Leu Asn Leu Arg Pro Arg Gln Val Glu Val
                165                 170                 175

Trp Phe Gln Asn Arg Arg Ala Arg Thr Lys Leu Lys Gln Thr Glu Val
            180                 185                 190

Asp Cys Glu Tyr Leu Lys Arg Cys Cys Glu Asn Leu Thr Glu Glu Asn
        195                 200                 205

Arg Arg Leu Gln Lys Glu Val Gln Glu Leu Arg Ala Leu Lys Leu Ser
    210                 215                 220

Pro Gln Leu Tyr Met His Met Asn Pro Pro Thr Thr Leu Thr Met Cys
225                 230                 235                 240

Pro Ser Cys Glu Arg Val Ala Val Ser Ser Ala Ser Ser Ser Ala
                245                 250                 255

Ala Ala Ala Ser Ser Ala Leu Ala Pro Thr Ala Ser Thr Arg Gln Pro
            260                 265                 270

Gln Arg Pro Val Pro Ile Asn Pro Trp Ala Thr Met Pro Val His Gln
        275                 280                 285

Arg Thr Phe Asp Ala Pro Ala Ser Arg Ser
        290                 295
```

<210> SEQ ID NO 15
<211> LENGTH: 318
<212> TYPE: PRT
<213> ORGANISM: Arabidopsis thaliana

<400> SEQUENCE: 15

Met Gly Glu Arg Asp Asp Gly Leu Gly Leu Ser Leu Ser Leu Gly Asn
1               5                   10                  15

Ser Gln Gln Lys Glu Pro Ser Leu Arg Leu Asn Leu Met Pro Leu Thr
            20                  25                  30

Thr Ser Ser Ser Ser Ser Phe Gln His Met His Asn Gln Asn Asn
        35                  40                  45

Asn Ser His Pro Gln Lys Ile His Asn Ile Ser Trp Thr His Leu Phe
    50                  55                  60

Gln Ser Ser Gly Ile Lys Arg Thr Thr Ala Glu Arg Asn Ser Asp Ala
65                  70                  75                  80

Gly Ser Phe Leu Arg Gly Phe Asn Val Asn Arg Ala Gln Ser Ser Val
                85                  90                  95

Ala Val Val Asp Leu Glu Glu Ala Ala Val Ser Ser Pro Asn
            100                 105                 110

Ser Ala Val Ser Ser Leu Ser Gly Asn Lys Arg Asp Leu Ala Val Ala
            115                 120                 125

Arg Gly Gly Asp Glu Asn Glu Ala Glu Arg Ala Ser Cys Ser Arg Gly
    130                 135                 140

Gly Gly Ser Gly Gly Ser Asp Asp Glu Asp Gly Gly Asn Gly Asp Gly
145                 150                 155                 160

Ser Arg Lys Lys Leu Arg Leu Ser Lys Asp Gln Ala Leu Val Leu Glu
                165                 170                 175

Glu Thr Phe Lys Glu His Ser Thr Leu Asn Pro Lys Gln Lys Leu Ala
            180                 185                 190

Leu Ala Lys Gln Leu Asn Leu Arg Ala Arg Gln Val Glu Val Trp Phe
        195                 200                 205

Gln Asn Arg Arg Ala Arg Thr Lys Leu Lys Gln Thr Glu Val Asp Cys
    210                 215                 220

Glu Tyr Leu Lys Arg Cys Cys Asp Asn Leu Thr Glu Glu Asn Arg Arg
225                 230                 235                 240

Leu Gln Lys Glu Val Ser Glu Leu Arg Ala Leu Lys Leu Ser Pro His
                245                 250                 255

Leu Tyr Met His Met Thr Pro Pro Thr Thr Leu Thr Met Cys Pro Ser
            260                 265                 270

Cys Glu Arg Val Ser Ser Ser Ala Ala Thr Val Thr Ala Ala Pro Ser
        275                 280                 285

Thr Thr Thr Thr Pro Thr Val Val Gly Arg Pro Ser Pro Gln Arg Leu
    290                 295                 300

Thr Pro Trp Thr Ala Ile Ser Leu Gln Gln Lys Ser Gly Arg
305                 310                 315

<210> SEQ ID NO 16
<211> LENGTH: 321
<212> TYPE: PRT
<213> ORGANISM: Brassica campestris

<400> SEQUENCE: 16

Met Gly Glu Ser Glu Asp Gly Leu Gly Leu Ser Leu Ser Leu Gly Leu
1               5                   10                  15

```
Ser Gln Leu Lys Glu Pro Ser Leu Gly Leu Gly Leu Asn Leu Leu Pro
            20                  25                  30

Leu Arg Thr Ser Ser Ser Ser Phe Ser His Met His Asn His Asn Asn
        35                  40                  45

Asn His Leu Gln Lys Lys Ile Asn His Asn Ser Trp Pro His Gln Phe
    50                  55                  60

His Ser Ser Glu Arg Asn Ser Asp Val Gly Ser Leu Leu Arg Gly Leu
65                  70                  75                  80

Glu Val Asn Arg Thr Pro Ser Ala Thr Val Val Ile Asn Leu Glu Glu
                85                  90                  95

Asp Leu Ala Gly Val Ser Ser Pro Asn Ser Asn Ile Ser Ser Val Ser
            100                 105                 110

Gly Asn Lys Arg Asp Leu Ala Ala Arg Gly Asp Gly Gly Asp
        115                 120                 125

Glu Asn Glu Ala Glu Arg Ala Ser Cys Ser His Gly Gly Gly Ser Asp
    130                 135                 140

Glu Glu Glu Gly Gly Asn Cys Glu Gly Thr Arg Lys Lys Leu Arg Leu
145                 150                 155                 160

Ser Lys Glu Gln Ala Leu Val Leu Glu Asp Thr Phe Lys Glu His Ser
                165                 170                 175

Thr Leu Asn Pro Lys Gln Lys Leu Ala Leu Ala Lys Gln Leu Asn Leu
            180                 185                 190

Arg Thr Arg Gln Val Glu Val Trp Phe Gln Asn Arg Arg Ala Arg Thr
        195                 200                 205

Lys Leu Lys Gln Thr Glu Val Asp Cys Glu Tyr Leu Lys Arg Cys Cys
    210                 215                 220

Asp Thr Leu Thr Glu Glu Asn Arg Arg Leu His Lys Glu Val Ala Glu
225                 230                 235                 240

Leu Arg Ala Leu Lys Leu Ser Pro His Leu Tyr Met His Met Thr Pro
                245                 250                 255

Pro Thr Thr Leu Thr Met Cys Pro Ser Cys Glu Arg Val Ser Ala Ser
            260                 265                 270

Ser Ser Ser Ser Ala Met Ala Ala Ala Ala Pro Pro Ser Ser Ile Thr
        275                 280                 285

Ser Gly Gly Gly Gly Arg Ile Pro Thr Val Val Gly Arg Pro Ser Pro
    290                 295                 300

Gln Arg Pro Thr Pro Cys Ala Ala Ile Ser Leu Gln Ser Arg Leu Ala
305                 310                 315                 320

His

<210> SEQ ID NO 17
<211> LENGTH: 318
<212> TYPE: PRT
<213> ORGANISM: Brassica oleracea

<400> SEQUENCE: 17

Met Gly Glu Ser Glu Asp Gly Leu Gly Leu Ser Leu Ser Leu Gly Leu
1               5                   10                  15

Ser Gln Leu Lys Glu Pro Ser Leu Gly Leu Gly Leu Asn Leu Leu Pro
            20                  25                  30

Leu Arg Thr Ser Ser Phe Ser His Met His Asn His Asn Asn Asn His
        35                  40                  45

Leu Gln Lys Lys Ile Tyr His Asn Ser Trp Pro His Gln Phe Gln Ser
    50                  55                  60
```

Ser Glu Arg Asn Ser Asp Val Gly Ser Leu Leu Arg Gly Leu Glu Val
65                  70                  75                  80

Asn Arg Thr Pro Ser Ala Thr Val Val Ile Asn Leu Glu Glu Asp Ala
                85                  90                  95

Ala Gly Val Ser Ser Pro Asn Ser Asn Val Ser Ser Val Ser Gly Asn
            100                 105                 110

Lys Arg Asp Leu Ala Ala Ala Arg Gly Asp Gly Gly Asp Glu Asn
        115                 120                 125

Glu Ala Glu Arg Ala Ser Cys Ser His Arg Gly Gly Ser Asp Glu Glu
    130                 135                 140

Glu Gly Gly Asn Cys Glu Gly Thr Arg Lys Lys Leu Arg Leu Ser Lys
145                 150                 155                 160

Glu Gln Ala Leu Val Leu Glu Glu Thr Phe Lys Glu His Ser Thr Leu
                165                 170                 175

Asn Pro Lys Gln Lys Leu Ala Leu Ala Lys Gln Leu Asn Leu Trp Thr
            180                 185                 190

Arg Gln Val Glu Val Trp Phe Gln Asn Arg Arg Ala Arg Thr Lys Leu
        195                 200                 205

Lys Gln Thr Glu Val Asp Cys Glu Tyr Leu Lys Arg Cys Cys Asp Thr
210                 215                 220

Leu Thr Glu Glu Asn Arg Arg Leu His Lys Glu Val Ser Glu Leu Arg
225                 230                 235                 240

Ala Leu Lys Leu Ser Pro His Leu Tyr Met His Met Thr Pro Pro Thr
                245                 250                 255

Thr Leu Thr Met Cys Pro Ser Cys Glu Arg Val Ser Ala Ser Ser Ser
            260                 265                 270

Ser Ser Ala Met Ala Ala Ala Pro Pro Ser Ser Thr Ala Ser Gly
        275                 280                 285

Gly Gly Arg Ile Pro Thr Val Val Gly Arg Pro Ser Pro Gln Arg Pro
    290                 295                 300

Thr Pro Cys Ala Ala Ile Ser Leu Gln Ser Arg Leu Ala His
305                 310                 315

<210> SEQ ID NO 18
<211> LENGTH: 319
<212> TYPE: PRT
<213> ORGANISM: Prunus persica

<400> SEQUENCE: 18

Met Met Val Glu Arg Asp Gln Asp Leu Gly Leu Ser Leu Ser Leu Ser
1               5                   10                  15

Phe Pro Gln Thr His Asn His His Asn Asn Asn Asn Asn Asn Ser Ser
                20                  25                  30

Ser Thr Thr Ser Thr Leu Gln Leu Asn Leu Met Pro Ser Leu Ala Pro
            35                  40                  45

Thr Ser Ala Ser Ser Pro Ser Gly Phe Leu Pro Gln Lys Pro Ser Trp
        50                  55                  60

Asn Glu Ala Leu Ile Ser Ser Asp Arg Asn Ser Asn Ser Glu Thr Phe
65                  70                  75                  80

Arg Val Gly Pro Arg Ser Phe Leu Arg Gly Ile Asp Val Asn Arg Leu
                85                  90                  95

Pro Ser Thr Gly Asp Cys Glu Asp Glu Ala Gly Val Ser Ser Pro Asn
            100                 105                 110

Ser Thr Val Ser Ser Val Ser Gly Lys Arg Ser Glu Arg Glu Ala Asn
        115                 120                 125

```
Gly Glu Asp Leu Asp Ile Glu Thr Arg Gly Ile Ser Asp Glu Glu Asp
            130                 135                 140

Gly Glu Thr Ser Arg Lys Lys Leu Arg Leu Ser Lys Asp Gln Ser Ala
145                 150                 155                 160

Ile Leu Glu Glu Ser Phe Lys Glu His Asn Thr Leu Asn Pro Lys Gln
                165                 170                 175

Lys Leu Ala Leu Ala Lys Gln Leu Gly Leu Arg Pro Arg Gln Val Glu
            180                 185                 190

Val Trp Phe Gln Asn Arg Arg Ala Arg Thr Lys Leu Lys Gln Thr Glu
        195                 200                 205

Val Asp Cys Glu Phe Leu Lys Arg Cys Cys Glu Asn Leu Thr Glu Glu
210                 215                 220

Asn Arg Arg Leu Gln Lys Glu Val Gln Glu Leu Arg Ala Leu Lys Leu
225                 230                 235                 240

Ser Pro Gln Phe Tyr Met Gln Met Thr Pro Thr Thr Leu Thr Met
                245                 250                 255

Cys Pro Ser Cys Glu Arg Val Ala Val Pro Pro Asn Ser Ser Ser Ser
                260                 265                 270

Thr Val Glu Pro Arg Pro His Pro His Pro His Pro Gln Met Gly Ser
            275                 280                 285

Val Gln Thr Arg Pro Val Pro Ile Asn Pro Trp Ala Ser Ala Thr Pro
290                 295                 300

Ile Pro His Arg Pro Leu Pro Phe Glu Ala Phe His Thr Arg Thr
305                 310                 315

<210> SEQ ID NO 19
<211> LENGTH: 299
<212> TYPE: PRT
<213> ORGANISM: Cicer arietinum

<400> SEQUENCE: 19

Met Gly Asp Lys Glu Asp Glu Leu Gly Leu Gly Leu Ser Leu Ser Leu
1               5                   10                  15

Ser Leu Gly Tyr Gly Ala Asn Ala Asn Asn Ala Pro Leu Lys Val Thr
            20                  25                  30

His Met His Lys Pro Pro Gln Ser Val Pro Asn Gln Arg Val Ser Phe
        35                  40                  45

Asn Asn Phe Phe His Phe His Asp Leu Ser Ser Glu Thr Arg Ser Phe
    50                  55                  60

Ile Gly Gly Ile Asp Val Asn Ser Pro Ala Thr Ala Ala Cys Asp Asp
65                  70                  75                  80

Glu Asn Gly Gly Ser Ser Pro Asn Ser Thr Val Ser Ser Ile Ser Gly
                85                  90                  95

Lys Arg Ser Glu Arg Glu Gly Asn Gly Glu Glu Asn Asp Ala Val Glu
            100                 105                 110

Arg Ala Ser Cys Ser Arg Gly Gly Ser Asp Asp Asp Gly Gly Gly
        115                 120                 125

Cys Gly Gly Asp Gly Asp Ser Ser Arg Lys Lys Leu Arg Leu Ser Lys
130                 135                 140

Glu Gln Ser Val Leu Leu Glu Glu Thr Phe Lys Glu His Asn Thr Leu
145                 150                 155                 160

Asn Pro Lys Gln Lys Gln Ala Leu Ala Lys Gln Leu Asn Leu Met Pro
                165                 170                 175

Arg Gln Val Glu Val Trp Phe Gln Asn Arg Arg Ala Arg Thr Lys Leu
```

```
            180                 185                 190
Lys Gln Thr Glu Val Asp Cys Glu Tyr Leu Lys Arg Cys Cys Glu Thr
            195                 200                 205
Leu Thr Glu Glu Asn Arg Arg Leu Gln Lys Glu Val Gln Glu Leu Arg
        210                 215                 220
Ala Leu Lys Leu Ser Pro Gln Leu Tyr Met His Met Asn Pro Pro Thr
225                 230                 235                 240
Thr Leu Thr Met Cys Pro Ser Cys Glu Arg Val Ala Val Ser Ser Ala
                245                 250                 255
Ser Ser Ser Ser Ala Asn Val Pro Ser Ala Leu Ala Pro Ala Asn Arg
            260                 265                 270
Asn Ser Ile Gly Pro Ser Val Gln Arg Pro Val Pro Leu Asn Pro Trp
        275                 280                 285
Ala Ala Met Ser Ile Gln Asn Arg Ser Arg Pro
            290                 295

<210> SEQ ID NO 20
<211> LENGTH: 317
<212> TYPE: PRT
<213> ORGANISM: Glycine max

<400> SEQUENCE: 20

Met Gly Glu Lys Asp Asp Gly Leu Gly Leu Gly Leu Ser Leu Lys Leu
1               5                   10                  15
Gly Trp Gly Glu Asn Asn Asp Asn Asn Asn Gln Gln Gln His Pro
            20                  25                  30
Phe Asn Val His Lys Pro Pro Gln Ser Val Pro Asn Gln Arg Val Ser
            35                  40                  45
Val Asn Ser Leu Phe His Phe His Asp Glu Asn His Ala Met Arg Asn
        50                  55                  60
Thr Asp Arg Ser Ser Glu Met Arg Ser Phe Phe Arg Gly Ile Asp Val
65                  70                  75                  80
Asn Leu Pro Pro Pro Pro Ser Ala Ala Leu Ala Ala Phe Asp Asp
                85                  90                  95
Glu Asn Gly Val Ser Ser Pro Asn Ser Thr Ile Ser Ser Ile Ser Gly
            100                 105                 110
Lys Arg Ser Glu Arg Glu Gly Asn Gly Glu Glu Asn Glu Arg Thr Ser
        115                 120                 125
Ser Ser Arg Gly Gly Gly Ser Asp Asp Asp Glu Gly Gly Ala Cys
    130                 135                 140
Gly Gly Asp Ala Asp Ala Asp Ala Ser Arg Lys Lys Leu Arg Leu Ser
145                 150                 155                 160
Lys Glu Gln Ala Leu Val Leu Glu Glu Thr Phe Lys Glu His Asn Thr
                165                 170                 175
Leu Asn Pro Lys Gln Lys Gln Ala Leu Ala Lys Gln Leu Asn Leu Met
            180                 185                 190
Pro Arg Gln Val Glu Val Trp Phe Gln Asn Arg Arg Ala Arg Thr Lys
        195                 200                 205
Leu Lys Gln Thr Glu Val Asp Cys Glu Tyr Leu Lys Arg Cys Cys Glu
    210                 215                 220
Asn Leu Thr Glu Glu Asn Arg Arg Leu Gln Lys Glu Val Gln Glu Leu
225                 230                 235                 240
Arg Ala Leu Lys Leu Ser Pro His Leu Tyr Met Gln Met Asn Pro Pro
                245                 250                 255
```

Thr Thr Leu Thr Met Cys Pro Ser Cys Glu Arg Val Ala Val Ser Ser
              260                 265                 270

Ala Ser Ser Ser Ser Ala Thr Met Pro Ser Ala Leu Pro Pro Ala
          275                 280                 285

Asn Leu Asn Pro Val Gly Pro Thr Ile Gln Arg Pro Met Pro Val Asn
    290                 295                 300

Pro Trp Ala Ala Met Leu Asn Gln His Arg Gly Arg Pro
305                 310                 315

<210> SEQ ID NO 21
<211> LENGTH: 296
<212> TYPE: PRT
<213> ORGANISM: Medicago truncatula

<400> SEQUENCE: 21

Met Ser Ile Glu Lys Glu Asp Phe Gly Leu Ser Leu Ser Leu Ser Phe
1               5                   10                  15

Pro Gln Asn Pro Pro Asn Pro Gln Tyr Leu Asn Leu Met Ser Ser Ser
            20                  25                  30

Thr His Ser Tyr Ser Pro Ser Thr Phe Asn Pro Gln Lys Pro Ser Trp
        35                  40                  45

Asn Asp Val Phe Thr Ser Ser Asp Arg Asp Ser Glu Thr Cys Arg Ile
    50                  55                  60

Glu Glu Arg Pro Leu Ile Leu Arg Gly Ile Asp Val Asn Arg Leu Pro
65                  70                  75                  80

Ser Gly Ala Asp Cys Glu Glu Ala Gly Val Ser Ser Pro Asn Ser
                85                  90                  95

Thr Val Ser Ser Val Ser Gly Lys Arg Ser Glu Arg Glu Val Thr Gly
            100                 105                 110

Glu Asp Leu Asp Met Glu Arg Asp Cys Ser Arg Gly Ile Ser Asp Glu
        115                 120                 125

Glu Asp Ala Glu Thr Ser Arg Lys Lys Leu Arg Leu Thr Lys Asp Gln
    130                 135                 140

Ser Ile Ile Leu Glu Glu Ser Phe Lys Glu His Asn Thr Leu Asn Pro
145                 150                 155                 160

Lys Gln Lys Leu Ala Leu Ala Lys Gln Leu Gly Leu Arg Ala Arg Gln
                165                 170                 175

Val Glu Val Trp Phe Gln Asn Arg Arg Ala Arg Thr Lys Leu Lys Gln
            180                 185                 190

Thr Glu Val Asp Cys Glu Phe Leu Lys Arg Cys Cys Glu Asn Leu Thr
        195                 200                 205

Asp Glu Asn Arg Arg Leu Gln Lys Glu Val Gln Glu Leu Arg Ala Leu
    210                 215                 220

Lys Leu Ser Pro Gln Phe Tyr Met Gln Met Thr Pro Thr Thr Leu
225                 230                 235                 240

Thr Met Cys Pro Ser Cys Glu Arg Val Ala Val Pro Ser Ser Ala Val
                245                 250                 255

Asp Ala Ala Thr Arg Arg His Pro Met Ala Ser Asn His Pro Arg Thr
            260                 265                 270

Phe Ser Val Gly Pro Trp Ala Thr Ala Ala Pro Ile Gln His Arg Thr
        275                 280                 285

Phe Asp Thr Leu Arg Pro Arg Ser
    290                 295

<210> SEQ ID NO 22

```
<211> LENGTH: 305
<212> TYPE: PRT
<213> ORGANISM: Phaseolus vulgaris

<400> SEQUENCE: 22
```

| | | | | | | | | | | | | | | |
|---|---|---|---|---|---|---|---|---|---|---|---|---|---|---|
|Met|Gly|Glu|Lys|Asp|Asp|Gly|Leu|Gly|Leu|Arg|Leu|Ser|Leu|Arg|Trp|
|1| | |5| | | | |10| | | | |15| |

Gly Glu Asn Asp Asp Asn Asn Met Asn Gln Gln His Pro Phe Asn Met
                20                  25                  30

His Lys Pro Pro Gln Pro Val Pro Asn Gln Arg Thr Ser Phe Asn Asn
             35                  40                  45

Leu Phe His Phe His Gly Ala Ser His Val Thr Asn Arg Asn Ser Glu
         50                  55                  60

Pro Pro Pro Phe Phe Phe Gly Ile Asp Val Asn Leu Pro Pro Pro
65              70                  75                  80

Thr Pro Thr Pro Ser Val Val Pro Cys Glu Glu Asp Asn Leu Val Ser
                 85                  90                  95

Ser Gln Asn Ser Ala Val Ser Ser Ile Ser Gly Lys Arg Ser Glu Arg
            100                 105                 110

Glu Glu Asn Glu Arg Gly Ser Cys Ser His Gly Ser Glu Asp Glu Asp
        115                 120                 125

Gly Gly Gly Phe Gly Gly Glu Gly Asp Gly Asp Met Ser Arg Lys Lys
    130                 135                 140

Leu Arg Leu Ser Lys Glu Gln Ala Leu Val Leu Glu Glu Thr Phe Lys
145                 150                 155                 160

Glu His Asn Thr Leu Asn Pro Lys Gln Lys Gln Ala Leu Ala Lys Gln
                165                 170                 175

Leu Asn Leu Ser Pro Arg Gln Val Glu Val Trp Phe Gln Asn Arg Arg
            180                 185                 190

Ala Arg Thr Lys Leu Lys Gln Thr Glu Val Asp Cys Glu Tyr Leu Lys
        195                 200                 205

Arg Cys Cys Glu Asn Leu Thr Glu Glu Asn Arg Arg Leu Gln Lys Glu
    210                 215                 220

Val Gln Glu Leu Arg Ala Leu Lys Phe Ser Pro Gln Leu Tyr Met His
225                 230                 235                 240

Met Asn Pro Pro Thr Thr Leu Thr Met Cys Pro Ser Cys Glu Arg Val
                245                 250                 255

Ala Val Ser Ser Ala Ser Ser Ser Ser Ala Ala Met Pro Ser Val
            260                 265                 270

Pro Pro Pro Ala Asn His Asn Pro Leu Gly Pro Thr Ile Gln Arg Pro
        275                 280                 285

Val Pro Val Asn Pro Trp Ala Ala Met Ser Ile Gln Arg Pro Cys Arg
    290                 295                 300

Asn
305

```
<210> SEQ ID NO 23
<211> LENGTH: 294
<212> TYPE: PRT
<213> ORGANISM: Ricinus communis

<400> SEQUENCE: 23
```

Met Glu Asp Lys Asp Asp Gly Leu Gly Leu Gly Leu Ser Leu Ser Leu
1               5                   10                  15

Gly Gly Gln Glu Lys His Gln Asn Gln Pro Ser Leu Lys Leu Asn Leu
                20                  25                  30

```
Met Pro Phe Pro Ser Leu Phe Met Gln Asn Thr His His Ser Thr Ser
            35                  40                  45

Leu Asn Asp Leu Phe Gln Ser Ser Asp Arg Asn Ala Asp Thr Arg Ser
 50                  55                  60

Phe Gln Arg Gly Ile Asp Met Asn Arg Met Pro Leu Phe Ala Asp Cys
 65                  70                  75                  80

Asp Asp Glu Asn Gly Val Ser Ser Pro Asn Ser Thr Ile Ser Ser Leu
                 85                  90                  95

Ser Gly Lys Arg Ser Glu Arg Glu Gln Ile Gly Gly Glu Glu Met Glu
                100                 105                 110

Ala Glu Arg Ala Ser Cys Ser Arg Gly Gly Ser Asp Asp Glu Asp Gly
                115                 120                 125

Gly Ala Gly Gly Asp Asp Gly Ser Arg Lys Lys Leu Arg Leu Ser Lys
            130                 135                 140

Glu Gln Ser Leu Leu Leu Glu Glu Thr Phe Lys Glu His Asn Thr Leu
145                 150                 155                 160

Asn Pro Lys Gln Lys Leu Ala Leu Ala Lys Gln Leu Asn Leu Lys Pro
                165                 170                 175

Arg Gln Val Glu Val Trp Phe Gln Asn Arg Arg Ala Arg Thr Lys Ser
                180                 185                 190

Lys Gln Thr Glu Val Asp Cys Glu Tyr Leu Lys Arg Cys Cys Glu Asn
                195                 200                 205

Leu Thr Gln Glu Asn Arg Arg Leu Gln Lys Glu Val Gln Glu Leu Arg
            210                 215                 220

Ala Leu Lys Leu Ser Pro Gln Leu Tyr Met His Met Asn Pro Pro Thr
225                 230                 235                 240

Thr Leu Thr Met Cys Pro Ser Cys Glu Arg Val Ala Val Ser Ser Ser
                245                 250                 255

Ala Ala Pro Ser Arg Gln Pro Pro Asn Ser Gln Pro Gln Arg Pro Val
                260                 265                 270

Pro Val Lys Pro Trp Ala Ala Leu Pro Ile Gln His Arg Pro Phe Asp
                275                 280                 285

Thr Pro Ala Ser Arg Ser
            290

<210> SEQ ID NO 24
<211> LENGTH: 293
<212> TYPE: PRT
<213> ORGANISM: Nicotiana sylvestris

<400> SEQUENCE: 24

Met Gly Gly Glu Lys Glu Asp Gly Leu Gly Leu Ser Leu Ser Leu Gly
1               5                   10                  15

Met Ser Cys Pro Gln Asn Asn Leu Lys Asn Asn Asp Phe Ile Ser Pro
                20                  25                  30

Ser Thr Pro Pro Phe Leu Leu Pro Phe Met His Asn His Gln Ile Ser
            35                  40                  45

Ala Glu Arg Asn Glu Glu Ala Arg Glu Phe Ile Arg Gly Glu Ile Asp
 50                  55                  60

Met Asn Arg Pro Val Arg Met Ile Glu Ala Cys Asp Glu Glu Leu Glu
 65                  70                  75                  80

Asp Glu Ala Val Ile Met Val Ser Ser Pro Asn Asn Ser Thr Val Ser
                 85                  90                  95

Ser Val Ser Gly Lys Arg Ser His Asp Arg Glu Asp Asn Glu Gly Glu
```

```
            100                 105                 110
Arg Pro Thr Ser Ser Leu Glu Asp Asp Gly Gly Asp Ala Ala Ala Arg
        115                 120                 125

Lys Lys Leu Arg Leu Ser Lys Glu Gln Ala Ala Val Leu Glu Glu Thr
        130                 135                 140

Phe Lys Glu His Asn Thr Leu Asn Pro Lys Gln Lys Leu Ala Leu Ser
145                 150                 155                 160

Lys Gln Leu Asn Leu Arg Pro Arg Gln Val Glu Val Trp Phe Gln Asn
                165                 170                 175

Arg Arg Ala Arg Thr Lys Leu Lys Gln Thr Glu Val Asp Cys Glu Tyr
                180                 185                 190

Leu Arg Arg Cys Cys Glu Asn Leu Thr Glu Glu Asn Arg Arg Leu Gln
                195                 200                 205

Lys Glu Val Thr Glu Leu Arg Ala Leu Lys Leu Ser Pro Gln Met Tyr
        210                 215                 220

Met Asn Met Thr Pro Pro Thr Thr Leu Thr Met Cys Pro Gln Cys Glu
225                 230                 235                 240

Arg Val Ala Val Ser Ser Ser Ser Ser Val Thr Ser Ala Gly Val
                245                 250                 255

Ser Arg Ser Asn His Pro Val Gly Ala Leu His Gln Pro Pro Val Pro
                260                 265                 270

Leu Asn Lys Pro Trp Ala Ala Ile Phe Ser Pro Lys Thr Leu Asp Asp
        275                 280                 285

Gln Arg Thr Gln Leu
        290

<210> SEQ ID NO 25
<211> LENGTH: 275
<212> TYPE: PRT
<213> ORGANISM: Solanum tuberosum

<400> SEQUENCE: 25

Met Val Glu Lys Glu Asp Leu Gly Leu Ser Leu Ser Leu Ser Phe Pro
1               5                   10                  15

Asp Asn Asn Asn Lys Lys Asn Thr Gln Leu Asn Leu Ser Pro Phe Asn
                20                  25                  30

Leu Ile Gln Lys Thr Ser Trp Thr Asp Ser Leu Phe Pro Ser Ser Asp
        35                  40                  45

Arg Asn Ile Glu Thr Cys Arg Val Glu Thr Arg Thr Phe Leu Lys Gly
    50                  55                  60

Ile Asp Val Asn Arg Leu Pro Ala Thr Gly Glu Ala Asp Glu Glu Ala
65                  70                  75                  80

Gly Val Ser Ser Pro Asn Ser Thr Ile Ser Ser Val Ser Gly Asn Lys
                85                  90                  95

Arg Thr Glu Arg Glu Ala Asn Asn Cys Asp Gln Glu Glu His Glu Met
            100                 105                 110

Glu Arg Gly Ser Asp Glu Glu Asp Gly Glu Thr Ser Arg Lys Lys Leu
        115                 120                 125

Arg Leu Ser Lys Asp Gln Ser Ala Ile Leu Glu Glu Ser Phe Lys Glu
        130                 135                 140

His Asn Thr Leu Asn Pro Lys Gln Lys Leu Ala Leu Ala Lys Arg Leu
145                 150                 155                 160

Gly Leu Arg Pro Arg Gln Val Glu Val Trp Phe Gln Asn Arg Arg Ala
                165                 170                 175
```

```
Arg Thr Lys Leu Lys Gln Thr Glu Val Asp Cys Glu Phe Leu Lys Arg
            180                 185                 190

Cys Cys Glu Asn Leu Thr Glu Leu Asn Arg Arg Leu Gln Lys Glu Val
        195                 200                 205

Gln Glu Leu Arg Ala Leu Lys Leu Ser Pro Gln Phe Tyr Met Gln Met
    210                 215                 220

Thr Pro Pro Thr Thr Leu Thr Met Cys Pro Ser Cys Glu Arg Val Ala
225                 230                 235                 240

Gly Pro Pro Ser Ser Ser Ser Gly Pro Thr Ser Thr Pro Met Gly Gln
                245                 250                 255

Ala Gln Pro Arg Pro Arg Pro Phe Asn Leu Trp Ala Asn Ala Leu His
        260                 265                 270

Pro Arg Ser
        275

<210> SEQ ID NO 26
<211> LENGTH: 323
<212> TYPE: PRT
<213> ORGANISM: Erythranthe guttata

<400> SEQUENCE: 26

Met Met Thr Ala Gly Lys Glu Asp Leu Gly Leu Ser Leu Ser Leu Thr
1               5                   10                  15

Phe Pro Pro Glu Lys Lys Ala Val Ser Asn Ile Pro Ser Ser Leu His
            20                  25                  30

Leu Asn Leu Met Pro Ser Ser Pro Ser Pro Asn Phe Thr Ile Phe Asn
        35                  40                  45

Asn Asn Phe Asn Trp Thr Ser Thr Gln Gln Ala Ala Ala Ala Phe Pro
50                  55                  60

Phe Ser Asp Arg Ser Ser Glu Thr Cys Arg Val Glu Thr Thr Arg Ser
65                  70                  75                  80

Phe Leu Lys Gly Ile Asp Val Asn Cys Leu Pro Ser Ala Ala Ala Ala
                85                  90                  95

Glu Glu Glu Glu Glu Glu Gly Gly Gly Val Ser Ser Pro Asn Ser
            100                 105                 110

Thr Ile Ser Ser Val Ser Gly Lys Arg Ser Glu Arg Glu Asp Ala Thr
        115                 120                 125

Glu Glu His Asp Gly Glu Arg Ala Cys Ser Arg Gly Ile Ser Asp Glu
    130                 135                 140

Glu Asp Ala Glu Asn Ala Arg Lys Lys Leu Arg Leu Ser Lys Asp Gln
145                 150                 155                 160

Ser Ala Thr Leu Glu Glu Ser Phe Lys Glu His Asn Thr Leu Asn Pro
                165                 170                 175

Lys Gln Lys Met Ala Leu Ala Lys Arg Leu Gly Leu Arg Pro Arg Gln
            180                 185                 190

Val Glu Val Trp Phe Gln Asn Arg Arg Ala Arg Thr Lys Leu Lys Gln
        195                 200                 205

Thr Glu Val Asp Cys Glu Phe Leu Lys Arg Cys Cys Glu Asn Leu Thr
    210                 215                 220

Glu Glu Asn Arg Arg Leu Gln Lys Glu Val Gln Glu Leu Arg Ala Leu
225                 230                 235                 240

Lys Leu Ser Pro Gln Phe Tyr Met Gln Met Thr Pro Thr Thr Leu
                245                 250                 255

Thr Met Cys Pro Ser Cys Glu Arg Val Ala Val Pro Thr Met Gly Gly
        260                 265                 270
```

```
Pro Pro Ser Asn Gly Gly Arg Ala Pro Pro Ala Ala Ser Ala Ala Ala
            275                 280                 285

Ala Val Gln Pro Arg Pro Ile Thr Phe Asn Pro Trp Ala Ala Val Met
290                 295                 300

Pro Ser Gln Gln Gln Gln Leu His Arg Pro Phe Asp Ala Ile Met
305                 310                 315                 320

His Ser Arg

<210> SEQ ID NO 27
<211> LENGTH: 302
<212> TYPE: PRT
<213> ORGANISM: Nelumbo nucifera

<400> SEQUENCE: 27

Met Met Val Glu Lys Glu Asp Leu Gly Leu Ser Leu Ser Leu Ser Thr
1               5                   10                  15

Ala Asp Ser Arg His Ser Leu Gln Leu Asn Leu Met Pro Ser Ser Val
            20                  25                  30

Ser Ser Ser Pro Ala Ser Pro Phe Val Ala Gln Lys Asn Thr Trp Asn
            35                  40                  45

Glu Ala Phe Ala Ser Ser Asp Arg Asn Ser Asp Met Phe Arg Gly Glu
50                  55                  60

Thr Arg Thr Phe Leu Arg Gly Ile Asp Val Asn Arg Met Pro Ser Thr
65                  70                  75                  80

Val Asp Cys Glu Glu Ala Ala Val Ser Ser Pro Asn Ser Thr Ile
                85                  90                  95

Ser Ser Val Ser Gly Lys Arg Ser Glu Arg Asp Thr Asn Gly Glu Glu
            100                 105                 110

His Glu Ile Glu Arg Ala Cys Ser Arg Gly Ile Ser Asp Glu Glu Asp
        115                 120                 125

Gly Asp Met Ser Arg Lys Lys Leu Arg Leu Ser Lys Asp Gln Ser Ala
    130                 135                 140

Val Leu Glu Glu Ser Phe Lys Glu His Asn Thr Leu Asn Pro Lys Gln
145                 150                 155                 160

Lys Leu Ala Leu Ala Lys Gln Leu Asn Leu Arg Pro Arg Gln Val Glu
                165                 170                 175

Val Trp Phe Gln Asn Arg Arg Ala Arg Thr Lys Leu Lys Gln Thr Glu
            180                 185                 190

Val Asp Cys Glu Phe Leu Lys Arg Cys Cys Glu Asn Leu Thr Glu Glu
        195                 200                 205

Asn Arg Arg Leu Gln Lys Glu Val Gln Glu Leu Arg Ala Leu Lys Leu
    210                 215                 220

Ser Pro Gln Phe Tyr Met His Met Thr Pro Thr Thr Leu Thr Met
225                 230                 235                 240

Cys Pro Ser Cys Glu Arg Val Ala Val Ser Ser Ser Ser Ala Ala
                245                 250                 255

Thr Ala Thr Val Ala Val Asp Ala Pro His His Pro Met Ala Met Ala
            260                 265                 270

Gly Pro His His His Arg Pro Ile Ala Ile Asn Pro Trp Ala Ala Ala
        275                 280                 285

Pro Ile His His Arg Pro Phe Asp Ala Pro Ala Pro Arg Ser
    290                 295                 300

<210> SEQ ID NO 28
```

<211> LENGTH: 224
<212> TYPE: PRT
<213> ORGANISM: Hordeum vulgare

<400> SEQUENCE: 28

Met Met Glu Arg Ala Asp Asp Leu Gly Leu Ser Leu Ser Leu Ser Ser
1               5                   10                  15

Pro Leu Ala Pro Arg Thr His His Val Ala Met Leu Leu His Ala Pro
            20                  25                  30

Glu Arg Arg Phe Leu Glu Met Pro Leu Leu Pro Ala Lys Arg Val Ser
        35                  40                  45

Ala Val Ser Ala Asp Glu Glu Arg Ser Gly Gln Arg Gly Gly Gly Ser
    50                  55                  60

Asp Asp Glu Asp Gly Gly Cys Gly Met Asp Gly Ser Arg Lys Lys Leu
65                  70                  75                  80

Arg Leu Ser Lys Asp Gln Ser Ala Val Leu Glu Asp Ser Phe Arg Glu
                85                  90                  95

His Pro Thr Leu Asn Pro Arg Gln Lys Ala Ala Leu Ala Gln Gln Leu
            100                 105                 110

Gly Leu Arg Ser Arg Gln Val Glu Val Trp Phe Gln Asn Arg Arg Ala
        115                 120                 125

Arg Thr Lys Leu Lys Gln Thr Glu Val Asp Cys Glu Phe Leu Lys Arg
    130                 135                 140

Cys Cys Glu Thr Leu Thr Glu Glu Asn Arg Arg Leu Gln Lys Glu Val
145                 150                 155                 160

Gln Glu Leu Arg Ala Leu Lys Leu Val Ser Pro His Gln Tyr Met His
                165                 170                 175

Met Ser Pro Pro Thr Thr Leu Thr Met Cys Pro Ser Cys Glu Arg Val
            180                 185                 190

Ser Asn Asn Asn Asn Thr Asn Thr Asn Phe Thr Gly Val Arg Arg Asn
        195                 200                 205

Val Val Asp Gly Ala Ile Cys His Arg Pro Ile Ala Val Arg Pro Gln
    210                 215                 220

<210> SEQ ID NO 29
<211> LENGTH: 247
<212> TYPE: PRT
<213> ORGANISM: Oryza rufipogon

<400> SEQUENCE: 29

Met Met Glu Arg Ala Glu Asp Leu Arg Leu Ser Leu Ser Leu Ser Ser
1               5                   10                  15

Pro Leu Ile Ala Pro Arg Thr His His Val Ala Met Leu Phe His Ala
            20                  25                  30

Pro Pro Glu Lys Arg Phe Leu Glu Met Pro Leu Leu Pro Ala Ala Lys
        35                  40                  45

Arg Ser Glu Val Val Ala Ala Glu Glu Glu Arg Ala Gly Leu Arg Gly
    50                  55                  60

Gly Gly Gly Ser Asp Glu Glu Asp Gly Gly Cys Gly Ile Asp Gly Ser
65                  70                  75                  80

Arg Lys Lys Leu Arg Leu Ser Lys Asp Gln Ser Ala Val Leu Glu Asp
                85                  90                  95

Ser Phe Arg Glu His Pro Thr Leu Asn Pro Arg Gln Lys Ala Thr Leu
            100                 105                 110

Ala Gln Gln Leu Gly Leu Arg Pro Arg Gln Val Glu Val Trp Phe Gln
        115                 120                 125

```
Asn Arg Arg Ala Arg Thr Lys Leu Lys Gln Thr Glu Val Asp Cys Glu
            130                 135                 140

Phe Leu Lys Arg Cys Cys Glu Thr Leu Thr Glu Glu Asn Arg Arg Leu
145                 150                 155                 160

Gln Lys Glu Val Gln Glu Leu Arg Ala Leu Lys Leu Val Ser Pro His
                165                 170                 175

Leu Tyr Met Asn Met Ser Pro Pro Thr Thr Leu Thr Met Cys Pro Ser
            180                 185                 190

Cys Glu Arg Val Ser Asn Thr Asn Asn Ser Ser Ala Ala Ala Ala Ala
                195                 200                 205

Ala Asp Arg Arg Gly Ile Arg Thr Thr Ala Ala Gly Gly Gly Ser
            210                 215                 220

Val Val Asp Thr Ala Ala Asp Gly Gly Ile Leu Cys His Arg Pro Ile
225                 230                 235                 240

Ala Val Arg Pro Gln Gln Ser
                245
```

```
<210> SEQ ID NO 30
<211> LENGTH: 247
<212> TYPE: PRT
<213> ORGANISM: Oryza sativa

<400> SEQUENCE: 30

Met Met Glu Arg Ala Glu Asp Leu Arg Leu Ser Leu Ser Leu Ser Ser
1               5                   10                  15

Pro Leu Ile Ala Pro Arg Thr His His Val Ala Met Leu Phe His Ala
            20                  25                  30

Pro Pro Glu Lys Arg Phe Leu Glu Met Pro Leu Leu Pro Ala Ala Lys
        35                  40                  45

Arg Ser Glu Val Val Ala Ala Glu Glu Arg Ala Gly Leu Arg Gly
    50                  55                  60

Gly Gly Gly Ser Asp Glu Glu Asp Gly Gly Cys Gly Ile Asp Gly Ser
65                  70                  75                  80

Arg Lys Lys Leu Arg Leu Ser Lys Asp Gln Ser Ala Val Leu Glu Asp
                85                  90                  95

Ser Phe Arg Glu His Pro Thr Leu Asn Pro Arg Gln Lys Ala Thr Leu
            100                 105                 110

Ala Gln Gln Leu Gly Leu Arg Pro Arg Gln Val Glu Val Trp Phe Gln
        115                 120                 125

Asn Arg Arg Ala Arg Thr Lys Leu Lys Gln Thr Glu Val Asp Cys Glu
    130                 135                 140

Phe Leu Lys Arg Cys Cys Glu Thr Leu Thr Glu Glu Asn Arg Arg Leu
145                 150                 155                 160

Gln Lys Glu Val Gln Glu Leu Arg Ala Leu Lys Leu Val Ser Pro His
                165                 170                 175

Leu Tyr Met Asn Met Ser Pro Pro Thr Thr Leu Thr Met Cys Pro Ser
            180                 185                 190

Cys Glu Arg Val Ser Asn Thr Asn Asn Ser Ser Ala Ala Ala Ala
        195                 200                 205

Ala Asp Arg Arg Gly Ile Arg Thr Thr Ala Ala Gly Gly Gly Ser
    210                 215                 220

Val Val Asp Thr Ala Ala Asp Gly Gly Ile Leu Cys His Arg Pro Ile
225                 230                 235                 240

Ala Val Arg Pro Gln Gln Ser
```

<210> SEQ ID NO 31
<211> LENGTH: 240
<212> TYPE: PRT
<213> ORGANISM: Oryza brachyantha

<400> SEQUENCE: 31

Met Met Glu Arg Ala Glu Asp Leu Arg Leu Ser Leu Ser Leu Ser Ser
1               5                   10                  15

Pro Leu Ala Pro Arg Thr His Val Ala Ala Met Leu Phe His Ser
            20                  25                  30

Pro Pro Glu Lys Arg Phe Leu Glu Met Pro Leu Leu Pro Ala Ala Lys
        35                  40                  45

Arg Ser Glu Val Ala Ala Ala Asp Glu Arg Ala Gly Leu Arg Gly
    50                  55                  60

Gly Ser Asp Glu Glu Asp Gly Gly Cys Gly Ile Asp Gly Ser Arg Lys
65                  70                  75                  80

Lys Leu Arg Leu Ser Lys Asp Gln Ser Ala Val Leu Glu Asp Ser Phe
                85                  90                  95

Arg Glu His Pro Thr Leu Asn Pro Arg Gln Lys Ala Ala Leu Ala Gln
            100                 105                 110

Gln Leu Gly Leu Arg Pro Arg Gln Val Glu Val Trp Phe Gln Asn Arg
        115                 120                 125

Arg Ala Arg Thr Lys Leu Lys Gln Thr Glu Val Asp Cys Glu Phe Leu
    130                 135                 140

Lys Arg Cys Cys Glu Thr Leu Thr Glu Glu Asn Arg Arg Leu Gln Lys
145                 150                 155                 160

Glu Val Gln Glu Leu Arg Ala Leu Lys Leu Val Ser Pro His Leu Tyr
                165                 170                 175

Met Asn Met Ser Pro Pro Thr Thr Leu Thr Met Cys Pro Ser Cys Glu
            180                 185                 190

Arg Val Ser Asn Ala Asn Asn Ser Ser Ser Ala Ala Pro Asp Arg Arg
        195                 200                 205

Gly Ala Gly Gly Val Thr Ala Ala Gly Gly Asn Asp Thr Ala Ala Asp
    210                 215                 220

Gly Gly Ile Leu Cys His Arg Pro Ile Ala Val Arg Pro Gln Gln Ser
225                 230                 235                 240

<210> SEQ ID NO 32
<211> LENGTH: 247
<212> TYPE: PRT
<213> ORGANISM: Oryza nivara

<400> SEQUENCE: 32

Met Met Glu Arg Ala Glu Asp Leu Arg Leu Ser Leu Ser Leu Ser Ser
1               5                   10                  15

Pro Leu Ile Ala Pro Arg Thr His His Val Ala Met Leu Phe His Ala
            20                  25                  30

Pro Pro Glu Lys Arg Phe Leu Glu Met Pro Leu Leu Pro Ala Ala Lys
        35                  40                  45

Arg Ser Glu Val Val Ala Ala Glu Glu Glu Arg Ala Gly Leu Arg Gly
    50                  55                  60

Gly Gly Gly Ser Asp Glu Glu Asp Gly Gly Cys Gly Ile Asp Gly Ser
65                  70                  75                  80

Arg Lys Lys Leu Arg Leu Ser Lys Asp Gln Ser Ala Val Leu Glu Asp

```
                    85                  90                  95
Ser Phe Arg Glu His Pro Thr Leu Asn Pro Arg Gln Lys Ala Thr Leu
                100                 105                 110

Ala Gln Gln Leu Gly Leu Arg Pro Arg Gln Val Glu Val Trp Phe Gln
            115                 120                 125

Asn Arg Arg Ala Arg Thr Lys Leu Lys Gln Thr Glu Val Asp Cys Glu
        130                 135                 140

Phe Leu Lys Arg Cys Cys Glu Thr Leu Thr Glu Glu Asn Arg Arg Leu
145                 150                 155                 160

Gln Lys Glu Val Gln Glu Leu Arg Ala Leu Lys Leu Val Ser Pro His
                165                 170                 175

Leu Tyr Met Asn Met Ser Pro Pro Thr Thr Leu Thr Met Cys Pro Ser
            180                 185                 190

Cys Glu Arg Val Ser Asn Thr Asn Asn Ser Ser Ala Ala Ala Ala
        195                 200                 205

Ala Asp Arg Arg Gly Ile Arg Thr Thr Thr Ala Ala Ala Gly Gly Ser
    210                 215                 220

Val Val Asp Thr Ala Ala Asp Gly Gly Ile Leu Cys His Arg Pro Ile
225                 230                 235                 240

Ala Val Arg Pro Gln Gln Ser
                245

<210> SEQ ID NO 33
<211> LENGTH: 242
<212> TYPE: PRT
<213> ORGANISM: Oryza punctata

<400> SEQUENCE: 33

Met Glu Arg Ala Glu Asp Leu Arg Leu Ser Leu Ser Leu Ser Ser Pro
1               5                   10                  15

Leu Ile Ala Pro Arg Thr His His Val Ala Met Leu Phe His Ala Pro
                20                  25                  30

Pro Glu Lys Arg Phe Leu Glu Met Pro Leu Leu Pro Ala Ala Lys Arg
            35                  40                  45

Ser Glu Val Val Ala Ala Asp Glu Glu Arg Ala Gly Leu Arg Gly Gly
        50                  55                  60

Ser Asp Glu Glu Asp Gly Gly Cys Gly Ile Asp Gly Ser Arg Lys Lys
65                  70                  75                  80

Leu Arg Leu Ser Lys Asp Gln Ser Ala Val Leu Glu Asp Ser Phe Arg
                85                  90                  95

Glu His Pro Thr Leu Asn Pro Arg Gln Lys Ala Thr Leu Ala Gln Gln
                100                 105                 110

Leu Gly Leu Arg Pro Arg Gln Val Glu Val Trp Phe Gln Asn Arg Arg
            115                 120                 125

Ala Arg Thr Lys Leu Lys Gln Thr Glu Val Asp Cys Glu Phe Leu Lys
        130                 135                 140

Arg Cys Cys Glu Thr Leu Thr Glu Glu Asn Arg Arg Leu Gln Lys Glu
145                 150                 155                 160

Val Gln Glu Leu Arg Ala Leu Lys Leu Val Ser Pro His Leu Tyr Met
                165                 170                 175

Asn Met Ser Pro Pro Thr Thr Leu Thr Met Cys Pro Ser Cys Glu Arg
            180                 185                 190

Val Ser Asn Thr Asn Asn Ser Ser Ala Ala Asp Arg Arg Gly
        195                 200                 205
```

```
Ile Ser Thr Thr Thr Ala Ala Ala Thr Gly Gly Ser Ile Asp Thr Ala
            210                 215                 220

Ala Asp Gly Gly Ile Leu Cys His Arg Pro Ile Ala Val Arg Pro Gln
225                 230                 235                 240

Gln Ser

<210> SEQ ID NO 34
<211> LENGTH: 247
<212> TYPE: PRT
<213> ORGANISM: Oryza glaberrima

<400> SEQUENCE: 34

Met Met Glu Arg Ala Glu Asp Leu Arg Leu Ser Leu Ser Leu Ser Ser
1               5                   10                  15

Pro Leu Ile Ala Pro Arg Thr His His Val Ala Met Leu Phe His Ala
            20                  25                  30

Pro Pro Glu Lys Arg Phe Leu Glu Met Pro Leu Leu Pro Ala Ala Lys
        35                  40                  45

Arg Ser Glu Val Val Ala Ala Glu Glu Arg Ala Gly Leu Arg Gly
    50                  55                  60

Gly Gly Gly Ser Asp Glu Glu Asp Gly Gly Cys Gly Ile Asp Gly Ser
65                  70                  75                  80

Arg Lys Lys Leu Arg Leu Ser Lys Asp Gln Ser Ala Val Leu Glu Asp
                85                  90                  95

Ser Phe Arg Glu His Pro Thr Leu Asn Pro Arg Gln Lys Ala Thr Leu
            100                 105                 110

Ala Gln Gln Leu Gly Leu Arg Pro Arg Gln Val Glu Val Trp Phe Gln
        115                 120                 125

Asn Arg Arg Ala Arg Thr Lys Leu Lys Gln Thr Glu Val Asp Cys Glu
130                 135                 140

Phe Leu Lys Arg Cys Cys Glu Thr Leu Thr Glu Glu Asn Arg Arg Leu
145                 150                 155                 160

Gln Lys Glu Val Gln Glu Leu Arg Ala Leu Lys Leu Val Ser Pro His
                165                 170                 175

Leu Tyr Met Asn Met Ser Pro Pro Thr Thr Leu Thr Met Cys Pro Ser
            180                 185                 190

Cys Glu Arg Val Ser Asn Thr Asn Asn Ser Ser Ala Ala Ala Ala
        195                 200                 205

Ala Asp Arg Arg Gly Ile Arg Thr Thr Thr Ala Ala Ala Gly Gly Ser
210                 215                 220

Val Val Asp Thr Ala Ala Asp Gly Gly Ile Leu Cys His Arg Pro Ile
225                 230                 235                 240

Ala Val Arg Pro Gln Gln Ser
                245

<210> SEQ ID NO 35
<211> LENGTH: 237
<212> TYPE: PRT
<213> ORGANISM: Setaria italica

<400> SEQUENCE: 35

Met Met Glu Arg Ala Glu Asp Leu Gly Leu Ser Leu Ser Leu Ser Ser
1               5                   10                  15

Ser Leu Ala Ala Pro Arg Thr His His Val Ser Ala Met Leu Leu Arg
            20                  25                  30

Ser Pro Glu Lys Arg Phe Leu Glu Met Pro Leu Leu Pro Ala Lys Arg
```

```
        35                  40                  45
Ser Glu Val Thr Ala Glu Glu Gly Leu Leu Arg Gly Ser Asp Glu
 50                  55                  60
Glu Asp Gly Ser Cys Gly Ile Asp Gly Ser Arg Lys Lys Leu Arg Leu
65                  70                  75                  80
Ser Lys Asp Gln Ser Ala Val Leu Glu Asp Ser Phe Arg Glu His Pro
                 85                  90                  95
Thr Leu Asn Pro Arg Gln Lys Ala Ala Leu Ala Gln Gln Leu Gly Leu
                100                 105                 110
Arg Pro Arg Gln Val Glu Val Trp Phe Gln Asn Arg Arg Ala Arg Thr
                115                 120                 125
Lys Leu Lys Gln Thr Glu Val Asp Cys Glu Phe Leu Lys Arg Cys Cys
130                 135                 140
Glu Thr Leu Thr Glu Glu Asn Arg Arg Leu Gln Lys Glu Val Gln Glu
145                 150                 155                 160
Leu Arg Ala Leu Lys Leu Val Ser Pro His Leu Tyr Met His Met Ser
                165                 170                 175
Pro Pro Thr Thr Leu Thr Met Cys Pro Ser Cys Glu Arg Val Ser Ser
                180                 185                 190
Ser Gly Ala Asn Ser Thr Gly Ala Ala Ala Ser Ser Asp Arg Arg Ala
                195                 200                 205
Gly Gly Ala Ile Ile Ser Thr Ala Ala Ala Ala Glu Gly Ala Ala
                210                 215                 220
Ile Cys His Arg Pro Ile Ala Val Arg Pro Gln Gln Ser
225                 230                 235
```

<210> SEQ ID NO 36
<211> LENGTH: 233
<212> TYPE: PRT
<213> ORGANISM: Sorghum bicolor

<400> SEQUENCE: 36

```
Met Met Glu Arg Val Glu Asp Leu Gly Leu Ser Leu Ser Leu Ser Ser
 1               5                  10                  15
Ser Leu Ala Ser Pro Arg Thr His His Val Ala Thr Met Leu Leu Arg
                 20                  25                  30
Ala Pro Pro Glu Lys Arg Phe Leu Glu Met Pro Leu Leu Leu Pro Ala
                 35                  40                  45
Lys Arg Ser Glu Leu Ala Thr Gly Glu Glu Gly Leu Arg Gly Gly Gly
 50                  55                  60
Ser Asp Glu Glu Asp Gly Gly Cys Gly Ile Asp Gly Ser Arg Lys Lys
65                  70                  75                  80
Leu Arg Leu Ser Lys Asp Gln Ser Ala Val Leu Glu Asp Ser Phe Arg
                 85                  90                  95
Glu His Pro Thr Leu Asn Pro Arg Gln Lys Ala Ala Leu Ala Gln Gln
                100                 105                 110
Leu Gly Leu Arg Pro Arg Gln Val Glu Val Trp Phe Gln Asn Arg Arg
                115                 120                 125
Ala Arg Thr Lys Leu Lys Gln Thr Glu Val Asp Cys Glu Tyr Leu Lys
                130                 135                 140
Arg Cys Cys Glu Thr Leu Thr Glu Glu Asn Arg Arg Leu His Lys Glu
145                 150                 155                 160
Val Gln Glu Leu Arg Ala Leu Lys Leu Val Ser Pro His Leu Tyr Met
                165                 170                 175
```

His Met Pro Pro Pro Thr Thr Leu Thr Met Cys Pro Ser Cys Glu Arg
                180                 185                 190

Val Ser Ser Ser Asn Ala Ser Asn Ala Asn Ser Ala Ala Ala Asp Arg
            195                 200                 205

Lys Ala Gly Ala Gly Val Ala Asp Gly Gly Ala Ile Val Cys His Arg
            210                 215                 220

Pro Ile Ala Val Arg Pro Gln Gln Ser
225                 230

<210> SEQ ID NO 37
<211> LENGTH: 156
<212> TYPE: PRT
<213> ORGANISM: Triticum urartu

<400> SEQUENCE: 37

Met Asp Gly Ser Arg Lys Lys Leu Arg Leu Ser Lys Asp Gln Ser Ala
1               5                   10                  15

Val Leu Glu Asp Ser Phe Arg Glu His Pro Thr Leu Asn Pro Arg Gln
            20                  25                  30

Lys Ala Ala Leu Ala Gln Gln Leu Gly Leu Arg Ser Arg Gln Val Glu
            35                  40                  45

Val Trp Phe Gln Asn Arg Arg Ala Arg Thr Lys Leu Lys Gln Thr Glu
    50                  55                  60

Val Asp Cys Glu Phe Leu Lys Arg Cys Cys Glu Thr Leu Thr Glu Glu
65                  70                  75                  80

Asn Arg Arg Leu Gln Lys Glu Val Gln Glu Leu Arg Ala Leu Lys Leu
                85                  90                  95

Val Ser Pro His His Tyr Met His Met Ser Pro Thr Thr Leu Thr
            100                 105                 110

Met Cys Pro Ser Cys Glu Arg Val Ser Asn Asn Asn Asn Asn Asn
            115                 120                 125

Asn Asn Ser Thr Thr Ala Asp Arg Arg Asn Gly Val Glu Gly Ala Ile
    130                 135                 140

Cys His Arg Pro Ile Ala Val Arg Pro Gln Gln Ser
145                 150                 155

<210> SEQ ID NO 38
<211> LENGTH: 227
<212> TYPE: PRT
<213> ORGANISM: Zea mays

<400> SEQUENCE: 38

Met Met Glu Arg Val Glu Asp Leu Gly Leu Ser Leu Ser Leu Ser Ser
1               5                   10                  15

Ser Leu Ala Ser Pro Arg Thr His His Val Ala Thr Met Leu Leu Arg
            20                  25                  30

Ala Pro Glu Lys Arg Phe Leu Glu Met Pro Leu Leu Leu Pro Ala Lys
            35                  40                  45

Arg Thr Thr Glu Val Thr Gly Glu Asp Gly Leu Arg Gly Gly Ser Asp
    50                  55                  60

Glu Glu Asp Gly Gly Cys Gly Ile Asp Gly Ser Arg Lys Lys Leu Arg
65                  70                  75                  80

Leu Ser Lys Asp Gln Ser Ala Val Leu Glu Asp Ser Phe Arg Glu His
                85                  90                  95

Pro Thr Leu Asn Pro Arg Gln Lys Ala Ala Leu Ala Gln Gln Leu Gly
            100                 105                 110

```
Leu Arg Pro Arg Gln Val Glu Val Trp Phe Gln Asn Arg Ala Arg
        115                 120                 125
Thr Lys Leu Lys Gln Thr Glu Val Asp Cys Glu Tyr Leu Lys Arg Cys
    130                 135                 140
Cys Glu Thr Leu Thr Glu Glu Asn Arg Arg Leu Gln Lys Glu Val Gln
145                 150                 155                 160
Glu Leu Arg Ala Leu Lys Leu Val Ser Pro His Leu Tyr Met His Met
                165                 170                 175
Ser Pro Pro Thr Thr Leu Thr Met Cys Pro Ser Cys Glu Arg Val Ser
                180                 185                 190
Ser Ser Asn Gly Asn Ser Ala Ala Ala Thr Ala Ala Arg Ala Arg
            195                 200                 205
Ala Gly Ala Gly Ala Gly Ala Ile Val Cys His Pro Ile Asp Arg Ala
    210                 215                 220
Thr Ser Thr
225

<210> SEQ ID NO 39
<211> LENGTH: 279
<212> TYPE: PRT
<213> ORGANISM: Musa acuminata

<400> SEQUENCE: 39

Met Leu Leu Glu Lys Glu Asp Leu Ala Leu Ser Leu Ser Leu Ser Ser
1               5                   10                  15
Ser Ala Asn Arg Phe Asp Arg Leu Gly Leu Val Pro Ser Ser Ser Ser
            20                  25                  30
Ser Pro Ser Arg Ser Leu Pro Ser Ser Cys Gln Gln Trp Ser Arg Leu
        35                  40                  45
Leu Leu Ala Arg Ser Ala Gly Glu Ala Arg Arg Gly Leu Arg Thr Ile
    50                  55                  60
Asp Val Asn Gln Pro Pro Ala Gly Ala Ala Gly Arg Pro Asp
65                  70                  75                  80
Ser Glu Glu Ala Asp Ala Ser Ser Pro Asn Ser Gly Val Ser Val
                85                  90                  95
Gly Gly Lys Arg Pro Ala Glu Arg Glu Ala Glu His Asp Ala Glu Pro
            100                 105                 110
Ser Cys Ser Arg Gly Ala Ser Asp Glu Glu Gly Asp Gly Asp Gly
        115                 120                 125
Ser Arg Lys Lys Leu Arg Leu Ser Lys Asp Gln Ser Ala Val Leu Glu
    130                 135                 140
Glu Ser Phe Lys Glu His Thr Thr Leu Ser Pro Lys Gln Lys Leu Ala
145                 150                 155                 160
Leu Ala Lys Gln Leu Asn Leu Arg Pro Arg Gln Val Glu Val Trp Phe
                165                 170                 175
Gln Asn Arg Arg Ala Arg Thr Lys Leu Lys Gln Thr Glu Val Asp Cys
            180                 185                 190
Glu Phe Leu Lys Arg Cys Cys Glu Asn Leu Thr Glu Glu Asn Arg Arg
        195                 200                 205
Leu Gln Lys Glu Val Gln Glu Leu Arg Ala Leu Lys Leu Ser Pro Gln
    210                 215                 220
Leu Tyr Met Gln Met Thr Pro Pro Thr Thr Leu Thr Met Cys Pro Ser
225                 230                 235                 240
Cys Glu Arg Val Ser Lys Pro Ser Phe Ser Thr Thr Ser Thr Thr Asn
                245                 250                 255
```

Pro Pro Pro Ser Glu Ala Ala Ala Pro Arg Ser Leu Arg Pro Pro Phe
            260                 265                 270

Leu Asp Ala Pro Pro Gln Arg
            275

<210> SEQ ID NO 40
<211> LENGTH: 266
<212> TYPE: PRT
<213> ORGANISM: Amborella trichopoda

<400> SEQUENCE: 40

Met Asn Arg Glu Asp Leu Asn Leu Ser Leu Ser Leu Arg Arg Val Gly
1               5                   10                  15

Asp Phe Glu Leu Asn Leu Leu Pro Arg Asn Cys Arg Asn Asp Ser Ser
            20                  25                  30

Ser Leu Asp Arg Ser Glu Thr Ala Arg Ser Ile Leu Lys Ser Phe Asp
        35                  40                  45

Val Asn Arg Ile Gln Ala Thr Ser Asp Arg Ile Pro Thr Thr Thr Asp
    50                  55                  60

Ala Ile Arg Ser Glu Ile Ser Arg Ile Pro Ala Thr Pro Asn Met Ala
65                  70                  75                  80

Gly Phe Asp Val Asn Arg Ile Pro Val Ile Ser Glu Cys Glu Glu Glu
                85                  90                  95

Ala Val Val Ser Ser Pro Met Ser Thr Val Ser Ser Leu Ser Met Ser
            100                 105                 110

Gly Gly Lys Arg Asp Glu Pro Glu Gly Glu Arg Ala Ser Ser Arg Gly
        115                 120                 125

Ser Ser Asp Glu Glu Asp Gly Gly Glu Ala Ala Arg Lys Lys Leu Arg
    130                 135                 140

Leu Ser Lys Asp Gln Ser Ala Val Leu Glu Glu Ser Phe Lys Glu His
145                 150                 155                 160

Asn Thr Leu Asn Pro Lys Gln Lys Leu Thr Leu Ala Lys Gln Leu Asn
                165                 170                 175

Leu Arg Pro Arg Gln Val Glu Val Trp Phe Gln Asn Arg Arg Ala Arg
            180                 185                 190

Thr Lys Leu Lys Gln Thr Glu Val Asp Cys Glu Phe Leu Lys Arg Cys
        195                 200                 205

Cys Glu Asn Leu Thr Glu Glu Asn Arg Arg Leu Gln Lys Glu Val Met
    210                 215                 220

Glu Leu Arg Ser Leu Lys Gln Thr Pro His Phe Tyr Met His Val Pro
225                 230                 235                 240

Pro Ala Ala Leu Thr Met Cys Pro Ser Cys Glu Arg Val Ala Val Ser
                245                 250                 255

Glu Ser Gln Phe Arg Pro Gln Ile Arg Ser
            260                 265

<210> SEQ ID NO 41
<211> LENGTH: 225
<212> TYPE: PRT
<213> ORGANISM: Brachypodium distachyon

<400> SEQUENCE: 41

Met Met Glu Arg Ala Glu Asp Leu Gly Leu Ser Leu Ser Leu Ser Ser
1               5                   10                  15

Ser Leu Ala Pro Arg Thr His His Val Ser Lys Leu Phe His Ala Pro
            20                  25                  30

```
Glu Arg Arg Phe Met Glu Met Pro Leu Leu Pro Ala Lys Arg Ser Ser
        35                  40                  45

Glu Ala Ala Gly Asp Asp Ser Leu Leu Gly Gly Ser Asp Glu Glu
 50                  55                  60

Asp Gly Gly Cys Gly Val Asp Gly Ser Arg Lys Leu Arg Leu Ser
 65                  70                  75                  80

Lys Asp Gln Ser Ala Val Leu Glu Asp Ser Phe Arg Glu His Pro Thr
                 85                  90                  95

Leu Asn Pro Arg Gln Lys Ala Ala Leu Ala Gln Gln Leu Gly Leu Arg
            100                 105                 110

Ser Arg Gln Val Glu Val Trp Phe Gln Asn Arg Arg Ala Arg Thr Lys
            115                 120                 125

Leu Lys Gln Thr Glu Val Asp Cys Glu Phe Leu Lys Arg Cys Cys Glu
130                 135                 140

Thr Leu Thr Glu Glu Asn Arg Arg Leu Gln Lys Glu Val Gln Glu Leu
145                 150                 155                 160

Arg Ala Leu Lys Leu Val Ser Pro Arg His Tyr Met His Met Ser Pro
                165                 170                 175

Pro Thr Thr Leu Thr Met Cys Pro Ser Cys Glu Arg Val Ser Asn Lys
            180                 185                 190

Asn Asn Asn Asn Asn Asn Asn Ser Ser Ala Ala Ala Asp Arg Arg
            195                 200                 205

Gly Asp Val Ala Ile Cys His Arg Pro Ile Ala Val Arg Pro Gln Gln
210                 215                 220

Ser
225

<210> SEQ ID NO 42
<211> LENGTH: 301
<212> TYPE: PRT
<213> ORGANISM: Gossypium raimondii

<400> SEQUENCE: 42

Met Met Val Gly Lys Glu Asp Leu Gly Leu Ser Leu Ser Leu Gly Phe
 1               5                  10                  15

Pro Gln Asn His His Ser Leu Gln Leu Asn Leu Arg Pro Ser Leu Leu
                20                  25                  30

Pro Ser Ser Val Asp Ser Cys Ser Ser Val Pro Ser Gly Phe Thr Ala
            35                  40                  45

Phe His Lys Ser Ser Trp Asn Asp Val Ser Ala Pro Ser Asp Pro Asn
 50                  55                  60

Ala Glu Ser Phe Arg Gly Glu Thr Arg Ser Phe Leu Arg Gly Ile Asp
 65                  70                  75                  80

Val Asn Arg Leu Pro Ser Thr Val Asp Cys Glu Glu Ala Gly Val
                 85                  90                  95

Ser Ser Pro Asn Ser Thr Ile Ser Val Ser Gly Lys Arg Ser Glu
            100                 105                 110

Arg Glu Gly Thr Asn Gly Asp Glu Leu Asp Ile Glu Arg Ala Cys Ser
            115                 120                 125

Arg Gly Ile Ser Asp Glu Glu Asp Gly Asp Ala Ser Arg Lys Lys Leu
130                 135                 140

Arg Leu Ser Lys Asp Gln Ser Ala Ile Leu Glu Glu Ser Phe Lys Glu
145                 150                 155                 160

His Asn Thr Leu Asn Pro Lys Gln Lys Met Ala Leu Ala Lys Gln Leu
```

```
            165                 170                 175
Gly Leu Arg Pro Arg Gln Val Glu Val Trp Phe Gln Asn Arg Arg Ala
            180                 185                 190

Arg Thr Lys Leu Lys Gln Thr Glu Val Asp Cys Glu Phe Leu Lys Arg
            195                 200                 205

Cys Cys Glu Asn Leu Thr Glu Asn Arg Arg Leu Gln Lys Glu Val
            210                 215                 220

Gln Glu Leu Arg Ala Leu Lys Leu Ser Pro Gln Phe Tyr Met Gln Met
225                 230                 235                 240

Thr Pro Pro Thr Thr Leu Thr Met Cys Pro Ser Cys Glu Arg Val Gly
            245                 250                 255

Ala Ser Ser Thr Val Asp Pro Arg Ser His His Gln Leu Pro Gln Thr
            260                 265                 270

His His Arg Ala Ile Pro Ile Asn Pro Trp Ala Pro Ala Ala Pro
            275                 280                 285

Ile Pro His Gly Pro Phe Asp Ala Leu Arg Pro Gln Ser
            290                 295                 300

<210> SEQ ID NO 43
<211> LENGTH: 285
<212> TYPE: PRT
<213> ORGANISM: Vitis vinifera

<400> SEQUENCE: 43

Met Val Asp Lys Asp Asp Asp Leu Gly Leu Ser Leu Ala Leu Lys Cys
1               5                   10                  15

Pro Glu Ala Leu Pro Gln Arg Pro Leu Asn Leu Phe Val Gln Lys Lys
            20                  25                  30

Ala Leu Cys Ser Asp Ala Phe His Ala Ser Glu Thr Arg Ala Tyr Leu
            35                  40                  45

Arg Gly Ile Asp Val Asn Arg Ala Pro Thr Met Ala Asp Cys Glu Asp
            50                  55                  60

Val Gly Val Ser Ser Pro Asn Ser Thr Ile Ser Ser Ile Ser Gly Lys
65                  70                  75                  80

Arg Asn Asp Arg Glu Thr Asn Glu Glu Asn Glu Asn Glu Asn Glu
            85                  90                  95

Ile Glu Ser Ser Glu Glu Asp Ala Gly Gly Thr Gly Asp Thr Val Arg
            100                 105                 110

Lys Lys Leu Arg Leu Ser Lys Glu Gln Ser Ala Ile Leu Glu Glu Thr
            115                 120                 125

Phe Lys Glu His Asn Thr Leu Asn Pro Lys Gln Lys Leu Ala Leu Ala
            130                 135                 140

Lys Gln Leu Asn Leu Arg Pro Arg Gln Val Glu Val Trp Phe Gln Asn
145                 150                 155                 160

Arg Arg Ala Arg Thr Lys Leu Lys Gln Thr Glu Val Asp Cys Glu Tyr
            165                 170                 175

Leu Lys Arg Cys Cys Glu Asn Leu Thr Glu Glu Asn Arg Arg Leu Gln
            180                 185                 190

Lys Glu Val Gln Glu Leu Arg Thr Leu Lys Leu Ser Pro Gln Leu Tyr
            195                 200                 205

Met His Met Asn Pro Pro Thr Thr Leu Thr Met Cys Pro Ser Cys Glu
            210                 215                 220

Arg Val Ala Val Ala Ser Ala Ser Ser Ser Ala Pro Ser Pro Ser Pro
225                 230                 235                 240
```

```
Ala Ser Asn Pro Leu Ala Ala Pro His Phe Pro Leu Gly Pro His
            245                 250                 255

Gln His Arg Pro Met Pro Ile Ala Gly Pro Trp Ala Gly Ala Ala Ser
            260                 265                 270

Met Arg His Arg Pro Phe Asp Ala His Gly Thr Arg Ser
            275                 280                 285

<210> SEQ ID NO 44
<211> LENGTH: 247
<212> TYPE: PRT
<213> ORGANISM: Oryza glumipatula

<400> SEQUENCE: 44

Met Met Glu Arg Ala Glu Asp Leu Arg Leu Ser Leu Ser Leu Ser Ser
1               5                   10                  15

Pro Leu Ile Ala Pro Arg Thr His His Val Ala Met Leu Phe His Ala
            20                  25                  30

Pro Pro Glu Lys Arg Phe Leu Glu Met Pro Leu Leu Pro Ala Ala Lys
        35                  40                  45

Arg Ser Glu Val Val Ala Ala Glu Glu Arg Ala Gly Leu Arg Gly
    50                  55                  60

Gly Gly Gly Ser Asp Glu Asp Gly Gly Cys Gly Ile Asp Gly Ser
65                  70                  75                  80

Arg Lys Lys Leu Arg Leu Ser Lys Asp Gln Ser Ala Val Leu Glu Asp
                85                  90                  95

Ser Phe Arg Glu His Pro Thr Leu Asn Pro Arg Gln Lys Ala Thr Leu
            100                 105                 110

Ala Gln Gln Leu Gly Leu Arg Pro Arg Gln Val Glu Val Trp Phe Gln
        115                 120                 125

Asn Arg Arg Ala Arg Thr Lys Leu Lys Gln Thr Glu Val Asp Cys Glu
130                 135                 140

Phe Leu Lys Arg Cys Cys Glu Thr Leu Thr Glu Glu Asn Arg Arg Leu
145                 150                 155                 160

Gln Lys Glu Val Gln Glu Leu Arg Ala Leu Lys Leu Val Ser Pro His
                165                 170                 175

Leu Tyr Met Asn Met Ser Pro Pro Thr Thr Leu Thr Met Cys Pro Ser
            180                 185                 190

Cys Glu Arg Val Ser Asn Thr Asn Asn Ser Ser Ala Ala Ala Ala
        195                 200                 205

Ala Asp Arg Arg Gly Ile Arg Thr Thr Thr Ala Ala Gly Gly Ser
    210                 215                 220

Val Val Asp Thr Ala Ala Asp Gly Gly Ile Leu Cys His Arg Pro Ile
225                 230                 235                 240

Ala Val Arg Pro Gln Gln Ser
            245

<210> SEQ ID NO 45
<211> LENGTH: 245
<212> TYPE: PRT
<213> ORGANISM: Oryza meridionalis

<400> SEQUENCE: 45

Met Met Glu Arg Ala Glu Asp Leu Arg Leu Ser Leu Ser Leu Ser Ser
1               5                   10                  15

Pro Leu Ile Ala Pro Arg Thr His His Val Ala Met Leu Phe His Ala
            20                  25                  30
```

```
Pro Pro Glu Lys Arg Phe Leu Glu Met Pro Leu Leu Pro Ala Ala Lys
            35                  40                  45

Arg Ser Glu Val Val Ala Ala Glu Glu Arg Ala Gly Leu Arg Gly
 50                  55                  60

Gly Gly Gly Ser Asp Glu Glu Asp Gly Cys Gly Ile Asp Gly Ser
 65                  70                  75                  80

Arg Lys Lys Leu Arg Leu Ser Lys Asp Gln Ser Ala Val Leu Glu Asp
                85                  90                  95

Ser Phe Arg Glu His Pro Thr Leu Asn Pro Arg Gln Lys Ala Thr Leu
            100                 105                 110

Ala Gln Gln Leu Gly Leu Arg Pro Arg Gln Val Glu Val Trp Phe Gln
            115                 120                 125

Asn Arg Arg Ala Arg Thr Lys Leu Lys Gln Thr Glu Val Asp Cys Glu
130                 135                 140

Phe Leu Lys Arg Cys Cys Glu Thr Leu Thr Glu Asn Arg Arg Leu
145                 150                 155                 160

Gln Lys Glu Val Gln Glu Leu Arg Ala Leu Lys Leu Val Ser Pro His
                165                 170                 175

Leu Tyr Met Asn Met Ser Pro Pro Thr Thr Leu Thr Met Cys Pro Ser
            180                 185                 190

Cys Glu Arg Val Ser Asn Thr Asn Asn Ser Ser Ala Ala Ala Asp
            195                 200                 205

Arg Arg Gly Ile Ser Thr Ser Thr Ala Ala Gly Ser Ser Val Val
            210                 215                 220

Asp Thr Ala Ala Asp Gly Gly Ile Leu Cys His Arg Pro Ile Ala Val
225                 230                 235                 240

Arg Pro Gln Gln Ser
            245

<210> SEQ ID NO 46
<211> LENGTH: 305
<212> TYPE: PRT
<213> ORGANISM: Arabis alpina

<400> SEQUENCE: 46

Met Gly Glu Arg Asp Asp Gly Leu Gly Leu Ser Leu Ser Leu Gly Leu
 1                   5                  10                  15

Gly Phe Asn Gln Lys Glu Gln Ser Pro Arg Leu Asn Pro Met Gln Phe
                20                  25                  30

Gly Ser Tyr Ser Ser Ser Ser Ser His Met His Met Gln Ser Asn His
            35                  40                  45

Ile Asn His Ser Gln Lys Ile Gln Asn Ser Trp Thr His Met Phe Gln
 50                  55                  60

Ser Ser Glu Arg Asn Ser Asp Val Arg Ser Phe Leu Arg Gly Ile Asp
 65                  70                  75                  80

Val Asn Arg Ala Pro Ser Thr Val Val Asp Val Glu Glu Asp Ala
                85                  90                  95

Gly Val Ser Ser Pro Asn Ser Thr Val Ser Val Met Ser Gly Lys
            100                 105                 110

Arg Asn Glu Arg Val Ala Thr Val Val Gly Gly Gly Val Ile Glu
            115                 120                 125

Asp His Asp Val Glu Arg Ala Ser Ser Ser Leu Gly Gly Ser Asp
            130                 135                 140

Asp Glu Asp Gly Gly Gly Asn Gly Asp Asp Gly Ser Arg Lys Lys Leu
145                 150                 155                 160
```

```
Arg Leu Ser Lys Glu Gln Ala Leu Val Leu Glu Thr Phe Lys Glu
            165                 170                 175

His Ser Thr Leu Asn Pro Lys Gln Lys Met Ala Leu Ala Lys Gln Leu
            180                 185                 190

Asn Leu Arg Thr Arg Gln Val Glu Val Trp Phe Gln Asn Arg Arg Ala
            195                 200                 205

Arg Thr Lys Leu Lys Gln Thr Glu Val Asp Cys Glu Tyr Leu Lys Arg
            210                 215                 220

Cys Cys Glu Asn Leu Thr Glu Glu Asn Arg Arg Leu Gln Lys Glu Val
225                 230                 235                 240

Ser Glu Leu Arg Ala Leu Lys Leu Ser Pro His Leu Tyr Met His Met
            245                 250                 255

Lys Pro Pro Thr Thr Leu Thr Met Cys Pro Ser Cys Glu Arg Val Ala
            260                 265                 270

Ala Thr Ser Ser Ser Ser Val Ala Pro Ala Met Asn Ser Ser
            275                 280                 285

Ser Pro Trp Ala Ala Ile Pro Leu Arg Gln Arg Pro Ala Ala Gly Ser
            290                 295                 300

His
305

<210> SEQ ID NO 47
<211> LENGTH: 315
<212> TYPE: PRT
<213> ORGANISM: Arabidopsis lyrata

<400> SEQUENCE: 47

Met Gly Glu Arg Asp Asp Gly Leu Gly Leu Ser Leu Ser Leu Gly Asn
1               5                   10                  15

Ser Gln Gln Lys Glu Pro Ser Leu Arg Leu Asn Leu Met Pro Leu Thr
            20                  25                  30

Thr Ser Ser Ser Ser Ser Phe Gln His Met His Asn Gln Asn Asn Asn
            35                  40                  45

Ser His Pro Gln Lys Ile His His Asn Ser Trp Thr His Leu Phe Gln
        50                  55                  60

Ser Ser Gly Ile Lys Arg Thr Thr Ala Glu Arg Asn Ser Asp Ala Gly
65                  70                  75                  80

Ser Phe Leu Arg Gly Phe Asn Val Ser Arg Ala Pro Ser Ala Val Ala
            85                  90                  95

Val Val Asp Leu Glu Glu Glu Ala Ala Val Ser Ser Pro Asn Ser
            100                 105                 110

Thr Val Ser Ser Leu Ser Gly Asn Lys Arg Asp Leu Ala Val Ala Arg
            115                 120                 125

Gly Gly Asp Glu Asn Glu Ala Glu Arg Ala Ser Cys Ser Arg Gly Gly
        130                 135                 140

Gly Ser Gly Gly Ser Asp Asp Glu Glu Gly Asn Gly Asp Gly Ser
145                 150                 155                 160

Arg Lys Lys Leu Arg Leu Ser Lys Glu Gln Ala Leu Val Leu Glu Glu
            165                 170                 175

Thr Phe Lys Glu His Ser Thr Leu Asn Pro Lys Gln Lys Leu Ala Leu
            180                 185                 190

Ala Lys Gln Leu Asn Leu Arg Ala Arg Gln Val Glu Val Trp Phe Gln
            195                 200                 205

Asn Arg Arg Ala Arg Thr Lys Leu Lys Gln Thr Glu Val Asp Cys Glu
```

```
                210                 215                 220
Tyr Leu Lys Arg Cys Cys Asp Ser Leu Thr Glu Glu Asn Arg Arg Leu
225                 230                 235                 240

Gln Lys Glu Val Ser Glu Leu Arg Ala Leu Lys Leu Ser Pro His Leu
                245                 250                 255

Tyr Met His Met Thr Pro Pro Thr Thr Leu Thr Met Cys Pro Ser Cys
                260                 265                 270

Glu Arg Val Ser Ser Ser Ala Ala Thr Val Thr Ala Ala Pro Pro Thr
                275                 280                 285

Thr Pro Thr Val Val Gly Arg Pro Ser Pro Gln Arg Leu Thr Pro Trp
                290                 295                 300

Thr Thr Ile Ser Leu Gln Gln Lys Ser Gly Arg
305                 310                 315

<210> SEQ ID NO 48
<211> LENGTH: 247
<212> TYPE: PRT
<213> ORGANISM: Oryza barthii

<400> SEQUENCE: 48

Met Met Glu Arg Ala Glu Asp Leu Arg Leu Ser Leu Ser Leu Ser Ser
1               5                   10                  15

Pro Leu Ile Ala Pro Arg Thr His Val Ala Met Leu Phe His Ala
                20                  25                  30

Pro Pro Glu Lys Arg Phe Leu Glu Met Pro Leu Leu Pro Ala Ala Lys
                35                  40                  45

Arg Ser Glu Val Val Ala Ala Glu Glu Arg Ala Gly Leu Arg Gly
    50                  55                  60

Gly Gly Gly Ser Asp Glu Glu Asp Gly Gly Cys Gly Ile Asp Gly Ser
65                  70                  75                  80

Arg Lys Lys Leu Arg Leu Ser Lys Asp Gln Ser Ala Val Leu Glu Asp
                85                  90                  95

Ser Phe Arg Glu His Pro Thr Leu Asn Pro Arg Gln Lys Ala Thr Leu
                100                 105                 110

Ala Gln Gln Leu Gly Leu Arg Pro Arg Gln Val Glu Val Trp Phe Gln
                115                 120                 125

Asn Arg Arg Ala Arg Thr Lys Leu Lys Gln Thr Glu Val Asp Cys Glu
                130                 135                 140

Phe Leu Lys Arg Cys Cys Glu Thr Leu Thr Glu Glu Asn Arg Arg Leu
145                 150                 155                 160

Gln Lys Glu Val Gln Glu Leu Arg Ala Leu Lys Leu Val Ser Pro His
                165                 170                 175

Leu Tyr Met Asn Met Ser Pro Pro Thr Thr Leu Thr Met Cys Pro Ser
                180                 185                 190

Cys Glu Arg Val Ser Asn Thr Asn Asn Ser Ser Ala Ala Ala Ala
        195                 200                 205

Ala Asp Arg Arg Gly Ile Arg Thr Thr Thr Ala Ala Ala Gly Gly Ser
    210                 215                 220

Val Val Asp Thr Ala Ala Asp Gly Gly Ile Leu Cys His Arg Pro Ile
225                 230                 235                 240

Ala Val Arg Pro Gln Gln Ser
                245

<210> SEQ ID NO 49
<211> LENGTH: 287
```

<212> TYPE: PRT
<213> ORGANISM: Eucalyptus grandis

<400> SEQUENCE: 49

```
Met Met Val Glu Arg Glu Asp Leu Gly Leu Ser Leu Ser Leu Ser Phe
1               5                   10                  15

Ser Asp Ser Ser Arg Pro Ser Gln Leu Gly Ala Ser Pro Phe Gly Phe
            20                  25                  30

Asn Leu Tyr Lys Pro Ser His Arg Asp Cys Glu Thr Phe Ala Ser Leu
        35                  40                  45

Asp Arg Ile Ser Glu Ala Asp Ala Arg Pro Ser Leu Arg Gly Ile Asp
    50                  55                  60

Val Asn Arg Pro Pro Ser Ala Ala Asp Cys Glu Glu Gln Glu Glu
65                  70                  75                  80

Ala Gly Val Ser Ser Pro Asn Ser Thr Ile Ser Ser Val Ser Gly Lys
                85                  90                  95

Arg Gly Glu Arg Glu Met Val Ser Gly Gly Glu Asp Asn Glu Ala Glu
            100                 105                 110

Arg Asp Cys Ser Arg Gly Gly Ser Asp Glu Glu Asp Gly Glu Asn Ser
        115                 120                 125

Arg Lys Lys Leu Arg Leu Ser Lys Asp Gln Ser Ala Val Leu Glu Glu
    130                 135                 140

Ser Phe Arg Glu His Asn Thr Leu Asn Pro Lys Gln Lys Leu Ala Leu
145                 150                 155                 160

Ala Lys Gln Leu Gly Leu Arg Pro Arg Gln Val Glu Val Trp Phe Gln
                165                 170                 175

Asn Arg Arg Ala Arg Thr Lys Leu Lys Gln Thr Glu Ile Asp Cys Glu
            180                 185                 190

Phe Leu Lys Arg Cys Cys Glu Asn Leu Thr Glu Glu Asn Arg Arg Leu
        195                 200                 205

Gln Lys Glu Val Gln Glu Leu Arg Ala Leu Lys Leu Ser Pro Gln Phe
    210                 215                 220

Tyr Met His Met Pro Pro Thr Thr Leu Thr Val Cys Pro Asn Cys
225                 230                 235                 240

Glu Arg Val Gly Ala Ala Pro Pro Leu Pro Ser Ala Gly Gly Gly
                245                 250                 255

Gly Arg Pro Ala His His Arg Glu Pro Val Pro Met Ile Pro Trp Ala
            260                 265                 270

Ala Arg Pro Gly Pro Val Ser His Gly Ala Leu Arg Pro Arg Thr
    275                 280                 285
```

<210> SEQ ID NO 50
<211> LENGTH: 323
<212> TYPE: PRT
<213> ORGANISM: Eutrema salsugineum

<400> SEQUENCE: 50

```
Met Gly Glu Arg Asp Asp Gly Leu Gly Leu Ser Leu Ser Leu Gly Phe
1               5                   10                  15

Ser Gln Gln Lys Glu Pro Cys Pro Arg Leu Asn Leu Leu Pro Leu Thr
            20                  25                  30

Thr Ser Ser Ser Ser Ser Phe His His Met His Asn His Asn Asn
        35                  40                  45

Asn His Leu Gln Lys Lys Ile Gln His Asn Ser Trp Pro His Leu Phe
    50                  55                  60
```

Gln Ser Ser Glu Lys Asn Pro Asp Ala Gly Ser Phe Gly Arg Gly Phe
65                  70                  75                  80

Asp Val Asn Arg Ala Pro Ser Ala Ala Val Val Asp Leu Glu Glu
            85                  90                  95

Asp Gly Thr Gly Val Ser Ser Pro Asn Ser Thr Val Ser Ser Val Ser
            100                 105                 110

Gly Asn Lys Arg Asp Leu Ala Ala Ala Arg Gly Gly Gly Gly Asp Glu
            115                 120                 125

Asn Glu Gly Glu Arg Ala Ser Cys Ser His Gly Gly Gly Ser Gly Gly
            130                 135                 140

Ser Asp Asp Glu Asp Gly Gly Asn Gly Asp Gly Ser Arg Lys Lys Leu
145                 150                 155                 160

Arg Leu Ser Lys Glu Gln Ala Val Val Leu Glu Glu Thr Phe Lys Glu
            165                 170                 175

His Thr Thr Leu Asn Pro Lys Gln Lys Leu Ala Leu Ala Arg Gln Leu
            180                 185                 190

Asn Leu Arg Thr Arg Gln Val Glu Val Trp Phe Gln Asn Arg Arg Ala
            195                 200                 205

Arg Thr Lys Leu Lys Gln Thr Glu Val Asp Cys Glu Tyr Leu Lys Arg
            210                 215                 220

Cys Cys Asp Asn Leu Thr Glu Glu Asn Arg Arg Leu His Lys Glu Val
225                 230                 235                 240

Ser Glu Leu Arg Ala Leu Lys Leu Ser Pro His Leu Tyr Met His Met
            245                 250                 255

Thr Pro Pro Thr Thr Leu Thr Met Cys Pro Ser Cys Glu Arg Val Ser
            260                 265                 270

Ala Ser Ser Ser Ser Thr Ala Val Ala Ala Pro Pro Ser Ser Ser Ser
            275                 280                 285

Ala Ala Ser Gly Gly Gly Gly Trp Ile Pro Thr Val Val Gly Arg Pro
            290                 295                 300

Ser Pro Gln Arg Pro Thr Pro Cys Ala Ala Ile Ser Leu Gln Ser Arg
305                 310                 315                 320

Leu Ala His

<210> SEQ ID NO 51
<211> LENGTH: 241
<212> TYPE: PRT
<213> ORGANISM: Leersia perrieri

<400> SEQUENCE: 51

Met Met Glu Arg Ala Glu Asp Leu Arg Leu Ser Leu Ser Leu Ser Ser
1               5                   10                  15

Pro Leu Ala Pro Arg Thr His His Val Ala Met Leu Phe His Ala Pro
            20                  25                  30

Pro Glu Lys Arg Phe Leu Glu Met Pro Leu Leu Pro Ala Ala Lys Arg
            35                  40                  45

Ser Glu Val Val Val Ala Ala Asp Glu Gly Met Arg Gly Gly Gly Gly
            50                  55                  60

Gly Ser Asp Glu Glu Gly Gly Cys Gly Ile Asp Gly Ser Arg Lys
65                  70                  75                  80

Lys Leu Arg Leu Ser Lys Asp Gln Ser Ala Val Leu Glu Asp Ser Phe
            85                  90                  95

Arg Glu His Pro Thr Leu Asn Pro Arg Gln Lys Ala Thr Leu Ala Gln
            100                 105                 110

Gln Leu Gly Leu Arg Pro Arg Gln Val Glu Val Trp Phe Gln Asn Arg
115                 120                 125

Arg Ala Arg Thr Lys Leu Lys Gln Thr Glu Val Asp Cys Glu Phe Leu
130                 135                 140

Lys Arg Cys Cys Glu Thr Leu Thr Glu Glu Asn Arg Arg Leu Gln Lys
145                 150                 155                 160

Glu Val Gln Glu Leu Arg Ala Leu Lys Leu Val Ser Pro His Leu Tyr
                165                 170                 175

Met Asn Met Ser Pro Pro Thr Thr Leu Thr Met Cys Pro Ser Cys Glu
            180                 185                 190

Arg Val Ser Asn Thr Asn Asn Ser Asn Ser Asn Ser Ser Ser Ser Ala
        195                 200                 205

Ala Ala Ala Ala Ala Asp Arg Arg Gly Val Gly Ser Asp Thr Ala Ala
    210                 215                 220

Glu Gly Gly Ile Leu Cys His Arg Pro Ile Ala Val Arg Pro Gln Gln
225                 230                 235                 240

Ser

<210> SEQ ID NO 52
<211> LENGTH: 320
<212> TYPE: PRT
<213> ORGANISM: Capsella rubella

<400> SEQUENCE: 52

Met Gly Glu Arg Asp Asp Gly Leu Gly Leu Ser Leu Ser Leu Gly Asn
1               5                   10                  15

Ser Ser Gln Leu Lys Glu Pro Ser Leu Arg Leu Asn Leu Thr Pro Phe
            20                  25                  30

Thr Ala Ser Thr Ser Ser Ser Phe Pro Pro His Met His Asn Gln Ile
        35                  40                  45

Ile Asn Asn Asn Ser His Pro Gln Lys Ile His His Asn Ser Trp Thr
    50                  55                  60

His Leu Phe Gln Ser Ser Gly Ile Lys Arg Thr Thr Ala Glu Arg Asn
65                  70                  75                  80

Ser Asp Ala Gly Ser Phe Leu Arg Ser Phe Asp Val Asn Arg Ala Pro
                85                  90                  95

Ser Ser Ser Val Ala Val Val Asn Leu Glu Glu Glu Ala Ala Val Val
            100                 105                 110

Ser Ser Pro Asn Ser Thr Val Ser Ser Leu Ser Gly Asn Lys Arg Asp
        115                 120                 125

Leu Ala Ala Ala Arg Gly Gly Asp Glu His Glu Ala Glu Arg Ala Ser
    130                 135                 140

Cys Ser Arg Gly Gly Gly Ser Asp Asp Glu Asp Cys Gly Asn Gly Asp
145                 150                 155                 160

Gly Ser Arg Lys Lys Leu Arg Leu Ser Lys Glu Gln Ala Leu Val Leu
                165                 170                 175

Glu Glu Thr Phe Lys Val His Ser Thr Leu Asn Pro Lys Gln Lys Leu
            180                 185                 190

Val Leu Ala Lys Gln Leu Asn Leu Arg Ala Arg Gln Val Glu Val Trp
        195                 200                 205

Phe Gln Asn Arg Arg Ala Arg Thr Lys Leu Lys Gln Thr Glu Val Asp
    210                 215                 220

Cys Glu Tyr Leu Lys Arg Cys Cys Asp Asn Leu Thr Glu Glu Asn Arg
225                 230                 235                 240

Arg Leu Gln Lys Glu Val Ser Glu Leu Arg Ala Leu Lys Leu Ser Pro
                    245                 250                 255

His Leu Tyr Met His Met Thr Pro Pro Thr Thr Leu Thr Met Cys Pro
            260                 265                 270

Ser Cys Glu Arg Val Ser Ser Thr Ser Ser Ala Asn Ala Ser Ile Ala
        275                 280                 285

Pro Pro Pro Pro Ala Thr Ser Val Val Gly Arg Pro Ser Pro Gln
    290                 295                 300

Arg Ser Thr His Trp Thr Ala Ile Ser Leu Gln Gln Arg Ser Gly Arg
305                 310                 315                 320

<210> SEQ ID NO 53
<211> LENGTH: 287
<212> TYPE: PRT
<213> ORGANISM: Citrus clementina

<400> SEQUENCE: 53

Met Gly Glu Lys Asp Asp Gly Leu Gly Leu Ser Leu Ser Leu Gly Cys
1               5                   10                  15

Ala Ala Arg Asn Glu Pro Ser Leu Arg Leu Asn His Met Pro Leu Ser
            20                  25                  30

Ser Ser Gln Ser Met Gln Asn His His Lys Arg Ser Pro Trp Thr Glu
        35                  40                  45

Leu Phe His Ser Ser Asp Arg Asn Ser Asp Thr Arg Ser Phe Leu Arg
    50                  55                  60

Gly Ile Asp Val Asn Gln Ala Pro Thr Val Ala Asp Cys Glu Glu Glu
65                  70                  75                  80

Asn Gly Val Ser Ser Pro Asn Ser Thr Val Ser Ser Ile Ser Gly Lys
                85                  90                  95

Arg Ser Glu Arg Glu Pro Ile Gly Asp Glu Thr Glu Ala Glu Arg Ala
            100                 105                 110

Ser Cys Ser Arg Gly Ser Asp Asp Glu Asp Gly Gly Ala Gly Asp Ala
        115                 120                 125

Ser Arg Lys Lys Leu Arg Leu Ser Lys Glu Gln Ser Leu Leu Leu Glu
    130                 135                 140

Glu Thr Phe Lys Glu His Ser Thr Leu Asn Pro Lys Gln Lys Leu Ala
145                 150                 155                 160

Leu Ala Lys Gln Leu Asn Leu Arg Pro Arg Gln Val Glu Val Trp Phe
                165                 170                 175

Gln Asn Arg Arg Ala Arg Thr Lys Leu Lys Gln Thr Glu Val Asp Cys
            180                 185                 190

Glu Tyr Leu Lys Arg Cys Cys Glu Asn Leu Thr Glu Glu Asn Arg Arg
        195                 200                 205

Leu Gln Lys Glu Val Gln Glu Leu Arg Ser Leu Lys Leu Ser Pro Gln
    210                 215                 220

Leu Tyr Met Asn Met Asn Pro Pro Thr Thr Leu Thr Met Cys Pro Ser
225                 230                 235                 240

Cys Glu Arg Val Ala Val Ser Ser Ser Ser Ser Ser Ala Ala
                245                 250                 255

Ala Asn Gly Thr Thr Arg Leu Pro Ile Gly Pro Asn His Gln Arg Leu
            260                 265                 270

Thr Pro Val Ser Pro Trp Ala Ala Leu Pro Ile His His Arg Ser
        275                 280                 285

<210> SEQ ID NO 54

-continued

<211> LENGTH: 333
<212> TYPE: PRT
<213> ORGANISM: Morus notabilis

<400> SEQUENCE: 54

Met Gly Glu Lys Asp Asp Gly Leu Gly Leu Gly Leu Ser Leu Ser
1               5                   10                  15

Leu Gly Ile Phe Gly Gly Thr Thr Thr Ala Thr Thr His Thr Thr
            20                  25                  30

Thr His Gln Pro Gly Ser Ser Ser Ser Leu Lys Phe Asn Leu
        35                  40                  45

Met Gln Lys Pro Ser Ser Ser Met Gln Tyr Gln Gln Lys Thr Thr
50                  55                  60

Asn Thr Thr Ala Thr Pro Trp Asn Glu Ile Phe Gln Leu Ser Asp Arg
65                  70                  75                  80

Asn Ser Asp Gly Arg Ser Phe Leu Arg Gly Leu Asp Val Asn Leu Thr
                85                  90                  95

Pro Ser Phe Ala Ala Ala Ala Ala Asp Tyr Asp Glu Glu Asn Gly
            100                 105                 110

Val Ser Ser Pro Asn Ser Thr Ile Ser Ser Ile Ser Gly Lys Lys Ser
            115                 120                 125

Glu Arg Glu Ala Pro Gly Gly Glu Ala Glu Gly Asp Arg Asp
    130                 135                 140

Ser Cys Ser Arg Gly Gly Gly Ser Asp Asp Glu Asp Gly Gly Asn
145                 150                 155                 160

Gly Gly Gly Asp Ala Ser Arg Lys Lys Leu Arg Leu Thr Lys Asp Gln
                165                 170                 175

Ser Leu Ile Leu Glu Glu Thr Phe Lys Glu His Asn Thr Leu Asn Pro
            180                 185                 190

Lys Gln Lys Leu Ala Leu Ala Lys Glu Leu Asn Leu Arg Pro Arg Gln
        195                 200                 205

Val Glu Val Trp Phe Gln Asn Arg Arg Ala Arg Thr Lys Leu Lys Gln
    210                 215                 220

Thr Glu Val Asp Cys Glu Tyr Leu Lys Arg Cys Cys Glu Asn Leu Thr
225                 230                 235                 240

Glu Glu Asn Arg Arg Leu Gln Lys Glu Val Gln Glu Leu Arg Ala Leu
                245                 250                 255

Lys Leu Ser Pro Gln Leu Tyr Met His Met Ser Pro Thr Thr Leu
            260                 265                 270

Thr Met Cys Pro Ser Cys Glu Arg Val Ala Ala Ser Ser Ser Leu Ser
        275                 280                 285

Ser Thr Ala Ala Ala Ala Pro Asn Gly Ser Asn Arg Gln Pro Ala Val
    290                 295                 300

Pro Ser Ile Pro Arg Pro Val Pro Ile Asn Pro Trp Ala Ala Leu Pro
305                 310                 315                 320

Ile Pro His Arg Pro Leu Asp Thr Pro Ala Ser Arg Ser
                325                 330

<210> SEQ ID NO 55
<211> LENGTH: 287
<212> TYPE: PRT
<213> ORGANISM: Citrus sinensis

<400> SEQUENCE: 55

Met Gly Glu Lys Asp Asp Gly Leu Gly Leu Ser Leu Ser Leu Gly Cys
1               5                   10                  15

```
Ala Ala Arg Asn Glu Pro Ser Leu Arg Leu Asn His Met Pro Leu Ser
            20                  25                  30

Ser Ser Gln Ser Met Gln Asn His His Lys Arg Ser Pro Trp Thr Glu
        35                  40                  45

Leu Phe His Ser Ser Asp Arg Asn Ser Asp Thr Arg Ser Phe Leu Arg
    50                  55                  60

Gly Ile Asp Val Asn Gln Ala Pro Thr Val Ala Asp Cys Glu Glu Glu
65                  70                  75                  80

Asn Gly Val Ser Ser Pro Asn Ser Thr Val Ser Ser Ile Ser Gly Lys
                85                  90                  95

Arg Ser Glu Arg Glu Pro Ile Gly Asp Glu Thr Glu Ala Glu Arg Ala
            100                 105                 110

Ser Cys Ser Arg Gly Ser Asp Asp Glu Asp Gly Gly Ala Gly Asp Ala
        115                 120                 125

Ser Arg Lys Lys Leu Arg Leu Ser Lys Glu Gln Ser Leu Leu Leu Glu
    130                 135                 140

Glu Thr Phe Lys Glu His Ser Thr Leu Asn Pro Lys Gln Lys Leu Ala
145                 150                 155                 160

Leu Ala Lys Gln Leu Asn Leu Arg Pro Arg Gln Val Glu Val Trp Phe
                165                 170                 175

Gln Asn Arg Arg Ala Arg Thr Lys Leu Lys Gln Thr Glu Val Asp Cys
            180                 185                 190

Glu Tyr Leu Lys Arg Cys Cys Glu Asn Leu Thr Glu Glu Asn Arg Arg
        195                 200                 205

Leu Gln Lys Glu Val Gln Glu Leu Arg Ser Leu Lys Leu Ser Pro Gln
    210                 215                 220

Leu Tyr Met Asn Met Asn Pro Pro Thr Thr Leu Thr Met Cys Pro Ser
225                 230                 235                 240

Cys Glu Arg Val Ala Val Ser Ser Ser Ser Ser Ser Ser Ser Ala Ala
                245                 250                 255

Ala Asn Gly Thr Thr Arg Leu Pro Ile Gly Pro Asn His Gln Arg Leu
            260                 265                 270

Thr Pro Val Ser Pro Trp Ala Ala Leu Pro Ile His His Arg Ser
        275                 280                 285

<210> SEQ ID NO 56
<211> LENGTH: 160
<212> TYPE: PRT
<213> ORGANISM: Physcomitrella patens subsp. patens

<400> SEQUENCE: 56

Met Ser Ser Arg Gly Gly Ser Asp Asp Glu Asp Glu Gly Thr Thr Arg
1               5                   10                  15

Lys Lys Leu Arg Leu Ser Lys Glu Gln Ser Ala Leu Leu Glu Glu Ser
            20                  25                  30

Phe Lys Glu His Ser Thr Leu Asn Pro Lys Gln Lys Asn Ala Leu Ala
        35                  40                  45

Lys Gln Leu Gly Leu Arg Pro Arg Gln Val Glu Val Trp Phe Gln Asn
    50                  55                  60

Arg Arg Ala Arg Thr Lys Leu Lys Gln Thr Glu Val Asp Cys Glu Leu
65                  70                  75                  80

Leu Lys Arg Cys Cys Asp Ser Leu Lys Glu Glu Asn Arg Arg Leu Gln
                85                  90                  95

Lys Glu Leu Leu Glu Leu Arg Ala Ile Lys Val Ala Pro Pro Cys Val
```

```
                    100                 105                 110
Ile Ser His Asp Tyr Tyr Met Pro Leu Pro Ala Ala Thr Leu Thr Met
            115                 120                 125

Cys Pro Ser Cys Glu Arg Val Ala Thr Val Asp Asn Arg Ser Leu Thr
        130                 135                 140

Phe Ala Lys Pro Gly Phe Ser His Leu Ser Gln Ser Ser Ala Ala Cys
145                 150                 155                 160

<210> SEQ ID NO 57
<211> LENGTH: 295
<212> TYPE: PRT
<213> ORGANISM: Theobroma cacao

<400> SEQUENCE: 57

Met Gly Ala Glu Lys Asp Asp Gly Leu Gly Leu Ser Leu Ser Leu Gly
1               5                   10                  15

Cys Ala Gln Asn His Pro Ser Leu Lys Leu Asn Leu Met Pro Leu Ala
            20                  25                  30

Ser Pro Arg Met Gln Asn Leu Gln Gln Lys Asn Thr Trp Asn Glu Leu
        35                  40                  45

Phe Gln Ser Ser Asp Arg Asn Leu Asp Thr Arg Ser Phe Leu Arg Gly
    50                  55                  60

Ile Asp Val Asn Arg Ala Pro Ala Thr Val Asp Cys Glu Glu Glu Gly
65                  70                  75                  80

Gly Val Ser Ser Pro Asn Ser Thr Ile Ser Ser Ile Ser Gly Lys Arg
                85                  90                  95

Asn Glu Arg Asp Pro Val Gly Asp Glu Thr Glu Ala Glu Arg Ala Ser
            100                 105                 110

Cys Ser Arg Ala Ser Asp Asp Glu Asp Gly Gly Ala Gly Gly Asp Ala
        115                 120                 125

Ser Arg Lys Lys Leu Arg Leu Ser Lys Glu Gln Ser Leu Leu Leu Glu
    130                 135                 140

Glu Thr Phe Lys Glu His Ser Thr Leu Asn Pro Lys Gln Lys Leu Ala
145                 150                 155                 160

Leu Ala Lys Gln Leu Asn Leu Arg Pro Arg Gln Val Glu Val Trp Phe
                165                 170                 175

Gln Asn Arg Arg Ala Arg Thr Lys Leu Lys Gln Thr Glu Val Asp Cys
            180                 185                 190

Glu Tyr Leu Lys Arg Cys Cys Glu Asn Leu Thr Glu Glu Asn Arg Arg
        195                 200                 205

Leu Gln Lys Glu Val Gln Glu Leu Arg Ala Leu Lys Leu Ser Pro Gln
    210                 215                 220

Leu Tyr Met His Met Asn Pro Pro Thr Thr Leu Thr Met Cys Pro Ser
225                 230                 235                 240

Cys Glu Arg Val Ala Val Ser Ser Ser Ser Ser Ala Ala Ala Thr
                245                 250                 255

Ala Ser Ser Thr Pro Thr Ser Thr Val Pro Asn Arg His His Arg Thr
            260                 265                 270

Ser Ser Val Ser Pro Trp Ala Ala Met Pro Ile Gly His Arg Pro Phe
        275                 280                 285

His Ala Pro Ala Ser Arg Ser
    290                 295

<210> SEQ ID NO 58
<211> LENGTH: 292
```

<212> TYPE: PRT
<213> ORGANISM: Cucumis melo

<400> SEQUENCE: 58

Met Gly Gly Arg Asp Asp Asp Leu Gly Leu Thr Leu Ser Leu Gly Phe
1               5                   10                  15

Gly Val Thr Thr Gln Pro Thr His Met Gln Arg Pro Ser Met His Asn
            20                  25                  30

His Leu Arg Lys Thr Ser Trp Asn Glu Leu Phe Gln Phe Ser Asp Arg
        35                  40                  45

Asn Ala Asp Ser Arg Ser Phe Leu Arg Gly Ile Asp Val Asn Arg Leu
    50                  55                  60

Pro Thr Gly Val Asp Gly Glu Glu Asn Gly Val Ser Ser Pro Asn
65                  70                  75                  80

Ser Thr Ile Ser Ser Ile Ser Gly Lys Arg Ser Glu Arg Glu Ala Ala
                85                  90                  95

Gly Asp Glu Ala Glu Ala Glu Ala Glu Ala Glu Ala Glu Ala Glu Ala
            100                 105                 110

Glu Ala Glu Ala Glu Arg Ala Ser Cys Ser Arg Gly Ser Asp Asp Glu
        115                 120                 125

Asp Gly Gly Gly Asp Gly Asp Ala Ser Arg Lys Lys Leu Arg Leu
    130                 135                 140

Ser Lys Glu Gln Ser Met Val Leu Glu Glu Thr Phe Lys Glu His Asn
145                 150                 155                 160

Thr Leu Asn Pro Lys Gln Lys Leu Ala Leu Ala Lys Gln Leu Asn Leu
                165                 170                 175

Thr Pro Arg Gln Val Glu Val Trp Phe Gln Asn Arg Arg Ala Arg Thr
            180                 185                 190

Lys Leu Lys Gln Thr Glu Val Asp Cys Glu Tyr Leu Lys Arg Cys Cys
        195                 200                 205

Glu Asn Leu Thr Glu Glu Asn Arg Arg Leu Gln Lys Glu Val Gln Glu
    210                 215                 220

Leu Arg Ala Leu Lys Leu Ser Pro Gln Leu Tyr Met His Met Asn Pro
225                 230                 235                 240

Pro Thr Thr Leu Thr Met Cys Pro Gln Cys Glu Arg Val Ala Val Ser
                245                 250                 255

Ser Ser Ser Ser Thr Ser Ala Ala Thr Thr Thr Arg His Pro Ala Ala
            260                 265                 270

Ala Gly Val Gln Arg Thr Ser Met Ala Ile Asn Pro Trp Ala Val Leu
        275                 280                 285

Pro Ile Gln Arg
    290

<210> SEQ ID NO 59
<211> LENGTH: 294
<212> TYPE: PRT
<213> ORGANISM: Cucumis sativus

<400> SEQUENCE: 59

Met Gly Gly Arg Asp Asp Asp Val Gly Leu Thr Leu Ser Leu Gly Phe
1               5                   10                  15

Gly Val Thr Thr Gln Ser Thr His Met Gln Arg Pro Ser Ser Met His
            20                  25                  30

Asn His His Leu Arg Lys Thr His Trp Asn Glu Leu Phe Gln Phe Ser
        35                  40                  45

Asp Arg Asn Ala Asp Ser Arg Ser Phe Leu Arg Gly Ile Asp Val Asn
    50                  55                  60

Arg Leu Pro Thr Gly Val Asp Gly Glu Glu Asn Gly Val Ser Ser
65              70                  75                  80

Pro Asn Ser Thr Ile Ser Ser Ile Ser Gly Lys Arg Ser Glu Arg Glu
                85                  90                  95

Ala Ala Gly Asp Glu Ala Glu Ala Glu Ala Glu Ala Glu Ala
            100                 105                 110

Glu Ala Glu Ala Glu Ala Glu Arg Ala Ser Cys Ser Arg Gly Ser Asp
        115                 120                 125

Asp Glu Asp Gly Gly Gly Gly Asp Gly Asp Ala Ser Arg Lys Lys Leu
    130                 135                 140

Arg Leu Ser Lys Glu Gln Ser Met Val Leu Glu Glu Thr Phe Lys Glu
145                 150                 155                 160

His Asn Thr Leu Asn Pro Lys Gln Lys Leu Ala Leu Ala Lys Gln Leu
                165                 170                 175

Asn Leu Thr Pro Arg Gln Val Glu Val Trp Phe Gln Asn Arg Arg Ala
            180                 185                 190

Arg Thr Lys Leu Lys Gln Thr Glu Val Asp Cys Glu Tyr Leu Lys Arg
        195                 200                 205

Cys Cys Glu Asn Leu Thr Glu Glu Asn Arg Arg Leu Gln Lys Glu Val
    210                 215                 220

Gln Glu Leu Arg Ala Leu Lys Leu Ser Pro Gln Leu Tyr Met His Met
225                 230                 235                 240

Asn Pro Pro Thr Thr Leu Thr Met Cys Pro Gln Cys Glu Arg Val Ala
                245                 250                 255

Val Ser Ser Ser Ser Thr Ser Ala Ala Thr Thr Thr Arg His Gln
            260                 265                 270

Ala Ala Ala Gly Val Gln Arg Pro Ser Met Ala Ile Asn Pro Trp Ala
        275                 280                 285

Val Leu Pro Ile Gln Arg
        290

<210> SEQ ID NO 60
<211> LENGTH: 298
<212> TYPE: PRT
<213> ORGANISM: Populus trichocarpa

<400> SEQUENCE: 60

Met Gly Asp Lys Asn Asp Gly Leu Gly Leu Ser Leu Ser Leu Gly Phe
1               5                   10                  15

Asp Ala Thr Gln Gln Asn His Gln Gln Gln Pro Ser Leu Lys Leu Asn
            20                  25                  30

Leu Met Pro Val Pro Ser Gln Asn Asn His Arg Lys Thr Ser Leu Thr
        35                  40                  45

Asp Leu Phe Gln Ser Ser Asp Arg Ala Cys Gly Thr Arg Phe Phe Gln
    50                  55                  60

Arg Gly Ile Asp Met Asn Arg Val Pro Ala Ala Val Thr Asp Cys Asp
65              70                  75                  80

Asp Glu Thr Gly Val Ser Ser Pro Asn Ser Thr Leu Ser Ser Leu Ser
                85                  90                  95

Gly Lys Arg Ser Glu Arg Glu Gln Ile Gly Glu Glu Thr Glu Ala Glu
            100                 105                 110

Arg Ala Ser Cys Ser Arg Asp Ser Asp Asp Glu Asp Gly Ala Gly Gly
        115                 120                 125

```
Asp Ala Ser Arg Lys Lys Leu Arg Leu Ser Lys Glu Gln Ser Leu Val
        130                 135                 140

Leu Glu Glu Thr Phe Lys Glu His Asn Thr Leu Asn Pro Lys Glu Lys
145                 150                 155                 160

Leu Ala Leu Ala Lys Gln Leu Asn Leu Arg Pro Arg Gln Val Glu Val
                165                 170                 175

Trp Phe Gln Asn Arg Arg Ala Arg Thr Lys Leu Lys Gln Thr Glu Val
                180                 185                 190

Asp Cys Glu Tyr Leu Lys Arg Cys Cys Glu Asn Leu Thr Glu Glu Asn
                195                 200                 205

Arg Arg Leu Gln Lys Glu Val Gln Glu Leu Arg Ala Leu Lys Leu Ser
    210                 215                 220

Pro Gln Leu Tyr Met His Met Asn Pro Pro Thr Thr Leu Thr Met Cys
225                 230                 235                 240

Pro Ser Cys Glu Arg Val Ala Val Ser Ser Ala Ser Ser Ser Ser Ala
                245                 250                 255

Ala Ala Ala Ser Ser Ala Leu Ala Pro Thr Ala Ser Thr Arg Gln Pro
                260                 265                 270

Gln Arg Pro Val Pro Ile Asn Pro Trp Ala Thr Met Pro Val His Gln
                275                 280                 285

Arg Thr Phe Asp Ala Pro Ala Ser Arg Ser
    290                 295

<210> SEQ ID NO 61
<211> LENGTH: 315
<212> TYPE: PRT
<213> ORGANISM: Arabidopsis thaliana

<400> SEQUENCE: 61

Met Ser Glu Arg Asp Asp Gly Leu Gly Leu Ser Leu Ser Leu Ser Leu
1               5                   10                  15

Gly Phe Asn Gln Lys Asp Pro Ser Ser Arg Leu Asn Pro Met Pro Leu
                20                  25                  30

Ala Ser Tyr Ala Ser Ser Ser His Met Gln His Met Gln Gln Ser Asn
                35                  40                  45

Tyr Asn His Pro Gln Lys Ile Gln Asn Thr Trp Ile Asn Met Phe Gln
            50                  55                  60

Ser Ser Glu Arg Asn Ser Asp Met Arg Ser Phe Leu Arg Gly Ile Asp
65                  70                  75                  80

Val Asn Arg Ala Pro Ser Thr Val Val Asp Val Glu Asp Glu Gly
                85                  90                  95

Ala Gly Val Ser Ser Pro Asn Ser Thr Val Ser Ser Val Met Ser Gly
                100                 105                 110

Lys Lys Ser Glu Arg Glu Leu Met Ala Ala Gly Ala Val Gly Gly
            115                 120                 125

Gly Arg Val Glu Asp Asn Glu Ile Glu Arg Ala Ser Cys Ser Leu Gly
    130                 135                 140

Gly Gly Ser Asp Asp Glu Asp Gly Ser Gly Asn Gly Asp Asp Ser Ser
145                 150                 155                 160

Arg Lys Lys Leu Arg Leu Ser Lys Glu Gln Ala Leu Val Leu Glu Glu
                165                 170                 175

Thr Phe Lys Glu His Ser Thr Leu Asn Pro Lys Gln Lys Met Ala Leu
            180                 185                 190

Ala Lys Gln Leu Asn Leu Arg Thr Arg Gln Val Glu Val Trp Phe Gln
```

```
            195                 200                 205
Asn Arg Arg Ala Arg Thr Lys Leu Lys Gln Thr Glu Val Asp Cys Glu
210                 215                 220

Tyr Leu Lys Arg Cys Cys Glu Asn Leu Thr Asp Glu Asn Arg Arg Leu
225                 230                 235                 240

Gln Lys Glu Val Ser Glu Leu Arg Ala Leu Lys Leu Ser Pro His Leu
                245                 250                 255

Tyr Met His Met Lys Pro Pro Thr Thr Leu Thr Met Cys Pro Ser Cys
                260                 265                 270

Glu Arg Val Ala Val Thr Ser Ser Ser Ser Val Ala Pro Pro Val
                275                 280                 285

Met Asn Ser Ser Pro Met Gly Pro Met Ser Pro Trp Ala Ala Met
290                 295                 300

Pro Leu Arg Gln Arg Pro Ala Ala Gly Ser His
305                 310                 315

<210> SEQ ID NO 62
<211> LENGTH: 311
<212> TYPE: PRT
<213> ORGANISM: Brassica campestris

<400> SEQUENCE: 62

Met Gly Glu Arg Asp Asp Gly Leu Gly Leu Ser Leu Ser Leu Ser Leu
1               5                   10                  15

Gly Leu Asn Gln Lys Glu Ser Ser Pro Arg Leu Asn Pro Met Pro Met
                20                  25                  30

Ala Ser Tyr Ser Ser Ser His Met His Met Gln Ser His Tyr Asn
            35                  40                  45

His Pro Gln Lys Ile Gln Asn Ser Trp Ile Gln Met Phe Gln Ser Ser
50                  55                  60

Glu Arg Asn Ser Asp Val Gly Ser Phe Leu Arg Gly Leu Asp Val Asn
65                  70                  75                  80

Arg Ala Pro Ser Arg Val Val Asp Val Glu Asp Ala Gly Val
                85                  90                  95

Ser Ser Pro Asn Ser Thr Val Ser Val Met Ser Gly Lys Arg Asn
                100                 105                 110

Glu Arg Glu Leu Val Ala Ala Ala Gly Thr Gly Gly Arg Thr Ile
            115                 120                 125

Glu Asp Asn Glu Ala Glu Arg Gly Ser Ser Ser Leu Gly Gly Gly Ser
130                 135                 140

Asp Asp Glu Asp Gly Gly Asn Gly Asp Asp Gly Ser Arg Lys Lys
145                 150                 155                 160

Leu Arg Leu Ser Lys Glu Gln Ala Leu Val Leu Glu Glu Thr Phe Lys
                165                 170                 175

Glu His Ser Thr Leu Asn Pro Lys Gln Lys Met Ala Leu Ala Lys Gln
            180                 185                 190

Leu Asn Leu Arg Thr Arg Gln Val Glu Val Trp Phe Gln Asn Arg Arg
            195                 200                 205

Ala Arg Thr Lys Leu Lys Gln Thr Glu Val Asp Cys Glu Tyr Leu Lys
210                 215                 220

Arg Cys Cys Glu Asn Leu Thr Glu Glu Asn Arg Arg Leu Gln Lys Glu
225                 230                 235                 240

Val Ser Glu Leu Arg Ala Leu Lys Leu Ser Pro Gln Leu Tyr Met His
                245                 250                 255
```

```
Met Lys Pro Pro Thr Thr Leu Thr Met Cys Pro Ser Cys Glu Arg Val
            260                 265                 270

Ala Val Ala Ser Ser Ser Val Ala Pro Ala Pro Val Met Ser Ser Ser
        275                 280                 285

Ser Pro Met Gly Pro Met Ser Pro Trp Ala Ala Ile Pro Leu Arg Gln
    290                 295                 300

Arg Pro Ala Ala Gly Ser Arg
305                 310

<210> SEQ ID NO 63
<211> LENGTH: 301
<212> TYPE: PRT
<213> ORGANISM: Brassica oleracea

<400> SEQUENCE: 63

Met Gly Glu Arg Asp Asp Gly Leu Gly Leu Ser Leu Ser Leu Ser Leu
1               5                   10                  15

Gly Leu Asn Gln Lys Glu Ser Thr Pro Arg Leu Asn Pro Thr Pro Met
            20                  25                  30

Ala Ser Tyr Ser Ser Ser Ser His Met His Met Gln Asn Ser Trp Ile
        35                  40                  45

Gln Met Phe Gln Ser Ser Glu Arg Asn Ser Asp Val Gly Ser Phe Leu
    50                  55                  60

Arg Gly Leu Asp Val Asn Arg Ala Pro Ser Arg Val Val Val Asp Val
65                  70                  75                  80

Glu Glu Asp Ala Gly Val Ser Ser Pro Asn Ser Thr Val Ser Ser Val
                85                  90                  95

Met Ser Gly Lys Arg Asn Glu Arg Glu Leu Val Ala Ala Ala Gly Ala
            100                 105                 110

Gly Gly Gly Arg Thr Ile Glu Asp Asn Glu Thr Glu Arg Gly Ser Ser
        115                 120                 125

Ser Leu Gly Gly Gly Ser Asp Asp Glu Asp Gly Gly Gly Asn Gly Asp
    130                 135                 140

Asp Gly Ser Arg Lys Lys Leu Arg Leu Ser Lys Glu Gln Ala Leu Val
145                 150                 155                 160

Leu Glu Glu Thr Phe Lys Glu His Ser Thr Leu Asn Pro Lys Gln Lys
                165                 170                 175

Met Ala Leu Ala Lys Gln Leu Asn Leu Arg Thr Arg Gln Val Glu Val
            180                 185                 190

Trp Phe Gln Asn Arg Arg Ala Arg Thr Lys Leu Lys Gln Thr Glu Val
        195                 200                 205

Asp Cys Glu Tyr Leu Lys Arg Cys Cys Glu Asn Leu Thr Glu Glu Asn
    210                 215                 220

Arg Arg Leu Gln Lys Glu Val Ser Glu Leu Arg Ala Leu Lys Leu Ser
225                 230                 235                 240

Pro Gln Leu Tyr Met His Met Lys Pro Pro Thr Thr Leu Thr Met Cys
                245                 250                 255

Pro Ser Cys Glu Arg Val Ala Val Ala Ser Ser Ser Val Ala Pro Ala
            260                 265                 270

Pro Val Met Ser Ser Ser Pro Met Gly Pro Met Ser Pro Trp Ala
        275                 280                 285

Ala Ile Pro Leu Arg Gln Arg Pro Ala Ala Gly Ser Arg
    290                 295                 300

<210> SEQ ID NO 64
```

```
<211> LENGTH: 319
<212> TYPE: PRT
<213> ORGANISM: Prunus persica

<400> SEQUENCE: 64

Met Met Val Glu Arg Asp Gln Asp Leu Gly Leu Ser Leu Ser Leu Ser
1               5                   10                  15

Phe Pro Gln Thr His Asn His His Asn Asn Asn Asn Asn Asn Ser Ser
                20                  25                  30

Ser Thr Thr Ser Thr Leu Gln Leu Asn Leu Met Pro Ser Leu Ala Pro
            35                  40                  45

Thr Ser Ala Ser Ser Pro Ser Gly Phe Leu Pro Gln Lys Pro Ser Trp
        50                  55                  60

Asn Glu Ala Leu Ile Ser Ser Asp Arg Asn Ser Asn Ser Glu Thr Phe
65                  70                  75                  80

Arg Val Gly Pro Arg Ser Phe Leu Arg Gly Ile Asp Val Asn Arg Leu
                85                  90                  95

Pro Ser Thr Gly Asp Cys Glu Asp Glu Ala Gly Val Ser Ser Pro Asn
            100                 105                 110

Ser Thr Val Ser Ser Val Ser Gly Lys Arg Ser Glu Arg Glu Ala Asn
        115                 120                 125

Gly Glu Asp Leu Asp Ile Glu Thr Arg Gly Ile Ser Asp Glu Glu Asp
    130                 135                 140

Gly Glu Thr Ser Arg Lys Lys Leu Arg Leu Ser Lys Asp Gln Ser Ala
145                 150                 155                 160

Ile Leu Glu Glu Ser Phe Lys Glu His Asn Thr Leu Asn Pro Lys Gln
                165                 170                 175

Lys Leu Ala Leu Ala Lys Gln Leu Gly Leu Arg Pro Arg Gln Val Glu
            180                 185                 190

Val Trp Phe Gln Asn Arg Arg Ala Arg Thr Lys Leu Lys Gln Thr Glu
        195                 200                 205

Val Asp Cys Glu Phe Leu Lys Arg Cys Cys Glu Asn Leu Thr Glu Glu
    210                 215                 220

Asn Arg Arg Leu Gln Lys Glu Val Gln Glu Leu Arg Ala Leu Lys Leu
225                 230                 235                 240

Ser Pro Gln Phe Tyr Met Gln Met Thr Pro Pro Thr Thr Leu Thr Met
                245                 250                 255

Cys Pro Ser Cys Glu Arg Val Ala Val Pro Pro Asn Ser Ser Ser Ser
            260                 265                 270

Thr Val Glu Pro Arg Pro His Pro His Pro His Pro Gln Met Gly Ser
        275                 280                 285

Val Gln Thr Arg Pro Val Pro Ile Asn Pro Trp Ala Ser Ala Thr Pro
    290                 295                 300

Ile Pro His Arg Pro Leu Pro Phe Glu Ala Phe His Thr Arg Thr
305                 310                 315

<210> SEQ ID NO 65
<211> LENGTH: 299
<212> TYPE: PRT
<213> ORGANISM: Cicer arietinum

<400> SEQUENCE: 65

Met Gly Asp Lys Glu Asp Glu Leu Gly Leu Gly Leu Ser Leu Ser Leu
1               5                   10                  15

Ser Leu Gly Tyr Gly Ala Asn Ala Asn Asn Ala Pro Leu Lys Val Thr
                20                  25                  30
```

His Met His Lys Pro Pro Gln Ser Val Pro Asn Gln Arg Val Ser Phe
            35                  40                  45

Asn Asn Phe Phe His Phe His Asp Leu Ser Ser Glu Thr Arg Ser Phe
 50                  55                  60

Ile Gly Gly Ile Asp Val Asn Ser Pro Ala Thr Ala Ala Cys Asp Asp
 65                  70                  75                  80

Glu Asn Gly Gly Ser Ser Pro Asn Ser Thr Val Ser Ser Ile Ser Gly
                85                  90                  95

Lys Arg Ser Glu Arg Glu Gly Asn Gly Glu Glu Asn Asp Ala Val Glu
                100                 105                 110

Arg Ala Ser Cys Ser Arg Gly Gly Ser Asp Asp Asp Gly Gly Gly
                115                 120                 125

Cys Gly Gly Asp Gly Asp Ser Ser Arg Lys Lys Leu Arg Leu Ser Lys
            130                 135                 140

Glu Gln Ser Val Leu Leu Glu Glu Thr Phe Lys Glu His Asn Thr Leu
145                 150                 155                 160

Asn Pro Lys Gln Lys Gln Ala Leu Ala Lys Gln Leu Asn Leu Met Pro
                165                 170                 175

Arg Gln Val Glu Val Trp Phe Gln Asn Arg Arg Ala Arg Thr Lys Leu
                180                 185                 190

Lys Gln Thr Glu Val Asp Cys Glu Tyr Leu Lys Arg Cys Cys Glu Thr
                195                 200                 205

Leu Thr Glu Glu Asn Arg Arg Leu Gln Lys Glu Val Gln Glu Leu Arg
            210                 215                 220

Ala Leu Lys Leu Ser Pro Gln Leu Tyr Met His Met Asn Pro Pro Thr
225                 230                 235                 240

Thr Leu Thr Met Cys Pro Ser Cys Glu Arg Val Ala Val Ser Ser Ala
                245                 250                 255

Ser Ser Ser Ser Ala Asn Val Pro Ser Ala Leu Ala Pro Ala Asn Arg
                260                 265                 270

Asn Ser Ile Gly Pro Ser Val Gln Arg Pro Val Pro Leu Asn Pro Trp
            275                 280                 285

Ala Ala Met Ser Ile Gln Asn Arg Ser Arg Pro
            290                 295

<210> SEQ ID NO 66
<211> LENGTH: 299
<212> TYPE: PRT
<213> ORGANISM: Glycine max

<400> SEQUENCE: 66

Met Met Val Gln Lys Glu Asp Leu Gly Leu Ser Leu Ser Leu Asn Phe
1               5                   10                  15

Pro His His Asn Thr Pro Asn Pro Gln His Pro Ser Leu Met Ser Ser
                20                  25                  30

Ser Thr His Ser Ser Ser Pro Ser Gly Cys Asn Pro Gln Lys Pro Ser
            35                  40                  45

Trp Asn Glu Ala Phe Thr Ser Ser Asp Arg Asn Ser Asp Thr Cys Arg
 50                  55                  60

Gly Glu Thr Arg Ser Phe Leu Arg Gly Ile Asp Val Asn Arg Leu Pro
 65                  70                  75                  80

Ser Ala Val Asp Thr Glu Glu Glu Thr Gly Val Ser Ser Pro Asn Ser
                85                  90                  95

Thr Val Ser Ser Val Ser Gly Lys Arg Ser Glu Arg Glu Glu Pro Asn

```
            100                 105                 110
Gly Glu Glu His Asp Met Asp Arg Ala Cys Ser Arg Gly Ile Ser Asp
        115                 120                 125

Glu Glu Asp Ala Glu Thr Ala Arg Lys Lys Leu Arg Leu Ser Lys Asp
    130                 135                 140

Gln Ser Ala Ile Leu Glu Glu Ser Phe Lys Glu His Asn Thr Leu Asn
145                 150                 155                 160

Pro Lys Gln Lys Leu Ala Leu Ala Lys Gln Leu Gly Leu Arg Pro Arg
                165                 170                 175

Gln Val Glu Val Trp Phe Gln Asn Arg Arg Ala Arg Thr Lys Leu Lys
            180                 185                 190

Gln Thr Glu Val Asp Cys Glu Val Leu Lys Arg Cys Cys Glu Asn Leu
        195                 200                 205

Thr Glu Glu Asn Arg Arg Leu Gln Lys Glu Val Gln Glu Leu Arg Ala
    210                 215                 220

Leu Lys Leu Ser Pro Gln Phe Tyr Met Gln Met Thr Pro Pro Thr Thr
225                 230                 235                 240

Leu Thr Met Cys Pro Ser Cys Glu Arg Val Ala Val Pro Ser Ser Ala
                245                 250                 255

Val Asp Ala Ala Thr Arg His His Pro Met Ala Gln Ala Gln Ala Gln
            260                 265                 270

Ala Gln Ile Arg His Arg Pro Ile Gly Pro Trp Ala Ser Ala Ser Pro
        275                 280                 285

Ile Thr His Arg Pro Phe Asp Val Phe His His
    290                 295

<210> SEQ ID NO 67
<211> LENGTH: 296
<212> TYPE: PRT
<213> ORGANISM: Medicago truncatula

<400> SEQUENCE: 67

Met Ser Ile Glu Lys Glu Asp Phe Gly Leu Ser Leu Ser Leu Ser Phe
1               5                   10                  15

Pro Gln Asn Pro Asn Pro Gln Tyr Leu Asn Leu Met Ser Ser Ser
            20                  25                  30

Thr His Ser Tyr Ser Pro Ser Thr Phe Asn Pro Gln Lys Pro Ser Trp
        35                  40                  45

Asn Asp Val Phe Thr Ser Ser Asp Arg Asp Ser Glu Thr Cys Arg Ile
    50                  55                  60

Glu Glu Arg Pro Leu Ile Leu Arg Gly Ile Asp Val Asn Arg Leu Pro
65                  70                  75                  80

Ser Gly Ala Asp Cys Glu Glu Ala Gly Val Ser Ser Pro Asn Ser
                85                  90                  95

Thr Val Ser Ser Val Ser Gly Lys Arg Ser Glu Arg Glu Val Thr Gly
            100                 105                 110

Glu Asp Leu Asp Met Glu Arg Asp Cys Ser Arg Gly Ile Ser Asp Glu
        115                 120                 125

Glu Asp Ala Glu Thr Ser Arg Lys Lys Leu Arg Leu Thr Lys Asp Gln
    130                 135                 140

Ser Ile Ile Leu Glu Glu Ser Phe Lys Glu His Asn Thr Leu Asn Pro
145                 150                 155                 160

Lys Gln Lys Leu Ala Leu Ala Lys Gln Leu Gly Leu Arg Ala Arg Gln
                165                 170                 175
```

```
Val Glu Val Trp Phe Gln Asn Arg Arg Ala Arg Thr Lys Leu Lys Gln
            180                 185                 190

Thr Glu Val Asp Cys Glu Phe Leu Lys Arg Cys Cys Glu Asn Leu Thr
        195                 200                 205

Asp Glu Asn Arg Arg Leu Gln Lys Glu Val Gln Glu Leu Arg Ala Leu
    210                 215                 220

Lys Leu Ser Pro Gln Phe Tyr Met Gln Met Thr Pro Thr Thr Leu
225                 230                 235                 240

Thr Met Cys Pro Ser Cys Glu Arg Val Ala Val Pro Ser Ser Ala Val
                245                 250                 255

Asp Ala Ala Thr Arg Arg His Pro Met Ala Ser Asn His Pro Arg Thr
            260                 265                 270

Phe Ser Val Gly Pro Trp Ala Thr Ala Ala Pro Ile Gln His Arg Thr
        275                 280                 285

Phe Asp Thr Leu Arg Pro Arg Ser
    290                 295

<210> SEQ ID NO 68
<211> LENGTH: 295
<212> TYPE: PRT
<213> ORGANISM: Phaseolus vulgaris

<400> SEQUENCE: 68

Met Met Val Gln Lys Glu Asp Leu Gly Leu Ser Leu Ser Leu Asn Phe
1               5                   10                  15

Arg His Asn Ile Pro Asn Pro Gln His Leu Thr Leu Ile Ser Ser Ser
            20                  25                  30

Thr His Ser Ser Ser Pro Ser Ala Ser Asn Pro Phe Lys Pro Ser Trp
        35                  40                  45

Asn Asp Pro Phe Ala Ser Ser Arg Asn Ser Asp Thr Cys Arg Gly
    50                  55                  60

Glu Thr Arg Ser Phe Leu Arg Gly Ile Asp Val Asn Arg Leu Pro Ser
65                  70                  75                  80

Ala Val Asp Met Glu Glu Ala Gly Val Ser Ser Pro Asn Ser Thr
                85                  90                  95

Val Ser Ser Val Ser Gly Lys Arg Ser Glu Arg Glu Pro Asn Gly Glu
            100                 105                 110

Glu His Asp Met Asn Arg Ala Cys Ser Arg Gly Ile Ser Asp Glu Glu
        115                 120                 125

Asp Gly Glu Thr Ser Arg Lys Lys Leu Arg Leu Ser Lys Asp Gln Ser
    130                 135                 140

Ala Ile Leu Glu Glu Ser Phe Lys Glu His Asn Thr Leu Asn Pro Lys
145                 150                 155                 160

Gln Lys Leu Ala Leu Ala Lys Gln Leu Gly Leu Leu Pro Arg Gln Val
                165                 170                 175

Glu Val Trp Phe Gln Asn Arg Arg Ala Arg Thr Lys Leu Lys Gln Thr
            180                 185                 190

Glu Val Asp Cys Glu Val Leu Lys Arg Cys Cys Glu Asn Leu Thr Glu
        195                 200                 205

Glu Asn Arg Arg Leu Gln Lys Glu Val Gln Glu Leu Arg Ala Leu Lys
    210                 215                 220

Leu Ser Pro Gln Phe Tyr Met Gln Met Thr Pro Pro Thr Thr Leu Thr
225                 230                 235                 240

Met Cys Pro Ser Cys Glu Arg Val Ala Val Pro Ser Ser Ala Val Asp
                245                 250                 255
```

```
Ala Ala Thr Arg His His Pro Met Ala Gln Ala Gln Thr His Gly Arg
            260                 265                 270

Pro Ile Pro Ile Gly Pro Trp Ala Ser Ala Gly Pro Ile Pro Gln Arg
        275                 280                 285

Ala Phe Asp Gly Phe His Gln
    290                 295

<210> SEQ ID NO 69
<211> LENGTH: 294
<212> TYPE: PRT
<213> ORGANISM: Ricinus communis

<400> SEQUENCE: 69

Met Glu Asp Lys Asp Asp Gly Leu Gly Leu Gly Leu Ser Leu Ser Leu
1               5                   10                  15

Gly Gly Gln Glu Lys His Gln Asn Gln Pro Ser Leu Lys Leu Asn Leu
            20                  25                  30

Met Pro Phe Pro Ser Leu Phe Met Gln Asn Thr His His Ser Thr Ser
        35                  40                  45

Leu Asn Asp Leu Phe Gln Ser Ser Asp Arg Asn Ala Asp Thr Arg Ser
    50                  55                  60

Phe Gln Arg Gly Ile Asp Met Asn Arg Met Pro Leu Phe Ala Asp Cys
65                  70                  75                  80

Asp Asp Glu Asn Gly Val Ser Ser Pro Asn Ser Thr Ile Ser Ser Leu
                85                  90                  95

Ser Gly Lys Arg Ser Glu Arg Glu Gln Ile Gly Gly Glu Glu Met Glu
            100                 105                 110

Ala Glu Arg Ala Ser Cys Ser Arg Gly Gly Ser Asp Asp Glu Asp Gly
        115                 120                 125

Gly Ala Gly Gly Asp Asp Gly Ser Arg Lys Lys Leu Arg Leu Ser Lys
    130                 135                 140

Glu Gln Ser Leu Leu Leu Glu Glu Thr Phe Lys Glu His Asn Thr Leu
145                 150                 155                 160

Asn Pro Lys Gln Lys Leu Ala Leu Ala Lys Gln Leu Asn Leu Lys Pro
                165                 170                 175

Arg Gln Val Glu Val Trp Phe Gln Asn Arg Arg Ala Arg Thr Lys Ser
            180                 185                 190

Lys Gln Thr Glu Val Asp Cys Glu Tyr Leu Lys Arg Cys Cys Glu Asn
        195                 200                 205

Leu Thr Gln Glu Asn Arg Arg Leu Gln Lys Glu Val Gln Glu Leu Arg
    210                 215                 220

Ala Leu Lys Leu Ser Pro Gln Leu Tyr Met His Met Asn Pro Pro Thr
225                 230                 235                 240

Thr Leu Thr Met Cys Pro Ser Cys Glu Arg Val Ala Val Ser Ser Ser
                245                 250                 255

Ala Ala Pro Ser Arg Gln Pro Pro Asn Ser Gln Pro Gln Arg Pro Val
            260                 265                 270

Pro Val Lys Pro Trp Ala Ala Leu Pro Ile Gln His Arg Pro Phe Asp
        275                 280                 285

Thr Pro Ala Ser Arg Ser
    290

<210> SEQ ID NO 70
<211> LENGTH: 300
<212> TYPE: PRT
```

<213> ORGANISM: Nicotiana sylvestris

<400> SEQUENCE: 70

Met Leu Glu Asn Gln Asp Leu Gly Leu Ser Leu Ser Leu Ser Phe Pro
1               5                   10                  15

Glu Asn Lys Thr Thr Asn Ser Leu Gln Leu Asn Leu Phe Ser Ser Leu
            20                  25                  30

Ala Ser Ser Thr Ser Pro Ser Pro Ser Pro Ser Pro Phe Asn Leu Leu
        35                  40                  45

Gln Lys Thr Cys Trp Thr Asp Ser Phe Pro Ser Ser Asp Arg Asn Leu
    50                  55                  60

Glu Thr Cys Arg Thr Phe Leu Lys Gly Ile Asp Val Asn Arg Ile Pro
65                  70                  75                  80

Thr Ile Thr Asp Thr Glu Glu Glu Ala Gly Val Ser Ser Pro Asn
                85                  90                  95

Ser Thr Ile Ser Ser Leu Ser Gly Asn Lys Arg Asn Glu Arg Glu Ile
                100                 105                 110

Asn Cys Glu Glu Glu Leu Asp Cys Cys Arg Gly Ile Ser Asp Glu Glu
            115                 120                 125

Asp Gly Glu Thr Cys Arg Lys Lys Leu Arg Leu Thr Lys Asp Gln Ser
    130                 135                 140

Ala Val Leu Glu Glu Ser Phe Lys Glu His Asn Thr Leu Asn Pro Lys
145                 150                 155                 160

Gln Lys Gln Ala Leu Ala Lys Arg Leu Gly Leu Arg Pro Arg Gln Val
                165                 170                 175

Glu Val Trp Phe Gln Asn Arg Arg Ala Arg Thr Lys Leu Lys Gln Thr
            180                 185                 190

Glu Val Asp Cys Glu Phe Leu Lys Arg Cys Cys Glu Asn Leu Thr Glu
        195                 200                 205

Glu Asn Arg Arg Leu Gln Lys Glu Val Gln Glu Leu Arg Thr Leu Lys
    210                 215                 220

Leu Ser Pro Gln Phe Tyr Met Gln Met Thr Pro Pro Thr Thr Leu Thr
225                 230                 235                 240

Met Cys Pro Ser Cys Glu Gln Val Ala Gly Pro Pro Thr Pro Ser Pro
                245                 250                 255

Pro Gly Pro Thr Asn Val Asp Pro Arg Ala His Gln Met Gly Leu Ala
            260                 265                 270

Gln Gln Gln Arg Pro Met Pro Phe Asn Leu Trp Ala Thr Ser Pro Val
        275                 280                 285

Pro His Arg Pro Ile Ser Ala Leu Asn Pro Arg Ser
    290                 295                 300

<210> SEQ ID NO 71
<211> LENGTH: 275
<212> TYPE: PRT
<213> ORGANISM: Solanum tuberosum

<400> SEQUENCE: 71

Met Val Glu Lys Glu Asp Leu Gly Leu Ser Leu Ser Leu Ser Phe Pro
1               5                   10                  15

Asp Asn Asn Asn Lys Lys Asn Thr Gln Leu Asn Leu Ser Pro Phe Asn
            20                  25                  30

Leu Ile Gln Lys Thr Ser Trp Thr Asp Ser Leu Phe Pro Ser Ser Asp
        35                  40                  45

Arg Asn Ile Glu Thr Cys Arg Val Glu Thr Arg Thr Phe Leu Lys Gly

```
              50                  55                  60
Ile Asp Val Asn Arg Leu Pro Ala Thr Gly Glu Ala Asp Glu Glu Ala
 65                  70                  75                  80

Gly Val Ser Ser Pro Asn Ser Thr Ile Ser Val Ser Gly Asn Lys
                 85                  90                  95

Arg Thr Glu Arg Glu Ala Asn Asn Cys Asp Gln Glu Glu His Glu Met
            100                 105                 110

Glu Arg Gly Ser Asp Glu Glu Asp Gly Glu Thr Ser Arg Lys Lys Leu
                115                 120                 125

Arg Leu Ser Lys Asp Gln Ser Ala Ile Leu Glu Glu Ser Phe Lys Glu
            130                 135                 140

His Asn Thr Leu Asn Pro Lys Gln Lys Leu Ala Leu Ala Lys Arg Leu
145                 150                 155                 160

Gly Leu Arg Pro Arg Gln Val Glu Val Trp Phe Gln Asn Arg Arg Ala
                165                 170                 175

Arg Thr Lys Leu Lys Gln Thr Glu Val Asp Cys Glu Phe Leu Lys Arg
                180                 185                 190

Cys Cys Glu Asn Leu Thr Glu Glu Asn Arg Arg Leu Gln Lys Glu Val
            195                 200                 205

Gln Glu Leu Arg Ala Leu Lys Leu Ser Pro Gln Phe Tyr Met Gln Met
    210                 215                 220

Thr Pro Pro Thr Thr Leu Thr Met Cys Pro Ser Cys Glu Arg Val Ala
225                 230                 235                 240

Gly Pro Pro Ser Ser Ser Gly Pro Thr Thr Pro Met Gly Gln
                245                 250                 255

Ala Gln Pro Arg Pro Arg Pro Phe Asn Leu Trp Ala Asn Ala Leu His
            260                 265                 270

Pro Arg Ser
        275

<210> SEQ ID NO 72
<211> LENGTH: 323
<212> TYPE: PRT
<213> ORGANISM: Erythranthe guttata

<400> SEQUENCE: 72

Met Met Thr Ala Gly Lys Glu Asp Leu Gly Leu Ser Leu Ser Leu Thr
 1               5                  10                  15

Phe Pro Pro Glu Lys Lys Ala Val Ser Asn Ile Pro Ser Ser Leu His
                20                  25                  30

Leu Asn Leu Met Pro Ser Ser Pro Asn Phe Thr Ile Phe Asn
            35                  40                  45

Asn Asn Phe Asn Trp Thr Ser Thr Gln Gln Ala Ala Ala Phe Pro
 50                  55                  60

Phe Ser Asp Arg Ser Ser Glu Thr Cys Arg Val Glu Thr Thr Arg Ser
 65                  70                  75                  80

Phe Leu Lys Gly Ile Asp Val Asn Cys Leu Pro Ser Ala Ala Ala
                85                  90                  95

Glu Glu Glu Glu Glu Glu Gly Gly Gly Val Ser Ser Pro Asn Ser
            100                 105                 110

Thr Ile Ser Ser Val Ser Gly Lys Arg Ser Glu Arg Glu Asp Ala Thr
            115                 120                 125

Glu Glu His Asp Gly Glu Arg Ala Cys Ser Arg Gly Ile Ser Asp Glu
            130                 135                 140
```

```
Glu Asp Ala Glu Asn Ala Arg Lys Lys Leu Arg Leu Ser Lys Asp Gln
145                 150                 155                 160

Ser Ala Thr Leu Glu Glu Ser Phe Lys Glu His Asn Thr Leu Asn Pro
            165                 170                 175

Lys Gln Lys Met Ala Leu Ala Lys Arg Leu Gly Leu Arg Pro Arg Gln
        180                 185                 190

Val Glu Val Trp Phe Gln Asn Arg Arg Ala Arg Thr Lys Leu Lys Gln
    195                 200                 205

Thr Glu Val Asp Cys Glu Phe Leu Lys Arg Cys Cys Glu Asn Leu Thr
210                 215                 220

Glu Glu Asn Arg Arg Leu Gln Lys Glu Val Gln Glu Leu Arg Ala Leu
225                 230                 235                 240

Lys Leu Ser Pro Gln Phe Tyr Met Gln Met Thr Pro Pro Thr Thr Leu
            245                 250                 255

Thr Met Cys Pro Ser Cys Glu Arg Val Ala Val Pro Thr Met Gly Gly
        260                 265                 270

Pro Pro Ser Asn Gly Gly Arg Ala Pro Pro Ala Ser Ala Ala Ala
    275                 280                 285

Ala Val Gln Pro Arg Pro Ile Thr Phe Asn Pro Trp Ala Ala Val Met
290                 295                 300

Pro Ser Gln Gln Gln Gln Leu His Arg Pro Phe Asp Ala Ile Met
305                 310                 315                 320

His Ser Arg

<210> SEQ ID NO 73
<211> LENGTH: 302
<212> TYPE: PRT
<213> ORGANISM: Nelumbo nucifera

<400> SEQUENCE: 73

Met Met Val Glu Lys Glu Asp Leu Gly Leu Ser Leu Ser Leu Ser Thr
1               5                   10                  15

Ala Asp Ser Arg His Ser Leu Gln Leu Asn Leu Met Pro Ser Ser Val
            20                  25                  30

Ser Ser Ser Pro Ala Ser Pro Phe Val Ala Gln Lys Asn Thr Trp Asn
        35                  40                  45

Glu Ala Phe Ala Ser Ser Asp Arg Asn Ser Asp Met Phe Arg Gly Glu
    50                  55                  60

Thr Arg Thr Phe Leu Arg Gly Ile Asp Val Asn Arg Met Pro Ser Thr
65                  70                  75                  80

Val Asp Cys Glu Glu Ala Ala Val Ser Ser Pro Asn Ser Thr Ile
            85                  90                  95

Ser Ser Val Ser Gly Lys Arg Ser Glu Arg Asp Thr Asn Gly Glu Glu
        100                 105                 110

His Glu Ile Glu Arg Ala Cys Ser Arg Gly Ile Ser Asp Glu Glu Asp
    115                 120                 125

Gly Asp Met Ser Arg Lys Lys Leu Arg Leu Ser Lys Asp Gln Ser Ala
130                 135                 140

Val Leu Glu Glu Ser Phe Lys Glu His Asn Thr Leu Asn Pro Lys Gln
145                 150                 155                 160

Lys Leu Ala Leu Ala Lys Gln Leu Asn Leu Arg Pro Arg Gln Val Glu
            165                 170                 175

Val Trp Phe Gln Asn Arg Arg Ala Arg Thr Lys Leu Lys Gln Thr Glu
        180                 185                 190
```

```
Val Asp Cys Glu Phe Leu Lys Arg Cys Cys Glu Asn Leu Thr Glu Glu
        195                 200                 205

Asn Arg Arg Leu Gln Lys Glu Val Gln Glu Leu Arg Ala Leu Lys Leu
210                 215                 220

Ser Pro Gln Phe Tyr Met His Met Thr Pro Thr Thr Leu Thr Met
225                 230                 235                 240

Cys Pro Ser Cys Glu Arg Val Ala Val Ser Ser Ser Ser Ala Ala
                    245                 250                 255

Thr Ala Thr Val Ala Val Asp Ala Pro His His Pro Met Ala Met Ala
            260                 265                 270

Gly Pro His His His Arg Pro Ile Ala Ile Asn Pro Trp Ala Ala Ala
        275                 280                 285

Pro Ile His His Arg Pro Phe Asp Ala Pro Ala Pro Arg Ser
        290                 295                 300

<210> SEQ ID NO 74
<211> LENGTH: 361
<212> TYPE: PRT
<213> ORGANISM: Hordeum vulgare

<400> SEQUENCE: 74

Met Glu Met Thr Val Asn Gly Arg Asp Thr Glu His His Leu Gly Leu
1               5                   10                  15

Gly Leu Gly Leu Gly Leu Ser Leu Gly Met Ala Gly Thr Thr Ser Pro
            20                  25                  30

Val Glu Ala Ala Ala Pro Gln Arg Ala Leu Ala Ala Ala Ala Pro Val
        35                  40                  45

Thr Leu Gly Arg Gln Gln Gln Leu Gln Gln Ser Trp Asn Gly Ala Gly
50                  55                  60

Leu Phe Phe Pro Ala Pro Ser Gly Glu Gln Arg Ser His Ala Asp Asp
65                  70                  75                  80

Arg Arg Leu Ala Ala Leu Ala Cys His Glu Met Pro Phe Leu Arg Gly
                85                  90                  95

Ile Asp Val Asn Arg Ala Pro Ala Thr Gly Gly Ala Ser Glu Asp Glu
            100                 105                 110

Glu Pro Gly Ala Ser Ser Pro Asp Ser Thr Leu Ser Ser Leu Ser Gly
        115                 120                 125

Lys Arg Arg Ala Pro Thr Arg Ser Gly Gly Glu Gln Glu Arg Ala
130                 135                 140

Gly Ala Gly Ser Asp Asp Glu Asp Asp Ser Gly Ala Gly Gly Gly
145                 150                 155                 160

Ser Arg Lys Lys Leu Arg Leu Ser Lys Asp Gln Ser Ala Val Leu Glu
            165                 170                 175

Glu Ser Phe Lys Glu His Ser Thr Leu Asn Pro Val Ser Ala Leu Thr
        180                 185                 190

Lys Ser Thr Lys Val Lys Lys Thr Lys Ile Pro Ile Phe Leu Leu
            195                 200                 205

Pro Phe His Pro Ser Lys Phe Ala Leu Arg Thr Leu Met Asp Met Glu
        210                 215                 220

Gln Lys Gln Lys Ala Ala Leu Ala Arg Gln Leu Arg Leu Arg Pro Arg
225                 230                 235                 240

Gln Val Glu Val Trp Phe Gln Asn Arg Arg Ala Arg Thr Lys Leu Lys
                245                 250                 255

Gln Thr Glu Val Asp Cys Glu Ser Leu Lys Arg Cys Cys Glu Thr Leu
            260                 265                 270
```

```
Thr Glu Glu Asn Arg Arg Leu Gln Arg Glu Val Gln Glu Leu Arg Ala
            275                 280                 285

Leu Lys Leu Leu Ala Pro Pro Ala Pro His Leu Tyr Met Arg Ala Pro
        290                 295                 300

Pro Pro Ala Thr Leu Thr Met Cys Pro Ser Cys Glu Arg Val Ala Pro
305                 310                 315                 320

Ser Gly Lys Pro Ala Gly Asp Glu Ser Arg Ala Ala Thr Met Val Thr
                325                 330                 335

Arg Pro Val Pro Thr Gly Pro Trp Gly Pro Val Pro Val Leu Pro Val
            340                 345                 350

Phe Val Gly Arg Pro Ala Gln Arg Ser
        355                 360

<210> SEQ ID NO 75
<211> LENGTH: 247
<212> TYPE: PRT
<213> ORGANISM: Oryza rufipogon

<400> SEQUENCE: 75

Met Met Glu Arg Ala Glu Asp Leu Arg Leu Ser Leu Ser Leu Ser Ser
1               5                   10                  15

Pro Leu Ile Ala Pro Arg Thr His His Val Ala Met Leu Phe His Ala
            20                  25                  30

Pro Pro Glu Lys Arg Phe Leu Glu Met Pro Leu Leu Pro Ala Ala Lys
        35                  40                  45

Arg Ser Glu Val Val Ala Ala Glu Glu Glu Arg Ala Gly Leu Arg Gly
    50                  55                  60

Gly Gly Gly Ser Asp Glu Glu Asp Gly Cys Gly Ile Asp Gly Ser
65                  70                  75                  80

Arg Lys Lys Leu Arg Leu Ser Lys Asp Gln Ser Ala Val Leu Glu Asp
                85                  90                  95

Ser Phe Arg Glu His Pro Thr Leu Asn Pro Arg Gln Lys Ala Thr Leu
            100                 105                 110

Ala Gln Gln Leu Gly Leu Arg Pro Arg Gln Val Glu Val Trp Phe Gln
        115                 120                 125

Asn Arg Arg Ala Arg Thr Lys Leu Lys Gln Thr Glu Val Asp Cys Glu
    130                 135                 140

Phe Leu Lys Arg Cys Cys Glu Thr Leu Thr Glu Asn Arg Arg Leu
145                 150                 155                 160

Gln Lys Glu Val Gln Glu Leu Arg Ala Leu Lys Leu Val Ser Pro His
                165                 170                 175

Leu Tyr Met Asn Met Ser Pro Thr Thr Leu Thr Met Cys Pro Ser
            180                 185                 190

Cys Glu Arg Val Ser Asn Thr Asn Asn Ser Ser Ala Ala Ala Ala
        195                 200                 205

Ala Asp Arg Arg Gly Ile Arg Thr Thr Thr Ala Ala Gly Gly Gly Ser
    210                 215                 220

Val Val Asp Thr Ala Ala Asp Gly Gly Ile Leu Cys His Arg Pro Ile
225                 230                 235                 240

Ala Val Arg Pro Gln Gln Ser
                245

<210> SEQ ID NO 76
<211> LENGTH: 311
<212> TYPE: PRT
```

<213> ORGANISM: Oryza sativa

<400> SEQUENCE: 76

Met Glu Met Met Val His Gly Arg Arg Asp Glu Gln Tyr Gly Gly Leu
1               5                   10                  15

Arg Leu Gly Leu Gly Leu Gly Leu Ser Leu Gly Val Ala Gly Gly Ala
            20                  25                  30

Ala Asp Asp Glu Gln Pro Pro Arg Arg Gly Ala Ala Pro Pro Pro
        35                  40                  45

Gln Gln Gln Leu Cys Gly Trp Asn Gly Gly Gly Leu Phe Ser Ser Ser
    50                  55                  60

Ser Ser Asp His Arg Gly Arg Ser Ala Met Met Ala Cys His Asp Val
65                  70                  75                  80

Ile Glu Met Pro Phe Leu Arg Gly Ile Asp Val Asn Arg Ala Pro Ala
                85                  90                  95

Ala Glu Thr Thr Thr Thr Thr Ala Arg Gly Pro Ser Cys Ser Glu Glu
            100                 105                 110

Asp Glu Glu Pro Gly Ala Ser Ser Pro Asn Ser Thr Leu Ser Ser Leu
        115                 120                 125

Ser Gly Lys Arg Gly Ala Pro Ser Ala Ala Thr Ala Ala Ala Ala
    130                 135                 140

Ala Ser Asp Asp Glu Asp Ser Gly Gly Gly Ser Arg Lys Lys Leu Arg
145                 150                 155                 160

Leu Ser Lys Asp Gln Ala Ala Val Leu Glu Asp Thr Phe Lys Glu His
                165                 170                 175

Asn Thr Leu Asn Pro Lys Gln Lys Ala Leu Ala Arg Gln Leu Asn
            180                 185                 190

Leu Lys Pro Arg Gln Val Glu Val Trp Phe Gln Asn Arg Arg Ala Arg
        195                 200                 205

Thr Lys Leu Lys Gln Thr Glu Val Asp Cys Glu Leu Leu Lys Arg Cys
    210                 215                 220

Cys Glu Thr Leu Thr Asp Glu Asn Arg Arg Leu His Arg Glu Leu Gln
225                 230                 235                 240

Glu Leu Arg Ala Leu Lys Leu Ala Thr Ala Ala Ala Pro His His
                245                 250                 255

Leu Tyr Gly Ala Arg Val Pro Pro Thr Thr Leu Thr Met Cys Pro
            260                 265                 270

Ser Cys Glu Arg Val Ala Ser Ala Ala Thr Thr Thr Arg Asn Asn Ser
        275                 280                 285

Gly Ala Ala Pro Ala Arg Pro Val Pro Thr Arg Pro Trp Pro Pro Ala
    290                 295                 300

Ala Ala Gln Arg Ser Ser Ala
305                 310

<210> SEQ ID NO 77
<211> LENGTH: 366
<212> TYPE: PRT
<213> ORGANISM: Oryza nivara

<400> SEQUENCE: 77

Met Glu Leu Gly Leu Ser Leu Gly Glu Ala Met Ala Asp Ala Gly Arg
1               5                   10                  15

Glu Leu Val Leu Gly Leu Gly Met Gly Arg Arg Glu Glu Ala Ala Glu
            20                  25                  30

Ala Gly Arg Arg Asp His Glu Val Arg Arg Glu Leu Glu Phe Gly Ser

```
            35                  40                  45
Met Ser Ser Arg Cys Gly Gly Ser Pro Glu Pro Thr Val Arg Leu
 50                  55                  60

Thr Leu Leu Pro Met Val Pro Gly Leu Gly Leu Pro Trp Pro Pro
 65                  70                  75                  80

Pro Pro Pro Pro Ser Glu Ser Ser Glu Cys Gly Asp Gly His Leu
                 85                  90                  95

Glu Ala Ser Thr Arg Gly Phe Asp Val Asn Arg Pro Ser Ser Gly
            100                 105                 110

Gly Gly Gly Gly Gly Glu Glu Gln Asp Asp Val Ala Gly Ala Ala
        115                 120                 125

Leu Ser Ser Pro Asn Asn Ser Ala Gly Ser Phe Pro Met Asp Asp
130                 135                 140

Phe Ser Gly His Gly Leu Gly Gly Asn Asp Ala Ala Pro Gly Gly
145                 150                 155                 160

Gly Gly Asp Arg Ser Cys Ser Arg Ala Ser Asp Glu Asp Gly Gly
                165                 170                 175

Ser Ala Arg Lys Lys Leu Arg Leu Ser Lys Glu Gln Ser Ala Phe Leu
            180                 185                 190

Glu Glu Ser Phe Lys Glu His Ser Thr Leu Asn Pro Lys Gln Lys Leu
        195                 200                 205

Ala Leu Ala Lys Gln Leu Asn Leu Arg Pro Arg Gln Val Glu Val Trp
    210                 215                 220

Phe Gln Asn Arg Arg Ala Arg Thr Lys Leu Lys Gln Thr Glu Val Asp
225                 230                 235                 240

Cys Glu Tyr Leu Lys Arg Cys Cys Glu Thr Leu Thr Glu Glu Asn Arg
                245                 250                 255

Arg Leu Gln Lys Glu Leu Ala Glu Leu Arg Ala Leu Lys Thr Val His
            260                 265                 270

Pro Phe Tyr Met His Leu Pro Ala Thr Thr Leu Ser Met Cys Pro Ser
        275                 280                 285

Cys Glu Arg Val Ala Ser Asn Ser Ala Pro Ala Thr Ala Ser Ser Ala
    290                 295                 300

Ala Thr Ser Ser Thr Ala Ala Pro Pro Ala Ala Pro Ser Ser Gly Gly
305                 310                 315                 320

Ile Ala Ala Thr Ser Ser Ser Ser Ala Ala Ala Ala Ala Pro Asp
                325                 330                 335

His Arg Pro Ser Ser Phe Ala Ala Leu Phe Ser Ser Pro Arg Gly Phe
            340                 345                 350

Pro Leu Ser Val Ala Pro Gln Ala Gln Pro Pro Thr Ser Ser
        355                 360                 365

<210> SEQ ID NO 78
<211> LENGTH: 297
<212> TYPE: PRT
<213> ORGANISM: Oryza punctata

<400> SEQUENCE: 78

Met Glu Met Met Val His Gly Arg Arg Asp Glu Gln Tyr Gly Gln His
  1               5                  10                  15

His His Leu Gly Leu Gly Leu Gly Leu Gly Leu Ser Leu Gly
             20                  25                  30

Val Ala Gly Gly Ala Ala Asp Glu Thr Pro Pro Gln Gln Leu Cys
         35                  40                  45
```

Gly Trp Asn Gly Ala Ala Gly Leu Phe Pro Ser Asp Arg Arg Thr Met
 50                  55                  60

Met Ala Cys His Asp Val Glu Met Pro Leu Phe Leu Arg Gly Ile Asp
 65                  70                  75                  80

Val Asn Arg Thr Pro Val Ala Glu Thr Thr Thr Val Arg Arg Ala
                 85                  90                  95

Pro Ser Cys Ser Asp Glu Glu Pro Gly Ala Ser Ser Pro Asn
                100                 105                 110

Ser Thr Leu Ser Ser Leu Ser Gly Lys Arg Gly Ala Pro Ser Ala Ala
            115                 120                 125

Thr Ala Ala Gly Ser Asp Asp Glu Asp Ser Gly Gly Ser Arg
130                 135                 140

Lys Lys Leu Arg Leu Ser Lys Asp Gln Ala Ala Val Leu Glu Asp Thr
145                 150                 155                 160

Phe Lys Glu His Asn Thr Leu Asn Pro Lys Gln Lys Ala Ala Leu Ala
                165                 170                 175

Arg Gln Leu Asn Leu Lys Pro Arg Gln Val Glu Val Trp Phe Gln Asn
            180                 185                 190

Arg Arg Ala Arg Thr Lys Leu Lys Gln Thr Glu Val Asp Cys Glu Leu
            195                 200                 205

Leu Lys Arg Cys Cys Glu Thr Leu Thr Asp Glu Asn Arg Arg Leu His
210                 215                 220

Arg Glu Leu Gln Glu Leu Arg Ala Leu Lys Leu Ala Ala Ala Pro
225                 230                 235                 240

His His Leu Tyr Ala Arg Val Pro Pro Thr Thr Leu Thr Met Cys
                245                 250                 255

Pro Ser Cys Glu Arg Ile Ala Ser Thr Thr His Asn Ser Gly Ala Gly
            260                 265                 270

Lys Val Val Asp Ala Pro Ala Arg Pro Val Pro Thr Arg Pro Trp Pro
            275                 280                 285

Pro Ala Ala Ala Gln Arg Ser Ser Ala
            290                 295

<210> SEQ ID NO 79
<211> LENGTH: 310
<212> TYPE: PRT
<213> ORGANISM: Oryza glaberrima

<400> SEQUENCE: 79

Met Glu Met Met Val His Gly Arg Arg Asp Glu Gln Tyr Gly Gly Leu
 1               5                  10                  15

Gly Leu Gly Leu Gly Leu Gly Leu Ser Leu Gly Val Ala Gly Gly Ala
                 20                  25                  30

Ala Asp Asp Glu Gln Pro Pro Arg Gly Ala Ala Pro Pro
            35                  40                  45

Gln Gln Gln Leu Cys Gly Trp Asn Gly Gly Leu Phe Ser Ser Ser
 50                  55                  60

Ser Ser Asp His Arg Gly Arg Ser Ala Met Met Ala Cys His Asp Val
 65                  70                  75                  80

Ile Glu Met Pro Phe Leu Arg Gly Ile Asp Val Asn Arg Ala Pro Ala
                 85                  90                  95

Ala Glu Thr Thr Thr Thr Thr Ala Arg Gly Pro Ser Cys Ser Glu Glu
                100                 105                 110

Asp Glu Glu Pro Gly Ala Ser Ser Pro Asn Ser Thr Leu Ser Ser Leu
            115                 120                 125

Ser Gly Lys Arg Gly Ala Pro Ser Ala Ala Thr Ala Ala Ala Ala
            130                 135                 140

Ser Asp Asp Glu Asp Ser Gly Gly Gly Ser Arg Lys Lys Leu Arg Leu
145                 150                 155                 160

Ser Lys Asp Gln Ala Ala Val Leu Glu Asp Thr Phe Lys Glu His Asn
                165                 170                 175

Thr Leu Asn Pro Lys Gln Lys Ala Ala Leu Ala Arg Gln Leu Asn Leu
            180                 185                 190

Lys Pro Arg Gln Val Glu Val Trp Phe Gln Asn Arg Arg Ala Arg Thr
        195                 200                 205

Lys Leu Lys Gln Thr Glu Val Asp Cys Glu Leu Leu Lys Arg Cys Cys
    210                 215                 220

Glu Thr Leu Thr Asp Glu Asn Arg Arg Leu His Arg Glu Leu Gln Glu
225                 230                 235                 240

Leu Arg Ala Leu Lys Leu Ala Thr Ala Ala Ala Pro His His Leu
                245                 250                 255

Tyr Gly Ala Arg Val Pro Pro Thr Thr Leu Thr Met Cys Pro Ser
                260                 265                 270

Cys Glu Arg Val Ala Ser Ala Ala Thr Thr Thr Arg Asn Asn Ser Gly
                275                 280                 285

Ala Ala Pro Ala Arg Pro Val Pro Thr Arg Pro Trp Pro Pro Ala Ala
290                 295                 300

Ala Gln Arg Ser Ser Ala
305                 310

<210> SEQ ID NO 80
<211> LENGTH: 352
<212> TYPE: PRT
<213> ORGANISM: Setaria italica

<400> SEQUENCE: 80

Met Glu Met Ala Val Asn Ala Arg Asp Arg Glu Gln His Gly His Gly
1               5                   10                  15

Gly Leu Gly Leu Gly Leu Ser Leu Ser Leu Ser Ile Ala Thr Ala Ala
            20                  25                  30

Pro Pro Pro Gln Gln Gln Arg Ala Ile Ser Val Ala Pro Ile Ser Ser
        35                  40                  45

His Pro Ala Pro Pro Val Pro Pro Gln Pro Gln Trp Trp Asn Gly Gly
    50                  55                  60

Ala Gly Leu Phe Phe Ser Pro Ser Ser Gly Met Val Asp Arg Ser Met
65                  70                  75                  80

Glu Arg Lys Leu Gln Gln Gln Pro Ala Val Ala Ala Ala Cys His Gly
                85                  90                  95

His Glu Met Pro Phe Leu Arg Gly Ile Asp Val Asn Arg Ala Pro Ala
            100                 105                 110

Ala Gly Glu Ser Arg Arg Gly Cys Cys Ser Glu Asp Glu Pro Ala
        115                 120                 125

Ala Ser Ser Pro Asn Ser Thr Leu Ser Ser Leu Ser Gly Lys Arg Pro
    130                 135                 140

Ala Ala Thr Arg Ser Gly Asp Leu Glu Gly Asp His Thr Pro Arg Ala
145                 150                 155                 160

Gly Gly Ala Ser Asp Asp Glu Asp Ser Gly Ala Gly Gly Gly Ser Arg
                165                 170                 175

Lys Lys Leu Arg Leu Ser Lys Asp Gln Ala Ala Val Leu Glu Glu Ser

```
                    180                 185                 190
Phe Lys Glu His Asn Thr Leu Asn Pro Val Arg Thr Leu Pro Lys Gln
                    195                 200                 205

Lys Ala Ala Leu Ala Lys Gln Leu Asn Leu Lys Pro Arg Gln Val Glu
    210                 215                 220

Val Trp Phe Gln Asn Arg Ala Arg Thr Lys Leu Lys Gln Thr Glu
225                 230                 235                 240

Val Asp Cys Glu Phe Leu Lys Arg Cys Cys Glu Thr Leu Thr Glu Glu
                    245                 250                 255

Asn Arg Arg Leu Gln Arg Glu Val Ala Glu Leu Arg Ala Leu Lys Leu
            260                 265                 270

Val Ala Pro His Gln Tyr Ala Arg Met Pro Pro Thr Thr Leu Thr
        275                 280                 285

Met Cys Pro Ser Cys Glu Arg Leu Ala Thr Ala Asp Glu Ala Gly Arg
        290                 295                 300

Ala Ala Arg Pro Ala Ala Pro Thr Gly Pro Trp Gly Pro Val Pro Val
305                 310                 315                 320

Arg Pro Val Phe Val Asp Gly Met Ile Ile Asp Ala Asp Ala Arg Pro
                325                 330                 335

Glu His Pro Asn Ser Gly Gly Pro Val Val Glu Lys Lys Ser Trp
                340                 345                 350

<210> SEQ ID NO 81
<211> LENGTH: 346
<212> TYPE: PRT
<213> ORGANISM: Sorghum bicolor

<400> SEQUENCE: 81

Met Glu Met Ala Val Asn Ala Arg Asp Glu Glu Lys Lys Tyr Asp Gly
1               5                   10                  15

Asp Asp Asn His Leu Gly Leu Gly Leu Ser Leu Ser Leu Gly Ile Ala
                20                  25                  30

Thr Thr Ala Ala Thr Pro Val Glu Val Asp Pro Pro Arg Gln Gln
            35                  40                  45

Gln Gln Gln Arg Ala Ile Ser Val Ala Pro Ile Ser Ser Leu Pro Ala
    50                  55                  60

Pro Gln Trp Trp Asn Gly Pro Ala Gly Leu Phe Phe Ser Pro Ser Ser
65                  70                  75                  80

Gly Met Lys Met Asp Pro Ser Leu Glu Arg Lys His Gln His Gln Gln
                85                  90                  95

Gln Gln Gln Gln Ala Ala Ala Thr Ser Tyr Ser His Asp Met Pro
            100                 105                 110

Phe Leu Arg Gly Ile Asp Val Asn Arg Arg Ala Thr Ala Gly Glu Thr
        115                 120                 125

Arg Arg Gly Arg Ser Cys Ser Glu Asp Glu Pro Gly Ala Ser Ser
    130                 135                 140

Pro Asn Ser Thr Leu Ser Ser Leu Ser Gly Lys Arg Ala Ala Pro Ala
145                 150                 155                 160

Arg Ser Ser Gly Glu Val Asp Arg Glu Ala Asp Gly His Thr Pro Arg
                165                 170                 175

Ala Gly Gly Gly Gly Ser Asp Asp Glu Asp Ser Gly Ala Gly Gly Gly
            180                 185                 190

Ser Arg Lys Lys Leu Arg Leu Ser Lys Asp Gln Ala Ala Val Leu Glu
        195                 200                 205
```

-continued

```
Asp Ser Phe Lys Glu His Asn Thr Leu Asn Pro Lys Gln Lys Ala Ala
    210                 215                 220

Leu Ala Lys Gln Leu Asn Leu Lys Pro Arg Gln Val Glu Val Trp Phe
225                 230                 235                 240

Gln Asn Arg Arg Ala Arg Thr Lys Leu Lys Gln Thr Glu Val Asp Cys
                245                 250                 255

Glu Phe Leu Lys Arg Cys Cys Glu Thr Leu Thr Glu Glu Asn Arg Arg
            260                 265                 270

Leu Gln Arg Glu Val Ala Glu Leu Arg Ala Leu Lys Leu Val Ala Pro
        275                 280                 285

His His Tyr Ala Arg Met Pro Pro Thr Thr Leu Thr Met Cys Pro
    290                 295                 300

Ser Cys Glu Arg Leu Ala Ser Ala Pro Ala Asp Glu Ala Val Ala Gly
305                 310                 315                 320

Arg Thr Ala Ala Pro Thr Gly Pro Trp Gly Pro Leu Pro Val Arg Pro
                325                 330                 335

Val Phe Val Asp Gly Pro Ala Arg Ser
            340                 345

<210> SEQ ID NO 82
<211> LENGTH: 156
<212> TYPE: PRT
<213> ORGANISM: Triticum urartu

<400> SEQUENCE: 82

Met Asp Gly Ser Arg Lys Lys Leu Arg Leu Ser Lys Asp Gln Ser Ala
1               5                   10                  15

Val Leu Glu Asp Ser Phe Arg Glu His Pro Thr Leu Asn Pro Arg Gln
            20                  25                  30

Lys Ala Ala Leu Ala Gln Gln Leu Gly Leu Arg Ser Arg Gln Val Glu
        35                  40                  45

Val Trp Phe Gln Asn Arg Arg Ala Arg Thr Lys Leu Lys Gln Thr Glu
    50                  55                  60

Val Asp Cys Glu Phe Leu Lys Arg Cys Cys Glu Thr Leu Thr Glu Glu
65                  70                  75                  80

Asn Arg Arg Leu Gln Lys Glu Val Gln Glu Leu Arg Ala Leu Lys Leu
                85                  90                  95

Val Ser Pro His His Tyr Met His Met Ser Pro Pro Thr Thr Leu Thr
            100                 105                 110

Met Cys Pro Ser Cys Glu Arg Val Ser Asn Asn Asn Asn Asn Asn
        115                 120                 125

Asn Asn Ser Thr Thr Ala Asp Arg Arg Asn Gly Val Glu Gly Ala Ile
    130                 135                 140

Cys His Arg Pro Ile Ala Val Arg Pro Gln Gln Ser
145                 150                 155

<210> SEQ ID NO 83
<211> LENGTH: 319
<212> TYPE: PRT
<213> ORGANISM: Zea mays

<400> SEQUENCE: 83

Met Asp Ile Met Ala Leu Asn Ala Arg Asp Glu Glu Gln Tyr Gly Asn
1               5                   10                  15

Asn His Leu Gly Leu Gly Leu Ser Leu Ser Leu Gly Leu Gly Val Ala
            20                  25                  30
```

```
Thr Ala Ala Pro Val Glu Val Glu Pro Pro Pro Pro Arg Gln Gln
            35                  40                  45

Gln Gln Arg Ala Ile Ser Val Ala Pro Ile Thr Ser Leu Pro Ala Pro
 50                  55                  60

Gln Trp Trp Lys Trp Asn Gly Pro Gly Leu Phe Phe Gly Thr Thr Met
 65                  70                  75                  80

Asp Gln Gln Gln Pro Ala Ala Ala Arg His Gly His Glu Met Pro
                85                  90                  95

Phe Leu Arg Gly Val Asp Val Asn Arg Ala Pro Ala Gly Asp Thr Arg
                100                 105                 110

Arg Gly Ser Cys Ser Glu Asp Glu Glu Pro Gly Gly Ala Ser Ser
            115                 120                 125

Ser Pro Asn Ser Thr Leu Ser Ser Ser Leu Ser Gly Lys Arg Ala Ala
            130                 135                 140

Pro Ala Arg Ser Gly Gly Glu Val Ala Asp His Thr Pro Arg Ala Gly
145                 150                 155                 160

Gly Gly Ser Asp Asp Glu Asp Ser Gly Gly Gly Ser Arg Lys Lys Leu
                165                 170                 175

Arg Leu Ser Lys Asp Gln Ala Ala Val Leu Glu Glu Ser Phe Lys Glu
            180                 185                 190

His Asn Thr Leu Asn Pro Lys Gln Lys Ala Ala Leu Ala Lys Gln Leu
            195                 200                 205

Asn Leu Lys Pro Arg Gln Val Glu Val Trp Phe Gln Asn Arg Arg Ala
            210                 215                 220

Arg Thr Lys Leu Lys Gln Thr Glu Val Asp Cys Glu Phe Leu Lys Arg
225                 230                 235                 240

Cys Cys Glu Thr Leu Thr Glu Glu Asn Arg Arg Leu Gln Arg Glu Val
                245                 250                 255

Ala Glu Leu Arg Val Leu Lys Leu Val Ala Pro His His Tyr Ala Arg
            260                 265                 270

Met Pro Pro Pro Thr Thr Leu Thr Met Cys Pro Ser Cys Glu Arg Leu
            275                 280                 285

Ala Ser Ala Ser Ala Ser Ala Asp Gln Ala Gly Arg Ala Gly Pro Cys
            290                 295                 300

Trp Gly Pro Leu Pro Val Phe Val Asp Gly Pro Ala Arg Arg Pro
305                 310                 315

<210> SEQ ID NO 84
<211> LENGTH: 312
<212> TYPE: PRT
<213> ORGANISM: Musa acuminata

<400> SEQUENCE: 84

Met Ala Arg Val Ala Ala Asn Arg Pro Ala Val Ser Ser Ala Cys Ser
 1               5                  10                  15

His Val Pro Arg Gln Gly His Ala Arg Pro Arg Asp Gly Glu Leu Pro
            20                  25                  30

Ser Pro Phe Leu Pro Arg Glu Ile Lys Pro His Pro Arg Arg Pro Thr
            35                  40                  45

Trp His Ala Ser Ala Gln Met Asp Arg Arg Arg Asp Ser Thr Cys Arg
 50                  55                  60

Thr Asp Pro Arg Pro Arg Pro Leu His Arg Gly Ile Asp Val Asn Gln
65                  70                  75                  80

Glu Pro Pro Gly Ala Ala Glu Arg Asp Ser Glu Glu Asp Ala Gly Ala
                85                  90                  95
```

```
Ser Ser Pro Asn Ser Thr Leu Ser Ser Ala Ser Gly Lys Arg Ala Glu
            100                 105                 110

Arg Gly His His Leu Gly Val Asp Glu His Asp Thr Asp Arg Asp Cys
        115                 120                 125

Ser Arg Gly Ile Ser Asp Glu Glu Asp Gly Glu Gly Ser Arg Lys Lys
130                 135                 140

Leu Arg Leu Ser Lys Asp Gln Ala Ala Ile Leu Glu Glu Ser Phe Lys
145                 150                 155                 160

Glu His Asn Thr Leu Asn Pro Lys Gln Lys Leu Ala Leu Ala Lys Arg
                165                 170                 175

Leu Asn Leu Arg Pro Arg Gln Val Glu Val Trp Phe Gln Asn Arg Arg
                180                 185                 190

Ala Arg Thr Lys Leu Lys Gln Thr Glu Val Asp Cys Glu Phe Leu Lys
        195                 200                 205

Arg Cys Cys Glu Thr Leu Thr Glu Glu Asn Arg Arg Leu Gln Lys Glu
210                 215                 220

Val Gln Glu Leu Arg Ala Leu Lys Val Ser Pro Arg Leu Tyr Met His
225                 230                 235                 240

Met Thr Pro Pro Thr Thr Leu Ser Met Cys Pro Ser Cys Glu Arg Val
                245                 250                 255

Ser Asn Ala Ala Thr Thr Thr Thr Ala Ala Ser Thr Pro Thr Pro
                260                 265                 270

Glu Thr Asn Thr Pro His Pro Met Ser Gln His His Gln Phe Ile His
                275                 280                 285

His Arg Pro Phe Pro Ala Pro Trp Ala Pro Ile Pro Leu Arg Pro Cys
        290                 295                 300

Leu Lys Thr Pro Pro Gln Arg Ser
305                 310

<210> SEQ ID NO 85
<211> LENGTH: 266
<212> TYPE: PRT
<213> ORGANISM: Amborella trichopoda

<400> SEQUENCE: 85

Met Asn Arg Glu Asp Leu Asn Leu Ser Leu Ser Leu Arg Arg Val Gly
1               5                   10                  15

Asp Phe Glu Leu Asn Leu Leu Pro Arg Asn Cys Arg Asn Asp Ser Ser
                20                  25                  30

Ser Leu Asp Arg Ser Glu Thr Ala Arg Ser Ile Leu Lys Ser Phe Asp
        35                  40                  45

Val Asn Arg Ile Gln Ala Thr Ser Asp Arg Ile Pro Thr Thr Thr Asp
50                  55                  60

Ala Ile Arg Ser Glu Ile Ser Arg Ile Pro Ala Thr Pro Asn Met Ala
65                  70                  75                  80

Gly Phe Asp Val Asn Arg Ile Pro Val Ile Ser Glu Cys Glu Glu
                85                  90                  95

Ala Val Val Ser Ser Pro Met Ser Thr Val Ser Ser Leu Ser Met Ser
            100                 105                 110

Gly Gly Lys Arg Asp Glu Pro Glu Gly Glu Arg Ala Ser Ser Arg Gly
        115                 120                 125

Ser Ser Asp Glu Glu Asp Gly Gly Glu Ala Ala Arg Lys Lys Leu Arg
130                 135                 140

Leu Ser Lys Asp Gln Ser Ala Val Leu Glu Glu Ser Phe Lys Glu His
```

```
145                 150                 155                 160

Asn Thr Leu Asn Pro Lys Gln Lys Leu Thr Leu Ala Lys Gln Leu Asn
            165                 170                 175

Leu Arg Pro Arg Gln Val Glu Val Trp Phe Gln Asn Arg Arg Ala Arg
            180                 185                 190

Thr Lys Leu Lys Gln Thr Glu Val Asp Cys Glu Phe Leu Lys Arg Cys
            195                 200                 205

Cys Glu Asn Leu Thr Glu Glu Asn Arg Arg Leu Gln Lys Glu Val Met
            210                 215                 220

Glu Leu Arg Ser Leu Lys Gln Thr Pro His Phe Tyr Met His Val Pro
225                 230                 235                 240

Pro Ala Ala Leu Thr Met Cys Pro Ser Cys Glu Arg Val Ala Val Ser
                245                 250                 255

Glu Ser Gln Phe Arg Pro Gln Ile Arg Ser
            260                 265

<210> SEQ ID NO 86
<211> LENGTH: 291
<212> TYPE: PRT
<213> ORGANISM: Gossypium raimondii

<400> SEQUENCE: 86

Met Gly Asp Lys Asp Asp Gly Leu Gly Leu Ser Leu Ser Leu Gly Cys
1               5                   10                  15

Gly Gln Asn Gln Pro Ser Ser Lys Leu Asn Phe Met Phe Leu Ala Ser
                20                  25                  30

Asn Pro Leu Gln Asn Leu Gln Asn Lys Thr Trp Asn Arg Leu Cys
            35                  40                  45

Leu Ser Ser Asp Gly His Met Asp Thr Gly Ser Phe Leu Arg Gly Ile
50                  55                  60

Asp Val Asn Arg Ala Pro Ala Ala Thr Val Asp Cys Glu Glu Glu Gly
65                  70                  75                  80

Gly Gly Val Ser Ser Pro Asn Ser Thr Ile Ser Thr Ile Ser Gly Lys
                85                  90                  95

Lys Asn Glu Arg Asp His Val Ala Asp Glu Thr Glu Ala Glu Arg Asp
            100                 105                 110

Ser Cys Ser Arg Ala Ser Asp Asp Glu Asp Gly Gly Gly Asn Ala Gly
            115                 120                 125

Gly Gly Asp Ala Ser Arg Lys Lys Leu Arg Leu Ser Lys Glu Gln Ser
130                 135                 140

Met Val Leu Glu Glu Thr Phe Lys Glu His Ser Thr Leu Asn Pro Lys
145                 150                 155                 160

Gln Lys Leu Ala Leu Ala Lys Gln Leu Asn Leu Lys Pro Arg Gln Val
                165                 170                 175

Glu Val Trp Phe Gln Asn Arg Arg Ala Arg Thr Lys Leu Lys Gln Thr
            180                 185                 190

Glu Val Asp Cys Glu Tyr Leu Lys Arg Cys Cys Glu Asn Leu Thr Glu
            195                 200                 205

Glu Asn Arg Arg Leu His Lys Glu Val Gln Glu Leu Arg Ala Leu Lys
            210                 215                 220

Leu Ser Pro Gln Leu Tyr Met His Met Lys Pro Pro Thr Thr Leu Thr
225                 230                 235                 240

Met Cys Pro Ser Cys Glu Arg Val Ala Ala Pro Gly Ser Ser Ala Val
                245                 250                 255
```

```
Lys Arg Cys Gln Thr Ser Pro Asp Arg Gln Gln Pro Val Pro Val Asn
                260                 265                 270

Pro Trp Ala Ala Met Pro Ile Thr His Gln Pro Phe Asn Ala Pro Ala
        275                 280                 285

Ser Arg Ser
    290

<210> SEQ ID NO 87
<211> LENGTH: 297
<212> TYPE: PRT
<213> ORGANISM: Vitis vinifera

<400> SEQUENCE: 87

Met Met Val Asp Lys Glu Asp Leu Gly Leu Ser Leu Ser Leu Ser Phe
1               5                   10                  15

Pro Gln Asp Ala His Arg Pro Leu Gln Leu Asn Leu Met Pro Ser Leu
            20                  25                  30

Leu Pro Ala Ser Ser Ser Pro Ser Pro Ser Pro Phe Ala Leu Gln
        35                  40                  45

Lys Pro Ser Trp His Asp Ala Phe Pro Ser Ser Asp Arg Thr Ser Glu
    50                  55                  60

Thr Cys Arg Gly Asp Ala Arg Ser Phe Leu Arg Gly Ile Asp Val Asn
65                  70                  75                  80

Arg Leu Pro Ser Thr Ala Asp Cys Glu Glu Ala Gly Val Ser Ser
                85                  90                  95

Pro Asn Ser Thr Ile Ser Ser Val Ser Gly Lys Arg Ser Glu Arg Glu
            100                 105                 110

Ala Asn Gly Asp Glu His Glu Met Glu Arg Ala Cys Ser Arg Gly Ile
        115                 120                 125

Ser Asp Glu Glu Asp Gly Asp Thr Ser Arg Lys Lys Leu Arg Leu Ser
    130                 135                 140

Lys Asp Gln Ser Ala Ile Leu Glu Glu Asn Phe Lys Glu His Asn Thr
145                 150                 155                 160

Leu Asn Pro Lys Gln Lys Leu Ala Leu Ala Lys Gln Leu Asn Leu Arg
                165                 170                 175

Pro Arg Gln Val Glu Val Trp Phe Gln Asn Arg Arg Ala Arg Thr Lys
            180                 185                 190

Leu Lys Gln Thr Glu Val Asp Cys Glu Phe Leu Lys Arg Cys Cys Glu
        195                 200                 205

Asn Leu Thr Glu Glu Asn Arg Arg Leu Gln Lys Glu Val Asn Glu Leu
    210                 215                 220

Arg Ala Leu Lys Leu Ser Pro Gln Phe Tyr Met Gln Met Thr Pro Pro
225                 230                 235                 240

Thr Thr Leu Thr Met Cys Pro Ser Cys Glu Arg Val Ala Val Pro Pro
                245                 250                 255

Pro Ser Ser Glu Ala Arg Ser His Gln Met Ala Thr Thr His His Arg
            260                 265                 270

Pro Ile Pro Ile Asn Pro Trp Ala Thr Ala Pro Ile Pro His Arg
        275                 280                 285

Pro Phe Asp Ala Leu His Pro Arg Ser
    290                 295

<210> SEQ ID NO 88
<211> LENGTH: 310
<212> TYPE: PRT
<213> ORGANISM: Oryza glumipatula
```

<400> SEQUENCE: 88

```
Met Glu Met Met Val His Gly Arg Arg Asp Glu Gln Tyr Gly Gly Leu
1               5                   10                  15

Gly Leu Gly Leu Gly Leu Gly Leu Ser Leu Gly Val Ala Gly Gly Ala
            20                  25                  30

Ala Asp Asp Glu Gln Pro Pro Arg Arg Gly Ala Ala Pro Pro Pro
        35                  40                  45

Gln Gln Gln Leu Cys Gly Trp Asn Gly Gly Leu Phe Ser Ser Ser
    50                  55                  60

Ser Ser Asp His Arg Gly Arg Ser Ala Met Met Ala Cys His Asp Val
65                  70                  75                  80

Ile Glu Met Pro Phe Leu Arg Gly Ile Asp Val Asn Arg Ala Pro Ala
                85                  90                  95

Ala Glu Thr Thr Thr Thr Thr Ala Arg Gly Pro Ser Cys Arg Glu Glu
            100                 105                 110

Asp Glu Glu Pro Gly Ala Ser Ser Pro Asn Ser Thr Leu Ser Ser Leu
            115                 120                 125

Ser Gly Lys Arg Gly Ala Pro Ser Ala Ala Thr Ala Ala Ala Ala
    130                 135                 140

Ser Asp Asp Glu Asp Ser Gly Gly Ser Arg Lys Lys Leu Arg Leu
145                 150                 155                 160

Ser Lys Asp Gln Ala Ala Val Leu Glu Asp Thr Phe Lys Glu His Asn
                165                 170                 175

Thr Leu Asn Pro Lys Gln Lys Ala Ala Leu Ala Arg Gln Leu Asn Leu
            180                 185                 190

Lys Pro Arg Gln Val Glu Val Trp Phe Gln Asn Arg Arg Ala Arg Thr
        195                 200                 205

Lys Leu Lys Gln Thr Glu Val Asp Cys Glu Leu Leu Lys Arg Cys Cys
    210                 215                 220

Glu Thr Leu Thr Asp Glu Asn Arg Arg Leu His Arg Glu Leu Gln Glu
225                 230                 235                 240

Leu Arg Ala Leu Lys Leu Ala Thr Ala Ala Ala Pro His His Leu
                245                 250                 255

Tyr Gly Ala Arg Val Pro Pro Thr Thr Leu Thr Met Cys Pro Ser
            260                 265                 270

Cys Glu Arg Val Ala Ser Ala Ala Thr Thr Arg Asn Asn Ser Gly
    275                 280                 285

Ala Ala Pro Ala Arg Pro Val Pro Thr Arg Pro Trp Pro Pro Ala Ala
        290                 295                 300

Ala Gln Arg Ser Ser Ala
305                 310
```

<210> SEQ ID NO 89
<211> LENGTH: 323
<212> TYPE: PRT
<213> ORGANISM: Oryza meridionalis

<400> SEQUENCE: 89

```
Met Glu Met Met Val His Gly Arg Arg Asp Glu Gln Tyr Gly Gly Leu
1               5                   10                  15

Gly Leu Gly Leu Gly Leu Gly Leu Ser Leu Gly Val Ala Gly
            20                  25                  30

Gly Ala Ala Asp Asp Glu Gln Pro Pro Arg Arg Gly Pro Ala Pro Pro
        35                  40                  45
```

-continued

```
Pro Gln Gln Gln Leu Cys Gly Trp Asn Gly Gly Gly Gly
    50                  55                  60

Leu Phe Ser Ser Ser Ser Ser Asp His Arg Gly Arg Arg Ser Ala
 65                  70                  75                  80

Met Met Ala Cys His Asp Val Val Glu Met Pro Phe Leu Arg Gly Ile
                 85                  90                  95

Asp Val Asn Arg Ala Pro Ala Ala Glu Thr Thr Thr Thr Ala Arg
                100                 105                 110

Gly Pro Ser Cys Ser Glu Glu Asp Glu Glu Pro Gly Ala Ser Ser Pro
                115                 120                 125

Asn Ser Thr Leu Ser Ser Leu Ser Gly Lys Arg Gly Ala Pro Pro Ser
    130                 135                 140

Ala Ala Thr Ala Ala Ile Ala Ala Ala Ala Ser Asp Asp Glu Asp
145                 150                 155                 160

Ser Gly Gly Gly Ser Arg Lys Lys Leu Arg Leu Ser Lys Asp Gln
                165                 170                 175

Ala Ala Val Leu Glu Asp Thr Phe Lys Glu His Asn Thr Leu Asn Pro
                180                 185                 190

Lys Gln Lys Ala Ala Leu Ala Arg Gln Leu Asn Leu Lys Pro Arg Gln
                195                 200                 205

Val Glu Val Trp Phe Gln Asn Arg Arg Ala Arg Thr Lys Leu Lys Gln
                210                 215                 220

Thr Glu Val Asp Cys Glu Leu Leu Lys Arg Cys Cys Glu Thr Leu Thr
225                 230                 235                 240

Asp Glu Asn Arg Arg Leu His Arg Glu Leu Gln Glu Leu Arg Ala Leu
                245                 250                 255

Lys Leu Ala Ala Ala Ala Ala Ala Pro His His Leu Tyr Gly Ala
                260                 265                 270

Arg Val Pro Pro Pro Thr Thr Leu Thr Met Cys Pro Ser Cys Glu Arg
                275                 280                 285

Val Ala Ser Ala Ala Thr Thr Thr Arg Asn Asn Ser Gly Ala Ala Pro
                290                 295                 300

Ala Arg Pro Val Pro Thr Arg Pro Trp Pro Pro Ala Ala Ala Gln Arg
305                 310                 315                 320

Ser Ser Ala
```

<210> SEQ ID NO 90
<211> LENGTH: 305
<212> TYPE: PRT
<213> ORGANISM: Arabis alpina

<400> SEQUENCE: 90

```
Met Gly Glu Arg Asp Asp Gly Leu Gly Leu Ser Leu Ser Leu Gly Leu
  1               5                  10                  15

Gly Phe Asn Gln Lys Glu Gln Ser Pro Arg Leu Asn Pro Met Gln Phe
                 20                  25                  30

Gly Ser Tyr Ser Ser Ser Ser Ser His Met His Met Gln Ser Asn His
             35                  40                  45

Ile Asn His Ser Gln Lys Ile Gln Asn Ser Trp Thr His Met Phe Gln
    50                  55                  60

Ser Ser Glu Arg Asn Ser Asp Val Arg Ser Phe Leu Arg Gly Ile Asp
 65                  70                  75                  80

Val Asn Arg Ala Pro Ser Thr Val Val Asp Val Glu Glu Asp Ala
                 85                  90                  95
```

Gly Val Ser Ser Pro Asn Ser Thr Val Ser Ser Val Met Ser Gly Lys
            100                 105                 110

Arg Asn Glu Arg Val Ala Thr Val Gly Gly Gly Val Ile Glu
        115                 120                 125

Asp His Asp Val Glu Arg Ala Ser Ser Ser Leu Gly Gly Gly Ser Asp
130                 135                 140

Asp Glu Asp Gly Gly Asn Gly Asp Asp Gly Ser Arg Lys Lys Leu
145                 150                 155                 160

Arg Leu Ser Lys Glu Gln Ala Leu Val Leu Glu Glu Thr Phe Lys Glu
                165                 170                 175

His Ser Thr Leu Asn Pro Lys Gln Lys Met Ala Leu Ala Lys Gln Leu
            180                 185                 190

Asn Leu Arg Thr Arg Gln Val Glu Val Trp Phe Gln Asn Arg Arg Ala
        195                 200                 205

Arg Thr Lys Leu Lys Gln Thr Glu Val Asp Cys Glu Tyr Leu Lys Arg
210                 215                 220

Cys Cys Glu Asn Leu Thr Glu Glu Asn Arg Arg Leu Gln Lys Glu Val
225                 230                 235                 240

Ser Glu Leu Arg Ala Leu Lys Leu Ser Pro His Leu Tyr Met His Met
                245                 250                 255

Lys Pro Pro Thr Thr Leu Thr Met Cys Pro Ser Cys Glu Arg Val Ala
            260                 265                 270

Ala Thr Ser Ser Ser Ser Val Ala Pro Ala Met Asn Ser Ser
        275                 280                 285

Ser Pro Trp Ala Ala Ile Pro Leu Arg Gln Arg Pro Ala Ala Gly Ser
    290                 295                 300

His
305

<210> SEQ ID NO 91
<211> LENGTH: 315
<212> TYPE: PRT
<213> ORGANISM: Arabidopsis lyrata

<400> SEQUENCE: 91

Met Gly Glu Arg Asp Asp Gly Leu Gly Leu Ser Leu Ser Leu Ser Leu
1               5                   10                  15

Gly Phe Asn Gln Lys Asp Pro Ser Ser Arg Leu Asn Pro Met Pro Leu
            20                  25                  30

Ala Ser Tyr Ser Thr Ser Ser His Met His Met Gln Gln Ser Asn Tyr
        35                  40                  45

Ser His Pro Gln Lys Ile Gln Asn Thr Trp Ile Asn Met Phe His Ser
    50                  55                  60

Ser Glu Arg Asn Thr Asp Met Arg Ser Phe Leu Arg Gly Ile Asp Val
65                  70                  75                  80

Asn Arg Ala Pro Ser Thr Val Val Asp Val Glu Asp Gly Ala
                85                  90                  95

Gly Val Ser Ser Pro Asn Ser Thr Val Ser Ser Val Met Ser Gly Lys
            100                 105                 110

Arg Ser Glu Arg Glu Leu Met Thr Ala Ala Thr Ala Gly Gly Gly
        115                 120                 125

Gly Arg Val Glu Asp Asn Glu Met Glu Arg Ala Ser Cys Ser Leu Gly
    130                 135                 140

Gly Gly Ser Asp Asp Glu Asp Gly Ser Gly Asn Gly Asp Asp Gly Ser

```
145                 150                 155                 160
Arg Lys Lys Leu Arg Leu Ser Lys Glu Gln Ala Leu Val Leu Glu Glu
                165                 170                 175

Thr Phe Lys Glu His Ser Thr Leu Asn Pro Lys Gln Lys Met Ala Leu
            180                 185                 190

Ala Lys Gln Leu Asn Leu Arg Thr Arg Gln Val Glu Val Trp Phe Gln
        195                 200                 205

Asn Arg Arg Ala Arg Thr Lys Leu Lys Gln Thr Glu Val Asp Cys Glu
    210                 215                 220

Tyr Leu Lys Arg Cys Cys Glu Asn Leu Thr Asp Glu Asn Arg Arg Leu
225                 230                 235                 240

Gln Lys Glu Val Ser Glu Leu Arg Ala Leu Lys Leu Ser Pro His Leu
                245                 250                 255

Tyr Met His Met Lys Pro Pro Thr Thr Leu Thr Met Cys Pro Ser Cys
            260                 265                 270

Glu Arg Val Ala Val Thr Ser Ser Ser Ser Val Ala Pro Pro Val
        275                 280                 285

Met Thr Ser Ser Ser Pro Met Gly Pro Met Ser Pro Trp Ala Ala Ile
    290                 295                 300

Pro Leu Arg Gln Arg Pro Ala Ala Gly Ser His
305                 310                 315
```

<210> SEQ ID NO 92
<211> LENGTH: 339
<212> TYPE: PRT
<213> ORGANISM: Oryza barthii

<400> SEQUENCE: 92

```
Met Glu Met Met Val His Gly Arg Arg Asp Glu Gln Tyr Gly Gly Leu
1               5                   10                  15

Gly Leu Gly Leu Gly Leu Gly Leu Ser Leu Gly Val Ala Gly Gly Ala
            20                  25                  30

Ala Asp Asp Glu Gln Pro Pro Pro Arg Arg Gly Ala Ala Pro Pro Pro
        35                  40                  45

Gln Gln Gln Leu Cys Gly Trp Asn Gly Gly Leu Phe Ser Ser Ser
    50                  55                  60

Ser Ser Asp His Arg Gly Arg Ser Ala Met Met Ala Cys His Asp Val
65                  70                  75                  80

Ile Glu Met Pro Phe Leu Arg Gly Ile Asp Val Asn Arg Ala Pro Ala
                85                  90                  95

Ala Glu Thr Thr Thr Thr Ala Arg Gly Pro Ser Cys Ser Glu Glu
            100                 105                 110

Asp Glu Glu Pro Gly Ala Ser Ser Pro Asn Ser Thr Leu Ser Ser Leu
        115                 120                 125

Ser Gly Lys Arg Gly Ala Pro Ser Ala Ala Thr Ala Ala Ala Ala
    130                 135                 140

Ser Asp Asp Glu Asp Ser Gly Gly Gly Ser Arg Lys Lys Leu Arg Leu
145                 150                 155                 160

Ser Lys Asp Gln Ala Ala Val Leu Glu Asp Thr Phe Lys Glu His Asn
                165                 170                 175

Thr Leu Asn Pro Lys Gln Lys Ala Ala Leu Ala Arg Gln Leu Asn Leu
            180                 185                 190

Lys Pro Arg Gln Val Glu Val Trp Phe Gln Asn Arg Arg Ala Arg Thr
        195                 200                 205
```

```
Lys Leu Lys Gln Thr Glu Val Asp Cys Glu Leu Leu Lys Arg Cys Cys
    210                 215                 220

Glu Thr Leu Thr Asp Glu Asn Arg Arg Leu His Arg Glu Leu Gln Val
225                 230                 235                 240

Arg Arg Arg Ala His Val Leu Arg Ala Gln Val Pro Asp Val Leu Arg
                245                 250                 255

Gln Glu Arg Ala Ala Val Glu Val Glu Pro Arg Pro Glu Arg Arg Arg
            260                 265                 270

Asp Gly Leu Ala Thr Ala Ala Ala Pro His His Leu Tyr Gly Ala
                275                 280                 285

Arg Val Pro Pro Pro Thr Thr Leu Thr Met Cys Pro Ser Cys Glu Arg
    290                 295                 300

Val Ala Ser Ala Ala Thr Thr Thr Arg Asn Asn Ser Gly Ala Ala Pro
305                 310                 315                 320

Ala Arg Pro Val Pro Thr Arg Pro Trp Pro Ala Ala Ala Gln Arg
                325                 330                 335

Ser Ser Ala
```

<210> SEQ ID NO 93
<211> LENGTH: 287
<212> TYPE: PRT
<213> ORGANISM: Eucalyptus grandis

<400> SEQUENCE: 93

```
Met Met Val Glu Arg Glu Asp Leu Gly Leu Ser Leu Ser Leu Ser Phe
1               5                   10                  15

Ser Asp Ser Ser Arg Pro Ser Gln Leu Gly Ala Ser Pro Phe Gly Phe
            20                  25                  30

Asn Leu Tyr Lys Pro Ser His Arg Asp Cys Glu Thr Phe Ala Ser Leu
        35                  40                  45

Asp Arg Ile Ser Glu Ala Asp Ala Arg Pro Ser Leu Arg Gly Ile Asp
    50                  55                  60

Val Asn Arg Pro Pro Ser Ala Ala Asp Cys Glu Glu Gln Glu Glu
65                  70                  75                  80

Ala Gly Val Ser Ser Pro Asn Ser Thr Ile Ser Ser Val Ser Gly Lys
                85                  90                  95

Arg Gly Glu Arg Glu Met Val Ser Gly Gly Glu Asp Asn Glu Ala Glu
            100                 105                 110

Arg Asp Cys Ser Arg Gly Gly Ser Asp Glu Leu Asp Gly Glu Asn Ser
        115                 120                 125

Arg Lys Lys Leu Arg Leu Ser Lys Asp Gln Ser Ala Val Leu Glu Glu
    130                 135                 140

Ser Phe Arg Glu His Asn Thr Leu Asn Pro Lys Gln Lys Leu Ala Leu
145                 150                 155                 160

Ala Lys Gln Leu Gly Leu Arg Pro Arg Gln Val Glu Val Trp Phe Gln
                165                 170                 175

Asn Arg Arg Ala Arg Thr Lys Leu Lys Gln Thr Glu Ile Asp Cys Glu
            180                 185                 190

Phe Leu Lys Arg Cys Cys Glu Asn Leu Thr Glu Glu Asn Arg Arg Leu
        195                 200                 205

Gln Lys Glu Val Gln Glu Leu Arg Ala Leu Lys Leu Ser Pro Gln Phe
    210                 215                 220

Tyr Met His Met Pro Pro Pro Thr Thr Leu Thr Val Cys Pro Asn Cys
225                 230                 235                 240
```

```
Glu Arg Val Gly Ala Ala Pro Pro Leu Pro Ser Ala Gly Gly Gly
                245                 250                 255

Gly Arg Pro Ala His His Arg Glu Pro Val Pro Met Ile Pro Trp Ala
            260                 265                 270

Ala Arg Pro Gly Pro Val Ser His Gly Ala Leu Arg Pro Arg Thr
        275                 280                 285
```

<210> SEQ ID NO 94
<211> LENGTH: 313
<212> TYPE: PRT
<213> ORGANISM: Eutrema salsugineum

<400> SEQUENCE: 94

```
Met Gly Glu Arg Asp Asp Gly Leu Gly Leu Ser Leu Ser Leu Ser Leu
1               5                   10                  15

Gly Ser Asn Gln Asn Glu Ser Ser Arg Phe Asn Pro Met Pro Leu
            20                  25                  30

Ala Ser Phe Pro Ser Ser Ser His Met His Met Gln Asn His Tyr Ser
        35                  40                  45

His Pro Gln Lys Ile Gln Asn Asn Trp Ile Gln Met Phe Gln Ser Ser
    50                  55                  60

Glu Arg Asn Ser Asp Val Arg Ser Phe Leu Arg Gly Ile Asp Val Asn
65                  70                  75                  80

Arg Ala Pro Ser Thr Val Val Asp Val Glu Glu Asp Ala Gly Val
                85                  90                  95

Ser Ser Pro Asn Ser Thr Val Ser Ser Val Met Ser Gly Lys Arg Ser
            100                 105                 110

Glu Arg Glu Leu Met Ala Ala Ala Ala Gly Gly Val Arg Val Ile
        115                 120                 125

Glu Asp Asn Glu Ala Glu Arg Ala Ser Cys Ser Leu Gly Gly Gly Gly
    130                 135                 140

Ser Asp Asp Asp Asp Gly Gly Gly Asn Gly Asp Asp Gly Ser Arg Lys
145                 150                 155                 160

Lys Leu Arg Leu Ser Lys Glu Gln Ala Leu Val Leu Glu Glu Thr Phe
                165                 170                 175

Lys Glu His Ser Thr Leu Asn Pro Lys Gln Lys Met Ala Leu Ala Lys
            180                 185                 190

Gln Leu Asn Leu Arg Thr Arg Gln Val Glu Val Trp Phe Gln Asn Arg
        195                 200                 205

Arg Ala Arg Thr Lys Leu Lys Gln Thr Glu Val Asp Cys Glu Tyr Leu
    210                 215                 220

Lys Arg Cys Cys Glu Asn Leu Thr Glu Glu Asn Arg Arg Leu Gln Lys
225                 230                 235                 240

Glu Val Ser Glu Leu Arg Ala Leu Lys Leu Ser Pro His Leu Tyr Met
                245                 250                 255

His Met Lys Pro Pro Thr Thr Leu Thr Met Cys Pro Ser Cys Glu Arg
            260                 265                 270

Val Ala Val Thr Ser Ser Ser Ser Val Ala Pro Pro Ala Met Thr
        275                 280                 285

Ser Ser Ser Pro Met Gly Pro Met Ser Pro Trp Ala Ala Ile Pro Leu
    290                 295                 300

Arg Gln Arg Pro Ala Ala Gly Ser His
305                 310
```

<210> SEQ ID NO 95

<211> LENGTH: 241
<212> TYPE: PRT
<213> ORGANISM: Leersia perrieri

<400> SEQUENCE: 95

Met Met Glu Arg Ala Glu Asp Leu Arg Leu Ser Leu Ser Leu Ser Ser
1               5                   10                  15

Pro Leu Ala Pro Arg Thr His Val Ala Met Leu Phe His Ala Pro
            20                  25                  30

Pro Glu Lys Arg Phe Leu Glu Met Pro Leu Leu Pro Ala Ala Lys Arg
            35                  40                  45

Ser Glu Val Val Val Ala Ala Asp Glu Gly Met Arg Gly Gly Gly Gly
50                  55                  60

Gly Ser Asp Glu Glu Glu Gly Gly Cys Gly Ile Asp Gly Ser Arg Lys
65                  70                  75                  80

Lys Leu Arg Leu Ser Lys Asp Gln Ser Ala Val Leu Glu Asp Ser Phe
                85                  90                  95

Arg Glu His Pro Thr Leu Asn Pro Arg Gln Lys Ala Thr Leu Ala Gln
            100                 105                 110

Gln Leu Gly Leu Arg Pro Arg Gln Val Glu Val Trp Phe Gln Asn Arg
        115                 120                 125

Arg Ala Arg Thr Lys Leu Lys Gln Thr Glu Val Asp Cys Glu Phe Leu
130                 135                 140

Lys Arg Cys Cys Glu Thr Leu Thr Glu Glu Asn Arg Arg Leu Gln Lys
145                 150                 155                 160

Glu Val Gln Glu Leu Arg Ala Leu Lys Leu Val Ser Pro His Leu Tyr
                165                 170                 175

Met Asn Met Ser Pro Pro Thr Thr Leu Thr Met Cys Pro Ser Cys Glu
            180                 185                 190

Arg Val Ser Asn Thr Asn Asn Ser Asn Ser Asn Ser Ser Ser Ser Ala
        195                 200                 205

Ala Ala Ala Ala Ala Asp Arg Arg Gly Val Gly Ser Asp Thr Ala Ala
    210                 215                 220

Glu Gly Gly Ile Leu Cys His Arg Pro Ile Ala Val Arg Pro Gln Gln
225                 230                 235                 240

Ser

<210> SEQ ID NO 96
<211> LENGTH: 339
<212> TYPE: PRT
<213> ORGANISM: Capsella rubella

<400> SEQUENCE: 96

Lys Asn Leu Arg Thr Gln Arg Gln Ile Phe Phe Phe Leu Leu Ser Val
1               5                   10                  15

Phe Gly Leu Gly Lys Thr Lys Lys Met Gly Glu Arg Asp Asp Gly Leu
            20                  25                  30

Gly Leu Ser Leu Ser Leu Ser Leu Gly Phe Thr Pro Lys Glu Pro Ser
        35                  40                  45

Ser Arg Phe Asn Pro Met Pro Met Ala Ser Tyr Ser Ser Ser His
50                  55                  60

Met His Met Gln Gln Gln Ser Asn Tyr Ser His Pro His Lys Ile Gln
65                  70                  75                  80

Asn Ser Trp Ile Asn Met Phe Gln Ser Ser Glu Arg Asn Ser Asp Met
                85                  90                  95

Arg Ser Phe Leu Arg Gly Ile Asp Val Asn Arg Ala Pro Ser Thr Val
            100                 105                 110

Val Val Asp Val Glu Asp Ala Ala Gly Val Ser Ser Pro Asn Ser
        115                 120                 125

Thr Val Ser Ser Val Val Ser Gly Lys Arg Ser Glu Arg Glu Leu Met
    130                 135                 140

Ala Ala Ala Ala Ala Gly Gly Arg Ala Glu Asp Asn Glu Met
145                 150                 155                 160

Glu Arg Ala Ser Cys Ser Leu Gly Gly Ser Asp Asp Glu Asp Gly
                165                 170                 175

Ser Gly Asn Gly Asp Asp Gly Ser Arg Lys Lys Leu Arg Leu Ser Lys
            180                 185                 190

Glu Gln Ala Leu Val Leu Glu Glu Thr Phe Lys Glu His Ser Thr Leu
    195                 200                 205

Asn Pro Lys Gln Lys Met Ala Leu Ala Lys Gln Leu Asn Leu Gln Thr
210                 215                 220

Arg Gln Val Glu Val Trp Phe Gln Asn Arg Arg Ala Arg Thr Lys Leu
225                 230                 235                 240

Lys Gln Thr Glu Val Asp Cys Glu Tyr Leu Arg Arg Arg Cys Glu Asn
                245                 250                 255

Leu Thr Glu Glu Asn Arg Arg Leu Gln Lys Glu Val Ser Glu Leu Arg
            260                 265                 270

Ala Leu Lys Leu Ser Pro His Leu Tyr Met His Met Lys Pro Pro Thr
    275                 280                 285

Thr Leu Thr Met Cys Pro Ser Cys Glu Arg Val Ala Val Thr Ser Ser
    290                 295                 300

Ser Ser Ser Val Ala Pro Pro Val Met Thr Ser Ser Ser Pro Met Gly
305                 310                 315                 320

Gln Met Ser Pro Trp Ala Ala Ile Pro Leu Arg Gln Arg Pro Ala Ala
                325                 330                 335

Gly Ser His

<210> SEQ ID NO 97
<211> LENGTH: 299
<212> TYPE: PRT
<213> ORGANISM: Citrus clementina

<400> SEQUENCE: 97

Met Ala Glu Lys Asp Asp Leu Gly Leu Ser Leu Ser Leu Ser Phe Pro
1               5                   10                  15

Gln Asn His His Ser Leu Gln Leu Asn Leu Met Pro Ser Ser Ala Cys
                20                  25                  30

Ser Thr Ser Pro Ser Gly Phe Ser Leu Gln Lys Thr Pro Trp Asn Glu
            35                  40                  45

Ala Leu Phe Pro Pro Ser Asp Pro Asn Ser Glu Ser Cys Arg Ala Glu
    50                  55                  60

Thr Arg Ser Phe Leu Arg Gly Ile Asp Val Asn Arg Leu Pro Ser His
65                  70                  75                  80

Ala Asp Asn Glu Glu Glu Val Gly Val Ser Ser Pro Asn Ser Thr Ile
                85                  90                  95

Ser Ser Val Ser Gly Lys Arg Ser Glu Arg Glu Pro Asn Gly Asp Glu
            100                 105                 110

Leu Glu Met Glu Arg Ala Cys Ser Arg Gly Ile Ser Asp Asp Glu Asp
    115                 120                 125

Gly Asp Thr Ser Arg Lys Lys Leu Arg Leu Ser Lys Asp Gln Ser Ala
            130                 135                 140

Ile Leu Glu Glu Ser Phe Lys Glu His Asn Thr Leu Asn Pro Lys Gln
145                 150                 155                 160

Lys Leu Ala Leu Ala Lys Gln Leu Gly Leu Arg Pro Arg Gln Val Glu
                165                 170                 175

Val Trp Phe Gln Asn Arg Arg Ala Arg Thr Lys Leu Lys Gln Thr Glu
            180                 185                 190

Val Asp Cys Glu Phe Leu Lys Arg Cys Cys Glu Asn Leu Thr Glu Glu
                195                 200                 205

Asn Arg Arg Leu Gln Lys Glu Val Gln Glu Leu Arg Ala Leu Lys Leu
210                 215                 220

Ser Pro Gln Phe Tyr Met Gln Met Thr Pro Thr Thr Leu Thr Met
225                 230                 235                 240

Cys Pro Ser Cys Glu Arg Val Ala Val Pro Ser Ala Ala Ala Ser
                245                 250                 255

Ala Val Asp Pro Ala Arg Pro Thr His Gln Met Ala Ala Pro Asn His
                260                 265                 270

His Arg Pro Ile Pro Ile Asn Pro Trp Ala Pro Ala Ala Ile Pro
            275                 280                 285

His Gly Pro Phe Asp Ala Leu Arg Pro Arg Ser
290                 295

<210> SEQ ID NO 98
<211> LENGTH: 333
<212> TYPE: PRT
<213> ORGANISM: Morus notabilis

<400> SEQUENCE: 98

Met Gly Glu Lys Asp Asp Asp Gly Leu Gly Leu Gly Leu Ser Leu Ser
1                   5                   10                  15

Leu Gly Ile Phe Gly Gly Thr Thr Thr Thr Ala Thr Thr His Thr Thr
            20                  25                  30

Thr His Gln Pro Gly Ser Ser Ser Ser Ser Leu Lys Phe Asn Leu
            35                  40                  45

Met Gln Lys Pro Ser Ser Ser Met Gln Tyr Gln Gln Lys Thr Thr
50                  55                  60

Asn Thr Thr Ala Thr Pro Trp Asn Glu Ile Phe Gln Leu Ser Asp Arg
65                  70                  75                  80

Asn Ser Asp Gly Arg Ser Phe Leu Arg Gly Leu Asp Val Asn Leu Thr
                85                  90                  95

Pro Ser Phe Ala Ala Ala Ala Ala Asp Tyr Asp Glu Glu Asn Gly
                100                 105                 110

Val Ser Ser Pro Asn Ser Thr Ile Ser Ser Ile Ser Gly Lys Lys Ser
            115                 120                 125

Glu Arg Glu Ala Pro Gly Gly Glu Glu Ala Glu Gly Asp Arg Asp
            130                 135                 140

Ser Cys Ser Arg Gly Gly Gly Ser Asp Asp Glu Asp Gly Gly Asn
145                 150                 155                 160

Gly Gly Gly Asp Ala Ser Arg Lys Lys Leu Arg Leu Thr Lys Asp Gln
                165                 170                 175

Ser Leu Ile Leu Glu Glu Thr Phe Lys Glu His Asn Thr Leu Asn Pro
            180                 185                 190

Lys Gln Lys Leu Ala Leu Ala Lys Glu Leu Asn Leu Arg Pro Arg Gln
            195                 200                 205

| | | | | | | | | | | | | |
|---|---|---|---|---|---|---|---|---|---|---|---|---|
|Val|Glu|Val|Trp|Phe|Gln|Asn|Arg|Arg|Ala|Arg|Thr|Lys|Leu|Lys|Gln|
| |210| | | |215| | | |220| | | |
|Thr|Glu|Val|Asp|Cys|Glu|Tyr|Leu|Lys|Arg|Cys|Cys|Glu|Asn|Leu|Thr|
|225| | | |230| | | |235| | | |240|
|Glu|Glu|Asn|Arg|Arg|Leu|Gln|Lys|Glu|Val|Gln|Glu|Leu|Arg|Ala|Leu|
| | | |245| | | |250| | | |255|
|Lys|Leu|Ser|Pro|Gln|Leu|Tyr|Met|His|Met|Ser|Pro|Pro|Thr|Thr|Leu|
| | |260| | | |265| | | |270|
|Thr|Met|Cys|Pro|Ser|Cys|Glu|Arg|Val|Ala|Ala|Ser|Ser|Ser|Leu|Ser|
| |275| | | |280| | | |285|
|Ser|Thr|Ala|Ala|Ala|Ala|Pro|Asn|Gly|Ser|Asn|Arg|Gln|Pro|Ala|Val|
| |290| | | |295| | | |300|
|Pro|Ser|Ile|Pro|Arg|Pro|Val|Pro|Ile|Asn|Pro|Trp|Ala|Ala|Leu|Pro|
|305| | | |310| | | |315| | | |320|
|Ile|Pro|His|Arg|Pro|Leu|Asp|Thr|Pro|Ala|Ser|Arg|Ser|
| | | |325| | | |330|

<210> SEQ ID NO 99
<211> LENGTH: 957
<212> TYPE: DNA
<213> ORGANISM: Arabidopsis thaliana

<400> SEQUENCE: 99

```
atgggggaaa gagatgatgg gttgggtttg agtctaagct tgggaaatag tcaacaaaaa      60
gaaccatctc tgaggttgaa tcttatgccg ttgacaactt cttcttcttc ttcttcgttt     120
caacacatgc acaatcagaa taacaatagc catccccaga agattcataa catctcttgg     180
actcatctgt ttcaatcttc tgggattaaa cgtacaactg cagagagaaa ctccgacgcc     240
gggtcatttc taagaggttt caacgtgaac agagctcagt cttcggtggc ggtagtggac     300
ttggaagaag aagccgccgt cgtctcgtct ccaaacagcg ccgtttcgag tctgagtgga     360
aataaaaggg atcttgcggt ggcgagagga ggagatgaaa cgaggcggaa gagagcttct     420
tgctcacgcg aggggggaag cggtggtagc gacgatgaag acggcggaaa cggcgacgga     480
tcaaggaaga aactacggtt atcgaaggat caagctcttg ttctcgagga gactttaaa      540
gaacatagca ctcttaatcc gaagcaaaag ctggctctag caaaacagtt gaatctaagg     600
gcaagacaag ttgaagtgtg gtttcagaac cgtagggcaa ggacgaagct gaaacaaacg     660
gaggttgatt gtgagtattt aaagagatgt tgcgataatc tgaccgagga gaatcgacgg     720
ctgcagaaag aagtgtcgga gctgagggcg ttgaagttgt ctccacatct ctacatgcac     780
atgactcctc ctactactct caccatgtgc ccttcttgcg aacgtgtctc ctcctctgcc     840
gccactgtga ccgctgctcc ttccactact actactccta cggtggtggg gcggccaagt     900
ccacagcgat taactccttg gactgctatt tctctccagc aaaaatcagg tcgctag       957
```

<210> SEQ ID NO 100
<211> LENGTH: 891
<212> TYPE: DNA
<213> ORGANISM: Medicago truncatula

<400> SEQUENCE: 100

```
atgagtattg aaaaggaaga ttttggtttg agcctaagtt tgagctttcc tcaaaatcca      60
ccaaatcctc aataccttaa tcttatgtct tcttcaactc attcatattc tccttctact     120
ttcaatcctc aaaaaccttc ttggaatgat gtttttactt cttcagatcg ggattcggag     180
```

| | |
|---|---|
| acatgcagaa tcgaagaacg tcctttaatt ctccgaggaa tcgatgtgaa tcggttacct | 240 |
| tcaggtgctg attgtgaaga agaagcagga gtttcatcac caaacagcac cgtttcaagt | 300 |
| gtgagtggta aaagaagcga agagaagtt accggtgaag atcttgacat ggaaagagat | 360 |
| tgttcaagag gaatcagtga tgaagaagac gctgaaactt caaggaaaaa acttagactc | 420 |
| accaaagacc aatcaatcat tctcgaagag agtttcaaag aacacaacac tcttaatccc | 480 |
| aaacaaaaat tggcacttgc aaaacaattg ggacttcgtg ctagacaagt tgaagtttgg | 540 |
| tttcaaaatc gtagagcaag gactaagttg aagcaaacag aggtagattg tgaattttg | 600 |
| aaaagatgtt gtgagaatct aacggatgaa aatagacggt tgcaaaaaga agtgcaagag | 660 |
| ttaagagcat tgaaactttc cccacaattc tacatgcaaa tgacaccacc aacaacactt | 720 |
| accatgtgcc cctcttgtga gcgtgtcgct gttccatcat ctgccgttga tgctgccacg | 780 |
| cgtcgtcatc ctatggcttc aaatcaccct cgtacgtttt ccgtgggacc atgggccaca | 840 |
| gctgctccaa tccaacatag gacctttgat acactccgtc ctagatctta a | 891 |

<210> SEQ ID NO 101
<211> LENGTH: 957
<212> TYPE: DNA
<213> ORGANISM: Arabidopsis thaliana

<400> SEQUENCE: 101

| | |
|---|---|
| atgggggaaa gagatgatgg gttgggtttg agtctaagct tgggaaatag tcaacaaaaa | 60 |
| gaaccatctc tgaggttgaa tcttatgccg ttgacaactt cttcttcttc ttcttcgttt | 120 |
| caacacatgc acaatcagaa taacaatagc catccccaga agattcataa catctcttgg | 180 |
| actcatctgt ttcaatcttc tgggattaaa cgtacaactg cagagagaaa ctccgacgcc | 240 |
| gggtcatttc taagaggttt caacgtgaac agagctcagt cttcggtggc ggtagtggac | 300 |
| ttggaagaag aagccgccgt cgtctcgtct ccaaacagcg ccgtttcgag tctgagtgga | 360 |
| aataaaaggg atcttgcggt ggcgagagga ggagatgaaa acgaggcgga gagagcttct | 420 |
| tgctcacgcg gaggggaag cggtggtagc gacgatgaag acggcggaaa cggcgacgga | 480 |
| tcaaggaaga aactacggtt atcgaaggat caagctcttg ttctcgagga gacttttaaa | 540 |
| gaacatagca ctcttaatcc gaagcaaaag ctggctctag caaacagtt gaatctaagg | 600 |
| gcaagacaag ttgaagtgtg gtttcagaac cgtagggcaa ggacgaagct gaaacaaacg | 660 |
| gaggttgatt gtgagtattt aaagagatgt tgcgataatc tgaccgagga gaatcgacgg | 720 |
| ctgcagaaag aagtgtcgga gctgagggcg ttgaagttgt ctccacatct ctacatgcac | 780 |
| atgactcctc ctactactct caccatgtgc ccttcttgcg aacgtgtctc ctcctctgcc | 840 |
| gccactgtga ccgctgctcc ttccactact actactccta cggtggtggg gcggccaagt | 900 |
| ccacagcgat taactccttg gactgctatt tctctccagc aaaaatcagg tcgctag | 957 |

<210> SEQ ID NO 102
<211> LENGTH: 891
<212> TYPE: DNA
<213> ORGANISM: Medicago truncatula

<400> SEQUENCE: 102

| | |
|---|---|
| atgagtattg aaaaggaaga ttttggtttg agcctaagtt tgagctttcc tcaaaatcca | 60 |
| ccaaatcctc aataccttaa tcttatgtct tcttcaactc attcatattc tccttctact | 120 |
| ttcaatcctc aaaaaccttc ttggaatgat gttttttactt cttcagatcg ggattcggag | 180 |
| acatgcagaa tcgaagaacg tcctttaatt ctccgaggaa tcgatgtgaa tcggttacct | 240 |

| | |
|---|---|
| tcaggtgctg attgtgaaga agaagcagga gtttcatcac caaacagcac cgtttcaagt | 300 |
| gtgagtggta aaagaagcga aagagaagtt accggtgaag atcttgacat ggaaagagat | 360 |
| tgttcaagag gaatcagtga tgaagaagac gctgaaactt caaggaaaaa acttagactc | 420 |
| accaaagacc aatcaatcat tctcgaagag agtttcaaag aacacaacac tcttaatccc | 480 |
| aaacaaaaat tggcacttgc aaaacaattg ggacttcgtg ctagacaagt tgaagtttgg | 540 |
| tttcaaaatc gtagagcaag gactaagttg aagcaaacag aggtagattg tgaattttg | 600 |
| aaagatgtt gtgagaatct aacggatgaa atagacggt tgcaaaaaga agtgcaagag | 660 |
| ttaagagcat tgaaactttc cccacaattc tacatgcaaa tgacaccacc aacaacactt | 720 |
| accatgtgcc cctcttgtga gcgtgtcgct gttccatcat ctgccgttga tgctgccacg | 780 |
| cgtcgtcatc ctatggcttc aaatcaccct cgtacgtttt ccgtgggacc atgggccaca | 840 |
| gctgctccaa tccaacatag gacctttgat acactccgtc ctagatctta a | 891 |

<210> SEQ ID NO 103
<211> LENGTH: 744
<212> TYPE: DNA
<213> ORGANISM: Oryza sativa

<400> SEQUENCE: 103

| | |
|---|---|
| atgatggaga gggccgagga cctgcgcctg agcctcagtc tcagctcgcc gcttattgct | 60 |
| cctcgtactc accatgtcgc catgctgttc cacgctcctc cagagaaaag attcctggag | 120 |
| atgccgctgc tccctgctgc gaagcggagc gaggtcgtcg cggcagaaga ggagcgcgcg | 180 |
| ggcctgcgcg gcggcggcgg cagcgacgag gaggacggtg gctgcggcat cgacggctca | 240 |
| cgcaagaagc tccggctttc caaggaccag tccgccgtgc tcgaggacag cttccgggag | 300 |
| caccccaccc tcaaccccag gcagaaggca actttggcgc agcagctcgg gcttcggcct | 360 |
| cggcaggtcg aggtgtggtt tcagaacaga cgcgcaagga cgaagctgaa gcagacggag | 420 |
| gtggactgcg agttcctgaa cgctgctgc gagacgctca cggaggagaa ccggaggctg | 480 |
| cagaaggagg tgcaggagct gcgagcgctc aagctcgtct cgccgcacct ctacatgaac | 540 |
| atgtccccgc ccaccacgct caccatgtgc cctcctgcg agcgcgtctc caacaccaat | 600 |
| aacaactcca gcgccgccgc cgccgccgac cgccgcggca tcaggactac tactgccgca | 660 |
| ggcggcggca cgtcgtcga caccgccgcc gacggggca tcctctgcca ccgcccgatc | 720 |
| gccgtccggc cgcagcagtc atga | 744 |

<210> SEQ ID NO 104
<211> LENGTH: 744
<212> TYPE: DNA
<213> ORGANISM: Oryza sativa

<400> SEQUENCE: 104

| | |
|---|---|
| atgatggaga gggccgagga cctgcgcctg agcctcagtc tcagctcgcc gcttattgct | 60 |
| cctcgtactc accatgtcgc catgctgttc cacgctcctc cagagaaaag attcctggag | 120 |
| atgccgctgc tccctgctgc gaagcggagc gaggtcgtcg cggcagaaga ggagcgcgcg | 180 |
| ggcctgcgcg gcggcggcgg cagcgacgag gaggacggtg gctgcggcat cgacggctca | 240 |
| cgcaagaagc tccggctttc caaggaccag tccgccgtgc tcgaggacag cttccgggag | 300 |
| caccccaccc tcaaccccag gcagaaggca actttggcgc agcagctcgg gcttcggcct | 360 |
| cggcaggtcg aggtgtggtt tcagaacaga cgcgcaagga cgaagctgaa gcagacggag | 420 |

```
gtggactgcg agttcctgaa gcgctgctgc gagacgctca cggaggagaa ccggaggctg    480
cagaaggagg tgcaggagct gcgagcgctc aagctcgtct cgccgcacct ctacatgaac    540
atgtccccgc ccaccacgct caccatgtgc cctcctgcg agcgcgtctc caacaccaat    600
aacaactcca gcgccgccgc cgccgccgac cgccgcggca tcaggactac tactgccgca    660
ggcggcggca gcgtcgtcga caccgccgcc gacggggca tcctctgcca ccgcccgatc    720
gccgtccggc cgcagcagtc atga                                            744
```

<210> SEQ ID NO 105
<211> LENGTH: 744
<212> TYPE: DNA
<213> ORGANISM: Oryza sativa

<400> SEQUENCE: 105

```
atgatggaga gggccgagga cctgcgcctg agcctcagtc tcagctcgcc gcttattgct     60
cctcgtactc accatgtcgc catgctgttc cacgctcctc cagagaaaag attcctggag    120
atgccgctgc tccctgctgc gaagcggagc gaggtcgtcg cggcagaaga ggagcgcgcg    180
ggcctgcgcg gcggcggcgg cagcgacgag gaggacggtg gctgcggcat cgacggctca    240
cgcaagaagc tccggctttc caaggaccag tccgccgtgc tcgaggacag cttccgggag    300 cacccccaccc tcaaccccag gcagaaggca actttggcgc agcagctcgg gcttcggcct    360
cggcaggtcg aggtgtggtt tcagaacaga gcgcaagga cgaagctgaa gcagacggag    420
gtggactgcg agttcctgaa gcgctgctgc gagacgctca cggaggagaa ccggaggctg    480
cagaaggagg tgcaggagct gcgagcgctc aagctcgtct cgccgcacct ctacatgaac    540
atgtccccgc ccaccacgct caccatgtgc cctcctgcg agcgcgtctc caacaccaat    600
aacaactcca gcgccgccgc cgccgccgac cgccgcggca tcaggactac tactgccgca    660
ggcggcggca gcgtcgtcga caccgccgcc gacggggca tcctctgcca ccgcccgatc    720
gccgtccggc cgcagcagtc atga                                            744
```

<210> SEQ ID NO 106
<211> LENGTH: 957
<212> TYPE: DNA
<213> ORGANISM: Arabidopsis thaliana

<400> SEQUENCE: 106

```
atgggggaaa gagatgatgg gttgggtttg agtctaagct tggaaatag tcaacaaaaa     60 gaaccatctc tgaggttgaa tcttatgccg ttgacaactt cttcttcttc ttcttcgttt    120
caacacatgc acaatcagaa taacaatagc catccccaga agattcataa catctcttgg    180
actcatctgt ttcaatcttc tgggattaaa cgtacaactg cagagagaaa ctccgacgcc    240
gggtcatttc taagaggttt caacgtgaac agagctcagt cttcggtggc ggtagtggac    300
ttggaagaag aagccgccgt cgtctcgtct ccaaacagcg ccgtttcgag tctgagtgga    360
aataaaaggg atcttgcggt ggcgagagga ggagatgaaa cgaggcgga gagagcttct    420 tgctcacgcg gaggggaag cggtggtagc gacgatgaag acggcggaaa cggcgacgga    480
tcaaggaaga aactacggtt atcgaaggat caagctcttg ttctcgagga gacttttaaa    540
gaacatagca ctcttaatcc gaagcaaaag ctggctctag caaaacagtt gaatctaagg    600
gcaagacaag ttgaagtgtg gtttcagaac gtagggcaa ggacgaagct gaaacaaacg    660
gaggttgatt gtgagtattt aaagagatgt tgcgataatc tgaccgagga gaatcgacgg    720
ctgcagaaag aagtgtcgga gctgagggcg ttgaagttgt ctccacatct ctacatgcac    780
```

| | |
|---|---|
| atgactcctc ctactactct caccatgtgc ccttcttgcg aacgtgtctc ctcctctgcc | 840 |
| gccactgtga ccgctgctcc ttccactact actactccta cggtggtggg gcggccaagt | 900 |
| ccacagcgat taactccttg gactgctatt tctctccagc aaaaatcagg tcgctag | 957 |

<210> SEQ ID NO 107
<211> LENGTH: 957
<212> TYPE: DNA
<213> ORGANISM: Arabidopsis thaliana

<400> SEQUENCE: 107

| | |
|---|---|
| atgggggaaa gagatgatgg gttgggtttg agtctaagct tgggaaatag tcaacaaaaa | 60 |
| gaaccatctc tgaggttgaa tcttatgccg ttgacaactt cttcttcttc ttcttcgttt | 120 |
| caacacatgc acaatcagaa taacaatagc catccccaga agattcataa catctcttgg | 180 |
| actcatctgt ttcaatcttc tgggattaaa cgtacaactg cagagagaaa ctccgacgcc | 240 |
| gggtcatttc taagaggttt caacgtgaac agagctcagt cttcggtggc ggtagtggac | 300 |
| ttggaagaag aagccgccgt cgtctcgtct ccaaacagcg ccgtttcgag tctgagtgga | 360 |
| aataaaaggg atcttgcggt ggcgagagga ggagatgaaa acgaggcgga gagagcttct | 420 |
| tgctcacgcg agggggaag cggtggtagc gacgatgaag acggcggaaa cggcgacgga | 480 |
| tcaaggaaga aactacggtt atcgaaggat caagctcttg ttctcgagga gactttttaaa | 540 |
| gaacatagca ctcttaatcc gaagcaaaag ctggctctag caaaacagtt gaatctaagg | 600 |
| gcaagacaag ttgaagtgtg gtttcagaac cgtagggcaa ggacgaagct gaaacaaacg | 660 |
| gaggttgatt gtgagtattt aaagagatgt tgcgataatc tgaccgagga gaatcgacgg | 720 |
| ctgcagaaag aagtgtcgga gctgagggcg ttgaagttgt ctccacatct ctacatgcac | 780 |
| atgactcctc ctactactct caccatgtgc ccttcttgcg aacgtgtctc ctcctctgcc | 840 |
| gccactgtga ccgctgctcc ttccactact actactccta cggtggtggg gcggccaagt | 900 |
| ccacagcgat taactccttg gactgctatt tctctccagc aaaaatcagg tcgctag | 957 |

<210> SEQ ID NO 108
<211> LENGTH: 744
<212> TYPE: DNA
<213> ORGANISM: Oryza sativa

<400> SEQUENCE: 108

| | |
|---|---|
| atgatggaga gggccgagga cctgcgcctg agcctcagtc tcagctcgcc gcttattgct | 60 |
| cctcgtactc accatgtcgc catgctgttc cacgctcctc cagagaaaag attcctggag | 120 |
| atgccgctgc tccctgctgc gaagcggagc gaggtcgtcg cggcagaaga ggagcgcgcg | 180 |
| ggcctgcgcg gcggcggcgg cagcgacgag gaggacggtg gctgcggcat cgacggctca | 240 |
| cgcaagaagc tccggctttc caaggaccag tccgccgtgc tcgaggacag cttccgggag | 300 |
| cacccccaccc tcaaccccag gcagaaggca actttggcgc agcagctcgg gcttcggcct | 360 |
| cggcaggtcg aggtgtggtt tcagaacaga cgcgcaagga cgaagctgaa gcagacggag | 420 |
| gtggactgcg agttcctgaa gcgctgctgc gagacgctca cggaggagaa ccggaggctg | 480 |
| cagaaggagg tgcaggagct gcgagcgctc aagctcgtct cgccgcacct ctacatgaac | 540 |
| atgtccccgc ccaccacgct caccatgtgc ccctcctgcg agcgcgtctc caacaccaat | 600 |
| aacaactcca gcgccgccgc cgccgccgac gccgcggca tcaggactac tactgccgca | 660 |
| ggcggcggca gcgtcgtcga caccgccgcc gacggggggca tcctctgcca ccgcccgatc | 720 |

```
gccgtccggc cgcagcagtc atga                                      744
```

<210> SEQ ID NO 109
<211> LENGTH: 858
<212> TYPE: DNA
<213> ORGANISM: Vitis vinifera
<400> SEQUENCE: 109

```
atggtcgaca aggacgacga cttaggcttg agtctagccc taaaatgccc cgaagcgctg    60
cctcagaggc ctctcaatct cttcgtgcaa aagaaggccc tctgcagcga cgcgtttcat   120
gcatctgaga cgagagcgta cctgagaggc atcgatgtga atcgggcacc gacgatggcg   180
gattgcgagg atgttggggt gtcgtcgcca acagcacga tatcgagcat aagcgggaag    240
aggaatgaca gggaaaccaa cgaagaagag aatgagaacg agaatgagat tgagagttcg   300
gaggaagacg ccggaggcac cggggacacc gtcaggaaga agctccggtt gtcgaaagaa   360
cagtcggcga ttctcgaaga gactttcaaa gaacacaaca ctctcaaccc gaagcaaaag   420
ttggcgctag cgaagcaatt gaatctgagg ccgaggcagg tggaagtttg gtttcagaac   480
agaagggcaa gaactaagtt gaagcagacg gaggtggact gcgagtatct gaagaggtgc   540
tgtgagaatc taaccgagga gaacagacgg ctgcagaagg aggtgcagga gctgagaaca   600
ctgaagcttt caccacagct ctacatgcac atgaaccctc ccaccactct caccatgtgc   660
ccatcgtgtg agcgcgtggc cgtcgcgtcc gcctcatcct cagcaccctc tccatcaccc   720
gcctccaacc cacttgctgc agcccctcat ttcccattgg gcccgcatca acatcggccc   780
atgcccatag ccgggccatg ggccggagca gcatcaatgc ccacagacc gttcgatgcc    840
catggcacca ggtcgtga                                                858
```

<210> SEQ ID NO 110
<211> LENGTH: 885
<212> TYPE: DNA
<213> ORGANISM: Ricinus communis
<400> SEQUENCE: 110

```
atggaagaca aagatgatgg gctgggtttg ggtttgagtc tgagtttggg aggtcaggaa    60
aaacatcaaa atcagccatc tttgaagctc aatctcatgc cgtttccgtc gctctttatg   120
caaaatactc accacagtac ctccttgaat gacctttttcc aatcatctga tagaaacgct  180
gatacgaggt catttcaacg agggattgat atgaatcgga tgcccctctt cgccgattgc   240
gacgatgaaa acggtgtttc ttcgccgaac agtacgattt ccagtttaag tggaaagaga   300
agcgagaggg aacagattgg aggagaggag atggaggcag agagagcatc atgctctcgc   360
ggcggaagtg acgacgaaga cggtggcgcc ggcggcgatg acggttctag gaaaaaactg   420
aggctctcaa aggaacaatc tttattgctt gaagagactt ttaaggagca caatactctc   480
aatccaaagc agaagctggc tttagctaaa cagttgaatc tcaagccaag acaggtggag   540
gtgtggtttc agaaccggag ggcaaggact aagtcgaagc aaactgaagt tgattgtgag   600
tacttaaaaa ggtgttgtga gaatctgaca caagagaaca ggaggttgca gaggaggtg   660
caggagctta gagcattgaa gctctcccca cagctgtaca tgcacatgaa ccctcccacc    720
acactcacaa tgtgcccttc atgcgagcgt gttgcagtct cctcatcggc tgctcccagc   780
cgccaaccac cgaattccca acccaacga ccggtgcctg ttaagccttg ggcagcattg    840
cctatccagc atcgaccgtt tgatacgcct gcttctagat cgtag                  885
```

<210> SEQ ID NO 111
<211> LENGTH: 702
<212> TYPE: DNA
<213> ORGANISM: Sorghum bicolor

<400> SEQUENCE: 111

| | | | | | |
|---|---|---|---|---|---|
| atgatggaga | gggtcgagga | cttagggctc | agcctcagcc | tcagctcgtc | cctcgcgtct | 60 |
| cctcgcactc | accatgtcgc | caccatgctg | ctacgcgctc | caccagagaa | gaggttcctg | 120 |
| gagatgccgc | tgctgctccc | cgcgaagcga | agcgagctgg | ccacgggcga | ggagggcctg | 180 |
| cgaggcggcg | gcagcgacga | ggaggacggc | ggctgcggca | tcgacggctc | caggaagaag | 240 |
| ctccggctgt | ccaaggacca | gtcggccgtg | ctcgaggata | gcttccggga | gcacccaact | 300 |
| ctcaaccctc | ggcagaaggc | agccttggcg | cagcagctgg | gcctgcggcc | ccgccaggtg | 360 |
| gaggtgtggt | tccagaacag | gcgcgccagg | acgaagctga | gcagacggag | ggtggactgc | 420 |
| gagtacctga | agcgctgctg | cgagacgctg | acggaggaga | accggcggct | gcacaaggag | 480 |
| gtgcaggagc | tccgcgcgct | caagctcgtc | tcgccgcacc | tctacatgca | catgccccg | 540 |
| cccaccaccc | tcaccatgtg | ccctcctgc | gagcgcgtct | cctcctccaa | cgcgtccaac | 600 |
| gccaactccg | ccgccgctga | ccgcaaggcg | ggcgccggcg | tcgccgacgg | tggcgccatc | 660 |
| gtctgccacc | gcccgatcgc | cgtccggccg | cagcagtcat | ga | | 702 |

<210> SEQ ID NO 112
<211> LENGTH: 948
<212> TYPE: DNA
<213> ORGANISM: Arabidopsis lyrata subsp. lyrata

<400> SEQUENCE: 112

| | | | | | |
|---|---|---|---|---|---|
| atgggtgaaa | gagatgatgg | gttgggtctg | agtctaagct | tgggaaatag | tcaacaaaaa | 60 |
| gaaccatctc | tgaggttgaa | tcttatgccg | ttgacaactt | cttcttcttc | ttcgtttcaa | 120 |
| cacatgcaca | atcagaataa | taatagccat | ccccagaaga | ttcatcacaa | ctcttggact | 180 |
| catctgtttc | aatcttctgg | aattaaacgt | acaactgcag | agagaaactc | tgacgccggg | 240 |
| tcttttctaa | gaggtttcaa | cgtgagcaga | gctccgtctg | cggtggcggt | ggtggacttg | 300 |
| gaagaagaag | ccgccgttgt | ctcgtctccg | aacagcaccg | tctcgagtct | gagtgggaat | 360 |
| aagagggatc | ttgcggtggc | aagaggagga | gatgaaaacg | aggcggagag | agcttcttgc | 420 |
| tcacgtggag | ggggaagcgg | tggaagtgac | gatgaagagg | gcgaaacgg | cgacggatca | 480 |
| aggaagaaac | tccggttatc | gaaggaacaa | gctcttgttc | tcgaggagac | ttttaaagaa | 540 |
| catagcactc | ttaatccgaa | gcaaaagctg | gctctagcaa | aacagttgaa | tctaagggca | 600 |
| agacaagtgg | aagtgtggtt | tcagaaccga | agggcaagga | cgaagctgaa | acaaacggag | 660 |
| gttgattgtg | agtatttgaa | gagatgttgc | gatagtctga | cggaggagaa | tcgacggttg | 720 |
| cagaaagaag | tgtcggagct | gagagcgttg | aagttgtctc | cacatctcta | catgcatatg | 780 |
| actccgccta | ctactctcac | catgtgccct | tcttgcgaac | gtgtctcctc | ctctgccgcc | 840 |
| actgtgacgg | ctgctcctcc | tactactcct | acggtggtgg | ggcggccaag | tccacagcgg | 900 |
| ttaactccgt | ggactactat | ttctctccag | caaaaatcag | gtcgctag | | 948 |

<210> SEQ ID NO 113
<211> LENGTH: 960
<212> TYPE: DNA
<213> ORGANISM: Prunus persica

<400> SEQUENCE: 113

| | | |
|---|---|---|
| atgatggttg agagagatca agatttgggt tgagtctga gcttgagttt tcctcagacc | 60 |
| cacaaccacc acaacaacaa caacaacaac agcagcagca ccaccagcac ccttcagctc | 120 |
| aatctcatgc cttctttggc ccctacttct gcttcttctc cttctgggtt tcttcctcaa | 180 |
| aaaccctctt ggaatgaggc cttgatttct tcagatcgaa actccaactc cgaaacgttc | 240 |
| cgggtcgggc cccgatcgtt ccttcggggc atcgacgtga accggttgcc ttcaacgggc | 300 |
| gactgcgaag acgaggcggg cgtgtcgtcg cccaacagca cggtgtcgag cgtgagcggc | 360 |
| aagcggagcg agagagaggc caatggcgaa gatctcgaca tcgagactcg aggcatcagc | 420 |
| gatgaagaag acggcgagac ctctagaaag aagctcaggc tctccaagga ccagtccgcc | 480 |
| attctcgaag agagcttcaa ggagcacaac actctcaacc caaagcaaaa gttggcgttg | 540 |
| gctaaacagc ttggcctccg gcctagacaa gtggaagtct ggtttcagaa cagaagagca | 600 |
| aggactaagt tgaagcaaac ggaggtggac tgtgagttct tgaagaggtg ctgtgagaat | 660 |
| ctgacagagg agaacaggcg gttgcagaag gaggttcagg agctgagagc actgaaactt | 720 |
| tccccacagt tctacatgca aatgacccca cccacgacac tcaccatgtg ccctcgtgt | 780 |
| gagcgtgtcg cggtcccacc caactcctca tcctcaaccg tcgagccccg gccccacccc | 840 |
| cacccccacc cccaaatggg ttcggtccag acccggcccg tccccatcaa cccgtgggca | 900 |
| tccgccaccc caatccccca ccggccgctg ccgttcgaag ccttccacac ccggacgtaa | 960 |

<210> SEQ ID NO 114
<211> LENGTH: 471
<212> TYPE: DNA
<213> ORGANISM: Triticum urartu

<400> SEQUENCE: 114

| | | |
|---|---|---|
| atggatggct cccgcaagaa gctccggttg tccaaggacc agtccgccgt gctcgaggac | 60 |
| agcttccggg agcaccccac tctgaacccg aggcagaagg cagccttggc gcagcagctg | 120 |
| ggcctgcggt cgcggcaggt ggaggtgtgg ttccagaaca cgcgcaag acgaagctg | 180 |
| aagcagacgg aggtggactg cgagttcctg aagcgatgct gcgagacgct gacggaggag | 240 |
| aaccggcggt gcagaagga ggtgcaggag ctccgcgcgc tcaagctcgt ctccccgcac | 300 |
| cactacatgc acatgtcccc gcccaccacc ctcaccatgt gcccctcctg cgagcgcgtc | 360 |
| tccaacaaca caacaacaa caacaacaac tccaccaccg ccgaccgccg caacggtgtc | 420 |
| gagggcgcca tctgccaccg acccatcgcc gtccggccgc agcagtcatg a | 471 |

<210> SEQ ID NO 115
<211> LENGTH: 963
<212> TYPE: DNA
<213> ORGANISM: Capsella rubella

<400> SEQUENCE: 115

| | | |
|---|---|---|
| atgggtgaac gagatgatgg gttgggtctg agtctaagct tgggaaatag tagtcagcta | 60 |
| aaagaaccat ctctgaggtt gaatcttacg cctttcacag cttctacttc ttcctcgttt | 120 |
| cctcctcaca tgcacaatca gattattaat aataatagcc atccccaaaa gattcatcac | 180 |
| aactcttgga ctcatctgtt tcaatcttct ggaattaaac gtacaactgc agagagaaac | 240 |
| tccgacgccg atctttcct aagaagtttc gacgtgaaca gagctccgtc tcttcggtg | 300 |
| gcggtggtga acctggaaga agaagcagcc gtcgtctcgt ctccgaacag caccgtatcg | 360 |
| agtctgagtg ggaataagag ggatcttgcg gcggctagag aggagatga gcacgaggcg | 420 |
| gagagagctt cttgctcacg cggcggagga agtgatgacg aagactgcgg aaatggcgac | 480 |

```
gggtcaagaa agaagctacg gttgtcgaag gaacaagctc ttgttctcga ggagactttc    540
aaagtacaca gcactcttaa tccgaagcaa agctggttc  tagcaaaaca gttgaatcta    600
agggcaagac aagtggaagt gtggtttcag aaccgaaggg caaggacgaa gctgaaacaa    660
acggaggttg attgtgagta tttgaagaga tgttgtgata atttgacgga ggagaatcga    720
cgattgcaaa agaagtgtc  ggagctgaga gcgttgaagt tgtctccaca tctctacatg    780
cacatgactc ctcctactac tctcaccatg tgcccttctt gcgagcgtgt ctcctccacc    840
tcatccgcca atgcgagcat cgctcctcct ccacctcctg ctactagtgt ggttgggcgg    900
ccaagtccgc agcgatcgac tcattggact gctatttccc tccagcaacg atcaggccgc    960
tag                                                                  963

<210> SEQ ID NO 116
<211> LENGTH: 888
<212> TYPE: DNA
<213> ORGANISM: Theobroma cacao

<400> SEQUENCE: 116
atgggtgctg aaaaagatga tggtttgggg ttgagcttga gcttgggatg tgctcaaaat     60 caccctttctt tgaagttaaa tctcatgcct ttagcgtcac cccgcatgca aaatcttcag   120
cagaagaaca cttggaatga gctgtttcaa tcttctgatc gaaacctgga tacgagatca   180
tttcttcgag ggattgatgt gaaccgggca ccagcaacgg ttgattgcga ggaggaaggt   240
ggggtctcgt ctcccaacag caccatttct agcataagtg ggaagagaaa cgagagagac   300
cctgtgggtg atgaaactga ggccgagaga gcgtcttgct ctcgtgccag tgatgatgaa   360
gacggcggtg ctggtggcga tgcctcgagg aaaaagctta ggctctcaaa ggaacagtcc   420
ttgctgcttg aagaaacctt caaggagcat agcactctta atccgaagca aaagttggca   480
ctggcaaagc aattgaatct gaggcctagg caagtggagg tctggttcca gaacagaagg   540
gccaggacaa agttgaagca gacggaagtt gactgtgagt atctaaagag atgttgcgag   600
aatctgaccg aggagaatag gcggctgcag aaggaagtgc aagagcttag gcttttgaaa   660
ctctctccac agctctacat gcacatgaac cctcccacaa ccctcactat gtgcccttct   720
tgtgaacgtg tggcggtttc ttcctcctcc tcctccgcag cagctactgc ttcctccacc   780
ccaacttcga cggtcccaaa ccgtcaccac cggacgagtt ccgttagccc ttgggcagca   840
atgccaattg gtcatcgacc cttccatgcc cctgcatcta gatcataa                888

<210> SEQ ID NO 117
<211> LENGTH: 801
<212> TYPE: DNA
<213> ORGANISM: Amborella trichopoda

<400> SEQUENCE: 117
atgaatagag aagatctgaa tctgagttta agcttgagga gagtcggaga tttcgagttg     60
aatctgttac ccagaaattg cagaaatgat tcttccagtt tagatagatc agagacagct   120
agatcaatcc taaaatcctt tgatgtgaac cggattcagg cgacatcaga taggattccg   180
acaacaaccg atgcgattcg atcagaaatc agccggattc cggcaacacc gaacatggct   240
ggattcgatg taaataggat cccagtcatt tcagagtgcg aagaagaggc agtggtgtcg   300
tcgccaatga gcacagtttc gagcttgagc atgagtggcg ggaagagaga tgagccggag   360
ggggagagag cgagctcgag gggatctagt gacgaggagg atggtggtga ggctgcaagg   420
```

```
aagaaacttc gattgtcaaa ggatcaatct gcagttctag aggagagttt caaggaacac    480
aatactctta acccgaagca gaagctcact ttggcaaagc agttgaatct tcgccctcgt    540
caagtcgaag tctggtttca gaaccgaaga gcaaggacta agttaaagca aacagaagta    600
gattgtgaat ttttaaagag gtgttgtgaa aacctgactg aagagaacag gaggctccaa    660
aaagaagtga tggagctaag gtcccttaag caaacccctc acttctatat gcacgtgcct    720
cccgctgccc tgacgatgtg cccctcatgc gagcgtgtgg cagtgtcgga gtcccagttt    780
cgaccacaga ttcgatcatg a                                              801

<210> SEQ ID NO 118
<211> LENGTH: 972
<212> TYPE: DNA
<213> ORGANISM: Eutrema salsugineum

<400> SEQUENCE: 118
atgggtgaaa gagatgatgg gttgggtctg agtctaagct tggggtttag tcaacagaag     60
gaaccatgtc cgaggttgaa tctactacct ttgacaactt cttcttcttc atcttcgttt    120
catcacatgc acaatcacaa caataaccat ctccagaaga agattcaaca caactcttgg    180
cctcatctgt ttcaatcttc tgagaaaaat cccgacgccg gatcttttgg acgaggtttc    240
gacgtgaaca gagctccgtc tgcggcggcg gtggttgact tagaggaaga cggcaccggc    300
gtgtcgtcgc cgaacagcac cgtctcgagt gttagtggga acaagagaga tcttgcggcg    360
gcgagaggag gaggaggaga tgaaaacgag ggggagagag cttcttgctc cacggcggc    420 ggaagcggtg gaagcgacga tgaagacggc ggaaacggcg acggatcgag gaagaaactc    480
cgtttatcta aggaacaagc tgtggttctc gaagagactt caaagaaca taccactcta    540 aatccgaagc aaaagctggc cctagcgaga cagttgaatc taaggacaag gcaagtagaa    600
gtgtggttcc agaaccgaag ggcaaggacg aagctgaaac aaacggaggt tgattgtgag    660
tatttgaaga gatgttgcga taatctaacg gaggagaatc gacggttgca caaggaagta    720
tctgagctca gagcgttgaa gctgtctcca catctctaca tgcacatgac tcctccaact    780
actcttacaa tgtgtccttc ttgcgaacgt gtctcggctt cctcctcctc caccgccgtt    840
gctgctcctc cgtcgtcttc ctccgctgca tctggcggtg gtggatggat tcctacggtg    900
gtgggacggc caagtccaca acgaccaact ccttgcgcag ctatttctct ccagtcaaga    960
ttagctcact ag                                                        972

<210> SEQ ID NO 119
<211> LENGTH: 864
<212> TYPE: DNA
<213> ORGANISM: Citrus clementina

<400> SEQUENCE: 119
atgggcgaga aggatgacgg attgggtttg agtctaagct tgggatgtgc tgcaagaaat     60
gaaccttctt tgaggttgaa tcacatgcct ttgtcttctt cacaatccat gcaaaatcat    120
cataaaagaa gcccttggac tgagctgttc cattcgtccg atcgaaactc agatacaaga    180
tcattcctta gaggaataga tgtgaatcag gcaccaacag tggcagattg cgaggaagaa    240 aatgggggttt catcaccaaa cagcactgtt tctagcataa gtggaaagag gagtgagaga    300
gagcccattg gagatgagac tgaggctgaa agagcgtctt gctctcgcgg cagtgacgac    360
gaagacggtg gcgctggtga tgcatcaaga aagaagctga gattgtcgaa agaacagtct    420
ttgttgcttg aagagacctt caaagagcat agcactctca atcctaagca aaagttggct    480
```

```
ttggcaaagc agttgaatct taggcctaga caagtagaag tgtggtttca gaacagaagg      540
gcaaggacaa agttgaagca aacagaggtt gattgtgagt acttaaagag atgctgcgag      600
aatctaacgg aggagaacag gagattgcag aaggaagtgc aagagcttag atcattgaag      660
ctttctcctc aactctacat gaatatgaat cctcccacga cactcacaat gtgtccctcc      720
tgtgagcgtg tggctgtatc atcgtcgtcg tcgtcatcct ctgctgctgc caacggcacc      780
acccgtctcc ccattggtcc taaccatcaa cgactgactc cagtgagccc ttgggcagca      840
ttaccaatcc accaccggtc gtaa                                             864

<210> SEQ ID NO 120
<211> LENGTH: 918
<212> TYPE: DNA
<213> ORGANISM: Phaseolus vulgaris

<400> SEQUENCE: 120
atgggtgaaa aagatgatgg gttggggtta aggttgagtt tgagatgggg agaaaatgat       60
gataataaca tgaatcaaca acacccttc aacatgcaca agcctcctca acctgttcca      120
aaccaaagga cttcttttcaa taatttgttc catttccatg gagcttctca tgtaacaaat      180
cggaactccg agccgccacc gttttctctt ggaatagatg ttaacttgcc gccgccacca      240
acaccaacac cgtcggtggt accatgcgaa gaggacaatc ttgtgtcttc gcagaacagc      300
gcagtatcaa gcatcagcgg gaagaggagc gaaagagagg agaatgagag agggtcgtgt      360
tcgcatggaa gtgaagatga ggatggcgga gggttcggtg gtgaaggcga tggcgacatg      420
tcaaggaaga aactgaggtt gtcgaaggaa caggccttgg tgctggaaga aacattcaag      480
gaacacaaca ctctgaatcc gaaacaaaag caagctttgg caaagcagtt gaatctgagt      540
cctagacagg ttgaggtgtg gtttcaaaac agaagagcaa ggaccaagct gaagcagact      600
gaagtggact gtgaatactt aaagagatgt tgtgagaatc taactgagga aataggagg      660 ctacagaagg aagtgcaaga gctaagagca ttgaagttttt ctccacagct ctacatgcac      720
atgaatcctc caaccactct tacaatgtgt ccttcctgtg agcgtgttgc tgtctcatct      780
gcatcctcct cctcatcagc tgccatgcct tctgtgccac ctccagctaa tcacaaccca      840
ttaggcccta ccatccagcg gccagtgccg gtcaaccctt gggcagcaat gtcaattcaa      900
cgcccctgcc gtaattga                                                   918

<210> SEQ ID NO 121
<211> LENGTH: 1002
<212> TYPE: DNA
<213> ORGANISM: Morus notabilis

<400> SEQUENCE: 121
atgggtgaga aagatgatga tgggttgggg ttggggttga gtttgagctt gggaatattt       60
ggtgaaacta caacaacagc aacaactcac actactactc atcaaccggg ttcttcttct      120
tcttcttctc tcaagtttaa tctcatgcaa aagccttctt cttcttccat gcaatatcaa      180
caaaagacta ctaataccac cgccactcct tggaatgaaa tctttcagct ttctgatcgg      240
aactccgacg gcaggtcgtt cctccggggg ctcgacgtga acctgacacc ctcgtttgcg      300
gcggcggcgg cggcggatta cgatgaggaa aacggcgtgt cgtctccgaa cagcacgata      360
tcgagcataa gcgggaagaa gagcgagaga gaggcaccgg gaggagagga ggccgaggag      420
ggagacagag actcctgctc tcgcggcggc ggaggaagtg atgacgaaga cggcggaaat      480
```

```
ggcggcggcg acgcctccag aaagaagctc cgcctcacca aggaccagtc tctcatcctt    540
gaagaaactt tcaaggagca caacactctc aacccgaagc aaaagctggc gttggctaag    600
gaactgaacc tgcggccaag acaagtggag gtgtggtttc agaacaggag ggcaaggact    660
aaattgaagc agacagaagt ggactgtgag tatctaaaga ggtgctgtga gaatctgact    720
gaagagaaca ggaggctgca aaaggaagtg caagagctta gagcattaaa gttgtcccca    780
cagctctaca tgcacatgag ccctcccacc accctcacaa tgtgcccttc atgtgagcgt    840
gtggcggcct cgtcgtcgtt gtcctctact gctgctgccg ctccaaacgg ttcaaaccgg    900
cagcccgccg ttcccagcat cccacggcct gtgcccatta cccgtgggc cgcattgcca     960 atcccacacc ggccgttgga tacacctgcc tctaggtcct aa                       1002

<210> SEQ ID NO 122
<211> LENGTH: 972
<212> TYPE: DNA
<213> ORGANISM: Erythranthe guttata

<400> SEQUENCE: 122
atgatgacgg ccggaaaaga agatttgggg ctgagtttga gcctgacctt ccgccggag     60 aagaaggccg tttcgaatat tccgagctca ctgcacctca tctcatgcc ttcttcgcct     120 tctcccaatt tcaccatttt caataataat ttcaattgga cgtcgacgca acaagctgct    180
gctgctttcc cttctcaga tcggagctcg agacatgca gagtggagac gacgaggtct      240
tttctgaaag gaatcgatgt caactgcctc ccgtcggcgg cggcggcgga ggaggaagag    300
gaggaggaag gcggcggcgt ctcctccccc aacagcacga tctcaagcgt gagcgggaag    360
cggagcgaga gggaagacgc cacggaggag cacgacggcg agagagcttg ctcccgcggc    420
atcagcgacg aagaagacgc tgagaacgcc cggaaaaagc tccgcctctc caagaccag    480 tccgccactc tcgaagaaag cttcaaagaa cacaacacac tcaatcccaa gcaaaagatg    540
gctttggcta aaagattagg gctaaggcca agacaagttg aagtctggtt ccaaaacaga    600
agggctagga caaaactgaa gcaaacagag gttgattgcg agttcctaaa gagatgctgc    660
gaaaacctaa cagaagagaa cagaaggctg caaaagagg tccaagaact aagggcactt     720
aagctatccc cacagttcta catgcagatg accctccaa ctactctcac catgtgccct     780
tcttgcgaga gagtcgcggt gccgacaatg gggggcccac cgtcgaacgg cggccgagca    840
ccaccagctg cgtccgctgc cgcggcagtt cagccgcggc cgatcacatt caatccgtgg    900
gctgccgtca tgcctagtca gcagcagcag cagctgcacc ggccgttcga tgctattatg    960
cattcgagat ga                                                        972

<210> SEQ ID NO 123
<211> LENGTH: 864
<212> TYPE: DNA
<213> ORGANISM: Eucalyptus grandis

<400> SEQUENCE: 123
atgatggtgg agagggaaga tctgggcttg tctctgagct tgagcttctc tgacagcagt    60
cggccttccc agctcggcgc ctctccttc gggttcaacc tctacaagcc atctcaccgc     120
gactgcgaga ccttcgcttc attagatcgg atctcggagg cggatgcgcg gccgtccctg    180
cggggcatcg acgtgaaccg gccgccgccg tcggcggcgg actgcgagga gcaggaggag    240 gcggggggtgt cgtccccgaa cagcactatc tcgagcgtca gcgggaagag gggcgagagg    300
gagatggtca gcggcgggga ggacaacgag gcggagaggg actgcagccg cggaggcagc    360
```

```
gacgaggagg acggcgagaa ctcgaggaag aagctgaggc tgtccaagga tcagtcggcc    420
gtcttggagg agagcttccg agagcacaac actctgaatc ccaagcaaaa gctggcgttg    480
gctaagcagc taggcctgcg acctagacaa gtagaagtct ggtttcagaa ccgcagagca    540
cggaccaagt tgaagcagac ggagatagac tgcgagttcc tgaagaggtg ctgcgagaac    600
ctgacggagg agaaccggcg gctgcagaag gaggtccagg agctgcgcgc tctcaagctc    660
tcccctcagt tctacatgca catgccccct cccaccaccc ttaccgtctg ccccaactgc    720
gagcgcgtcg gggcggccgc accgccgctc ccatccgccg gcggcggcgg caggcccgcc    780
caccatcggg agccggtgcc catgatccca tgggccgcgc ggcccggccc ggtctcgcac    840
ggggctctcc ggcccaggac gtga                                           864
```

<210> SEQ ID NO 124
<211> LENGTH: 864
<212> TYPE: DNA
<213> ORGANISM: Citrus sinensis

<400> SEQUENCE: 124

```
atgggcgaga aggatgacgg attgggtttg agtctaagct tgggatgtgc tgcaagaaat     60
gaaccttctt tgaggttgaa tcacatgcct ttgtcttctt cacaatccat gcaaaatcat    120
cataaaagaa gcccttggac tgagctgttc cattcgtccg atcgaaactc agatacaaga    180
tcattcctta gaggaataga tgtgaatcag gcaccaacag tggcagattg cgaggaagaa    240
aatggggttt catcaccaaa cagcactgtt tctagcataa gtggaaagag gagtgagaga    300
gagcccattg agatgagac tgaggctgaa agagcgtctt gctctcgcgg cagtgacgac    360
gaagacggtg gcgctggtga tgcatcaaga aagaagctga gattgtcgaa agaacagtct    420
ttgttgcttg aagagacctt caaagagcat agcactctca atcctaagca aaagttggct    480
ttggcaaagc agttgaatct taggcctaga caagtagaag tgtggtttca gaacagaagg    540
gcaaggacaa agttgaagca aacagaggtt gattgtgagt acttaaagag atgctgcgag    600
aatctaacgg aggagaacag gagattgcag aaggaagtgc aagagcttag atcattgaag    660
ctttctcctc aactctacat gaatatgaat cctcccacga cactcacaat gtgtccctcc    720
tgtgagcgtg tggctgtatc atcgtcgtcg tcgtcatcct ctgctgctgc caacggcacc    780
acccgtctcc ccattggtcc taaccatcaa cgactgactc cagtgagccc ttgggcagca    840
ttaccaatcc accaccggtc gtaa                                           864
```

<210> SEQ ID NO 125
<211> LENGTH: 918
<212> TYPE: DNA
<213> ORGANISM: Arabis alpina

<400> SEQUENCE: 125

```
atgggtgaga gagatgatgg attggggtta agtttgagct tgggattagg gtttaatcaa     60
aaggagcaat ctccgaggtt aaatccaatg cagtttggtt cttattcttc ttcgtcttca    120
cacatgcata tgcagagcaa tcatattaac cattctcaaa agattcagaa tagttggact    180
cacatgtttc aatcttcaga gagaaactct gacgtgagat catttctccg ggggattgac    240
gtgaacagag caccatcaac ggtggtggtt gacgtggagg aagacgccgg agtgtcgtct    300
ccgaacagca ccgtttcgag cgtgatgagt gggaagagaa acgagcgagt tgccacggtg    360
gtcggaggag gaggagttat agaagatcac gacgtggaga gagcttcttc ctcgcttggt    420
```

```
ggtggtagtg atgatgaaga cggtggtgga aatggagacg acggttctag gaagaaacta    480
cggttgtcta aagaacaagc tttggttctt gaagaaactt ttaaagaaca tagcactctt    540
aatccgaagc aaaagatggc tttggctaaa caattgaatc tgaggacaag gcaagttgaa    600
gtgtggttcc aaaaccgaag ggcaaggacg aagctgaagc aaacgaagt ggattgtgaa     660
tatctaaaaa gatgttgtga aatctaacg gaagagaatc ggagattgca aaaggaagtg    720
agtgagctta gggcttttaaa gctttcacct catttataca tgcacatgaa acctcccact    780
acactcacaa tgtgtccttc gtgtgagcga gtcgctgcta catcgtcatc ttcctcggtg    840
gctcctcctg cgatgaattc gtcgtcgccg tgggctgcga ttcctctccg gcaacgacct    900
gctgctggtt ctcattag                                                  918

<210> SEQ ID NO 126
<211> LENGTH: 885
<212> TYPE: DNA
<213> ORGANISM: Cucumis sativus

<400> SEQUENCE: 126
atgggcggga gagatgatga cgtgggactc actttgagtt taggttttgg tgttacgact    60
cagtccactc acatgcaaag gccgtcgtcg atgcataatc accacctccg caagactcat    120
tggaacgagc tttttcaatt ttctgatcga acgccgatt cgaggtcgtt tcttagagga    180
atcgacgtga atcggttgcc gacgggcgtg gacggcgagg aagagaacgg cgtttcatct    240
ccgaacagta cgatttctag cattagtgga aagagaagcg agagagaagc ggctggagac    300
gaggcggagg cggaggctga gcggaggct gaagcggaag cggaagcgga agccgaaaga    360
gcctcgtgct cgcgagggag tgatgatgaa gacggcggag gcggggacgg tgacgcgtcg    420
agaaagaagc tgaggctatc gaaggaacag tcaatggttc ttgaagagac gttcaaagag    480
cacaatacgc tgaatcctaa gcaaaagctg gcacttgcaa agcagctgaa tctgacacca    540
agacaagtgg aggtgtggtt tcaaaacaga agggcaagga ccaaattgaa gcaaacagaa    600
gtggattgtg agtacttgaa gaggtgctgt gagaatctaa cagaggaaaa caggaggcta    660
cagaaggagg tgcaagagtt gagagcactc aagctttctc cacagcttta tatgcacatg    720
aatcctccta ccaccctcac catgtgccct caatgtgagc gtgtggcggt tcttcatct     780
tcttcgacct cagctgctac caccactcgc catcaagcag cagctggtgt gcagcgtccc    840
tctatggcca tcaacccgtg ggcagtgttg ccgattcaac gttga                    885

<210> SEQ ID NO 127
<211> LENGTH: 906
<212> TYPE: DNA
<213> ORGANISM: Gossypium raimondii

<400> SEQUENCE: 127
atgatggtgg gaaaagaaga tctgggtttg agtcttagtt tgggttttcc tcagaatcac    60
cactccttgc agctgaatct aaggccttct ttgcttcctt cctccgttga ttcttgctct    120
tcggtccctt ctgggtttac agcctttcac aaatcgtcgt ggaacgatgt ttctgctcct    180
tcagatccta acgcagaatc tttccgaggc gagactagat catttcttag aggaatcgac    240
gtgaacagat tgccatctac ggtcgactgc gaagaagaag ctggagtttc atctccgaac    300
agcacgatat cgagtgtgag tgggaaaagg agcgaagggg aaggcactaa tggagatgag    360
cttgatattg aaagagcttg ttctcgtggc atcagtgacg aggaagatgg tgacgcttcg    420
agaaaaaaac ttagactttc gaaggatcag tctgctattc ttgaagaaag ctttaaagaa    480
```

```
cacaacactc tgaacccaaa acaaaagatg gctttggcta agcagctggg attgcgaccc    540
agacaagttg aagtttggtt ccaaaacaga agggcgagga ccaagctgaa gcaaactgag    600
gttgactgtg agttcctaaa gagatgctgt gagaatctga cggaggaaaa caggcggttg    660
cagaaggaag ttcaggagct gagagcactg aaactttccc ctcagttcta catgcaaatg    720
accccaccta ccaccctcac catgtgccca tcgtgtgaga gagtgggtgc atcatccacc    780
gttgatccaa gatcccatca tcaactaccc caaaccacc acagggccat ccccatcaac    840
ccttgggctc cggctgctgc cccaatccct catggaccgt tcgatgctct tcggcctcaa    900
tcgtaa                                                                906
```

```
<210> SEQ ID NO 128
<211> LENGTH: 678
<212> TYPE: DNA
<213> ORGANISM: Brachypodium distachyon

<400> SEQUENCE: 128
atgatggaga gggccgagga cttggggctc agtctcagtc tcagctcatc acttgctcct     60
cgcactcacc atgtctccaa gctgttccat gcgccagaga ggagattcat ggagatgccg    120
ttgctccccg caaagaggag tagcgaggct gctggcgacg attcaagcct acttggcggc    180
agcgacgagg aggacggtgg ctgcggtgta cacggctccc gcaagaagct ccggttgtcc    240
aaagaccagt ccgccgtgct ggaggacagc ttccgggagc acccgactct aaacccgagg    300
cagaaggcag cgttggcgca gcagctcggg ctgcggtcgc ggcaggttga ggtgtggttc    360
cagaatagac gcgccaggac gaagctgaag cagacggagg tggactgcga gttcctgaag    420
cgctgctgcg agacgctgac cgaggagaac cggcggctgc agaaggaggt gcaggagctc    480
cgggcgctca gctcgtctc cccgcgccac tacatgcaca tgtccccgcc caccacgctc    540
accatgtgcc cctcctgcga gcgcgtctcc aacaagaaca caacaacaa taacaacaac    600 agctccgctg ccgccgaccg ccgcggcgac gtcgcaatct gccaccgccc gatcgccgtc    660
cggccgcagc agtcatga                                                  678
```

```
<210> SEQ ID NO 129
<211> LENGTH: 954
<212> TYPE: DNA
<213> ORGANISM: Glycine max

<400> SEQUENCE: 129
atgggtgaga aagatgatgg cttgggtttg gggttgagtt tgaagttagg atggggagaa     60
aataatgata caataataa tcaacaacaa caccctttca acgtgcacaa gcctcctcaa    120
tcggttccaa accaaagggt ttccgtcaat agcttgttcc atttcatga cgaaaatcat    180 gcaatgagga acacagatcg gagctccgag atgcggtcgt tcttccgcgg aatagacgtg    240
aatttgccac cgccccgcc ttcggcggct ctggcggcgt tcgatgacga aacggggtg     300 tcctcgccga acagcacgat atcgagcatc agcgggaagc ggagcgagag agagggaaac    360
ggagaggaga acgagagaac gtcgagttct cgcggcggcg gcggaagcga cgacgatgaa    420
ggcggcgcgt gtggtggaga cgccgacgcc gatgcgtcga ggaagaagct gaggttgtct    480
aaggaacagg ccttggtgct ggaagaaaca ttcaaggaac acaatactct gaacccgaag    540
caaaagcaag ctttggcaaa gcagttgaat ttgatgccta ggcaggtgga ggtgtggttt    600
caaaacagaa gagcaaggac caaattgaag cagactgaag tggattgtga atatttgaag    660
```

| | |
|---|---|
| aggtgctgtg agaatctaac tgaagagaat aggaggcttc aaaaggaagt gcaagagctc | 720 |
| agggcattga agttatcccc acatctttac atgcaaatga accctcccac cactctcaca | 780 |
| atgtgccctt catgtgagcg tgttgctgtc tcatccgcat cctcttcctc atcggccacc | 840 |
| atgccctctg ccctgcctcc agctaatctc aacccgtggg ccctaccat ccagcggcca | 900 |
| atgcccgtca acccttgggc agcaatgttg aatcagcacc gtggccggcc ataa | 954 |

<210> SEQ ID NO 130
<211> LENGTH: 960
<212> TYPE: DNA
<213> ORGANISM: Prunus persica

<400> SEQUENCE: 130

| | |
|---|---|
| atgatggttg agagagatca agatttgggt ttgagtctga gcttgagttt tcctcagacc | 60 |
| cacaaccacc acaacaacaa caacaacaac agcagcagca ccaccagcac ccttcagctc | 120 |
| aatctcatgc cttctttggc ccctacttct gcttcttctc cttctgggtt tcttcctcaa | 180 |
| aaaccctctt ggaatgaggc cttgatttct tcagatcgaa actccaactc cgaaacgttc | 240 |
| cgggtcgggc cccgatcgtt ccttcggggc atcgacgtga accggttgcc ttcaacgggc | 300 |
| gactgcgaag acgaggcggg cgtgtcgtcg cccaacagca cggtgtcgag cgtgagcggc | 360 |
| aagcggagcg agagagaggc caatggcgaa gatctcgaca tcgagactcg aggcatcagc | 420 |
| gatgaagaag acggcgagac ctctagaaag aagctcaggc tctccaagga ccagtccgcc | 480 |
| attctcgaag agagcttcaa ggagcacaac actctcaacc caaagcaaaa gttggcgttg | 540 |
| gctaaacagc ttggcctccg gcctagacaa gtggaagtct ggtttcagaa cagaagagca | 600 |
| aggactaagt tgaagcaaac ggaggtggac tgtgagttct tgaagaggtg ctgtgagaat | 660 |
| ctgacagagg agaacaggcg gttgcagaag gaggttcagg agctgagagc actgaaactt | 720 |
| tccccacagt tctacatgca aatgaccccca cccacgacac tcaccatgtg ccctcgtgt | 780 |
| gagcgtgtcg cggtcccacc caactcctca tcctcaaccg tcgagccccg gccccacccc | 840 |
| caccccaccc cccaaatggg ttcggtccag accggcccg tccccatcaa cccgtgggca | 900 |
| tccgccaccc caatccccca ccggccgctg ccgttcgaag ccttccacac ccggacgtaa | 960 |

<210> SEQ ID NO 131
<211> LENGTH: 897
<212> TYPE: DNA
<213> ORGANISM: Populus trichocarpa

<400> SEQUENCE: 131

| | |
|---|---|
| atgggtgata aaaatgatgg actgggcttg agtttgagct tgggattcga tgctacacaa | 60 |
| caaaatcatc aacagcagcc ttctttgaag ctaaatctca tgcccgtacc ttcacaaaac | 120 |
| aatcatagaa aaacttcctt gactgacctc tttcaatcat cagatagagc atgtggtacg | 180 |
| aggttttttc aacgaggaat tgacatgaac agggtgccag ctgcagtgac agattgtgat | 240 |
| gacgaaactg gggtttcttc accaaacagt acgctatcca gcttaagtgg taaaagaagc | 300 |
| gaaagagaac agattggaga agaaacagaa gcggagaggg cctcttgctc tcgtgacagt | 360 |
| gatgatgaag atggtgctgg tggtgatgct tctaggaaga agctgagact ctcaaaggaa | 420 |
| cagtctttag tgcttgaaga gactttcaag gaacataata ctcttaatcc caaggagaag | 480 |
| ctggccttgg caaagcagtt gaatctcagg cctaggcaag tggaggtgtg gtttcagaac | 540 |
| cgaagagcaa ggactaagtt gaagcaaact gaagtcgatt gcgagtacct aaagaggtgc | 600 |
| tgtgaaaatc taacagagga gaacaggagg ttacagaagg aggtgcaaga gcttagagca | 660 |

```
ctgaaacttt cccctcagct ctacatgcac atgaaccctc ccaccaccct caccatgtgc    720
ccttcatgcg agcgagttgc tgtctcgtca gcctcatcat cttctgctgc tgccgcgtcc    780
tctgctcttg ctccaactgc ctcaacccgc caaccacaac gacccgtgcc cattaaccct    840
tgggcaacaa tgcccgtcca ccaacgaact tttgatgctc ctgcttccag gtcatga      897
```

<210> SEQ ID NO 132
<211> LENGTH: 684
<212> TYPE: DNA
<213> ORGANISM: Zea mays

<400> SEQUENCE: 132

```
atgatggaga gggtcgagga cttagggctc agcctcagcc tcagctcgtc cctcgcgtct     60
cctcgaactc accatgtcgc caccatgctg ctacgcgctc cagagaagag gttcctggag    120
atgccactgc tgctgcccgc gaagcggacg accgaggtca ccggcgagga tggcctgcga    180
ggcggcagcg acgaggagga cggcggctgc ggcatcgacg gctccaggaa gaagctccgg    240
ctgtccaagg accagtccgc cgtgctcgag gatagcttcc gggagcaccc aactctcaac    300
cctcggcaga aggcagcctt ggcgcagcag ctaggcctgc ggccccgcca ggtggaggtg    360
tggttccaga acaggcgcgc caggacgaag ctgaagcaga cggaggtgga ctgcgagtac    420
ctgaagcgct gctgcgagac gctgacggag gagaaccggc ggctgcagaa ggaggtgcag    480
gagctccgcg cgctcaagct cgtgtcgccg cacctctaca tgcacatgtc cccgcccacc    540
accctcacca tgtgcccctc ctgcgagcgc gtctcctcgt ccaacggcaa ctccgcagct    600
gccacggccg ccgcgcgcgc gcgcgccggc gccggcgccg cgccatcgt ctgccacccg    660 atcgaccgag ccactagtac gtag                                           684
```

<210> SEQ ID NO 133
<211> LENGTH: 714
<212> TYPE: DNA
<213> ORGANISM: Setaria italica

<400> SEQUENCE: 133

```
atgatggaga gggccgagga cttagggctc agcctcagcc tcagctcgtc gctcgccgct     60
cctcgcactc accatgtctc cgccatgctg ctccgctctc cagagaagag gttcctggag    120
atgccactgc taccggcaaa gcggagcgag gtcacggctg aggagggcct gctgcgcggc    180
ggcagcgacg aggaggacgg cagctgcggc atcgacggct ccaggaagaa gctccggctt    240
tccaaggacc agtcggccgt gctcgaggac agcttccggg agcacccac tctgaaccct    300 cgtcagaagg cagccttggc gcagcagctc ggcctgcggc ccggcaggt ggaggtgtgg    360 ttccagaaca gacgcgcgag gacgaagctg aagcaaacgg aggtggactg cgagttcctg    420
aagcgctgct gcgagacact gacggaggag aaccggcggc tgcagaagga ggtgcaggag    480
ctccgcgcgc tcaagctcgt ctcgccgcac ctctatatgc acatgtcccc gcccaccacc    540
ctcaccatgt gcccctcctg cgagcgcgtc tcctccagcg gcgccaactc caccggcgcc    600
gcggcgtcgt cagaccgacg cgccggcggc gccatcatca gcacggccgc cgccgccgcc    660
gaaggcgccg ccatctgcca ccgcccgatc gccgtccggc cgcagcagtc atga         714
```

<210> SEQ ID NO 134
<211> LENGTH: 891
<212> TYPE: DNA
<213> ORGANISM: Medicago truncatula

<400> SEQUENCE: 134

```
atgagtattg aaaaggaaga ttttggtttg agcctaagtt tgagctttcc tcaaaatcca      60
ccaaatcctc aataccttaa tcttatgtct tcttcaactc attcatattc tccttctact     120
ttcaatcctc aaaaaccttc ttggaatgat gttttttactt cttcagatcg ggattcggag    180
acatgcagaa tcgaagaacg tcctttaatt ctccgaggaa tcgatgtgaa tcggttacct    240
tcaggtgctg attgtgaaga agaagcagga gtttcatcac caaacagcac cgtttcaagt    300
gtgagtggta aagaagcga aagagaagtt accggtgaag atcttgacat ggaaagagat    360
tgttcaagag gaatcagtga tgaagaagac gctgaaactt caaggaaaaa acttagactc    420
accaaagacc aatcaatcat tctcgaagag agtttcaaag aacacaacac tcttaatccc    480
aaacaaaaat tggcacttgc aaaacaattg ggacttcgtg ctagacaagt tgaagtttgg    540
tttcaaaatc gtagagcaag gactaagttg aagcaaacag aggtagattg tgaattttg     600
aaaagatgtt gtgagaatct aacgatgaa aatagacggt tgcaaaaaga agtgcaagag     660
ttaagagcat tgaaactttc cccacaattc tacatgcaaa tgacaccacc aacaacactt    720
accatgtgcc cctcttgtga gcgtgtcgct gttccatcat ctgccgttga tgctgccacg    780
cgtcgtcatc ctatggcttc aaatcaccct cgtacgtttt ccgtgggacc atgggccaca    840
gctgctccaa tccaacatag gacctttgat acactccgtc ctagatctta a             891
```

<210> SEQ ID NO 135
<211> LENGTH: 948
<212> TYPE: DNA
<213> ORGANISM: Arabidopsis thaliana

<400> SEQUENCE: 135

```
atgagtgaaa agatgatgg attggggcta agtttgagct tgagtttagg ttttaatcaa      60
aaggacccgt cttcgaggtt aaatccaatg cctctggctt cttatgcatc ttcatcacac    120
atgcagcata tgcagcagag caattataac catcctcaaa agattcagaa cacttggatt    180
aacatgtttc agtcatcaga gagaaactcg gacatgagat cgtttctccg gggaatagac    240
gtgaacagag ctccatcgac ggtggtggtt gacgtggagg atgaaggcgc ggagtttcg     300
tctccgaaca gcaccgtctc aagcgtgatg agcgggaaga gagcgagcg agagctaatg     360
gctgcggcag gtgcagttgg aggaggtaga gtagaagata tgagattga gagagcttct    420
tgctcgctcg gcggtggtag cgacgatgaa gacggtagcg ggaacggaga tgacagttcg    480
aggaagaaac tccgattgtc taagaacaa gctttggttc ttgaagaaac ttttaaagaa    540
catagtacac tcaatccgaa gcaaaagatg gctttggcta agcagttgaa tctgaggacg    600
agacaagttg aagtgtggtt ccaaaaccga aggcaaagga cgaagctgaa gcaaacggaa    660
gtagactgtg aatatcttaa gagatgttgc gagaatctaa cggatgagaa tcggagattg    720
caaaaggaag tgagtgagct tagggcttta aagctttctc acacttata catgcacatg     780
aaacctccca ctactctcac aatgtgtcct tcttgcgagc gagtcgctgt tacgtcatct    840
ccgtcatcgg tggctcctcc tgtgatgaat tcatcgtctc cgatgggtcc gatgagtccg    900
tgggctgcca tgcctctacg gcaacgacct gctgctggtt ctcattag                 948
```

<210> SEQ ID NO 136
<211> LENGTH: 948
<212> TYPE: DNA
<213> ORGANISM: Arabidopsis thaliana

<400> SEQUENCE: 136

```
atgagtgaaa gagatgatgg attggggcta agtttgagct tgagtttagg tttaatcaa        60
aaggacccgt cttcgaggtt aaatccaatg cctctggctt cttatgcatc ttcatcacac      120
atgcagcata tgcagcagag caattataac catcctcaaa agattcagaa cacttggatt      180
aacatgtttc agtcatcaga gagaaactcg gacatgagat cgtttctccg gggaatagac      240
gtgaacagag ctccatcgac ggtggtggtt gacgtggagg atgaaggcgc cggagtttcg      300
tctccgaaca gcaccgtctc aagcgtgatg agcgggaaga gagcgagcg agagctaatg       360
gctgcggcag gtgcagttgg aggaggtaga gtagaagata atgagattga gagagcttct      420
tgctcgctcg gcggtggtag cgacgatgaa acggtagcg ggaacggaga tgacagttcg       480
aggaagaaac tccgattgtc taaagaacaa gctttggttc ttgaagaaac ttttaaagaa      540
catagtacac tcaatccgaa gcaaaagatg gctttggcta agcagttgaa tctgaggacg      600
agacaagttg aagtgtggtt ccaaaaccga aggcaaagga cgaagctgaa gcaaacggaa      660
gtagactgtg aatatcttaa gagatgttgc gagaatctaa cggatgagaa tcggagattg      720
caaaaggaag tgagtgagct tagggcttta agctttctc cacacttata catgcacatg       780
aaacctccca ctactctcac aatgtgtcct tcttgcgagc gagtcgctgt tacgtcatct      840
ccgtcatcgg tggctcctcc tgtgatgaat tcatcgtctc cgatgggtcc gatgagtccg      900
tgggctgcca tgcctctacg gcaacgacct gctgctggtt ctcattag                   948
```

<210> SEQ ID NO 137
<211> LENGTH: 936
<212> TYPE: DNA
<213> ORGANISM: Oryza sativa

<400> SEQUENCE: 137

```
atggagatga tggttcatgg gaggagagac gagcagtatg gcgggctcag gctcgggctt      60
gggcttgggc tcagcctcgg cgtcgccggt ggtgcagccg acgacgagca gccgccgccg     120
cgccgtggtg ccgccccgcc gccgcagcag cagctgtgcg gctggaacgg cggcggtctc     180
ttctcctcgt cttcctccga tcatcggggg aggtcggcga tgatggcgtg ccacgacgtc     240
atcgagatgc cgttcctgcg ggggatcgac gtgaaccgtg cgccggcggc agagacgacc     300
acgacgacgg cgagggggcc cagctgcagc gaggaagacg aggagcccgg cgcgtcctcc     360
cccaacagca cgctctccag cctcagcggc aagcgcggcg caccatctgc cgccaccgcc     420
gccgccgccg ccgccagcga cgacgaggac tccggcggcg gatcccgcaa gaagctccgc     480
ctctccaagg accaagccgc cgtcctcgag gacaccttca aagagcacaa caccctcaat     540
cccaagcaga aggcggcgct ggcgaggcag ctgaatctga gccgcggca ggtggaggtg      600
tggttccaga acaggagggc gaggacgaag ctgaagcaga cggaggtgga ctgcgagctg     660
ctcaagcgct gctgcgagac gctcaccgac gagaaccgcc gcctccaccg cgagctccag     720
gagctccgcg ccctcaagct cgccaccgcc gcgccgcgc cgcaccacct ctacggcgcc      780
cgcgtcccgc cgcccaccac cctcaccatg tgcccctcct gcgagcgcgt cgcctccgca     840
gccaccacca cccgcaacaa ctccggcgcc gccccgcgc ggccggtgcc cacccgcccg      900
tggccgccgg cggcggcgca gaggtcgtcg gcgtag                                936
```

<210> SEQ ID NO 138
<211> LENGTH: 948
<212> TYPE: DNA
<213> ORGANISM: Arabidopsis thaliana

<400> SEQUENCE: 138

```
atgagtgaaa gagatgatgg attggggcta agtttgagct tgagtttagg ttttaatcaa        60
aaggacccgt cttcgaggtt aaatccaatg cctctggctt cttatgcatc ttcatcacac       120
atgcagcata tgcagcagag caattataac catcctcaaa agattcagaa cacttggatt       180
aacatgtttc agtcatcaga gagaaactcg gacatgagat cgtttctccg gggaatagac       240
gtgaacagag ctccatcgac ggtggtggtt gacgtggagg atgaaggcgc cggagtttcg       300
tctccgaaca gcaccgtctc aagcgtgatg agcgggaaga gagcgagcg agagctaatg        360
gctgcggcag gtgcagttgg aggaggtaga gtagaagata tgagattga gagagcttct        420
tgctcgctcg gcggtggtag cgacgatgaa gacggtagcg ggaacggaga tgacagttcg       480
aggaagaaac tccgattgtc taagaacaa gctttggttc ttgaagaaac ttttaaagaa        540
catagtacac tcaatccgaa gcaaaagatg gctttggcta agcaattgaa tctgaggacg       600
agacaagttg aagtgtggtt ccaaaaccga agggcaagga cgaagctgaa gcaaacggaa       660
gtagactgtg aatatcttaa gagatgttgc gagaatctaa cggatgagaa tcggagattg       720
caaaaggaag tgagtgagct tagggcttta aagctttctc cacacttata catgcacatg       780
aaacctccca ctactctcac aatgtgtcct tcttgcgagc gagtcgctgt tacgtcatct       840
tcgtcatcgg tggctcctcc tgtgatgaat tcatcgtctc cgatgggtcc gatgagtccg       900
tgggctgcca tgcctctacg gcaacgacct gctgctggtt ctcattag                    948
```

<210> SEQ ID NO 139
<211> LENGTH: 948
<212> TYPE: DNA
<213> ORGANISM: Arabidopsis thaliana

<400> SEQUENCE: 139

```
atgagtgaaa gagatgatgg attggggcta agtttgagct tgagtttagg ttttaatcaa        60
aaggacccgt cttcgaggtt aaatccaatg cctctggctt cttatgcatc ttcatcacac       120
atgcagcata tgcagcagag caattataac catcctcaaa agattcagaa cacttggatt       180
aacatgtttc agtcatcaga gagaaactcg gacatgagat cgtttctccg gggaatagac       240
gtgaacagag ctccatcgac ggtggtggtt gacgtggagg atgaaggcgc cggagtttcg       300
tctccgaaca gcaccgtctc aagcgtgatg agcgggaaga gagcgagcg agagctaatg        360
gctgcggcag gtgcagttgg aggaggtaga gtagaagata tgagattga gagagcttct        420
tgctcgctcg gcggtggtag cgacgatgaa gacggtagcg ggaacggaga tgacagttcg       480
aggaagaaac tccgattgtc taagaacaa gctttggttc ttgaagaaac ttttaaagaa        540
catagtacac tcaatccgaa gcaaaagatg gctttggcta agcaattgaa tctgaggacg       600
agacaagttg aagtgtggtt ccaaaaccga agggcaagga cgaagctgaa gcaaacggaa       660
gtagactgtg aatatcttaa gagatgttgc gagaatctaa cggatgagaa tcggagattg       720
caaaaggaag tgagtgagct tagggcttta aagctttctc cacacttata catgcacatg       780
aaacctccca ctactctcac aatgtgtcct tcttgcgagc gagtcgctgt tacgtcatct       840
tcgtcatcgg tggctcctcc tgtgatgaat tcatcgtctc cgatgggtcc gatgagtccg       900
tgggctgcca tgcctctacg gcaacgacct gctgctggtt ctcattag                    948
```

<210> SEQ ID NO 140
<211> LENGTH: 936
<212> TYPE: DNA
<213> ORGANISM: Oryza sativa

<400> SEQUENCE: 140

```
atggagatga tggttcatgg aggagagac gagcagtatg gcgggctcag gctcgggctt      60
gggcttgggc tcagcctcgg cgtcgccggt ggtgcagccg acgacgagca gccgccgccg     120
cgccgtggtg ccgccccgcc gccgcagcag cagctgtgcg gctggaacgg cggcggtctc     180
ttctcctcgt cttcctccga tcatcggggg aggtcggcga tgatggcgtg ccacgacgtc     240
atcgagatgc cgttcctgcg ggggatcgac gtgaaccgtg cgccggcggc agagacgacc     300
acgacgacgg cgagggggcc cagctgcagc gaggaagacg aggagcccgg cgcgtcctcc     360
cccaacagca cgctctccag cctcagcggc aagcgcggcg caccatctgc cgccaccgcc     420
gccgccgccg ccgccagcga cgacgaggac tccggcggcg gatcccgcaa gaagctccgc     480
ctctccaagg accaagccgc cgtcctcgag gacaccttca agagcacaa caccctcaat     540
cccaagcaga aggcggcgct ggcgaggcag ctgaatctga gccgcggca ggtggaggtg     600
tggttccaga acaggagggc gaggacgaag ctgaagcaga cggaggtgga ctgcgagctg     660
ctcaagcgct gctgcgagac gctcaccgac gagaaccgcc gcctccaccg cgagctccag     720
gagctccgcg ccctcaagct cgccaccgcc gccgccgcgc cgcaccacct ctacggcgcc     780
cgcgtcccgc cgcccaccac cctcaccatg tgcccctcct gcgagcgcgt cgcctccgca     840
gccaccacca cccgcaacaa ctccggcgcc gcccccgcgc ggccggtgcc cacccgcccg     900
tggccgccgg cggcggcgca gaggtcgtcg gcgtag                              936
```

<210> SEQ ID NO 141
<211> LENGTH: 891
<212> TYPE: DNA
<213> ORGANISM: Medicago truncatula

<400> SEQUENCE: 141

```
atgagtattg aaaaggaaga ttttggtttg agcctaagtt tgagctttcc tcaaaatcca      60
ccaaatcctc aataccttaa tcttatgtct tcttcaactc attcatattc tccttctact     120
ttcaatcctc aaaaaccttc ttggaatgat gttttactt cttcagatcg ggattcggag      180
acatgcagaa tcgaagaacg tcctttaatt ctccgaggaa tcgatgtgaa tcggttacct     240
tcaggtgctg attgtgaaga agaagcagga gtttcatcac caaacagcac cgtttcaagt     300
gtgagtggta aagaagcga aagagaagtt accggtgaag atcttgacat ggaaagagat     360
tgttcaagag gaatcagtga tgaagaagac gctgaaactt caaggaaaaa acttagactc     420
accaaagacc aatcaatcat tctcgaagag agtttcaaag aacacaacac tcttaatccc     480
aaacaaaaat tggcacttgc aaaacaattg ggacttcgtg ctagacaagt tgaagtttgg     540
tttcaaaatc gtagagcaag gactaagttg aagcaaacag aggtagattg tgaattttg     600
aaaagatgtt gtgagaatct aacggatgaa aatagacggt tgcaaaaaga agtgcaagag     660
ttaagagcat tgaaactttc cccacaattc tacatgcaaa tgacaccacc aacaacactt     720
accatgtgcc cctcttgtga gcgtgtcgct gttccatcat ctgccgttga tgctgccacg     780
cgtcgtcatc ctatggcttc aaaatcaccct cgtacgtttt ccgtgggacc atgggccaca     840
gctgctccaa tccaacatag gacctttgat acactccgtc ctagatctta a              891
```

<210> SEQ ID NO 142
<211> LENGTH: 948
<212> TYPE: DNA
<213> ORGANISM: Arabidopsis thaliana

<400> SEQUENCE: 142

```
atgagtgaaa gagatgatgg attggggcta agtttgagct tgagtttagg ttttaatcaa        60
aaggacccgt cttcgaggtt aaatccaatg cctctggctt cttatgcatc ttcatcacac       120
atgcagcata tgcagcagag caattataac catcctcaaa agattcagaa cacttggatt       180
aacatgtttc agtcatcaga gagaaactcg gacatgagat cgttctccg gggaatagac        240
gtgaacagag ctccatcgac ggtggtggtt gacgtggagg atgaaggcgc cggagtttcg       300
tctccgaaca gcaccgtctc aagcgtgatg agcgggaaga gagcgagcg agagctaatg        360
gctgcggcag gtgcagttgg aggaggtaga gtagaagata tgagattga gagagcttct        420
tgctcgctcg gcggtggtag cgacgatgaa gacggtagcg ggaacggaga tgacagttcg       480
aggaagaaac tccgattgtc taagaacaa gctttggttc ttgaagaaac ttttaaagaa        540
catagtacac tcaatccgaa gcaaaagatg gctttggcta agcaattgaa tctgaggacg       600
agacaagttg aagtgtggtt ccaaaaccga agggcaagga cgaagctgaa gcaaacggaa       660
gtagactgtg aatatcttaa gagatgttgc gagaatctaa cggatgagaa tcggagattg       720
caaaaggaag tgagtgagct tagggcttta aagcttctc cacacttata catgcacatg        780
aaacctccca ctactctcac aatgtgtcct tcttgcgagc gagtcgctgt tacgtcatct       840
tcgtcatcgg tggctcctcc tgtgatgaat tcatcgtctc cgatgggtcc gatgagtccg       900
tgggctgcca tgcctctacg gcaacgacct gctgctggtt ctcattag                    948
```

<210> SEQ ID NO 143
<211> LENGTH: 891
<212> TYPE: DNA
<213> ORGANISM: Medicago truncatula

<400> SEQUENCE: 143

```
atgagtattg aaaaggaaga ttttggtttg agcctaagtt tgagctttcc tcaaaatcca        60
ccaaatcctc aataccttaa tcttatgtct tcttcaactc attcatattc tccttctact       120
ttcaatcctc aaaaaccttc ttggaatgat gttttttactt cttcagatcg ggattcggag      180
acatgcagaa tcgaagaacg tcctttaatt ctccgaggaa tcgatgtgaa tcggttacct      240
tcaggtgctg attgtgaaga agaagcagga gtttcatcac caaacagcac cgtttcaagt      300
gtgagtggta aagaagcga aagagaagtt accggtgaag atcttgacat ggaaagagat       360
tgttcaagag gaatcagtga tgaagaagac gctgaaactt caaggaaaaa acttagactc      420
accaaagacc aatcaatcat tctcgaagag agttttcaaag aacacaacac tcttaatccc     480
aaacaaaaat tggcacttgc aaaacaattg ggacttcgtg ctagacaagt tgaagtttgg      540
tttcaaaatc gtagagcaag gactaagttg aagcaaacag aggtagattg tgaattttg       600
aaagatgtt gtgagaatct aacggatgaa aatagacggt tgcaaaaaga agtgcaagag      660
ttaagagcat tgaaactttc cccacaattc tacatgcaaa tgcaccacc aacaacactt      720
accatgtgcc cctcttgtga gcgtgtcgct gttccatcat ctgccgttga tgctgccacg      780
cgtcgtcatc ctatggcttc aaatcacccct cgtacgtttt ccgtgggacc atgggccaca    840
gctgctccaa tccaacatag gacctttgat acactccgtc ctagatctta a               891
```

<210> SEQ ID NO 144
<211> LENGTH: 936
<212> TYPE: DNA
<213> ORGANISM: Oryza sativa

<400> SEQUENCE: 144

```
atggagatga tggttcatgg gaggagagac gagcagtatg gcgggctcag gctcgggctt    60
gggcttgggc tcagcctcgg cgtcgccggt ggtgcagccg acgacgagca gccgccgccg   120
cgccgtggtg ccgccccgcc gccgcagcag cagctgtgcg gctggaacgg cggcggtctc   180
ttctcctcgt cttcctccga tcatcggggg aggtcggcga tgatggcgtg ccacgacgtc   240
atcgagatgc cgttcctgcg ggggatcgac gtgaaccgtg cgccggcggc agagacgacc   300
acgacgacgg cgagggggcc cagctgcagc gaggaagacg aggagcccgg cgcgtcctcc   360
cccaacagca cgctctccag cctcagcggc aagcgcggcg caccatctgc cgccaccgcc   420
gccgccgccg ccgccagcga cgacgaggac tccggcggcg gatcccgcaa gaagctccgc   480
ctctccaagg accaagccgc cgtcctcgag gacaccttca aagagcacaa caccctcaat   540
cccaagcaga aggcggcgct ggcgaggcag ctgaatctga gccgcggca ggtggaggtg    600 tggttccaga acaggagggc gaggacgaag ctgaagcaga cggaggtgga ctgcgagctg   660
ctcaagcgct gctgcgagac gctcaccgac gagaaccgcc gcctccaccg cgagctccag   720
gagctccgcg ccctcaagct cgccaccgcc gccgccgcgc cgcaccacct ctacggcgcc   780
cgcgtcccgc cgcccaccac cctcaccatg tgccctcct gcgagcgcgt cgcctccgca   840
gccaccacca cccgcaacaa ctccggcgcc gccccgcgc ggccggtgcc cacccgcccg   900
tggccgccgg cggcggcgca gaggtcgtcg gcgtag                              936
```

<210> SEQ ID NO 145
<211> LENGTH: 936
<212> TYPE: DNA
<213> ORGANISM: Oryza sativa

<400> SEQUENCE: 145

```
atggagatga tggttcatgg gaggagagac gagcagtatg gcgggctcag gctcgggctt    60
gggcttgggc tcagcctcgg cgtcgccggt ggtgcagccg acgacgagca gccgccgccg   120
cgccgtggtg ccgccccgcc gccgcagcag cagctgtgcg gctggaacgg cggcggtctc   180
ttctcctcgt cttcctccga tcatcggggg aggtcggcga tgatggcgtg ccacgacgtc   240
atcgagatgc cgttcctgcg ggggatcgac gtgaaccgtg cgccggcggc agagacgacc   300
acgacgacgg cgagggggcc cagctgcagc gaggaagacg aggagcccgg cgcgtcctcc   360
cccaacagca cgctctccag cctcagcggc aagcgcggcg caccatctgc cgccaccgcc   420
gccgccgccg ccgccagcga cgacgaggac tccggcggcg gatcccgcaa gaagctccgc   480
ctctccaagg accaagccgc cgtcctcgag gacaccttca aagagcacaa caccctcaat   540
cccaagcaga aggcggcgct ggcgaggcag ctgaatctga gccgcggca ggtggaggtg    600 tggttccaga acaggagggc gaggacgaag ctgaagcaga cggaggtgga ctgcgagctg   660
ctcaagcgct gctgcgagac gctcaccgac gagaaccgcc gcctccaccg cgagctccag   720
gagctccgcg ccctcaagct cgccaccgcc gccgccgcgc cgcaccacct ctacggcgcc   780
cgcgtcccgc cgcccaccac cctcaccatg tgccctcct gcgagcgcgt cgcctccgca   840
gccaccacca cccgcaacaa ctccggcgcc gccccgcgc ggccggtgcc cacccgcccg   900
tggccgccgg cggcggcgca gaggtcgtcg gcgtag                              936
```

<210> SEQ ID NO 146
<211> LENGTH: 936
<212> TYPE: DNA
<213> ORGANISM: Oryza sativa

<400> SEQUENCE: 146

```
atggagatga tggttcatgg gaggagagac gagcagtatg gcgggctcag gctcgggctt      60
gggcttgggc tcagcctcgg cgtcgccggt ggtgcagccg acgacgagca gccgccgccg     120
cgccgtggtg ccgccccgcc gccgcagcag cagctgtgcg gctggaacgg cggcggtctc     180
ttctcctcgt cttcctccga tcatcggggg aggtcggcga tgatggcgtg ccacgacgtc     240
atcgagatgc cgttcctgcg ggggatcgac gtgaaccgtg cgccggcggc agagacgacc     300
acgacgacgg cgagggggcc cagctgcagc gaggaagacg aggagcccgg cgcgtcctcc     360
cccaacagca cgctctccag cctcagcggc aagcgcggcg caccatctgc cgccaccgcc     420
gccgccgccg ccgccagcga cgacgaggac tccggcggcg gatcccgcaa gaagctccgc     480
ctctccaagg accaagccgc cgtcctcgag gacaccttca agagcacaa cacccctcaat    540
cccaagcaga aggcggcgct ggcgaggcag ctgaatctga gccgcggca ggtggaggtg     600
tggttccaga acaggagggc gaggacgaag ctgaagcaga cggaggtgga ctgcgagctg     660
ctcaagcgct gctgcgagac gctccaccgac gagaaccgcc gcctccaccg cgagctccag     720
gagctccgcg ccctcaagct cgccaccgcc gccgccgcgc cgcaccacct ctacggcgcc     780
cgcgtcccgc cgcccaccac cctcaccatg tgcccctcct gcgagcgcgt cgcctccgca     840
gccaccacca cccgcaacaa ctccggcgcc gccccgcgc ggccggtgcc cacccgcccg     900
tggccgccgg cggcggcgca gaggtcgtcg gcgtag                                936
```

<210> SEQ ID NO 147
<211> LENGTH: 948
<212> TYPE: DNA
<213> ORGANISM: Arabidopsis thaliana

<400> SEQUENCE: 147

```
atgagtgaaa gagatgatgg attggggcta agtttgagct tgagtttagg ttttaatcaa      60
aaggacccgt cttcgaggtt aaatccaatg cctctggctt cttatgcatc ttcatcacac     120
atgcagcata tgcagcagag caattataac catcctcaaa agattcagaa cacttggatt     180
aacatgtttc agtcatcaga gagaaactcg gacatgagat cgtttctccg ggaatagac      240
gtgaacagag ctccatcgac ggtggtggtt gacgtggagg atgaaggcgc cggagtttcg     300
tctccgaaca gcaccgtctc aagcgtgatg agcgggaaga gagcgagcg agagctaatg     360
gctgcggcag gtgcagttgg aggaggtaga gtagaagata tgagattga gagagcttct      420
tgctcgctcg gcggtggtag cgacgatgaa gacggtagcg ggaacggaga tgacagttcg     480
aggaagaaac tccgattgtc taaagaacaa gctttggttc ttgaagaaac ttttaaagaa     540
catagtacac tcaatccgaa gcaaaagatg gctttggcta agcaattgaa tctgaggacg     600
agacaagttg aagtgtggtt ccaaaaccga agggcaagga cgaagctgaa gcaaacggaa     660
gtagactgtg aatatcttaa gagatgttgc gagaatctaa cggatgagaa tcggagattg     720
caaaaggaag tgagtgagct tagggcttta aagctttctc cacacttata catgcacatg     780
aaacctccca ctactctcac aatgtgtcct tcttgcgagc gagtcgctgt tacgtcatct     840
tcgtcatcgg tggctcctcc tgtgatgaat tcatcgtctc cgatgggtcc gatgagtccg     900
tgggctgcca tgcctctacg gcaacgacct gctgctggtt ctcattag                   948
```

<210> SEQ ID NO 148
<211> LENGTH: 948
<212> TYPE: DNA
<213> ORGANISM: Arabidopsis thaliana

<400> SEQUENCE: 148

```
atgagtgaaa gagatgatgg attggggcta agtttgagct tgagtttagg ttttaatcaa      60
aaggacccgt cttcgaggtt aaatccaatg cctctggctt cttatgcatc ttcatcacac     120
atgcagcata tgcagcagag caattataac catcctcaaa agattcagaa cacttggatt     180
aacatgtttc agtcatcaga gagaaactcg gacatgagat cgtttctccg gggaatagac     240
gtgaacagag ctccatcgac ggtggtggtt gacgtggagg atgaaggcgc cggagtttcg     300
tctccgaaca gcaccgtctc aagcgtgatg agcgggaaga agagcgagcg agagctaatg     360
gctgcggcag gtgcagttgg aggaggtaga gtagaagata atgagattga gagagcttct     420
tgctcgctcg gcggtggtag cgacgatgaa gacggtagcg ggaacggaga tgacagttcg     480
aggaagaaac tccgattgtc taagaacaa gctttggttc ttgaagaaac ttttaaagaa      540
catagtacac tcaatccgaa gcaaaagatg gctttggcta agcaattgaa tctgaggacg     600
agacaagttg aagtgtggtt ccaaaaccga agggcaagga cgaagctgaa gcaaacggaa     660
gtagactgtg aatatcttaa gagatgttgc gagaatctaa cggatgagaa tcggagattg     720
caaaaggaag tgagtgagct tagggcttta aagctttctc cacacttata catgcacatg     780
aaacctccca ctactctcac aatgtgtcct tcttgcgagc gagtcgctgt tacgtcatct     840
tcgtcatcgg tggctcctcc tgtgatgaat tcatcgtctc cgatgggtcc gatgagtccg     900
tgggctgcca tgcctctacg gcaacgacct gctgctggtt ctcattag               948
```

<210> SEQ ID NO 149
<211> LENGTH: 894
<212> TYPE: DNA
<213> ORGANISM: Vitis vinifera

<400> SEQUENCE: 149

```
atgatggttg acaaggagga cttgggtttg agcttgagct taagctttcc tcaggacgca      60
catcgtccgc tacagttgaa tctgatgcct tcgttgcttc ctgcctcttc ctcttctcct     120
tctccttctc ccttcgctct tcagaaacct tcatggcacg acgcctttcc ctcttctgat     180
cgaacctcag agacatgcag aggcgatgcc agatcgttcc tccgtggaat agatgtgaac     240
cgcttgccat cgacggccga ctgcgaagaa gaggccggcg tttcatcacc aaacagcacg     300
atttccagcg taagcgggaa aagaagcgag agaagcaa acggagacga gcatgagatg       360
gagagagctt gttctcgcgg aatcagcgac gaagaagatg gcgacacttc gagaagaag      420
cttagactct ctaaggatca gtccgcgatt ctcgaagaaa acttcaaaga acacaacact     480
ctcaatccaa gcaaaagct ggccttggct aagcaactga acctgagacc aagacaggtg      540
gaggtgtggt tcagaacag aagggcaagg accaagttga agcaaacgga ggttgactgt     600
gagttcttga agagatgctg cgagaatctg acggaggaga acagacggtt gcagaaggag     660
gtgaatgagc tgagagcact gaaactttcc ccacagttct acatgcaaat gaccccaccc     720
acaacccctca ccatgtgccc atcatgtgag cgtgtggcgg tcccacctcc ctcgtcggag    780
gctcgctccc accagatggc caccaccac caccgtccca tccccatcaa cccttgggcc       840
accgccactc ccatccccca ccgcccttc gacgccctcc atcctcgctc ctga            894
```

<210> SEQ ID NO 150
<211> LENGTH: 936
<212> TYPE: DNA
<213> ORGANISM: Oryza sativa

```
<400> SEQUENCE: 150
atggagatga tggttcatgg gaggagagac gagcagtatg gcgggctcag gctcgggctt    60
gggcttgggc tcagcctcgg cgtcgccggt ggtgcagccg acgacgagca gccgccgccg   120
cgccgtggtg ccgccccgcc gccgcagcag cagctgtgcg gctggaacgg cggcggtctc   180
ttctcctcgt cttcctccga tcatcggggg aggtcggcga tgatggcgtg ccacgacgtc   240
atcgagatgc cgttcctgcg ggggatcgac gtgaaccgtg cgccggcggc agagacgacc   300
acgacgacgg cgaggggggcc cagctgcagc gaggaagacg aggagcccgg cgcgtcctcc   360
cccaacagca cgctctccag cctcagcggc aagcgcggcg caccatctgc cgccaccgcc   420
gccgccgccg ccgccagcga cgacgaggac tccggcggcg gatcccgcaa gaagctccgc   480
ctctccaagg accaagccgc cgtcctcgag gacaccttca aagagcacaa cacccctcaat   540 cccaagcaga aggcggcgct ggcgaggcag ctgaatctga gccgcggca ggtggaggtg    600 tggttccaga acaggagggc gaggacgaag ctgaagcaga cggaggtgga ctgcgagctg   660
ctcaagcgct gctgcgagac gctcaccgac gagaaccgcc gcctccaccg cgagctccag   720
gagctccgcg ccctcaagct cgccaccgcc gccgccgcgc cgcaccacct ctacggcgcc   780
cgcgtcccgc cgcccaccac cctcaccatg tgccctcct gcgagcgcgt cgcctccgca    840
gccaccacca cccgcaacaa ctccggcgcc gccccgcgc ggccggtgcc cacccgcccg     900
tggccgccgg cggcggcgca gaggtcgtcg gcgtag                             936

<210> SEQ ID NO 151
<211> LENGTH: 483
<212> TYPE: DNA
<213> ORGANISM: Physcomitrella patens

<400> SEQUENCE: 151
atgagctcgc gggggggaag cgacgatgag gacgaaggga cgacgcggaa gaagctgcga    60
ctgtcgaagg aacagtcggc actgctggag gagagtttca aggagcacag tacgctgaac   120
ccgaagcaga agaacgctct ggcgaagcag ctgggtctcc ggccgcggca ggtggaagtg   180
tggttccaga acaggagggc tcggacaaag ctgaaacaga ccgaagtgga ctgcgagttg   240
cttaagcgat gctgcgattc gctgaaggag gagaacagga ggttgcagaa agagttgctg   300
gagttgcgag ccatcaaggt ggcgcctcca tgtgtgatat cgcacgatta ctacatgcct   360
ctgcccgcgg cgacgctgac gatgtgtccg tcatgcgaga gagtggcgac ggtggacaac   420
aggtcgttga cgtttgcgaa gccagggttt tcacatttgt cgcaatcaag cgcagcatgt   480
tag                                                                 483

<210> SEQ ID NO 152
<211> LENGTH: 885
<212> TYPE: DNA
<213> ORGANISM: Ricinus communis

<400> SEQUENCE: 152
atggaagaca agatgatgg gctgggtttg ggttgagtc tgagtttggg aggtcaggaa     60
aaacatcaaa atcagccatc tttgaagctc aatctcatgc cgtttccgtc gctctttatg   120
caaaatactc accacagtac ctccttgaat gaccttttcc aatcatctga tagaaacgct   180
gatacgaggt catttcaacg agggattgat atgaatcgga tgcccctctt cgccgattgc   240
gacgatgaaa acggtgtttc ttcgccgaac agtacgattt ccagtttaag tggaaagaga   300
agcgagaggg aacagattgg aggagaggag atggaggcag agagagcatc atgctctcgc   360
```

```
ggcggaagtg acgacgaaga cggtggcgcc ggcggcgatg acggttctag gaaaaaactg      420
aggctctcaa aggaacaatc tttattgctt gaagagactt ttaaggagca caatactctc      480
aatccaaagc agaagctggc tttagctaaa cagttgaatc tcaagccaag acaggtggag      540
gtgtggtttc agaaccggag ggcaaggact aagtcgaagc aaactgaagt tgattgtgag      600
tacttaaaaa ggtgttgtga gaatctgaca caagagaaca ggaggttgca gaaggaggtg      660
caggagctta gagcattgaa gctctcccca cagctgtaca tgcacatgaa ccctcccacc      720
acactcacaa tgtgcccttc atgcgagcgt gttgcagtct cctcatcggc tgctcccagc      780
cgccaaccac cgaattccca accccaacga ccggtgcctg ttaagccttg ggcagcattg      840
cctatccagc atcgaccgtt tgatacgcct gcttctagat cgtag                     885
```

<210> SEQ ID NO 153
<211> LENGTH: 1041
<212> TYPE: DNA
<213> ORGANISM: Sorghum bicolor

<400> SEQUENCE: 153

```
atggagatgg cggttaatgc gagagacgag gagaagaagt acgacgggga cgacaaccat       60
ctcgggcttg ggctaagcct cagcctcggc atcgccacca ccgcggctac tccggtcgag      120
gtcgacccgc cgccgcggca gcagcagcag cagcgagcta tcagcgtcgc gcccatctcc      180
tccctccccg cgccgcagtg gtggaacgga cccgccggtc tcttcttctc cccctcctcc      240
gggatgaaga tggatccatc tctggagagg aagcatcagc atcagcagca gcagcagcag      300
caggcggcgg ccacgagcta cagccacgat atgccgttcc tgcgtgggat cgacgtgaac      360
cggcgggcca ccgccggaga gacccggagg ggccgcagct gcagcgagga cgaggagccc      420
ggcgcgtcgt cgccgaacag cacgctctcc agcctcagcg ggaagcgcgc cgcgccggcg      480
aggagcagcg gagaagtgga tcgagaggcc gacggccaca ccccgagagc cggaggcggc      540
ggcagcgacg acgaggactc cggcgccggc ggtgggtcgc gcaagaagct ccgcctctcc      600
aaggaccagg ccgccgtcct cgaggacagc ttcaaggagc acaacaccct caaccccaag      660
cagaaggcgg cgctggcgaa gcagctgaac ctgaagccac gtcaggttga ggtctggttc      720
cagaaccgca gagccaggac gaagctgaag cagacggagg tggactgcga gttcctgaag      780
cgctgctgcg agacgctgac ggaggagaac cggcggctgc agcgggaggt ggcggagctg      840
cgcgcgctca gctcgtggc gccgcaccac tacgcgcgga tgccgccgcc aaccacgctc      900
accatgtgcc cctcctgcga gcgcctcgcc tccgcgcccg ccgacgaggc ggtggcgggc      960
cgtaccgccg cgcccacagg gccctggggc cctctccccg tgcggccagt gttcgtcgac     1020 ggccccggccc ggaggtcatg a                                               1041
```

<210> SEQ ID NO 154
<211> LENGTH: 948
<212> TYPE: DNA
<213> ORGANISM: Arabidopsis lyrata

<400> SEQUENCE: 154

```
atgggtgaaa gagatgatgg attggggcta agcttgagct tgagtttagg ttttaatcaa       60
aaggacccgt cttcgagatt aaatccaatg cctttggctt cttattcaac ttcatcacac      120
atgcatatgc agcagagcaa ttatagccat cctcaaaaga ttcagaacac ttggattaac      180
atgtttcatt catcagagag aaacaccgac atgagatcgt ttctccgggg aatagacgtg      240
```

| | | |
|---|---|---|
| aacagagctc catcgacggt ggttgttgat gtggaggatg acggagccgg agtctcgtct | 300 |
| ccgaatagca ccgtatcaag cgtgatgagc gggaagagga gcgagcggga gctaatgact | 360 |
| gcggcagcta cagccggagg aggaggtaga gtagaagata acgagatgga gagagcttct | 420 |
| tgctcgctcg gcggtggtag cgacgatgaa gacggtagcg ggaacggaga cgatggttcg | 480 |
| aggaagaaac tgcgtttgtc taaagaacaa gctttggttc tcgaagaaac ttttaaagaa | 540 |
| catagcacac tcaatccgaa gcaaaagatg gcgttggcta agcaattgaa tctgaggacg | 600 |
| aggcaagtag aagtgtggtt ccaaaaccga agggcaagga cgaagctgaa gcaaacggaa | 660 |
| gtagactgtg aatatcttaa gagatgttgc gagaatctaa ctgatgagaa tcggagattg | 720 |
| caaaaggaag tgagtgagct tagggctttg aagctttctc cacacttata catgcacatg | 780 |
| aaacctccca ctactctcac tatgtgccct tcttgcgagc gagtcgctgt tacatcatct | 840 |
| tcgtcatctg tggctcctcc tgtgatgact tcatcgtctc cgatgggacc gatgagtccg | 900 |
| tgggctgcca ttcctctccg gcaacgacct gctgctggtt ctcattag | 948 |

<210> SEQ ID NO 155
<211> LENGTH: 960
<212> TYPE: DNA
<213> ORGANISM: Prunus persica

<400> SEQUENCE: 155

| | | |
|---|---|---|
| atgatggttg agagagatca agatttgggt ttgagtctga gcttgagttt tcctcagacc | 60 |
| cacaaccacc acaacaacaa caacaacaac agcagcagca ccaccagcac ccttcagctc | 120 |
| aatctcatgc cttctttggc ccctactcct gcttcttctc cttctgggtt tcttcctcaa | 180 |
| aaaccctctt ggaatgaggc cttgatttct tcagatcgaa actccaactc cgaaacgttc | 240 |
| cgggtcgggc cccgatcgtt ccttcggggc atcgacgtga accggttgcc ttcaacgggc | 300 |
| gactgcgaag acgaggcggg cgtgtcgtcg cccaacagca cggtgtcgag cgtgagcggc | 360 |
| aagcggagcg agagagaggc caatggcgaa gatctcgaca tcgagactcg aggcatcagc | 420 |
| gatgaagaag acggcgagac ctctagaaag aagctcaggc tctccaagga ccagtccgcc | 480 |
| attctcgaag agagcttcaa ggagcacaac actctcaacc caaagcaaaa gttggcgttg | 540 |
| gctaaacagc ttggcctccg gcctagacaa gtggaagtct ggtttcagaa cagaagagca | 600 |
| aggactaagt tgaagcaaac ggaggtggac tgtgagttct tgaagaggtg ctgtgagaat | 660 |
| ctgacagagg agaacaggcg gttgcagaag gaggttcagg agctgagagc actgaaactt | 720 |
| tccccacagt tctacatgca aatgaccccca cccacgacac tcaccatgtg ccctcgtgt | 780 |
| gagcgtgtcg cggtcccacc caactcctca tcctcaaccg tcgagccccg gccccacccc | 840 |
| caccccacc cccaaatggg ttcggtccag accggcccg tccccatcaa cccgtgggca | 900 |
| tccgccaccc caatccccca ccggccgctg ccgttcgaag ccttccacac ccggacgtaa | 960 |

<210> SEQ ID NO 156
<211> LENGTH: 471
<212> TYPE: DNA
<213> ORGANISM: Triticum urartu

<400> SEQUENCE: 156

| | | |
|---|---|---|
| atggatggct cccgcaagaa gctccggttg tccaaggacc agtccgccgt gctcgaggac | 60 |
| agcttccggg agcaccccac tctgaacccg aggcagaagg cagccttggc gcagcagctg | 120 |
| ggcctgcggt cgcggcaggt ggaggtgtgg ttccagaaca cacgcgcaag gacgaagctg | 180 |
| aagcagacgg aggtggactg cgagttcctg aagcgatgct gcgagacgct gacggaggag | 240 |

| | |
|---|---|
| aaccggcggc tgcagaagga ggtgcaggag ctccgcgcgc tcaagctcgt ctccccgcac | 300 |
| cactacatgc acatgtcccc gcccaccacc ctcaccatgt gcccctcctg cgagcgcgtc | 360 |
| tccaacaaca acaacaacaa caacaacaac tccaccaccg ccgaccgccg caacggtgtc | 420 |
| gagggcgcca tctgccaccg acccatcgcc gtccggccgc agcagtcatg a | 471 |

<210> SEQ ID NO 157
<211> LENGTH: 1020
<212> TYPE: DNA
<213> ORGANISM: Capsella rubella

<400> SEQUENCE: 157

| | |
|---|---|
| aaaaacctga gaacccagag acaaattttc ttctttcttc tttctgtttt tgggctagga | 60 |
| aaaaccaaaa aaatgggtga agagatgat ggattgggtc taagcttgag cttgagttta | 120 |
| ggttttactc caaaggagcc gtcttctagg tttaatccaa tgcctatggc ttcttattca | 180 |
| tcttcttcac acatgcatat gcagcagcag agcaattata gccatcctca caagattcag | 240 |
| aacagttgga tcaacatgtt ccagtcttca gagagaaact ccgacatgag atcgtttctc | 300 |
| cggggaatcg acgtgaacag agctccatcg acggtggtgg ttgacgtgga ggatgacgcc | 360 |
| gccggagtct cgtccccgaa cagcaccgtg tcaagcgtgg tgagcgggaa gaggagcgag | 420 |
| cgggagctaa tggctgcggc agctgcagcc ggaggaggca gagcagaaga taacgagatg | 480 |
| gagagagctt cttgttcgct cggtggtggt agcgacgatg aggacgggag tgggaacgga | 540 |
| gacgacggtt cgaggaagaa actccgtttg tctaaagaac aagctttggt tcttgaagag | 600 |
| acttttaaag aacatagcac actcaatccg aagcaaaaga tggcgttggc taagcaattg | 660 |
| aatctgcaga cgaggcaagt ggaagtgtgg ttccaaaacc gaagggcaag gacgaagctg | 720 |
| aagcaaacgg aagtagactg tgaatatctg aggagacgtt gcgagaatct aacggaggag | 780 |
| aatcgaagat tgcaaaagga agtgagtgag ctaagggctt tgaagctttc gccacactta | 840 |
| tacatgcaca tgaaacctcc cactacgcta acaatgtgcc cttcttgcga acgagtggct | 900 |
| gttacatcat catcctcgtc ggtggctcct cctgtcatga cttcttcgtc tcctatgggg | 960 |
| caaatgagtc catgggctgc cattcctctc cgacaacgac ctgctgctgg ttctcattag | 1020 |

<210> SEQ ID NO 158
<211> LENGTH: 888
<212> TYPE: DNA
<213> ORGANISM: Theobroma cacao

<400> SEQUENCE: 158

| | |
|---|---|
| atgggtgctg aaaaagatga tggtttgggg ttgagcttga gcttgggatg tgctcaaaat | 60 |
| caccttctt tgaagttaaa tctcatgcct ttagcgtcac cccgcatgca aaatcttcag | 120 |
| cagaagaaca cttggaatga gctgtttcaa tcttctgatc gaaacctgga tacgagatca | 180 |
| tttcttcgag ggattgatgt gaaccgggca ccagcaacgg ttgattgcga ggaggaaggt | 240 |
| ggggtctcgt ctcccaacag caccatttct agcataagtg ggaagagaaa cgagagagac | 300 |
| cctgtgggtg atgaaactga ggccgagaga gcgtcttgct ctcgtgccag tgatgatgaa | 360 |
| gacggcggtg ctggtggcga tgcctcgagg aaaaagctta ggctctcaaa ggaacagtcc | 420 |
| ttgctgcttg aagaaccttt caaggagcat agcactctta atccgaagca aagttggca | 480 |
| ctggcaaagc aattgaatct gaggcctagg caagtggagg tctggttcca aacagaagg | 540 |
| gccaggacaa agttgaagca gacggaagtt gactgtgagt atctaaagag atgttgcgag | 600 |

```
aatctgaccg aggagaatag gcggctgcag aaggaagtgc aagagcttag agctttgaaa      660
ctctctccac agctctacat gcacatgaac cctcccacaa ccctcactat gtgcccttct      720
tgtgaacgtg tggcggtttc ttcctcctcc tcctccgcag cagctactgc ttcctccacc      780
ccaacttcga cggtcccaaa ccgtcaccac cggacgagtt ccgttagccc ttgggcagca      840
atgccaattg gtcatcgacc cttccatgcc cctgcatcta gatcataa                  888

<210> SEQ ID NO 159
<211> LENGTH: 801
<212> TYPE: DNA
<213> ORGANISM: Amborella trichopoda

<400> SEQUENCE: 159
atgaatagag aagatctgaa tctgagttta agcttgagga gagtcggaga tttcgagttg       60
aatctgttac ccagaaattg cagaaatgat tcttccagtt tagatagatc agagacagct      120
agatcaatcc taaaatcctt tgatgtgaac cggattcagg cgacatcaga taggattccg      180
acaacaaccg atgcgattcg atcagaaatc agccggattc cggcaacacc gaacatggct      240
ggattcgatg taaataggat cccagtcatt tcagagtgcg aagaagaggc agtggtgtcg      300
tcgccaatga gcacagtttc gagcttgagc atgagtggcg gaagagaga tgagccggag       360 ggggagagag cgagctcgag gggatctagt gacgaggagg atggtggtga ggctgcaagg      420
aagaaacttc gattgtcaaa ggatcaatct gcagttctag aggagagttt caaggaacac      480
aatactctta acccgaagca gaagctcact ttggcaaagc agttgaatct tcgccctcgt      540
caagtcgaag tctggtttca gaaccgaaga gcaaggacta agttaaagca aacagaagta      600
gattgtgaat ttttaaagag gtgttgtgaa aacctgactg aagagaacag gaggctccaa      660
aaagaagtga tggagctaag gtcccttaag caaaccccctc acttctatat gcacgtgcct      720
cccgctgccc tgacgatgtg cccctcatgc gagcgtgtgg cagtgtcgga gtcccagttt      780
cgaccacaga ttcgatcatg a                                                 801

<210> SEQ ID NO 160
<211> LENGTH: 942
<212> TYPE: DNA
<213> ORGANISM: Eutrema salsugineum

<400> SEQUENCE: 160
atgggtgaga gagatgatgg attggggcta agcttgagct tgagtttagg ttcaaatcaa       60
aacgagtcgt cttcgaggtt taatcctatg cctctggctt cttttccatc ttcatcacac      120
atgcatatgc agaaccatta tagccatcct cagaagattc agaacaactg gattcaaatg      180
tttcaatctt cagagaggaa ctccgacgtg agatcttttc tccggggaat cgacgtgaac      240
agagctccat cgacggtggt ggttgacgtt gaggaagacg ccggagtctc gtctccgaac      300
agcacagtct caagcgtgat gagcgggaag agaagtgagc gagagctgat ggctgcggcg      360
gcggctggag gagtaagagt aatagaagac aacgaggcgg agagagcttc ttgctcgcta      420
ggcggcggtg gtagcgacga tgatgatggt ggcgggaacg gagacgacgg ttcgaggaag      480
aaactccgat tgtctaaaga acaagcttta gtcctcgagg agacttttaa gaacatagc       540 actctcaatc gaagcaaaaa gatggctttg gctaagcaat gaatctaag aacaaggcaa       600 gtggaagtgt ggttccaaaa ccgaagggca aggacgaagc tgaagcaaac ggaagtagat      660
tgtgaatatc tgaaaagatg ctgcgagaat ctaacggagg agaatcgaag attgcaaaag      720
gaagtgagtg agctcagggc tttaaagctt tcaccacatt tatacatgca catgaaacct      780
```

| | |
|---|---|
| cccactactc tcacaatgtg cccttcttgt gagcgagtcg ctgttacatc gtcgtcgtca | 840 |
| tcggtggccc ctcctgcgat gacgtcatca tctccgatgg ggccaatgag tccttgggct | 900 |
| gccattcctc tccggcaacg acctgctgct ggttctcatt ag | 942 |

<210> SEQ ID NO 161
<211> LENGTH: 900
<212> TYPE: DNA
<213> ORGANISM: Citrus clementina

<400> SEQUENCE: 161

| | |
|---|---|
| atggctgaga aagatgatct gggtttgagt cttagcttga gctttcctca aaatcaccat | 60 |
| tctttacagc taaatctcat gccttcttct gcttgttcca cttctccttc tggtttcagt | 120 |
| ctccaaaaaa ccccttggaa cgaggcctta ttcccacctt cagatccaaa ctctgagtct | 180 |
| tgtcgcgccg agacccgatc atttcttaga ggaatcgacg tgaatcgatt gccgtcacat | 240 |
| gcagataacg aagaagaagt gggcgtctca tctcctaaca gcacgatttc gagcgttagc | 300 |
| ggcaagagaa gcgagcggga acctaatgga gatgagctcg aaatggagag agcttgctct | 360 |
| cgtggtatca gcgacgatga agatggtgac acttcaagaa agaagctgag actttctaaa | 420 |
| gatcagtcag ccattcttga agagagcttc aaagagcaca acactctcaa cccaaagcaa | 480 |
| aagttggcgt tggcaaagca gcttggtctc agacctagac aggtggaagt gtggttccag | 540 |
| aacagaaggg caaggaccaa attgaagcaa actgaggttg actgcgaatt cttgaagaga | 600 |
| tgctgtgaga atctgacgga ggagaacagg cggttcagaa agaagttca ggagctgaga | 660 |
| gcactgaagc tttccccgca gttctacatg caaatgaccc cacccacaac acttacgatg | 720 |
| tgtccttcgt gtgagcgtgt ggcagtccca ccatccgctg cagcatcagc cgttgatccg | 780 |
| gctaggccta ctcatcagat ggctgctccc aatcatcaca gacccatccc catcaaccct | 840 |
| tgggccccg ctgctgccat ccctcatgga ccctttgatg cactccgtcc tcgatcgtga | 900 |

<210> SEQ ID NO 162
<211> LENGTH: 888
<212> TYPE: DNA
<213> ORGANISM: Phaseolus vulgaris

<400> SEQUENCE: 162

| | |
|---|---|
| atgatggttc aaaaggaaga tttgggtttg agtctgagcc tcaacttccg tcacaatatc | 60 |
| ccaaatcctc aacatcttac actcatctcc tcctcaactc attcatcttc cccttcggct | 120 |
| tcaaatcctt ttaaaccctc ttggaacgac cctttcgcct cttcggatcg aaactcggac | 180 |
| acatgcagag gcgaaacccg atctttcctc cgcggaatcg acgtgaatcg gttaccttcg | 240 |
| gccgtggaca tggaagagga gcgggagtt tcgtccccga cagcaccgt ctcgagcgtg | 300 |
| agcggaaagc ggagcgagcg agaacccaac ggtgaagaac acgacatgaa cagagcgtgt | 360 |
| tcccgcggaa tcagcgacga agaagacggc gaaacctcaa ggaaaaaact ccgactctcc | 420 |
| aaagaccaat cagctattct tgaagaaagt ttcaaagagc acaataccct caacccgaag | 480 |
| caaaagctgg cactggcaaa acagctaggc cttctaccaa gacaagttga ggtgtggttc | 540 |
| cagaaccgga gggcaaggac taaactgaag cagactgagg tggattgcga ggtgttgaaa | 600 |
| aggtgttgcg agaatctgac ggaggaaaat agaaggttgc agaaggaagt tcaggagctt | 660 |
| agagcactca aactttcccc tcagttttac atgcaaatga ccccacccac cacactcact | 720 |
| atgtgcccat cttgcgagcg ggtggctgtt ccgtcctccg ccgttgatgc cgccacacgt | 780 |

| | |
|---|---|
| catcatccca tggcccaggc ccagacacac ggtcggccca tacccattgg gccgtgggct | 840 |
| tcggctggtc ccattccgca gcgggccttt gatggtttcc accagtga | 888 |

<210> SEQ ID NO 163
<211> LENGTH: 1002
<212> TYPE: DNA
<213> ORGANISM: Morus notabilis

<400> SEQUENCE: 163

| | |
|---|---|
| atgggtgaga aagatgatga tgggttgggg ttggggttga gtttgagctt gggaatattt | 60 |
| ggtggaacta caacaacagc aacaactcac actactactc atcaaccggg ttcttcttct | 120 |
| tcttcttctc tcaagtttaa tctcatgcaa aagccttctt cttcttccat gcaatatcaa | 180 |
| caaaagacta ctaataccac cgccactcct tggaatgaaa tctttcagct ttctgatcgg | 240 |
| aactccgacg gcaggtcgtt cctccggggg ctcgacgtga acctgacacc ctcgtttgcg | 300 |
| gcggcggcgg cggcggatta cgatgaggaa acggcgtgt cgtctccgaa cagcacgata | 360 |
| tcgagcataa gcgggaagaa gagcgagaga gaggcaccgg gaggagagga ggccgaggag | 420 |
| ggagacagag actcctgctc tcgcggcggc ggaggaagtg atgacgaaga cggcggaaat | 480 |
| ggcggcggcg acgcctccag aaagaagctc cgcctcacca aggaccagtc tctcatcctt | 540 |
| gaagaaactt tcaaggagca caacactctc aacccgaagc aaaagctggc gttggctaag | 600 |
| gaactgaacc tgcggccaag acaagtggag gtgtggtttc agaacaggag ggcaaggact | 660 |
| aaattgaagc agacagaagt ggactgtgag tatctaaaga ggtgctgtga aatctgact | 720 |
| gaagagaaca ggaggctgca aaaggaagtg caagagctta gagcattaaa gttgtcccca | 780 |
| cagctctaca tgcacatgag ccctcccacc accctcacaa tgtgcccttc atgtgagcgt | 840 |
| gtggcggcct cgtcgtcgtt gtcctctact gctgctgccg ctccaaacgg ttcaaaccgg | 900 |
| cagcccgccg ttcccagcat cccacggcct gtgcccatta cccgtgggc cgcattgcca | 960 |
| atcccacacc ggccgttgga tacacctgcc tctaggtcct aa | 1002 |

<210> SEQ ID NO 164
<211> LENGTH: 972
<212> TYPE: DNA
<213> ORGANISM: Erythranthe guttata

<400> SEQUENCE: 164

| | |
|---|---|
| atgatgacgg ccggaaaaga agatttgggg ctgagtttga gcctgacctt cccgccggag | 60 |
| aagaaggccg tttcgaatat tccgagctca ctgcacctca atctcatgcc ttcttcgcct | 120 |
| tctcccaatt tcaccatttt caataataat ttcaattgga cgtcgacgca acaagctgct | 180 |
| gctgctttcc ccttctcaga tcggagctcg gagacatgca gagtggagac gacgaggtct | 240 |
| tttctgaaag gaatcgatgt caactgcctc ccgtcggcgg cggcggcgga ggaggaagag | 300 |
| gaggaggaag gcggcggcgt ctcctcccccc aacagcacga tctcaagcgt gagcgggaag | 360 |
| cggagcgaga gggaagacgc cacggaggag cacgacggcg agagagcttg ctcccgcggc | 420 |
| atcagcgacg aagaagacgc tgagaacgcc cggaaaaagc tccgcctctc caaagaccag | 480 |
| tccgccactc tcgaagaaag cttcaagaa cacaacacac tcaatcccaa gcaaaagatg | 540 |
| gctttggcta aagattagg gctaaggcca agacaagttg aagtctggtt ccaaaacaga | 600 |
| agggctagga caaactgaa gcaaacagag gttgattgcg agttcctaaa gagatgctgc | 660 |
| gaaaacctaa cagaagagaa cagaaggctg caaaagagg tccaagaact aagggcactt | 720 |
| aagctatccc cacagttcta catgcagatg acccctccaa ctactctcac catgtgccct | 780 |

| | |
|---|---|
| tcttgcgaga gagtcgcggt gccgacaatg ggggcccac cgtcgaacgg cggccgagca | 840 |
| ccaccagctg cgtccgctgc cgcggcagtt cagccgcggc cgatcacatt caatccgtgg | 900 |
| gctgccgtca tgcctagtca gcagcagcag cagctgcacc ggccgttcga tgctattatg | 960 |
| cattcgagat ga | 972 |

<210> SEQ ID NO 165
<211> LENGTH: 864
<212> TYPE: DNA
<213> ORGANISM: Eucalyptus grandis

<400> SEQUENCE: 165

| | |
|---|---|
| atgatggtgg agagggaaga tctgggcttg tctctgagct tgagcttctc tgacagcagt | 60 |
| cggccttccc agctcggcgc ctctcctttc gggttcaacc tctacaagcc atctcaccgc | 120 |
| gactgcgaga ccttcgcttc attagatcgg atctcggagg cggatgcgcg ccgtccctg | 180 |
| cggggcatcg acgtgaaccg gccgccgccg tcggcggcgg actgcgagga gcaggaggag | 240 |
| gcggggggtgt cgtccccgaa cagcactatc tcgagcgtca gcgggaagag gggcgagagg | 300 |
| gagatggtca gcggcgggga ggacaacgag gcggagaggg actgcagccg cggaggcagc | 360 |
| gacgaggagg acggcgagaa ctcgaggaag aagctgaggc tgtccaagga tcagtcggcc | 420 |
| gtcttggagg agagcttccg agagcacaac actctgaatc ccaagcaaaa gctggcgttg | 480 |
| gctaagcagc taggcctgcg acctagacaa gtagaagtct ggtttcagaa ccgcagagca | 540 |
| cggaccaagt tgaagcagac ggagatagac tgcgagttcc tgaagaggtg ctgcgagaac | 600 |
| ctgacggagg agaaccggcg gctgcagaag gaggtccagg agctgcgcgc tctcaagctc | 660 |
| tccctcagt tctacatgca catgcccct ccaccaccc ttaccgtctg ccccaactgc | 720 |
| gagcgcgtcg gggcggccgc accgccgctc ccatccgccg gcggcggcgg caggcccgcc | 780 |
| caccatcggg agccggtgcc catgatccca tgggccgcgc ggcccggccc ggtctcgcac | 840 |
| ggggctctcc ggcccaggac gtga | 864 |

<210> SEQ ID NO 166
<211> LENGTH: 918
<212> TYPE: DNA
<213> ORGANISM: Arabis alpina

<400> SEQUENCE: 166

| | |
|---|---|
| atgggtgaga gagatgatgg attggggtta agtttgagct tgggattagg gtttaatcaa | 60 |
| aaggagcaat ctccgaggtt aaatccaatg cagtttggtt cttattcttc ttcgtcttca | 120 |
| cacatgcata tgcagagcaa tcatattaac cattctcaaa agattcagaa tagttggact | 180 |
| cacatgtttc aatcttcaga gagaaactct gacgtgagat catttctccg ggggattgac | 240 |
| gtgaacagag caccatcaac ggtggtggtt gacgtggagg aagacgccgg agtgtcgtct | 300 |
| ccgaacagca ccgtttcgag cgtgatgagt gggaagagaa cgagcgagt tgccacggtg | 360 |
| gtcggaggag gaggagttat agaagatcac gacgtggaga gagcttcttc ctcgcttggt | 420 |
| ggtggtagtg atgatgaaga cggtggtgga aatggagacg acggttctag gaagaaacta | 480 |
| cggttgtcta agaacaagc tttggttctt gaagaaactt ttaaagaaca tagcactctt | 540 |
| aatccgaagc aaaagatggc tttggctaaa caattgaatc tgaggacaag gcaagttgaa | 600 |
| gtgtggttcc aaaaccgaag ggcaaggacg aagctgaagc aaacggaagt ggattgtgaa | 660 |
| tatctaaaaa gatgttgtga gaatctaacg gaagagaatc ggagattgca aaaggaagtg | 720 |

```
agtgagctta gggctttaaa gctttcacct catttataca tgcacatgaa acctcccact    780
acactcacaa tgtgtccttc gtgtgagcga gtcgctgcta catcgtcatc ttcctcggtg    840
gctcctcctg cgatgaattc gtcgtcgccg tgggctgcga ttcctctccg gcaacgacct    900
gctgctggtt ctcattag                                                 918
```

<210> SEQ ID NO 167
<211> LENGTH: 885
<212> TYPE: DNA
<213> ORGANISM: Cucumis sativus

<400> SEQUENCE: 167

```
atgggcggga gagatgatga cgtgggactc actttgagtt taggttttgg tgttacgact     60
cagtccactc acatgcaaag gccgtcgtcg atgcataatc accacctccg caagactcat    120
tggaacgagc ttttttcaatt ttctgatcga aacgccgatt cgaggtcgtt tcttagagga    180
atcgacgtga atcggttgcc gacgggcgtg gacggcgagg aagagaacgg cgtttcatct    240
ccgaacagta cgatttctag cattagtgga aagaaagcg agagagaagc ggctggagac    300
gaggcggagg cggaggctga ggcggaggct gaagcggaag cggaagcgga agccgaaaga    360
gcctcgtgct cgcgagggag tgatgatgaa gacggcggag gcgggacgg tgacgcgtcg    420 agaagaagc tgaggctatc gaaggaacag tcaatggttc ttgaagagac gttcaaagag    480
cacaatacgc tgaatcctaa gcaaaagctg gcacttgcaa agcagctgaa tctgacacca    540
agacaagtgg aggtgtggtt caaaacaga agggcaagga ccaaattgaa gcaaacagaa    600
gtggattgtg agtacttgaa gaggtgctgt gagaatctaa cagaggaaaa caggaggcta    660
cagaaggagg tgcaagagtt gagagcactc aagctttctc cacagcttta tgcacatg    720 aatcctccta ccaccctcac catgtgccct caatgtgagc gtgtggcggt ttcttcatct    780
tcttcgacct cagctgctac caccactcgc catcaagcag cagctggtgt gcagcgtccc    840
tctatggcca tcaacccgtg ggcagtgttg ccgattcaac gttga                    885
```

<210> SEQ ID NO 168
<211> LENGTH: 876
<212> TYPE: DNA
<213> ORGANISM: Gossypium raimondii

<400> SEQUENCE: 168

```
atgggtgata aagatgatgg tttggggttg agtttgagct tgggttgtgg tcagaatcag     60
ccttcttcta aattaaattt catgttttta gcttcaaacc ccttgcaaaa tcttcagcag    120
aacaaaactt ggaaccgact gtgtctgtct tctgatggac acatggatac aggatcattt    180
cttcgaggaa tcgatgtgaa ccgagcaccg gcagcaacgg tcgattgcga ggaagaaggt    240 ggggggggtgt cgtcgcccaa cagcactatt tccaccataa gtgggaagaa aaacgagaga    300
gatcatgtcg ctgatgaaac cgaggccgag agagattctt gctctcgtgc cagcgatgac    360
gaagatggcg gtggcaatgc tggtggcggg gatgcctcga ggaagaagct taggctttca    420
aaggaacaat ccatggtgct ggaagaaact ttcaaggagc atagtactct gaatccgaaa    480
caaaagttgg cattggctaa gcaattgaat ctcaagccca gcaagtggaa ggtttggttt    540
caaaacagaa gggcaaggac aaagttgaag cagacggaag tcgactgcga gtatctaaaa    600
aggtgttgcg agaatctaac ggaggagaac cggaggttgc ataaggaagt acaagaactt    660
agagcactga aactatcccc acagctttac atgcacatga aacctcctac gacactcacc    720
atgtgcccgt cttgtgaacg tgtggctgcc cctggttctt ctgctgtgaa gcgttgccaa    780
```

```
acgagccctg accgtcaaca gccagtgcct gttaaccctt gggctgcaat gccgattact      840
catcaacctt tcaatgcccc tgcatctaga tcataa                                876

<210> SEQ ID NO 169
<211> LENGTH: 900
<212> TYPE: DNA
<213> ORGANISM: Glycine max

<400> SEQUENCE: 169
atgatggttc aaaaggaaga tttgggtttg agtttaagcc tcaacttccc tcatcacaat       60
accccaaatc ctcaacatcc gagtctcatg tcatcctcta ctcattcctc ttctccttct      120
ggttgcaacc ctcaaaaacc ctcttggaac gaggctttca cttcttcgga tcgaaactcc      180
gacacatgca gaggcgaaac gcgatcgttc ctgcgcggaa tcgacgtgaa ccggttacct      240
tccgccgtgg acaccgagga ggaaacggga gtttcgtctc cgaacagcac cgtctctagc      300
gtgagtggaa acgtagcgag agagaagaa ccgaacggcg aagaaacgga catggacaga       360
gcctgttccc gcggaatcag cgacgaggaa gacgctgaaa ccgcaaggaa aaaacttaga      420
ctctccaaag accaatccgc tatactcgaa gaaagcttca agaacacaa caccctcaac       480 cccaagcaaa aattggcact ggcgaaacag ctaggacttc gacctagaca agtggaggtg      540
tggttccaga acagaagagc aaggactaag ctgaagcaaa ccgaggtgga ctgcgaagta      600
ttgaaaaggt gctgcgagaa tctgacggag gaaaatagaa ggttgcagaa ggaggttcag      660
gagcttagag cactgaaact tccccacag ttttacatgc aaatgacccc acccacgacg       720
ctcaccatgt gccctcttg cgagcgtgtg gctgttccgt cctccgccgt cgatgctgcc       780
acgcgtcatc atcccatggc ccaggccag gcccaggccc agattcggca caggcccatt       840
ggcccgtggg cttccgcctc tcccattacg caccggccgt tgatgtcttc caccactga      900

<210> SEQ ID NO 170
<211> LENGTH: 960
<212> TYPE: DNA
<213> ORGANISM: Prunus persica

<400> SEQUENCE: 170
atgatggttg agagagatca agatttgggt ttgagtctga gcttgagttt tcctcagacc       60
cacaaccacc acaacaacaa caacaacaac agcagcagca ccaccagcac ccttcagctc      120
aatctcatgc cttctttggc ccctacttct gcttcttctc cttctgggtt tcttcctcaa      180
aaaccctctt ggaatgaggc cttgatttct tcagatcgaa actccaactc cgaaacgttc      240
cgggtcgggc cccgatcgtt ccttcggggc atcgacgtga accggttgcc ttcaacgggc      300
gactgcgaag acgaggcggg cgtgtcgtcg cccaacagca cggtgtcgag cgtgagcggc      360
aagcggagcg agagagaggc caatggcgaa gatctcgaca tcgagactcg aggcatcagc      420
gatgaagaag acggcgagac ctctagaaag aagctcaggc tctccaagga ccagtccgcc      480
attctcgaag agagcttcaa ggagcacaac actctcaacc caaagcaaaa gttggcgttg      540
gctaaacagc ttggcctccg gcctagacaa gtggaagtct ggtttcagaa cagaagagca      600
aggactaagt tgaagcaaac ggaggtggac tgtgagttct tgaagaggtg ctgtgagaat      660
ctgacagagg agaacaggcg gttgcagaag gaggttcagg agctgagagc actgaaactt      720
tccccacagt tctacatgca aatgacccca cccacgacac tcaccatgtg ccctcgtgt       780 gagcgtgtcg cggtcccacc caactcctca tcctcaaccg tcgagcccg gccccacccc       840
```

| | |
|---|---|
| caccccacc cccaaatggg ttcggtccag acccggcccg tccccatcaa cccgtgggca | 900 |
| tccgccaccc caatccccca ccggccgctg ccgttcgaag ccttccacac ccggacgtaa | 960 |

<210> SEQ ID NO 171
<211> LENGTH: 960
<212> TYPE: DNA
<213> ORGANISM: Zea mays

<400> SEQUENCE: 171

| | |
|---|---|
| atggatatta tggcgcttaa tgcgagagac gaggagcagt acgggaacaa ccatctcggg | 60 |
| ctcgggctga gcctcagcct cggcctcggc gtcgccaccg cggctccggt cgaggtcgag | 120 |
| cccccgccac cgccgcggca gcagcagcag cgagctatca gcgtcgcgcc catcacctcc | 180 |
| ctccccgcgc cgcagtggtg gaagtggaac ggccccggtc tcttcttcgg acgacaatg | 240 |
| gatcagcagc agcagccggc ggccgcgcgc cacgccacg atgccgtt cctgcggggg | 300 |
| gtggacgtga accgggcccc tgccggggat accaggaggg gtagctgcag cgaggacgac | 360 |
| gaggagcctg gcggcgcgtc gtcgtcgcca acagcacgc tctccagcag cctcagcggg | 420 |
| aagcgcgcag ctccggcgag gagcggcgga gaggtggccg accacacccc gagagccgga | 480 |
| ggcggcagcg acgacgagga ctccggcggt gggtcgcgca agaagctccg cctgtccaag | 540 |
| gaccaggccg ccgtcctcga ggagagcttc aaggagcata acacactcaa ccccaagcag | 600 |
| aaggcggcgc tggcgaagca gctgaacctg aagccgcgtc aggtggaggt gtggttccag | 660 |
| aaccgcagag ccaggacgaa gctgaagcag acggaggtgg actgcgagtt cctgaagcgc | 720 |
| tgctgcgaga cgctgacgga ggagaaccgg cggctgcagc gggaggtggc ggagctgcgc | 780 |
| gtgctcaagc tcgtggcgcc gcaccactac gcgcgcatgc cgccgcccac cacgctcacc | 840 |
| atgtgcccct cctgcgagcg cctcgcctcc cgtccgcgt ccgccgacca ggcgggccgt | 900 |
| gcagggccct gctggggccc tctccccgtg ttcgtcgacg gcccagcccg gaggccgtga | 960 |

<210> SEQ ID NO 172
<211> LENGTH: 897
<212> TYPE: DNA
<213> ORGANISM: Populus trichocarpa

<400> SEQUENCE: 172

| | |
|---|---|
| atgggtgata aaaatgatgg actgggcttg agtttgagct tgggattcga tgctacacaa | 60 |
| caaaatcatc aacagcagcc ttctttgaag ctaaatctca tgcccgtacc ttcacaaaac | 120 |
| aatcatagaa aaacttcctt gactgacctc tttcaatcat cagatagagc atgtggtacg | 180 |
| aggtttttc aacgaggaat tgacatgaac agggtgccag ctgcagtgac agattgtgat | 240 |
| gacgaaactg ggtttcttc accaaacagt acgctatcca gcttaagtgg taaaagaagc | 300 |
| gaaagagaac agattggaga agaaacagaa gcggagaggg cctcttgctc tcgtgacagt | 360 |
| gatgatgaag atggtgctgg tggtgatgct tctaggaaga agctgagact ctcaaaggaa | 420 |
| cagtctttag tgcttgaaga ctttcaag gaacataata ctcttaatcc caaggagaag | 480 |
| ctggccttgg caaagcagtt gaatctcagg cctaggcaag tggaggtgtg gtttcagaac | 540 |
| cgaagagcaa ggactaagtt gaagcaaact gaagtcgatt gcgagtacct aaagaggtgc | 600 |
| tgtgaaaatc taacagagga gaacaggagg ttacagaagg aggtgcaaga gcttagagca | 660 |
| ctgaaacttt ccctcagct ctacatgcac atgaaccctc ccaccaccct caccatgtgc | 720 |
| ccttcatgcg agcgagttgc tgtctcgtca gcctcatcat cttctgctgc tgccgcgtcc | 780 |
| tctgctcttg ctccaactgc ctcaacccgc caaccacaac gacccgtgcc cattaaccct | 840 |

| | | |
|---|---|---|
| tgggcaacaa tgcccgtcca ccaacgaact tttgatgctc ctgcttccag gtcatga | | 897 |

<210> SEQ ID NO 173
<211> LENGTH: 1059
<212> TYPE: DNA
<213> ORGANISM: Setaria italica

<400> SEQUENCE: 173

| | |
|---|---|
| atggagatgg cggttaatgc gagggatcgg gagcagcacg gccacggcgg tctcgggctc | 60 |
| gggctcagcc tcagcctgag catcgccacc gcggcaccgc cgccgcagca gcagcgagcc | 120 |
| atcagcgtcg cgcccatctc ctcccacccc gcgccgccgg tgccgccgca gccgcagtgg | 180 |
| tggaacggcg gcgccggtct cttcttctct ccctcctccg ggatggtgga tcgatctatg | 240 |
| gagaggaagc tgcagcagca gccggcagtg cggcggcgt gccacggcca cgagatgccg | 300 |
| ttcctgcggg ggatcgacgt gaaccgggcg ccggccgccg gggagagccg gaggggctgc | 360 |
| tgcagcgagg acgaggagcc cgccgcgtcg tctcccaaca gcacgctgtc cagcctcagc | 420 |
| gggaagcggc ccgcggcgac gaggagcggg gacctagagg gcgaccacac cccgagggcc | 480 |
| ggcggcgcca cgacgacga ggacagtggc gccggcggcg ggtcccgcaa gaagctccgc | 540 |
| ctgtccaagg accaggccgc cgtcctcgag gagagcttca aggagcacaa caccctcaac | 600 |
| cccgtacgta ctctccccaa gcagaaggcg cgctggcga agcagctgaa cctgaagccg | 660 |
| cgccaggtcg aggtctggtt ccagaaccgc agagccagga cgaagctgaa gcagacggag | 720 |
| gtggactgcg agttcctgaa gcgctgctgc gagacgctga cggaggagaa ccggcggctg | 780 |
| cagcgggagg tggcggagct gcgcgcgctc aagctcgtcg cgccgcacca gtacgcgcgc | 840 |
| atgccgccgc ccaccacact caccatgtgc ccctcctgcg agcgcctcgc caccgccgac | 900 |
| gaggccggcc gcgcggcccg tcccgccgcg cccacggggc cctggggccc cgtccccgtg | 960 |
| cgccccgtgt tcgtcgacgg catgatcatc gacgcagacg cgcgccccga acaccccaac | 1020 |
| agcggtggac cggtggttgt agaaaaaaaa agttggtag | 1059 |

<210> SEQ ID NO 174
<211> LENGTH: 891
<212> TYPE: DNA
<213> ORGANISM: Medicago truncatula

<400> SEQUENCE: 174

| | |
|---|---|
| atgagtattg aaaaggaaga ttttggtttg agcctaagtt tgagctttcc tcaaaatcca | 60 |
| ccaaatcctc aataccttaa tcttatgtct tcttcaactc attcatattc tccttctact | 120 |
| ttcaatcctc aaaaaccttc ttggaatgat gtttttactt cttcagatcg ggattcggag | 180 |
| acatgcagaa tcgaagaacg tcctttaatt ctccgaggaa tcgatgtgaa tcggttacct | 240 |
| tcaggtgctg attgtgaaga agaagcagga gtttcatcac caaacagcac cgtttcaagt | 300 |
| gtgagtggta aagaagcga agagaagtt accggtgaag atcttgacat ggaaagagat | 360 |
| tgttcaagag gaatcagtga tgaagaagac gctgaaactt caaggaaaaa acttagactc | 420 |
| accaaagacc aatcaatcat tctcgaagag agtttcaaag aacacaacac tcttaatccc | 480 |
| aaacaaaaat tggcacttgc aaaacaattg ggacttcgtg ctagacaagt tgaagtttgg | 540 |
| tttcaaaatc gtagagcaag gactaagttg aagcaaacag aggtagattg tgaattttg | 600 |
| aaaagatgtt gtgagaatct aacgatgaa aatagacggt tgcaaaaaga agtgcaagag | 660 |
| ttaagagcat tgaaactttc cccacaattc tacatgcaaa tgcacaccacc aacaacactt | 720 |

-continued

```
accatgtgcc cctcttgtga gcgtgtcgct gttccatcat ctgccgttga tgctgccacg    780
cgtcgtcatc ctatggcttc aaatcaccct cgtacgtttt ccgtgggacc atgggccaca    840
gctgctccaa tccaacatag gacctttgat acactccgtc ctagatctta a             891
```

<210> SEQ ID NO 175
<211> LENGTH: 23
<212> TYPE: DNA
<213> ORGANISM: Artificial Sequence
<220> FEATURE:
<223> OTHER INFORMATION: Synthetic spacer

<400> SEQUENCE: 175

```
ccgtgctcga ggatagcttc cgg                                             23
```

<210> SEQ ID NO 176
<211> LENGTH: 23
<212> TYPE: DNA
<213> ORGANISM: Artificial Sequence
<220> FEATURE:
<223> OTHER INFORMATION: Synthetic spacer

<400> SEQUENCE: 176

```
ggtactcgca gtccacctcc gtc                                             23
```

<210> SEQ ID NO 177
<211> LENGTH: 23
<212> TYPE: DNA
<213> ORGANISM: Artificial Sequence
<220> FEATURE:
<223> OTHER INFORMATION: Synthetic spacer

<400> SEQUENCE: 177

```
ggagcaccca actctcaacc ctg                                             23
```

<210> SEQ ID NO 178
<211> LENGTH: 23
<212> TYPE: DNA
<213> ORGANISM: Artificial Sequence
<220> FEATURE:
<223> OTHER INFORMATION: Synthetic spacer

<400> SEQUENCE: 178

```
cctccgtctg cttcagcttc gtc                                             23
```

<210> SEQ ID NO 179
<211> LENGTH: 23
<212> TYPE: DNA
<213> ORGANISM: Artificial Sequence
<220> FEATURE:
<223> OTHER INFORMATION: Synthetic spacer

<400> SEQUENCE: 179

```
aggagcataa cacactcaac ccc                                             23
```

<210> SEQ ID NO 180
<211> LENGTH: 23
<212> TYPE: DNA
<213> ORGANISM: Artificial Sequence
<220> FEATURE:
<223> OTHER INFORMATION: Synthetic spacer

<400> SEQUENCE: 180

```
ggacgaagct gaagcagacg gag                                             23
```

<210> SEQ ID NO 181
<211> LENGTH: 23
<212> TYPE: DNA
<213> ORGANISM: Artificial Sequence
<220> FEATURE:
<223> OTHER INFORMATION: Synthetic spacer

<400> SEQUENCE: 181
aggaccaggc cgccgtcctc gag                                          23

<210> SEQ ID NO 182
<211> LENGTH: 23
<212> TYPE: DNA
<213> ORGANISM: Artificial Sequence
<220> FEATURE:
<223> OTHER INFORMATION: Synthetic spacer

<400> SEQUENCE: 182
ggaactcgca gtccacctcc gtc                                          23

<210> SEQ ID NO 183
<211> LENGTH: 166
<212> TYPE: PRT
<213> ORGANISM: Escherichia coli

<400> SEQUENCE: 183

Ser Glu Val Glu Phe Ser His Glu Tyr Trp Met Arg His Ala Leu Thr
1               5                   10                  15

Leu Ala Lys Arg Ala Trp Asp Glu Arg Glu Val Pro Val Gly Ala Val
            20                  25                  30

Leu Val His Asn Asn Arg Val Ile Gly Glu Gly Trp Asn Arg Pro Ile
        35                  40                  45

Gly Arg His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Leu Glu Pro Cys Val Met Cys Ala Gly Ala Met Ile His Ser
                85                  90                  95

Arg Ile Gly Arg Val Val Phe Gly Ala Arg Asp Ala Lys Thr Gly Ala
            100                 105                 110

Ala Gly Ser Leu Met Asp Val Leu His His Pro Gly Met Asn His Arg
        115                 120                 125

Val Glu Ile Thr Glu Gly Ile Leu Ala Asp Glu Cys Ala Ala Leu Leu
    130                 135                 140

Ser Asp Phe Phe Arg Met Arg Arg Gln Glu Ile Lys Ala Gln Lys Lys
145                 150                 155                 160

Ala Gln Ser Ser Thr Asp
                165

<210> SEQ ID NO 184
<211> LENGTH: 166
<212> TYPE: PRT
<213> ORGANISM: Artificial Sequence
<220> FEATURE:
<223> OTHER INFORMATION: Synthetic tRNA-specific adenosine deaminase

<400> SEQUENCE: 184

Ser Glu Val Glu Phe Ser His Glu Tyr Trp Met Arg His Ala Leu Thr
1               5                   10                  15

Leu Ala Lys Arg Ala Arg Asp Glu Arg Glu Val Pro Val Gly Ala Val
            20                  25                  30

Leu Val Leu Asn Asn Arg Val Ile Gly Glu Gly Trp Asn Arg Ala Ile
                35                  40                  45

Gly Leu His Asp Pro Thr Ala His Ala Glu Ile Met Ala Leu Arg Gln
 50                  55                  60

Gly Gly Leu Val Met Gln Asn Tyr Arg Leu Ile Asp Ala Thr Leu Tyr
 65                  70                  75                  80

Val Thr Phe Glu Pro Cys Val Met Cys Ala Gly Ala Met Ile His Ser
                 85                  90                  95

Arg Ile Gly Arg Val Val Phe Gly Val Arg Asn Ala Lys Thr Gly Ala
                100                 105                 110

Ala Gly Ser Leu Met Asp Val Leu His Tyr Pro Gly Met Asn His Arg
            115                 120                 125

Val Glu Ile Thr Glu Gly Ile Leu Ala Asp Glu Cys Ala Ala Leu Leu
        130                 135                 140

Cys Tyr Phe Phe Arg Met Pro Arg Gln Val Phe Asn Ala Gln Lys Lys
145                 150                 155                 160

Ala Gln Ser Ser Thr Asp
                165

<210> SEQ ID NO 185
<211> LENGTH: 166
<212> TYPE: PRT
<213> ORGANISM: Artificial Sequence
<220> FEATURE:
<223> OTHER INFORMATION: Synthetic tRNA-specific adenosine deaminase

<400> SEQUENCE: 185

Ser Glu Val Glu Phe Ser His Glu Tyr Trp Met Arg His Ala Leu Thr
1                5                  10                  15

Leu Ala Lys Arg Ala Trp Asp Glu Arg Glu Val Pro Val Gly Ala Val
                20                  25                  30

Leu Val Leu Asn Asn Arg Val Ile Gly Glu Gly Trp Asn Arg Ser Ile
                35                  40                  45

Gly Leu His Asp Pro Thr Ala His Ala Glu Ile Met Ala Leu Arg Gln
 50                  55                  60

Gly Gly Leu Val Met Gln Asn Tyr Arg Leu Ile Asp Ala Thr Leu Tyr
 65                  70                  75                  80

Val Thr Phe Glu Pro Cys Val Met Cys Ala Gly Ala Met Ile His Ser
                 85                  90                  95

Arg Ile Gly Arg Val Val Phe Gly Val Arg Asn Ala Lys Thr Gly Ala
                100                 105                 110

Ala Gly Ser Leu Met Asp Val Leu His Tyr Pro Gly Met Asn His Arg
            115                 120                 125

Val Glu Ile Thr Glu Gly Ile Leu Ala Asp Glu Cys Ala Ala Leu Leu
        130                 135                 140

Cys Tyr Phe Phe Arg Met Arg Arg Gln Val Phe Asn Ala Gln Lys Lys
145                 150                 155                 160

Ala Gln Ser Ser Thr Asp
                165

<210> SEQ ID NO 186
<211> LENGTH: 166
<212> TYPE: PRT
<213> ORGANISM: Artificial Sequence
<220> FEATURE:
<223> OTHER INFORMATION: Synthetic tRNA-specific adenosine deaminase

<400> SEQUENCE: 186

Ser Glu Val Glu Phe Ser His Glu Tyr Trp Met Arg His Ala Leu Thr
1               5                   10                  15

Leu Ala Lys Arg Ala Leu Asp Glu Arg Glu Val Pro Val Gly Ala Val
            20                  25                  30

Leu Val Leu Asn Asn Arg Val Ile Gly Glu Gly Trp Asn Arg Ala Ile
        35                  40                  45

Gly Leu His Asp Pro Thr Ala His Ala Glu Ile Met Ala Leu Arg Gln
50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
            100                 105                 110

Ala Gly Ser Leu Met Asp Val Leu His Tyr Pro Gly Met Asn His Arg
        115                 120                 125

Val Glu Ile Thr Glu Gly Ile Leu Ala Asp Glu Cys Asn Ala Leu Leu
    130                 135                 140

Cys Tyr Phe Phe Arg Met Arg Arg Gln Val Phe Asn Ala Gln Lys Lys
145                 150                 155                 160

Ala Gln Ser Ser Thr Asp
                165

<210> SEQ ID NO 187
<211> LENGTH: 166
<212> TYPE: PRT
<213> ORGANISM: Artificial Sequence
<220> FEATURE:
<223> OTHER INFORMATION: Synthetic tRNA-specific adenosine deaminase

<400> SEQUENCE: 187

Ser Glu Val Glu Phe Ser His Glu Tyr Trp Met Arg His Ala Leu Thr
1               5                   10                  15

Leu Ala Lys Arg Ala Leu Asp Glu Arg Glu Val Pro Val Gly Ala Val
            20                  25                  30

Leu Val Leu Asn Asn Arg Val Ile Gly Glu Gly Trp Asn Arg Ala Ile
        35                  40                  45

Gly Leu His Asp Pro Thr Ala His Ala Glu Ile Met Ala Leu Arg Gln
50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
            100                 105                 110

Ala Gly Ser Leu Met Asp Val Leu His Tyr Pro Gly Met Asn His Arg
        115                 120                 125

Val Glu Ile Thr Glu Gly Ile Leu Ala Asp Glu Cys Asn Ala Leu Leu
    130                 135                 140

Cys Tyr Phe Phe Arg Met Pro Arg Gln Val Phe Asn Ala Gln Lys Lys
145                 150                 155                 160

Ala Gln Ser Ser Thr Asp
                165

```
<210> SEQ ID NO 188
<211> LENGTH: 228
<212> TYPE: PRT
<213> ORGANISM: Rattus norvegicus

<400> SEQUENCE: 188
```

Ser Ser Glu Thr Gly Pro Val Ala Val Asp Pro Thr Leu Arg Arg Arg
1               5                   10                  15

Ile Glu Pro His Glu Phe Glu Val Phe Phe Asp Pro Arg Glu Leu Arg
            20                  25                  30

Lys Glu Thr Cys Leu Leu Tyr Glu Ile Asn Trp Gly Gly Arg His Ser
        35                  40                  45

Ile Trp Arg His Thr Ser Gln Asn Thr Asn Lys His Val Glu Val Asn
    50                  55                  60

Phe Ile Glu Lys Phe Thr Thr Glu Arg Tyr Phe Cys Pro Asn Thr Arg
65                  70                  75                  80

Cys Ser Ile Thr Trp Phe Leu Ser Trp Ser Pro Cys Gly Glu Cys Ser
                85                  90                  95

Arg Ala Ile Thr Glu Phe Leu Ser Arg Tyr Pro His Val Thr Leu Phe
            100                 105                 110

Ile Tyr Ile Ala Arg Leu Tyr His His Ala Asp Pro Arg Asn Arg Gln
        115                 120                 125

Gly Leu Arg Asp Leu Ile Ser Ser Gly Val Thr Ile Gln Ile Met Thr
    130                 135                 140

Glu Gln Glu Ser Gly Tyr Cys Trp Arg Asn Phe Val Asn Tyr Ser Pro
145                 150                 155                 160

Ser Asn Glu Ala His Trp Pro Arg Tyr Pro His Leu Trp Val Arg Leu
                165                 170                 175

Tyr Val Leu Glu Leu Tyr Cys Ile Ile Leu Gly Leu Pro Pro Cys Leu
            180                 185                 190

Asn Ile Leu Arg Arg Lys Gln Pro Gln Leu Thr Phe Phe Thr Ile Ala
        195                 200                 205

Leu Gln Ser Cys His Tyr Gln Arg Leu Pro Pro His Ile Leu Trp Ala
    210                 215                 220

Thr Gly Leu Lys
225

```
<210> SEQ ID NO 189
<211> LENGTH: 199
<212> TYPE: PRT
<213> ORGANISM: Homo sapiens

<400> SEQUENCE: 189
```

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45

Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Trp Gly Cys Ala Gly Glu Val Arg Ala

```
                100                 105                 110
Phe Leu Gln Glu Asn Thr His Val Arg Leu Arg Ile Phe Ala Ala Arg
            115                 120                 125

Ile Tyr Asp Tyr Asp Pro Leu Tyr Lys Glu Ala Leu Gln Met Leu Arg
        130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn
        195

<210> SEQ ID NO 190
<211> LENGTH: 621
<212> TYPE: DNA
<213> ORGANISM: Petromyzon marinus

<400> SEQUENCE: 190
acagatgcag agtatgtgag aattcacgaa aagctggaca tctatacctt caagaagcag      60
ttctttaaca ataagaagtc tgtgagccat aggtgctacg tgctgttcga gctgaagaga     120 agggtgaaa gaagggcatg tttttggggg tatgctgtga acaagcccca gtctggaact      180
gagagaggca ttcacgccga aattttcagc atcagaaagg tggaggaata cctgagggat     240
aaccctggac agtttacaat taattggtat tctagctggt ctccatgcgc tgactgtgcc     300
gagaagatcc tggaatggta caaccaggag ctgagaggaa atggccatac cctgaagatt     360
tgggcctgca agctgtacta tgaaaagaac gcaagaaatc agatcggact gtggaacctg     420
agggataatg gtgtggggct gaacgtgatg gtgtccgagc actatcagtg ctgtagaaag     480
attttcattc agtcctcaca taatcagctg aacgagaata gatggctgga aaagactctg     540
aagagggctg agaagagaag gtccgaactg tcaattatga tccaggtgaa gatcctgcac     600
accactaagt cacctgccgt g                                               621

<210> SEQ ID NO 191
<211> LENGTH: 160
<212> TYPE: PRT
<213> ORGANISM: Artificial Sequence
<220> FEATURE:
<223> OTHER INFORMATION: Synthetic FERNY deaminase

<400> SEQUENCE: 191

Phe Glu Arg Asn Tyr Asp Pro Arg Glu Leu Arg Lys Glu Thr Tyr Leu
1               5                   10                  15

Leu Tyr Glu Ile Lys Trp Gly Lys Ser Gly Lys Leu Trp Arg His Trp
            20                  25                  30

Cys Gln Asn Asn Arg Thr Gln His Ala Glu Val Tyr Phe Leu Glu Asn
        35                  40                  45

Ile Phe Asn Ala Arg Arg Phe Asn Pro Ser Thr His Cys Ser Ile Thr
    50                  55                  60

Trp Tyr Leu Ser Trp Ser Pro Cys Ala Glu Cys Ser Gln Lys Ile Val
65                  70                  75                  80

Asp Phe Leu Lys Glu His Pro Asn Val Leu Glu Ile Tyr Val Ala Arg
                85                  90                  95

Leu Tyr Tyr His Glu Asp Glu Arg Asn Arg Gln Gly Leu Arg Asp Leu
```

```
                100             105             110
Val Asn Ser Gly Val Thr Ile Arg Ile Met Asp Leu Pro Asp Tyr Asn
            115                 120                 125

Tyr Cys Trp Lys Thr Phe Val Ser Asp Gln Gly Gly Asp Glu Asp Tyr
            130                 135                 140

Trp Pro Gly His Phe Ala Pro Trp Ile Lys Gln Tyr Ser Leu Lys Leu
145                 150                 155                 160

<210> SEQ ID NO 192
<211> LENGTH: 207
<212> TYPE: PRT
<213> ORGANISM: Artificial Sequence
<220> FEATURE:
<223> OTHER INFORMATION: Synthetic cytosine deaminase

<400> SEQUENCE: 192

Thr Asp Ala Glu Tyr Val Arg Ile His Glu Lys Leu Asp Ile Tyr Thr
1               5                   10                  15

Phe Lys Lys Gln Phe Ser Asn Asn Lys Lys Ser Val Ser His Arg Cys
            20                  25                  30

Tyr Val Leu Phe Glu Leu Lys Arg Arg Gly Glu Arg Arg Ala Cys Phe
        35                  40                  45

Trp Gly Tyr Ala Val Asn Lys Pro Gln Ser Gly Thr Glu Arg Gly Ile
    50                  55                  60

His Ala Glu Ile Phe Ser Ile Arg Lys Val Glu Glu Tyr Leu Arg Asp
65                  70                  75                  80

Asn Pro Gly Gln Phe Thr Ile Asn Trp Tyr Ser Ser Trp Ser Pro Cys
                85                  90                  95

Ala Asp Cys Ala Glu Lys Ile Leu Glu Trp Tyr Asn Gln Glu Leu Arg
            100                 105                 110

Gly Asn Gly His Thr Leu Lys Ile Trp Val Cys Lys Leu Tyr Tyr Glu
        115                 120                 125

Lys Asn Ala Arg Asn Gln Ile Gly Leu Trp Asn Leu Arg Asp Asn Gly
    130                 135                 140

Val Gly Leu Asn Val Met Val Ser Glu His Tyr Gln Cys Cys Arg Lys
145                 150                 155                 160

Ile Phe Ile Gln Ser Ser His Asn Gln Leu Asn Glu Asn Arg Trp Leu
                165                 170                 175

Glu Lys Thr Leu Lys Arg Ala Glu Lys Arg Arg Ser Glu Leu Ser Ile
            180                 185                 190

Met Phe Gln Val Lys Ile Leu His Thr Thr Lys Ser Pro Ala Val
        195                 200                 205

<210> SEQ ID NO 193
<211> LENGTH: 228
<212> TYPE: PRT
<213> ORGANISM: Artificial Sequence
<220> FEATURE:
<223> OTHER INFORMATION: Synthetic cytosine deaminase

<400> SEQUENCE: 193

Ser Ser Lys Thr Gly Pro Val Ala Val Asp Pro Thr Leu Arg Arg Arg
1               5                   10                  15

Ile Glu Pro His Glu Phe Glu Val Phe Phe Asp Pro Arg Glu Leu Arg
            20                  25                  30

Lys Glu Thr Cys Leu Leu Tyr Glu Ile Asn Trp Gly Gly Arg His Ser
        35                  40                  45
```

```
Ile Trp Arg His Thr Ser Gln Asn Thr Asn Lys His Val Glu Val Asn
 50                  55                  60
Phe Ile Glu Lys Phe Thr Thr Glu Arg Tyr Phe Cys Pro Asn Thr Arg
 65                  70                  75                  80
Cys Ser Ile Thr Trp Phe Leu Ser Trp Ser Pro Cys Gly Glu Cys Ser
                 85                  90                  95
Arg Ala Ile Thr Glu Phe Leu Ser Arg Tyr Pro Asn Val Thr Leu Phe
            100                 105                 110
Ile Tyr Ile Ala Arg Leu Tyr His Leu Ala Asn Pro Arg Asn Arg Gln
        115                 120                 125
Gly Leu Arg Asp Leu Ile Ser Ser Gly Val Thr Ile Gln Ile Met Thr
130                 135                 140
Glu Gln Glu Ser Gly Tyr Cys Trp His Asn Phe Val Asn Tyr Ser Pro
145                 150                 155                 160
Ser Asn Glu Ser His Trp Pro Arg Tyr Pro His Leu Trp Val Arg Leu
                165                 170                 175
Tyr Val Leu Glu Leu Tyr Cys Ile Ile Leu Gly Leu Pro Pro Cys Leu
            180                 185                 190
Asn Ile Leu Arg Arg Lys Gln Ser Gln Leu Thr Ser Phe Thr Ile Ala
        195                 200                 205
Leu Gln Ser Cys His Tyr Gln Arg Leu Pro Pro His Ile Leu Trp Ala
210                 215                 220
Thr Gly Leu Lys
225
```

<210> SEQ ID NO 194
<211> LENGTH: 162
<212> TYPE: PRT
<213> ORGANISM: Artificial Sequence
<220> FEATURE:
<223> OTHER INFORMATION: Synthetic cytosine deaminase

<400> SEQUENCE: 194

```
Ser Phe Glu Arg Asn Tyr Asp Pro Arg Glu Leu Arg Lys Glu Thr Tyr
 1                   5                  10                  15
Leu Leu Tyr Glu Ile Lys Trp Gly Lys Ser Gly Lys Leu Trp Arg His
             20                  25                  30
Trp Cys Gln Asn Asn Arg Thr Gln His Ala Glu Val Tyr Phe Leu Glu
         35                  40                  45
Asn Ile Phe Asn Ala Arg Arg Phe Asn Pro Ser Thr His Cys Ser Ile
     50                  55                  60
Thr Trp Tyr Leu Ser Trp Ser Pro Cys Ala Glu Cys Ser Gln Lys Ile
 65                  70                  75                  80
Val Asp Phe Leu Lys Glu His Pro Asn Val Asn Leu Glu Ile Tyr Val
                 85                  90                  95
Ala Arg Leu Tyr Tyr Pro Glu Asn Glu Arg Asn Arg Gln Gly Leu Arg
            100                 105                 110
Asp Leu Val Asn Ser Gly Val Thr Ile Arg Ile Met Asp Leu Pro Asp
        115                 120                 125
Tyr Asn Tyr Cys Trp Lys Thr Phe Val Ser Asp Gln Gly Gly Asp Glu
130                 135                 140
Asp Tyr Trp Pro Gly His Phe Ala Pro Trp Ile Lys Gln Tyr Ser Leu
145                 150                 155                 160
Lys Leu
```

<210> SEQ ID NO 195
<211> LENGTH: 83
<212> TYPE: PRT
<213> ORGANISM: Bacillus phage AR9

<400> SEQUENCE: 195

```
Thr Asn Leu Ser Asp Ile Ile Glu Lys Glu Thr Gly Lys Gln Leu Val
1               5                   10                  15

Ile Gln Glu Ser Ile Leu Met Leu Pro Glu Glu Val Glu Val Ile
            20                  25                  30

Gly Asn Lys Pro Glu Ser Asp Ile Leu Val His Thr Ala Tyr Asp Glu
            35                  40                  45

Ser Thr Asp Glu Asn Val Met Leu Leu Thr Ser Asp Ala Pro Glu Tyr
        50                  55                  60

Lys Pro Trp Ala Leu Val Ile Gln Asp Ser Asn Gly Glu Asn Lys Ile
65                  70                  75                  80

Lys Met Leu
```

<210> SEQ ID NO 196
<211> LENGTH: 1592
<212> TYPE: DNA
<213> ORGANISM: Medicago truncatula

<400> SEQUENCE: 196

```
actgttaata attttaaac gtcagcgcac taaaaaaacg aaaagacgga cacgtgaaaa      60
taaaaaacac acactagttt atgacgcaat actattttac ttatgatttg ggtacattag    120
acaaaccgt gaaagagatg tatcagctat gaaacctgta tacttcaata cagagactta    180
ctcatatcgg atacgtacgc acgaagtatc atattaatta ttttaatttt taataaatat    240
tttatcggat acttatgtga tactctacat atacacaagg atatttctaa gatactttat    300
agatacgtat cctagaaaaa catgaagagt aaaaagtga gacaatgttg taaaaattca    360
ttataaatgt atatgattca attttagata tgcatcagta taattgattc tcgatgaaac    420
acttaaaatt atatttcttg tggaagaacg tagcgagaga ggtgattcag ttagacaaca    480
ttaaataaaa ttaatgttaa gttctttttaa tgatgtttct ctcaatatca catcatatga    540
aaatgtaata tgatttataa gaaattttt aaaaaattta ttttaataat cacatgtact    600
attttttaaa aattgtatct tttataataa tacaataata aagagtaatc agtgttaatt    660
tttcttcaaa tataagtttt attataaatc attgttaacg tatcataagt cattaccgta    720
tcgtatctta atttttttt aaaaaccgct aattcacgta cccgtattgt attgtacccg    780
cacctgtatc acaatcgatc ttagttagaa gaattgtctc gaggcggtgc aagacagcat    840
ataatagacg tggactctct tataccaaac gttgtcgtat cacaaagggt taggtaacaa    900
gtcacagttt gtccacgtgt cacgttttaa ttggaagagg tgccgttggc gtaatataac    960
agccaatcga ttttgctat aaaagcaaat caggtaaact aaacttcttc attcttttct   1020
tccccatcgc tacaaaaccg gttcctttgg aaaagagatt cattcaaacc tagcacccaa   1080
ttccgtttca aggtataatc tactttctat tcttcgatta ttttattatt attagctact   1140
atcgttaat cgatcttttc ttttgatccg tcaaatttaa attcaattag gttttgttc    1200
ttttctttca tctgattgaa atccttctga attgaaccgt ttacttgatt ttactgttta   1260
ttgtatgatt taatccttg ttttcaaag acagtcttta gattgtgatt aggggttcat    1320
ataaattttt agatttggat ttttgtattg tatgattcaa aaaatacgtc ctttaattag   1380
attagtacat ggatattttt tacccgattt attgattgtc agggagaatt tgatgagcaa   1440
```

```
gttttttttga tgtctgttgt aaattgaatt gattataatt gctgatctgc tgcttccagt    1500
tttcataacc catattcttt taaccttgtt gtacacacaa tgaaaaattg gtgattgatt    1560
catttgtttt tctttgtttt ggattataca gg                                  1592
```

<210> SEQ ID NO 197
<211> LENGTH: 2000
<212> TYPE: DNA
<213> ORGANISM: Zea mays

<400> SEQUENCE: 197

```
gtcgtgcccc tctctagaga taaagagcat tgcatgtcta aagtataaaa aattaccaca      60 tattttttg tcacacttat ttgaagtgta gtttatctat ctctatacat atatttaaac     120
ttcactctac aaataatata gtctataata ctaaaataat attagtgttt tagaggatca     180
tataaataaa ctgctagaca tggtctaaag gataattgaa tattttgaca atctacagtt     240
ttatcttttt agtgtgcatg tgatctctct gttttttttg caaatagctt gacctatata     300
atacttcatc cattttatta gtacatccat ttaggattta gggttgatgg tttctataga     360
ctaattttta gtacatccat tttattcttt ttagtctcta aattttttaa aactaaaact     420
ctattttagt tttttattta ataatttaga tataaaatga aataaaataa attgactaca     480
aataaaacaa ataccctta agaaataaaa aaactaagca aacatttttc ttgtttcgag     540
tagataatga caggctgttc aacgccgtcg acgagtctaa cggacaccaa ccagcgaacc     600
agcagcgtcg cgtcgggcca agcgaagcag acggcacggc atctctgtag ctgcctctgg     660
acccctctcg agagttccgc tccaccgttg gacttgctcc gctgtcggca tccagaaatt     720
gcgtggcgga gcggcagacg tgaggcggca cggcaggcgg cctcttcctc ctctcacggc     780
accggcagct acggggggatt cctttcccac cgctccttcg ctttcccttc ctcgcccgcc     840
gtaataaata gacacccccct ccacacccctc tttcccccaac ctcgtgttcg ttcggagcgc     900
acacacacgc aaccagatct cccccaaatc cagccgtcgg cacctccgct tcaaggtacg     960
ccgctcatcc tcccccccccc cctctctcta ccttctctag atcggcgatc cggtccatgg    1020
ttagggcccg gtagttctac ttctgttcat gtttgtgtta gagcaaacat gttcatgttc    1080
atgtttgtga tgatgtggtc tggttgggcg gtcgttctag atcggagtag gatactgttt    1140
caagctacct ggtggattta ttaatttgt atctgtatgt gtgtgccata catcttcata    1200
gttacgagtt taagatgatg gatggaaata tcgatctagg ataggtatac atgttgatgc    1260
gggttttact gatgcatata cagagatgct tttttctcg cttggttgtg atgatatggt    1320
ctggttgggc ggtcgttcta gatcggagta gaatactgtt tcaaactacc tggtggattt    1380
attaaaggat aaagggtcgt tctagatcgg agtagaatac tgtttcaaac tacctggtgg    1440
atttattaaa ggatctgtat gtatgtgcct acatcttcat agttacgagt taagatgat    1500 ggatggaaat atcgatctag gataggtata catgttgatg cgggttttac tgatgcatat    1560
acagagatgc ttttttcgc ttggttgtga tgatgtggtc tggttgggcg gtcgttctag    1620
atcggagtag aatactgttt caaactacct ggtggattta ttaatttgt atctttatgt    1680 gtgtgccata catcttcata gttacgagtt taagatgatg gatggaaata ttgatctagg    1740
ataggtatac atgttgatgt gggttttact gatgcatata catgatggca tatgcggcat    1800
ctattcatat gctctaacct tgagtaccta tctattataa taaacaagta tgttttataa    1860
ttattttgat cttgatatac ttggatgatg gcatatgcag cagctatatg tggattttt    1920
```

-continued

```
agccctgcct tcatacgcta tttatttgct tggtactgtt tcttttgtcc gatgctcacc    1980
ctgttgtttg gtgatacttc                                                2000
```

<210> SEQ ID NO 198
<211> LENGTH: 19
<212> TYPE: DNA
<213> ORGANISM: Artificial Sequence
<220> FEATURE:
<223> OTHER INFORMATION: Synthetic spacer
<220> FEATURE:
<221> NAME/KEY: misc_feature
<222> LOCATION: (1)..(19)
<223> OTHER INFORMATION: n is a, c, g, or t

<400> SEQUENCE: 198

```
nnnnnnnnnn nnnnnnnnn                                                 19
```

<210> SEQ ID NO 199
<211> LENGTH: 22
<212> TYPE: DNA
<213> ORGANISM: Artificial Sequence
<220> FEATURE:
<223> OTHER INFORMATION: Synthetic target strand
<220> FEATURE:
<221> NAME/KEY: misc_feature
<222> LOCATION: (4)..(22)
<223> OTHER INFORMATION: n is a, c, g, or t

<400> SEQUENCE: 199

```
aaannnnnnn nnnnnnnnnn nn                                             22
```

<210> SEQ ID NO 200
<211> LENGTH: 22
<212> TYPE: DNA
<213> ORGANISM: Artificial Sequence
<220> FEATURE:
<223> OTHER INFORMATION: Synthetic non-target strand
<220> FEATURE:
<221> NAME/KEY: misc_feature
<222> LOCATION: (4)..(22)
<223> OTHER INFORMATION: n is a, c, g, or t

<400> SEQUENCE: 200

```
tttnnnnnnn nnnnnnnnnn nn                                             22
```

<210> SEQ ID NO 201
<211> LENGTH: 207
<212> TYPE: PRT
<213> ORGANISM: Artificial Sequence
<220> FEATURE:
<223> OTHER INFORMATION: Synthetic HB78 polypeptide

<400> SEQUENCE: 201

```
Met Asp Ile Met Ala Leu Asn Ala Arg Asp Glu Glu Gln Tyr Gly Asn
1               5                   10                  15

Asn His Leu Gly Leu Gly Leu Ser Leu Ser Leu Gly Leu Gly Val Ala
            20                  25                  30

Thr Ala Ala Pro Val Glu Val Glu Pro Pro Pro Pro Arg Gln Gln
        35                  40                  45

Gln Gln Arg Ala Ile Ser Val Ala Pro Ile Thr Ser Leu Pro Ala Pro
    50                  55                  60

Gln Trp Trp Lys Trp Asn Gly Pro Gly Leu Phe Phe Met His Ala Gly
65                  70                  75                  80

Thr Thr Met Asp Gln Gln Gln Pro Ala Ala Ala Arg His Gly His
            85                  90                  95
```

```
Glu Met Pro Phe Leu Arg Gly Val Asp Val Asn Arg Ala Pro Ala Gly
            100                 105                 110

Asp Thr Arg Arg Gly Ser Cys Ser Glu Asp Glu Pro Gly Gly
        115                 120                 125

Ala Ser Ser Pro Asn Ser Thr Leu Ser Ser Leu Ser Gly Lys
130                 135                 140

Arg Ala Ala Pro Ala Arg Ser Gly Gly Glu Val Ala Asp His Thr Pro
145                 150                 155                 160

Arg Ala Gly Gly Gly Ser Asp Asp Glu Asp Ser Gly Gly Gly Ser Arg
                165                 170                 175

Lys Lys Leu Arg Leu Ser Lys Asp Gln Ala Ala Val Leu Glu Glu Ser
                180                 185                 190

Phe Lys Glu His Asn Thr Ser Arg Arg Arg Trp Arg Ser Ser
        195                 200                 205
```

<210> SEQ ID NO 202
<211> LENGTH: 947
<212> TYPE: DNA
<213> ORGANISM: Artificial Sequence
<220> FEATURE:
<223> OTHER INFORMATION: Synthetic HB78 nucleic acid molecule

<400> SEQUENCE: 202

```
atggatatta tggcgcttaa tgcgagagac gaggagcagt acgggaacaa ccatctcggg      60
ctcgggctga gcctcagcct cggcctcggc gtcgccaccg cggctccggt cgaggtcgag     120
cccccgccac cgccgcggca gcagcagcag cgagctatca gcgtcgcgcc catcacctcc     180
ctccccgcgc cgcagtggtg gaagtggaac ggccccggtc tcttcttcat gcatgcaggg     240
acgacaatgg atcagcagca gcagccggcg ccgcgcgcc acggccacga gatgccgttc     300
ctgcgggggg tggacgtgaa ccgggccccct gccggggata ccaggagggg tagctgcagc     360
gaggacgacg aggagcctgg cggcgcgtcg tcgtcgccaa cagcacgct ctccagcagc      420
ctcagcggga agcgcgcagc tccggcgagg agcggcggag aggtggccga ccacaccccg     480
agagccggag gcggcagcga cgacgaggac tccggcggtg gtcgcgcaa gaagctccgc      540
ctgtccaagg accaggccgc cgtcctcgag gagagcttca aggagcataa cacaagcaga     600
aggcggcgct ggcgaagcag ctgaacctga agccgcgtca ggtggaggtg tggttccaga     660
accgcagagc cacgaagctg aaggtggact gcgagttcct gaagcgctgc tgcgagacgc     720
tgacggagga gaaccggcgg ctgcagcggg aggtggcgga gctgcgcgtg ctcaagctcg     780
tggcgccgca ccactacgcg cgcatgccgc cgcccaccac gctcaccatg tgcccctcct     840
gcgagcgcct cgcctccgcg tccgcgtccg ccgaccaggc gggccgtgca gggccctgct     900
ggggccctct ccccgtgttc gtcgacggcc cagcccggag gccgtga                  947
```

<210> SEQ ID NO 203
<211> LENGTH: 53
<212> TYPE: PRT
<213> ORGANISM: Amborella trichopoda

<400> SEQUENCE: 203

```
Leu Ala Lys Gln Leu Asn Leu Arg Pro Arg Gln Val Glu Val Trp Phe
1               5                   10                  15

Gln Asn Arg Arg Ala Arg Thr Lys Leu Lys Gln Thr Glu Val Asp Cys
                20                  25                  30

Glu Phe Leu Lys Arg Cys Cys Glu Asn Leu Thr Glu Glu Asn Arg Arg
```

```
                35                  40                  45

Leu Gln Lys Glu Val
    50

<210> SEQ ID NO 204
<211> LENGTH: 53
<212> TYPE: PRT
<213> ORGANISM: Arabidopsis lyrata

<400> SEQUENCE: 204

Leu Ala Lys Gln Leu Asn Leu Arg Thr Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Tyr Leu Lys Arg Cys Cys Glu Asn Leu Thr Asp Glu Asn Arg Arg
        35                  40                  45

Leu Gln Lys Glu Val
    50

<210> SEQ ID NO 205
<211> LENGTH: 53
<212> TYPE: PRT
<213> ORGANISM: Arabidopsis thaliana

<400> SEQUENCE: 205

Leu Ala Lys Gln Leu Asn Leu Arg Thr Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Tyr Leu Lys Arg Cys Cys Glu Asn Leu Thr Asp Glu Asn Arg Arg
        35                  40                  45

Leu Gln Lys Glu Val
    50

<210> SEQ ID NO 206
<211> LENGTH: 53
<212> TYPE: PRT
<213> ORGANISM: Arabis alpina

<400> SEQUENCE: 206

Leu Ala Lys Gln Leu Asn Leu Arg Thr Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Tyr Leu Lys Arg Cys Cys Glu Asn Leu Thr Glu Glu Asn Arg Arg
        35                  40                  45

Leu Gln Lys Glu Val
    50

<210> SEQ ID NO 207
<211> LENGTH: 53
<212> TYPE: PRT
<213> ORGANISM: Brassica campestris

<400> SEQUENCE: 207

Leu Ala Lys Gln Leu Asn Leu Arg Thr Arg Gln Val Glu Val Trp Phe
1               5                   10                  15

Gln Asn Arg Arg Ala Arg Thr Lys Leu Lys Gln Thr Glu Val Asp Cys
            20                  25                  30
```

Glu Tyr Leu Lys Arg Cys Cys Glu Asn Leu Thr Glu Asn Arg Arg
            35                  40                  45

Leu Gln Lys Glu Val
    50

<210> SEQ ID NO 208
<211> LENGTH: 53
<212> TYPE: PRT
<213> ORGANISM: Brassica oleracea

<400> SEQUENCE: 208

Leu Ala Lys Gln Leu Asn Leu Arg Thr Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Tyr Leu Lys Arg Cys Cys Glu Asn Leu Thr Glu Asn Arg Arg
            35                  40                  45

Leu Gln Lys Glu Val
    50

<210> SEQ ID NO 209
<211> LENGTH: 53
<212> TYPE: PRT
<213> ORGANISM: Capsella rubella

<400> SEQUENCE: 209

Leu Ala Lys Gln Leu Asn Leu Gln Thr Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Tyr Leu Arg Arg Cys Glu Asn Leu Thr Glu Asn Arg Arg
            35                  40                  45

Leu Gln Lys Glu Val
    50

<210> SEQ ID NO 210
<211> LENGTH: 53
<212> TYPE: PRT
<213> ORGANISM: Cicer arietinum

<400> SEQUENCE: 210

Leu Ala Lys Gln Leu Asn Leu Met Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Tyr Leu Lys Arg Cys Cys Glu Thr Leu Thr Glu Asn Arg Arg
            35                  40                  45

Leu Gln Lys Glu Val
    50

<210> SEQ ID NO 211
<211> LENGTH: 53
<212> TYPE: PRT
<213> ORGANISM: Citrus clementina

<400> SEQUENCE: 211

Leu Ala Lys Gln Leu Gly Leu Arg Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

```
Glu Phe Leu Lys Arg Cys Cys Glu Asn Leu Thr Glu Glu Asn Arg Arg
        35                  40                  45

Leu Gln Lys Glu Val
    50

<210> SEQ ID NO 212
<211> LENGTH: 53
<212> TYPE: PRT
<213> ORGANISM: Citrus sinensis

<400> SEQUENCE: 212

Leu Ala Lys Gln Leu Asn Leu Arg Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Tyr Leu Lys Arg Cys Cys Glu Asn Leu Thr Glu Glu Asn Arg Arg
        35                  40                  45

Leu Gln Lys Glu Val
    50

<210> SEQ ID NO 213
<211> LENGTH: 53
<212> TYPE: PRT
<213> ORGANISM: Cucumis melo

<400> SEQUENCE: 213

Leu Ala Lys Gln Leu Asn Leu Thr Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Tyr Leu Lys Arg Cys Cys Glu Asn Leu Thr Glu Glu Asn Arg Arg
        35                  40                  45

Leu Gln Lys Glu Val
    50

<210> SEQ ID NO 214
<211> LENGTH: 53
<212> TYPE: PRT
<213> ORGANISM: Cucumis sativus

<400> SEQUENCE: 214

Leu Ala Lys Gln Leu Asn Leu Thr Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Tyr Leu Lys Arg Cys Cys Glu Asn Leu Thr Glu Glu Asn Arg Arg
        35                  40                  45

Leu Gln Lys Glu Val
    50

<210> SEQ ID NO 215
<211> LENGTH: 53
<212> TYPE: PRT
<213> ORGANISM: Erythranthe guttata

<400> SEQUENCE: 215

Leu Ala Lys Arg Leu Gly Leu Arg Pro Arg Gln Val Glu Val Trp Phe
1               5                   10                  15

Gln Asn Arg Arg Ala Arg Thr Lys Leu Lys Gln Thr Glu Val Asp Cys
```

```
                    20                  25                  30

Glu Phe Leu Lys Arg Cys Cys Glu Asn Leu Thr Glu Glu Asn Arg Arg
            35                  40                  45

Leu Gln Lys Glu Val
        50

<210> SEQ ID NO 216
<211> LENGTH: 53
<212> TYPE: PRT
<213> ORGANISM: Eucalyptus grandis

<400> SEQUENCE: 216

Leu Ala Lys Gln Leu Gly Leu Arg Pro Arg Gln Val Glu Val Trp Phe
1               5                   10                  15

Gln Asn Arg Arg Ala Arg Thr Lys Leu Lys Gln Thr Glu Ile Asp Cys
            20                  25                  30

Glu Phe Leu Lys Arg Cys Cys Glu Asn Leu Thr Glu Glu Asn Arg Arg
            35                  40                  45

Leu Gln Lys Glu Val
        50

<210> SEQ ID NO 217
<211> LENGTH: 53
<212> TYPE: PRT
<213> ORGANISM: Eutrema salsugineum

<400> SEQUENCE: 217

Leu Ala Lys Gln Leu Asn Leu Arg Thr Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Tyr Leu Lys Arg Cys Cys Glu Asn Leu Thr Glu Glu Asn Arg Arg
            35                  40                  45

Leu Gln Lys Glu Val
        50

<210> SEQ ID NO 218
<211> LENGTH: 53
<212> TYPE: PRT
<213> ORGANISM: Glycine max

<400> SEQUENCE: 218

Leu Ala Lys Gln Leu Gly Leu Arg Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Val Leu Lys Arg Cys Cys Glu Asn Leu Thr Glu Glu Asn Arg Arg
            35                  40                  45

Leu Gln Lys Glu Val
        50

<210> SEQ ID NO 219
<211> LENGTH: 53
<212> TYPE: PRT
<213> ORGANISM: Gossypium raimondii

<400> SEQUENCE: 219

Leu Ala Lys Gln Leu Asn Leu Lys Pro Arg Gln Val Glu Val Trp Phe
1               5                   10                  15
```

Gln Asn Arg Arg Ala Arg Thr Lys Leu Lys Gln Thr Glu Val Asp Cys
            20                  25                  30

Glu Tyr Leu Lys Arg Cys Cys Glu Asn Leu Thr Glu Glu Asn Arg Arg
        35                  40                  45

Leu His Lys Glu Val
        50

<210> SEQ ID NO 220
<211> LENGTH: 53
<212> TYPE: PRT
<213> ORGANISM: Leersia perrieri

<400> SEQUENCE: 220

Leu Ala Gln Gln Leu Gly Leu Arg Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Phe Leu Lys Arg Cys Cys Glu Thr Leu Thr Glu Glu Asn Arg Arg
        35                  40                  45

Leu Gln Lys Glu Val
        50

<210> SEQ ID NO 221
<211> LENGTH: 53
<212> TYPE: PRT
<213> ORGANISM: Medicago truncatula

<400> SEQUENCE: 221

Leu Ala Lys Gln Leu Gly Leu Arg Ala Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Phe Leu Lys Arg Cys Cys Glu Asn Leu Thr Asp Glu Asn Arg Arg
        35                  40                  45

Leu Gln Lys Glu Val
        50

<210> SEQ ID NO 222
<211> LENGTH: 53
<212> TYPE: PRT
<213> ORGANISM: Morus notabilis

<400> SEQUENCE: 222

Leu Ala Lys Glu Leu Asn Leu Arg Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Tyr Leu Lys Arg Cys Cys Glu Asn Leu Thr Glu Glu Asn Arg Arg
        35                  40                  45

Leu Gln Lys Glu Val
        50

<210> SEQ ID NO 223
<211> LENGTH: 53
<212> TYPE: PRT
<213> ORGANISM: Musa acuminata

<400> SEQUENCE: 223

Leu Ala Lys Arg Leu Asn Leu Arg Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Phe Leu Lys Arg Cys Cys Glu Thr Leu Thr Glu Asn Arg Arg
        35                  40                  45

Leu Gln Lys Glu Val
    50

<210> SEQ ID NO 224
<211> LENGTH: 53
<212> TYPE: PRT
<213> ORGANISM: Nelumbo nucifera

<400> SEQUENCE: 224

Leu Ala Lys Gln Leu Asn Leu Arg Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Phe Leu Lys Arg Cys Cys Glu Asn Leu Thr Glu Glu Asn Arg Arg
        35                  40                  45

Leu Gln Lys Glu Val
    50

<210> SEQ ID NO 225
<211> LENGTH: 53
<212> TYPE: PRT
<213> ORGANISM: Nicotiana sylvestris

<400> SEQUENCE: 225

Leu Ala Lys Arg Leu Gly Leu Arg Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Phe Leu Lys Arg Cys Cys Glu Asn Leu Thr Glu Glu Asn Arg Arg
        35                  40                  45

Leu Gln Lys Glu Val
    50

<210> SEQ ID NO 226
<211> LENGTH: 53
<212> TYPE: PRT
<213> ORGANISM: Oryza barthii

<400> SEQUENCE: 226

Leu Ala Arg Gln Leu Asn Leu Lys Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Leu Leu Lys Arg Cys Cys Glu Thr Leu Thr Asp Glu Asn Arg Arg
        35                  40                  45

Leu His Arg Glu Leu
    50

<210> SEQ ID NO 227
<211> LENGTH: 53
<212> TYPE: PRT
<213> ORGANISM: Oryza brachyantha

<400> SEQUENCE: 227

Leu Ala Arg Gln Leu Gly Leu Lys Pro Arg Gln Val Glu Val Trp Phe

```
                1               5                  10                 15
              Gln Asn Arg Arg Ala Arg Thr Lys Leu Lys Gln Thr Glu Val Asp Cys
                         20                  25                  30
              Glu Leu Leu Lys Arg Cys Cys Glu Thr Leu Thr Glu Glu Asn Arg Arg
                     35                  40                  45
              Leu His Lys Glu Leu
                     50
```

```
<210> SEQ ID NO 228
<211> LENGTH: 53
<212> TYPE: PRT
<213> ORGANISM: Oryza glaberrima

<400> SEQUENCE: 228

Leu Ala Arg Gln Leu Asn Leu Lys Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Leu Leu Lys Arg Cys Cys Glu Thr Leu Thr Asp Glu Asn Arg Arg
        35                  40                  45

Leu His Arg Glu Leu
        50

<210> SEQ ID NO 229
<211> LENGTH: 53
<212> TYPE: PRT
<213> ORGANISM: Oryza glumipatula

<400> SEQUENCE: 229

Leu Ala Arg Gln Leu Asn Leu Lys Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Leu Leu Lys Arg Cys Cys Glu Thr Leu Thr Asp Glu Asn Arg Arg
        35                  40                  45

Leu His Arg Glu Leu
        50

<210> SEQ ID NO 230
<211> LENGTH: 53
<212> TYPE: PRT
<213> ORGANISM: Oryza meridionalis

<400> SEQUENCE: 230

Leu Ala Arg Gln Leu Asn Leu Lys Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Leu Leu Lys Arg Cys Cys Glu Thr Leu Thr Asp Glu Asn Arg Arg
        35                  40                  45

Leu His Arg Glu Leu
        50

<210> SEQ ID NO 231
<211> LENGTH: 53
<212> TYPE: PRT
<213> ORGANISM: Oryza nivara

<400> SEQUENCE: 231
```

```
Leu Ala Lys Gln Leu Asn Leu Arg Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Tyr Leu Lys Arg Cys Cys Glu Thr Leu Thr Glu Glu Asn Arg Arg
        35                  40                  45

Leu Gln Lys Glu Leu
    50

<210> SEQ ID NO 232
<211> LENGTH: 53
<212> TYPE: PRT
<213> ORGANISM: Oryza punctata

<400> SEQUENCE: 232

Leu Ala Arg Gln Leu Asn Leu Lys Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Leu Leu Lys Arg Cys Cys Glu Thr Leu Thr Asp Glu Asn Arg Arg
        35                  40                  45

Leu His Arg Glu Leu
    50

<210> SEQ ID NO 233
<211> LENGTH: 53
<212> TYPE: PRT
<213> ORGANISM: Oryza rufipogon

<400> SEQUENCE: 233

Leu Ala Gln Gln Leu Gly Leu Arg Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Phe Leu Lys Arg Cys Cys Glu Thr Leu Thr Glu Glu Asn Arg Arg
        35                  40                  45

Leu Gln Lys Glu Val
    50

<210> SEQ ID NO 234
<211> LENGTH: 53
<212> TYPE: PRT
<213> ORGANISM: Oryza sativa

<400> SEQUENCE: 234

Leu Ala Arg Gln Leu Asn Leu Lys Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Leu Leu Lys Arg Cys Cys Glu Thr Leu Thr Asp Glu Asn Arg Arg
        35                  40                  45

Leu His Arg Glu Leu
    50

<210> SEQ ID NO 235
<211> LENGTH: 53
<212> TYPE: PRT
<213> ORGANISM: Phaseolus vulgaris

<400> SEQUENCE: 235
```

-continued

```
Leu Ala Lys Gln Leu Gly Leu Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Val Leu Lys Arg Cys Cys Glu Asn Leu Thr Glu Glu Asn Arg Arg
        35                  40                  45

Leu Gln Lys Glu Val
    50

<210> SEQ ID NO 236
<211> LENGTH: 53
<212> TYPE: PRT
<213> ORGANISM: Physcomitrella patens

<400> SEQUENCE: 236

Leu Ala Lys Gln Leu Gly Leu Arg Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Leu Leu Lys Arg Cys Cys Asp Ser Leu Lys Glu Glu Asn Arg Arg
        35                  40                  45

Leu Gln Lys Glu Leu
    50

<210> SEQ ID NO 237
<211> LENGTH: 53
<212> TYPE: PRT
<213> ORGANISM: Populus trichocarpa

<400> SEQUENCE: 237

Leu Ala Lys Gln Leu Asn Leu Arg Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Tyr Leu Lys Arg Cys Cys Glu Asn Leu Thr Glu Glu Asn Arg Arg
        35                  40                  45

Leu Gln Lys Glu Val
    50

<210> SEQ ID NO 238
<211> LENGTH: 53
<212> TYPE: PRT
<213> ORGANISM: Prunus persica

<400> SEQUENCE: 238

Leu Ala Lys Gln Leu Gly Leu Arg Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Phe Leu Lys Arg Cys Cys Glu Asn Leu Thr Glu Glu Asn Arg Arg
        35                  40                  45

Leu Gln Lys Glu Val
    50

<210> SEQ ID NO 239
<211> LENGTH: 53
<212> TYPE: PRT
<213> ORGANISM: Ricinus communis
```

-continued

```
<400> SEQUENCE: 239

Leu Ala Lys Gln Leu Asn Leu Lys Pro Arg Gln Val Glu Val Trp Phe
1               5                   10                  15

Gln Asn Arg Arg Ala Arg Thr Lys Ser Lys Gln Thr Glu Val Asp Cys
            20                  25                  30

Glu Tyr Leu Lys Arg Cys Cys Glu Asn Leu Thr Gln Glu Asn Arg Arg
        35                  40                  45

Leu Gln Lys Glu Val
    50

<210> SEQ ID NO 240
<211> LENGTH: 53
<212> TYPE: PRT
<213> ORGANISM: Setaria italica

<400> SEQUENCE: 240

Leu Ala Lys Gln Leu Asn Leu Lys Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Phe Leu Lys Arg Cys Cys Glu Thr Leu Thr Glu Glu Asn Arg Arg
        35                  40                  45

Leu Gln Arg Glu Val
    50

<210> SEQ ID NO 241
<211> LENGTH: 53
<212> TYPE: PRT
<213> ORGANISM: Solanum tuberosum

<400> SEQUENCE: 241

Leu Ala Lys Arg Leu Gly Leu Arg Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Phe Leu Lys Arg Cys Cys Glu Asn Leu Thr Glu Glu Asn Arg Arg
        35                  40                  45

Leu Gln Lys Glu Val
    50

<210> SEQ ID NO 242
<211> LENGTH: 53
<212> TYPE: PRT
<213> ORGANISM: Sorghum bicolor

<400> SEQUENCE: 242

Leu Ala Lys Gln Leu Asn Leu Lys Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Phe Leu Lys Arg Cys Cys Glu Thr Leu Thr Glu Glu Asn Arg Arg
        35                  40                  45

Leu Gln Arg Glu Val
    50

<210> SEQ ID NO 243
<211> LENGTH: 53
<212> TYPE: PRT
<213> ORGANISM: Theobroma cacao
```

```
<400> SEQUENCE: 243

Leu Ala Lys Gln Leu Asn Leu Arg Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Tyr Leu Lys Arg Cys Cys Glu Asn Leu Thr Glu Glu Asn Arg Arg
        35                  40                  45

Leu Gln Lys Glu Val
        50

<210> SEQ ID NO 244
<211> LENGTH: 53
<212> TYPE: PRT
<213> ORGANISM: Triticum urartu

<400> SEQUENCE: 244

Leu Ala Gln Gln Leu Gly Leu Arg Ser Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Phe Leu Lys Arg Cys Cys Glu Thr Leu Thr Glu Glu Asn Arg Arg
        35                  40                  45

Leu Gln Lys Glu Val
        50

<210> SEQ ID NO 245
<211> LENGTH: 53
<212> TYPE: PRT
<213> ORGANISM: Vitis vinifera

<400> SEQUENCE: 245

Leu Ala Lys Gln Leu Asn Leu Arg Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Phe Leu Lys Arg Cys Cys Glu Asn Leu Thr Glu Glu Asn Arg Arg
        35                  40                  45

Leu Gln Lys Glu Val
        50

<210> SEQ ID NO 246
<211> LENGTH: 53
<212> TYPE: PRT
<213> ORGANISM: Zea mays

<400> SEQUENCE: 246

Leu Ala Lys Gln Leu Asn Leu Lys Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Phe Leu Lys Arg Cys Cys Glu Thr Leu Thr Glu Glu Asn Arg Arg
        35                  40                  45

Leu Gln Arg Glu Val
        50

<210> SEQ ID NO 247
<211> LENGTH: 114
<212> TYPE: PRT
```

<213> ORGANISM: Amborella trichopoda

<400> SEQUENCE: 247

Arg Lys Lys Leu Arg Leu Ser Lys Asp Gln Ser Ala Val Leu Glu Glu
1               5                   10                  15

Ser Phe Lys Glu His Asn Thr Leu Asn Pro Lys Gln Lys Leu Thr Leu
            20                  25                  30

Ala Lys Gln Leu Asn Leu Arg Pro Arg Gln Val Glu Val Trp Phe Gln
        35                  40                  45

Asn Arg Arg Ala Arg Thr Lys Leu Lys Gln Thr Glu Val Asp Cys Glu
    50                  55                  60

Phe Leu Lys Arg Cys Cys Glu Asn Leu Thr Glu Asn Arg Arg Leu
65                  70                  75                  80

Gln Lys Glu Val Met Glu Leu Arg Ser Leu Lys Gln Thr Pro His Phe
                85                  90                  95

Tyr Met His Val Pro Pro Ala Ala Leu Thr Met Cys Pro Ser Cys Glu
                100                 105                 110

Arg Val

<210> SEQ ID NO 248
<211> LENGTH: 115
<212> TYPE: PRT
<213> ORGANISM: Arabidopsis lyrata

<400> SEQUENCE: 248

Arg Lys Lys Leu Arg Leu Ser Lys Glu Gln Ala Leu Val Leu Glu Glu
1               5                   10                  15

Thr Phe Lys Glu His Ser Thr Leu Asn Pro Lys Gln Lys Leu Ala Leu
            20                  25                  30

Ala Lys Gln Leu Asn Leu Arg Ala Arg Gln Val Glu Val Trp Phe Gln
        35                  40                  45

Asn Arg Arg Ala Arg Thr Lys Leu Lys Gln Thr Glu Val Asp Cys Glu
    50                  55                  60

Tyr Leu Lys Arg Cys Cys Asp Ser Leu Thr Glu Glu Asn Arg Arg Leu
65                  70                  75                  80

Gln Lys Glu Val Ser Glu Leu Arg Ala Leu Lys Leu Ser Pro His Leu
                85                  90                  95

Tyr Met His Met Thr Pro Pro Thr Thr Leu Thr Met Cys Pro Ser Cys
                100                 105                 110

Glu Arg Val
        115

<210> SEQ ID NO 249
<211> LENGTH: 115
<212> TYPE: PRT
<213> ORGANISM: Arabidopsis thaliana

<400> SEQUENCE: 249

Arg Lys Lys Leu Arg Leu Ser Lys Asp Gln Ala Leu Val Leu Glu Glu
1               5                   10                  15

Thr Phe Lys Glu His Ser Thr Leu Asn Pro Lys Gln Lys Leu Ala Leu
            20                  25                  30

Ala Lys Gln Leu Asn Leu Arg Ala Arg Gln Val Glu Val Trp Phe Gln
        35                  40                  45

Asn Arg Arg Ala Arg Thr Lys Leu Lys Gln Thr Glu Val Asp Cys Glu
    50                  55                  60

```
Tyr Leu Lys Arg Cys Cys Asp Asn Leu Thr Glu Glu Asn Arg Arg Leu
 65                  70                  75                  80

Gln Lys Glu Val Ser Glu Leu Arg Ala Leu Lys Leu Ser Pro His Leu
                 85                  90                  95

Tyr Met His Met Thr Pro Pro Thr Thr Leu Thr Met Cys Pro Ser Cys
            100                 105                 110

Glu Arg Val
        115

<210> SEQ ID NO 250
<211> LENGTH: 115
<212> TYPE: PRT
<213> ORGANISM: Arabis alpina

<400> SEQUENCE: 250

Arg Lys Lys Leu Arg Leu Ser Lys Glu Gln Ala Leu Val Leu Glu Glu
  1               5                  10                  15

Thr Phe Lys Glu His Ser Thr Leu Asn Pro Lys Gln Lys Met Ala Leu
                 20                  25                  30

Ala Lys Gln Leu Asn Leu Arg Thr Arg Gln Val Glu Val Trp Phe Gln
             35                  40                  45

Asn Arg Arg Ala Arg Thr Lys Leu Lys Gln Thr Glu Val Asp Cys Glu
 50                  55                  60

Tyr Leu Lys Arg Cys Cys Glu Asn Leu Thr Glu Glu Asn Arg Arg Leu
 65                  70                  75                  80

Gln Lys Glu Val Ser Glu Leu Arg Ala Leu Lys Leu Ser Pro His Leu
                 85                  90                  95

Tyr Met His Met Lys Pro Pro Thr Thr Leu Thr Met Cys Pro Ser Cys
            100                 105                 110

Glu Arg Val
        115

<210> SEQ ID NO 251
<211> LENGTH: 116
<212> TYPE: PRT
<213> ORGANISM: Brachypodium distachyon

<400> SEQUENCE: 251

Arg Lys Lys Leu Arg Leu Ser Lys Asp Gln Ser Ala Val Leu Glu Asp
  1               5                  10                  15

Ser Phe Arg Glu His Pro Thr Leu Asn Pro Arg Gln Lys Ala Ala Leu
                 20                  25                  30

Ala Gln Gln Leu Gly Leu Arg Ser Arg Gln Val Glu Val Trp Phe Gln
             35                  40                  45

Asn Arg Arg Ala Arg Thr Lys Leu Lys Gln Thr Glu Val Asp Cys Glu
 50                  55                  60

Phe Leu Lys Arg Cys Cys Glu Thr Leu Thr Glu Glu Asn Arg Arg Leu
 65                  70                  75                  80

Gln Lys Glu Val Gln Glu Leu Arg Ala Leu Lys Leu Val Ser Pro Arg
                 85                  90                  95

His Tyr Met His Met Ser Pro Pro Thr Thr Leu Thr Met Cys Pro Ser
            100                 105                 110

Cys Glu Arg Val
            115

<210> SEQ ID NO 252
<211> LENGTH: 115
```

```
<212> TYPE: PRT
<213> ORGANISM: Brassica campestris

<400> SEQUENCE: 252

Arg Lys Lys Leu Arg Leu Ser Lys Glu Gln Ala Leu Val Leu Glu Asp
1               5                   10                  15

Thr Phe Lys Glu His Ser Thr Leu Asn Pro Lys Gln Lys Leu Ala Leu
            20                  25                  30

Ala Lys Gln Leu Asn Leu Arg Thr Arg Gln Val Glu Val Trp Phe Gln
        35                  40                  45

Asn Arg Arg Ala Arg Thr Lys Leu Lys Gln Thr Glu Val Asp Cys Glu
    50                  55                  60

Tyr Leu Lys Arg Cys Cys Asp Thr Leu Thr Glu Glu Asn Arg Arg Leu
65                  70                  75                  80

His Lys Glu Val Ala Glu Leu Arg Ala Leu Lys Leu Ser Pro His Leu
                85                  90                  95

Tyr Met His Met Thr Pro Pro Thr Thr Leu Thr Met Cys Pro Ser Cys
            100                 105                 110

Glu Arg Val
        115

<210> SEQ ID NO 253
<211> LENGTH: 115
<212> TYPE: PRT
<213> ORGANISM: Brassica oleracea

<400> SEQUENCE: 253

Arg Lys Lys Leu Arg Leu Ser Lys Glu Gln Ala Leu Val Leu Glu Glu
1               5                   10                  15

Thr Phe Lys Glu His Ser Thr Leu Asn Pro Lys Gln Lys Leu Ala Leu
            20                  25                  30

Ala Lys Gln Leu Asn Leu Trp Thr Arg Gln Val Glu Val Trp Phe Gln
        35                  40                  45

Asn Arg Arg Ala Arg Thr Lys Leu Lys Gln Thr Glu Val Asp Cys Glu
    50                  55                  60

Tyr Leu Lys Arg Cys Cys Asp Thr Leu Thr Glu Glu Asn Arg Arg Leu
65                  70                  75                  80

His Lys Glu Val Ser Glu Leu Arg Ala Leu Lys Leu Ser Pro His Leu
                85                  90                  95

Tyr Met His Met Thr Pro Pro Thr Thr Leu Thr Met Cys Pro Ser Cys
            100                 105                 110

Glu Arg Val
        115

<210> SEQ ID NO 254
<211> LENGTH: 115
<212> TYPE: PRT
<213> ORGANISM: Capsella rubella

<400> SEQUENCE: 254

Arg Lys Lys Leu Arg Leu Ser Lys Glu Gln Ala Leu Val Leu Glu Glu
1               5                   10                  15

Thr Phe Lys Val His Ser Thr Leu Asn Pro Lys Gln Lys Leu Val Leu
            20                  25                  30

Ala Lys Gln Leu Asn Leu Arg Ala Arg Gln Val Glu Val Trp Phe Gln
        35                  40                  45

Asn Arg Arg Ala Arg Thr Lys Leu Lys Gln Thr Glu Val Asp Cys Glu
```

```
                    50                  55                  60
Tyr Leu Lys Arg Cys Cys Asp Asn Leu Thr Glu Glu Asn Arg Arg Leu
 65                  70                  75                  80

Gln Lys Glu Val Ser Glu Leu Arg Ala Leu Lys Leu Ser Pro His Leu
                 85                  90                  95

Tyr Met His Met Thr Pro Pro Thr Thr Leu Thr Met Cys Pro Ser Cys
                100                 105                 110

Glu Arg Val
        115

<210> SEQ ID NO 255
<211> LENGTH: 115
<212> TYPE: PRT
<213> ORGANISM: Cicer arietinum

<400> SEQUENCE: 255

Arg Lys Lys Leu Arg Leu Ser Lys Glu Gln Ser Val Leu Leu Glu Glu
  1               5                  10                  15

Thr Phe Lys Glu His Asn Thr Leu Asn Pro Lys Gln Lys Gln Ala Leu
                 20                  25                  30

Ala Lys Gln Leu Asn Leu Met Pro Arg Gln Val Glu Val Trp Phe Gln
                 35                  40                  45

Asn Arg Arg Ala Arg Thr Lys Leu Lys Gln Thr Glu Val Asp Cys Glu
 50                  55                  60

Tyr Leu Lys Arg Cys Cys Glu Thr Leu Thr Glu Glu Asn Arg Arg Leu
 65                  70                  75                  80

Gln Lys Glu Val Gln Glu Leu Arg Ala Leu Lys Leu Ser Pro Gln Leu
                 85                  90                  95

Tyr Met His Met Asn Pro Pro Thr Thr Leu Thr Met Cys Pro Ser Cys
                100                 105                 110

Glu Arg Val
        115

<210> SEQ ID NO 256
<211> LENGTH: 115
<212> TYPE: PRT
<213> ORGANISM: Citrus clementina

<400> SEQUENCE: 256

Arg Lys Lys Leu Arg Leu Ser Lys Glu Gln Ser Leu Leu Leu Glu Glu
  1               5                  10                  15

Thr Phe Lys Glu His Ser Thr Leu Asn Pro Lys Gln Lys Leu Ala Leu
                 20                  25                  30

Ala Lys Gln Leu Asn Leu Arg Pro Arg Gln Val Glu Val Trp Phe Gln
                 35                  40                  45

Asn Arg Arg Ala Arg Thr Lys Leu Lys Gln Thr Glu Val Asp Cys Glu
 50                  55                  60

Tyr Leu Lys Arg Cys Cys Glu Asn Leu Thr Glu Asn Arg Arg Leu
 65                  70                  75                  80

Gln Lys Glu Val Gln Glu Leu Arg Ser Leu Lys Leu Ser Pro Gln Leu
                 85                  90                  95

Tyr Met Asn Met Asn Pro Pro Thr Thr Leu Thr Met Cys Pro Ser Cys
                100                 105                 110

Glu Arg Val
        115
```

<210> SEQ ID NO 257
<211> LENGTH: 115
<212> TYPE: PRT
<213> ORGANISM: Citrus sinensis

<400> SEQUENCE: 257

Arg Lys Lys Leu Arg Leu Ser Lys Glu Gln Ser Leu Leu Glu Glu
1               5                   10                  15

Thr Phe Lys Glu His Ser Thr Leu Asn Pro Lys Gln Lys Leu Ala Leu
            20                  25                  30

Ala Lys Gln Leu Asn Leu Arg Pro Arg Gln Val Glu Val Trp Phe Gln
        35                  40                  45

Asn Arg Arg Ala Arg Thr Lys Leu Lys Gln Thr Glu Val Asp Cys Glu
    50                  55                  60

Tyr Leu Lys Arg Cys Cys Glu Asn Leu Thr Glu Glu Asn Arg Arg Leu
65                  70                  75                  80

Gln Lys Glu Val Gln Glu Leu Arg Ser Leu Lys Leu Ser Pro Gln Leu
                85                  90                  95

Tyr Met Asn Met Asn Pro Pro Thr Thr Leu Thr Met Cys Pro Ser Cys
            100                 105                 110

Glu Arg Val
        115

<210> SEQ ID NO 258
<211> LENGTH: 115
<212> TYPE: PRT
<213> ORGANISM: Cucumis melo

<400> SEQUENCE: 258

Arg Lys Lys Leu Arg Leu Ser Lys Glu Gln Ser Met Val Leu Glu Glu
1               5                   10                  15

Thr Phe Lys Glu His Asn Thr Leu Asn Pro Lys Gln Lys Leu Ala Leu
            20                  25                  30

Ala Lys Gln Leu Asn Leu Thr Pro Arg Gln Val Glu Val Trp Phe Gln
        35                  40                  45

Asn Arg Arg Ala Arg Thr Lys Leu Lys Gln Thr Glu Val Asp Cys Glu
    50                  55                  60

Tyr Leu Lys Arg Cys Cys Glu Asn Leu Thr Glu Glu Asn Arg Arg Leu
65                  70                  75                  80

Gln Lys Glu Val Gln Glu Leu Arg Ala Leu Lys Leu Ser Pro Gln Leu
                85                  90                  95

Tyr Met His Met Asn Pro Pro Thr Thr Leu Thr Met Cys Pro Gln Cys
            100                 105                 110

Glu Arg Val
        115

<210> SEQ ID NO 259
<211> LENGTH: 115
<212> TYPE: PRT
<213> ORGANISM: Cucumis sativus

<400> SEQUENCE: 259

Arg Lys Lys Leu Arg Leu Ser Lys Glu Gln Ser Met Val Leu Glu Glu
1               5                   10                  15

Thr Phe Lys Glu His Asn Thr Leu Asn Pro Lys Gln Lys Leu Ala Leu
            20                  25                  30

Ala Lys Gln Leu Asn Leu Thr Pro Arg Gln Val Glu Val Trp Phe Gln
        35                  40                  45

```
Asn Arg Arg Ala Arg Thr Lys Leu Lys Gln Thr Glu Val Asp Cys Glu
            50                  55                  60

Tyr Leu Lys Arg Cys Cys Glu Asn Leu Thr Glu Glu Asn Arg Arg Leu
 65                  70                  75                  80

Gln Lys Glu Val Gln Glu Leu Arg Ala Leu Lys Leu Ser Pro Gln Leu
                85                  90                  95

Tyr Met His Met Asn Pro Pro Thr Thr Leu Thr Met Cys Pro Gln Cys
                100                 105                 110

Glu Arg Val
        115

<210> SEQ ID NO 260
<211> LENGTH: 115
<212> TYPE: PRT
<213> ORGANISM: Erythranthe guttata

<400> SEQUENCE: 260

Arg Lys Lys Leu Arg Leu Ser Lys Asp Gln Ser Ala Thr Leu Glu Glu
 1               5                  10                  15

Ser Phe Lys Glu His Asn Thr Leu Asn Pro Lys Gln Lys Met Ala Leu
                20                  25                  30

Ala Lys Arg Leu Gly Leu Arg Pro Arg Gln Val Glu Val Trp Phe Gln
                35                  40                  45

Asn Arg Arg Ala Arg Thr Lys Leu Lys Gln Thr Glu Val Asp Cys Glu
            50                  55                  60

Phe Leu Lys Arg Cys Cys Glu Asn Leu Thr Glu Glu Asn Arg Arg Leu
 65                  70                  75                  80

Gln Lys Glu Val Gln Glu Leu Arg Ala Leu Lys Leu Ser Pro Gln Phe
                85                  90                  95

Tyr Met Gln Met Thr Pro Pro Thr Thr Leu Thr Met Cys Pro Ser Cys
                100                 105                 110

Glu Arg Val
        115

<210> SEQ ID NO 261
<211> LENGTH: 115
<212> TYPE: PRT
<213> ORGANISM: Eucalyptus grandis

<400> SEQUENCE: 261

Arg Lys Lys Leu Arg Leu Ser Lys Asp Gln Ser Ala Val Leu Glu Glu
 1               5                  10                  15

Ser Phe Arg Glu His Asn Thr Leu Asn Pro Lys Gln Lys Leu Ala Leu
                20                  25                  30

Ala Lys Gln Leu Gly Leu Arg Pro Arg Gln Val Glu Val Trp Phe Gln
                35                  40                  45

Asn Arg Arg Ala Arg Thr Lys Leu Lys Gln Thr Glu Ile Asp Cys Glu
            50                  55                  60

Phe Leu Lys Arg Cys Cys Glu Asn Leu Thr Glu Glu Asn Arg Arg Leu
 65                  70                  75                  80

Gln Lys Glu Val Gln Glu Leu Arg Ala Leu Lys Leu Ser Pro Gln Phe
                85                  90                  95

Tyr Met His Met Pro Pro Pro Thr Thr Leu Thr Val Cys Pro Asn Cys
                100                 105                 110

Glu Arg Val
        115
```

<210> SEQ ID NO 262
<211> LENGTH: 115
<212> TYPE: PRT
<213> ORGANISM: Eutrema salsugineum

<400> SEQUENCE: 262

Arg Lys Lys Leu Arg Leu Ser Lys Glu Gln Ala Val Val Leu Glu Glu
1               5                   10                  15

Thr Phe Lys Glu His Thr Thr Leu Asn Pro Lys Gln Lys Leu Ala Leu
            20                  25                  30

Ala Arg Gln Leu Asn Leu Arg Thr Arg Gln Val Glu Val Trp Phe Gln
        35                  40                  45

Asn Arg Arg Ala Arg Thr Lys Leu Lys Gln Thr Glu Val Asp Cys Glu
    50                  55                  60

Tyr Leu Lys Arg Cys Cys Asp Asn Leu Thr Glu Asn Arg Arg Leu
65                  70                  75                  80

His Lys Glu Val Ser Glu Leu Arg Ala Leu Lys Leu Ser Pro His Leu
                85                  90                  95

Tyr Met His Met Thr Pro Pro Thr Thr Leu Thr Met Cys Pro Ser Cys
            100                 105                 110

Glu Arg Val
        115

<210> SEQ ID NO 263
<211> LENGTH: 115
<212> TYPE: PRT
<213> ORGANISM: Glycine max

<400> SEQUENCE: 263

Arg Lys Lys Leu Arg Leu Ser Lys Glu Gln Ala Leu Val Leu Glu Glu
1               5                   10                  15

Thr Phe Lys Glu His Asn Thr Leu Asn Pro Lys Gln Lys Gln Ala Leu
            20                  25                  30

Ala Lys Gln Leu Asn Leu Met Pro Arg Gln Val Glu Val Trp Phe Gln
        35                  40                  45

Asn Arg Arg Ala Arg Thr Lys Leu Lys Gln Thr Glu Val Asp Cys Glu
    50                  55                  60

Tyr Leu Lys Arg Cys Cys Glu Asn Leu Thr Glu Glu Asn Arg Arg Leu
65                  70                  75                  80

Gln Lys Glu Val Gln Glu Leu Arg Ala Leu Lys Leu Ser Pro His Leu
                85                  90                  95

Tyr Met Gln Met Asn Pro Pro Thr Thr Leu Thr Met Cys Pro Ser Cys
            100                 105                 110

Glu Arg Val
        115

<210> SEQ ID NO 264
<211> LENGTH: 115
<212> TYPE: PRT
<213> ORGANISM: Gossypium raimondii

<400> SEQUENCE: 264

Arg Lys Lys Leu Arg Leu Ser Lys Asp Gln Ser Ala Ile Leu Glu Glu
1               5                   10                  15

Ser Phe Lys Glu His Asn Thr Leu Asn Pro Lys Gln Lys Met Ala Leu
            20                  25                  30

```
Ala Lys Gln Leu Gly Leu Arg Pro Arg Gln Val Glu Val Trp Phe Gln
             35                  40                  45

Asn Arg Arg Ala Arg Thr Lys Leu Lys Gln Thr Glu Val Asp Cys Glu
         50                  55                  60

Phe Leu Lys Arg Cys Cys Glu Asn Leu Thr Glu Glu Asn Arg Arg Leu
 65                  70                  75                  80

Gln Lys Glu Val Gln Glu Leu Arg Ala Leu Lys Leu Ser Pro Gln Phe
                 85                  90                  95

Tyr Met Gln Met Thr Pro Pro Thr Thr Leu Thr Met Cys Pro Ser Cys
             100                 105                 110

Glu Arg Val
        115
```

<210> SEQ ID NO 265
<211> LENGTH: 116
<212> TYPE: PRT
<213> ORGANISM: Hordeum vulgare

<400> SEQUENCE: 265

```
Arg Lys Lys Leu Arg Leu Ser Lys Asp Gln Ser Ala Val Leu Glu Asp
 1               5                  10                  15

Ser Phe Arg Glu His Pro Thr Leu Asn Pro Arg Gln Lys Ala Ala Leu
             20                  25                  30

Ala Gln Gln Leu Gly Leu Arg Ser Arg Gln Val Glu Val Trp Phe Gln
             35                  40                  45

Asn Arg Arg Ala Arg Thr Lys Leu Lys Gln Thr Glu Val Asp Cys Glu
         50                  55                  60

Phe Leu Lys Arg Cys Cys Glu Thr Leu Thr Glu Glu Asn Arg Arg Leu
 65                  70                  75                  80

Gln Lys Glu Val Gln Glu Leu Arg Ala Leu Lys Leu Val Ser Pro His
                 85                  90                  95

Gln Tyr Met His Met Ser Pro Pro Thr Thr Leu Thr Met Cys Pro Ser
             100                 105                 110

Cys Glu Arg Val
        115
```

<210> SEQ ID NO 266
<211> LENGTH: 116
<212> TYPE: PRT
<213> ORGANISM: Leersia perrieri

<400> SEQUENCE: 266

```
Arg Lys Lys Leu Arg Leu Ser Lys Asp Gln Ser Ala Val Leu Glu Asp
 1               5                  10                  15

Ser Phe Arg Glu His Pro Thr Leu Asn Pro Arg Gln Lys Ala Thr Leu
             20                  25                  30

Ala Gln Gln Leu Gly Leu Arg Pro Arg Gln Val Glu Val Trp Phe Gln
             35                  40                  45

Asn Arg Arg Ala Arg Thr Lys Leu Lys Gln Thr Glu Val Asp Cys Glu
         50                  55                  60

Phe Leu Lys Arg Cys Cys Glu Thr Leu Thr Glu Glu Asn Arg Arg Leu
 65                  70                  75                  80

Gln Lys Glu Val Gln Glu Leu Arg Ala Leu Lys Leu Val Ser Pro His
                 85                  90                  95

Leu Tyr Met Asn Met Ser Pro Thr Thr Leu Thr Met Cys Pro Ser
             100                 105                 110
```

Cys Glu Arg Val
        115

<210> SEQ ID NO 267
<211> LENGTH: 115
<212> TYPE: PRT
<213> ORGANISM: Medicago truncatula

<400> SEQUENCE: 267

Arg Lys Lys Leu Arg Leu Thr Lys Asp Gln Ser Ile Ile Leu Glu Glu
1               5                   10                  15

Ser Phe Lys Glu His Asn Thr Leu Asn Pro Lys Gln Lys Leu Ala Leu
            20                  25                  30

Ala Lys Gln Leu Gly Leu Arg Ala Arg Gln Val Glu Val Trp Phe Gln
        35                  40                  45

Asn Arg Arg Ala Arg Thr Lys Leu Lys Gln Thr Glu Val Asp Cys Glu
    50                  55                  60

Phe Leu Lys Arg Cys Cys Glu Asn Leu Thr Asp Glu Asn Arg Arg Leu
65                  70                  75                  80

Gln Lys Glu Val Gln Glu Leu Arg Ala Leu Lys Leu Ser Pro Gln Phe
                85                  90                  95

Tyr Met Gln Met Thr Pro Pro Thr Leu Thr Met Cys Pro Ser Cys
            100                 105                 110

Glu Arg Val
        115

<210> SEQ ID NO 268
<211> LENGTH: 115
<212> TYPE: PRT
<213> ORGANISM: Morus notabilis

<400> SEQUENCE: 268

Arg Lys Lys Leu Arg Leu Thr Lys Asp Gln Ser Leu Ile Leu Glu Glu
1               5                   10                  15

Thr Phe Lys Glu His Asn Thr Leu Asn Pro Lys Gln Lys Leu Ala Leu
            20                  25                  30

Ala Lys Glu Leu Asn Leu Arg Pro Arg Gln Val Glu Val Trp Phe Gln
        35                  40                  45

Asn Arg Arg Ala Arg Thr Lys Leu Lys Gln Thr Glu Val Asp Cys Glu
    50                  55                  60

Tyr Leu Lys Arg Cys Cys Glu Asn Leu Thr Glu Glu Asn Arg Arg Leu
65                  70                  75                  80

Gln Lys Glu Val Gln Glu Leu Arg Ala Leu Lys Leu Ser Pro Gln Leu
                85                  90                  95

Tyr Met His Met Ser Pro Pro Thr Thr Leu Thr Met Cys Pro Ser Cys
            100                 105                 110

Glu Arg Val
        115

<210> SEQ ID NO 269
<211> LENGTH: 115
<212> TYPE: PRT
<213> ORGANISM: Musa acuminata

<400> SEQUENCE: 269

Arg Lys Lys Leu Arg Leu Ser Lys Asp Gln Ser Ala Val Leu Glu Glu
1               5                   10                  15

Ser Phe Lys Glu His Thr Thr Leu Ser Pro Lys Gln Lys Leu Ala Leu

```
                      20                  25                  30

Ala Lys Gln Leu Asn Leu Arg Pro Arg Gln Val Glu Val Trp Phe Gln
            35                  40                  45

Asn Arg Arg Ala Arg Thr Lys Leu Lys Gln Thr Glu Val Asp Cys Glu
        50                  55                  60

Phe Leu Lys Arg Cys Cys Glu Asn Leu Thr Glu Glu Asn Arg Arg Leu
65                  70                  75                  80

Gln Lys Glu Val Gln Glu Leu Arg Ala Leu Lys Leu Ser Pro Gln Leu
                85                  90                  95

Tyr Met Gln Met Thr Pro Pro Thr Thr Leu Thr Met Cys Pro Ser Cys
            100                 105                 110

Glu Arg Val
        115

<210> SEQ ID NO 270
<211> LENGTH: 115
<212> TYPE: PRT
<213> ORGANISM: Nelumbo nucifera

<400> SEQUENCE: 270

Arg Lys Lys Leu Arg Leu Ser Lys Asp Gln Ser Ala Val Leu Glu Glu
1               5                   10                  15

Ser Phe Lys Glu His Asn Thr Leu Asn Pro Lys Gln Lys Leu Ala Leu
                20                  25                  30

Ala Lys Gln Leu Asn Leu Arg Pro Arg Gln Val Glu Val Trp Phe Gln
            35                  40                  45

Asn Arg Arg Ala Arg Thr Lys Leu Lys Gln Thr Glu Val Asp Cys Glu
        50                  55                  60

Phe Leu Lys Arg Cys Cys Glu Asn Leu Thr Glu Glu Asn Arg Arg Leu
65                  70                  75                  80

Gln Lys Glu Val Gln Glu Leu Arg Ala Leu Lys Leu Ser Pro Gln Phe
                85                  90                  95

Tyr Met His Met Thr Pro Pro Thr Thr Leu Thr Met Cys Pro Ser Cys
            100                 105                 110

Glu Arg Val
        115

<210> SEQ ID NO 271
<211> LENGTH: 115
<212> TYPE: PRT
<213> ORGANISM: Nicotiana sylvestris

<400> SEQUENCE: 271

Arg Lys Lys Leu Arg Leu Ser Lys Glu Gln Ala Ala Val Leu Glu Glu
1               5                   10                  15

Thr Phe Lys Glu His Asn Thr Leu Asn Pro Lys Gln Lys Leu Ala Leu
                20                  25                  30

Ser Lys Gln Leu Asn Leu Arg Pro Arg Gln Val Glu Val Trp Phe Gln
            35                  40                  45

Asn Arg Arg Ala Arg Thr Lys Leu Lys Gln Thr Glu Val Asp Cys Glu
        50                  55                  60

Tyr Leu Arg Arg Cys Cys Glu Asn Leu Thr Glu Glu Asn Arg Arg Leu
65                  70                  75                  80

Gln Lys Glu Val Thr Glu Leu Arg Ala Leu Lys Leu Ser Pro Gln Met
                85                  90                  95

Tyr Met Asn Met Thr Pro Pro Thr Thr Leu Thr Met Cys Pro Gln Cys
```

```
                    100                 105                 110

Glu Arg Val
        115

<210> SEQ ID NO 272
<211> LENGTH: 116
<212> TYPE: PRT
<213> ORGANISM: Oryza barthii

<400> SEQUENCE: 272

Arg Lys Lys Leu Arg Leu Ser Lys Asp Gln Ser Ala Val Leu Glu Asp
1               5                   10                  15

Ser Phe Arg Glu His Pro Thr Leu Asn Pro Arg Gln Lys Ala Thr Leu
            20                  25                  30

Ala Gln Gln Leu Gly Leu Arg Pro Arg Gln Val Glu Val Trp Phe Gln
        35                  40                  45

Asn Arg Arg Ala Arg Thr Lys Leu Lys Gln Thr Glu Val Asp Cys Glu
    50                  55                  60

Phe Leu Lys Arg Cys Cys Glu Thr Leu Thr Glu Asn Arg Arg Leu
65                  70                  75                  80

Gln Lys Glu Val Gln Glu Leu Arg Ala Leu Lys Leu Val Ser Pro His
                85                  90                  95

Leu Tyr Met Asn Met Ser Pro Pro Thr Thr Leu Thr Met Cys Pro Ser
                100                 105                 110

Cys Glu Arg Val
        115

<210> SEQ ID NO 273
<211> LENGTH: 116
<212> TYPE: PRT
<213> ORGANISM: Oryza brachyantha

<400> SEQUENCE: 273

Arg Lys Lys Leu Arg Leu Ser Lys Asp Gln Ser Ala Val Leu Glu Asp
1               5                   10                  15

Ser Phe Arg Glu His Pro Thr Leu Asn Pro Arg Gln Lys Ala Ala Leu
            20                  25                  30

Ala Gln Gln Leu Gly Leu Arg Pro Arg Gln Val Glu Val Trp Phe Gln
        35                  40                  45

Asn Arg Arg Ala Arg Thr Lys Leu Lys Gln Thr Glu Val Asp Cys Glu
    50                  55                  60

Phe Leu Lys Arg Cys Cys Glu Thr Leu Thr Glu Asn Arg Arg Leu
65                  70                  75                  80

Gln Lys Glu Val Gln Glu Leu Arg Ala Leu Lys Leu Val Ser Pro His
                85                  90                  95

Leu Tyr Met Asn Met Ser Pro Pro Thr Thr Leu Thr Met Cys Pro Ser
                100                 105                 110

Cys Glu Arg Val
        115

<210> SEQ ID NO 274
<211> LENGTH: 116
<212> TYPE: PRT
<213> ORGANISM: Oryza glaberrima

<400> SEQUENCE: 274

Arg Lys Lys Leu Arg Leu Ser Lys Asp Gln Ser Ala Val Leu Glu Asp
1               5                   10                  15
```

```
Ser Phe Arg Glu His Pro Thr Leu Asn Pro Arg Gln Lys Ala Thr Leu
            20                  25                  30

Ala Gln Gln Leu Gly Leu Arg Pro Arg Gln Val Glu Val Trp Phe Gln
        35                  40                  45

Asn Arg Arg Ala Arg Thr Lys Leu Lys Gln Thr Glu Val Asp Cys Glu
 50                  55                  60

Phe Leu Lys Arg Cys Cys Glu Thr Leu Thr Glu Glu Asn Arg Arg Leu
 65                  70                  75                  80

Gln Lys Glu Val Gln Glu Leu Arg Ala Leu Lys Leu Val Ser Pro His
                85                  90                  95

Leu Tyr Met Asn Met Ser Pro Pro Thr Thr Leu Thr Met Cys Pro Ser
            100                 105                 110

Cys Glu Arg Val
        115

<210> SEQ ID NO 275
<211> LENGTH: 116
<212> TYPE: PRT
<213> ORGANISM: Oryza glumipatula

<400> SEQUENCE: 275

Arg Lys Lys Leu Arg Leu Ser Lys Asp Gln Ser Ala Val Leu Glu Asp
1               5                   10                  15

Ser Phe Arg Glu His Pro Thr Leu Asn Pro Arg Gln Lys Ala Thr Leu
            20                  25                  30

Ala Gln Gln Leu Gly Leu Arg Pro Arg Gln Val Glu Val Trp Phe Gln
        35                  40                  45

Asn Arg Arg Ala Arg Thr Lys Leu Lys Gln Thr Glu Val Asp Cys Glu
 50                  55                  60

Phe Leu Lys Arg Cys Cys Glu Thr Leu Thr Glu Glu Asn Arg Arg Leu
 65                  70                  75                  80

Gln Lys Glu Val Gln Glu Leu Arg Ala Leu Lys Leu Val Ser Pro His
                85                  90                  95

Leu Tyr Met Asn Met Ser Pro Pro Thr Thr Leu Thr Met Cys Pro Ser
            100                 105                 110

Cys Glu Arg Val
        115

<210> SEQ ID NO 276
<211> LENGTH: 116
<212> TYPE: PRT
<213> ORGANISM: Oryza meridionalis

<400> SEQUENCE: 276

Arg Lys Lys Leu Arg Leu Ser Lys Asp Gln Ser Ala Val Leu Glu Asp
1               5                   10                  15

Ser Phe Arg Glu His Pro Thr Leu Asn Pro Arg Gln Lys Ala Thr Leu
            20                  25                  30

Ala Gln Gln Leu Gly Leu Arg Pro Arg Gln Val Glu Val Trp Phe Gln
        35                  40                  45

Asn Arg Arg Ala Arg Thr Lys Leu Lys Gln Thr Glu Val Asp Cys Glu
 50                  55                  60

Phe Leu Lys Arg Cys Cys Glu Thr Leu Thr Glu Glu Asn Arg Arg Leu
 65                  70                  75                  80

Gln Lys Glu Val Gln Glu Leu Arg Ala Leu Lys Leu Val Ser Pro His
                85                  90                  95
```

```
Leu Tyr Met Asn Met Ser Pro Pro Thr Thr Leu Thr Met Cys Pro Ser
                100                 105                 110

Cys Glu Arg Val
        115

<210> SEQ ID NO 277
<211> LENGTH: 116
<212> TYPE: PRT
<213> ORGANISM: Oryza nivara

<400> SEQUENCE: 277

Arg Lys Lys Leu Arg Leu Ser Lys Asp Gln Ser Ala Val Leu Glu Asp
1               5                   10                  15

Ser Phe Arg Glu His Pro Thr Leu Asn Pro Arg Gln Lys Ala Thr Leu
            20                  25                  30

Ala Gln Gln Leu Gly Leu Arg Pro Arg Gln Val Glu Val Trp Phe Gln
        35                  40                  45

Asn Arg Arg Ala Arg Thr Lys Leu Lys Gln Thr Glu Val Asp Cys Glu
    50                  55                  60

Phe Leu Lys Arg Cys Cys Glu Thr Leu Thr Glu Glu Asn Arg Arg Leu
65                  70                  75                  80

Gln Lys Glu Val Gln Glu Leu Arg Ala Leu Lys Leu Val Ser Pro His
                85                  90                  95

Leu Tyr Met Asn Met Ser Pro Pro Thr Thr Leu Thr Met Cys Pro Ser
                100                 105                 110

Cys Glu Arg Val
        115

<210> SEQ ID NO 278
<211> LENGTH: 116
<212> TYPE: PRT
<213> ORGANISM: Oryza punctata

<400> SEQUENCE: 278

Arg Lys Lys Leu Arg Leu Ser Lys Asp Gln Ser Ala Val Leu Glu Asp
1               5                   10                  15

Ser Phe Arg Glu His Pro Thr Leu Asn Pro Arg Gln Lys Ala Thr Leu
            20                  25                  30

Ala Gln Gln Leu Gly Leu Arg Pro Arg Gln Val Glu Val Trp Phe Gln
        35                  40                  45

Asn Arg Arg Ala Arg Thr Lys Leu Lys Gln Thr Glu Val Asp Cys Glu
    50                  55                  60

Phe Leu Lys Arg Cys Cys Glu Thr Leu Thr Glu Glu Asn Arg Arg Leu
65                  70                  75                  80

Gln Lys Glu Val Gln Glu Leu Arg Ala Leu Lys Leu Val Ser Pro His
                85                  90                  95

Leu Tyr Met Asn Met Ser Pro Pro Thr Thr Leu Thr Met Cys Pro Ser
                100                 105                 110

Cys Glu Arg Val
        115

<210> SEQ ID NO 279
<211> LENGTH: 116
<212> TYPE: PRT
<213> ORGANISM: Oryza rufipogon

<400> SEQUENCE: 279
```

Arg Lys Lys Leu Arg Leu Ser Lys Asp Gln Ser Ala Val Leu Glu Asp
1               5                   10                  15

Ser Phe Arg Glu His Pro Thr Leu Asn Pro Arg Gln Lys Ala Thr Leu
                20                  25                  30

Ala Gln Gln Leu Gly Leu Arg Pro Arg Gln Val Glu Val Trp Phe Gln
            35                  40                  45

Asn Arg Arg Ala Arg Thr Lys Leu Lys Gln Thr Glu Val Asp Cys Glu
50                  55                  60

Phe Leu Lys Arg Cys Cys Glu Thr Leu Thr Glu Glu Asn Arg Arg Leu
65                  70                  75                  80

Gln Lys Glu Val Gln Glu Leu Arg Ala Leu Lys Leu Val Ser Pro His
                85                  90                  95

Leu Tyr Met Asn Met Ser Pro Pro Thr Thr Leu Thr Met Cys Pro Ser
            100                 105                 110

Cys Glu Arg Val
            115

<210> SEQ ID NO 280
<211> LENGTH: 116
<212> TYPE: PRT
<213> ORGANISM: Oryza sativa

<400> SEQUENCE: 280

Arg Lys Lys Leu Arg Leu Ser Lys Asp Gln Ser Ala Val Leu Glu Asp
1               5                   10                  15

Ser Phe Arg Glu His Pro Thr Leu Asn Pro Arg Gln Lys Ala Thr Leu
                20                  25                  30

Ala Gln Gln Leu Gly Leu Arg Pro Arg Gln Val Glu Val Trp Phe Gln
            35                  40                  45

Asn Arg Arg Ala Arg Thr Lys Leu Lys Gln Thr Glu Val Asp Cys Glu
50                  55                  60

Phe Leu Lys Arg Cys Cys Glu Thr Leu Thr Glu Glu Asn Arg Arg Leu
65                  70                  75                  80

Gln Lys Glu Val Gln Glu Leu Arg Ala Leu Lys Leu Val Ser Pro His
                85                  90                  95

Leu Tyr Met Asn Met Ser Pro Pro Thr Thr Leu Thr Met Cys Pro Ser
            100                 105                 110

Cys Glu Arg Val
            115

<210> SEQ ID NO 281
<211> LENGTH: 115
<212> TYPE: PRT
<213> ORGANISM: Phaseolus vulgaris

<400> SEQUENCE: 281

Arg Lys Lys Leu Arg Leu Ser Lys Glu Gln Ala Leu Val Leu Glu Glu
1               5                   10                  15

Thr Phe Lys Glu His Asn Thr Leu Asn Pro Lys Gln Lys Gln Ala Leu
                20                  25                  30

Ala Lys Gln Leu Asn Leu Ser Pro Arg Gln Val Glu Val Trp Phe Gln
            35                  40                  45

Asn Arg Arg Ala Arg Thr Lys Leu Lys Gln Thr Glu Val Asp Cys Glu
50                  55                  60

Tyr Leu Lys Arg Cys Cys Glu Asn Leu Thr Glu Glu Asn Arg Arg Leu
65                  70                  75                  80

```
Gln Lys Glu Val Gln Glu Leu Arg Ala Leu Lys Phe Ser Pro Gln Leu
            85                  90                  95

Tyr Met His Met Asn Pro Pro Thr Thr Leu Thr Met Cys Pro Ser Cys
            100                 105                 110

Glu Arg Val
        115

<210> SEQ ID NO 282
<211> LENGTH: 115
<212> TYPE: PRT
<213> ORGANISM: Populus trichocarpa

<400> SEQUENCE: 282

Arg Lys Lys Leu Arg Leu Ser Lys Glu Gln Ser Leu Val Leu Glu Glu
1               5                   10                  15

Thr Phe Lys Glu His Asn Thr Leu Asn Pro Lys Glu Lys Leu Ala Leu
            20                  25                  30

Ala Lys Gln Leu Asn Leu Arg Pro Arg Gln Val Glu Val Trp Phe Gln
            35                  40                  45

Asn Arg Arg Ala Arg Thr Lys Leu Lys Gln Thr Glu Val Asp Cys Glu
50                  55                  60

Tyr Leu Lys Arg Cys Cys Glu Asn Leu Thr Glu Glu Asn Arg Arg Leu
65                  70                  75                  80

Gln Lys Glu Val Gln Glu Leu Arg Ala Leu Lys Leu Ser Pro Gln Leu
            85                  90                  95

Tyr Met His Met Asn Pro Pro Thr Thr Leu Thr Met Cys Pro Ser Cys
            100                 105                 110

Glu Arg Val
        115

<210> SEQ ID NO 283
<211> LENGTH: 115
<212> TYPE: PRT
<213> ORGANISM: Prunus persica

<400> SEQUENCE: 283

Arg Lys Lys Leu Arg Leu Ser Lys Asp Gln Ser Ala Ile Leu Glu Glu
1               5                   10                  15

Ser Phe Lys Glu His Asn Thr Leu Asn Pro Lys Gln Lys Leu Ala Leu
            20                  25                  30

Ala Lys Gln Leu Gly Leu Arg Pro Arg Gln Val Glu Val Trp Phe Gln
            35                  40                  45

Asn Arg Arg Ala Arg Thr Lys Leu Lys Gln Thr Glu Val Asp Cys Glu
50                  55                  60

Phe Leu Lys Arg Cys Cys Glu Asn Leu Thr Glu Glu Asn Arg Arg Leu
65                  70                  75                  80

Gln Lys Glu Val Gln Glu Leu Arg Ala Leu Lys Leu Ser Pro Gln Phe
            85                  90                  95

Tyr Met Gln Met Thr Pro Pro Thr Thr Leu Thr Met Cys Pro Ser Cys
            100                 105                 110

Glu Arg Val
        115

<210> SEQ ID NO 284
<211> LENGTH: 115
<212> TYPE: PRT
<213> ORGANISM: Ricinus communis
```

<400> SEQUENCE: 284

Arg Lys Lys Leu Arg Leu Ser Lys Glu Gln Ser Leu Leu Glu Glu
1               5                   10                  15

Thr Phe Lys Glu His Asn Thr Leu Asn Pro Lys Gln Lys Leu Ala Leu
            20                  25                  30

Ala Lys Gln Leu Asn Leu Lys Pro Arg Gln Val Glu Val Trp Phe Gln
        35                  40                  45

Asn Arg Arg Ala Arg Thr Lys Ser Lys Gln Thr Glu Val Asp Cys Glu
50                  55                  60

Tyr Leu Lys Arg Cys Cys Glu Asn Leu Thr Gln Glu Asn Arg Arg Leu
65                  70                  75                  80

Gln Lys Glu Val Gln Glu Leu Arg Ala Leu Lys Leu Ser Pro Gln Leu
                85                  90                  95

Tyr Met His Met Asn Pro Pro Thr Thr Leu Thr Met Cys Pro Ser Cys
            100                 105                 110

Glu Arg Val
        115

<210> SEQ ID NO 285
<211> LENGTH: 116
<212> TYPE: PRT
<213> ORGANISM: Setaria italica

<400> SEQUENCE: 285

Arg Lys Lys Leu Arg Leu Ser Lys Asp Gln Ser Ala Val Leu Glu Asp
1               5                   10                  15

Ser Phe Arg Glu His Pro Thr Leu Asn Pro Arg Gln Lys Ala Ala Leu
            20                  25                  30

Ala Gln Gln Leu Gly Leu Arg Pro Arg Gln Val Glu Val Trp Phe Gln
        35                  40                  45

Asn Arg Arg Ala Arg Thr Lys Leu Lys Gln Thr Glu Val Asp Cys Glu
50                  55                  60

Phe Leu Lys Arg Cys Cys Glu Thr Leu Thr Glu Glu Asn Arg Arg Leu
65                  70                  75                  80

Gln Lys Glu Val Gln Glu Leu Arg Ala Leu Lys Leu Val Ser Pro His
                85                  90                  95

Leu Tyr Met His Met Ser Pro Pro Thr Thr Leu Thr Met Cys Pro Ser
            100                 105                 110

Cys Glu Arg Val
115

<210> SEQ ID NO 286
<211> LENGTH: 115
<212> TYPE: PRT
<213> ORGANISM: Solanum tuberosum

<400> SEQUENCE: 286

Arg Lys Lys Leu Arg Leu Ser Lys Asp Gln Ser Ala Ile Leu Glu Glu
1               5                   10                  15

Ser Phe Lys Glu His Asn Thr Leu Asn Pro Lys Gln Lys Leu Ala Leu
            20                  25                  30

Ala Lys Arg Leu Gly Leu Arg Pro Arg Gln Val Glu Val Trp Phe Gln
        35                  40                  45

Asn Arg Arg Ala Arg Thr Lys Leu Lys Gln Thr Glu Val Asp Cys Glu
50                  55                  60

Phe Leu Lys Arg Cys Cys Glu Asn Leu Thr Glu Glu Asn Arg Arg Leu

```
                    65                  70                  75                  80
        Gln Lys Glu Val Gln Glu Leu Arg Ala Leu Lys Leu Ser Pro Gln Phe
                        85                  90                  95

Tyr Met Gln Met Thr Pro Pro Thr Thr Leu Thr Met Cys Pro Ser Cys
                       100                 105                 110

Glu Arg Val
               115

<210> SEQ ID NO 287
<211> LENGTH: 116
<212> TYPE: PRT
<213> ORGANISM: Sorghum bicolor

<400> SEQUENCE: 287

Arg Lys Lys Leu Arg Leu Ser Lys Asp Gln Ser Ala Val Leu Glu Asp
        1               5                  10                  15

Ser Phe Arg Glu His Pro Thr Leu Asn Pro Arg Gln Lys Ala Ala Leu
                        20                  25                  30

Ala Gln Gln Leu Gly Leu Arg Pro Arg Gln Val Glu Val Trp Phe Gln
                        35                  40                  45

Asn Arg Arg Ala Arg Thr Lys Leu Lys Gln Thr Glu Val Asp Cys Glu
                50                  55                  60

Tyr Leu Lys Arg Cys Cys Glu Thr Leu Thr Glu Glu Asn Arg Arg Leu
        65                  70                  75                  80

His Lys Glu Val Gln Glu Leu Arg Ala Leu Lys Leu Val Ser Pro His
                        85                  90                  95

Leu Tyr Met His Met Pro Pro Pro Thr Thr Leu Thr Met Cys Pro Ser
                       100                 105                 110

Cys Glu Arg Val
                   115

<210> SEQ ID NO 288
<211> LENGTH: 115
<212> TYPE: PRT
<213> ORGANISM: Theobroma cacao

<400> SEQUENCE: 288

Arg Lys Lys Leu Arg Leu Ser Lys Glu Gln Ser Leu Leu Leu Glu Glu
        1               5                  10                  15

Thr Phe Lys Glu His Ser Thr Leu Asn Pro Lys Gln Lys Leu Ala Leu
                        20                  25                  30

Ala Lys Gln Leu Asn Leu Arg Pro Arg Gln Val Glu Val Trp Phe Gln
                        35                  40                  45

Asn Arg Arg Ala Arg Thr Lys Leu Lys Gln Thr Glu Val Asp Cys Glu
                50                  55                  60

Tyr Leu Lys Arg Cys Cys Glu Asn Leu Thr Glu Glu Asn Arg Arg Leu
        65                  70                  75                  80

Gln Lys Glu Val Gln Glu Leu Arg Ala Leu Lys Leu Ser Pro Gln Leu
                        85                  90                  95

Tyr Met His Met Asn Pro Pro Thr Thr Leu Thr Met Cys Pro Ser Cys
                       100                 105                 110

Glu Arg Val
               115

<210> SEQ ID NO 289
<211> LENGTH: 116
<212> TYPE: PRT
```

-continued

<213> ORGANISM: Triticum urartu

<400> SEQUENCE: 289

Arg Lys Lys Leu Arg Leu Ser Lys Asp Gln Ser Ala Val Leu Glu Asp
1               5                   10                  15

Ser Phe Arg Glu His Pro Thr Leu Asn Pro Arg Gln Lys Ala Ala Leu
            20                  25                  30

Ala Gln Gln Leu Gly Leu Arg Ser Arg Gln Val Glu Val Trp Phe Gln
        35                  40                  45

Asn Arg Arg Ala Arg Thr Lys Leu Lys Gln Thr Glu Val Asp Cys Glu
    50                  55                  60

Phe Leu Lys Arg Cys Cys Glu Thr Leu Thr Glu Asn Arg Arg Leu
65                  70                  75                  80

Gln Lys Glu Val Gln Glu Leu Arg Ala Leu Lys Leu Val Ser Pro His
                85                  90                  95

His Tyr Met His Met Ser Pro Pro Thr Thr Leu Thr Met Cys Pro Ser
            100                 105                 110

Cys Glu Arg Val
        115

<210> SEQ ID NO 290
<211> LENGTH: 115
<212> TYPE: PRT
<213> ORGANISM: Vitis vinifera

<400> SEQUENCE: 290

Arg Lys Lys Leu Arg Leu Ser Lys Glu Gln Ser Ala Ile Leu Glu Glu
1               5                   10                  15

Thr Phe Lys Glu His Asn Thr Leu Asn Pro Lys Gln Lys Leu Ala Leu
            20                  25                  30

Ala Lys Gln Leu Asn Leu Arg Pro Arg Gln Val Glu Val Trp Phe Gln
        35                  40                  45

Asn Arg Arg Ala Arg Thr Lys Leu Lys Gln Thr Glu Val Asp Cys Glu
    50                  55                  60

Tyr Leu Lys Arg Cys Cys Glu Asn Leu Thr Glu Glu Asn Arg Arg Leu
65                  70                  75                  80

Gln Lys Glu Val Gln Glu Leu Arg Thr Leu Lys Leu Ser Pro Gln Leu
                85                  90                  95

Tyr Met His Met Asn Pro Pro Thr Thr Leu Thr Met Cys Pro Ser Cys
            100                 105                 110

Glu Arg Val
    115

<210> SEQ ID NO 291
<211> LENGTH: 116
<212> TYPE: PRT
<213> ORGANISM: Zea mays

<400> SEQUENCE: 291

Arg Lys Lys Leu Arg Leu Ser Lys Asp Gln Ser Ala Val Leu Glu Asp
1               5                   10                  15

Ser Phe Arg Glu His Pro Thr Leu Asn Pro Arg Gln Lys Ala Ala Leu
            20                  25                  30

Ala Gln Gln Leu Gly Leu Arg Pro Arg Gln Val Glu Val Trp Phe Gln
        35                  40                  45

Asn Arg Arg Ala Arg Thr Lys Leu Lys Gln Thr Glu Val Asp Cys Glu
    50                  55                  60

```
Tyr Leu Lys Arg Cys Cys Glu Thr Leu Thr Glu Glu Asn Arg Arg Leu
 65                  70                  75                  80

Gln Lys Glu Val Gln Glu Leu Arg Ala Leu Lys Leu Val Ser Pro His
                 85                  90                  95

Leu Tyr Met His Met Ser Pro Pro Thr Thr Leu Thr Met Cys Pro Ser
            100                 105                 110

Cys Glu Arg Val
        115

<210> SEQ ID NO 292
<211> LENGTH: 56
<212> TYPE: RNA
<213> ORGANISM: Artificial Sequence
<220> FEATURE:
<223> OTHER INFORMATION: Synthetic oligonucleotide

<400> SEQUENCE: 292
ccgccaggug gagguguggu uccagaacag gcgcgccagg acgaagcuga agcaga         56

<210> SEQ ID NO 293
<211> LENGTH: 56
<212> TYPE: RNA
<213> ORGANISM: Artificial Sequence
<220> FEATURE:
<223> OTHER INFORMATION: Synthetic oligonucleotide

<400> SEQUENCE: 293
ggcgguccac cuccacacca aggucuuguc cgcgcggucc ugcuucgacu ucgucu         56

<210> SEQ ID NO 294
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 294

Arg Gln Val Glu Val Trp Phe Gln Asn Arg Arg Ala Arg Thr Lys Leu
 1               5                  10                  15

Lys Gln

<210> SEQ ID NO 295
<211> LENGTH: 116
<212> TYPE: DNA
<213> ORGANISM: Artificial Sequence
<220> FEATURE:
<223> OTHER INFORMATION: Synthetic oligonucleotide

<400> SEQUENCE: 295
aagaagctcc gcctgtccaa ggaccaggcc gccgtcctcg aggagagctt caaggagcat     60
aacacactca accccgtacg tgtataatta cttatatcct ccaaaaagaa acatcg        116

<210> SEQ ID NO 296
<211> LENGTH: 25
<212> TYPE: PRT
<213> ORGANISM: Artificial sequence
<220> FEATURE:
<223> OTHER INFORMATION: Synthetic peptide

<400> SEQUENCE: 296

Lys Lys Leu Arg Leu Ser Lys Asp Gln Ala Ala Val Leu Glu Glu Ser
 1               5                  10                  15
```

Phe Lys Glu His Asn Thr Leu Asn Pro
            20                  25

<210> SEQ ID NO 297
<211> LENGTH: 106
<212> TYPE: DNA
<213> ORGANISM: Artificial Sequence
<220> FEATURE:
<223> OTHER INFORMATION: Synthetic oligonucleotide

<400> SEQUENCE: 297
aagaagctcc gcctgtccaa ggaccaggcc gccgtcctcg aggagagctt caaggagcat    60
aacacgtacg tgtataatta cttatatcct ccaaaaagaa acatcg                  106

<210> SEQ ID NO 298
<211> LENGTH: 126
<212> TYPE: DNA
<213> ORGANISM: Artificial Sequence
<220> FEATURE:
<223> OTHER INFORMATION: Synthetic oligonucleotide

<400> SEQUENCE: 298
caaggaccag gccgccgtcc tcgaggagag cttcaaggag cataacacaa gcagaaggcg    60
gcgctggcga agcagctgaa cctgaagccg cgtcaggtgg aggtgtggtt ccagaaccgc   120
agagcc                                                              126

<210> SEQ ID NO 299
<211> LENGTH: 126
<212> TYPE: DNA
<213> ORGANISM: Artificial Sequence
<220> FEATURE:
<223> OTHER INFORMATION: Synthetic oligonucleotide

<400> SEQUENCE: 299
gttcctggtc cggcggcagg agctcctctc gaagttcctc gtattgtgtt cgtcttccgc    60
cgcgaccgct tcgtcgactt ggacttcggc gcagtccacc tccacaccaa ggtcttggcg   120
tctcgg                                                              126

<210> SEQ ID NO 300
<211> LENGTH: 25
<212> TYPE: PRT
<213> ORGANISM: Artificial Sequence
<220> FEATURE:
<223> OTHER INFORMATION: Synthetic peptide

<400> SEQUENCE: 300

Lys Asp Gln Ala Ala Val Leu Glu Glu Ser Phe Lys Glu His Asn Thr
1               5                   10                  15

Ser Arg Arg Arg Arg Trp Arg Ser Ser
            20                  25

<210> SEQ ID NO 301
<211> LENGTH: 14
<212> TYPE: PRT
<213> ORGANISM: Artificial Sequence
<220> FEATURE:
<223> OTHER INFORMATION: Synthetic peptide

<400> SEQUENCE: 301

Ser Arg Val Arg Trp Arg Cys Gly Ser Arg Thr Ala Glu Pro
1               5                   10

```
<210> SEQ ID NO 302
<211> LENGTH: 53
<212> TYPE: PRT
<213> ORGANISM: Hordeum vulgare

<400> SEQUENCE: 302

Leu Ala Arg Gln Leu Arg Leu Arg Pro Arg Gln Val Glu Val Trp Phe
1               5                   10                  15

Gln Asn Arg Arg Ala Arg Thr Lys Leu Lys Gln Thr Glu Val Asp Cys
            20                  25                  30

Glu Ser Leu Lys Arg Cys Cys Glu Thr Leu Thr Glu Glu Asn Arg Arg
        35                  40                  45

Leu Gln Arg Glu Val
    50

<210> SEQ ID NO 303
<211> LENGTH: 323
<212> TYPE: PRT
<213> ORGANISM: Oryza_brachyantha
<220> FEATURE:
<221> NAME/KEY: misc_feature
<222> LOCATION: (243)..(291)
<223> OTHER INFORMATION: Xaa can be any naturally occurring amino acid

<400> SEQUENCE: 303

Met Glu Thr Met Val His Gly Arg Arg Glu Gln Gln Arg His Val Gly
1               5                   10                  15

Leu Gly Leu Gly Leu Gly Leu Gly Leu Ser Leu Gly Val Gly Ala Val
            20                  25                  30

Asp Glu Gln Pro Cys Arg Gly Ala Arg Val Pro Ser Pro Ala Ala Pro
        35                  40                  45

Pro Pro Pro Ser Gln Glu Cys Ser Trp Ser Gly Ala Gly Leu Phe Ser
    50                  55                  60

Ser Ser Ser Ser Asp Arg Arg Ser Thr Thr Met Met Thr Ala Met Ala
65                  70                  75                  80

Ala Cys His Asp Val Glu Met Pro Phe Leu Arg Gly Ile Asp Val Asn
                85                  90                  95

Arg Ala Pro Ala Glu Thr Thr Arg Pro Gly Leu Ser Cys Ser Glu Glu
            100                 105                 110

Asp Glu Glu Thr Gly Ala Ser Ser Pro Asn Ser Thr Leu Ser Ser Leu
        115                 120                 125

Ser Gly Lys Arg Gly Ala Pro Ala Ala Arg Thr Ala Ala Ala Gly
    130                 135                 140

Gly Ser Asp Asp Glu Asp Ser Gly Ala Gly Ala Gly Ser Arg Lys Lys
145                 150                 155                 160

Leu Arg Leu Ser Lys Asp Gln Ala Ala Val Leu Glu Asp Thr Phe Lys
                165                 170                 175

Glu His Asn Thr Leu Asn Pro Lys Gln Lys Ala Ala Leu Ala Arg Gln
            180                 185                 190

Leu Gly Leu Lys Pro Arg Gln Val Glu Val Trp Phe Gln Asn Arg Arg
        195                 200                 205

Ala Arg Thr Lys Leu Lys Gln Thr Glu Val Asp Cys Glu Leu Leu Lys
    210                 215                 220

Arg Cys Cys Glu Thr Leu Thr Glu Glu Asn Arg Arg Leu His Lys Glu
225                 230                 235                 240

Leu Ala Xaa Xaa Xaa Xaa Xaa Xaa Xaa Xaa Xaa Xaa Xaa Xaa Xaa Xaa
                245                 250                 255
```

| | | | | | | | | | | | | |
|---|---|---|---|---|---|---|---|---|---|---|---|---|
| Xaa | Xaa | Xaa | Xaa | Xaa | Xaa | Xaa | Xaa | Xaa | Xaa | Xaa | Xaa | Xaa |
| | | 260 | | | | | 265 | | | | 270 | |

Xaa Xaa Xaa Xaa Xaa Xaa Xaa Xaa Xaa Xaa Xaa Xaa Xaa
    275              280              285

Xaa Xaa Xaa Pro Arg Gln His Pro Pro Arg Pro Ala Asp Val Val Pro
    290              295              300

Pro Gln Ala Gly Gly Glu Glu Ala Ala Ala Val Val Glu Val Leu His
305            310              315              320

Trp Arg Gly

<210> SEQ ID NO 304
<211> LENGTH: 1648
<212> TYPE: DNA
<213> ORGANISM: Zea mays

<400> SEQUENCE: 304

| | | | | | |
|---|---|---|---|---|---|
| actgccacac | cacatcgaca | gctccatcga | ttcatccacc | gctatctctc | tctctctctc | 60 |
| tctctctctc | tctctctctc | tctttcaact | gtaagggaaa | ccgagctcaa | agtggcaacc | 120 |
| atcaatggat | attatggcgc | ttaatgcgag | agacgaggag | cagtacggga | acaaccatct | 180 |
| cgggctcggg | ctgagcctca | gcctcggcct | cggcgtcgcc | accgcggctc | cggtcgaggt | 240 |
| cgagcccccg | ccaccgccgc | ggcagcagca | gcagcgagct | atcagcgtcg | cgcccatcac | 300 |
| ctccctcccc | gcgccgcagt | ggtggaagtg | gaacggcccc | ggtctcttct | tcggtgagta | 360 |
| attgattcaa | agagcagaca | ccgcatgcat | gacgccgttc | ctctaatcct | gacagagata | 420 |
| ctgcgcgcat | gcatgcaggg | acgacaatgg | atcagcagca | gcagccggcg | gccgcgcgcc | 480 |
| acggccacga | gatgccgttc | ctgcgggggg | tggacgtgaa | ccgggcccct | gccggggata | 540 |
| ccaggagggg | tagctgcagc | gaggacgacg | aggagcctgg | cggcgcgtcg | tcgtcgccaa | 600 |
| acagcacgct | ctccagcagc | ctcagcggga | agcgcgcagc | tccggcgagg | agcggcggag | 660 |
| aggtggccga | ccacaccccg | agagccggag | gcggcagcga | cgacgaggac | tccggcggtg | 720 |
| ggtcgcgcaa | gaagctccgc | ctgtccaagg | accaggccgc | cgtcctcgag | gagagcttca | 780 |
| aggagcataa | cacactcaac | cccgtacgtg | tataattact | tatatcctcc | aaaaagaaac | 840 |
| atcgatcaac | cttcaactcg | atctaataat | aataagaacc | gttggctgat | cagaagcaga | 900 |
| aggcggcgct | ggcgaagcag | ctgaacctga | agccgcgtca | ggtggaggtg | tggttccaga | 960 |
| accgcagagc | caggtgaaca | agcagcgcc | cttgaagcag | cacacgcatg | ccatttatac | 1020 |
| tgactcatcc | tccgtggcta | atactagtct | aataataata | ttatcgttca | ggacgaagct | 1080 |
| gaagcagacg | gaggtggact | gcgagttcct | gaagcgctgc | tgcgagacgc | tgacggagga | 1140 |
| gaaccggcgg | ctgcagcggg | aggtggcgga | gctgcgcgtg | ctcaagctcg | tggcgccgca | 1200 |
| ccactacgcg | cgcatgccgc | cgcccaccac | gctccaccatg | tgcccctcct | gcgagcgcct | 1260 |
| cgcctccgcg | tccgcgtccg | ccgaccagge | gggccgtgca | gggccctgct | ggggccctct | 1320 |
| ccccgtgttc | gtcgacggcc | cagcccggag | gccgtgatcc | acgaccacga | tatggcatga | 1380 |
| gatggatgcg | cttgctaatc | gctaccgcta | gctaagtagc | tagtgctaat | tagggctgga | 1440 |
| tcttcttttt | ttctttgttt | ggttcttatt | atactcgcag | gctattacag | cttagtagtg | 1500 |
| tttattagtc | cgatatgata | aaaatcttcg | ttgtttggca | gtgtttatt | tgctgaaaaa | 1560 |
| tagataacga | tgtcttatgt | ctttgtactc | ataagtgatg | caaaattgtc | ttactactac | 1620 |
| tttgcatata | taaggtttca | gttgttaa | | | | 1648 |

<210> SEQ ID NO 305
<211> LENGTH: 1375
<212> TYPE: DNA
<213> ORGANISM: Zea mays

<400> SEQUENCE: 305

| | | | | | |
|---|---|---|---|---|---|
| actgccacac | cacatcgaca | gctccatcga | ttcatccacc | gctatctctc | tctctctctc | 60 |
| tctctctctc | tctctctctc | tctttcaact | gtaagggaaa | ccgagctcaa | agtggcaacc | 120 |
| atcaatggat | attatggcgc | ttaatgcgag | agacgaggag | cagtacggga | acaaccatct | 180 |
| cgggctcggg | ctgagcctca | gcctcggcct | cggcgtcgcc | accgcggctc | cggtcgaggt | 240 |
| cgagcccccg | ccaccgccgc | ggcagcagca | gcagcgagct | atcagcgtcg | cgcccatcac | 300 |
| ctccctcccc | gcgccgcagt | ggtggaagtg | gaacggcccc | ggtctcttct | tcgggacgac | 360 |
| aatggatcag | cagcagcagc | cggcggccgc | gcgccacggc | cacgagatgc | cgttcctgcg | 420 |
| gggggtggac | gtgaaccggg | ccctgccgg | ggataccagg | aggggtagct | gcagcgagga | 480 |
| cgacgaggag | cctggcggcg | cgtcgtcgtc | gccaaacagc | acgctctcca | gcagcctcag | 540 |
| cgggaagcgc | gcagctccgg | cgaggagcgg | cggagaggtg | gccgaccaca | ccccgagagc | 600 |
| cggaggcggc | agcgacgacg | aggactccgg | cggtgggtcg | cgcaagaagc | tccgcctgtc | 660 |
| caaggaccag | gccgccgtcc | tcgaggagag | cttcaaggag | cataacacac | tcaacccca | 720 |
| gcagaaggcg | cgctggcga | agcagctgaa | cctgaagccg | cgtcaggtgg | aggtgtggtt | 780 |
| ccagaaccgc | agagccagga | cgaagctgaa | gcagacggag | gtggactgcg | agttcctgaa | 840 |
| gcgctgctgc | gagacgctga | cggaggagaa | ccggcggctg | cagcgggagg | tggcggagct | 900 |
| gcgcgtgctc | aagctcgtgg | cgccgcacca | ctacgcgcgc | atgccgccgc | ccaccacgct | 960 |
| caccatgtgc | ccctcctgcg | agcgcctcgc | ctccgcgtcc | gcgtccgccg | accaggcggg | 1020 |
| ccgtgcaggg | ccctgctggg | gccctctccc | cgtgttcgtc | gacggcccag | cccggaggcc | 1080 |
| gtgatccacg | accacgatat | ggcatgagat | ggatgcgctt | gctaatcgct | accgctagct | 1140 |
| aagtagctag | tgctaattag | ggctggatct | tctttttttc | tttgtttggt | tcttattata | 1200 |
| ctcgcaggct | attacagctt | agtagtgttt | attagtccga | tatgataaaa | atcttcgttg | 1260 |
| tttggcagtg | ttttatttgc | tgaaaaatag | ataacgatgt | cttatgtctt | tgtactcata | 1320 |
| agtgatgcaa | aattgtctta | ctactacttt | gcatatataa | ggtttcagtt | gttaa | 1375 |

<210> SEQ ID NO 306
<211> LENGTH: 314
<212> TYPE: PRT
<213> ORGANISM: Artificial Sequence
<220> FEATURE:
<223> OTHER INFORMATION: Synthetic polypeptide

<400> SEQUENCE: 306

Met Asp Ile Met Ala Leu Asn Ala Arg Asp Glu Glu Gln Tyr Gly Asn
1               5                   10                  15

Asn His Leu Gly Leu Gly Leu Ser Leu Ser Leu Gly Leu Gly Val Ala
            20                  25                  30

Thr Ala Ala Pro Val Glu Val Glu Pro Pro Pro Pro Arg Gln Gln
        35                  40                  45

Gln Gln Arg Ala Ile Ser Val Ala Pro Ile Thr Ser Leu Pro Ala Pro
    50                  55                  60

Gln Trp Trp Lys Trp Asn Gly Pro Gly Leu Phe Phe Gly Thr Thr Met
65                  70                  75                  80

Asp Gln Gln Gln Gln Pro Ala Ala Ala Arg His Gly His Glu Met Pro

```
                    85                  90                  95
Phe Leu Arg Gly Val Asp Val Asn Arg Ala Pro Ala Gly Asp Thr Arg
                100                 105                 110

Arg Gly Ser Cys Ser Glu Asp Glu Glu Pro Gly Gly Ala Ser Ser
            115                 120                 125

Ser Pro Asn Ser Thr Leu Ser Ser Ser Leu Ser Gly Lys Arg Ala Ala
        130                 135                 140

Pro Ala Arg Ser Gly Gly Glu Val Ala Asp His Thr Pro Arg Ala Gly
145                 150                 155                 160

Gly Gly Ser Asp Asp Glu Asp Ser Gly Gly Gly Ser Arg Lys Lys Leu
                165                 170                 175

Arg Leu Ser Lys Asp Gln Ala Ala Val Leu Glu Glu Ser Phe Lys Glu
            180                 185                 190

His Asn Thr Leu Asn Pro Lys Gln Lys Ala Ala Leu Ala Lys Gln Leu
        195                 200                 205

Asn Leu Lys Pro Arg Gln Val Glu Val Trp Phe Gln Asn Arg Arg Ala
    210                 215                 220

Arg Thr Lys Leu Met Arg Val Pro Glu Ala Leu Leu Arg Asp Ala Asp
225                 230                 235                 240

Gly Gly Glu Pro Ala Ala Ala Gly Gly Gly Ala Ala Arg Ala
                245                 250                 255

Gln Ala Arg Gly Ala Ala Pro Leu Arg Ala His Ala Ala His His
            260                 265                 270

Ala His His Val Pro Leu Leu Arg Ala Pro Arg Leu Arg Val Arg Val
        275                 280                 285

Arg Arg Pro Gly Gly Pro Cys Arg Ala Leu Leu Gly Pro Ser Pro Arg
    290                 295                 300

Val Arg Arg Arg Pro Ser Pro Glu Ala Val
305                 310

<210> SEQ ID NO 307
<211> LENGTH: 1631
<212> TYPE: DNA
<213> ORGANISM: Artificial Sequence
<220> FEATURE:
<223> OTHER INFORMATION: Synthethic polynucleotide

<400> SEQUENCE: 307
actgccacac cacatcgaca gctccatcga ttcatccacc gctatctctc tctctctctc      60
tctctctctc tctctctctc tctttcaact gtaagggaaa ccgagctcaa agtggcaacc     120
atcaatggat attatggcgc ttaatgcgag agacgaggag cagtacggga acaaccatct     180
cgggctcggg ctgagcctca gcctcggcct cggcgtcgcc accgcggctc cggtcgaggt     240
cgagcccccg ccaccgccgc ggcagcagca gcagcgagct atcagcgtcg cgcccatcac     300
ctccctcccc gcgccgcagt ggtggaagtg gaacggcccc ggtctcttct tcggtgagta     360
attgattcaa agagcagaca ccgcatgcat gacgccgttc ctctaatcct gacagagata     420
ctgcgcgcat gcatgcaggg acgacaatgg atcagcagca gcagccggcg gccgcgcgcc     480
acggccacga gatgccgttc ctgcgggggg tggacgtgaa ccgggcccct gccggggata     540
ccaggagggg tagctgcagc gaggacgacg aggagcctgg cggcgcgtcg tcgtcgccaa     600
acagcacgct ctccagcagc tcagcgggga gcgcgcagc tccggcgagg agcggcggag     660
aggtggccga ccacaccccg agagccggag gcggcagcga cgacgaggac tccggcggtg     720
ggtcgcgcaa gaagctccgc ctgtccaagg accaggccgc cgtcctcgag gagagcttca     780
```

```
aggagcataa cacactcaac cccgtacgtg tataattact tatatcctcc aaaaagaaac    840
atcgatcaac cttcaactcg atctaataat aataagaacc gttggctgat cagaagcaga    900
aggcggcgct ggcgaagcag ctgaacctga agccgcgtca ggtggaggtg tggttccaga    960
accgcagagc caggtgaaca aagcagcgcc cttgaagcag cacacgcatg ccatttatac   1020
tgactcatcc tccgtggcta atactagtct aataataata ttatcgttca ggacgaagct   1080
gatgcgagtt cctgaagcgc tgctgcgaga cgctgacgga ggagaaccgg cggctgcagc   1140
gggaggtggc ggagctgcgc gtgctcaagc tcgtggcgcc gcaccactac gcgcgcatgc   1200
cgccgcccac cacgctcacc atgtgcccct cctgcgagcg cctcgcctcc gcgtccgcgt   1260
ccgccgacca ggcgggccgt gcagggccct gctgggccc tctccccgtg ttcgtcgacg    1320
gcccagcccg gaggccgtga tccacgacca cgatatggca tgagatggat gcgcttgcta   1380
atcgctaccg ctagctaagt agctagtgct aattagggct ggatcttctt tttttctttg   1440
tttggttctt attatactcg caggctatta cagcttagta gtgtttatta gtccgatatg   1500
ataaaaatct tcgttgtttg gcagtgtttt atttgctgaa aaatagataa cgatgtctta   1560
tgtctttgta ctcataagtg atgcaaaatt gtcttactac tactttgcat atataaggtt   1620
tcagttgtta a                                                        1631
```

<210> SEQ ID NO 308
<211> LENGTH: 943
<212> TYPE: DNA
<213> ORGANISM: Artificial Sequence
<220> FEATURE:
<223> OTHER INFORMATION: Synthetic polynucleotide

<400> SEQUENCE: 308

```
atggatatta tggcgcttaa tgcgagagac gaggagcagt acgggaacaa ccatctcggg     60
ctcgggctga gcctcagcct cggcctcggc gtcgccaccg cggctccggt cgaggtcgag    120
cccccgccac cgccgcggca gcagcagcag cgagctatca gcgtcgcgcc catcacctcc    180
ctccccgcgc cgcagtggtg gaagtggaac ggccccggtc tcttcttcgg gacgacaatg    240
gatcagcagc agcagccggc ggccgcgcgc cacgccacg agatgccgtt cctgcggggg    300
gtggacgtga accgggcccc tgccggggat accaggaggg gtagctgcag cgaggacgac    360
gaggagcctg gcgcgcgtc gtcgtcgcca acagcacgc tctccagcag cctcagcggg     420
aagcgcgcag ctccggcgag gagcggcgga gaggtggccg accacacccc gagagccgga    480
ggcggcagcg acgacgagga ctccggcggt gggtcgcgca agaagctccg cctgtccaag    540
gaccaggccg ccgtcctcga ggagagcttc aaggagcata acacactcaa ccccaagcag    600
aagcggcgc tggcgaagca gctgaacctg agccgcgtc aggtggaggt gtggttccag     660
aaccgcagag ccaggacgaa gctgatgcga gttcctgaag cgctgctgcg agacgctgac    720
ggaggagaac cggcggctgc agcgggaggt ggcggagctg cgcgtgctca agctcgtggc    780
gccgcaccac tacgcgcgca tgccgccgcc caccacgctc accatgtgcc cctcctgcga    840
gcgcctcgcc tccgcgtccg cgtccgccga ccaggcgggc cgtgcagggc cctgctgggg    900
ccctctcccc gtgttcgtcg acgggccagc ccggaggccg tga                     943
```

<210> SEQ ID NO 309
<211> LENGTH: 1358
<212> TYPE: DNA
<213> ORGANISM: Artificial Sequence
<220> FEATURE:

<223> OTHER INFORMATION: Synthetic polynucleotide

<400> SEQUENCE: 309

| | | |
|---|---|---|
| actgccacac cacatcgaca gctccatcga ttcatccacc gctatctctc tctctctctc | 60 |
| tctctctctc tctctctctc tctttcaact gtaagggaaa ccgagctcaa agtggcaacc | 120 |
| atcaatggat attatggcgc ttaatgcgag agacgaggag cagtacggga acaaccatct | 180 |
| cgggctcggg ctgagcctca gcctcggcct cggcgtcgcc accgcggctc cggtcgaggt | 240 |
| cgagccccg ccaccgccgc ggcagcagca gcagcgagct atcagcgtcg cgcccatcac | 300 |
| ctccctcccc gcgccgcagt ggtggaagtg gaacggcccc ggtctcttct tcgggacgac | 360 |
| aatggatcag cagcagcagc cggcggccgc gcgccacggc cacgagatgc cgttcctgcg | 420 |
| ggggtggac gtgaaccggg cccctgccgg ggataccagg aggggtagct gcagcgagga | 480 |
| cgacgaggag cctggcggcg cgtcgtcgtc gccaaacagc acgctctcca gcagcctcag | 540 |
| cgggaagcgc gcagctccgg cgaggagcgg cggagaggtg gccgaccaca ccccgagagc | 600 |
| cggaggcggc agcgacgacg aggactccgg cggtgggtcg cgcaagaagc tccgcctgtc | 660 |
| caaggaccag gccgccgtcc tcgaggagag cttcaaggag cataacacac tcaaccccaa | 720 |
| gcagaaggcg gcgctggcga agcagctgaa cctgaagccg cgtcaggtgg aggtgtggtt | 780 |
| ccagaaccgc agagccagga cgaagctgat gcgagttcct gaagcgctgc tgcgagacgc | 840 |
| tgacggagga gaaccggcgg ctgcagcggg aggtggcgga gctgcgcgtg ctcaagctcg | 900 |
| tggcgccgca ccactacgcg cgcatgccgc cgcccaccac gctcaccatg tgcccctcct | 960 |
| gcgagcgcct cgcctccgcg tccgcgtccg ccgaccaggc gggccgtgca gggccctgct | 1020 |
| ggggccctct ccccgtgttc gtcgacggcc cagcccggag gccgtgatcc acgaccacga | 1080 |
| tatggcatga gatggatgcg cttgctaatc gctaccgcta gctaagtagc tagtgctaat | 1140 |
| tagggctgga tcttcttttt ttctttgttt ggttcttatt atactcgcag gctattacag | 1200 |
| cttagtagtg tttattagtc cgatatgata aaaatcttcg ttgtttggca gtgttttatt | 1260 |
| tgctgaaaaa tagataacga tgtcttatgt ctttgtactc ataagtgatg caaaattgtc | 1320 |
| ttactactac tttgcatata taaggtttca gttgttaa | 1358 |

<210> SEQ ID NO 310
<211> LENGTH: 1708
<212> TYPE: DNA
<213> ORGANISM: Artificial Sequence
<220> FEATURE:
<223> OTHER INFORMATION: Synthetic polynucleotide

<400> SEQUENCE: 310

| | | |
|---|---|---|
| cttcttttat caccttcatc tatatctact gctactctca gtactatata tctatcccca | 60 |
| gttccatagt tcttccagct ctacacatac acatacacgc agcacgctag ctctagctct | 120 |
| cacatcgatt gagatcatca gagggtgga agaagaagga gctaagatac cagatcgagg | 180 |
| aagagaggcg gtgcggtcgg tagatgatgg agagggtcga ggacttaggg ctcagcctca | 240 |
| gcctcagctc gtccctcgcg tctcctcgaa ctcaccatgt cgccaccatg ctgctacgcg | 300 |
| ctccaggtaa atataatgca atttgctata tatatatata tatatatata tctctgtact | 360 |
| aagtagctat atatgctgct tggatgatct atcagagagt atttagctag ctcctgcagg | 420 |
| cacgcgcgct actgctagca gctaactgtg aatgaccata tcaattaagc tatagctagc | 480 |
| tctagtgtac atgtgtgagt tttatgtctg tctgactata tgtaagatta gtagtcagca | 540 |
| actacaaacc gtacgtgtat ggctggcact ctgatgcatc acatataatg tatcagagaa | 600 |

-continued

```
gaggttcctg agatgccac tgctgctgcc cgcgaagcgg acgaccgagg tcaccggcga        660
ggatggcctg cgaggcggca gcgacgagga ggacggcggc tgcggcatcg acggctccag        720
gaagaagctc cggctgtcca aggaccagtc cgccgtgctc aggatagct tccgggagca         780 cccaactctc aaccctgtaa gtactagtag tatagtagta gcagtagca ttaagagcta         840 cagttctgtg gttcatcctc ccggccgctc accaagactc ctgatggacg aacgtacagc        900
taggctaggc agcagtagct ttcaatcatt cgccggttct cgaccttatc aacctgcctg        960
tgactgtgag ctgtactaac ttgcttatta atggcgtgca gcggcagaag gcagccttgg       1020
cgcagcagct aggcctgcgg ccccgccagg tggaggtgtg gttccagaac aggcgcgcca       1080
ggtacgtacg tagcgcacat gcgatatgtc gccgcgcgct agctgcttcg cgtgtgctga       1140
tgatcagcaa gcatgcactg catgtctgca tgggatttct ctctcttttc tgcccctcgc       1200
tcgatcgctt cattcgttcg tgcaggacga agctgaagca gacggaggtg gactgcgagt       1260
acctgaagcg ctgctgcgag acgctgacgg aggagaaccg gcggctgcag aaggaggtgc       1320
aggagctccg cgcgctcaag ctcgtgtcgc cgcacctcta catgcacatg tccccgccca       1380
ccaccctcac catgtgcccc tcctgcgagc gcgtctcctc gtccaacggc aactccgcag       1440
ctgccacggc cgccgcgcgc gcgcgcgccg gcgccggcgc cggcgccatc gtctgccacc       1500
cgatcgaccg agccactagt acgtagtagt agtagctgct acactagcta gctgtacacg       1560
ggcgccggcc gtaacgtgta aaagccaaca aaacagtctc tctgcgcatt tattcgaccg       1620
tgcaaacgac tgttccctcg ttaatcttag tattggtatt gactagtcac ccacagtatt       1680
agacttgaag atccagcaga ttacagtt                                           1708

<210> SEQ ID NO 311
<211> LENGTH: 1069
<212> TYPE: DNA
<213> ORGANISM: Zea mays

<400> SEQUENCE: 311
cttcttttat caccttcatc tatatctact gctactctca gtactatata tctatcccca         60
gttccatagt tcttccagct ctacacatac acatacacgc agcacgctag ctctagctct        120
cacatcgatt gagatcatca gagaggtgga agaagaagga gctaagatac cagatcgagg        180
aagagaggcg gtgcggtcgg tagatgatgg agagggtcga ggacttaggg ctcagcctca        240
gcctcagctc gtccctcgcg tctcctcgaa ctcaccatgt cgccaccatg ctgctacgcg        300
ctccagagaa gaggttcctg gagatgccac tgctgctgcc cgcgaagcgg acgaccgagg        360
tcaccggcga ggatggcctg cgaggcggca gcgacgagga ggacggcggc tgcggcatcg        420
acggctccag gaagaagctc cggctgtcca aggaccagtc cgccgtgctc gaggatagct        480
tccgggagca cccaactctc aaccctcggc agaaggcagc cttggcgcag cagctaggcc        540
tgcggccccg ccaggtggag gtgtggttcc agaacaggcg cgccaggacg aagctgaagc        600
agacggaggt ggactgcgag tacctgaagc gctgctgcga gacgctgacg gaggagaacc        660
ggcggctgca gaaggaggtg caggagctcc gcgcgctcaa gctcgtgtcg ccgcacctct        720
acatgcacat gtccccgccc accaccctca ccatgtgccc ctcctgcgag cgcgtctcct       780
cgtccaacgg caactccgca gctgccacgg ccgccgcgcg cgcgcgcgcc ggcgccggcg        840
ccggcgccat cgtctgccac ccgatcgacc gagccactag tacgtagtag tagtagctgc        900
tacactagct agctgtacac gggcgccggc cgtaacgtgt aaaagccaac aaaacagtct        960
```

```
ctctgcgcat ttattcgacc gtgcaaacga ctgttccctc gttaatctta gtattggtat    1020
tgactagtca cccacagtat tagacttgaa gatccagcag attacagtt               1069

<210> SEQ ID NO 312
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 312

Met Met Glu Arg Val Glu Asp Leu Gly Leu Ser Leu Ser Ser
1               5                   10                  15

Ser Leu Ala Ser Pro Arg Thr His Val Ala Thr Met Leu Leu Arg
            20                  25                  30

Ala Pro Glu Lys Arg Phe Leu Glu Met Pro Leu Leu Pro Ala Lys
        35                  40                  45

Arg Thr Thr Glu Val Thr Gly Glu Asp Gly Leu Arg Gly Gly Ser Asp
    50                  55                  60

Glu Glu Asp Gly Gly Cys Gly Ile Asp Gly Ser Arg Lys Lys Leu Arg
65                  70                  75                  80

Leu Ser Lys Asp Gln Ser Ala Val Leu Glu Asp Ser Phe Arg Glu His
                85                  90                  95

Pro Thr Asn Gly Arg Arg Gln Pro Trp Arg Ser Ser
            100                 105

<210> SEQ ID NO 313
<211> LENGTH: 1697
<212> TYPE: DNA
<213> ORGANISM: Artificial Sequence
<220> FEATURE:
<223> OTHER INFORMATION: Synthetic Polynucleotide

<400> SEQUENCE: 313
cttcttttat caccttcatc tatatctact gctactctca gtactatata tctatcccca     60
gttccatagt tcttccagct ctacacatac acatacacgc agcacgctag ctctagctct    120
cacatcgatt gagatcatca gagaggtgga agaagaagga gctaagatac cagatcgagg    180
aagagaggcg gtgcggtcgg tagatgatgg agagggtcga ggacttaggg ctcagcctca    240
gcctcagctc gtccctcgcg tctcctcgaa ctcaccatgt cgccaccatg ctgctacgcg    300
ctccaggtaa atataatgca atttgctata tatatatata tatatatata tctctgtact    360
aagtagctat atatgctgct tggatgatct atcagagagt atttagctag ctcctgcagg    420
cacgcgcgct actgctagca gctaactgtg aatgaccata tcaattaagc tatagctagc    480
tctagtgtac atgtgtgagt tttatgtctg tctgactata tgtaagatta gtagtcagca    540
actacaaacc gtacgtgtat ggctggcact ctgatgcatc acatataatg tatcagagaa    600
gaggttcctg gagatgccac tgctgctgcc cgcgaagcgg acgaccgagg tcaccggcga    660
ggatggcctg cgaggcggca gcgacgagga ggacggcggc tgcggcatcg acggctccag    720
gaagaagctc cggctgtcca aggaccagtc cgccgtgctc gaggatagct ccgggagca    780 cccaactaag tactagtagt atagtagtag cagctagcat taagagctac agttctgtgg    840
ttcatcctcc cggccgctca ccaagactcc tgatggacga acgtacagct aggctaggca    900
gcagtagctt tcaatcattc gccggttctc gaccttatca acctgcctgt gactgtgagc    960
tgtactaact tgcttattaa tggcgtgcag cggcagaagg cagccttggc gcagcagcta   1020
```

| | |
|---|---:|
| ggcctgcggc cccgccaggt ggaggtgtgg ttccagaaca ggcgcgccag gtacgtacgt | 1080 |
| agcgcacatg cgatatgtcg ccgcgcgcta gctgcttcgc gtgtgctgat gatcagcaag | 1140 |
| catgcactgc atgtctgcat gggatttctc tctcttttct gccctcgct cgatcgcttc | 1200 |
| attcgttcgt gcaggacgaa gctgaagcag acggagtgg actgcgagta cctgaagcgc | 1260 |
| tgctgcgaga cgctgacgga ggagaaccgg cggctgcaga aggaggtgca ggagctccgc | 1320 |
| gcgctcaagc tcgtgtcgcc gcacctctac atgcacatgt ccccgcccac caccctcacc | 1380 |
| atgtgcccct cctgcgagcg cgtctcctcg tccaacggca actccgcagc tgccacggcc | 1440 |
| gccgcgcgcg cgcgcgccgg cgccggcgcc ggcgccatcg tctgccaccc gatcgaccga | 1500 |
| gccactagta cgtagtagta gtagctgcta cactagctag ctgtacacgg gcgccggccg | 1560 |
| taacgtgtaa aagccaacaa aacagtctct ctgcgcattt attcgaccgt gcaaacgact | 1620 |
| gttccctcgt taatcttagt attggtattg actagtcacc cacagtatta gacttgaaga | 1680 |
| tccagcagat tacagtt | 1697 |

<210> SEQ ID NO 314
<211> LENGTH: 677
<212> TYPE: DNA
<213> ORGANISM: Artificial Sequence
<220> FEATURE:
<223> OTHER INFORMATION: Synthetic Polynucleotide

<400> SEQUENCE: 314

| | |
|---|---:|
| atgatggaga gggtcgagga cttagggctc agcctcagcc tcagctcgtc cctcgcgtct | 60 |
| cctcgaactc accatgtcgc caccatgctg ctacgcgctc cagagaagag gttcctggag | 120 |
| atgccactgc tgctgcccgc gaagcggacg accgaggtca ccggcgagga tggcctgcga | 180 |
| ggcggcagcg acgaggagga cggcggctgc ggcatcgacg gctccaggaa gaagctccgg | 240 |
| ctgtccaagg accagtccgc cgtgctcgag gatagcttcc gggagcaccc aactaacggc | 300 |
| agaaggcagc cttggcgcag cagctaggcc tgccggcccg ccaggtggag gtgtggttcc | 360 |
| agaacaggcg cgccaggacg aagctgaagc agacggaggt ggactgcgag tacctgaagc | 420 |
| gctgctgcga gacgctgacg gaggagaacc ggcggctgca gaaggaggtg caggagctcc | 480 |
| gcgcgctcaa gctcgtgtcg ccgcacctct acatgcacat gtccccgccc accaccctca | 540 |
| ccatgtgccc ctcctgcgag cgcgtctcct cgtccaacgg caactccgca gctgccacgg | 600 |
| ccgccgcgcg cgcgcgcgcc ggcgccggcg ccggcgccat cgtctgccac ccgatcgacc | 660 |
| gagccactag tacgtag | 677 |

<210> SEQ ID NO 315
<211> LENGTH: 1062
<212> TYPE: DNA
<213> ORGANISM: Artificial Sequence
<220> FEATURE:
<223> OTHER INFORMATION: Synthetic polynucleotide

<400> SEQUENCE: 315

| | |
|---|---:|
| cttcttttat caccttcatc tatatctact gctactctca gtactatata tctatcccca | 60 |
| gttccatagt tcttccagct ctacacatac acatacacgc agcacgctag ctctagctct | 120 |
| cacatcgatt gagatcatca gagaggtgga agaagaagga gctaagatac cagatcgagg | 180 |
| aagagaggcg gtgcggtcgg tagatgatgg agagggtcga ggacttaggg ctcagcctca | 240 |
| gcctcagctc gtccctcgcg tctcctcgaa ctcaccatgt cgccaccatg ctgctacgcg | 300 |
| ctccagagaa gaggttcctg gagatgccac tgctgctgcc cgcgaagcgg acgaccgagg | 360 |

```
tcaccggcga ggatggcctg cgaggcggca gcgacgagga ggacggcggc tgcggcatcg      420
acggctccag gaagaagctc cggctgtcca aggaccagtc cgccgtgctc gaggatagct      480
tccgggagca cccaactaac ggcagaaggc agccttggcg cagcagctag gcctgcggcc      540
ccgccaggtg gaggtgtggt tccagaacag gcgcgccagg acgaagctga agcagacgga      600
ggtggactgc gagtacctga agcgctgctg cgagacgctg acggaggaga accggcggct      660
gcagaaggag gtgcaggagc tccgcgcgct caagctcgtg tcgccgcacc tctacatgca      720
catgtccccg cccaccaccc tcaccatgtg ccctcctgc gagcgcgtct cctcgtccaa      780
cggcaactcc gcagctgcca cggccgccg gcgcgcgcgc gccggcgccg gcgccggcgc      840
catcgtctgc cacccgatcg accgagccac tagtacgtag tagtagtagc tgctacacta      900
gctagctgta cacgggcgcc ggccgtaacg tgtaaaagcc aacaaaacag tctctctgcg      960
catttattcg accgtgcaaa cgactgttcc ctcgttaatc ttagtattgg tattgactag     1020
tcacccacag tattagactt gaagatccag cagattacag tt                       1062
```

<210> SEQ ID NO 316
<211> LENGTH: 109
<212> TYPE: PRT
<213> ORGANISM: Artificial Sequence
<220> FEATURE:
<223> OTHER INFORMATION: Synthetic polypeptide

<400> SEQUENCE: 316

```
Met Met Glu Arg Val Glu Asp Leu Gly Leu Ser Leu Ser Ser
1               5                   10              15

Ser Leu Ala Ser Pro Arg Thr His His Val Ala Thr Met Leu Leu Arg
                20                  25                  30

Ala Pro Glu Lys Arg Phe Leu Glu Met Pro Leu Leu Pro Ala Lys
            35                  40                  45

Arg Thr Thr Glu Val Thr Gly Glu Asp Gly Leu Arg Gly Gly Ser Asp
        50                  55                  60

Glu Glu Asp Gly Gly Cys Gly Ile Asp Gly Ser Arg Lys Lys Leu Arg
65                  70                  75                  80

Leu Ser Lys Asp Gln Ser Ala Val Leu Glu Asp Ser Phe Arg Glu His
                85                  90                  95

Pro Thr Leu Asn Gly Arg Arg Gln Pro Trp Arg Ser Ser
            100                 105
```

<210> SEQ ID NO 317
<211> LENGTH: 1700
<212> TYPE: DNA
<213> ORGANISM: Artificial Sequence
<220> FEATURE:
<223> OTHER INFORMATION: Synthetic polynucleotide

<400> SEQUENCE: 317

```
cttcttttat caccttcatc tatatctact gctactctca gtactatata tctatcccca       60
gttccatagt tcttccagct ctacacatac acatacacgc agcacgctag ctctagctct      120
cacatcgatt gagatcatca gagaggtgga agaagaagga gctaagatac cagatcgagg      180
aagagaggcg gtgcggtcgg tagatgatgg agagggtcga ggacttaggg ctcagcctca      240
gcctcagctc gtccctcgcg tctcctcgaa ctcaccatgt cgccaccatg ctgctacgcg      300
ctccaggtaa atataatgca atttgctata tatatatata tatatatata tctctgtact      360
aagtagctat atatgctgct tggatgatct atcagagagt atttagctag ctcctgcagg      420
```

```
cacgcgcgct actgctagca gctaactgtg aatgaccata tcaattaagc tatagctagc    480
tctagtgtac atgtgtgagt tttatgtctg tctgactata tgtaagatta gtagtcagca    540
actacaaacc gtacgtgtat ggctggcact ctgatgcatc acatataatg tatcagagaa    600
gaggttcctg gagatgccac tgctgctgcc cgcgaagcgg acgaccgagg tcaccggcga    660
ggatggcctg cgaggcggca gcgacgagga ggacggcggc tgcggcatcg acggctccag    720
gaagaagctc cggctgtcca aggaccagtc cgccgtgctc gaggatagct ccgggagca    780 cccaactctt aagtactagt agtatagtag tagcagctag cattaagagc tacagttctg    840
tggttcatcc tcccggccgc tcaccaagac tcctgatgga cgaacgtaca gctaggctag    900
gcagcagtag ctttcaatca ttcgccggtt ctcgacctta tcaacctgcc tgtgactgtg    960
agctgtacta acttgcttat taatggcgtg cagcggcaga aggcagcctt ggcgcagcag   1020
ctaggcctgc ggccccgcca ggtggaggtg tggttccaga acaggcgcgc caggtacgta   1080
cgtagcgcac atgcgatatg tcgccgcgcg ctagctgctt cgcgtgtgct gatgatcagc   1140
aagcatgcac tgcatgtctg catgggattt ctctctcttt tctgcccctc gctcgatcgc   1200
ttcattcgtt cgtgcaggac gaagctgaag cagacggagg tggactgcga gtacctgaag   1260
cgctgctgcg agacgctgac ggaggagaac cggcggctgc agaaggaggt gcaggagctc   1320
cgcgcgctca gctcgtgtc gccgcacctc tacatgcaca tgtccccgcc caccaccctc   1380
accatgtgcc cctcctgcga gcgcgtctcc tcgtccaacg gcaactccgc agctgccacg   1440
gccgccgcgc gcgcgcgcgc cggcgccggc gccggcgcca tcgtctgcca cccgatcgac   1500
cgagccacta gtacgtagta gtagtagctg ctacactagc tagctgtaca cgggcgccgg   1560
ccgtaacgtg taaaagccaa caaaacagtc tctctgcgca tttattcgac cgtgcaaacg   1620
actgttccct cgttaatctt agtattggta ttgactagtc acccacagta ttagacttga   1680
agatccagca gattacagtt                                                1700
```

<210> SEQ ID NO 318
<211> LENGTH: 680
<212> TYPE: DNA
<213> ORGANISM: Artificial Sequence
<220> FEATURE:
<223> OTHER INFORMATION: Synthetic polynucleotide

<400> SEQUENCE: 318

```
atgatggaga gggtcgagga cttagggctc agcctcagcc tcagctcgtc cctcgcgtct     60
cctcgaactc accatgtcgc caccatgctg ctacgcgctc cagagaagag gttcctggag    120
atgccactgc tgctgcccgc gaagcggacg accgaggtca ccggcgagga tggcctgcga    180
ggcggcagcg acgaggagga cggcggctgc ggcatcgacg gctccaggaa gaagctccgg    240
ctgtccaagg accagtccgc cgtgctcgag gatagcttcc gggagcaccc aactcttaac    300
ggcagaaggc agccttggcg cagcagctag gcctgcggcc ccgccaggtg gaggtgtggt    360
tccagaacag gcgcgccagg acgaagctga agcagacgga ggtggactgc gagtacctga    420
agcgctgctg cgagacgctg acggaggaga accggcggct gcagaaggag gtgcaggagc    480
tccgcgcgct caagctcgtg tcgccgcacc tctacatgca catgtccccg cccaccaccc    540
tcaccatgtg cccctcctgc gagcgcgtct cctcgtccaa cggcaactcc gcagctgcca    600
cggccgccgc gcgcgcgcgc gccggcgccg cgccggcgc catcgtctgc cacccgatcg    660
accgagccac tagtacgtag                                                680
```

<210> SEQ ID NO 319
<211> LENGTH: 1065
<212> TYPE: DNA
<213> ORGANISM: Artificial Sequence
<220> FEATURE:
<223> OTHER INFORMATION: Synthetic polynucleotide

<400> SEQUENCE: 319

```
cttcttttat caccttcatc tatatctact gctactctca gtactatata tctatcccca      60
gttccatagt tcttccagct ctacacatac acatacacgc agcacgctag ctctagctct     120
cacatcgatt gagatcatca gagaggtgga agaagaagga gctaagatac cagatcgagg     180
aagagaggcg gtgcggtcgg tagatgatgg agagggtcga ggacttaggg ctcagcctca     240
gcctcagctc gtccctcgcg tctcctcgaa ctcaccatgt cgccaccatg ctgctacgcg     300
ctccagagaa gaggttcctg gagatgccac tgctgctgcc cgcgaagcgg acgaccgagg     360
tcaccggcga ggatggcctg cgaggcggca gcgacgagga ggacggcggc tgcggcatcg     420
acggctccag gaagaagctc cggctgtcca aggaccagtc cgccgtgctc gaggatagct     480
tccgggagca cccaactctt aacggcagaa ggcagccttg gcgcagcagc taggcctgcg     540
gccccgccag gtggaggtgt ggttccagaa caggcgcgcc aggacgaagc tgaagcagac     600
ggaggtggac tgcgagtacc tgaagcgctg ctgcgagacg ctgacggagg agaaccggcg     660
gctgcagaag gaggtgcagg agctccgcgc gctcaagctc gtgtcgccgc acctctacat     720
gcacatgtcc ccgcccacca ccctcaccat gtgcccctcc tgcgagcgcg tctcctcgtc     780
caacggcaac tccgcagctg ccacggccgc cgcgcgcgcg cgcgccggcg ccggcgccgg     840
cgccatcgtc tgccacccga tcgaccgagc cactagtacg tagtagtagt agctgctaca     900
ctagctagct gtacacgggc gccggccgta acgtgtaaaa gccaacaaaa cagtctctct     960
gcgcatttat tcgaccgtgc aaacgactgt tccctcgtta atcttagtat tggtattgac    1020
tagtcaccca cagtattaga cttgaagatc cagcagatta cagtt                    1065
```

<210> SEQ ID NO 320
<211> LENGTH: 90
<212> TYPE: DNA
<213> ORGANISM: Artificial Sequence
<220> FEATURE:
<223> OTHER INFORMATION: Synthetic polynucleotide

<400> SEQUENCE: 320

```
ccaaggacca gtccgccgtg ctcgaggata gcttccggga gcacccaact aagtactagt      60
agtatagtag tagcagctag cattaagagc                                       90
```

<210> SEQ ID NO 321
<211> LENGTH: 101
<212> TYPE: DNA
<213> ORGANISM: Zea mays

<400> SEQUENCE: 321

```
ccaaggacca gtccgccgtg ctcgaggata gcttccggga gcacccaact ctcaaccctg      60
taagtactag tagtatagta gtagcagcta gcattaagag c                         101
```

<210> SEQ ID NO 322
<211> LENGTH: 96
<212> TYPE: DNA
<213> ORGANISM: Artificial Sequence
<220> FEATURE:
<223> OTHER INFORMATION: Synthetic polynucleotide

<400> SEQUENCE: 322
ccaaggacca gtccgccgtg ctcgaggata gcttccggga gcacccaact ccctgtaagt    60
actagtagta tagtagtagc agctagcatt aagagc    96

<210> SEQ ID NO 323
<211> LENGTH: 78
<212> TYPE: DNA
<213> ORGANISM: Artificial Sequence
<220> FEATURE:
<223> OTHER INFORMATION: Synthetic polynucleotide

<400> SEQUENCE: 323
ccaaggacca gtccgccgtg ctcgaggata gcttccggga gtactagtag tatagtagta    60
gcagctagca ttaagagc    78

<210> SEQ ID NO 324
<211> LENGTH: 92
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (42)..(44)
<223> OTHER INFORMATION: n is a, c, g, or t

<400> SEQUENCE: 324
agtccgccgt gctcgaggat agcttccggg agcacccaac tnnnaagtac tagtagtata    60
gtagtagcag ctagcattaa gagctacagt tc    92

<210> SEQ ID NO 325
<211> LENGTH: 100
<212> TYPE: DNA
<213> ORGANISM: Zea mays

<400> SEQUENCE: 325
agtccgccgt gctcgaggat agcttccggg agcacccaac tctcaaccct gtaagtacta    60
gtagtatagt agtagcagct agcattaaga gctacagttc    100

<210> SEQ ID NO 326
<211> LENGTH: 92
<212> TYPE: DNA
<213> ORGANISM: Artificial Sequence
<220> FEATURE:
<223> OTHER INFORMATION: Synthetic polynucleotide

<400> SEQUENCE: 326
agtccgccgt gctcgaggat agcttccggg agcacccaac tcttaagtac tagtagtata    60
gtagtagcag ctagcattaa gagctacagt tc    92

<210> SEQ ID NO 327
<211> LENGTH: 89
<212> TYPE: DNA
<213> ORGANISM: Artificial Sequence
<220> FEATURE:
<223> OTHER INFORMATION: Synthetic polynucleotide

<400> SEQUENCE: 327
agtccgccgt gctcgaggat agcttccggg agcacccaac taagtactag tagtatagta    60
gtagcagcta gcattaagag ctacagttc    89

```
<210> SEQ ID NO 328
<211> LENGTH: 132
<212> TYPE: DNA
<213> ORGANISM: Artificial Sequence
<220> FEATURE:
<223> OTHER INFORMATION: Synthetic polynucleotide

<400> SEQUENCE: 328
ccgcagagcc aggtgaacaa agcagcgccc ttgaagcagc acacgcatgc catttatact      60
gactcatcct ccgtggctaa tactagtcta ataataatat tatcgttcag gacgaagctg     120
atgcgagttc ct                                                         132

<210> SEQ ID NO 329
<211> LENGTH: 149
<212> TYPE: DNA
<213> ORGANISM: Zea mays

<400> SEQUENCE: 329
ccgcagagcc aggtgaacaa agcagcgccc ttgaagcagc acacgcatgc catttatact      60
gactcatcct ccgtggctaa tactagtcta ataataatat tatcgttcag gacgaagctg     120
aagcagacgg aggtggactg cgagttcct                                       149
```

SUPPRESSION OF SHADE AVOIDANCE RESPONSE IN PLANTS

STATEMENT OF PRIORITY

This application claims the benefit, under 35 U.S.C. § 119 (e), of U.S. Provisional Application No. 62/968,596 filed on Jan. 31, 2020, the entire contents of which is incorporated by reference herein.

STATEMENT REGARDING ELECTRONIC FILING OF A SEQUENCE LISTING

A Sequence Listing in ASCII text format, submitted under 37 C.F.R. § 1.821, entitled 1499.17.WO_ST25.txt, 465,866 bytes in size, generated on Jan. 28, 2021 and filed via EFS-Web, is provided in lieu of a paper copy. This Sequence Listing is hereby incorporated herein by reference into the specification for its disclosures.

FIELD OF THE INVENTION

This invention relates to compositions and methods for modifying Homeodomain-leucine zipper (HD-Zip) transcription factors to suppress shade avoidance response in plants. The invention further relates to plants produced using the methods and compositions of the invention.

BACKGROUND OF THE INVENTION

Shade avoidance response (SAR) is a response to a decrease in the quality or quantity of available light (Kebrom and Brutnell, *J Exp Bot* 58:3079-3089 (2007)) in which a plant attempts to outcompete neighboring plants by growing toward resources (primarily light). Overcrowding of plants can lead to shade avoidance syndrome (SAS) where plants lack vigor and decreased yield. Shade avoidance relates to the relative proportion of red light to far-red light that is present in a plant's environment (Ballare et al. *Science*, 247:329-332 (1990)). Plants absorb most of the red light available to them, but reflect far-red light, including reflecting this light on nearby plants. When a plant detects consistent far-red light in its environment, it will undergo a morphological and physiological response. These responses can include reduced branching, increased plant height, decreased leaf blade area, redistribution of auxin, enhanced ethylene production and acceleration of flowering. SAS is characterized by increased root/shoot ratio, increased plant height, and reduced individual plant yield. In a typical monoculture crop setting, interplant competition through shade avoidance is considered a wasteful survival mechanism.

SUMMARY OF THE INVENTION

One aspect of the invention provides a plant or plant part thereof comprising at least one non-natural mutation in an endogenous Homeodomain-leucine zipper (HD-Zip) transcription factor, wherein the mutation disrupts the binding of the HD-Zip transcription factor to DNA.

Another aspect of the invention provides a plant cell comprising an editing system, the editing system comprising: (a) a CRISPR-associated effector protein; and (b) a guide nucleic acid (gRNA, gDNA, crRNA, crDNA) having a spacer sequence with complementarity to an endogenous target gene encoding an HD-Zip transcription factor.

A further aspect of the invention provides a plant cell comprising a non-natural mutation within a DNA binding site of an HD-Zip transcription factor gene that prevents or reduces binding of the HD-Zip transcription factor to DNA, wherein the mutation is a substitution, insertion and/or a deletion that is introduced using an editing system that comprises a nucleic acid binding domain that binds to a target site in the HD-Zip transcription factor gene, wherein the HD-Zip transcription factor gene encodes: (a) a polypeptide comprising a sequence having at least 80% sequence identity to the amino acid sequence of SEQ ID NO:38 or SEQ ID NO:83; (b) a polypeptide comprising a sequence having at least 80% sequence identity to the amino acid sequence of: RKKLRLSKDQSAVLEDSFREHPTLNPRQ-KAALAQQLGLRPRQVEVWFQNRRARTKLK QTEVD CEYLKRCCETLTEENRRLQKEVQELRALKLVSP HLY MHMSPPTTLTMCPSCER V (SEQ ID NO:1) (*Zea mays* HB53) or RKKLRLSKDQAAVLEESFKEHNTLNPKQKA ALAKQLNLKPRQ VEVWFQNRRARTKL KQTEVDCE-FLKRCCETLTEENRRLQREVAELRVLKLVAPHHYA RMPPPTTLTMCPSCE RL (SEQ ID NO:2) (*Zea mays* HB78); (c) a polypeptide comprising a sequence having at least 80% sequence identity to the amino acid sequence of LAKQLNLKPRQVEVWFQNRRARTKLKQTEVDCE-FLKRCCETLTEENRRLQREV (SEQ ID NO:3); (d) a polypeptide comprising a sequence having at least 95% sequence identity to the nucleotide sequence of RQVEVWFQNR-RARTKLKQTEVDCE (SEQ ID NO:4); (e) a polypeptide comprising a sequence having the amino acid sequence of RQVEVWFQNRRARTKXKQTEVDCE (SEQ ID NO:5), wherein X is L or S; (f) a polypeptide comprising: (i) sequence having the amino acid sequence of KKLRLX$_1$KX$_2$QX$_3$ (SEQ ID NO:6), wherein X$_1$ is S or T, X$_2$ is D or E and X$_3$ is S or A; (ii) a sequence having the amino acid sequence of PX$_1$X$_2$X$_2$LTX$_3$CPX$_4$CER (SEQ ID NO:8), wherein X$_1$ is P or A, X$_2$ is T or A, X$_3$ is V or M and X$_4$ is Q, S or N; (iii) a sequence having the amino acid sequence of ENRRLX$_1$X$_2$EX$_3$, (SEQ ID NO:7), wherein X$_1$ is Q or H, X$_2$ is R or K and X$_3$ is V or L; and (iv) a sequence having the amino acid sequence of VWFQNRRA (SEQ ID NO:9); and/or (g) a polypeptide comprising a sequence having the amino acid sequence of VWFQNRRA (SEQ ID NO:9).

Another aspect of the invention provides a plant or part thereof comprising a mutation (e.g., at least one mutation) in an endogenous HD-Zip transcription factor, which mutation reduces DNA binding by the endogenous HD-Zip transcription factor, wherein the endogenous HD-Zip transcription factor comprises a polypeptide comprising a sequence having at least 80% sequence identity to the amino acid sequence of SEQ ID NO:1 or SEQ ID NO:2; wherein the mutation is a deletion, substitution, and/or insertion of at least one amino acid residue of amino acid residues 45-52 (VWFQNRRA (SEQ ID NO:9)) of the amino acid sequence of SEQ ID NO:1 or SEQ ID NO:2, optionally wherein the mutation is a non-natural mutation.

Another aspect of the invention provides a plant or part thereof comprising an HD-Zip transcription factor gene that encodes an amino acid sequence of SEQ ID NO:201.

A further aspect of the invention provides a corn plant comprising an HD-Zip transcription factor gene that comprises an amino acid sequence of SEQ ID NO:201.

Another aspect of the invention provides a plant or part thereof comprising an HD-Zip transcription factor gene that comprises the nucleotide sequence of SEQ ID NO:202.

A further aspect of the invention provides a corn plant comprising an HD-Zip transcription factor gene that comprises the nucleotide sequence of SEQ ID NO:202.

The invention further provides a method of producing/breeding a transgene-free genome-edited plant, comprising: (a) crossing a plant of the invention with a transgene free plant, thereby introducing the mutation present in the plant of the invention into the plant that is transgene-free; and (b) selecting a progeny plant that comprises the mutation but is transgene-free, thereby producing a transgene free genome-edited plant.

Another aspect of the invention provides a method for editing a specific site in the genome of a plant cell, the method comprising: cleaving, in a site specific manner, a target site within an endogenous HD-Zip transcription factor gene in the plant cell, the endogenous HD-Zip transcription factor gene encoding: (a) a polypeptide comprising a sequence having at least 80% sequence identity to the amino acid sequence of SEQ ID NO:38 or SEQ ID NO:83; (b) a polypeptide comprising a sequence having at least 80% sequence identity to the amino acid sequence of: SEQ ID NO:1 or SEQ ID NO:2; (c) a polypeptide comprising a sequence having at least 80% sequence identity to the amino acid sequence of SEQ ID NO:3; (d) a polypeptide comprising a sequence having at least 95% sequence identity to the nucleotide sequence of SEQ ID NO:4; (e) a polypeptide comprising a sequence having the amino acid sequence of SEQ ID NO:5, wherein X is L or S; (f) a polypeptide comprising: (i) sequence having the amino acid sequence of RKKLRLX$_1$KX$_2$QX$_3$ (SEQ ID NO:6), wherein X$_1$ is S or T, X$_2$ is D or E and X$_3$ is S or A; (ii) a sequence having the amino acid sequence of PX$_1$X$_2$ X$_2$LTX$_3$CPX$_4$CER (SEQ ID NO:8), wherein X$_1$ is P or A, X$_2$ is T or A, X$_3$ is V or M and X$_4$ is Q, S or N; (iii) a sequence having the amino acid sequence of ENRRLX$_1$X$_2$EX$_3$, (SEQ ID NO:7), wherein X$_1$ is Q or H, X$_2$ is R or K and X$_3$ is V or L; and (iv) a sequence having the amino acid sequence of VWFQNRRA (SEQ ID NO:9); and/or (g) a polypeptide comprising a sequence having the amino acid sequence of VWFQNRRA (SEQ ID NO:9), thereby generating an edit in the endogenous HD-Zip transcription factor gene of the plant cell.

An additional aspect of the invention provides a method for making a plant, comprising: (a) contacting a population of plant cells that comprising a wild-type endogenous gene encoding an HD-Zip transcription factor with a nuclease targeted to the wild-type endogenous gene, wherein the nuclease is linked to a DNA binding domain that binds to a nucleic acid sequence encoding: (i) a polypeptide comprising a sequence having at least 80% sequence identity to the amino acid sequence of SEQ ID NO:38 or SEQ ID NO:83; (ii) a polypeptide comprising a sequence having at least 80% sequence identity to the amino acid sequence of: SEQ ID NO:1 or SEQ ID NO:2; (iii) a polypeptide comprising a sequence having at least 80% sequence identity to the amino acid sequence of SEQ ID NO:3; (iv) a polypeptide comprising a sequence having at least 95% sequence identity to the nucleotide sequence of SEQ ID NO:4; (v) a polypeptide comprising a sequence having the amino acid sequence of SEQ ID NO:5, wherein X is L or S; (vi) a polypeptide comprising: (1) a sequence having the amino acid sequence of RKKLRLX$_1$KX$_2$QX$_3$ (SEQ ID NO:6), wherein X$_1$ is S or T, X$_2$ is D or E and X$_3$ is S or A; (2) a sequence having the amino acid sequence of PX$_1$X$_2$ X$_2$LTX$_3$CPX$_4$CER (SEQ ID NO:8), wherein X$_1$ is P or A, X$_2$ is T or A, X$_3$ is V or M and X$_4$ is Q, S or N; (3) a sequence having the amino acid sequence of ENRRLX$_1$X$_2$EX$_3$, (SEQ ID NO:7), wherein X$_1$ is Q or H, X$_2$ is R or K and X$_3$ is V or L; and (4) a sequence having the amino acid sequence of VWFQNRRA (SEQ ID NO:9); and/or (vii) a polypeptide comprising a sequence having the amino acid sequence of VWFQNRRA (SEQ ID NO:9); (b) selecting a plant cell from said population comprising a mutation in the wild-type endogenous gene encoding an HD-Zip transcription factor, wherein the mutation is a substitution and/or a deletion of at least one amino acid residue in the polypeptide of any one of (i)-(v), wherein the mutation reduces or eliminates the ability of the HD-Zip transcription factor to bind DNA; and (c) growing the selected plant cell into a plant.

In some aspects, the invention provides a method for reducing a Shade Avoidance Response in a plant, comprising (a) contacting a plant cell comprising a wild-type endogenous gene encoding an HD-Zip transcription factor with a nuclease targeted to the wild-type endogenous gene, wherein the nuclease is linked to a DNA binding domain that binds to a target site in the wild type endogenous gene, the wild type endogenous gene encoding: (i) a polypeptide comprising a sequence having at least 80% sequence identity to the amino acid sequence of SEQ ID NO:38 or SEQ ID NO:83; (ii) a polypeptide comprising a sequence having at least 80% sequence identity to the amino acid sequence of: SEQ ID NO:1 or SEQ ID NO:2; (iii) a polypeptide comprising a sequence having at least 80% sequence identity to the amino acid sequence of SEQ ID NO:3; (iv) a polypeptide comprising a sequence having at least 95% sequence identity to the nucleotide sequence of SEQ ID NO:4; (v) a polypeptide comprising a sequence having the amino acid sequence of SEQ ID NO:5, wherein X is L or S; (vi) a polypeptide comprising: (1) a sequence having the amino acid sequence of RKKLRLX$_1$KX$_2$QX$_3$ (SEQ ID NO:6), wherein X$_1$ is S or T, X$_2$ is D or E and X$_3$ is S or A; (2) a sequence having the amino acid sequence of PX$_1$X$_2$ X$_2$LTX$_3$CPX$_4$CER (SEQ ID NO:8), wherein X$_1$ is P or A, X$_2$ is T or A, X$_3$ is V or M and X$_4$ is Q, S or N; (3) a sequence having the amino acid sequence of ENRRLX$_1$X$_2$EX$_3$, (SEQ ID NO:7), wherein X$_1$ is Q or H, X$_2$ is R or K and X$_3$ is V or L; and (4) a sequence having the amino acid sequence of VWFQNRRA (SEQ ID NO:9); and/or (vii) a polypeptide comprising a sequence having the amino acid sequence of VWFQNRRA (SEQ ID NO:9), thereby producing a plant cell comprising a mutation in the wild-type endogenous gene encoding an HD-Zip transcription factor; and (b) growing the plant cell into a plant, thereby reducing the Shade Avoidance Response.

In another aspect, a method for producing a plant or part thereof comprising at least one cell having a mutated endogenous HD-Zip transcription factor gene is provided, the method comprising contacting a target site in the HD-Zip transcription factor gene in the plant or plant part with a nuclease comprising a cleavage domain and a DNA-binding domain, wherein the DNA binding domain binds to a target site in the HD-Zip transcription factor gene, wherein the HD-Zip transcription factor gene encodes: (a) a polypeptide comprising a sequence having at least 80% sequence identity to the amino acid sequence of SEQ ID NO:38 or SEQ ID NO:83; (b) a polypeptide comprising a sequence having at least 80% sequence identity to the amino acid sequence of: SEQ ID NO:1 or SEQ ID NO:2; (c) a polypeptide comprising a sequence having at least 80% sequence identity to the amino acid sequence of SEQ ID NO:3; (d) a polypeptide comprising a sequence having at least 95% sequence identity to the nucleotide sequence of SEQ ID NO:4; (e) a polypeptide comprising a sequence having the amino acid sequence of SEQ ID NO:5, wherein X is L or S; (0 a polypeptide comprising: (i) a sequence having the amino acid sequence of RKKLRLX$_1$KX$_2$QX$_3$ (SEQ ID NO:6), wherein X$_1$ is S or T, X$_2$ is D or E and X$_3$ is S or A; (ii) a sequence having the amino acid sequence of PX$_1$X$_2$ X$_2$LTX$_3$CPX$_4$CER (SEQ ID NO:8), wherein X$_1$ is P or A, X$_2$ is T or A, X$_3$ is V or M and X$_4$ is Q, S or N; (iii) a sequence having the amino acid sequence of ENRRLX$_1$X$_2$EX$_3$, (SEQ ID NO:7), wherein X$_1$ is Q or H, X$_2$ is R or K and X$_3$ is V or L; and (iv) a sequence having the amino acid sequence of VWFQNRRA (SEQ ID NO:9); and/or (g) a polypeptide comprising a sequence having the amino acid sequence of VWFQNRRA (SEQ ID NO:9), thereby producing a plant or part thereof comprising at least one cell having a mutation in the endogenous HD-Zip transcription factor gene.

In a further aspect, a method of producing a plant or part thereof comprising a mutated endogenous HD-Zip transcription factor having reduced DNA binding is provided, the method comprising contacting a target site in an endogenous HD-Zip transcription factor gene in the plant or plant part with a nuclease comprising a cleavage domain and a DNA-binding domain, wherein the DNA binding domain binds to a target site in the HD-Zip transcription factor gene wherein the HD-Zip transcription factor gene encodes: (a) a polypeptide comprising a sequence having at least 80% sequence identity to the amino acid sequence of SEQ ID NO:38 or SEQ ID NO:83; (b) a polypeptide comprising a sequence having at least 80% sequence identity to the amino acid sequence of: SEQ ID NO:1 or SEQ ID NO:2; (c) a polypeptide comprising a sequence having at least 80% sequence identity to the amino acid sequence of SEQ ID NO:3; (d) a polypeptide comprising a sequence having at least 95% sequence identity to the nucleotide sequence of SEQ ID NO:4; (e) a polypeptide comprising a sequence having the amino acid sequence of SEQ ID NO:5, wherein X is L or S; (f) a polypeptide comprising: (i) sequence having the amino acid sequence of RKKLRLX$_1$KX$_2$QX$_3$ (SEQ ID NO:6), wherein X$_1$ is S or T, X$_2$ is D or E and X$_3$ is S or A; (ii) a sequence having the amino acid sequence of PX$_1$X$_2$ X$_2$LTX$_3$CPX$_4$CER (SEQ ID NO:8), wherein X$_1$ is P or A, X$_2$ is T or A, X$_3$ is V or M and X$_4$ is Q, S or N; (iii) a sequence having the amino acid sequence of ENRRLX$_1$X$_2$EX$_3$, (SEQ ID NO:7), wherein X$_1$ is Q or H, X$_2$ is R or K and X$_3$ is V or L; and (iv) a sequence having the amino acid sequence of VWFQNRRA (SEQ ID NO:9); and/or (g) a polypeptide comprising a sequence having the amino acid sequence of VWFQNRRA (SEQ ID NO:9), thereby producing a plant or part thereof having a mutated endogenous HD-Zip transcription factor having reduced DNA binding.

An additional aspect of the invention provides a guide nucleic acid that binds to a target site in a HD-Zip transcription factor gene, the target site comprising a nucleotide sequence encoding: (a) a polypeptide comprising a sequence having at least 80% sequence identity to the amino acid sequence of SEQ ID NO:1 or SEQ ID NO:2; (b) a polypeptide comprising a sequence having at least 80% sequence identity to the amino acid sequence of SEQ ID NO:3; (c) a polypeptide comprising a sequence having at least 95% sequence identity to the nucleotide sequence of SEQ ID NO:4; (d) a polypeptide comprising a sequence having the amino acid sequence of SEQ ID NO:5, wherein X is L or S; (e) a polypeptide comprising: (i) a sequence having the amino acid sequence of RKKLRLX$_1$KX$_2$QX$_3$ (SEQ ID NO:6), wherein X$_1$ is S or T, X$_2$ is D or E and X$_3$ is S or A; (ii) a sequence having the amino acid sequence of PX$_1$X$_2$ X$_2$LTX$_3$CPX$_4$CER (SEQ ID NO:8), wherein X$_1$ is P or A, X$_2$ is T or A, X$_3$ is V or M and X$_4$ is Q, S or N; (iii) a sequence having the amino acid sequence of ENRRLX$_1$X$_2$EX$_3$, (SEQ ID NO:7), wherein X$_1$ is Q or H, X$_2$ is R or K and X$_3$ is V or L; and a sequence having the amino acid sequence of VWFQNRRA (SEQ ID NO:9) and/or (0 a polypeptide comprising a sequence having the amino acid sequence of VWFQNRRA (SEQ ID NO:9).

A further aspect of the invention provides a system comprising the guide nucleic acid of the invention and a CRISPR-Cas effector protein that associates with the guide nucleic acid.

Another aspect of the invention provides gene editing system comprising a CRISPR-Cas effector protein in association with a guide nucleic acid, wherein the guide nucleic acid comprises a spacer sequence that binds to a HD-Zip transcription factor gene.

An additional aspect of the invention provides a complex comprising a CRISPR-Cas effector protein comprising a cleavage domain and a guide nucleic acid, wherein the guide nucleic acid binds to a target site in a HD-Zip transcription factor gene encoding (a) a polypeptide comprising a sequence having at least 80% sequence identity to the amino acid sequence of SEQ ID NO:1 or SEQ ID NO:2; (b) a polypeptide comprising a sequence having at least 80% sequence identity to the amino acid sequence of SEQ ID NO:3; (c) a polypeptide comprising a sequence having at least 95% sequence identity to the nucleotide sequence of SEQ ID NO:4; (d) a polypeptide comprising a sequence having the amino acid sequence of SEQ ID NO:5, wherein X is L or S; (e) a polypeptide comprising: (i) a sequence having the amino acid sequence of RKKLRLX$_1$KX$_2$QX$_3$ (SEQ ID NO:6), wherein X$_1$ is S or T, X$_2$ is D or E and X$_3$ is S or A; (ii) a sequence having the amino acid sequence of PX$_1$X$_2$ X$_2$LTX$_3$CPX$_4$CER (SEQ ID NO:8), wherein X$_1$ is P or A, X$_2$ is T or A, X$_3$ is V or M and X$_4$ is Q, S or N; (iii) a sequence having the amino acid sequence of ENRRLX$_1$X$_2$EX$_3$, (SEQ ID NO:7), wherein X$_1$ is Q or H, X$_2$ is R or K and X$_3$ is V or L; and a sequence having the amino acid sequence of VWFQNRRA (SEQ ID NO:9) and/or (f) a polypeptide comprising a sequence having the amino acid sequence of VWFQNRRA (SEQ ID NO:9), wherein the cleavage domain cleaves a target strand in the HD-Zip transcription factor gene A further aspect of the invention provides a nucleic acid encoding HD-Zip transcription factor having a mutated DNA binding site, wherein the mutated DNA binding site comprises a mutation that disrupts DNA binding.

Further provided are plants comprising in their genome one or more mutated HD-Zip transcription factors that have reduced ability to bind to DNA that are produced by the methods of the invention as well as polypeptides, polynucleotides, nucleic acid constructs, expression cassettes and vectors for making a plant of this invention.

These and other aspects of the invention are set forth in more detail in the description of the invention below.

BRIEF DESCRIPTION OF THE SEQUENCES

SEQ ID NO:1 shows a portion of the *Zea mays* HB 53 transcription factor (amino acid residues 173-288 of SEQ ID NO:38).

SEQ ID NO:2 shows a portion of the *Zea mays* HB 78 transcription factor (amino acid residues 76-191 of SEQ ID NO:83).

SEQ ID NOs:3-9 are partial sequences of HD-zip transcription factors.

SEQ ID NOs:10-54 are examples of HB53 transcription factors from a variety of different plant species.

SEQ ID NOs:55-98 and 303 are examples of HB78 transcription factors from a variety of different plant species.

SEQ ID NOs:99-134 are cDNA sequences of HB53 transcription factors from a variety of different plant species.

SEQ ID NOs:135-174 are cDNA sequences of HB78 transcription factors from a variety of different plant species.

SEQ ID NOs:175-182 show example spacer sequences for guide nucleic acids for targeting HB78 and HB53 transcription factors.

SEQ ID NOs:183-194 are example cytosine deaminase amino acid sequences useful with this invention.

SEQ ID NO:195 is an exemplary uracil-DNA glycosylase inhibitor (UGI) useful with this invention.

SEQ ID NO:196-197 are exemplary regulatory sequences encoding a promoter and intron.

SEQ ID NOs:198-200 provide examples of a protospacer adjacent motif position for a Type V CRISPR-Cas12a nuclease.

SEQ ID NOs: 201 provides an example HB78 mutated amino acid sequence produced using the methods and compositions of this invention.

SEQ ID NOs: 202 provides an example HB78 mutated nucleotide sequence produced using the methods and compositions of this invention. SEQ ID NO:202 encodes the amino acid sequence of SEQ ID NO:201.

SEQ ID NOs: 203-246 and 302 are the portions of HB78 amino acid sequences for different plant species shown in the alignment in FIGS. 1A-1B.

SEQ ID NOs:247-291 are the portions of HB53 amino acid sequences for different plant species shown in the alignment in FIGS. 2A-2D.

SEQ ID NOs:292-294 are the HB53 sequences shown in FIG. 6.

SEQ ID NOs:295-297 are the HB78 sequences shown in FIG. 8.

SEQ ID NOs:298-301 are the HB78 sequences shown in FIG. 9.

SEQ ID NO:304 and SEQ ID NO:305 provide a wild type HB78 genomic sequence and cDNA (corresponding to the WT HB78 amino acid sequence of SEQ ID NO:83 and the WT HB78 coding sequence of SEQ ID NO:171), respectively, from Z. mays.

SEQ ID NOs:306-309 provide the protein sequence, genomic sequence, coding sequence and cDNA, respectively, of an edited HB78 having a 17 base pair deletion.

SEQ ID NO:310 and SEQ ID NO:311 provide a wild type HB53 genomic sequence and cDNA (corresponding to the WT HB53 amino acid sequence of SEQ ID NO:38 and the WT HB53 coding sequence of SEQ ID NO:132), respectively, from Z. mays.

SEQ ID NOs:312-315 provide the protein sequence, genomic sequence, coding sequence and cDNA, respectively, of an edited HB53 having an 11 base pair deletion.

SEQ ID NOs:316-319 provide the protein sequence, genomic sequence, coding sequence and cDNA, respectively, of an edited HB53 having an 8 base pair deletion.

SEQ ID NOs:320-329 are the sequences shown in FIGS. 10-12.

BRIEF DESCRIPTION OF THE DRAWINGS

FIGS. 1A-1B provides an alignment of HD-Zip (HB78) amino acid sequences from 44 different plant species. The sequences are a portion of consecutive amino acids (53 amino acid residues) from the full length HB78 sequences.

FIGS. 2A-2D provides an alignment of HD-Zip (HB53) amino acid sequences from 45 different plant species. The sequences are a portion of consecutive amino acid residues (e.g., about 116 amino acid residues) from the full length HB53 sequences.

FIG. 4 provides an example illustrating a dominant negative strategy. By removing the DNA binding capability of a bifunctional protein, dimerized complex will not activate gene expression.

DETAILED DESCRIPTION

Figure 3:
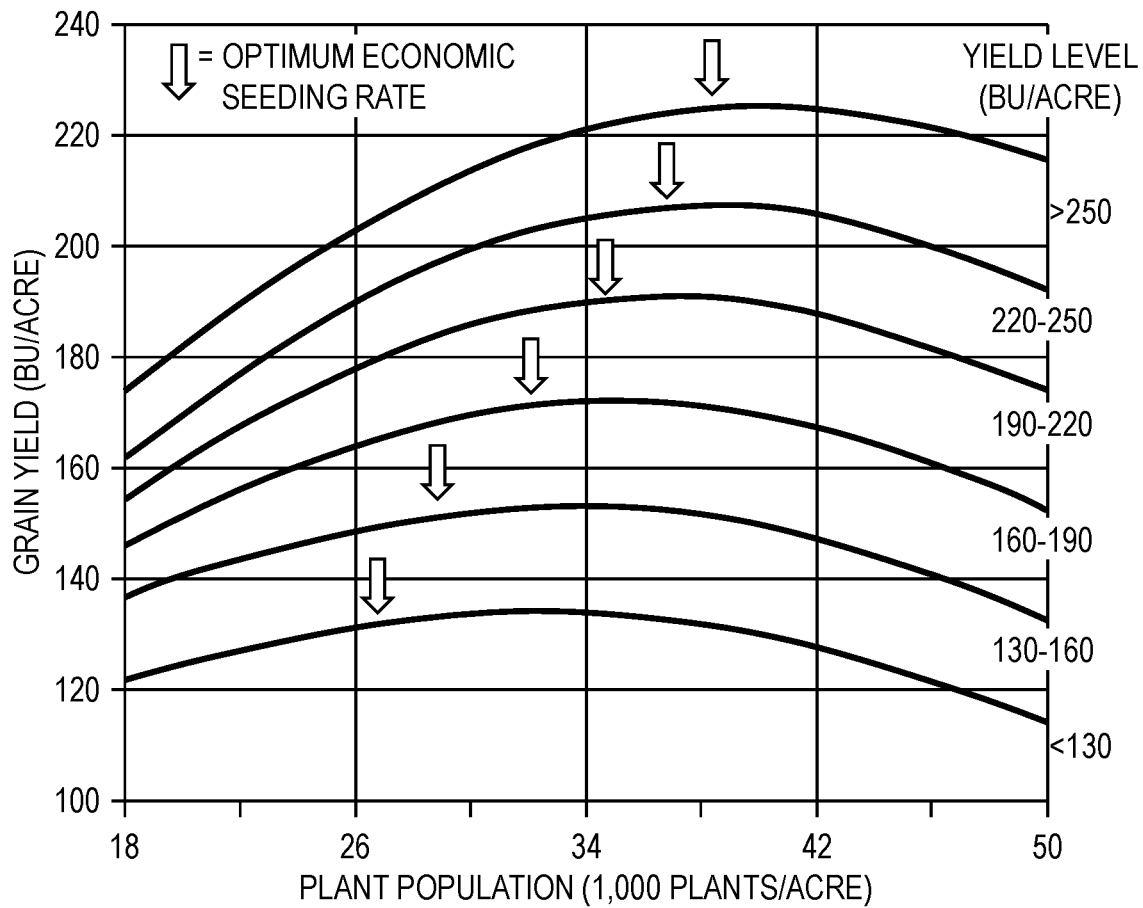
FIG. 3 provides an example illustrating the relationship between planting density and yield in corn. Increasing planting density increases plant yield up to an inflection point (arrows—Optimum economic seeding rate). Variants with attenuated shade avoidance would have inflection points at a higher planting density.

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations, and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measurable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to15 is disclosed, then 11, 12, 13, and 14 are also disclosed.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "increased," "enhance," "enhanced," "enhancing," and "enhancement" (and grammatical variations thereof) describe an elevation of at least about 15%, 20%, 25%, 50%, 75%, 100%, 150%, 200%, 300%, 400%, 500% or more as compared to a control.

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 96%, 97%, 98%, 99%, 99.5%, 99.6%, 99.7%, 99.8%, 99.9%, or 100% as compared to a control. In particular embodiments, the reduction can result in no or essentially no (i.e., an insignificant amount, e.g., less than about 10% or even 5%) detectable activity or amount.

As used herein, the terms "express," "expresses," "expressed" or "expression," and the like, with respect to a nucleic acid molecule and/or a nucleotide sequence (e.g., RNA or DNA) indicates that the nucleic acid molecule and/or a nucleotide sequence is transcribed and, optionally, translated. Thus, a nucleic acid molecule and/or a nucleotide sequence may express a polypeptide of interest or, for example, a functional untranslated RNA.

A "heterologous" or a "recombinant" nucleotide sequence is a nucleotide sequence not naturally associated with a host cell into which it is introduced, including non-naturally occurring multiple copies of a naturally occurring nucleotide sequence.

A "native" or "wild type" nucleic acid, nucleotide sequence, polypeptide or amino acid sequence refers to a naturally occurring or endogenous nucleic acid, nucleotide sequence, polypeptide, or amino acid sequence. Thus, for example, a "wild type mRNA" is an mRNA that is naturally occurring in or endogenous to the reference organism.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "allele" refers to one of two or more different nucleotides or nucleotide sequences that occur at a specific locus.

A "locus" is a position on a chromosome where a gene or marker or allele is located. In some embodiments, a locus may encompass one or more nucleotides.

As used herein, the terms "desired allele," "target allele" and/or "allele of interest" are used interchangeably to refer to an allele associated with a desired trait. In some embodiments, a desired allele may be associated with either an increase or a decrease (relative to a control) of or in a given trait, depending on the nature of the desired phenotype. In some embodiments of this invention, the phrase "desired allele," "target allele" or "allele of interest" refers to an allele(s) that is associated with increased yield under non-water stress conditions in a plant relative to a control plant not having the target allele or alleles.

A marker is "associated with" a trait when said trait is linked to it and when the presence of the marker is an indicator of whether and/or to what extent the desired trait or trait form will occur in a plant/germplasm comprising the marker. Similarly, a marker is "associated with" an allele or chromosome interval when it is linked to it and when the presence of the marker is an indicator of whether the allele or chromosome interval is present in a plant/germplasm comprising the marker.

As used herein, the terms "backcross" and "backcrossing" refer to the process whereby a progeny plant is crossed back to one of its parents one or more times (e.g., 1, 2, 3, 4, 5, 6, 7, 8, etc.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in TECHNIQUES ET UTILISATIONS DES MARQUEURS MOLECULAIRES LES COLLOQUES, Vol. 72, pp. 45-56 (1995); and Openshaw et al., *Marker-assisted Selection in Backcross Breeding*, in PROCEEDINGS OF THE SYMPOSIUM "ANALYSIS OF MOLECULAR MARKER DATA," pp. 41-43 (1994). The initial cross gives rise to the F1 generation. The term "BC1" refers to the second use of the recurrent parent, "BC2" refers to the third use of the recurrent parent, and so on.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be backcrossed one or more times (e.g., 1, 2, 3, 4, or more times) to a line having a desired genetic background, selecting for the desired allele, with the result being that the desired allele becomes fixed in the desired genetic background. For example, a marker associated with increased yield under non-water stress conditions may be introgressed from a donor into a recurrent parent that does not comprise the marker and does not exhibit increased yield under non-water stress conditions. The resulting offspring could then be backcrossed one or more times and selected until the progeny possess the genetic marker(s) associated with increased yield under non-water stress conditions in the recurrent parent background.

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific genetic makeup that provides a foundation for some or all of the hereditary qualities of an organism or cell culture. As used herein, germplasm includes cells, seed or tissues from which new plants may be grown, as well as plant parts that can be cultured into a whole plant (e.g., leaves, stems, buds, roots, pollen, cells, etc.).

As used herein, the terms "cultivar" and "variety" refer to a group of similar plants that by structural or genetic features and/or performance can be distinguished from other varieties within the same species.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the term "heterologous" refers to a nucleotide/polypeptide that originates from a foreign species, or, if from the same species, is substantially modified from its native form in composition and/or genomic locus by deliberate human intervention.

As used herein, "shade avoidance response" is defined as the growth of a plant in response to a low red:far-red (R:FR) light ratio. Suppression of a shade avoidance refers to the suppression of the growth changes in response to a low R:FR light ratio. In one aspect, suppression of a shade avoidance response can be shown by measuring the height of a plant comprising the trait of the invention (e.g., mutation of HD-Zip as described herein) and an isogenic plant without the trait in a controlled environment with a low R:FR light ratio. When grown under identical conditions in the presence of a R:FR ratio of 0.16, a plant comprising the trait of the invention will be at least 5% shorter (e.g., height measured at coleoptile, V1 sheath or V2 sheath) than an isogenic plant not comprising the trait (e.g., about 5, 6, 7, 8, 9, 11, 12, 13, 14, 15, 16, 17, 18, 19, 20, 21, 22, 23, 24, 25, 26, 27, 28, 29, 30, 31, 32, 33, 34, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 86, 87, 88, 89, 90, 91, 92, 93, 94, 95, 96, 97, 98, 99, 100, 110, 120, 130, 140, 150%, or more shorter, or any range or value therein; e.g., about 5, 6, 7, 8, 9, 10, 11, 12, 13, 14, 15, 16, 17, 18, 19, 20, 21, 22, 23, 24, 25% shorter to about 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150%, or more shorter) (e.g., about 5% to about 10% shorter, about 5% to about 15% shorter, about 5% to about 20% shorter, about 5% to about 25% shorter, about 5% to about 30% shorter, about 5% to about 40% shorter, about 5% to about 50% shorter, about 10% to about 20% shorter, about 10% to about 30% shorter, about 10% to about 50% shorter, 10% to about 70% shorter, about 15% to about 20% shorter, about 15% to about 30% shorter, 15% to about 50% shorter, about 20% to about 30% shorter, about 20% to about 50% shorter, about 20% to about 70% shorter, about 40% to about 50% shorter, about 40% to about 60% shorter, about 40% to about 80% shorter, about 40% to about 100% shorter, about 50% to about 70% shorter, about 50% to about 100% shorter, about 50% to about 125% shorter, about 75% to about 100% shorter, about 75% to about 120% shorter, about 75% to about 140% shorter, and the like).

Plants exhibiting SAR show exaggerated elongation of hypocotyl and internodes, longer leaf, impaired root growth, early flowering and reduced seed set, low photosynthesis efficiency, enhanced green snap, high lodging rate, hastened senescence, reduced grain filling; and active suppression of disease and herbivory response mechanisms.

A plant in which SAR is reduced as described herein may have increased yield as compared to a plant that does not comprise the reduction in SAR. As used herein, "increased yield" refers to any plant trait associated with growth, for example, biomass, yield, nitrogen use efficiency (NUE), inflorescence size/weight, fruit yield, fruit quality, fruit size, seed size, seed number, foliar tissue weight, nodulation number, nodulation mass, nodulation activity, number of seed heads, number of tillers, number of flowers, number of tubers, tuber mass, bulb mass, number of seeds, total seed mass, rate of leaf emergence, rate of tiller emergence, rate of seedling emergence, length of roots, number of roots, size and/or weight of root mass, or any combination thereof. Thus, in some aspects, "increased yield" may include, but is not limited to, increased inflorescence production, increased fruit production (e.g., increased number, weight and/or size of fruit; e.g., increase number, weight, and/or size of ears for, e.g., maize), increased fruit quality, increased number, size and/or weight of roots, increased meristem size, increased seed size, increased biomass, increased leaf size, increased nitrogen use efficiency, increased height and/or increased internode length as compared to a control plant or part thereof (e.g., a plant that does not comprise a mutated endogenous nucleic acid encoding an HD-Zip transcription factor as described herein grown in an environment with a low R:FR light ratio (e.g., a shaded environment; e.g., a R:FR ratio of about 0.16) including when grown in close proximity with other plants). In some aspects, increased yield can be expressed as quantity of grain produced per area of land (e.g. bushels per acre of land).

"Seed weight" is jointly determined by grain morphology traits such as seed length, seed width and seed thickness as well as grain filling and these traits are all governed by quantitative genetics.

As used herein "decreased height" means repression of stem elongation in response to enriched far-red light.

As used herein, "decreased shoot:root ratio" means reduction of the proportion of above ground biomass relative to below ground biomass.

As used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "nucleic acid construct," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. A "5' region" as used herein can mean the region of a polynucleotide that is nearest the 5' end of the polynucleotide. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end of the polynucleotide. Thus, for example, an element in the 3' region of a polynucleotide can be located anywhere from the first nucleotide located at the 3' end of the polynucleotide to the nucleotide located halfway through the polynucleotide.

As used herein with respect to nucleic acids, the term "fragment" or "portion" refers to a nucleic acid that is reduced in length relative (e.g., reduced by 1, 2, 3, 4, 5, 6, 7, 8, 9, 10, 11, 12, 13, 14, 15, 16, 17, 18, 19, 20 or more nucleotides) to a reference nucleic acid and that comprises, consists essentially of and/or consists of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to a corresponding portion of the reference nucleic acid. Such a nucleic acid fragment may be, where appropriate, included in a larger polynucleotide of which it is a constituent. As an example, a repeat sequence of guide nucleic acid of this invention may comprise a portion of a wild type CRISPR-Cas repeat sequence (e.g., a wild Type CRISR-Cas repeat; e.g., a repeat from the CRISPR Cas system of, for example, a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or a Cas14c, and the like). In some embodiments, a nucleic acid fragment may comprise, consist essentially of or consist of about 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 300, 350, 400, 450, 500, 550, 600, 660, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000 or more consecutive nucleotides of a nucleotide sequence encoding an HD-Zip transcription factor for which a reduction in activity, e.g., a reduction in DNA binding, can result in a reduced shade avoidance response in a plant.

In some embodiments, a fragment or portion may be a fragment or portion of an HD-Zip transcription factor. In some embodiments, a fragment or portion of a nucleic acid may be a fragment or portion of nucleic acid encoding an amino acid sequence of any one of (a) a polypeptide comprising a sequence having at least 80% sequence identity to the amino acid sequence of SEQ ID NO:38 or SEQ ID NO:83; (b) a polypeptide comprising a sequence having at least 80% sequence identity to the amino acid sequence of: SEQ ID NO:1 or SEQ ID NO:2; (c) a polypeptide comprising a sequence having at least 80% sequence identity to the amino acid sequence of SEQ ID NO:3; (d) a polypeptide comprising a sequence having at least 95% sequence identity to the nucleotide sequence of SEQ ID NO:4; (e) a polypeptide comprising a sequence having the amino acid sequence of SEQ ID NO:5, wherein X is L or S; (f) a polypeptide comprising: (i) sequence having the amino acid sequence of RKKLRLX$_1$KX$_2$QX$_3$ (SEQ ID NO:6), wherein X$_1$ is S or T, X$_2$ is D or E and X$_3$ is S or A; (ii) a sequence having the amino acid sequence of PX$_1$X$_2$X$_2$LTX$_3$CPX$_4$CER (SEQ ID NO:8), wherein X$_1$ is P or A, X$_2$ is T or A, X$_3$ is V or M and X$_4$ is Q, S or N; (iii) a sequence having the amino acid sequence of ENRRLX$_1$X$_2$EX$_3$, (SEQ ID NO:7), wherein X$_1$ is Q or H, X$_2$ is R or K and X$_3$ is V or L; and (iv) a sequence having the amino acid sequence of VWFQNRRA (SEQ ID NO:9); and/or (g) a polypeptide comprising a sequence having the amino acid sequence of VWFQNRRA (SEQ ID NO:9), wherein the fragment or portion comprises about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 130, 140, 150, 175, 200, 225, 250, 300, 350 or more consecutive nucleotides, or any range or value therein of a nucleic acid encoding any one of the polypeptides of (a)-(g) as described above. In some embodiments, a "portion" may be related to the number of amino acids deleted from a polypeptide. Thus, for example, a deletion of a portion of an HD-Zip transcription factor may comprise the deletion of at least two consecutive nucleotides (e.g., 2, 3, 4, 5, 6, 7, 8, 9, 10, 11, 12, 13, 14, 15, 16, 17, 18, 19, 20, 21) of a nucleotide sequence encoding an HD-Zip transcription factor polypeptide that comprises the amino acid sequence of SEQ ID NO:9 (VWFQNRRA). In some embodiments, a deletion may comprise a portion of the HD-Zip transcription factor that comprises exon 3 and exon 4, wherein exon 3 encodes the HD-Zip DNA binding region. In some embodiments, a deletion may comprise a portion of the HD-Zip transcription factor, wherein the portion comprises all of exon 3 and exon 4 and optionally, a portion of exon 2. In some embodiments, a deletion may comprise the portion of the HD-Zip polynucleotide encoding about the last 96 to 125 consecutive amino acid residues at the C-terminal portion of the HD-Zip polypeptide.

In some embodiments, a "sequence-specific DNA binding domain" may bind to one or more fragments or portions of nucleotide sequences encoding HD-Zip transcription factors as described herein.

As used herein with respect to polypeptides, the term "fragment" or "portion" may refer to a polypeptide that is reduced in length relative to a reference polypeptide and that comprises, consists essentially of and/or consists of an amino acid sequence of contiguous amino acids identical or almost identical (e.g., 90%, 91%, 92%, 93%, 94%, 95%, 96%, 97%, 98%, 99% identical) to a corresponding portion of the reference polypeptide. Such a polypeptide fragment may be, where appropriate, included in a larger polypeptide of which it is a constituent. In some embodiments, the polypeptide fragment comprises, consists essentially of or consists of at least about 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 300, 350, 400 or more consecutive amino acids of a reference polypeptide. In some embodiments, a polypeptide fragment may comprise, consist essentially of or consist of about 5, 6, 7, 8, 9, 11, 12, 13, 14, 15, 20, 25, 30, 35, 40, 45, 50, 55, 60, 65, 70, 75, 80, 85, 90, 95, 100, 125, 150, 175, 200, 225, 250, 300, 350, 400, 450, 500, 550, 600, 660, 700 or more consecutive amino acid residues of a HD-Zip transcription factor (e.g., (a) a polypeptide comprising a sequence having at least 80% sequence identity to the amino acid sequence of SEQ ID NO:38 or SEQ ID NO:83; (b) a polypeptide comprising a sequence having at least 80% sequence identity to the amino acid sequence of: SEQ ID NO:1 or SEQ ID NO:2; (c) a polypeptide comprising a sequence having at least 80% sequence identity to the amino acid sequence of SEQ ID NO:3; (d) a polypeptide comprising a sequence having at least 95% sequence identity to the nucleotide sequence of SEQ ID NO:4; (e) a polypeptide comprising a sequence having the amino acid sequence of SEQ ID NO:5, wherein X is L or S; (f) a polypeptide comprising: (i) sequence having the amino acid sequence of RKKLRLX$_1$KX$_2$QX$_3$ (SEQ ID NO:6), wherein X$_1$ is S or T, X$_2$ is D or E and X$_3$ is S or A; (ii) a sequence having the amino acid sequence of PX$_1$X$_2$ X$_2$LTX$_3$CPX$_4$CER (SEQ ID NO:8), wherein X$_1$ is P or A, X$_2$ is T or A, X$_3$ is V or M and X$_4$ is Q, S or N; (iii) a sequence having the amino acid sequence of ENRRLX$_1$X$_2$EX$_3$, (SEQ ID NO:7), wherein X$_1$ is Q or H, X$_2$ is R or K and X$_3$ is V or L; and (iv) a sequence having the amino acid sequence of VWFQNRRA (SEQ ID NO:9); and/or (g) a polypeptide comprising a sequence having the amino acid sequence of VWFQNRRA (SEQ ID NO:9).

In some embodiments, a fragment or portion may be a fragment or portion of an HD-Zip transcription factor. In some embodiments, a fragment or portion may be a fragment or portion of an amino acid sequence of any one of (a) a polypeptide comprising a sequence having at least 80% sequence identity to the amino acid sequence of (a) to (g) described above, wherein the fragment or portion comprises about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 140, 150, 175, 200, 225, 250, 300, 350 or more consecutive amino acids, or any range or value therein of any one of (a) a polypeptide comprising a sequence having at least 80% sequence identity to the amino acid sequence of (a) to (g) described above. In some embodiments, a "portion" may be related to the number of amino acids that are deleted from a polypeptide. Thus, for example, a deleted "portion" of an HD-Zip transcription factor may comprise at least one amino acid residue (e.g., at least 1, 2, 3, 4, 5, 6, 7, 8 amino acid residues), and/or at least two (e.g., at least 2, 3, 4, 5, 6, 7, 8 amino acid residues) amino acid residues of the amino acid sequence of SEQ ID NO:9 (VWFQNRRA) of any HD-Zip transcription factor described herein. In some embodiments, a deletion of a portion of an HD-Zip transcription factor may comprise a portion of consecutive amino acid residues of SEQ ID NO:9 (e.g., at least 2, 3, 4, 5, 6, 7, or 8 consecutive amino acid residues). In some embodiments, the deletion includes at least a portion of consecutive amino acid residues of SEQ ID NO:9 (e.g., at least 1, 2, 3, 4, 5, 6, 7, or 8 consecutive amino acid residues), wherein the deletion may be at least 1 amino acid residue to about 120 amino acid residues in length (e.g., at least 1, 2, 3, 4, 5, 6, 7, 8, 9, 10, 11, 12, 13, 14, 15, 16, 17, 18, 19, 20, 21, 22, 23, 24, 26, 27, 28, 29, 30, 31, 32, 33, 34, 35, 36, 37, 38, 39, 40, 41, 42, 43, 44, 45, 46, 47, 48, 49, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, or more consecutive amino acid residues up to the full length of the HD-Zip transcription factor, and any range or value therein) and wherein at least 1 amino acid residue that is deleted is from the DNA binding region of the HD-Zip transcription factor. In some embodiments, the deletion may be a truncation that includes at least a portion of consecutive amino acid residues of SEQ ID NO:9 (e.g., at least 1, 2, 3, 4, 5, 6, 7, or 8 consecutive amino acid residues). In some embodiments, the truncation may be a C-terminal truncation and comprise a length of at least 96 consecutive amino acid residues. In some embodiments, the truncation may be a C-terminal truncation and comprise a length of about 96 amino acid residues to about 125 amino acid residues (e.g., at least 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, or more consecutive amino acid residues up to the full length of the HD-Zip transcription factor, and any range or value therein) and wherein at least 1 amino acid residue that is truncated is from the DNA binding region of the HD-Zip transcription factor. In some embodiments, a deletion may include a deletion of exon 3, which comprises the DNA binding region of the HD-Zip transcription factor (e.g., the portion of the HD-Zip transcription factor that is deleted may be about 27 amino acid residues in length). In some embodiments, the truncation may be a result of a deletion in exon 2 (e.g., a portion of exon 2) that results in a truncation of a portion of the amino acid residues encoded by exon2 and all remaining amino acids following the deletion, thereby, for example, truncating all of the amino acids encoded by exon 3 and exon 4. Thus, in some embodiments, a deletion may result in a truncation of the C-terminal region of the HD-Zip transcription factor polypeptide that includes the DNA binding region or at least a portion of the DNA binding region. In some embodiments, a deletion may cause a frameshift mutation that results a stop codon and a truncation of the C-terminus of the HD-Zip transcription factor polypeptide. In some embodiments, a C-terminal truncation may result in a polypeptide that comprises 207 amino acids (e.g., the deleted or truncated portion includes all amino acid residues after amino acid residue 207; see, e.g., maize HD-Zip edited polypeptide SEQ ID NO:201).

In some embodiments, a "sequence-specific DNA binding domain" may bind to one or more fragments or portions of nucleotide sequences encoding HD-Zip transcription factors as described herein.

As used herein with respect to nucleic acids, the term "functional fragment" refers to nucleic acid that encodes a functional fragment of a polypeptide.

The term "gene," as used herein, refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The term "mutation" refers to point mutations (e.g., missense, or nonsense, or insertions or deletions of single base pairs that result in frame shifts), insertions, deletions, and/or truncations. When the mutation is a substitution of a residue within an amino acid sequence with another residue, or a deletion or insertion of one or more residues within a sequence, the mutations are typically described by identifying the original residue followed by the position of the residue within the sequence and by the identity of the newly substituted residue. In some embodiments, a deletion may result in a frameshift mutation that generates a premature stop codon, thereby truncating the protein.

The terms "complementary" or "complementarity," as used herein, refer to the natural binding of polynucleotides under permissive salt and temperature conditions by base-pairing. For example, the sequence "A-G-T" (5' to 3') binds to the complementary sequence "T-C-A" (3' to 5'). Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement," as used herein, can mean 100% complementarity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity) to the comparator nucleotide sequence.

Different nucleic acids or proteins having homology are referred to herein as "homologues." The term homologue includes homologous sequences from the same and from other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention.

"Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to said nucleotide sequence of the invention.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence as compared to a reference polypeptide.

As used herein, the phrase "substantially identical," or "substantial identity" in the context of two nucleic acid molecules, nucleotide sequences or polypeptide sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% nucleotide or amino acid residue identity, when compared and aligned for maximum correspondence, as measured using one of the following sequence comparison algorithms or by visual inspection.

In some embodiments of the invention, the substantial identity exists over a region of consecutive nucleotides of a nucleotide sequence of the invention that is about 10 nucleotides to about 20 nucleotides, about 10 nucleotides to about 25 nucleotides, about 10 nucleotides to about 30 nucleotides, about 15 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, or more nucleotides in length, and any range therein, up to the full length of the sequence. In some embodiments, nucleotide sequences can be substantially identical over at least about 20 nucleotides (e.g., about 20, 21, 22, 23, 24, 25, 26, 27, 28, 29, 30, 31, 32, 33, 34, 35, 36, 37, 38, 39, 40 nucleotides). In some embodiments of the invention, the substantial identity exists over a region of consecutive amino acid residues of a polypeptide of the invention that is about 3 amino acid residues to about 20 amino acid residues, about 5 amino acid residues to about 25 amino acid residues, about 7 amino acid residues to about 30 amino acid residues, about 10 amino acid residues to about 25 amino acid residues, about 15 amino acid residues to about amino acid residues, about 20 amino acid residues to about 40 amino acid residues, about amino acid residues to about 40 amino acid residues, about 25 amino acid residues to about 50 amino acid residues, about 30 amino acid residues to about 50 amino acid residues, about 40 amino acid residues to about 50 amino acid residues, about 40 amino acid residues to about 70 amino acid residues, about 50 amino acid residues to about 70 amino acid residues, about 60 amino acid residues to about 80 amino acid residues, about 70 amino acid residues to about 80 amino acid residues, about 90 amino acid residues to about 100 amino acid residues, or more amino acid residues in length, and any range therein, up to the full length of the sequence. In some embodiments, polypeptide sequences can be substantially identical to one another over at least about 8 consecutive amino acid residues (e.g., about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 130, 140, 150, 175, 200, 225, 250, 275, 300, 325, 350 or more amino acids in length or more consecutive amino acid residues). In some embodiments, two or more HD-Zip transcription factors may be substantially identical to one another over at least about 8 consecutive amino acid residues (e.g., SEQ ID NO:9), over at least about 9 consecutive amino acid residues (e.g., SEQ ID NO:7), over at least about 11 consecutive amino acid residues (e.g., SEQ ID NO:6), at least about 13 consecutive amino acid residues (e.g., SEQ ID NO:8), over at least about 24 consecutive amino acid residues (e.g., SEQ ID NOs:4-5), over at least about 53 consecutive amino acid residues (e.g., SEQ ID NO:3), over at least about 116 consecutive amino acid residues (e.g., SEQ ID NOs:1-2), and the like, or an combination thereof. In some embodiments, a substantially identical nucleotide or protein sequence performs substantially the same function as the nucleotide (or encoded protein sequence) to which it is substantially identical.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, CA). An "identity fraction" for aligned segments of a test sequence and a reference sequence is the number of identical components which are shared by the two aligned sequences divided by the total number of components in the reference sequence segment, e.g., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Two nucleotide sequences may also be considered substantially complementary when the two sequences hybridize to each other under stringent conditions. In some embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen Laboratory Techniques in Biochemistry and Molecular Biology-Hybridization with Nucleic Acid Probes part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

A polynucleotide and/or recombinant nucleic acid construct of this invention (e.g., expression cassettes and/or vectors) may be codon optimized for expression. In some embodiments, the polynucleotides, nucleic acid constructs, expression cassettes, and/or vectors of the editing systems of the invention (e.g., comprising/encoding a sequence-specific DNA binding domain (e.g., a sequence-specific DNA binding domain from a polynucleotide-guided endonuclease, a zinc finger nuclease, a transcription activator-like effector nuclease (TALEN), an Argonaute protein, and/or a CI 1SPR-Cas endonuclease (e.g., CR1SPR-Cas effector protein) (e.g., a Type I CRISPR-Cas effector protein, a Type II CRISPR-Cas effector protein, a Type III CRISPR-Cas effector protein, a Type IV CRISPR-Cas effector protein, a Type V CRISPR-Cas effector protein or a Type VI CRISPR-Cas effector protein)), a nuclease (e.g., an endonuclease (e.g., Fok1), a polynucleotide-guided endonuclease, a CR1SPR-Cas endonuclease (e.g., CR1SPR-Cas effector protein), a zinc finger nuclease, and/or a transcription activator-like effector nuclease (TALEN)), deaminase proteins/domains (e.g., adenine deaminase, cytosine deaminase), a polynucleotide encoding a reverse transcriptase protein or domain, a polynucleotide encoding a 5'-3' exonuclease polypeptide, and/or affinity polypeptides, peptide tags, etc.) may be codon optimized for expression in a plant. In some embodiments, the codon optimized nucleic acids, polynucleotides, expression cassettes, and/or vectors of the invention have about 70% to about 99.9% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% or 100%) identity or more to the reference nucleic acids, polynucleotides, expression cassettes, and/or vectors that have not been codon optimized.

In any of the embodiments described herein, a polynucleotide or nucleic acid construct of the invention may be operatively associated with a variety of promoters and/or other regulatory elements for expression in a plant and/or a cell of a plant. Thus, in some embodiments, a polynucleotide or nucleic acid construct of this invention may further comprise one or more promoters, introns, enhancers, and/or terminators operably linked to one or more nucleotide sequences. In some embodiments, a promoter may be operably associated with an intron (e.g., Ubi1 promoter and intron). In some embodiments, a promoter associated with an intron may be referred to as a "promoter region" (e.g., Ubi1 promoter and intron).

By "operably linked" or "operably associated" as used herein in reference to polynucleotides, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, nucleic acid sequences can be present between a promoter and the nucleotide sequence, and the promoter can still be considered "operably linked" to the nucleotide sequence.

As used herein, the term "linked," in reference to polypeptides, refers to the attachment of one polypeptide to another. A polypeptide may be linked to another polypeptide (at the N-terminus or the C-terminus) directly (e.g., via a peptide bond) or through a linker.

The term "linker" is art-recognized and refers to a chemical group, or a molecule linking two molecules or moieties, e.g., two domains of a fusion protein, such as, for example, a DNA binding polypeptide or domain and peptide tag and/or a reverse transcriptase and an affinity polypeptide that binds to the peptide tag; or a DNA endonuclease polypeptide or domain and peptide tag and/or a reverse transcriptase and an affinity polypeptide that binds to the peptide tag. A linker may be comprised of a single linking molecule or may comprise more than one linking molecule. In some embodiments, the linker can be an organic molecule, group, polymer, or chemical moiety such as a bivalent organic moiety. In some embodiments, the linker may be an amino acid or it may be a peptide. In some embodiments, the linker is a peptide.

In some embodiments, a peptide linker useful with this invention may be about 2 to about 100 or more amino acids in length, for example, about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 2 to about 40, about 2 to about 50, about 2 to about 60, about 4 to about 40, about 4 to about about 4 to about 60, about 5 to about 40, about 5 to about 50, about 5 to about 60, about 9 to about 40, about 9 to about 50, about 9 to about 60, about 10 to about 40, about 10 to about about 10 to about 60, or about 2, 3, 4, 5, 6, 7, 8, 9, 10, 11, 12, 13, 14, 15, 16, 17, 18, 19, 21, 22, 23, 24, 25 amino acids to about 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 105, 110, 115, 120, 130, 140 150 or more amino acids in length). In some embodiments, a peptide linker may be a GS linker.

As used herein, the term "linked," or "fused" in reference to polynucleotides, refers to the attachment of one polynucleotide to another. In some embodiments, two or more polynucleotide molecules may be linked by a linker that can be an organic molecule, group, polymer, or chemical moiety such as a bivalent organic moiety. A polynucleotide may be linked or fused to another polynucleotide (at the 5' end or the 3' end) via a covalent or non-covenant linkage or binding, including e.g., Watson-Crick base-pairing, or through one or more linking nucleotides. In some embodiments, a polynucleotide motif of a certain structure may be inserted within another polynucleotide sequence (e.g. extension of the hairpin structure in the guide RNA). In some embodiments, the linking nucleotides may be naturally occurring nucleotides. In some embodiments, the linking nucleotides may be non-naturally occurring nucleotides.

A "promoter" is a nucleotide sequence that controls or regulates the transcription of a nucleotide sequence (e.g., a coding sequence) that is operably associated with the promoter. The coding sequence controlled or regulated by a promoter may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. A promoter may comprise other elements that act as regulators of gene expression; e.g., a promoter region. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in *Genetic Engineering of Plants*, T. Kosuge, C. Meredith and A. Hollaender (eds.), Plenum Press, pp. 211-227).

Promoters useful with this invention can include, for example, constitutive, inducible, temporally regulated, developmentally regulated, chemically regulated, tissue-preferred and/or tissue-specific promoters for use in the preparation of recombinant nucleic acid molecules, e.g., "synthetic nucleic acid constructs" or "protein-RNA complex." These various types of promoters are known in the art.

The choice of promoter may vary depending on the temporal and spatial requirements for expression, and also may vary based on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments, a promoter functional in a plant may be used with the constructs of this invention. Non-limiting examples of a promoter useful for driving expression in a plant include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735

(2005); Li et al. *Gene* 403:132-142 (2007); Li et al. *Mol Biol. Rep.* 37:1143-1154 (2010)). PrbcS1 and Pactin are constitutive promoters and Pnr and Pdca1 are inducible promoters. Pnr is induced by nitrate and repressed by ammonium (Li et al. *Gene* 403:132-142 (2007)) and Pdca1 is induced by salt (Li et al. *Mol Biol. Rep.* 37:1143-1154 (2010)). In some embodiments, a promoter useful with this invention is RNA polymerase II (Pol II) promoter. In some embodiments, a U6 promoter or a 7SL promoter from *Zea mays* may be useful with constructs of this invention. In some embodiments, the U6c promoter and/or 7SL promoter from *Zea mays* may be useful for driving expression of a guide nucleic acid. In some embodiments, a U6c promoter, U6i promoter and/or 7SL promoter from *Glycine max* may be useful with constructs of this invention. In some embodiments, the U6c promoter, U6i promoter and/or 7SL promoter from *Glycine max* may be useful for driving expression of a guide nucleic acid.

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) Nature 313:810-812), CaMV 19S promoter (Lawton et al. (1987) *Plant Mol. Biol.* 9:315-324), nos promoter (Ebert et al. (1987) Proc. Natl. Acad. Sci USA 84:5745-5749), Adh promoter (Walker et al. (1987) *Proc. Natl. Acad. Sci. USA* 84:6624-6629), sucrose synthase promoter (Yang & Russell (1990) Proc. Natl. Acad. Sci. USA 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and *arabidopsis* (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231: 150-160 (1991)) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Tissue specific or preferred expression patterns include, but are not limited to, green tissue specific or preferred, root specific or preferred, stem specific or preferred, flower specific or preferred or pollen specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of the nucleotide sequences of the invention in plants, particularly maize, include but are not limited to those that direct expression in root, pith, leaf or pollen. Such promoters are disclosed, for example, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604, 121; the root specific promoter described by de Framond (*FEBS* 290:103-106 (1991); EP 0 452 269 to Ciba-Geigy); the stem specific promoter described in U.S. Pat. No. 5,625,136 (to Ciba-Geigy) and which drives expression of the maize trpA gene; the cestrum yellow leaf curling virus promoter disclosed in WO 01/73087; and pollen specific or preferred promoters including, but not limited to, ProOsLPS10 and ProOsLPS11 from rice (Nguyen et al. *Plant Biotechnol. Reports* 9(5):297-306 (2015)), ZmSTK2 USP from maize (Wang et al. *Genome* 60(6):485-495 (2017)), LAT52 and LAT59 from tomato (Twell et al. *Development* 109(3):705-713 (1990)), Zm13 (U.S. Pat. No. 10,421,972), PLA2-6 promoter from *arabidopsis* (U.S. Pat. No. 7,141, 424), and/or the ZmC5 promoter from maize (International PCT Publication No. WO1999/042587.

Additional examples of plant tissue-specific/tissue preferred promoters include, but are not limited to, the root hair—specific cis-elements (RHEs) (Kim et al. *The Plant Cell* 18:2958-2970 (2006)), the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adePosyi-L-methionine synthetase (SAMS) (Vander Mijnsbrugge et al. (1996) *Plant and Cell Physiology,* 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986) *Mol. Gen. Genet.* 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), *petunia* chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989)*Mol. Gen. Genet.* 215:431-440), PEP-Case promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612).

Useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched at the onset of senescence, such as the SAG promoter from *Arabidopsis* (Gan et al. (1995) *Science* 270:1986-1988).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

Additional regulatory elements useful with this invention include, but are not limited to, introns, enhancers, termination sequences and/or 5' and 3' untranslated regions.

An intron useful with this invention can be an intron identified in and isolated from a plant and then inserted into an expression cassette to be used in transformation of a plant. As would be understood by those of skill in the art, introns can comprise the sequences required for self-excision and are incorporated into nucleic acid constructs/expression cassettes in frame. An intron can be used either as a spacer to separate multiple protein-coding sequences in one nucleic acid construct, or an intron can be used inside one protein-coding sequence to, for example, stabilize the mRNA. If they are used within a protein-coding sequence, they are inserted "in-frame" with the excision sites included. Introns may also be associated with promoters to improve or modify expression. As an example, a promoter/intron combination useful with this invention includes but is not limited to that of the maize Ubi1 promoter and intron (see, e.g, SEQ ID NO:196 and SEQ ID NO:197).

Non-limiting examples of introns useful with the present invention include introns from the ADHI gene (e.g., Adhl-S introns 1, 2 and 6), the ubiquitin gene (Ubi1), the RuBisCO small subunit (rbcS) gene, the RuBisCO large subunit (rbcL) gene, the actin gene (e.g., actin-1 intron), the pyruvate dehydrogenase kinase gene (pdk), the nitrate reductase gene (nr), the duplicated carbonic anhydrase gene 1 (Tdcal), the psbA gene, the atpA gene, or any combination thereof.

In some embodiments, a polynucleotide and/or a nucleic acid construct of the invention can be an "expression cassette" or can be comprised within an expression cassette. As used herein, "expression cassette" means a recombinant nucleic acid molecule comprising, for example, a one or more polynucleotides of the invention (e.g., a polynucleotide encoding a sequence-specific DNA binding domain, a polynucleotide encoding a deaminase protein or domain, a polynucleotide encoding a reverse transcriptase protein or domain, a polynucleotide encoding a 5'-3' exonuclease polypeptide or domain, a guide nucleic acid and/or reverse transcriptase (RT) template), wherein polynucleotide(s) is/are operably associated with one or more control sequences (e.g., a promoter, terminator and the like). Thus, in some embodiments, one or more expression cassettes may be provided, which are designed to express, for example, a nucleic acid construct of the invention (e.g., a polynucleotide encoding a sequence-specific DNA binding domain, a polynucleotide encoding a nuclease polypeptide/domain, a polynucleotide encoding a deaminase protein/domain, a polynucleotide encoding a reverse transcriptase protein/domain, a polynucleotide encoding a 5'-3' exonuclease polypeptide/domain, a polynucleotide encoding a peptide tag, and/or a polynucleotide encoding an affinity polypeptide, and the like, or comprising a guide nucleic acid, an extended guide nucleic acid, and/or RT template, and the like). When an expression cassette of the present invention comprises more than one polynucleotide, the polynucleotides may be operably linked to a single promoter that drives expression of all of the polynucleotides or the polynucleotides may be operably linked to one or more separate promoters (e.g., three polynucleotides may be driven by one, two or three promoters in any combination). When two or more separate promoters are used, the promoters may be the same promoter or they may be different promoters. Thus, a polynucleotide encoding a sequence specific DNA binding domain, a polynucleotide encoding a nuclease protein/domain, a polynucleotide encoding a CRISPR-Cas effector protein/domain, a polynucleotide encoding an deaminase protein/domain, a polynucleotide encoding a reverse transcriptase polypeptide/domain (e.g., RNA-dependent DNA polymerase), and/or a polynucleotide encoding a 5'-3' exonuclease polypeptide/domain, a guide nucleic acid, an extended guide nucleic acid and/or RT template when comprised in a single expression cassette may each be operably linked to a single promoter, or separate promoters in any combination.

An expression cassette comprising a nucleic acid construct of the invention may be chimeric, meaning that at least one of its components is heterologous with respect to at least one of its other components (e.g., a promoter from the host organism operably linked to a polynucleotide of interest to be expressed in the host organism, wherein the polynucleotide of interest is from a different organism than the host or is not normally found in association with that promoter). An expression cassette may also be one that is naturally occurring but has been obtained in a recombinant form useful for heterologous expression.

An expression cassette can optionally include a transcriptional and/or translational termination region (i.e., termination region) and/or an enhancer region that is functional in the selected host cell. A variety of transcriptional terminators and enhancers are known in the art and are available for use in expression cassettes. Transcriptional terminators are responsible for the termination of transcription and correct mRNA polyadenylation. A termination region and/or the enhancer region may be native to the transcriptional initiation region, may be native to, for example, a gene encoding a sequence-specific DNA binding protein, a gene encoding a nuclease, a gene encoding a reverse transcriptase, a gene encoding a deaminase, and the like, or may be native to a host cell, or may be native to another source (e.g., foreign or heterologous to, for example, to a promoter, to a gene encoding a sequence-specific DNA binding protein, a gene encoding a nuclease, a gene encoding a reverse transcriptase, a gene encoding a deaminase, and the like, or to the host cell, or any combination thereof).

An expression cassette of the invention also can include a polynucleotide encoding a selectable marker, which can be used to select a transformed host cell. As used herein, "selectable marker" means a polynucleotide sequence that when expressed imparts a distinct phenotype to the host cell expressing the marker and thus allows such transformed cells to be distinguished from those that do not have the marker. Such a polynucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Many examples of suitable selectable markers are known in the art and can be used in the expression cassettes described herein.

In addition to expression cassettes, the nucleic acid molecules/constructs and polynucleotide sequences described herein can be used in connection with vectors. The term "vector" refers to a composition for transferring, delivering or introducing a nucleic acid (or nucleic acids) into a cell. A vector comprises a nucleic acid construct (e.g. expression cassette(s)) comprising the nucleotide sequence(s) to be transferred, delivered or introduced. Vectors for use in transformation of host organisms are well known in the art. Non-limiting examples of general classes of vectors include viral vectors, plasmid vectors, phage vectors, phagemid vectors, cosmid vectors, fosmid vectors, bacteriophages, artificial chromosomes, minicircles, or *Agrobacterium* binary vectors in double or single stranded linear or circular form which may or may not be self-transmissible or mobilizable. In some embodiments, a viral vector can include, but is not limited, to a retroviral, lentiviral, adenoviral, adeno-associated, or herpes simplex viral vector. A vector as defined herein can transform a prokaryotic or eukaryotic host either by integration into the cellular genome or exist extrachromosomally (e.g. autonomous replicating plasmid with an origin of replication). Additionally included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells). In some embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter and/or other regulatory elements and in the case of cDNA this may be under the control of an appropriate promoter and/or other regulatory elements for expression in the host cell. Accordingly, a nucleic acid or polynucleotide of this invention and/or expression cassettes comprising the same may be comprised in vectors as described herein and as known in the art.

As used herein, "contact," "contacting," "contacted," and grammatical variations thereof, refer to placing the components of a desired reaction together under conditions suitable for carrying out the desired reaction (e.g., transformation, transcriptional control, genome editing, nicking, and/or cleavage). As an example, a target nucleic acid may be contacted with a sequence-specific DNA binding protein (e.g., polynucleotide-guided endonuclease, a. CRISPR-Cas endonuclease CRISPR-Cas effector protein), a zinc finger nuclease, a transcription activator-like effector nuclease (TALEN) and/or an Argonaute protein)) and a deaminase or a nucleic acid construct encoding the same, under conditions whereby the sequence-specific DNA binding protein, the reverse transcriptase and the deaminase are expressed and the sequence-specific DNA binding protein binds to the target nucleic acid, and the reverse transcriptase and/or deaminase may be fused to either the sequence-specific DNA binding protein or recruited to the sequence-specific DNA binding protein (via, for example, a peptide tag fused to the sequence-specific DNA binding protein and an affinity tag fused to the reverse transcriptase and/or deaminase) and thus, the deaminase and/or reverse transcriptase is positioned in the vicinity of the target nucleic acid, thereby modifying the target nucleic acid. Other methods for recruiting reverse transcriptase and/or deaminase may be used that take advantage of other protein-protein interactions, and also RNA-protein interactions and chemical interactions may be used for protein-protein and protein-nucleic acid recruitment.

As used herein, "modifying," "modification," "mutating" or "mutation" (which terms may be used interchangeably herein) in reference to a target nucleic acid includes editing (e.g., mutating), covalent modification, exchanging/substituting nucleic acids/nucleotide bases, deleting, cleaving, nicking, and/or altering transcriptional control of a target nucleic acid. In some embodiments, a modification may include one or more single base changes (SNPs) of any type.

"Introducing," "introduce," "introduced" (and grammatical variations thereof) in the context of a polynucleotide of interest means presenting a nucleotide sequence of interest (e.g., polynucleotide, RT template, a nucleic acid construct, and/or a guide nucleic acid) to a plant, plant part thereof, or cell thereof, in such a manner that the nucleotide sequence gains access to the interior of a cell.

The terms "transformation" or transfection" may be used interchangeably and as used herein refer to the introduction of a heterologous nucleic acid into a cell. Transformation of a cell may be stable or transient. Thus, in some embodiments, a host cell or host organism (e.g., a plant) may be stably transformed with a polynucleotide/nucleic acid molecule of the invention. In some embodiments, a host cell or host organism may be transiently transformed with a polynucleotide/nucleic acid molecule of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear and the plastid genome, and therefore includes integration of the nucleic acid into, for example, the chloroplast or mitochondrial genome. Stable transformation as used herein can also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a host organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Accordingly, in some embodiments, nucleotide sequences, polynucleotides, nucleic acid constructs, and/or expression cassettes of the invention may be expressed transiently and/or they can be stably incorporated into the genome of the host organism. Thus, in some embodiments, a nucleic acid construct of the invention (e.g., one or more expression cassettes comprising polynucleotides for editing as described herein) may be transiently introduced into a cell with a guide nucleic acid and as such, no DNA is maintained in the cell.

A nucleic acid construct of the invention may be introduced into a plant cell by any method known to those of skill in the art. Non-limiting examples of transformation methods include transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. Procedures for transforming both eukaryotic and prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013)). General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol.* Lett. 7:849-858 (2002)).

In some embodiments of the invention, transformation of a cell may comprise nuclear transformation. In other embodiments, transformation of a cell may comprise plastid transformation (e.g., chloroplast transformation). In still further embodiments, nucleic acids of the invention may be introduced into a cell via conventional breeding techniques. In some embodiments, one or more of the polynucleotides, expression cassettes and/or vectors may be introduced into a plant cell via *Agrobacterium* transformation.

A polynucleotide therefore can be introduced into a plant, plant part, plant cell in any number of ways that are well known in the art. The methods of the invention do not depend on a particular method for introducing one or more nucleotide sequences into a plant, only that they gain access to the interior the cell. Where more than polynucleotide is to be introduced, they can be assembled as part of a single nucleic acid construct, or as separate nucleic acid constructs, and can be located on the same or different nucleic acid constructs. Accordingly, the polynucleotide can be introduced into the cell of interest in a single transformation event, or in separate transformation events, or, alternatively, a polynucleotide can be incorporated into a plant as part of a breeding protocol.

Yield (bushels/acre) in, for example, corn has increased steadily through high intensity breeding. However, incremental increases in yield have recently started to plateau and require large investments in field evaluation and breeding to clearly demonstrate genetic gain. New approaches to genetic modification are required to deliver significant improvements to yield that are not possible through traditional methods. Crop yields may be improved in two fundamentally distinct ways: 1) yield improvements per se, where an engineered plant has gained an advantage such as improved photosynthesis or optimized carbohydrate partitioning or 2) the removal of vestigial survival mechanisms that are not consistent with high production agriculture. Shade avoidance response (SAR) or shade avoidance syndrome (SAS) is such a survival mechanism. SAS/SAR is characterized by increased root/shoot ratio, increased plant height, and reduced individual plant yield and in a typical monoculture crop setting, this response to competition a wasteful survival mechanism.

Thus, the present invention addresses problems associated with increased planting density tolerance (see, FIG. 3) and reduction in yield loss (on an acre basis) due to planting variability. The present invention describes the use of gene editing to modify key regulatory factors that trigger shade avoidance in crops (e.g., dominant negative mutants) (see, e.g., FIG. 4). Plants with such edited genomes will have reduced shade avoidance capability. An example of a mutation useful for addressing (e.g., reducing/attenuating) SAR/SAS, may be one that removes the DNA binding function of transcription factors that dimerize to be functional. In in some cases such a mutation may be a dominant negative mutation (see, e.g., FIG. 4).

Figure 5:
FIG. 5 shows the relationship between HDLZ Class II proteins.

The HD (homeodomain)-LZ (leucine zipper) (HD-Zip) class of transcription factors have multiple functions within the plant. The Type II class have been associated with light perception and shade avoidance. One specific HD-LZ Class II member (HB53) has been shown to be induced by shade treatment. In maize, ZmHB53 is the closest maize homolog of ATHB2, an HDLZ closely associated with the Shade Avoidance Response in *Arabidopsis* (Carabelli et al., 1996; Steindler et al., 1999) (see, e.g., FIG. 5). A closely related HDLZ protein, ZmHB78, has been identified as a further target for attenuating shade avoidance. One approach for attenuating the DNA binding capability of a transcription factor useful with this invention (e.g., HB53, HB78) can include modifying individual amino acids (deletions, insertions or substitutions) or removing all or a portion of the DNA binding domain through an in-frame deletion.

An alignment of HD-Zip (HB78) amino acid sequences from 44 different plant species is provided in FIGS. 1A-1B. The sequences shown in FIGS. 1A-1B are a portion of consecutive amino acids (53 amino acid residues) from the full length HB78 sequences. Also provided is an alignment of HD-Zip (HB53) amino acid sequences from 45 different plant species (FIGS. 2A-2D). The sequences shown in FIGS. 2A-2D are a portion of consecutive amino acid residues (e.g., about 116 amino acid residues) from the full length HB53 sequences. These alignments show that there is substantial conservation in the targeted region of these two genes and demonstrate that the present invention of targeting an endogenous Homeodomain-leucine zipper (HD-Zip) transcription factor, wherein the mutation disrupts the binding of the HD-Zip transcription factor to DNA, would be predicted to work across diverse plant species to produce a plant having an attenuated Shade Avoidance Response.

Figure 6:
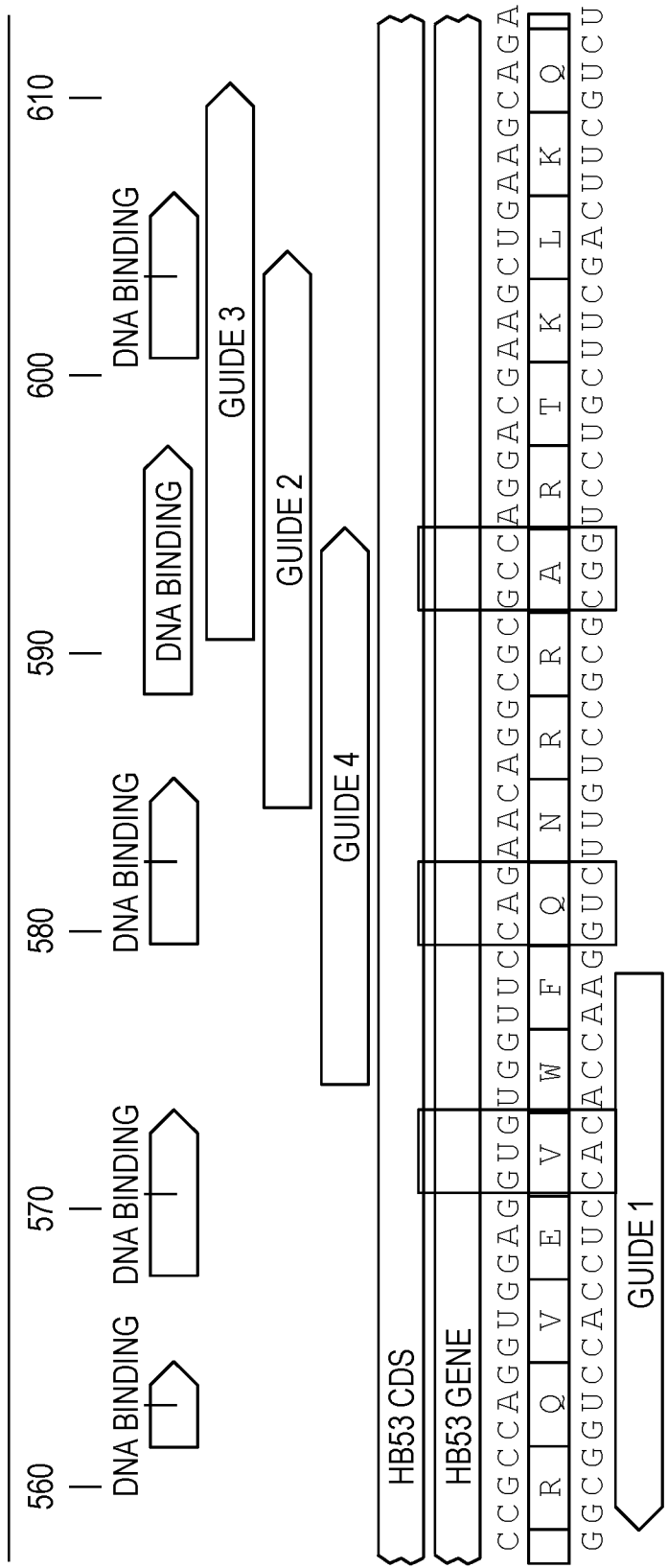
FIG. 6 provides an example of editing of the DNA binding domain of HB53 in Z. mays and shows target example amino acid residues for modification in the boxes. Coding (SEQ ID NO:292) and non-coding (SEQ ID NO:293) strands and the HB53 amino acid sequence (SEQ ID NO:294) are shown.
Figure 7:
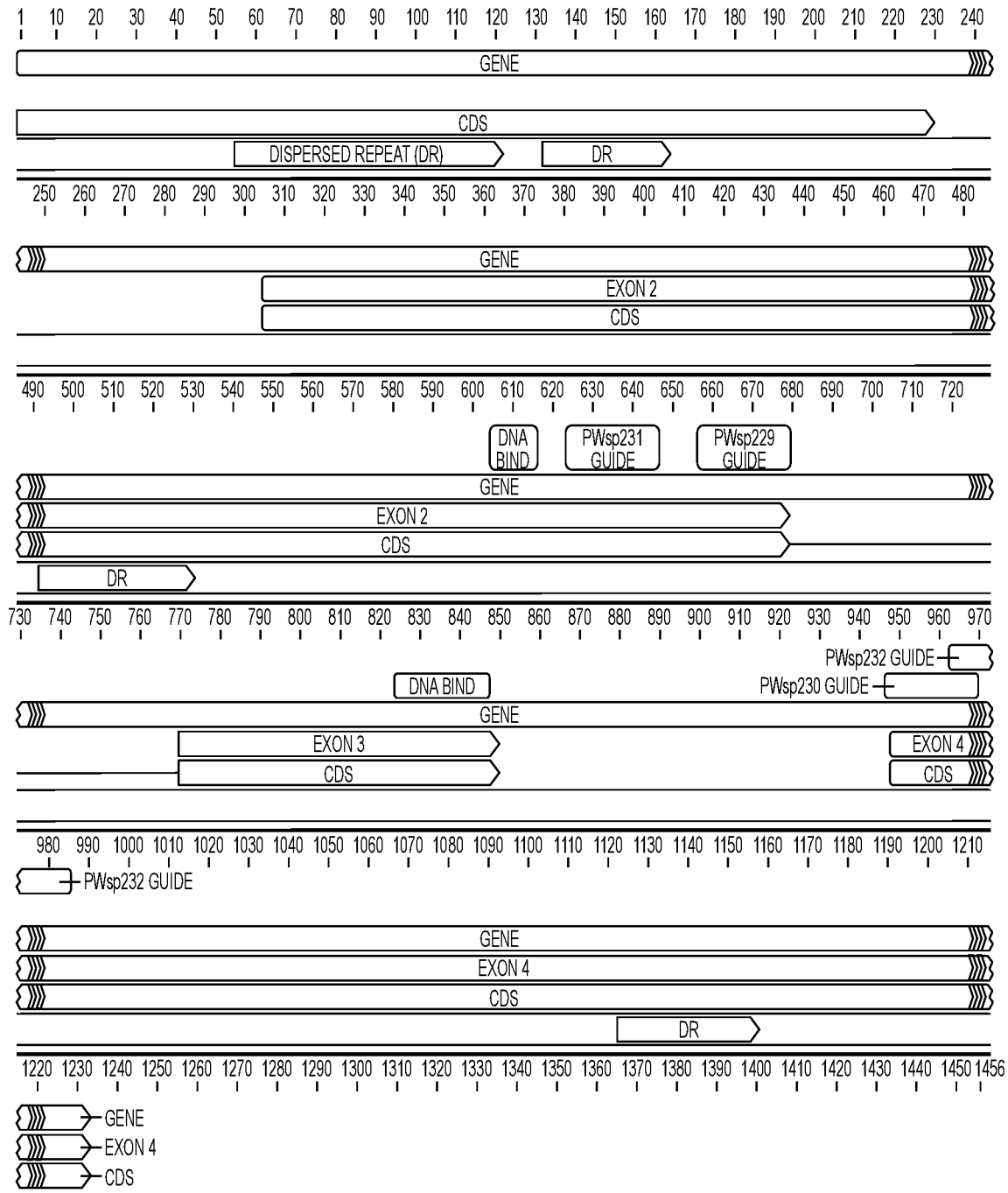
FIG. 7 provides an annotated HB78 gene with example guide nucleic acids.
Figure 8:
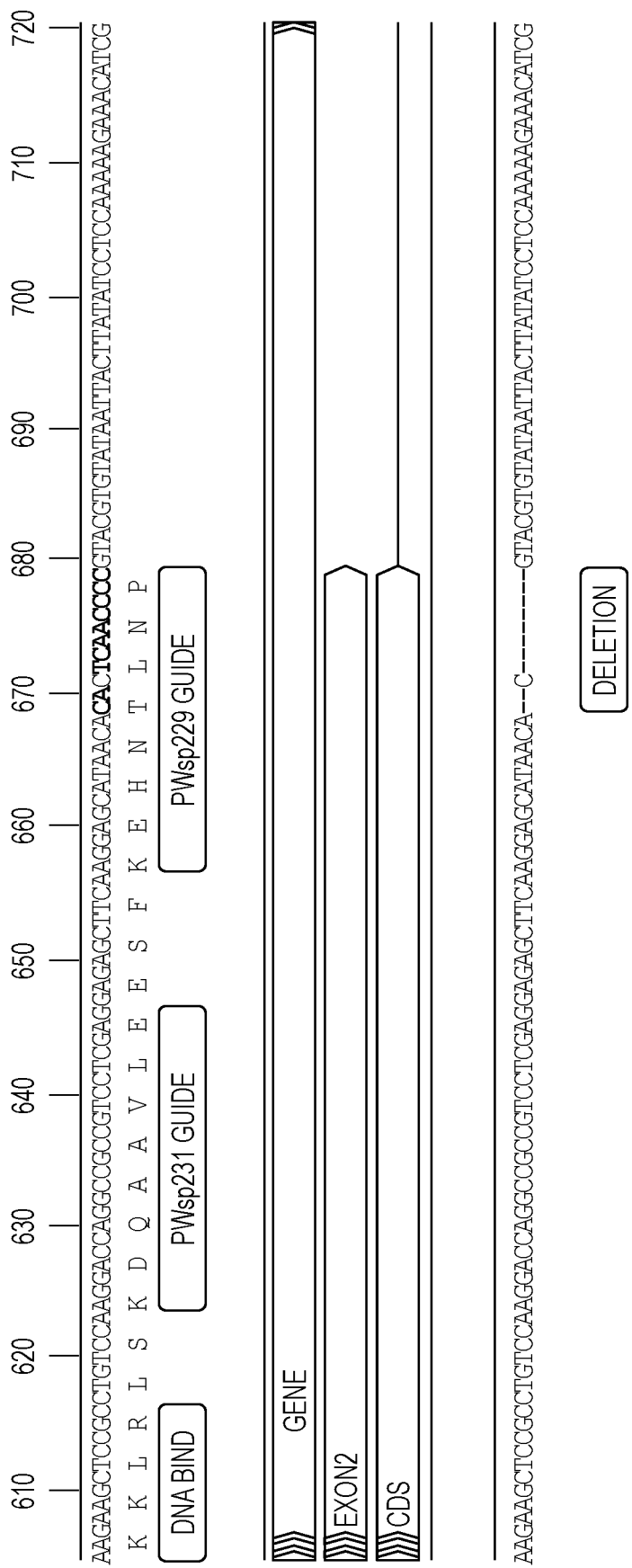
FIG. 8 provides an example of a deletion in an HB78 gene (SEQ ID NO:295) showing that a deletion (SEQ ID NO:297) in, for example, Exon 2 results in a truncation that deletes Exon 3, Exon 4 and the DNA binding domain. The protein sequence (SEQ ID NO:296) at the site of the deletion is also shown.
Figure 9:
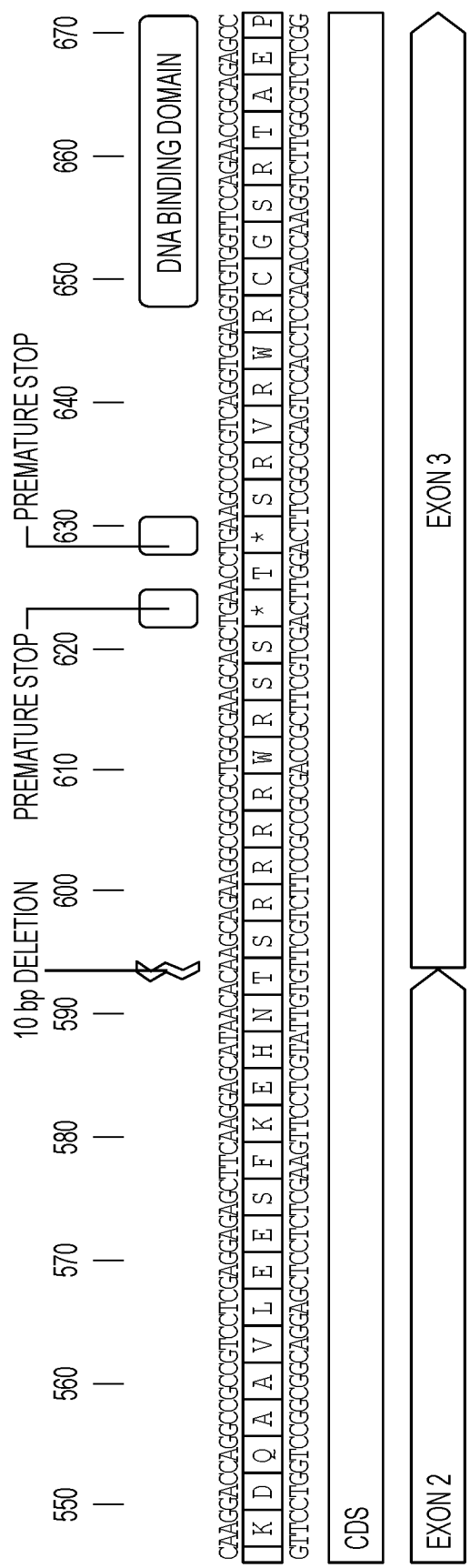
FIG. 9 provides a representative genomic sequence (coding strand (SEQ ID NO:298) and non-coding strand (SEQ ID NO:299)) of an edited plant showing a premature stop upstream of the HB78 DNA binding domain. The protein sequence (SEQ ID NO:300 and SEQ ID NO:301) resulting from this premature stop is shown.
Figure 13:
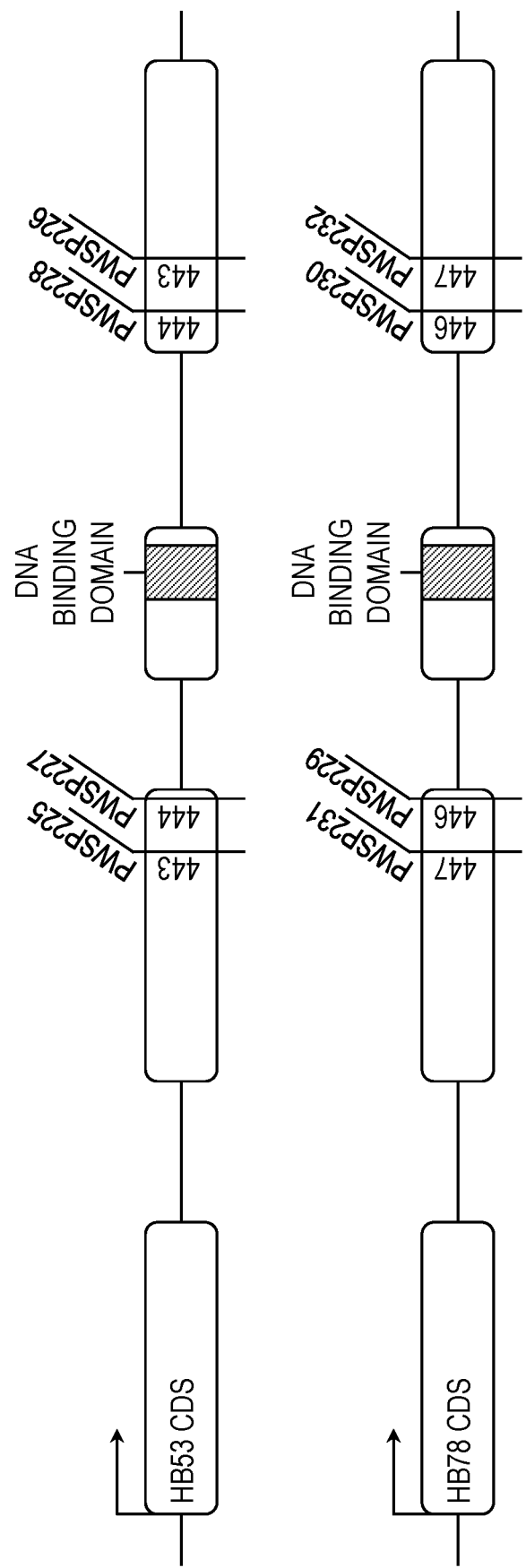
FIG. 13 provides examples for targeting of HB53 (upper schematic) and HB78 (lower schematic). Plasmids pWISE443 and pWISE444 are shown with corresponding spacers. Plasmid pWISE445 contains all 4 spacers shown for HB53. Plasmids pWISE446 and pWISE447 are shown with corresponding spacers. Plasmid pWISE448 contains all 4 spacers shown for HB78. Plasmid pWISE451 contains all 8 spacers (4 for HB53 and 4 for HB78, as shown in FIG. 13).

Examples of possible editing of these genes are provided in FIGS. 6, 7, 8 and 9. FIG. 6 provides an example of editing of the DNA binding domain of HB53 in *Z. mays* and shows target example amino acid residues for modification in the boxes. FIG. 7 provides an annotated HB78 gene with example guide nucleic acids and FIG. 8 provides an example of a deletion in an HB78 gene (SEQ ID NO:295) showing that a deletion (SEQ ID NO:297) in, for example, Exon 2 results in a truncation that deletes Exon 3, Exon 4 and the DNA binding domain resulting in a deletion in the protein sequence (SEQ ID NO:296). FIG. 9 provides a representative genomic sequence (coding strand (SEQ ID NO:298) and non-coding strand (SEQ ID NO:299)) of an edited plant showing a premature stop upstream of the HB78 DNA binding domain. FIG. 13 provides a schematic of exemplary targeting of HB53 (upper schematic) and HB78 (lower schematic) using plasmids pWISE443, pWISE444, pWISE446 and pWISE447 with their corresponding spacers. Plasmid pWISE448 contains all four spacers shown for HB78 and plasmid pWISE445 contains all four spacers shown for HB53, while plasmid pWISE451 contains all eight spacers (four for HB53 and four for HB78, as shown in FIG. 13).

In some embodiments, the present invention provides a plant or plant part thereof comprising at least one non-natural mutation in an endogenous Homeodomain-leucine zipper (HD-Zip) transcription factor, wherein the mutation disrupts the binding of the HD-Zip transcription factor to DNA. In some embodiments, an HD-Zip transcription factor may be an HD-Zip Type II (HD-Zip II) transcription factor, wherein the HD-Zip II transcription factor is capable of regulating response to illumination in the plant (e.g., regulating the shade avoidance response (SAR)). In some embodiments, an HD-Zip II transcription factor useful with this invention may include, but is not limited to, an ortholog of AtHB2, HB53, and/or HB78. In some embodiments, an HD-Zip II transcription factor useful with this invention may be HOMEOBOX PROTEIN 53 (HB53) or HOMEOBOX PROTEIN 78 (HB78). An HD-Zip transcription factor useful with this invention is an HD-Zip transcription factor that comprises: (a) a polypeptide comprising a sequence having at least 80% sequence identity (e.g., at least about 80, 81, 82, 83, 84, 85, 86, 87, 88, 89, 90, 91, 92, 93, 94, 95, 96, 97, 99 or 100% sequence identity) to the amino acid sequence of SEQ ID NO:38 or SEQ ID NO:83; (b) a polypeptide comprising a sequence having at least 80% sequence identity (e.g., at least about 80, 81, 82, 83, 84, 85, 86, 87, 88, 89, 90, 91, 92, 93, 94, 95, 96, 97, 99 or 100% sequence identity) to the amino acid sequence of: RKKLRLSKDQSAVLED-SFREHPTLNPRQKAALAQQLGLRPRQVEVWFQNRR ARTKLK QTEVDCEYLKRCCETLTEENRRLQKEVQE LRALKLVSPHLYMHMSPPTTLTMCPSCER V (SEQ ID NO:1) (Zea mays HB53) or RKKLRLSKDQA AVL EESFKEHNTLNPKQKAALAKQLNLKPRQ VEVWFQN RRARTKL KQTEVDCEFLKRCCETLTEENRRLQRE-VAELRVLKLVAPHHYARMPPPTTLTMCPSCE RL SEQ ID NO:2) (Zea mays HB78); (c) a polypeptide comprising a sequence having at least 80% sequence identity (e.g., at least about 80, 81, 82, 83, 84, 85, 86, 87, 88, 89, 90, 91, 92, 93, 94, 95, 96, 97, 99 or 100% sequence identity) to the amino acid sequence of LAKQLNLKPRQVEVWFQNRRART KLKQTEVDCEFLKRCCETLTEENRRLQREV (SEQ ID NO:3); (d) a polypeptide comprising a sequence having at least 95% sequence identity (e.g., at least about 95, 96, 97, 99, 99.5, or 100% sequence identity) to the nucleotide sequence of RQVEVWFQNRRARTKLKQTEVDCE (SEQ ID NO:4); (e) a polypeptide comprising a sequence having the amino acid sequence of RQVEVWFQNRRARTK XKQTEVDCE (SEQ ID NO:5), wherein X is L or S; (f) a polypeptide comprising: (i) sequence having the amino acid sequence of RKKLRLX$_1$KX$_2$QX$_3$ (SEQ ID NO:6), wherein X$_1$ is S or T, X$_2$ is D or E and X$_3$ is S or A; (ii) a sequence having the amino acid sequence of PX$_1$X$_2$ X$_2$LTX$_3$ CPX$_4$CER (SEQ ID NO:8), wherein X$_1$ is P or A, X$_2$ is T or A, X$_3$ is V or M and X$_4$ is Q, S or N; (iii) a sequence having the amino acid sequence of ENRRLX$_1$X$_2$EX$_3$, (SEQ ID NO:7), wherein X$_1$ is Q or H, X$_2$ is R or K and X$_3$ is V or L; and (iv) a sequence having the amino acid sequence of VWFQNRRA (SEQ ID NO:9); and/or (g) a polypeptide comprising a sequence having the amino acid sequence of VWFQNRRA (SEQ ID NO:9).

In some embodiments, a plant or plant part of the invention comprises an HD-Zip transcription factor that comprises: (a) a polypeptide comprising a sequence having at least 80% sequence identity (e.g., at least about 80, 81, 82, 83, 84, 85, 86, 87, 88, 89, 90, 91, 92, 93, 94, 95, 96, 97, 99 or 100% sequence identity) to the amino acid sequence of SEQ ID NO:38 or SEQ ID NO:83; (b) a polypeptide comprising a sequence having at least 80% sequence identity (e.g., at least about 80, 81, 82, 83, 84, 85, 86, 87, 88, 89, 90, 91, 92, 93, 94, 95, 96, 97, 99 or 100% sequence identity) to the amino acid sequence of: RKKLRLSKDQSAVLED-SFREHPTLNPRQKAALAQQLGLRPRQVEVWFQNRR ARTKLK QTEVDCEYLKRCCETLTEENRRLQKEVQEL RA LKLVSPHLYMHMSPPTTLTMCPSCER V (SEQ ID NO:1) (Zea mays HB53) or RKKLRLSKDQAA VLEE SFKEHNTLNPKQKAALAKQLNLKPRQ VEVWFQNR-RARTKL KQTEVDCEFLKRCCETLTEENRRLQREVAE LRVLKLVAPHHYARMPPPTTLTMCPSCE RL SEQ ID NO:2) (Zea mays HB78); (c) a polypeptide comprising a sequence having at least 80% sequence identity (e.g., at least about 80, 81, 82, 83, 84, 85, 86, 87, 88, 89, 90, 91, 92, 93, 94, 95, 96, 97, 99 or 100% sequence identity) to the amino acid sequence of LAKQLNLKPRQVEVWFQNRRARTKL KQTEVDCEFLKRCCETLTEENRRLQREV (SEQ ID NO:3); (d) a polypeptide comprising a sequence having at least 95% sequence identity (e.g., at least about 95, 96, 97, 99, 99.5, or 100% sequence identity) to the nucleotide sequence of RQVEVWFQNRRARTKLKQTEVDCE (SEQ ID NO:4); (e) a polypeptide comprising a sequence having the amino acid sequence of RQVEVWFQNR-RARTKXKQTEVDCE (SEQ ID NO:5), wherein X is L or S; (f) a polypeptide comprising: (i) sequence having the amino acid sequence of RKKLRLX$_1$KX$_2$QX$_3$ (SEQ ID NO:6), wherein X$_1$ is S or T, X$_2$ is D or E and X$_3$ is S or A; (ii) a sequence having the amino acid sequence of PX$_1$X$_2$ X$_2$LTX$_3$CPX$_4$CER (SEQ ID NO:8), wherein X$_1$ is P or A, X$_2$ is T or A, X$_3$ is V or M and X$_4$ is Q, S or N; (iii) a sequence having the amino acid sequence of ENRRLX$_1$X$_2$EX$_3$, (SEQ ID NO:7), wherein X$_1$ is Q or H, X$_2$ is R or K and X$_3$ is V or L; and (iv) a sequence having the amino acid sequence of VWFQNRRA (SEQ ID NO:9); and/or (g) a polypeptide comprising a sequence having the amino acid sequence of VWFQNRRA (SEQ ID NO:9). Accordingly, an HD-Zip transcription factor useful with this invention may comprise the amino acid sequence of any one of SEQ ID NOs: 1-8 or 10-98, which comprises a DNA binding domain comprising the amino acid sequence of VWFQNRRA (SEQ ID NO:9). As an example, residues 173-288 of the HD-Zip transcription factor comprising the amino acid sequence of SEQ ID NO:38 comprise the amino acid sequence of SEQ ID NO:9. As a further example, residues 76-191 of the HD-Zip transcription factor comprising the amino acid sequence of SEQ ID NO:83 comprises the amino acid sequence of SEQ ID NO:9. In addition, to SEQ ID NO:9, other polypeptide domains identified in HD-Zip transcription factors useful with this invention include polypeptides comprising at least 80% sequence identity to the amino acid sequence of SEQ ID NO:1 and/or SEQ ID NO:2, polypeptides comprising a sequence having at least 80% sequence identity to the amino acid sequence of SEQ ID NO:3), polypeptides comprising a sequence having at least 95% sequence identity to the nucleotide sequence of SEQ ID NO:4, polypeptides comprising a sequence having the amino acid sequence of SEQ ID NO:5, wherein X is L or S, polypeptides comprising a sequence having the amino acid sequence of SEQ ID NO:6, wherein $X_1$ is S or T, $X_2$ is D or E and $X_3$ is S or A, polypeptides comprising a sequence having the amino acid sequence of ENRRL$X_1X_2$E$X_3$, (SEQ ID NO:7), wherein $X_1$ is Q or H, $X_2$ is R or K and $X_3$ is V or L, and/or polypeptides comprising a sequence having the amino acid sequence of SEQ ID NO:8, wherein $X_1$ is P or A, $X_2$ is T or A, $X_3$ is V or M and $X_4$ is Q, S or N.

In some embodiments, the at least one non-natural mutation in an endogenous Homeodomain-leucine zipper (HD-Zip) transcription factor in a plant may be a substitution, a deletion and/or an insertion that disrupts the binding of the HD-Zip transcription factor to DNA. For example, the mutation may be a substitution, a deletion and/or an insertion of one or more amino acid residues of the transcription factor. The at least one non-natural mutation may comprise a base substitution to an A, a T, a G, or a C, which results in an amino acid substitution, thereby disrupting the binding of the HD-Zip transcription factor to DNA. In some embodiments, the at least one non-natural mutation in an endogenous gene encoding an HD-Zip transcription factor may comprise a deletion. Such a deletion may comprise, for example, a deletion of all or a portion of the DNA binding domain (e.g., a deletion of at least 1, 2, 3, 4, 5, 6, 7, or 8 amino acid residues of SEQ ID NO:9 (VWFQNRRA) of the HD-Zip transcription factor. In some embodiments, the deletion may be a truncation that includes the portion of consecutive amino acid residues of SEQ ID NO:9 (e.g., at least 2, 3, 4, 5, 6, 7, or 8 consecutive amino acid residues). In some embodiments, the deletion may be a truncation that includes at least a portion of consecutive amino acid residues of SEQ ID NO:9 (e.g., at least 2, 3, 4, 5, 6, 7, or 8 consecutive amino acid residues). Thus, a deletion may be about 1 amino acid residue to about 120 amino acid residues, or more in length (e.g., at least 1, 2, 3, 4, 5, 6, 7, 8, 9, 10, 11, 12, 13, 14, 15, 20, 21, 22, 23, 24, 25, 26, 27, 28, 29, 30, 31, 32, 33, 34, 36, 37, 38, 39, 40, 41, 42, 43, 44, 45, 46, 47, 48, 49, 50, 51, 52, 53, 54, 55, 56, 57, 58, 59, 61, 62, 63, 64, 65, 66, 67, 68, 69, 70, 71, 72, 73, 74, 75, 76, 77, 78, 79, 80, 81, 82, 83, 84, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, or more consecutive amino acid residues) up to the full length of the HD-Zip polypeptide, wherein the deletion includes at least a portion of consecutive amino acid residues of SEQ ID NO:9. In some embodiments, a deletion produces a truncated HD-Zip transcription factor that includes a deletion of at least a portion of consecutive amino acid residues of SEQ ID NO:9. In some embodiments, a deletion in an HD-Zip transcription factor polynucleotide may result in a premature stop codon that generates a truncated HD-Zip transcription factor, optionally a truncation at the C-terminus of the HD-Zip transcription factor, wherein at least a portion of consecutive amino acid residues of SEQ ID NO:9 are deleted.

A non-natural mutation in an endogenous gene encoding a HD-Zip transcription factor mutation useful with this invention may be a dominant recessive mutation. A dominant negative may remove the DNA binding function of the transcription factor that dimerizes to be functional. The transcription factor can still dimerize but will have lost the ability to bind to the regulatory regions of downstream genes and therefore will be non-functional. Thus, by removing the DNA binding capability of a bifunctional protein, dimerized complex will not activate gene expression (see, e.g., FIG. 5).

In some embodiments, a plant cell comprising an editing system is provided, the editing system comprising: (a) a CRISPR-associated effector protein; and (c) a guide nucleic acid (gRNA, gDNA, crRNA, crDNA) having a spacer sequence with complementarity to an endogenous target gene encoding a wild type HD-Zip transcription factor. The wild type HD-Zip transcription factor may be any HD-Zip transcription factor involved in the shade avoidance response. In some embodiments, the HD-Zip transcription factor may be a type HD-Zip II transcription factor, optionally a HB53 transcription factor or a HB78 transcription factor. In some embodiments, the HD-Zip transcription factor gene to which the spacer sequence of the guide nucleic acid shares complementarity may encode (a) a polypeptide comprising a sequence having at least 80% sequence identity to the amino acid sequence of SEQ ID NO:38 or SEQ ID NO:83; (b) a polypeptide comprising a sequence having at least 80% sequence identity to the amino acid sequence of: SEQ ID NO:1 or SEQ ID NO:2; (c) a polypeptide comprising a sequence having at least 80% sequence identity to the amino acid sequence of SEQ ID NO:3; (d) a polypeptide comprising a sequence having at least 95% sequence identity to the nucleotide sequence of SEQ ID NO:4; (e) a polypeptide comprising a sequence having the amino acid sequence of SEQ ID NO:5, wherein X is L or S; (0 a polypeptide comprising: (i) sequence having the amino acid sequence of RKKLRL$X_1$K$X_2$Q$X_3$ (SEQ ID NO:6), wherein $X_1$ is S or T, $X_2$ is D or E and $X_3$ is S or A; (ii) a sequence having the amino acid sequence of P$X_1X_2X_2$LT$X_3$CP$X_4$CER (SEQ ID NO:8), wherein $X_1$ is P or A, $X_2$ is T or A, $X_3$ is V or M and $X_4$ is Q, S or N; (iii) a sequence having the amino acid sequence of ENRRL$X_1X_2$E$X_3$, (SEQ ID NO:7), wherein $X_1$ is Q or H, $X_2$ is R or K and $X_3$ is V or L; and (iv) a sequence having the amino acid sequence of VWFQNRRA (SEQ ID NO:9); and/or (g) a polypeptide comprising a sequence having the amino acid sequence of VWFQNRRA (SEQ ID NO:9). In some embodiments, a spacer sequence of a guide nucleic acid of an editing system of this invention may comprise a nucleotide sequence of any one of SEQ ID NOs:175 to 182. In some embodiments, the nucleic acid binding domain of an editing system useful with this invention may be from a polynucleotide-guided endonuclease. a CRISPR-Cas endonuclease CMSPR-Cas effector protein), a zinc finger nuclease, a transcription activator-like effector nuclease (TALEN) and/or an Argonaute protein. In some embodiments, a plant cell edited as described herein may be regenerated into a plant, thereby providing a plant with a mutation in an HD-Zip transcription factor that is involved in the shade avoidance response and having an attenuated shade avoidance response.

In some embodiments, the invention provides a plant cell comprising at least one non-naturally occurring mutation (e.g., 1, 2, 3, 4, 5, or more mutation) to a DNA binding site of an HD-Zip transcription factor gene that prevents or reduces binding of the encoded HD-Zip transcription factor to DNA, wherein the mutation is a substitution, insertion and/or a deletion that is introduced using an editing system that comprises a nucleic acid binding domain that binds to a target site in the HD-Zip transcription factor gene, and wherein the HD-Zip transcription factor gene encodes: (a) a polypeptide comprising a sequence having at least 80% sequence identity to the amino acid sequence of SEQ ID NO:38 or SEQ ID NO:83; (b) a polypeptide comprising a sequence having at least 80% sequence identity to the amino acid sequence of: SEQ ID NO:1 or SEQ ID NO:2; (c) a polypeptide comprising a sequence having at least 80% sequence identity to the amino acid sequence of SEQ ID NO:3; (d) a polypeptide comprising a sequence having at least 95% sequence identity to the nucleotide sequence of SEQ ID NO:4; (e) a polypeptide comprising a sequence having the amino acid sequence of SEQ ID NO:5, wherein X is L or S; (0 a polypeptide comprising: (i) sequence having the amino acid sequence of RKKLRLX$_1$KX$_2$QX$_3$ (SEQ ID NO:6), wherein X$_1$ is S or T, X$_2$ is D or E and X$_3$ is S or A; (ii) a sequence having the amino acid sequence of PX$_1$X$_2$ X$_2$LTX$_3$CPX$_4$CER (SEQ ID NO:8), wherein X$_1$ is P or A, X$_2$ is T or A, X$_3$ is V or M and X$_4$ is Q, S or N; (iii) a sequence having the amino acid sequence of ENRRLX$_1$X$_2$EX$_3$, (SEQ ID NO:7), wherein X$_1$ is Q or H, X$_2$ is R or K and X$_3$ is V or L; and (iv) a sequence having the amino acid sequence of VWFQNRRA (SEQ ID NO:9); and/or (g) a polypeptide comprising a sequence having the amino acid sequence of VWFQNRRA (SEQ ID NO:9).

In some embodiments, a plant or part thereof is provided, the plant or part thereof comprising a mutation in an endogenous HD-Zip transcription factor, which mutation reduces DNA binding by the endogenous HD-Zip transcription factor, wherein the endogenous HD-Zip transcription factor comprises a polypeptide comprising a sequence having at least 80% sequence identity to the amino acid sequence of SEQ ID NO:1 or SEQ ID NO:2; wherein the mutation is a deletion, substitution, and/or insertion of at least one amino acid residue of amino acid residues 45-52 (VWFQNRRA) (SEQ ID NO:9)) of the amino acid sequence of SEQ ID NO:1 or SEQ ID NO:2. In some embodiments, the mutation of the at least one amino acid residue of amino acid residues 45-52 of the amino acid sequence of SEQ ID NO:1 or SEQ ID NO:2 is made following cleavage by a nuclease comprising a DNA-binding domain that binds to a target site within a target nucleic acid encoding a sequence having at least 80% sequence identity to the amino acid sequence of SEQ ID NO:1) (*Zea mays* HB53) or SEQ ID NO:2) (*Zea mays* HB78).

A mutation of an endogenous HD-Zip transcription factor in a plant or part thereof may be an insertion, substitution and/or a deletion of at least one amino acid. In some embodiments, the mutation may comprise a deletion of all or a portion (e.g., a deletion of at least 1, 2, 3, 4, 5, 6, 7, or 8 amino acid residues of SEQ ID NO:9 (VWFQNRRA) of a DNA binding domain within the endogenous HD-Zip transcription factor.

In some embodiments, non-limiting examples of a plant or part thereof include corn, soy, canola, wheat, rice, cotton, sugarcane, sugar beet, barley, oats, alfalfa, sunflower, safflower, oil palm, sesame, coconut, tobacco, potato, sweet potato, cassava, coffee, apple, plum, apricot, peach, cherry, pear, fig, banana, citrus, cocoa, avocado, olive, almond, walnut, strawberry, watermelon, pepper, grape, tomato, cucumber, blackberry, raspberry, black raspberry or a *Brassica* spp. In some embodiments, the plant part may be a cell from a plant that includes but is not limited to, corn, soy, canola, wheat, rice, cotton, sugarcane, sugar beet, barley, oats, alfalfa, sunflower, safflower, oil palm, sesame, coconut, tobacco, potato, sweet potato, cassava, coffee, apple, plum, apricot, peach, cherry, pear, fig, banana, citrus, cocoa, avocado, olive, almond, walnut, strawberry, watermelon, pepper, grape, tomato, cucumber, blackberry, raspberry, black raspberry or a *Brassica* spp. In some embodiments, a plant may be regenerated from a cell or plant part of this invention. A plant of this invention comprising at least one mutation in an HD-Zip transcription factor comprises an attenuated Shade Avoidance Response (SAR).

In some embodiments, the invention provides a plant or plant part thereof comprising an HD-Zip transcription factor gene that comprises the nucleotide sequence of SEQ ID NO:202 and/or that encodes an amino acid sequence of any one of SEQ ID NO:201. In some embodiments, the invention provides a corn plant or plant part thereof comprising an HD-Zip transcription factor gene that comprises the nucleotide sequence of SEQ ID NO:202 and/or that encodes an amino acid sequence of any one of SEQ ID NO:201.

The invention further provides a method of producing/breeding a transgene-free genome-edited (e.g., base-edited) plant, comprising: (a) crossing a plant of the present invention with a transgene free plant, thereby introducing the mutation or modification from the plant of the present invention into the plant that is transgene-free; and (b) selecting a progeny plant that comprises the mutation or modification but is transgene-free, thereby producing a transgene free genome-edited (e.g., base-edited) plant.

In some embodiments, a method of providing a plurality of plants having increased yield when each plant of the plurality of plants is planted in close proximity to one another is provided, the method comprising planting two or more plants of the present invention in close proximity to one another, thereby providing a plurality of plants having increased yield as compared to a plurality of control plants (e.g., plants not having an edited HD-Zip transcription factor gene and reduced SAR) planted in close proximity to one another.

"Close proximity" refers to a high planting density for any particular plant species that can result in SAR. For example, in some embodiments, "close proximity" includes a density of plants resulting from planting seeds of the plant about 6.1 inches or less apart (e.g., about 6.1, 6, 5.9, 5.8, 5.7, 5.6, 5.5, 5.4, 5.3, 5.2, 5.2, 5.1, 5, 4.9, 4.8, 4.7, 4.6, 4.5, 4.4, 4.3, 4.2, 4.1, 4 3.9, 3.8, 3.7, 3.6, 3.5, 3.4, 3.3, 3.2, 3.1, 3, 2.9, 2.8, 2.7, 2.6, 2.5, 2.4, 2.3, 2.2, 2.1, 2, 1.9, 1.8, 1.7, 1.6, 1.5, 1.4, 1.3, 1.2, 1.1, 1, 0.9, 0.8, 0.7, 0.6, 0.5, inches apart, and the like or any range or value therein). In some embodiments, a high density planting includes about 35K seeds per acre at 36 in and 38 in row spacing; or anything more than 35K per acre at 30 in or more row spacing. As would be understood by one of skill in the art, the number of seeds planted per acre to achieve a high density planting will vary by plant species.

In some embodiments, a method for editing a specific site in the genome of a plant cell is provided, the method comprising: cleaving, in a site specific manner, a target site within an endogenous HD-Zip transcription factor gene in the plant cell, the endogenous HD-Zip transcription factor gene encoding: (a) a polypeptide comprising a sequence having at least 80% sequence identity to the amino acid sequence of SEQ ID NO:38 or SEQ ID NO:83; (b) a polypeptide comprising a sequence having at least 80% sequence identity to the amino acid sequence of: SEQ ID NO:1 or SEQ ID NO:2; (c) a polypeptide comprising a sequence having at least 80% sequence identity to the amino acid sequence of SEQ ID NO:3; (d) a polypeptide comprising a sequence having at least 95% sequence identity to the nucleotide sequence of SEQ ID NO:4; (e) a polypeptide comprising a sequence having the amino acid sequence of SEQ ID NO:5, wherein X is L or S; (0 a polypeptide comprising: (i) sequence having the amino acid sequence of RKKLRLX$_1$KX$_2$QX$_3$ (SEQ ID NO:6), wherein X$_1$ is S or T, X$_2$ is D or E and X$_3$ is S or A; (ii) a sequence having the amino acid sequence of PX$_1$X$_2$ X$_2$LTX$_3$CPX$_4$CER (SEQ ID NO:8), wherein $X_1$ is P or A, $X_2$ is T or A, $X_3$ is V or M and $X_4$ is Q, S or N; (iii) a sequence having the amino acid sequence of ENRRL$X_1X_2$E$X_3$, (SEQ ID NO:7), wherein $X_1$ is Q or H, $X_2$ is R or K and $X_3$ is V or L; and (iv) a sequence having the amino acid sequence of VWFQNRRA (SEQ ID NO:9); and/or (g) a polypeptide comprising a sequence having the amino acid sequence of VWFQNRRA (SEQ ID NO:9), thereby generating an edit in the endogenous HD-Zip transcription factor gene of the plant cell. The method for editing a plant may further comprise regenerating a plant from the plant cell comprising the edit in the endogenous HD-Zip transcription factor gene to produce a plant comprising the edit in its endogenous HD-Zip transcription factor gene. In some embodiments, the edit results in a non-naturally occurring mutation in the endogenous HD-Zip transcription factor gene that produces an HD-Zip transcription factor with reduced DNA binding.

A plant comprising an endogenous HD-Zip transcription factor gene that is edited as described herein to provide an HD-Zip transcription factor with reduced DNA binding has an attenuated Shade Avoidance Response when compared to a control plant that has does not comprise the edited endogenous HD-Zip transcription factor gene. A plant comprising an edited endogenous HD-Zip transcription factor gene as described herein may be compared to a plant that is not so edited when grown under the same environmental conditions, e.g., an environment with a low R:FR light ratio, e.g., shaded conditions (e.g., an R:FR ratio of about or a range of an R:FR ratio of about 0.09 to about 0.7 (e.g., about 0.09, 0.10, 0.11, 0.12, 0.14, 0.15, 0.16, 0.17, 018, 0.19, 0.2, 0.21, 0.23, 0.24, 0.25, to about 0.26, 0.27, 0.28, 0.29, 0.3, 0.35, 0.4, 0.45, 0.5, 0.55, 0.6, 0.65, 0.7, or any range or value therein))

In some embodiments, a method for making a plant is provided, the method comprising: (a) contacting a population of plant cells that comprising a wild-type endogenous gene encoding an HD-Zip transcription factor with a nuclease targeted to the wild-type endogenous gene, wherein the nuclease is linked to a DNA binding domain that binds to a nucleic acid sequence encoding: (i) a polypeptide comprising a sequence having at least 80% sequence identity to the amino acid sequence of SEQ ID NO:38 or SEQ ID NO:83; (ii) a polypeptide comprising a sequence having at least 80% sequence identity to the amino acid sequence of: SEQ ID NO:1 or SEQ ID NO:2; (iii) a polypeptide comprising a sequence having at least 80% sequence identity to the amino acid sequence of SEQ ID NO:3; (iv) a polypeptide comprising a sequence having at least 95% sequence identity to the nucleotide sequence of SEQ ID NO:4; (v) a polypeptide comprising a sequence having the amino acid sequence of SEQ ID NO:5, wherein X is L or S; (vi) a polypeptide comprising: (1) a sequence having the amino acid sequence of RKKLRL$X_1$K$X_2$Q$X_3$ (SEQ ID NO:6), wherein $X_1$ is S or T, $X_2$ is D or E and $X_3$ is S or A; (2) a sequence having the amino acid sequence of P$X_1X_2$ $X_2$LT$X_3$CP$X_4$CER (SEQ ID NO:8), wherein $X_1$ is P or A, $X_2$ is T or A, $X_3$ is V or M and $X_4$ is Q, S or N; (3) a sequence having the amino acid sequence of ENRRL$X_1X_2$E$X_3$, (SEQ ID NO:7), wherein $X_1$ is Q or H, $X_2$ is R or K and $X_3$ is V or L; and (4) a sequence having the amino acid sequence of VWFQNRRA (SEQ ID NO:9); and/or (vii) a polypeptide comprising a sequence having the amino acid sequence of VWFQNRRA (SEQ ID NO:9); (b) selecting a plant cell from said population comprising a mutation in the wild-type endogenous gene encoding an HD-Zip transcription factor, wherein the mutation is a substitution and/or a deletion of at least one amino acid residue in the polypeptide of any one of (i)-(v), wherein the mutation reduces or eliminates the ability of the HD-Zip transcription factor to bind DNA; and (c) growing the selected plant cell into a plant.

In some embodiments, a method for reducing a Shade Avoidance Response in a plant is provided, the method comprising (a) contacting a plant cell comprising a wild-type endogenous gene encoding an HD-Zip transcription factor with a nuclease targeted to the wild-type endogenous gene, wherein the nuclease is linked to a DNA binding domain that binds to a target site in the wild type endogenous gene, the wild type endogenous gene encoding: (i) a polypeptide comprising a sequence having at least 80% sequence identity to the amino acid sequence of SEQ ID NO:38 or SEQ ID NO:83; (ii) a polypeptide comprising a sequence having at least 80% sequence identity to the amino acid sequence of: SEQ ID NO:1 or SEQ ID NO:2; (iii) a polypeptide comprising a sequence having at least 80% sequence identity to the amino acid sequence of SEQ ID NO:3; (iv) a polypeptide comprising a sequence having at least 95% sequence identity to the nucleotide sequence of SEQ ID NO:4; (v) a polypeptide comprising a sequence having the amino acid sequence of SEQ ID NO:5, wherein X is L or S; (vi) a polypeptide comprising: (1) a sequence having the amino acid sequence of RKKLRL$X_1$K$X_2$Q$X_3$ (SEQ ID NO:6), wherein $X_1$ is S or T, $X_2$ is D or E and $X_3$ is S or A; (2) a sequence having the amino acid sequence of P$X_1X_2$ $X_2$LT$X_3$CP$X_4$CER (SEQ ID NO:8), wherein $X_1$ is P or A, $X_2$ is T or A, $X_3$ is V or M and $X_4$ is Q, S or N; (3) a sequence having the amino acid sequence of ENRRL$X_1X_2$E$X_3$, (SEQ ID NO:7), wherein $X_1$ is Q or H, $X_2$ is R or K and $X_3$ is V or L; and (4) a sequence having the amino acid sequence of VWFQNRRA (SEQ ID NO:9); and/or (vii) a polypeptide comprising a sequence having the amino acid sequence of VWFQNRRA (SEQ ID NO:9), thereby producing a plant cell comprising a mutation in the wild-type endogenous gene encoding an HD-Zip transcription factor; and (b) growing the plant cell into a plant, thereby reducing the Shade Avoidance Response in the plant.

In some embodiments, a method for producing a plant or part thereof comprising at least one cell having a mutated endogenous HD-Zip transcription factor gene is provided, the method comprising contacting a target site in an endogenous HD-Zip transcription factor gene in the plant or plant part with a nuclease comprising a cleavage domain and a DNA-binding domain, wherein the DNA binding domain binds to a target site in the endogenous HD-Zip transcription factor gene, wherein the endogenous HD-Zip transcription factor gene encodes: (a) a polypeptide comprising a sequence having at least 80% sequence identity to the amino acid sequence of SEQ ID NO:38 or SEQ ID NO:83; (b) a polypeptide comprising a sequence having at least 80% sequence identity to the amino acid sequence of: SEQ ID NO:1 or SEQ ID NO:2; (c) a polypeptide comprising a sequence having at least 80% sequence identity to the amino acid sequence of SEQ ID NO:3; (d) a polypeptide comprising a sequence having at least 95% sequence identity to the nucleotide sequence of SEQ ID NO:4; (e) a polypeptide comprising a sequence having the amino acid sequence of SEQ ID NO:5, wherein X is L or S; (f) a polypeptide comprising: (i) sequence having the amino acid sequence of RKKLRL$X_1$K$X_2$Q$X_3$ (SEQ ID NO:6), wherein $X_1$ is S or T, $X_2$ is D or E and $X_3$ is S or A; (ii) a sequence having the amino acid sequence of P$X_1X_2$ $X_2$LT$X_3$CP$X_4$CER (SEQ ID NO:8), wherein $X_1$ is P or A, $X_2$ is T or A, $X_3$ is V or M and $X_4$ is Q, S or N; (iii) a sequence having the amino acid sequence of ENRRL$X_1X_2$E$X_3$, (SEQ ID NO:7), wherein $X_1$ is Q or H, $X_2$ is R or K and $X_3$ is V or L; and (iv) a sequence having the amino acid sequence of VWFQNRRA (SEQ ID NO:9); and/or (g) a polypeptide comprising a sequence having the amino acid sequence of VWFQNRRA (SEQ ID NO:9), thereby producing a plant or part thereof comprising at least one cell having a mutation in the endogenous HD-Zip transcription factor gene. In some embodiments, the at least one cell in the plant or part thereof having a mutated endogenous HD-Zip transcription factor gene produces an HD-Zip transcription factor having reduced binding of DNA.

In some embodiments, a method of producing a plant or part thereof comprising a mutated endogenous HD-Zip transcription factor having reduced DNA binding, the method comprising contacting a target site in an endogenous HD-Zip transcription factor gene in the plant or plant part with a nuclease comprising a cleavage domain and a DNA-binding domain, wherein the DNA binding domain binds to a target site in the HD-Zip transcription factor gene, wherein the HD-Zip transcription factor gene encodes:

(a) a polypeptide comprising a sequence having at least 80% sequence identity to the amino acid sequence of SEQ ID NO:38 or SEQ ID NO:83; (b) a polypeptide comprising a sequence having at least 80% sequence identity to the amino acid sequence of: SEQ ID NO:1 or SEQ ID NO:2; (c) a polypeptide comprising a sequence having at least 80% sequence identity to the amino acid sequence of SEQ ID NO:3; (d) a polypeptide comprising a sequence having at least 95% sequence identity to the nucleotide sequence of SEQ ID NO:4; (e) a polypeptide comprising a sequence having the amino acid sequence of SEQ ID NO:5, wherein X is L or S; (0 a polypeptide comprising: (i) sequence having the amino acid sequence of RKKLRLX$_1$KX$_2$QX$_3$ (SEQ ID NO:6), wherein $X_1$ is S or T, $X_2$ is D or E and $X_3$ is S or A; (ii) a sequence having the amino acid sequence of PX$_1$X$_2$X$_2$LTX$_3$CPX$_4$CER (SEQ ID NO:8), wherein $X_1$ is P or A, $X_2$ is T or A, $X_3$ is V or M and $X_4$ is Q, S or N; (iii) a sequence having the amino acid sequence of ENRRLX$_1$X$_2$EX$_3$, (SEQ ID NO:7), wherein $X_1$ is Q or H, $X_2$ is R or K and $X_3$ is V or L; and (iv) a sequence having the amino acid sequence of VWFQNRRA (SEQ ID NO:9); and/or (g) a polypeptide comprising a sequence having the amino acid sequence of VWFQNRRA (SEQ ID NO:9), thereby producing a plant or part thereof having a mutated endogenous HD-Zip transcription factor having reduced DNA binding. In some embodiments, the endogenous HD-Zip transcription factor gene encodes an endogenous HD-Zip transcription factor that comprises the amino acid sequence of SEQ ID NO: 38 or SEQ ID NO:83, wherein the amino acid sequence of SEQ ID NO: 38 or SEQ ID NO:83 comprises the amino acid sequence of VWFQNRRA (SEQ ID NO:9) and the mutated endogenous HD-Zip transcription factor comprises a mutation in the amino acid sequence of VWFQNRRA (SEQ ID NO:9). In some embodiments, an endogenous HD-Zip transcription factor gene encodes an endogenous HD-Zip transcription factor that comprises the amino acid sequence of any one of SEQ ID NO: 10-98, wherein the amino acid sequence of any one of SEQ ID NO: 10-98 comprises the amino acid sequence of VWFQNRRA (SEQ ID NO:9), and the mutated endogenous HD-Zip transcription factor comprises a mutation in the amino acid sequence of VWFQNRRA (SEQ ID NO:9).

In some embodiments, the plant or part thereof comprising a mutated endogenous HD-Zip transcription factor as described herein exhibits an attenuated/reduced Shade Avoidance Response as compared to a control plant that does not comprise the mutation in the endogenous HD-Zip transcription factor gene, e.g., the plant or plant part has not been contacted with the editing system. In some embodiments, the comparison with a control plant may be made between the edited plant and control plant when grown under the same environmental conditions; e.g., a shaded environment, e.g., a low R:FR ratio environment. A plant that comprises a mutated endogenous HD-Zip transcription factor that results in an attenuated/reduced Shade Avoidance Response in the plant exhibits phenotypes that include, but are not limited to, increased yield, decreased height, decreased shoot:root ratio, decreased leaf length; increased mechanical strength of stems; reduced lodging rate; delayed senescence; increased photosynthesis efficiency and grain filling; and/or enhanced defense responses against pathogens and herbivores when planted in close proximity with one or more other plants as compared to a plant that does not comprise mutated endogenous HD-Zip transcription factor that results in an attenuated/reduced Shade Avoidance Response, which is planted in close proximity with one or more other plants. In some embodiments, a plant having a reduced SAR is at least about 5% shorter than the control plant grown under the same environmental conditions (.g., a shaded environment, e.g., a low R:FR ratio environment) (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150%, or more shorter, or any range or value therein).

In some embodiments, a nuclease contacting a plant cell, a population of plant cells and/or a target site cleaves an endogenous HD-Zip transcription factor gene and a mutation is introduced into the DNA binding site of an endogenous HD-Zip transcription factor encoded by the endogenous HD-Zip transcription factor gene.

In some embodiments, the mutation in an endogenous HD-Zip transcription factor gene may be a non-naturally occurring mutation. In some embodiments, the non-naturally occurring mutation may be a substitution, an insertion and/or a deletion. In some embodiments, the non-naturally occurring mutation that is a substitution, an insertion and/or a deletion may result in a substitution, an insertion and/or a deletion of one or more amino acids in the endogenous HD-Zip transcription factor encoded by the endogenous HD-Zip transcription factor gene. A nuclease useful with the invention includes but is not limited to a zinc finger nuclease, a transcription activator-like effector nuclease (TALEN), an endonuclease (e.g., Fok1) or a CRISPR-Cas effector protein.

In some embodiments, an HD-Zip transcription factor useful with this invention may be a HD-Zip Type II (HD-Zip II) transcription factor, wherein the HD-Zip II transcription factor is capable of regulating a plant's the response to illumination (e.g., shade avoidance response (SAR)). In some embodiments, the HD-Zip II transcription factor may include, but is not limited to, an ortholog of AtHB2, HB53, and/or HB78. In some embodiments, the HD-Zip II transcription factor may be HOMEOBOX PROTEIN 53 (HB53) or HOMEOBOX PROTEIN 78 (HB78).

In some embodiments, the present invention provides a guide nucleic acid (e.g., gRNA, gDNA, crRNA, crDNA) that binds to a target site in a HD-Zip transcription factor gene, the target site comprising a nucleotide sequence encoding: ((a) a polypeptide comprising a sequence having at least 80% sequence identity to the amino acid sequence of SEQ ID NO:1 or SEQ ID NO:2; (b) a polypeptide comprising a sequence having at least 80% sequence identity to the amino acid sequence of SEQ ID NO:3; (c) a polypeptide comprising a sequence having at least 95% sequence identity to the nucleotide sequence of SEQ ID NO:4; (d) a polypeptide comprising a sequence having the amino acid sequence of SEQ ID NO:5, wherein X is L or S; (e) a polypeptide comprising: (i) a sequence having the amino acid sequence of RKKLRLX$_1$KX$_2$QX$_3$ (SEQ ID NO:6), wherein X$_1$ is S or T, X$_2$ is D or E and X$_3$ is S or A; (ii) a sequence having the amino acid sequence of PX$_1$X$_2$X$_2$LTX$_3$CPX$_4$CER (SEQ ID NO:8), wherein X$_1$ is P or A, X$_2$ is T or A, X$_3$ is V or M and X$_4$ is Q, S or N; (iii) a sequence having the amino acid sequence of ENRRLX$_1$X$_2$EX$_3$, (SEQ ID NO:7), wherein X$_1$ is Q or H, X$_2$ is R or K and X$_3$ is V or L; and a sequence having the amino acid sequence of VWFQNRRA (SEQ ID NO:9) and/or (f) a polypeptide comprising a sequence having the amino acid sequence of VWFQNRRA (SEQ ID NO:9).

A spacer sequence of a guide of this invention may be complementary to a fragment or portion of the nucleotide sequence encoding (a) a polypeptide comprising a sequence having at least 80% sequence identity to the amino acid sequence of SEQ ID NO:1 or SEQ ID NO:2; (b) a polypeptide comprising a sequence having at least 80% sequence identity to the amino acid sequence of SEQ ID NO:3; (c) a polypeptide comprising a sequence having at least 95% sequence identity to the nucleotide sequence of SEQ ID NO:4; (d) a polypeptide comprising a sequence having the amino acid sequence of SEQ ID NO:5, wherein X is L or S; (e) a polypeptide comprising: (i) a sequence having the amino acid sequence of RKKLRLX$_1$KX$_2$QX$_3$ (SEQ ID NO:6), wherein X$_1$ is S or T, X$_2$ is D or E and X$_3$ is S or A; (ii) a sequence having the amino acid sequence of PX$_1$X$_2$X$_2$LTX$_3$CPX$_4$CER (SEQ ID NO:8), wherein X$_1$ is P or A, X$_2$ is T or A, X$_3$ is V or M and X$_4$ is Q, S or N; (iii) a sequence having the amino acid sequence of ENRRLX$_1$X$_2$EX$_3$, (SEQ ID NO:7), wherein X$_1$ is Q or H, X$_2$ is R or K and X$_3$ is V or L; and a sequence having the amino acid sequence of VWFQNRRA (SEQ ID NO:9) and/or (0 a polypeptide comprising a sequence having the amino acid sequence of VWFQNRRA (SEQ ID NO:9).

In some embodiments, a target nucleic acid is an endogenous HD-Zip transcription factor gene that is capable of regulating response to illumination in a plant. In some embodiments, a target site in a target nucleic acid may encode (a) a polypeptide comprising a sequence having at least 80% sequence identity to the amino acid sequence of SEQ ID NO:1 or SEQ ID NO:2; (b) a polypeptide comprising a sequence having at least 80% sequence identity to the amino acid sequence of SEQ ID NO:3; (c) a polypeptide comprising a sequence having at least 95% sequence identity to the nucleotide sequence of SEQ ID NO:4; (d) a polypeptide comprising a sequence having the amino acid sequence of SEQ ID NO:5, wherein X is L or S; (e) a polypeptide comprising: (i) a sequence having the amino acid sequence of RKKLRLX$_1$KX$_2$QX$_3$ (SEQ ID NO:6), wherein X$_1$ is S or T, X$_2$ is D or E and X$_3$ is S or A; (ii) a sequence having the amino acid sequence of PX$_1$X$_2$X$_2$LTX$_3$CPX$_4$CER (SEQ ID NO:8), wherein X$_1$ is P or A, X$_2$ is T or A, X$_3$ is V or M and X$_4$ is Q, S or N; (iii) a sequence having the amino acid sequence of ENRRLX$_1$X$_2$EX$_3$, (SEQ ID NO:7), wherein X$_1$ is Q or H, X$_2$ is R or K and X$_3$ is V or L; and a sequence having the amino acid sequence of VWFQNRRA (SEQ ID NO:9) and/or (f) a polypeptide comprising a sequence having the amino acid sequence of VWFQNRRA (SEQ ID NO:9).

In some embodiments, the guide nucleic acid comprises a spacer having the nucleotide sequence of any one of SEQ ID NOs:175-182. In some embodiments, the HD-Zip transcription factor may be a HD-Zip Type II (HD-Zip II) transcription factor, optionally wherein the HD-Zip II transcription factor may be HB53 or HB78.

In some embodiments, a system is provided that comprises a guide nucleic acid of the present invention and a CRISPR-Cas effector protein that associates with the guide nucleic acid. In some embodiments, the system may further comprise a tracr nucleic acid that associates with the guide nucleic acid and a CRISPR-Cas effector protein, optionally wherein the tracr nucleic acid and the guide nucleic acid are covalently linked.

In some embodiments, a gene editing system is provided, the gene editing system comprising a CRISPR-Cas effector protein in association with a guide nucleic acid, wherein the guide nucleic acid comprises a spacer sequence that binds to a HD-Zip transcription factor gene. In some embodiments, a HD-Zip transcription factor gene useful with the gene editing system encodes: (a) a polypeptide comprising a sequence having at least 80% sequence identity to the amino acid sequence of SEQ ID NO:1 or SEQ ID NO:2; (b) a polypeptide comprising a sequence having at least 80% sequence identity to the amino acid sequence of SEQ ID NO:3; (c) a polypeptide comprising a sequence having at least 95% sequence identity to the nucleotide sequence of SEQ ID NO:4; (d) a polypeptide comprising a sequence having the amino acid sequence of SEQ ID NO:5, wherein X is L or S; (e) a polypeptide comprising: (i) a sequence having the amino acid sequence of RKKLRLX$_1$KX$_2$QX$_3$ (SEQ ID NO:6), wherein X$_1$ is S or T, X$_2$ is D or E and X$_3$ is S or A; (ii) a sequence having the amino acid sequence of PX$_1$X$_2$ X$_2$LTX$_3$CPX$_4$CER (SEQ ID NO:8), wherein X$_1$ is P or A, X$_2$ is T or A, X$_3$ is V or M and X$_4$ is Q, S or N; (iii) a sequence having the amino acid sequence of ENRRLX$_1$X$_2$EX$_3$, (SEQ ID NO:7), wherein X$_1$ is Q or H, X$_2$ is R or K and X$_3$ is V or L; and a sequence having the amino acid sequence of VWFQNRRA (SEQ ID NO:9) and/or (0 a polypeptide comprising a sequence having the amino acid sequence of VWFQNRRA (SEQ ID NO:9). In some embodiments, the HD-Zip transcription factor may be a HD-Zip Type II (HD-Zip II) transcription factor, optionally wherein the HD-Zip II transcription factor may be HB53 or HB78.

In some embodiments, the guide nucleic acid of a gene editing system may comprise a spacer sequence having a nucleotide sequence that is complementary to a nucleotide sequence encoding (a) a polypeptide comprising a sequence having at least 80% sequence identity to the amino acid sequence of SEQ ID NO:1 or SEQ ID NO:2; (b) a polypeptide comprising a sequence having at least 80% sequence identity to the amino acid sequence of SEQ ID NO:3; (c) a polypeptide comprising a sequence having at least 95% sequence identity to the nucleotide sequence of SEQ ID NO:4; (d) a polypeptide comprising a sequence having the amino acid sequence of SEQ ID NO:5, wherein X is L or S; (e) a polypeptide comprising: (i) a sequence having the amino acid sequence of RKKLRLX$_1$KX$_2$QX$_3$ (SEQ ID NO:6), wherein X$_1$ is S or T, X$_2$ is D or E and X$_3$ is S or A; (ii) a sequence having the amino acid sequence of PX$_1$X$_2$ X$_2$LTX$_3$CPX$_4$CER (SEQ ID NO:8), wherein X$_1$ is P or A, X$_2$ is T or A, X$_3$ is V or M and X$_4$ is Q, S or N; (iii) a sequence having the amino acid sequence of ENRRLX$_1$X$_2$EX$_3$, (SEQ ID NO:7), wherein X$_1$ is Q or H, X$_2$ is R or K and X$_3$ is V or L; and a sequence having the amino acid sequence of VWFQNRRA (SEQ ID NO:9)

and/or (0 a polypeptide comprising a sequence having the amino acid sequence of VWFQNRRA (SEQ ID NO:9). In some embodiments, the guide nucleic acid of a gene editing system may comprise a spacer sequence having a nucleotide sequence of any one of SEQ ID NOs:175-182. In some embodiments, a gene editing system may further comprise a tracr nucleic acid that associates with the guide nucleic acid and a CRISPR-Cas effector protein, optionally wherein the tracr nucleic acid and the guide nucleic acid are covalently linked.

The present invention further provides a complex comprising a CRISPR-Cas effector protein comprising a cleavage domain and a guide nucleic acid, wherein the guide nucleic acid binds to a target site in a HD-Zip transcription factor gene encoding (a) a polypeptide comprising a sequence having at least 80% sequence identity to the amino acid sequence of SEQ ID NO:1 or SEQ ID NO:2; (b) a polypeptide comprising a sequence having at least 80% sequence identity to the amino acid sequence of SEQ ID NO:3; (c) a polypeptide comprising a sequence having at least 95% sequence identity to the nucleotide sequence of SEQ ID NO:4; (d) a polypeptide comprising a sequence having the amino acid sequence of SEQ ID NO:5, wherein X is L or S; (e) a polypeptide comprising: (i) a sequence having the amino acid sequence of RKKLRLX$_1$KX$_2$QX$_3$ (SEQ ID NO:6), wherein X$_1$ is S or T, X$_2$ is D or E and X$_3$ is S or A; (ii) a sequence having the amino acid sequence of PX$_1$X$_2$X$_2$LTX$_3$CPX$_4$CER (SEQ ID NO:8), wherein X$_1$ is P or A, X$_2$ is T or A, X$_3$ is V or M and X$_4$ is Q, S or N; (iii) a sequence having the amino acid sequence of ENRRLX$_1$X$_2$EX$_3$, (SEQ ID NO:7), wherein X$_1$ is Q or H, X$_2$ is R or K and X$_3$ is V or L; and a sequence having the amino acid sequence of VWFQNRRA (SEQ ID NO:9) and/or (0 a polypeptide comprising a sequence having the amino acid sequence of VWFQNRRA (SEQ ID NO:9), wherein the cleavage domain cleaves a target strand in the HD-Zip transcription factor gene.

Also provided herein are expression cassettes comprising a (a) polynucleotide encoding CRISPR-Cas effector protein comprising a cleavage domain and (b) a guide nucleic acid that binds to a target site in a HD-Zip transcription factor gene, wherein the guide nucleic acid comprises a spacer sequence that is complementary to and binds to a nucleotide sequence encoding: (a) a polypeptide comprising a sequence having at least 80% sequence identity to the amino acid sequence of SEQ ID NO:1 or SEQ ID NO:2; (b) a polypeptide comprising a sequence having at least 80% sequence identity to the amino acid sequence of SEQ ID NO:3; (c) a polypeptide comprising a sequence having at least 95% sequence identity to the nucleotide sequence of SEQ ID NO:4; (d) a polypeptide comprising a sequence having the amino acid sequence of SEQ ID NO:5, wherein X is L or S; (e) a polypeptide comprising: (i) a sequence having the amino acid sequence of RKKLRLX$_1$KX$_2$QX$_3$ (SEQ ID NO:6), wherein X$_1$ is S or T, X$_2$ is D or E and X$_3$ is S or A; (ii) a sequence having the amino acid sequence of PX$_1$X$_2$X$_2$LTX$_3$CPX$_4$CER (SEQ ID NO:8), wherein X$_1$ is P or A, X$_2$ is T or A, X$_3$ is V or M and X$_4$ is Q, S or N; (iii) a sequence having the amino acid sequence of ENRRLX$_1$X$_2$EX$_3$, (SEQ ID NO:7), wherein X$_1$ is Q or H, X$_2$ is R or K and X$_3$ is V or L; and a sequence having the amino acid sequence of VWFQNRRA (SEQ ID NO:9) and/or (0 a polypeptide comprising a sequence having the amino acid sequence of VWFQNRRA (SEQ ID NO:9). In some embodiments, the HD-Zip transcription factor is a HD-Zip Type II (HD-Zip II) transcription factor, optionally wherein the HD-Zip II transcription factor is HB53 or HB78.

In some embodiments, a nucleic acid encoding HD-Zip transcription factor (e.g., HD-Zip II, e.g., HB53 or HB78) having a mutated DNA binding site is provided, wherein the mutated DNA binding site of the HD-Zip transcription factor comprises a mutation that disrupts DNA binding by the HD-Zip transcription factor. In some embodiments, the mutation may eliminate the binding of the HD-Zip transcription factor to DNA or may reduce the ability of the HD-Zip transcription factor to bind to DNA by at least 75% (e.g., at least about 75, 76, 77, 78, 79, 80, 81, 82, 83, 84, 85, 86, 87, 88, 89, 90, 91, 92, 93, 94, 95, 96, 97, 98, 99, 100%). The present invention further provides plants or parts thereof comprising the nucleic acid of the invention. In some embodiments, when the plant is a corn plant, the corn plant may comprise a short stature/semi-dwarf phenotype. In some embodiments, the plant may be a whet plant or part thereof, optionally wherein the nucleic acid may be comprised in the A genome, the B genome, the D genome or in any combination thereof. In some embodiments, a plant, a corn plant and/or a wheat plant of the invention having a reduced SAR may exhibit increased yield, decreased height, decreased shoot:root ratio, decreased leaf length; increased mechanical strength of stems; reduced lodging rate; delayed senescence; increased photosynthesis efficiency and grain filling; and/or enhanced defense responses against pathogens and herbivores when they are planted in close proximity with one or more other as compared to a control plant that does not comprise a nucleic acid encoding HD-Zip transcription factor (e.g., HD-Zip II, e.g., HB53 or HB78) having a mutated DNA binding site and therefore does not comprise a reduced Shade Avoidance Response, which is planted in close proximity with one or more other plants. In some embodiments, when planted in close proximity to one another, plants of this invention comprising reduced SAR may be at least about 5% shorter than a control plant grown under the same conditions (e.g., a shaded environment, e.g., a low R:FR ratio environment).

In some embodiments, a method of the present invention may further comprise regenerating a plant from a plant cell or plant part comprising at least one non-natural mutation in an endogenous Homeodomain-leucine zipper (HD-Zip) transcription factor, wherein the mutation disrupts the binding of the HD-Zip transcription factor to DNA. In some embodiments, the plant comprise comprising at least one non-natural mutation in an endogenous Homeodomain-leucine zipper (HD-Zip) transcription factor may have increased yield, decreased height, decreased shoot:root ratio, decreased leaf length; increased mechanical strength of stems; reduced lodging rate; delayed senescence; increased photosynthesis efficiency and grain filling; and/or enhanced defense responses against pathogens and herbivores when they are planted in close proximity with one or more other plants compared to a control plant that does not comprise the at least one non-natural mutation in an endogenous Homeodomain-leucine zipper (HD-Zip) transcription factor, and therefore, does not comprise a reduced Shade Avoidance Response, which plant is planted in close proximity with one or more other plants. In some embodiments, the mutation is a non-naturally occurring mutation. In some embodiments, the mutation is a deletion. In some embodiments, the deletion is a dominant recessive mutation.

An editing system useful with this invention can be any site-specific (sequence-specific) genome editing system now known or later developed, which system can introduce mutations in target specific manner. For example, an editing system (e.g., site- or sequence-specific editing system) can include, but is not limited to, a CRISPR-Cas editing system, a meganuclease editing system, a zinc finger nuclease (ZFN) editing system, a transcription activator-like effector nuclease (TALEN) editing system, a base editing system and/or a prime editing system, each of which can comprise one or more polypeptides and/or one or more polynucleotides that when expressed as a system in a cell can modify (mutate) a target nucleic acid in a sequence specific manner. In some embodiments, an editing system (e.g., site- or sequence-specific editing system) can comprise one or more polynucleotides and/or one or more polypeptides, including but not limited to a nucleic acid binding domain (DNA binding domain), a nuclease, and/or other polypeptide, and/or a polynucleotide.

In some embodiments, an editing system can comprise one or more sequence-specific nucleic acid binding domains (DNA binding domains) that can be from, for example, a polynucleotide-guided endonuclease, a CRISPR-Cas endonuclease (e CRISPR-Cas effector protein), a zinc finger nuclease, a transcription activator-like effector nuclease (TALEN) and/or an Argonaute protein. In some embodiments, an editing system can comprise one or more cleavage domains (e.g., nucleases) including, but not limited to, an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN). In some embodiments, an editing system can comprise one or more polypeptides that include, but are not limited to, a deaminase (e.g., a cytosine deaminase, an adenine deaminase), a reverse transcriptase, a Dna2 polypeptide, and/or a 5' flap endonuclease (FEN). In some embodiments, an editing system can comprise one or more polynucleotides, including, but is not limited to, a CRISPR array (CRISPR guide) nucleic acid, extended guide nucleic acid, and/or a reverse transcriptase template.

In some embodiments, a method of modifying or editing an HD-Zip transcription factor may comprise contacting a target nucleic acid (e.g., a nucleic acid encoding an HD-Zip transcription factor) with a base-editing fusion protein (e.g., a sequence specific DNA binding protein (e.g., a CRISPR-Cas effector protein or domain) fused to a deaminase domain (e.g., an adenine deaminase and/or a cytosine deaminase) and a guide nucleic acid, wherein the guide nucleic acid is capable of guiding/targeting the base editing fusion protein to the target nucleic acid, thereby editing a locus within the target nucleic acid. In some embodiments, a base editing fusion protein and guide nucleic acid may be comprised in one or more expression cassettes. In some embodiments, the target nucleic acid may be contacted with a base editing fusion protein and an expression cassette comprising a guide nucleic acid. In some embodiments, the sequence-specific DNA binding fusion proteins and guides may be provided as ribonucleoproteins (RNPs). In some embodiments, a cell may be contacted with more than one base-editing fusion protein and/or one or more guide nucleic acids that may target one or more target nucleic acids in the cell.

In some embodiments, a method of modifying or editing an HD-Zip transcription factor may comprise contacting a target nucleic acid (e.g., a nucleic acid encoding an HD-Zip transcription factor) with a sequence-specific DNA binding fusion protein (e.g., a sequence-specific DNA binding protein (e.g., a CRISPR-Cas effector protein or domain) fused to a peptide tag, a deaminase fusion protein comprising a deaminase domain (e.g., an adenine deaminase and/or a cytosine deaminase) fused to an affinity polypeptide that is capable of binding to the peptide tag, and a guide nucleic acid, wherein the guide nucleic acid is capable of guiding/targeting the sequence-specific DNA binding fusion protein to the target nucleic acid and the sequence-specific DNA binding fusion protein is capable of recruiting the deaminase fusion protein to the target nucleic acid via the peptide tag-affinity polypeptide interaction, thereby editing a locus within the target nucleic acid. In some embodiments, the sequence-specific DNA binding fusion protein may be fused to the affinity polypeptide that binds the peptide tag and the deaminase may be fuse to the peptide tag, thereby recruiting the deaminase to the sequence-specific DNA binding fusion protein and to the target nucleic acid. In some embodiments, the sequence-specific binding fusion protein, deaminase fusion protein, and guide nucleic acid may be comprised in one or more expression cassettes. In some embodiments, the target nucleic acid may be contacted with a sequence-specific binding fusion protein, deaminase fusion protein, and an expression cassette comprising a guide nucleic acid. In some embodiments, the sequence-specific DNA binding fusion proteins, deaminase fusion proteins and guides may be provided as ribonucleoproteins (RNPs).

In some embodiments, methods such as prime editing may be used to generate a mutation in an endogenous HD-Zip transcription factor gene. In prime editing, RNA-dependent DNA polymerase (reverse transcriptase, RT) and reverse transcriptase templates (RT template) are used in combination with sequence specific DNA binding domains that confer the ability to recognize and bind the target in a sequence-specific manner, and which can also cause a nick of the PAM-containing strand within the target. The DNA binding domain may be a CRISPR-Cas effector protein and in this case, the CRISPR array or guide RNA may be an extended guide that comprises an extended portion comprising a primer binding site (PSB) and the edit to be incorporated into the genome (the template). Similar to base editing, prime editing can take advantageous of the various methods of recruiting proteins for use in the editing to the target site, such methods including both non-covalent and covalent interactions between the proteins and nucleic acids used in the selected process of genome editing.

In some embodiments, the mutation of an HD-Zip transcription factor gene may be an insertion, a deletion and/or a point mutation in that produces an HD-Zip transcription factor having reduced DNA binding (e.g., a mutated HD-Zip transcription factor). In some embodiments, a plant part may be a cell. In some embodiments, the plant or plant part thereof may be any plant or part thereof as described herein. In some embodiments, a plant useful with this invention may be corn, soy, canola, wheat, rice, cotton, sugarcane, sugar beet, barley, oats, alfalfa, sunflower, safflower, oil palm. sesame, coconut, tobacco, potato, sweet potato, cassava, coffee, apple, plum, apricot, peach, cherry, pear, fig, banana, citrus, cocoa, avocado, olive, almond, walnut, strawberry, watermelon, pepper, grape, tomato, cucumber, or a *Brassica* spp. In some embodiments, a plant comprising a mutated endogenous HD-Zip transcription factor having DNA binding may comprise increased yield, decreased height, decreased shoot:root ratio, decreased leaf length; increased mechanical strength of stems; reduced lodging rate; delayed senescence; increased photosynthesis efficiency and grain filling; and/or enhanced defense responses against pathogens and herbivores when they are planted in close proximity with one or more other plants compared to a control plant that does not comprise the at least one non-natural mutation in an endogenous Homeodomain-leucine zipper (HD-Zip) transcription factor, and therefore, does not comprise a reduced Shade Avoidance Response, which plant is planted in close proximity with one or more other plants. In some embodiments, the plant may be a corn plant, optionally wherein the corn plant comprises a short stature/semi-dwarf phenotype.

In some embodiments, a mutation that is introduced into an endogenous HD-Zip transcription factor and resulting in reduced DNA binding may be a non-naturally occurring mutation. In some embodiments, a mutation that is introduced into an endogenous HD-Zip transcription factor and resulting in reduced DNA binding may be a substitution, an insertion and/or a deletion of one or more amino acid residues. In some embodiments, a mutation that is introduced into an endogenous HD-Zip transcription factor gene that results in reduced DNA binding may be a deletion, optionally a deletion of all or a portion of the amino acid sequence of SEQ ID NO:9 (e.g., 1, 2, 3, 4, 5, 6, 7, or 8 amino acid residues of SEQ ID NO:9).

In some embodiments, an HD-Zip transcription factor may be an HD-Zip Type II (HD-Zip II) transcription factor, optionally wherein the HD-Zip II transcription factor may bea HOMEOBOX PROTEIN 53 (HB53) or a HOMEOBOX PROTEIN 78 (HB78)

In some embodiments, a sequence-specific nucleic acid binding domain (DNA binding domains) of an editing system useful with this invention can be from, for example, a polynucleotide-guided endonuclease. a CRISPR-Cas endonuclease CMSPR-Cas effector protein), a zinc finger nuclease, a transcription activator-like effector nuclease (TALEN) and/or an Argonaute protein.

In some embodiments, a sequence-specific DNA binding domain may be a CRISPR-Cas effector protein, optionally wherein the CRISPR-Cas effector protein may be from a Type I CRISPR-Cas system, a Type II CRISPR-Cas system, a Type III CRISPR-Cas system, a Type IV CRISPR-Cas system, Type V CRISPR-Cas system, or a Type VI CRISPR-Cas system. In some embodiments, a CRISPR-Cas effector protein of the invention may be from a Type II CRISPR-Cas system or a Type V CRISPR-Cas system. In some embodiments, a CRISPR-Cas effector protein may be Type II CRISPR-Cas effector protein, for example, a Cas9 effector protein. In some embodiments, a CRISPR-Cas effector protein may be Type V CRISPR-Cas effector protein, for example, a Cas12 effector protein.

In some embodiments, a CRISPR-Cas effector protein may include, but is not limited to, a Cas9, C2c1, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5 nuclease, optionally wherein the CRISPR-Cas effector protein may be a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or Cas14c effector protein.

In some embodiments, a CRISPR-Cas effector protein useful with the invention may comprise a mutation in its nuclease active site (e.g., RuvC, HNH, e.g., RuvC site of a Cas12a nuclease domain, e.g., RuvC site and/or HNH site of a Cas9 nuclease domain). A CRISPR-Cas effector protein having a mutation in its nuclease active site, and therefore, no longer comprising nuclease activity, is commonly referred to as "dead," e.g., dCas. In some embodiments, a CRISPR-Cas effector protein domain or polypeptide having a mutation in its nuclease active site may have impaired activity or reduced activity as compared to the same CRISPR-Cas effector protein without the mutation, e.g., a nickase, e.g, Cas9 nickase, Cas12a nickase.

A CRISPR Cas9 effector protein or CRISPR Cas9 effector domain useful with this invention may be any known or later identified Cas9 nuclease. In some embodiments, a CRISPR Cas9 polypeptide can be a Cas9 polypeptide from, for example, *Streptococcus* spp. (e.g., *S. pyogenes, S. thermophiles*), *Lactobacillus* spp., *Bifidobacterium* spp., *Kandleria* spp., *Leuconostoc* spp., *Oenococcus* spp., *Pediococcus* spp., *Weissella* spp., and/or *Olsenella* spp.

In some embodiments, the CRISPR-Cas effector protein may be a Cas9 polypeptide derived from *Streptococcus pyogenes* and recognizes the PAM sequence motif NGG, NAG, NGA (Mali et al, *Science* 2013; 339(6121): 823-826). In some embodiments, the CRISPR-Cas effector protein may be a Cas9 polypeptide derived from *Streptococcus thermophiles* and recognizes the PAM sequence motif NGGNG and/or NNAGAAW (W=A or T) (See, e.g., Horvath et al, *Science,* 2010; 327(5962): 167-170, and Deveau et al, *J Bacteriol* 2008; 190(4): 1390-1400). In some embodiments, the CRISPR-Cas effector protein may be a Cas9 polypeptide derived from *Streptococcus mutans* and recognizes the PAM sequence motif NGG and/or NAAR (R=A or G) (See, e.g., Deveau et al, *J BACTERIOL* 2008; 190(4): 1390-1400). In some embodiments, the CRISPR-Cas effector protein may be a Cas9 polypeptide derived from *Streptococcus aureus* and recognizes the PAM sequence motif NNGRR (R=A or G). In some embodiments, the CRISPR-Cas effector protein may be a Cas9 protein derived from *S. aureus*, which recognizes the PAM sequence motif N GRRT (R=A or G). In some embodiments, the CRISPR-Cas effector protein may be a Cas9 polypeptide derived from *S. aureus*, which recognizes the PAM sequence motif N GRRV (R=A or G). In some embodiments, the CRISPR-Cas effector protein may be a Cas9 polypeptide that is derived from *Neisseria meningitidis* and recognizes the PAM sequence motif N GATT or N GCTT (R=A or G, V=A, G or C) (See, e.g., Hou et ah, *PNAS* 2013, 1-6). In the aforementioned embodiments, N can be any nucleotide residue, e.g., any of A, G, C or T. In some embodiments, the CRISPR-Cas effector protein may be a Cas13a protein derived from Leptotrichia shahii, which recognizes a protospacer flanking sequence (PFS) (or RNA PAM (rPAM)) sequence motif of a single 3' A, U, or C, which may be located within the target nucleic acid.

In some embodiments, the CRISPR-Cas effector protein may be derived from Cas12a, which is a Type V Clustered Regularly Interspaced Short Palindromic Repeats (CRISPR)-Cas nuclease. Cas12a differs in several respects from the more well-known Type II CRISPR Cas9 nuclease. For example, Cas9 recognizes a G-rich protospacer-adjacent motif (PAM) that is 3' to its guide RNA (gRNA, sgRNA, crRNA, crDNA, CRISPR array) binding site (protospacer, target nucleic acid, target DNA) (3'-NGG), while Cas12a recognizes a T-rich PAM that is located 5' to the target nucleic acid (5'-TTN, 5'-TTTN. In fact, the orientations in which Cas9 and Cas12a bind their guide RNAs are very nearly reversed in relation to their N and C termini. Furthermore, Cas12a enzymes use a single guide RNA (gRNA, CRISPR array, crRNA) rather than the dual guide RNA (sgRNA (e.g., crRNA and tracrRNA)) found in natural Cas9 systems, and Cas12a processes its own gRNAs. Additionally, Cas12a nuclease activity produces staggered DNA double stranded breaks instead of blunt ends produced by Cas9 nuclease activity, and Cas12a relies on a single RuvC domain to cleave both DNA strands, whereas Cas9 utilizes an HNH domain and a RuvC domain for cleavage.

A CRISPR Cas12a effector protein/domain useful with this invention may be any known or later identified Cas12a polypeptide (previously known as Cpf1) (see, e.g., U.S. Pat. No. 9,790,490, which is incorporated by reference for its disclosures of Cpf1 (Cas12a) sequences). The term "Cas12a", "Cas12a polypeptide" or "Cas12a domain" refers to an RNA-guided nuclease comprising a Cas12a polypeptide, or a fragment thereof, which comprises the guide nucleic acid binding domain of Cas12a and/or an active, inactive, or partially active DNA cleavage domain of Cas12a. In some embodiments, a Cas12a useful with the invention may comprise a mutation in the nuclease active site (e.g., RuvC site of the Cas12a domain). A Cas12a domain or Cas12a polypeptide having a mutation in its nuclease active site, and therefore, no longer comprising nuclease activity, is commonly referred to as deadCas12a (e.g., dCas12a). In some embodiments, a Cas12a domain or Cas12a polypeptide having a mutation in its nuclease active site may have impaired activity, e.g., may have nickase activity.

Any deaminase domain/polypeptide useful for base editing may be used with this invention. In some embodiments, the deaminase domain may be a cytosine deaminase domain or an adenine deaminase domain. A cytosine deaminase (or cytidine deaminase) useful with this invention may be any known or later identified cytosine deaminase from any organism (see, e.g., U.S. Pat. No. 10,167,457 and Thuronyi et al. *Nat. Biotechnol.* 37:1070-1079 (2019), each of which is incorporated by reference herein for its disclosure of cytosine deaminases). Cytosine deaminases can catalyze the hydrolytic deamination of cytidine or deoxycytidine to uridine or deoxyuridine, respectively. Thus, in some embodiments, a deaminase or deaminase domain useful with this invention may be a cytidine deaminase domain, catalyzing the hydrolytic deamination of cytosine to uracil. In some embodiments, a cytosine deaminase may be a variant of a naturally occurring cytosine deaminase, including but not limited to a primate (e.g., a human, monkey, chimpanzee, gorilla), a dog, a cow, a rat or a mouse. Thus, in some embodiments, an cytosine deaminase useful with the invention may be about 70% to about 100% identical to a wild type cytosine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring cytosine deaminase).

In some embodiments, a cytosine deaminase useful with the invention may be an apolipoprotein B mRNA-editing complex (APOBEC) family deaminase. In some embodiments, the cytosine deaminase may be an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, an APOBEC3H deaminase, an APOBEC4 deaminase, a human activation induced deaminase (hAID), an rAPOBEC1, FERNY, and/or a CDA1, optionally a pmCDA1, an atCDA1 (e.g., At2g19570), and evolved versions of the same. In some embodiments, the cytosine deaminase may be an APOBEC1 deaminase having the amino acid sequence of SEQ ID NO:188. In some embodiments, the cytosine deaminase may be an APOBEC3A deaminase having the amino acid sequence of SEQ ID NO:189. In some embodiments, the cytosine deaminase may be an CDA1 deaminase, optionally a CDA1 having the amino acid sequence of SEQ ID NO:190. In some embodiments, the cytosine deaminase may be a FERNY deaminase, optionally a FERNY having the amino acid sequence of SEQ ID NO:191. In some embodiments, the cytosine deaminase may be an evolved deaminase, e.g., SEQ ID NO:192, SEQ ID NO:193, or SEQ ID NO:194. In some embodiments, a cytosine deaminase useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical) to the amino acid sequence of a naturally occurring cytosine deaminase (e.g., an evolved deaminase). In some embodiments, a cytosine deaminase useful with the invention may be about 70% to about 99.5% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical) to the amino acid sequence of SEQ ID NO:188, SEQ ID NO:189, SEQ ID NO:190, SEQ ID NO:191, SEQ ID NO:192, SEQ ID NO:193, or SEQ ID NO:194 (e.g., at least 80%, at least 85%, at least 90%, at least 92%, at least 95%, at least 96%, at least 97%, at least 98%, at least 99%, or at least 99.5% identical to the amino acid sequence of SEQ ID NO:188, SEQ ID NO:189, SEQ ID NO:190, SEQ ID NO:191, SEQ ID NO:192, SEQ ID NO:193, or SEQ ID NO:194). In some embodiments, a polynucleotide encoding a cytosine deaminase may be codon optimized for expression in a plant and the codon optimized polypeptide may be about 70% to 99.5% identical to the reference polynucleotide.

In some embodiments, a nucleic acid construct of this invention may further encode a uracil glycosylase inhibitor (UGI) (e.g., uracil-DNA glycosylase inhibitor) polypeptide/domain. Thus, in some embodiments, a nucleic acid construct encoding a CRISPR-Cas effector protein and a cytosine deaminase domain (e.g., encoding a fusion protein comprising a CRISPR-Cas effector protein domain fused to a cytosine deaminase domain, and/or a CRISPR-Cas effector protein domain fused to a peptide tag or to an affinity polypeptide capable of binding a peptide tag and/or a deaminase protein domain fused to a peptide tag or to an affinity polypeptide capable of binding a peptide tag) may further encode a uracil-DNA glycosylase inhibitor (UGI), optionally wherein the UGI may be codon optimized for expression in a plant. In some embodiments, the invention provides fusion proteins comprising a CRISPR-Cas effector polypeptide, a deaminase domain, and a UGI and/or one or more polynucleotides encoding the same, optionally wherein the one or more polynucleotides may be codon optimized for expression in a plant. In some embodiments, the invention provides fusion proteins, wherein a CRISPR-Cas effector polypeptide, a deaminase domain, and a UGI may be fused to any combination of peptide tags and affinity polypeptides as described herein, thereby recruiting the deaminase domain and UGI to the CRISPR-Cas effector polypeptide and a target nucleic acid. In some embodiments, a guide nucleic acid may be linked to a recruiting RNA motif and one or more of the deaminase domain and/or UGI may be fused to an affinity polypeptide that is capable of interacting with the recruiting RNA motif, thereby recruiting the deaminase domain and UGI to a target nucleic acid.

A "uracil glycosylase inhibitor" useful with the invention may be any protein that is capable of inhibiting a uracil-DNA glycosylase base-excision repair enzyme. In some embodiments, a UGI domain comprises a wild type UGI or a fragment thereof. In some embodiments, a UGI domain useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical and any range or value therein) to the amino acid sequence of a naturally occurring UGI domain. In some embodiments, a UGI domain may comprise the amino acid sequence of SEQ ID NO: 195 or a polypeptide having about 70% to about 99.5% sequence identity to the amino acid sequence of SEQ ID NO: 195 (e.g., at least 80%, at least 85%, at least 90%, at least 92%, at least 95%, at least 96%, at least 97%, at least 98%, at least 99%, or at least 99.5% identical to the amino acid sequence of SEQ ID NO:195). For example, in some embodiments, a UGI domain may comprise a fragment of the amino acid sequence of SEQ ID NO:195 that is 100% identical to a portion of consecutive nucleotides (e.g., 10, 15, 20, 25, 30, 35, 40, 45, 50, 55, 60, 65, 70, 75, 80 consecutive nucleotides; e.g., about 10, 15, 20, 25, 30, 35, 40, 45, to about 50, 55, 60, 65, 70, 75, 80 consecutive nucleotides) of the amino acid sequence of SEQ ID NO:195. In some embodiments, a UGI domain may be a variant of a known UGI (e.g., SEQ ID NO:195) having about 70% to about 99.5% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% sequence identity, and any range or value therein) to the known UGI. In some embodiments, a polynucleotide encoding a UGI may be codon optimized for expression in a plant (e.g., a plant) and the codon optimized polypeptide may be about 70% to about 99.5% identical to the reference polynucleotide.

An adenine deaminase (or adenosine deaminase) useful with this invention may be any known or later identified adenine deaminase from any organism (see, e.g., U.S. Pat. No. 10,113,163, which is incorporated by reference herein for its disclosure of adenine deaminases). An adenine deaminase can catalyze the hydrolytic deamination of adenine or adenosine. In some embodiments, the adenine deaminase may catalyze the hydrolytic deamination of adenosine or deoxyadenosine to inosine or deoxyinosine, respectively. In some embodiments, the adenosine deaminase may catalyze the hydrolytic deamination of adenine or adenosine in DNA. In some embodiments, an adenine deaminase encoded by a nucleic acid construct of the invention may generate an A→G conversion in the sense (e.g., "+"; template) strand of the target nucleic acid or a T→C conversion in the antisense (e.g., "−", complementary) strand of the target nucleic acid.

In some embodiments, an adenosine deaminase may be a variant of a naturally occurring adenine deaminase. Thus, in some embodiments, an adenosine deaminase may be about 70% to 100% identical to a wild type adenine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring adenine deaminase). In some embodiments, the deaminase or deaminase does not occur in nature and may be referred to as an engineered, mutated or evolved adenosine deaminase. Thus, for example, an engineered, mutated or evolved adenine deaminase polypeptide or an adenine deaminase domain may be about 70% to 99.9% identical to a naturally occurring adenine deaminase polypeptide/domain (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% identical, and any range or value therein, to a naturally occurring adenine deaminase polypeptide or adenine deaminase domain). In some embodiments, the adenosine deaminase may be from a bacterium, (e.g., *Escherichia coli, Staphylococcus aureus, Haemophilus influenzae, Caulobacter crescentus*, and the like). In some embodiments, a polynucleotide encoding an adenine deaminase polypeptide/domain may be codon optimized for expression in a plant.

In some embodiments, an adenine deaminase domain may be a wild type tRNA-specific adenosine deaminase domain, e.g., a tRNA-specific adenosine deaminase (TadA) and/or a mutated/evolved adenosine deaminase domain, e.g., mutated/evolved tRNA-specific adenosine deaminase domain (TadA*). In some embodiments, a TadA domain may be from *E. coli*. In some embodiments, the TadA may be modified, e.g., truncated, missing one or more N-terminal and/or C-terminal amino acids relative to a full-length TadA (e.g., 1, 2, 3, 4, 6, 7, 8, 9, 10, 11, 12, 13, 14, 15, 6, 17, 18, 19, or 20 N-terminal and/or C terminal amino acid residues may be missing relative to a full length TadA. In some embodiments, a TadA polypeptide or TadA domain does not comprise an N-terminal methionine. In some embodiments, a wild type *E. coli* TadA comprises the amino acid sequence of SEQ ID NO:183. In some embodiments, a mutated/evolved *E. coli* TadA* comprises the amino acid sequence of SEQ ID NOs:184-187 (e.g., SEQ ID NOs: 184, 185, 186, or 187). In some embodiments, a polynucleotide encoding a TadA/TadA* may be codon optimized for expression in a plant.

A cytosine deaminase catalyzes cytosine deamination and results in a thymidine (through a uracil intermediate), causing a C to T conversion, or a G to A conversion in the complementary strand in the genome. Thus, in some embodiments, the cytosine deaminase encoded by the polynucleotide of the invention generates a C→T conversion in the sense (e.g., "+"; template) strand of the target nucleic acid or a G→A conversion in antisense (e.g., "−", complementary) strand of the target nucleic acid.

In some embodiments, the adenine deaminase encoded by the nucleic acid construct of the invention generates an A→G conversion in the sense (e.g., "+"; template) strand of the target nucleic acid or a T→C conversion in the antisense (e.g., "−", complementary) strand of the target nucleic acid.

The nucleic acid constructs of the invention encoding a base editor comprising a sequence-specific DNA binding protein and a cytosine deaminase polypeptide, and nucleic acid constructs/expression cassettes/vectors encoding the same, may be used in combination with guide nucleic acids for modifying target nucleic acid including, but not limited to, generation of C→T or G→A mutations in a target nucleic acid including, but not limited to, a plasmid sequence; generation of C→T or G→A mutations in a coding sequence to alter an amino acid identity; generation of C→T or G→A mutations in a coding sequence to generate a stop codon; generation of C→T or G→A mutations in a coding sequence to disrupt a start codon; generation of point mutations in genomic DNA to disrupt transcription factor binding; and/or generation of point mutations in genomic DNA to disrupt splice junctions.

The nucleic acid constructs of the invention encoding a base editor comprising a sequence-specific DNA binding protein and an adenine deaminase polypeptide, and expression cassettes and/or vectors encoding the same may be used in combination with guide nucleic acids for modifying a target nucleic acid including, but not limited to, generation of A→G or T→C mutations in a target nucleic acid including, but not limited to, a plasmid sequence; generation of A→G or T→C mutations in a coding sequence to alter an amino acid identity; generation of A→G or T→C mutations in a coding sequence to generate a stop codon; generation of A→G or T→C mutations in a coding sequence to disrupt a start codon; generation of point mutations in genomic DNA to disrupt transcription factor binding; and/or generation of point mutations in genomic DNA to disrupt splice junctions.

The nucleic acid constructs of the invention comprising a CRISPR-Cas effector protein or a fusion protein thereof may be used in combination with a guide RNA (gRNA, CRISPR array, CRISPR RNA, crRNA), designed to function with the encoded CRISPR-Cas effector protein or domain, to modify a target nucleic acid. A guide nucleic acid useful with this invention comprises at least one spacer sequence and at least one repeat sequence. The guide nucleic acid is capable of forming a complex with the CRISPR-Cas nuclease domain encoded and expressed by a nucleic acid construct of the invention and the spacer sequence is capable of hybridizing to a target nucleic acid, thereby guiding the complex (e.g., a CRISPR-Cas effector fusion protein (e.g., CRISPR-Cas effector domain fused to a deaminase domain and/or a CRISPR-Cas effector domain fused to a peptide tag or an affinity polypeptide to recruit a deaminase domain and optionally, a UGI) to the target nucleic acid, wherein the target nucleic acid may be modified (e.g., cleaved or edited) or modulated (e.g., modulating transcription) by the deaminase domain.

As an example, a nucleic acid construct encoding a Cas9 domain linked to a cytosine deaminase domain (e.g., fusion protein) may be used in combination with a Cas9 guide nucleic acid to modify a target nucleic acid, wherein the cytosine deaminase domain of the fusion protein deaminates a cytosine base in the target nucleic acid, thereby editing the target nucleic acid. In a further example, a nucleic acid construct encoding a Cas9 domain linked to an adenine deaminase domain (e.g., fusion protein) may be used in combination with a Cas9 guide nucleic acid to modify a target nucleic acid, wherein the adenine deaminase domain of the fusion protein deaminates an adenosine base in the target nucleic acid, thereby editing the target nucleic acid.

Likewise, a nucleic acid construct encoding a Cas12a domain (or other selected CRISPR-Cas nuclease, e.g., C2c1, C2c3, Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5) linked to a cytosine deaminase domain or adenine deaminase domain (e.g., fusion protein) may be used in combination with a Cas12a guide nucleic acid (or the guide nucleic acid for the other selected CRISPR-Cas nuclease) to modify a target nucleic acid, wherein the cytosine deaminase domain or adenine deaminase domain of the fusion protein deaminates a cytosine base in the target nucleic acid, thereby editing the target nucleic acid.

A "guide nucleic acid," "guide RNA," "gRNA," "CRISPR RNA/DNA" "crRNA" or "crDNA" as used herein means a nucleic acid that comprises at least one spacer sequence, which is complementary to (and hybridizes to) a target DNA (e.g., protospacer), and at least one repeat sequence (e.g., a repeat of a Type V Cas12a CRISPR-Cas system, or a fragment or portion thereof; a repeat of a Type II Cas9 CRISPR-Cas system, or fragment thereof; a repeat of a Type V C2c1 CRISPR Cas system, or a fragment thereof; a repeat of a CRISPR-Cas system of, for example, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5, or a fragment thereof), wherein the repeat sequence may be linked to the 5' end and/or the 3' end of the spacer sequence. The design of a gRNA of this invention may be based on a Type I, Type II, Type III, Type IV, Type V, or Type VI CRISPR-Cas system.

In some embodiments, a Cas12a gRNA may comprise, from 5' to 3', a repeat sequence (full length or portion thereof ("handle"); e.g., pseudoknot-like structure) and a spacer sequence.

In some embodiments, a guide nucleic acid may comprise more than one repeat sequence-spacer sequence (e.g., 2, 3, 4, 5, 6, 7, 8, 9, 10, or more repeat-spacer sequences) (e.g., repeat-spacer-repeat, e.g., repeat-spacer-repeat-spacer-repeat-spacer-repeat-spacer-repeat-spacer, and the like). The guide nucleic acids of this invention are synthetic, human-made and not found in nature. A gRNA can be quite long and may be used as an aptamer (like in the MS2 recruitment strategy) or other RNA structures hanging off the spacer.

A "repeat sequence" as used herein, refers to, for example, any repeat sequence of a wild-type CRISPR Cas locus (e.g., a Cas9 locus, a Cas12a locus, a C2c1 locus, etc.) or a repeat sequence of a synthetic crRNA that is functional with the CRISPR-Cas effector protein encoded by the nucleic acid constructs of the invention. A repeat sequence useful with this invention can be any known or later identified repeat sequence of a CRISPR-Cas locus (e.g., Type I, Type II, Type III, Type IV, Type V or Type VI) or it can be a synthetic repeat designed to function in a Type I, II, III, IV, V or VI CRISPR-Cas system. A repeat sequence may comprise a hairpin structure and/or a stem loop structure. In some embodiments, a repeat sequence may form a pseudoknot-like structure at its 5' end (i.e., "handle"). Thus, in some embodiments, a repeat sequence can be identical to or substantially identical to a repeat sequence from wild-type Type I CRISPR-Cas loci, Type II, CRISPR-Cas loci, Type III, CRISPR-Cas loci, Type IV CRISPR-Cas loci, Type V CRISPR-Cas loci and/or Type VI CRISPR-Cas loci. A repeat sequence from a wild-type CRISPR-Cas locus may be determined through established algorithms, such as using the CRISPRfinder offered through CRISPRdb (see, Grissa et al. *Nucleic Acids Res.* 35 (Web Server issue):W52-7). In some embodiments, a repeat sequence or portion thereof is linked at its 3' end to the 5' end of a spacer sequence, thereby forming a repeat-spacer sequence (e.g., guide nucleic acid, guide RNA/DNA, crRNA, crDNA).

In some embodiments, a repeat sequence comprises, consists essentially of, or consists of at least 10 nucleotides depending on the particular repeat and whether the guide nucleic acid comprising the repeat is processed or unprocessed (e.g., about 10, 11, 12, 13, 14, 16, 17, 18, 19, 20, 21, 22, 23, 24, 25, 26, 27, 28, 29, 30, 31, 32, 33, 34, 35, 36, 37, 38, 39, 41, 42, 43, 44, 45, 46, 47, 48, 49, 50 to 100 or more nucleotides, or any range or value therein). In some embodiments, a repeat sequence comprises, consists essentially of, or consists of about 10 to about 20, about 10 to about 30, about 10 to about 45, about 10 to about 50, about 15 to about 30, about 15 to about 40, about 15 to about 45, about 15 to about about 20 to about 30, about 20 to about 40, about 20 to about 50, about 30 to about 40, about 40 to about 80, about 50 to about 100 or more nucleotides.

A repeat sequence linked to the 5' end of a spacer sequence can comprise a portion of a repeat sequence (e.g., 5, 6, 7, 8, 9, 10, 11, 12, 13, 14, 15, 16, 17, 18, 19, 20, 21, 22, 23, 24, 26, 27, 28, 29, 30, 31, 32, 33, 34, 35 or more contiguous nucleotides of a wild type repeat sequence). In some embodiments, a portion of a repeat sequence linked to the 5' end of a spacer sequence can be about five to about ten consecutive nucleotides in length (e.g., about 6, 7, 8, 9, 10 nucleotides) and have at least 90% sequence identity (e.g., at least about 90%, 91%, 92%, 93%, 94%, 95%, 96%, 97%, 98%, 99%, or more) to the same region (e.g., 5' end) of a wild type CRISPR Cas repeat nucleotide sequence. In some embodiments, a portion of a repeat sequence may comprise a pseudoknot-like structure at its 5' end (e.g., "handle").

A "spacer sequence" as used herein is a nucleotide sequence that is complementary to a target nucleic acid (e.g., target DNA) (e.g, protospacer) (e.g., consecutive nucleotides of any one of SEQ ID NOs:1-9; e.g., SEQ ID NOs: 175-182). The spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a target nucleic acid. Thus, in some embodiments, the spacer sequence can have one, two, three, four, or five mismatches as compared to the target nucleic acid, which mismatches can be contiguous or noncontiguous. In some embodiments, the spacer sequence can have 70% complementarity to a target nucleic acid. In other embodiments, the spacer nucleotide sequence can have 80% complementarity to a target nucleic acid. In still other embodiments, the spacer nucleotide sequence can have 85%, 90%, 95%, 96%, 97%, 98%, 99% or 99.5% complementarity, and the like, to the target nucleic acid (protospacer). In some embodiments, the spacer sequence is 100% complementary to the target nucleic acid. A spacer sequence may have a length from about 15 nucleotides to about 30 nucleotides (e.g., 15, 16, 17, 18, 19, 20, 21, 22, 23, 24, 25, 26, 27, 28, 29, or 30 nucleotides, or any range or value therein). Thus, in some embodiments, a spacer sequence may have complete complementarity or substantial complementarity over a region of a target nucleic acid (e.g., protospacer) that is at least about 15 nucleotides to about 30 nucleotides in length. In some embodiments, the spacer is about 20 nucleotides in length. In some embodiments, the spacer is about 21, 22, or 23 nucleotides in length.

In some embodiments, the 5' region of a spacer sequence of a guide nucleic acid may be identical to a target DNA, while the 3' region of the spacer may be substantially complementary to the target DNA (e.g., Type V CRISPR-Cas), or the 3' region of a spacer sequence of a guide nucleic acid may be identical to a target DNA, while the 5' region of the spacer may be substantially complementary to the target DNA (e.g., Type II CRISPR-Cas), and therefore, the overall complementarity of the spacer sequence to the target DNA may be less than 100%. Thus, for example, in a guide for a Type V CRISPR-Cas system, the first 1, 2, 3, 4, 5, 6, 7, 8, 9, 10 nucleotides in the 5' region (i.e., seed region) of, for example, a 20 nucleotide spacer sequence may be 100% complementary to the target DNA, while the remaining nucleotides in the 3' region of the spacer sequence are substantially complementary (e.g., at least about 70% complementary) to the target DNA. In some embodiments, the first 1 to 8 nucleotides (e.g., the first 1, 2, 3, 4, 5, 6, 7, 8, nucleotides, and any range therein) of the 5' end of the spacer sequence may be 100% complementary to the target DNA, while the remaining nucleotides in the 3' region of the spacer sequence are substantially complementary (e.g., at least about 50% complementary (e.g., 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target DNA.

As a further example, in a guide for a Type II CRISPR-Cas system, the first 1, 2, 3, 4, 6, 7, 8, 9, 10 nucleotides in the 3' region (i.e., seed region) of, for example, a 20 nucleotide spacer sequence may be 100% complementary to the target DNA, while the remaining nucleotides in the 5' region of the spacer sequence are substantially complementary (e.g., at least about 70% complementary) to the target DNA. In some embodiments, the first 1 to 10 nucleotides (e.g., the first 1, 2, 3, 4, 5, 6, 7, 8, 9, 10 nucleotides, and any range therein) of the 3' end of the spacer sequence may be 100% complementary to the target DNA, while the remaining nucleotides in the 5' region of the spacer sequence are substantially complementary (e.g., at least about 50% complementary (e.g., at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range or value therein)) to the target DNA.

In some embodiments, a seed region of a spacer may be about 8 to about 10 nucleotides in length, about 5 to about 6 nucleotides in length, or about 6 nucleotides in length.

As used herein, a "target nucleic acid", "target DNA," "target nucleotide sequence," "target region," or a "target region in the genome" refers to a region of a plant's genome that is fully complementary (100% complementary) or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a guide nucleic acid of this invention. A target region useful for a CRISPR-Cas system may be located immediately 3' (e.g., Type V CRISPR-Cas system) or immediately 5' (e.g., Type II CRISPR-Cas system) to a PAM sequence in the genome of the organism (e.g., a plant genome). A target region may be selected from any region of at least 15 consecutive nucleotides (e.g., 16, 17, 18, 19, 20, 21, 22, 23, 24, 25, 26, 27, 28, 29, 30 nucleotides, and the like) located immediately adjacent to a PAM sequence.

A "protospacer sequence" refers to the target double stranded DNA and specifically to the portion of the target DNA (e.g., or target region in the genome) that is fully or substantially complementary (and hybridizes) to the spacer sequence of the CRISPR repeat-spacer sequences (e.g., guide nucleic acids, CRISPR arrays, crRNAs).

In the case of Type V CRISPR-Cas (e.g., Cas12a) systems and Type II CRISPR-Cas (Cas9) systems, the protospacer sequence is flanked by (e.g., immediately adjacent to) a protospacer adjacent motif (PAM). For Type IV CRISPR-Cas systems, the PAM is located at the 5' end on the non-target strand and at the 3' end of the target strand (see below, as an example).

```
RNA Spacer
                                        (SEQ ID NO: 198)
5'-NNNNNNNNNNNNNNNNNNNN-3'

Target strand
                                        (SEQ ID NO: 199)
3'AAANNNNNNNNNNNNNNNNNNNNN-5'

Non-target strand
                                        (SEQ ID NO: 200)
5'TTTNNNNNNNNNNNNNNNNNNNNN-3'
```

In the case of Type II CRISPR-Cas (e.g., Cas9) systems, the PAM is located immediately 3' of the target region. The PAM for Type I CRISPR-Cas systems is located 5' of the target strand. There is no known PAM for Type III CRISPR-Cas systems. Makarova et al. describes the nomenclature for all the classes, types and subtypes of CRISPR systems (*Nature Reviews Microbiology* 13:722-736 (2015)). Guide structures and PAMs are described in by R. Barrangou (*Genome Biol.* 16:247 (2015)).

Canonical Cas12a PAMs are T rich. In some embodiments, a canonical Cas12a PAM sequence may be 5'-TTN, 5'-TTTN, or 5'-TTTV. In some embodiments, canonical Cas9 (e.g., *S. pyogenes*) PAMs may be 5'-NGG-3'. In some embodiments, non-canonical PAMs may be used but may be less efficient.

Additional PAM sequences may be determined by those skilled in the art through established experimental and computational approaches. Thus, for example, experimental approaches include targeting a sequence flanked by all possible nucleotide sequences and identifying sequence members that do not undergo targeting, such as through the transformation of target plasmid DNA (Esvelt et al. 2013. *Nat. Methods* 10:1116-1121; Jiang et al. 2013. *Nat. Biotechnol.* 31:233-239). In some aspects, a computational approach can include performing BLAST searches of natural spacers to identify the original target DNA sequences in bacteriophages or plasmids and aligning these sequences to determine conserved sequences adjacent to the target sequence (Briner and Barrangou. 2014. *Appl. Environ. Microbiol.* 80:994-1001; Mojica et al. 2009. *Microbiology* 155:733-740).

In some embodiments, the present invention provides expression cassettes and/or vectors comprising the nucleic acid constructs of the invention (e.g, one or more components of an editing system of the invention). In some embodiments, expression cassettes and/or vectors comprising the nucleic acid constructs of the invention and/or one or more guide nucleic acids may be provided. In some embodiments, a nucleic acid construct of the invention encoding a base editor (e.g., a construct comprising a CRISPR-Cas effector protein and a deaminase domain (e.g., a fusion protein)) or the components for base editing (e.g., a CRISPR-Cas effector protein fused to a peptide tag or an affinity polypeptide, a deaminase domain fused to a peptide tag or an affinity polypeptide, and/or a UGI fused to a peptide tag or an affinity polypeptide), may be comprised on the same or on a separate expression cassette or vector from that comprising the one or more guide nucleic acids. When the nucleic acid construct encoding a base editor or the components for base editing is/are comprised on separate expression cassette(s) or vector(s) from that comprising the guide nucleic acid, a target nucleic acid may be contacted with (e.g., provided with) the expression cassette(s) or vector(s) encoding the base editor or components for base editing in any order from one another and the guide nucleic acid, e.g., prior to, concurrently with, or after the expression cassette comprising the guide nucleic acid is provided (e.g., contacted with the target nucleic acid).

Fusion proteins of the invention may comprise sequence-specific DNA binding domains, CRISPR-Cas polypeptides, and/or deaminase domains fused to peptide tags or affinity polypeptides that interact with the peptide tags, as known in the art, for use in recruiting the deaminase to the target nucleic acid. Methods of recruiting may also comprise guide nucleic acids linked to RNA recruiting motifs and deaminases fused to affinity polypeptides capable of interacting with RNA recruiting motifs, thereby recruiting the deaminase to the target nucleic acid. Alternatively, chemical interactions may be used to recruit polypeptides (e.g., deaminases) to a target nucleic acid.

A peptide tag (e.g., epitope) useful with this invention may include, but is not limited to, a GCN4 peptide tag (e.g., Sun-Tag), a c-Myc affinity tag, an HA affinity tag, a His affinity tag, an S affinity tag, a methionine-His affinity tag, an RGD-His affinity tag, a FLAG octapeptide, a strep tag or strep tag II, a V5 tag, and/or a A,ISV-G epitope. Any epitope that may be linked to a polypeptide and for which there is a corresponding affinity polypeptide that may be linked to another polypeptide may be used with this invention as a peptide tag. In some embodiments, a peptide tag may comprise 1 or 2 or more copies of a peptide tag (e.g., repeat unit, multimerized epitope (e.g., tandem repeats)) (e.g., 1, 2, 3, 4, 5, 6, 7, 8, 9, 10, 11, 12, 13, 14, 15, 16, 17, 18, 19, 20, 21, 22, 23, 24, 25 or more repeat units. In some embodiments, an affinity polypeptide that interacts with/binds to a peptide tag may be an antibody. In some embodiments, the antibody may be a scFv antibody. In some embodiments, an affinity polypeptide that binds to a peptide tag may be synthetic (e.g., evolved for affinity interaction) including, but not limited to, an affibody, an anticalin, a monobody and/or a DARPin (see, e.g., Sha et al., *Protein Sci.* 26(5): 910-924 (2017)); Gilbreth (*Curr Opin Struc Biol* 22(4):413-420 (2013)), U.S. Pat. No. 9,982,053, each of which are incorporated by reference in their entireties for the teachings relevant to affibodies, anticalins, monobodies and/or DARPins.

In some embodiments, a guide nucleic acid may be linked to an RNA recruiting motif, and a polypeptide to be recruited (e.g., a deaminase) may be fused to an affinity polypeptide that binds to the RNA recruiting motif, wherein the guide binds to the target nucleic acid and the RNA recruiting motif binds to the affinity polypeptide, thereby recruiting the polypeptide to the guide and contacting the target nucleic acid with the polypeptide (e.g., deaminase). In some embodiments, two or more polypeptides may be recruited to a guide nucleic acid, thereby contacting the target nucleic acid with two or more polypeptides (e.g., deaminases).

In some embodiments, a polypeptide fused to an affinity polypeptide may be a reverse transcriptase and the guide nucleic acid may be an extended guide nucleic acid linked to an RNA recruiting motif. In some embodiments, an RNA recruiting motif may be located on the 3' end of the extended portion of an extended guide nucleic acid (e.g., 5'-3', repeat—spacer—extended portion (RT template-primer binding site)-RNA recruiting motif). In some embodiments, an RNA recruiting motif may be embedded in the extended portion.

In some embodiments of the invention, an extended guide RNA and/or guide RNA may be linked to one or to two or more RNA recruiting motifs (e.g., 1, 2, 3, 4, 5, 6, 7, 8, 9, 10 or more motifs, e.g., at least 10 to about 25 motifs), optionally wherein the two or more RNA recruiting motifs may be the same RNA recruiting motif or different RNA recruiting motifs. In some embodiments, an RNA recruiting motif and corresponding affinity polypeptide may include, but is not limited to, a telomerase Ku binding motif (e.g., Ku binding hairpin) and the corresponding affinity polypeptide Ku (e.g., Ku heterodimer), a telomerase Sm7 binding motif and the corresponding affinity polypeptide Sm7, an MS2 phage operator stem-loop and the corresponding affinity polypeptide MS2 Coat Protein (MCP), a PP7 phage operator stem-loop and the corresponding affinity polypeptide PP7 Coat Protein (PCP), an SfMu phage Com stem-loop and the corresponding affinity polypeptide Com RNA binding protein, a PUF binding site (PBS) and the affinity polypeptide Pumilio/fem-3 mRNA binding factor (PUF), and/or a synthetic RNA-aptamer and the aptamer ligand as the corresponding affinity polypeptide. In some embodiments, the RNA recruiting motif and corresponding affinity polypeptide may be an MS2 phage operator stem-loop and the affinity polypeptide MS2 Coat Protein (MCP). In some embodiments, the RNA recruiting motif and corresponding affinity polypeptide may be a PUF binding site (PBS) and the affinity polypeptide *Pumilio*/fem-3 mRNA binding factor (PUF).

In some embodiments, the components for recruiting polypeptides and nucleic acids may those that function through chemical interactions that may include, but are not limited to, rapamycin-inducible dimerization of FRB—FKBP; Biotin-streptavidin; SNAP tag; Halo tag; CLIP tag; DmrA-DmrC heterodimer induced by a compound; bifunctional ligand (e.g., fusion of two protein-binding chemicals together, e.g., dihydrofolate reductase (DHFR).

In some embodiments, the nucleic acid constructs, expression cassettes or vectors of the invention that are optimized for expression in a plant may be about 70% to 100% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to the nucleic acid constructs, expression cassettes or vectors comprising the same polynucleotide(s) but which have not been codon optimized for expression in a plant.

In some embodiments, the invention provides cells comprising one or more polynucleotides, guide nucleic acids, nucleic acid constructs, expression cassettes or vectors of the invention.

In some embodiments, a method of editing an endogenous HD-Zip transcription factor gene in a plant or plant part is provided, the method comprising contacting a target site in the HD-Zip transcription factor gene in the plant or plant part with a cytosine base editing system comprising a cytosine deaminase and a nucleic acid binding domain that binds to a target site in the HD-Zip transcription factor, the HD-Zip transcription factor gene encoding (a) a polypeptide comprising a sequence having at least 80% sequence identity to the amino acid sequence of SEQ ID NO:1 or SEQ ID NO:2; (b) a polypeptide comprising a sequence having at least 80% sequence identity to the amino acid sequence of SEQ ID NO:3; (c) a polypeptide comprising a sequence having at least 95% sequence identity to the nucleotide sequence of SEQ ID NO:4; (d) a polypeptide comprising a sequence having the amino acid sequence of SEQ ID NO:5, wherein X is L or S; (e) a polypeptide comprising: (i) a sequence having the amino acid sequence of RKKLRLX$_1$KX$_2$QX$_3$ (SEQ ID NO:6), wherein X$_1$ is S or T, X$_2$ is D or E and X$_3$ is S or A; (ii) a sequence having the amino acid sequence of PX$_1$X$_2$ X$_2$LTX$_3$CPX$_4$CER (SEQ ID NO:8), wherein X$_1$ is P or A, X$_2$ is T or A, X$_3$ is V or M and X$_4$ is Q, S or N; (iii) a sequence having the amino acid sequence of ENRRLX$_1$X$_2$EX$_3$, (SEQ ID NO:7), wherein X$_1$ is Q or H, X$_2$ is R or K and X$_3$ is V or L; and a sequence having the amino acid sequence of VWFQNRRA (SEQ ID NO:9) and/or (f) a polypeptide comprising a sequence having the amino acid sequence of VWFQNRRA (SEQ ID NO:9), thereby editing the endogenous HD-Zip transcription factor gene in the plant or part thereof and producing a plant or part thereof comprising at least one cell having a mutation in the endogenous HD-Zip transcription factor gene.

In some embodiments, a method of editing an endogenous HD-Zip transcription factor gene in a plant or plant part is provided, the method comprising contacting a target site in the HD-Zip transcription factor gene in the plant or plant part with a adenosine base editing system comprising an adenosine deaminase and a nucleic acid binding domain that binds to a target site in the HD-Zip transcription factor, the HD-Zip transcription factor gene encoding (a) a polypeptide comprising a sequence having at least 80% sequence identity to the amino acid sequence of SEQ ID NO:1 or SEQ ID NO:2; (b) a polypeptide comprising a sequence having at least 80% sequence identity to the amino acid sequence of SEQ ID NO:3; (c) a polypeptide comprising a sequence having at least 95% sequence identity to the nucleotide sequence of SEQ ID NO:4; (d) a polypeptide comprising a sequence having the amino acid sequence of SEQ ID NO:5, wherein X is L or S; (e) a polypeptide comprising: (i) a sequence having the amino acid sequence of RKKLRLX$_1$KX$_2$QX$_3$ (SEQ ID NO:6), wherein X$_1$ is S or T, X$_2$ is D or E and X$_3$ is S or A; (ii) a sequence having the amino acid sequence of PX$_1$X$_2$ X$_2$LTX$_3$CPX$_4$CER (SEQ ID NO:8), wherein X$_1$ is P or A, X$_2$ is T or A, X$_3$ is V or M and X$_4$ is Q, S or N; (iii) a sequence having the amino acid sequence of ENRRLX$_1$X$_2$EX$_3$, (SEQ ID NO:7), wherein X$_1$ is Q or H, X$_2$ is R or K and X$_3$ is V or L; and a sequence having the amino acid sequence of VWFQNRRA (SEQ ID NO:9) and/or (0 a polypeptide comprising a sequence having the amino acid sequence of VWFQNRRA (SEQ ID NO:9), thereby editing the endogenous HD-Zip transcription factor gene in the plant or part thereof and producing a plant or part thereof comprising at least one cell having a mutation in the endogenous HD-Zip transcription factor gene.

In some embodiments, a method of detecting a mutant HD-Zip (a mutation in an endogenous HD-Zip transcription factor gene) is provide, the method comprising detecting in the genome of a plant a deletion in a nucleic acid encoding the amino acid sequence of any one of SEQ ID NOs:1-98, wherein the amino acid sequence of any one of SEQ ID NOs:1-98 comprises the amino acid sequence of SEQ ID NO:9, and the deletion is in the nucleotide sequence encoding the amino acid sequence of SEQ ID NO:9.

In some embodiments, the present invention provides a method of detecting a mutation in an endogenous HD-Zip gene, comprising detecting in the genome of a plant a nucleotide sequence encoding at least one of any one of the polypeptide sequences of SEQ ID NOs:1-98.

In some embodiments, the present invention provides a method of producing a plant comprising a mutation in an endogenous HD-Zip transcription factor gene and at least one polynucleotide of interest, the method comprising crossing a plant of the invention comprising at least one mutation in an endogenous HD-Zip transcription factor gene (a first plant) with a second plant that comprises the at least one polynucleotide of interest to produce progeny plants; and selecting progeny plants comprising at least one mutation in the HD-Zip transcription factor gene and the at least one polynucleotide of interest, thereby producing the plant comprising a mutation in an endogenous HD-Zip transcription factor gene and at least one polynucleotide of interest.

The present invention further provides a method of producing a plant comprising a mutation in an endogenous HD-Zip transcription factor gene and at least one polynucleotide of interest, the method comprising introducing at least one polynucleotide of interest into a plant of the present invention comprising at least one mutation in a HD-Zip transcription factor gene, thereby producing a plant comprising at least one mutation in a HD-Zip transcription factor gene and at least one polynucleotide of interest.

In some embodiments, the present invention provides a method of producing a plant comprising a mutation in an endogenous HD-Zip transcription factor gene and at least one polynucleotide of interest, the method comprising introducing at least one polynucleotide of interest into a plant of the invention comprising at least one mutation in an endogenous HD-Zip transcription factor gene, thereby producing a plant comprising at least one mutation in a HD-Zip transcription factor gene and at least one polynucleotide of interest.

A polynucleotide of interest may be any polynucleotide that can confer a desirable phenotype or otherwise modify the phenotype or genotype of a plant. In some embodiments, a polynucleotide of interest may be polynucleotide that confers herbicide tolerance, insect resistance, disease resistance, increased yield, increased nutrient use efficiency or abiotic stress resistance.

In some embodiments, a method of producing a plant comprising a mutation in an endogenous HD-Zip transcription factor gene and having a dwarf or short stature phenotype is provided, the method comprising crossing a plant of the invention (a first plant) having at least one mutation in an endogenous HD-Zip transcription factor gene with a second plant that comprises the dwarf or short stature phenotype to produce progeny plants; and selecting progeny plants comprising the at least one mutation in the HD-Zip transcription factor gene and the dwarf or short stature phenotype, thereby producing the plant having a dwarf or short stature and comprising at least one mutation in an endogenous HD-Zip transcription factor gene.

The present invention further provides a method of controlling weeds in a container (e.g., pot, or seed tray and the like), a growth chamber, a greenhouse, a field (e.g., a cultivated field), a recreational area, a lawn, and/or a roadside comprising one or more (a plurality) plants of the present invention, comprising applying an herbicide to one or more (a plurality) plants of the present invention growing in the container, growth chamber, field or greenhouse, thereby controlling the weeds in the container, growth chamber, greenhouse, field, recreational area, a lawn, and/or a roadside in which the one or more plants are growing.

In some embodiments, a method of reducing insect predation on a plant (or a plurality of plants) is provided, comprising applying an insecticide to one or more (a plurality) plants of the present invention, thereby reducing the insect predation on the one or more (a plurality) plants. In some embodiments the one or more plants may be growing in a container, a growth chamber, a field, a recreational area (e.g., playing field, golf course), a lawn, roadside, or a greenhouse.

In some embodiments, the present invention provides a method of reducing fungal disease on a plant, comprising applying a fungicide to one or more (a plurality) plants of the present invention, thereby reducing fungal disease on the on the one or more (a plurality) plants. In some embodiments the one or more plants may be growing in a container, a growth chamber, a field, a recreational area (e.g., playing field, golf course), a lawn, a roadside, or a greenhouse.

The nucleic acid constructs of the invention (e.g., a construct comprising a sequence specific DNA binding domain, a CRISPR-Cas effector domain, a deaminase domain, reverse transcriptase (RT), RT template and/or a guide nucleic acid, etc.) and expression cassettes/vectors comprising the same may be used as an editing system of this invention for modifying target nucleic acids and/or their expression.

A target nucleic acid of any plant or plant part (or groupings of plants, for example, into a genus or higher order classification) may be modified (e.g., mutated, e.g., base edited, cleaved, nicked, etc.) using the polypeptides, polynucleotides, RNPs, nucleic acid constructs, expression cassettes, and/or vectors of the invention including an angiosperm, a gymnosperm, a monocot, a dicot, a C3, C4, CAM plant, a bryophyte, a fern and/or fern ally, a microalgae, and/or a macroalgae. A plant and/or plant part that may be modified as described herein may be a plant and/or plant part of any plant species/variety/cultivar. In some embodiments, a plant that may be modified as described herein is a monocot. In some embodiments, a plant that may be modified as described herein is a dicot.

The term "plant part," as used herein, includes but is not limited to reproductive tissues (e.g., petals, sepals, stamens, pistils, receptacles, anthers, pollen, flowers, fruits, flower bud, ovules, seeds, embryos, nuts, kernels, ears, cobs and husks); vegetative tissues (e.g., petioles, stems, roots, root hairs, root tips, pith, coleoptiles, stalks, shoots, branches, bark, apical meristem, axillary bud, cotyledon, hypocotyls, and leaves); vascular tissues (e.g., phloem and xylem); specialized cells such as epidermal cells, parenchyma cells, chollenchyma cells, schlerenchyma cells, stomates, guard cells, cuticle, mesophyll cells; callus tissue; and cuttings. The term "plant part" also includes plant cells, including plant cells that are intact in plants and/or parts of plants, plant protoplasts, plant tissues, plant organs, plant cell tissue cultures, plant calli, plant clumps, and the like. As used herein, "shoot" refers to the above ground parts including the leaves and stems. As used herein, the term "tissue culture" encompasses cultures of tissue, cells, protoplasts and callus.

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ. In some embodiments, a plant cell can be an algal cell. A "protoplast" is an isolated plant cell without a cell wall or with only parts of the cell wall. Thus, in some embodiments of the invention, a transgenic cell comprising a nucleic acid molecule and/or nucleotide sequence of the invention is a cell of any plant or plant part including, but not limited to, a root cell, a leaf cell, a tissue culture cell, a seed cell, a flower cell, a fruit cell, a pollen cell, and the like. In some aspects of the invention, the plant part can be a plant germplasm. In some aspects, a plant cell can be non-propagating plant cell that does not regenerate into a plant.

"Plant cell culture" means cultures of plant units such as, for example, protoplasts, cell culture cells, cells in plant tissues, pollen, pollen tubes, ovules, embryo sacs, zygotes and embryos at various stages of development.

As used herein, a "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

In some embodiments of the invention, a transgenic tissue culture or transgenic plant cell culture is provided, wherein the transgenic tissue or cell culture comprises a nucleic acid molecule/nucleotide sequence of the invention. In some embodiments, transgenes may be eliminated from a plant developed from the transgenic tissue or cell by breeding of the transgenic plant with a non-transgenic plant and selecting among the progeny for the plants comprising the desired gene edit and not the transgenes used in producing the edit.

Any plant comprising an endogenous HD-Zip transcription factor gene that is capable of regulating a Shade Avoidance Response (SAR) in a plant may be modified as described herein to reduce/attenuate or eliminate SAR in the plant. In some embodiments, a plant may be a monocot. In some embodiments, a plant may be a dicot.

Non-limiting examples of plants that may be modified as described herein may include, but are not limited to, turf grasses (e.g., bluegrass, bentgrass, ryegrass, fescue), feather reed grass, tufted hair grass, miscanthus, arundo, switchgrass, vegetable crops, including artichokes, kohlrabi, arugula, leeks, asparagus, lettuce (e.g., head, leaf, romaine), malanga, melons (e.g., muskmelon, watermelon, crenshaw, honeydew, cantaloupe), cole crops (e.g., brussels sprouts, cabbage, cauliflower, broccoli, collards, kale, chinese cabbage, bok choy), cardoni, carrots, napa, okra, onions, celery, parsley, chick peas, parsnips, chicory, peppers, potatoes, cucurbits (e.g., marrow, cucumber, zucchini, squash, pumpkin, honeydew melon, watermelon, cantaloupe), radishes, dry bulb onions, rutabaga, eggplant, salsify, escarole, shallots, endive, garlic, spinach, green onions, squash, greens, beet (sugar beet and fodder beet), sweet potatoes, chard, horseradish, tomatoes, turnips, and spices; a fruit crop such as apples, apricots, cherries, nectarines, peaches, pears, plums, prunes, cherry, quince, fig, nuts (e.g., chestnuts, pecans, pistachios, hazelnuts, pistachios, peanuts, walnuts, macadamia nuts, almonds, and the like), citrus (e.g., clementine, kumquat, orange, grapefruit, tangerine, mandarin, lemon, lime, and the like), blueberries, black raspberries, boysenberries, cranberries, currants, gooseberries, loganberries, raspberries, strawberries, blackberries, grapes (wine and table), avocados, bananas, kiwi, persimmons, pomegranate, pineapple, tropical fruits, pomes, melon, mango, papaya, and lychee, a field crop plant such as clover, alfalfa, timothy, evening primrose, meadow foam, corn/maize (field, sweet, popcorn), hops, jojoba, buckwheat, safflower, quinoa, wheat, rice, barley, rye, millet, sorghum, oats, triticale, sorghum, tobacco, kapok, a leguminous plant (beans (e.g., green and dried), lentils, peas, soybeans), an oil plant (rape, canola, mustard, poppy, olive, sunflower, coconut, castor oil plant, cocoa bean, groundnut, oil palm), duckweed, *Arabidopsis*, a fiber plant (cotton, flax, hemp, jute), *Cannabis* (e.g., *Cannabis sativa, Cannabis indica*, and *Cannabis ruderalis*), lauraceae (cinnamon, camphor), or a plant such as coffee, sugar cane, tea, and natural rubber plants; and/or a bedding plant such as a flowering plant, a cactus, a succulent and/or an ornamental plant (e.g., roses, tulips, violets), as well as trees such as forest trees (broad-leaved trees and evergreens, such as conifers; e.g., elm, ash, oak, maple, fir, spruce, cedar, pine, birch, cypress, eucalyptus, willow), as well as shrubs and other nursery stock. In some embodiments, the nucleic acid constructs of the invention and/or expression cassettes and/or vectors encoding the same may be used to modify maize, soybean, wheat, canola, rice, tomato, pepper, or sunflower.

In some embodiments, a plant that may be modified as described herein may include, but is not limited to, corn, soy, canola, wheat, rice, cotton, sugarcane, sugar beet, barley, oats, alfalfa, sunflower, safflower, oil palm, sesame, coconut, tobacco, potato, sweet potato, cassava, coffee, apple, plum, apricot, peach, cherry, pear, fig, banana, citrus, cocoa, avocado, olive, almond, walnut, strawberry, watermelon, pepper, grape, tomato, cucumber, or a *Brassica* spp (e.g., *B. napus, B. oleraceae, B. rapa, B. juncea*, and/or *B. nigra*). In some embodiments, a plant that may be modified as described herein is corn (i.e., maize, *Zea mays*, optionally wherein the corn plant comprises a short stature/semi-dwarf phenotype.

In some embodiments, a plant that may be modified as described herein is wheat (e.g., *Triticum aestivum, T. durum*, and/or *T. compactum*). In some embodiments, a wheat plant may comprise at least one non-natural mutation in an endogenous HD-Zip transcription factor in its A genome, in its B genome, and/or in its D genome.

Thus, plants or plant cultivars which are to be treated with preference in accordance with the invention include all plants which, through genetic modification, received genetic material which imparts particular advantageous useful properties ("traits") to these plants. Examples of such properties are better plant growth, vigor, stress tolerance, standability, lodging resistance, nutrient uptake, plant nutrition, and/or yield, in particular improved growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processability of the harvested products.

Further and particularly emphasized examples of such properties are an increased resistance against animal and microbial pests, such as against insects, arachnids, nematodes, mites, slugs and snails owing, for example, to toxins formed in the plants. Among DNA sequences encoding proteins which confer properties of tolerance to such animal and microbial pests, in particular insects, mention will particularly be made of the genetic material from *Bacillus thuringiensis* encoding the Bt proteins widely described in the literature and well known to those skilled in the art. Mention will also be made of proteins extracted from bacteria such as *Photorhabdus* (WO97/17432 and WO98/08932). In particular, mention will be made of the Bt Cry or VIP proteins which include the Cry1A, Cry1Ab, Cry1Ac, CryIIA, CryIIIA, CryIIIB2, Cry9c Cry2Ab, Cry3Bb and CryIF proteins or toxic fragments thereof and also hybrids or combinations thereof, especially the Cry1F protein or hybrids derived from a Cry1F protein (e.g. hybrid Cry1A-Cry1F proteins or toxic fragments thereof), the Cry1A-type proteins or toxic fragments thereof, preferably the Cry1Ac protein or hybrids derived from the Cry1Ac protein (e.g. hybrid Cry1Ab-Cry1Ac proteins) or the Cry1Ab or Bt2 protein or toxic fragments thereof, the Cry2Ae, Cry2Af or Cry2Ag proteins or toxic fragments thereof, the Cry1A.105 protein or a toxic fragment thereof, the VIP3Aa19 protein, the VIP3Aa20 protein, the VIP3A proteins produced in the COT202 or COT203 cotton events, the VIP3Aa protein or a toxic fragment thereof as described in Estruch et al. (1996), *Proc Natl Acad Sci US A*. 28; 93(11):5389-94, the Cry proteins as described in WO2001/47952, the insecticidal proteins from Xenorhabdus (as described in WO98/50427), *Serratia* (particularly from *S. entomophila*) or *Photorhabdus* species strains, such as Tc-proteins from *Photorhabdus* as described in WO98/08932. Also, any variants or mutants of any one of these proteins differing in some amino acids (1-10, preferably 1-5) from any of the above-named sequences, particularly the sequence of their toxic fragment, or which are fused to a transit peptide, such as a plastid transit peptide, or another protein or peptide, is included herein.

Another and particularly emphasized example of such properties is conferred tolerance to one or more herbicides, for example imidazolinones, sulphonylureas, glyphosate or phosphinothricin. Among DNA sequences encoding proteins (i.e., polynucleotides of interest) which confer properties of tolerance to certain herbicides on the transformed plant cells and plants, mention will be particularly be made to the bar or PAT gene or the *Streptomyces coelicolor* gene described in WO2009/152359 which confers tolerance to glufosinate herbicides, a gene encoding a suitable EPSPS (5-Enolpyruvylshikimat-3-phosphat-Synthase) which confers tolerance to herbicides having EPSPS as a target, especially herbicides such as glyphosate and its salts, a gene encoding glyphosate-n-acetyltransferase, or a gene encoding glyphosate oxidoreductase. Further suitable herbicide tolerance traits include at least one ALS (acetolactate synthase) inhibitor (e.g., WO2007/024782), a mutated *Arabidopsis* ALS/AHAS gene (e.g., U.S. Pat. No. 6,855,533), genes encoding 2,4-D-monooxygenases conferring tolerance to 2,4-D (2,4-dichlorophenoxyacetic acid) and genes encoding Dicamba monooxygenases conferring tolerance to dicamba (3,6-dichloro-2-methoxybenzoic acid).

Further and particularly emphasized examples of such properties are increased resistance against phytopathogenic fungi, bacteria and/or viruses owing, for example, to systemic acquired resistance (SAR), systemin, phytoalexins, elicitors and also resistance genes and correspondingly expressed proteins and toxins.

Particularly useful transgenic events in transgenic plants or plant cultivars which can be treated with preference in accordance with the invention include Event 531/PV-GHBK04 (cotton, insect control, described in WO2002/040677), Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US-A 2002-120964 or WO2002/034946); Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control-herbicide tolerance, deposited as PTA-6233, described in WO2005/103266 or US-A 2005-216969); Event 3006-210-23 (cotton, insect control-herbicide tolerance, deposited as PTA-6233, described in US-A 2007-143876 or WO2005/103266); Event 3272 (corn, quality trait, deposited as PTA-9972, described in WO2006/098952 or US-A 2006-230473); Event 33391 (wheat, herbicide tolerance, deposited as PTA-2347, described in WO2002/027004), Event 40416 (corn, insect control-herbicide tolerance, deposited as ATCC PTA-11508, described in WO 11/075593); Event 43A47 (corn, insect control-herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US-A 2006-162007 or WO2004/053062); Event B16 (corn, herbicide tolerance, not deposited, described in US-A 2003-126634); Event BPS-CV127-9 (soybean, herbicide tolerance, deposited as NCIMB No. 41603, described in WO2010/080829); Event BLRI (oilseed rape, restoration of male sterility, deposited as NCIMB 41193, described in WO2005/074671), Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US-A 2006-130175 or WO2004/039986); Event COT202 (cotton, insect control, not deposited, described in US-A 2007-067868 or WO2005/054479); Event COT203 (cotton, insect control, not deposited, described in WO2005/054480);); Event DAS21606-3/1606 (soybean, herbicide tolerance, deposited as PTA-11028, described in WO2012/033794), Event DAS40278 (corn, herbicide tolerance, deposited as ATCC PTA-10244, described in WO2011/022469); Event DAS-44406-6/pDAB8264.44.06.1 (soybean, herbicide tolerance, deposited as PTA-11336, described in WO2012/075426), Event DAS-14536-7/pDAB8291.45.36.2 (soybean, herbicide tolerance, deposited as PTA-11335, described in WO2012/075429), Event DAS-59122-7 (corn, insectcontrol-herbicide tolerance, deposited as ATCC PTA 11384, described in US-A2006-070139); Event DAS-59132 (corn, insect control-herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US-A 2009-137395 orWO 08/112019); Event DP-305423-1 (soybean, quality trait, not deposited, described in US-A 2008-312082 or WO2008/054747); Event DP-32138-1 (corn, hybridization system, deposited as ATCC PTA-9158, described in US-A 2009-0210970 or WO2009/103049); Event DP-356043-5 (soybean, herbicide tolerance, deposited as ATCC PTA-8287, described in US-A 2010-0184079 or WO2008/002872); EventEE-I (brinjal, insect control, not deposited, described in WO 07/091277); Event Fil 17 (corn, herbicide tolerance, deposited as ATCC 209031, described in US-A 2006-059581 or WO 98/044140); Event FG72 (soybean, herbicide tolerance, deposited as PTA-11041, described in WO2011/063413), Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO98/044140); Event GHB119 (cotton, insect control-herbicide tolerance, deposited as ATCC PTA-8398, described in WO2008/151780); Event GHB614 (cotton, herbicide tolerance, deposited as ATCC PTA-6878, described in US-A 2010-050282 or WO2007/017186); Event GJ11 (corn, herbicide tolerance, deposited as ATCC 209030, described in US-A 2005-188434 or WO98/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US-A 2004-172669 or WO 2004/074492); Event JOPLIN1 (wheat, disease tolerance, not deposited, described in US-A 2008-064032); Event LL27 (soybean, herbicide tolerance, deposited as NCIMB41658, described in WO2006/108674 or US-A 2008-320616); Event LL55 (soybean, herbicide tolerance, deposited as NCIMB 41660, described in WO 2006/108675 or US-A 2008-196127); Event LLcotton25 (cotton, herbicide tolerance, deposited as ATCC PTA-3343, described in WO2003/013224 or US-A 2003-097687); Event LLRICE06 (rice, herbicide tolerance, deposited as ATCC 203353, described in U.S. Pat. No. 6,468,747 or WO2000/026345); Event LLRice62 (rice, herbicide tolerance, deposited as ATCC 203352, described in WO2000/026345), Event LLRICE601 (rice, herbicide tolerance, deposited as ATCC PTA-2600, described in US-A 2008-2289060 or WO2000/026356); Event LY038 (corn, quality trait, deposited as ATCC PTA-5623, described in US-A 2007-028322 or WO2005/061720); Event MIR162 (corn, insect control, deposited as PTA-8166, described in US-A 2009-300784 or WO2007/142840); Event MIR604 (corn, insect control, not deposited, described in US-A 2008-167456 or WO2005/103301); Event MON15985 (cotton, insect control, deposited as ATCC PTA-2516, described in US-A 2004-250317 or WO2002/100163); Event MON810 (corn, insect control, not deposited, described in US-A 2002-102582); Event MON863 (corn, insect control, deposited as ATCC PTA-2605, described in WO2004/011601 or US-A 2006-095986); Event MON87427 (corn, pollination control, deposited as ATCC PTA-7899, described in WO2011/062904); Event MON87460 (corn, stress tolerance, deposited as ATCC PTA-8910, described in WO2009/111263 or US-A 2011-0138504); Event MON87701 (soybean, insect control, deposited as ATCC PTA-8194, described in US-A 2009-130071 or WO2009/064652); Event MON87705 (soybean, quality trait-herbicide tolerance, deposited as ATCC PTA-9241, described in US-A 2010-0080887 or WO2010/037016); Event MON87708 (soybean, herbicide tolerance, deposited as ATCC PTA-9670, described in WO2011/034704); Event MON87712 (soybean, yield, deposited as PTA-10296, described in WO2012/051199), Event MON87754 (soybean, quality trait, deposited as ATCC PTA-9385, described in WO2010/024976); Event MON87769 (soybean, quality trait, deposited as ATCC PTA-8911, described in US-A 2011-0067141 or WO2009/102873); Event MON88017 (corn, insect control-herbicide tolerance, deposited as ATCC PTA-5582, described in US-A 2008-028482 or WO2005/059103); Event MON88913 (cotton, herbicide tolerance, deposited as ATCC PTA-4854, described in WO2004/072235 or US-A 2006-059590); Event MON88302 (oilseed rape, herbicide tolerance, deposited as PTA-10955, described in WO2011/153186), Event MON88701 (cotton, herbicide tolerance, deposited as PTA-11754, described in WO2012/134808), Event MON89034 (corn, insect control, deposited as ATCC PTA-7455, described in WO 07/140256 or US-A 2008-260932); Event MON89788 (soybean, herbicide tolerance, deposited as ATCC PTA-6708, described in US-A 2006-282915 or WO2006/130436); Event MS1 1 (oilseed rape, pollination control-herbicide tolerance, deposited as ATCC PTA-850 or PTA-2485, described in WO2001/031042); Event MS8 (oilseed rape, pollination control-herbicide tolerance, deposited as ATCC PTA-730, described in WO2001/041558 or US-A 2003-188347); Event NK603 (corn, herbicide tolerance, deposited as ATCC PTA-2478, described in US-A 2007-292854); Event PE-7 (rice, insect control, not deposited, described in WO2008/114282); Event RF3 (oilseed rape, pollination control-herbicide tolerance, deposited as ATCC PTA-730, described in WO2001/041558 or US-A 2003-188347); Event RT73 (oilseed rape, herbicide tolerance, not deposited, described in WO2002/036831 or US-A 2008-070260); Event SYHT0H2/SYN-000H2-5 (soybean, herbicide tolerance, deposited as PTA-11226, described in WO2012/082548), Event T227-1 (sugar beet, herbicide tolerance, not deposited, described in WO2002/44407 or US-A 2009-265817); Event T25 (corn, herbicide tolerance, not deposited, described in US-A 2001-029014 or WO2001/051654); Event T304-40 (cotton, insect control-herbicide tolerance, deposited as ATCC PTA-8171, described in US-A 2010-077501 or WO2008/122406); Event T342-142 (cotton, insect control, not deposited, described in WO2006/128568); Event TC1507 (corn, insect control-herbicide tolerance, not deposited, described in US-A 2005-039226 or WO2004/099447); Event VIP1034 (corn, insect control-herbicide tolerance, deposited as ATCC PTA-3925, described in WO2003/052073), Event 32316 (corn, insect control-herbicide tolerance, deposited as PTA-11507, described in WO2011/084632), Event 4114 (corn, insect control-herbicide tolerance, deposited as PTA-11506, described in WO2011/084621), event EE-GM3/FG72 (soybean, herbicide tolerance, ATCC Accession N° PTA-11041) optionally stacked with event EE-GM1/LL27 or event EE-GM2/LL55 (WO2011/063413A2), event DAS-68416-4 (soybean, herbicide tolerance, ATCC Accession N° PTA-10442, WO2011/066360A1), event DAS-68416-4 (soybean, herbicide tolerance, ATCC Accession N° PTA-10442, WO2011/066384A1), event DP-040416-8 (corn, insect control, ATCC Accession N° PTA-11508, WO2011/075593A1), event DP-043A47-3 (corn, insect control, ATCC Accession N° PTA-11509, WO2011/075595A1), event DP-004114-3 (corn, insect control, ATCC Accession N° PTA-11506, WO2011/084621A1), event DP-032316-8 (corn, insect control, ATCC Accession N° PTA-11507, WO2011/084632A1), event MON-88302-9 (oilseed rape, herbicide tolerance, ATCC Accession N° PTA-10955, WO2011/153186A1), event DAS-21606-3 (soybean, herbicide tolerance, ATCC Accession No. PTA-11028, WO2012/033794A2), event MON-87712-4 (soybean, quality trait, ATCC Accession N°. PTA-10296, WO2012/051199A2), event DAS-44406-6 (soybean, stacked herbicide tolerance, ATCC Accession N°. PTA-11336, WO2012/075426A1), event DAS-14536-7 (soybean, stacked herbicide tolerance, ATCC Accession N°. PTA-11335, WO2012/075429A1), event SYN-000H2-5 (soybean, herbicide tolerance, ATCC Accession N°. PTA-11226, WO2012/082548A2), event DP-061061-7 (oilseed rape, herbicide tolerance, no deposit N° available, WO2012071039A1), event DP-073496-4 (oilseed rape, herbicide tolerance, no deposit N° available, US2012131692), event 8264.44.06.1 (soybean, stacked herbicide tolerance, Accession N° PTA-11336, WO2012075426A2), event 8291.45.36.2 (soybean, stacked herbicide tolerance, Accession N°. PTA-11335, WO2012075429A2), event SYHT0H2 (soybean, ATCC Accession N°. PTA-11226, WO2012/082548A2), event MON88701 (cotton, ATCC Accession N° PTA-11754, WO2012/134808A1), event KK179-2 (alfalfa, ATCC Accession N° PTA-11833, WO2013/003558A1), event pDAB8264.42.32.1 (soybean, stacked herbicide tolerance, ATCC Accession N° PTA-11993, WO2013/010094A1), event MZDT09Y (corn, ATCC Accession N° PTA-13025, WO2013/012775A1).

The genes/events (e.g., polynucleotides of interest), which impart the desired traits in question, may also be present in combinations with one another in the transgenic plants. Examples of transgenic plants which may be mentioned are the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits such as apples, pears, citrus fruits and grapes), with particular emphasis being given to maize, soya beans, wheat, rice, potatoes, cotton, sugar cane, tobacco and oilseed rape. Traits which are particularly emphasized are the increased resistance of the plants to insects, arachnids, nematodes and slugs and snails, as well as the increased resistance of the plants to one or more herbicides.

Commercially available examples of such plants, plant parts or plant seeds that may be treated with preference in accordance with the invention include commercial products, such as plant seeds, sold or distributed under the GENUITY®, DROUGHTGARD®, SMARTSTAX®, RIB COMPLETE®, ROUNDUP READY®, VT DOUBLE PRO®, VT TRIPLE PRO®, BOLLGARD II®, ROUNDUP READY 2 YIELD®, YIELDGARD®, ROUNDUP READY® 2 XTEN$^{DTM}$, INTACTA RR2 PRO®, VISTIVE GOLD®, and/or XTENDFLEX™ trade names.

The invention will now be described with reference to the following examples. It should be appreciated that these examples are not intended to limit the scope of the claims to the invention but are rather intended to be exemplary of certain embodiments. Any variations in the exemplified methods that occur to the skilled artisan are intended to fall within the scope of the invention.

EXAMPLES

Example 1. Design of the Genomic Editing Construct for HB53 and HB78

The genomic sequences of Zm00001d002754 (HB53) and Zm00001d029934 (HB78) (*Zea mays*) were identified from a proprietary maize line. From this reference line, spacer sequences SEQ ID NO: 175-182 were identified. The editing constructs (pWISE444 targeting HB53 and pWISE451 targeting both HB53/HB78) contained a CRISPR-Cas effector protein (FIG. 13, pWISE451 used all the guides from illustrated pWISE). The CRISPR-Cas effector protein associates with a spacer nucleic acid that is specific to the DNA sequence of HB53/HB78 transcription factor of maize. A Cpf1 cutting enzyme was used to create unique disruptions of the DNA binding domain of the gene targets.

Example 2. Transformation and Selection of Edited E0 Plants

Dried excised maize embryos were transformed using *Agrobacterium* to deliver the editing construct. Healthy non-chimeric plants (E0) were selected and plugged in growth trays. Genotyping of E0 plants was performed to assess transgene copy and editing efficacy. Plants identified to be (1) healthy, non-chimeric and fertile, with (2) low transgene copy and (3) a disrupted DNA binding domain were advanced to the next generation. E0 plants that satisfy all the above criteria were selfed to produce E1 generation.

Figure 10:
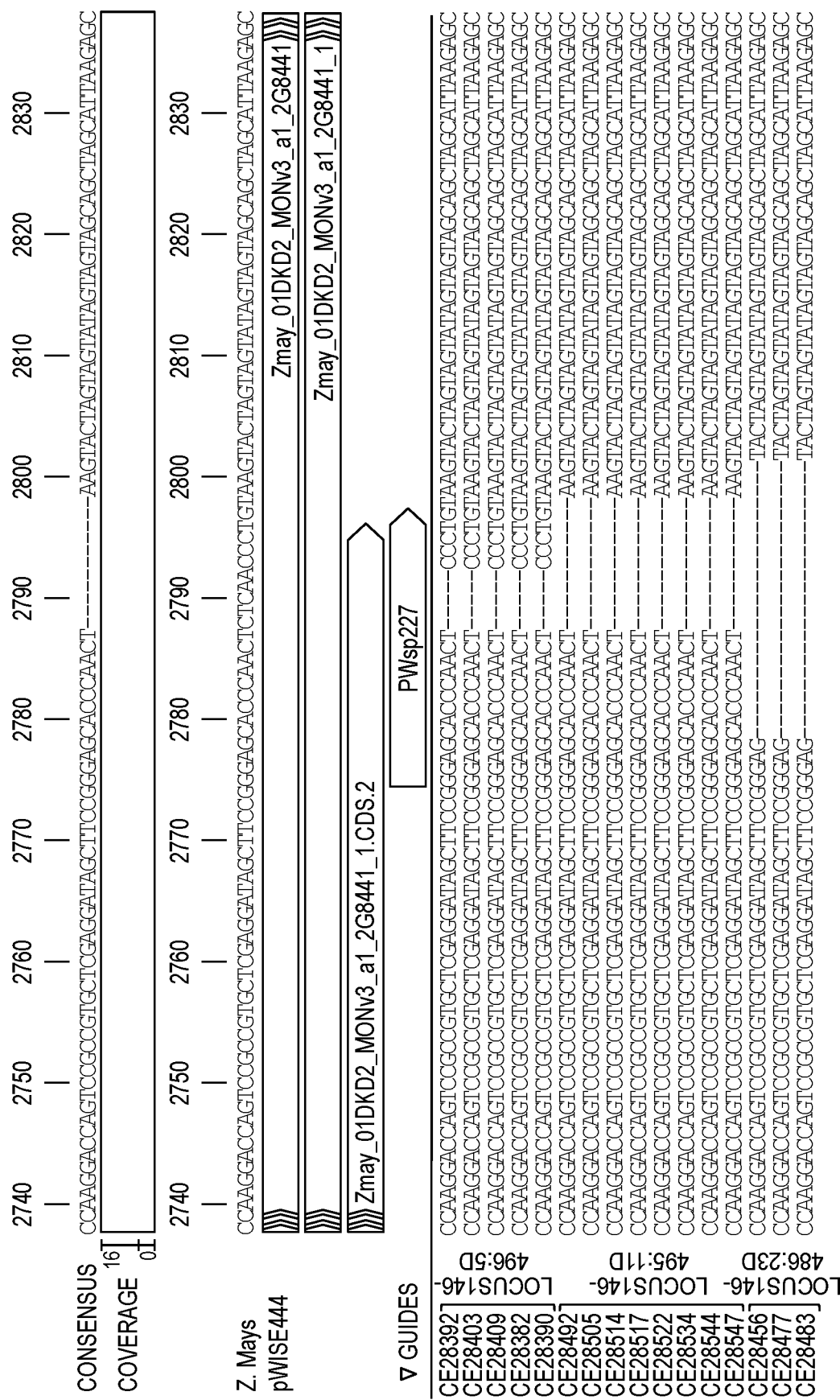
FIG. 10 provides an alignment showing the location of the guide PWsp227 and resulting edits in Zea mays HB53 (consensus SEQ ID NO:320; Z. mays SEQ ID NO:321; CE28392, CE28403, CE28409, CE28382, CE28390 SEQ ID NO:322; CE28492, CE28505, CE28514, CE28517, CE28522, CE28534, CE28544, CE28547 SEQ ID NO:320); CE28456, CE28477, CE28483 SEQ ID NO:323).

For pWISE444, 110 E0 plants were derived from a single transformation experiment. From this pool of E0 plants, we identified plants possessing out-of-frame deletions leading to disruption of the HB53 DNA binding domain. Table 1 provides plant identifiers, identified deletions and the ultimately advanced E1 alleles. FIG. 10 shows the genotypes of E1 progenies derived from advanced E0 parents.

TABLE 1

| HB53 E0 Parent plants and identified alleles | | |
|---|---|---|
| E0 parent | E0 alleles | E1 allele (advanced) |
| CE-9775 | Heterozygous (5 bp and 7bp deletion) | Homozygous 5 bp deletion |
| CE-9787 | Heterozygous (11 bp and 14bp deletion) | Homozygous 11 bp deletion |
| CE-9778 | Het-WT (23 bp deletion) | Homozygous 23 bp deletion |

Figure 11:
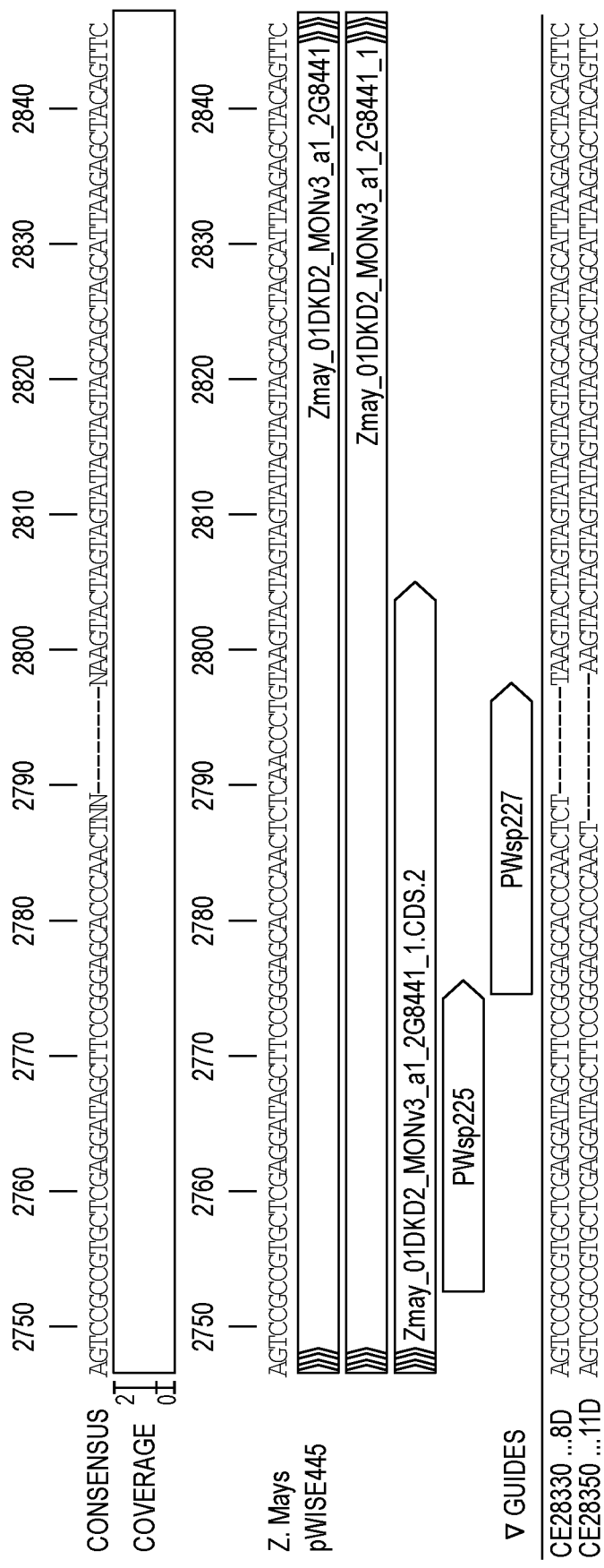
FIG. 11 provides an alignment showing the location of the guide PWsp227 and PWsp225 and resulting edits in Z. mays HB53 (consensus SEQ ID NO:324; Z. mays SEQ ID NO:325; CE28330 . . . 8D SEQ ID NO:326; CE28350 . . . 11D SEQ ID NO:327.
Figure 12:
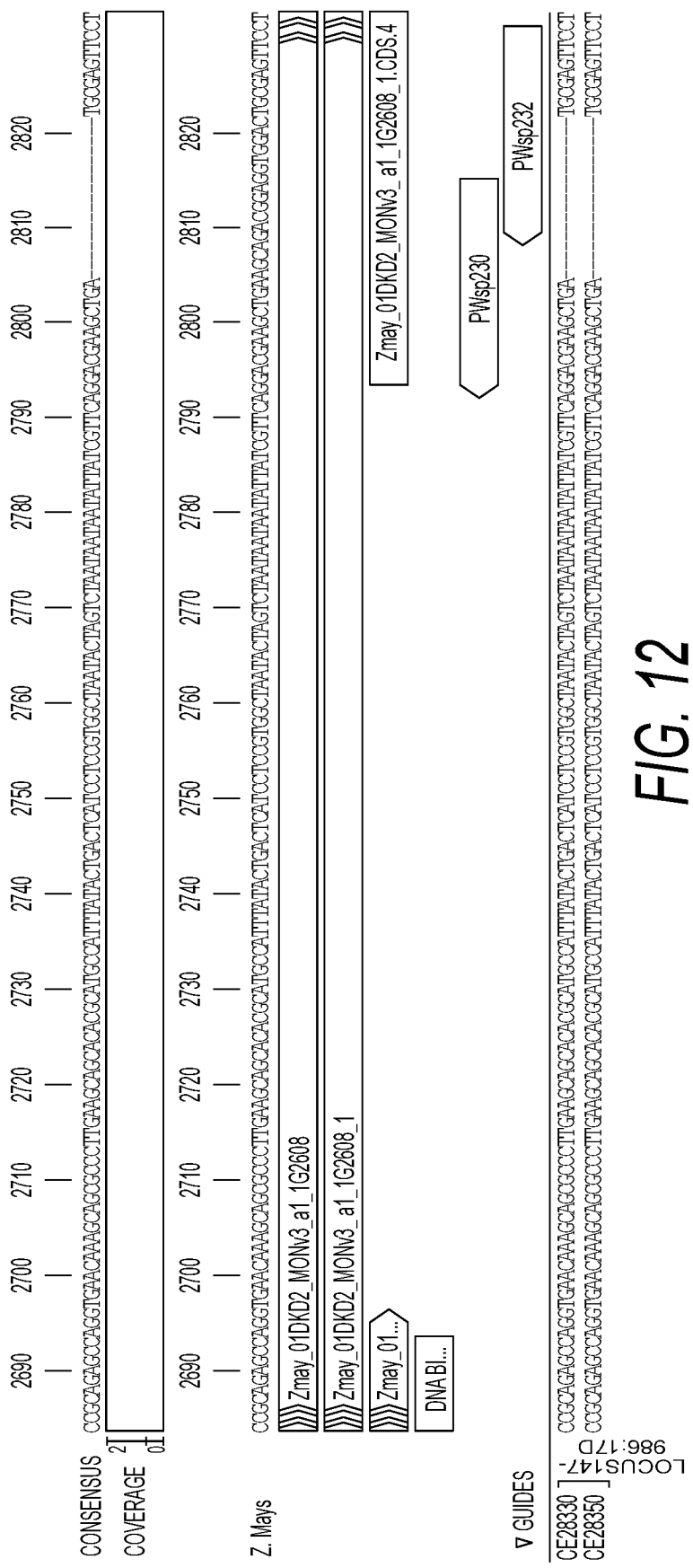
FIG. 12 provides an alignment showing the location of the guide PWsp230 and PWsp232 and resulting edits in Z. mays HB78 (consensus SEQ ID NO:328; Z. mays SEQ ID NO:329; CE28330 SEQ ID NO:328; CE28350 SEQ ID NO:328).

For pWISE451, a single transformation experiment produced 44 E0 events. Of these, a single E0 plant with the desired out-of-frame deletions was advanced. FIG. 11 and FIG. 12 show the nature of the edits for HB53 and HB78 E1 progenies, respectively.

In addition to pWISE444 and pWISE451, other transformation experiments produced desired edits on HB78. FIG. 9 shows the genomic sequence of a representative edited plant. It shows that the 10-bp out-of-frame deletion upstream the target DNA binding domain resulted in a premature stop codon and therefore loss of the DNA binding domain.

Example 3. Phenotypic Assessment of Trait Activity

For each E1 family, 100 seeds were planted and screened. Plants identified as being (1) healthy, non-chimeric and fertile, (2) transgene free, (3) having a disrupted DNA binding domain were advanced to the next generation. Trait activity is generally assessed at the E2 stage. To assess trait activity of the advanced desired edits, 10-day old seedlings were exposed to a simulated shade environment. A custom lighting array was built from 12 CREE 6500k 36V COBs supplemented with over 330 2.25V CREE Far Red LEDs (720-740) with a Bluefish controller. Other similar lighting may be used to simulate a shade environment.

Edited corn seedlings and control (wild-type and GUS controls) corn seedlings were grown in a growth tent with simulated shade environment in which they experienced red to far red wavelength ratio of 0.15 at 400 µmol m$^{-2}$ s$^{-1}$ PAR (photosynthetically active radiation). The edited corn seedlings and control corn seedlings were also grown in a separate growth tent where they experienced red to far-red ratio of 1.3 and 400 Ξmol m$^{-2}$ s$^{-1}$ PAR (non-shade). Plant height was measured at the three height markers (coleoptile, V1 sheath, V2 sheath) and compared between controls and edited plants in the simulated shade and non-shade environment. An editing event was considered trait-active when edited plants grown in simulated shade were 5%, 10%, 15% (or more) shorter than the control plants (wild-type).

Figure 14:
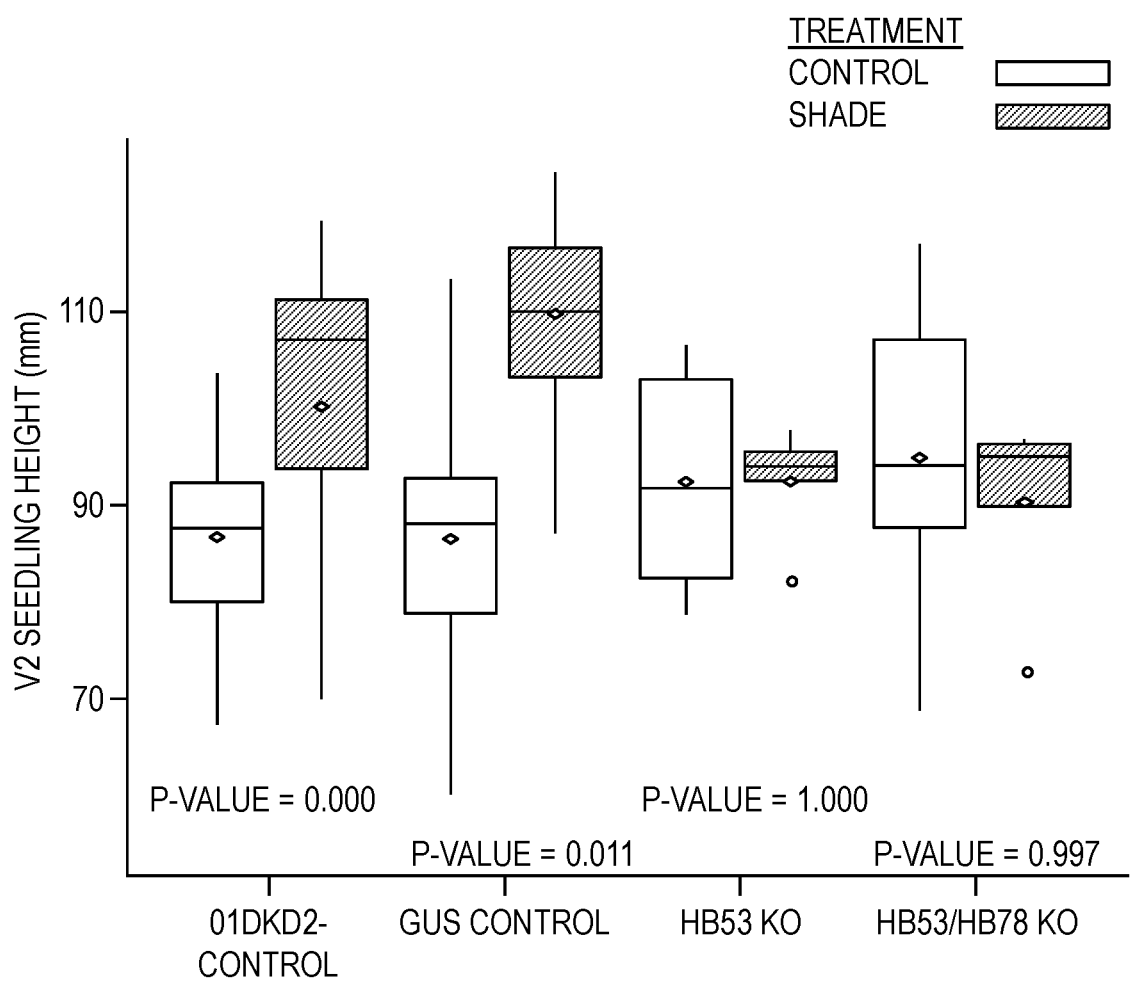
FIG. 14 provides the results of an example E2 shade avoidance assay of an HB53 knock-out and an HB53/HB78 knock-out showing no stem elongation in the edited lines when grown in the shade.
Figure 15:
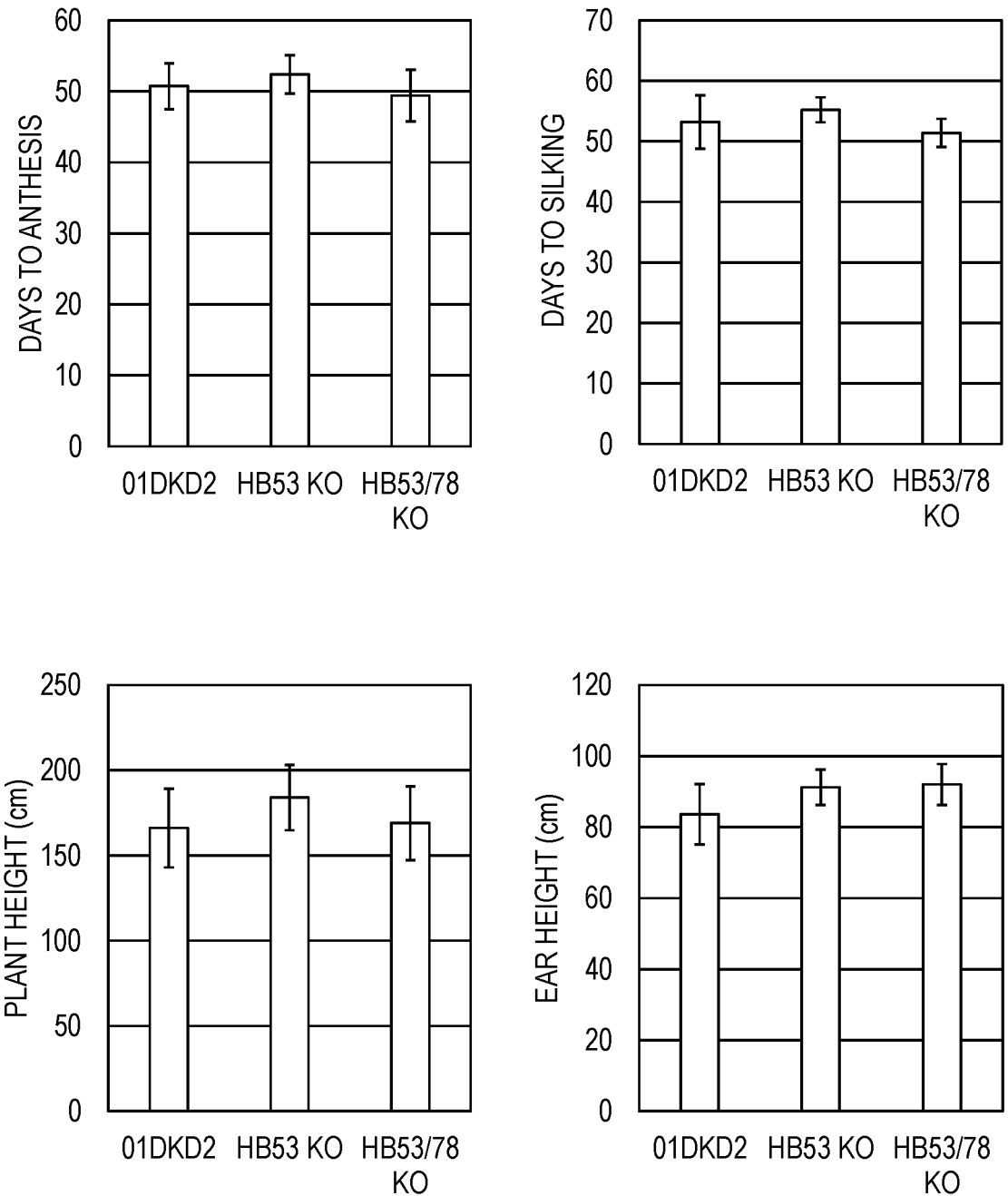
FIG. 15 provides an off-type analysis showing no evidence of morphological off-types or developmental delays in the edited plants.

Example 4. Modification of Endogenous Maize Homeodomain-Leucine Zipper (HD-Zip) Transcription Factor Represses Shade Avoidance Response Editing of HD-Zip transcription factors represses the exaggerated elongation of the stem in simulated shade condition. Homozygous edits of HD-Zip transcription factors HB53 and HB53/HB78 demonstrate statistically significant repressed shade avoidance response as shown in the V2 stage (FIG. 14) but no significant off-types (FIG. 15). In contrast, wild type plants (01DKD2 CONTROL) and plants transformed with guide-free vectors (GUS CONTROL) show statistically significant shade avoidance response. In addition to edited alleles generated from pWISE444 (HB53) and pWISE451 (HB53/HB78), homozygous HB78 edit (FIG. 8 and FIG. 9) were also tested. Our results indicate trait activity (i.e., no shade avoidance response) in the E1 stage but no significant difference in plant height between unedited vs edited HB78 in the E2 stage. As the two tests (E1 vs E2 stage) vary in growth chamber placement, further testing is warranted.

Taken together, our results show that HD-Zip transcription factors are potent regulators of shade avoidance response. Furthermore, we have demonstrated that the editing these transcription factors lead to repression of an evolutionarily conserved exaggerated response to shading.

The foregoing is illustrative of the present invention and is not to be construed as limiting thereof. The invention is defined by the following claims, with equivalents of the claims to be included therein.

That which is claimed is:

1. A plant or part thereof comprising at least one non-natural mutation in an endogenous Homeodomain-leucine zipper (HD-Zip) Type II (HD-Zip II) transcription factor, wherein the mutation disrupts the binding of the endogenous HD-Zip II transcription factor to DNA, wherein the at least one non-natural mutation results in a mutated HD-Zip transcription factor comprising the amino acid sequence of SEQ ID NO:312 or SEQ ID NO:316; and/or results in a nucleic acid having the sequence of any one of SEQ ID NO:313, SEQ ID NO:314, SEQ ID NO:315, SEQ ID NO:317, SEQ ID NO:318, SEQ ID NO:319, SEQ ID NO:320, SEQ ID NO:322, SEQ ID NO:323, SEQ ID NO:326 or SEQ ID NO:327, and the plant exhibits a reduced Shade Avoidance Response as compared to a control plant.

2. A guide nucleic acid that binds to a target site in a HD-Zip Type II transcription factor gene, wherein the HD-Zip Type II transcription factor gene is HOMEOBOX PROTEIN 53 (HB53) and the guide nucleic acid comprises a spacer having the nucleotide sequence of any one of SEQ ID NOs:175 and 177.

3. A system comprising the guide nucleic acid of claim 2 and a CRISPR-Cas effector protein that associates with the guide nucleic acid.

* * * * *

UNITED STATES PATENT AND TRADEMARK OFFICE
CERTIFICATE OF CORRECTION

PATENT NO. : 11,959,072 B2
APPLICATION NO. : 17/162075
DATED : April 16, 2024
INVENTOR(S) : Bate et al.

It is certified that error appears in the above-identified patent and that said Letters Patent is hereby corrected as shown below:

In the Specification

Column 6, Line 5: Please correct "(0" to read --(f)--

Column 13, Line 22: Please correct "9, 11," to read --9, 10, 11,--

Column 13, Line 24: Please correct "34, 36," to read --34, 35, 36,--

Column 13, Line 27: Please correct "84, 86," to read --84, 85, 86,--

Column 16, Line 51: Please correct "9, 11," to read --9, 10, 11,--

Column 17, Line 50: Please correct "24, 26," to read --24, 25, 26,--

Column 17, Line 52: Please correct "49, 51," to read --49, 50, 51,--

Column 20, Line 33: Please correct "about amino" to read --about 30 amino--

Column 20, Line 35: Please correct "about amino" to read --about 25 amino--

Column 22, Lines 38-39: Please correct "CI 1SPR-Cas" to read --CRISPR-Cas--

Column 22, Lines 45-46: Please correct "CR1SPR-Cas" to read --CRISPR-Cas--

Column 23, Line 61: Please correct "about 4 to about about" to read --about 4 to about 50,--

Column 23, Line 64: Please correct "about 10 to about about" to read --about 10 to about 50, about--

Column 23, Line 66: Please correct "19, 21," to read --19, 20, 21,--

Signed and Sealed this
Seventh Day of October, 2025

John A. Squires
*Director of the United States Patent and Trademark Office*

CERTIFICATE OF CORRECTION (continued)
U.S. Pat. No. 11,959,072 B2

Column 26, Line 25: Please correct "PLA-6" to read --$PLA_2$-δ--

Column 26, Line 37: Please correct "S-adePosyi-L-methionine" to read --S-adenosyl-L-methionine--

Column 29, Line 52: Please correct "CRISPR-Cas" to read --(e.g., CRISPR-Cas--

Column 36, Line 30: Please correct "(0" to read --(f)--

Column 36, Line 48: Please correct "CMSPR-Cas" to read --(e.g., CRISPR-Cas--

Column 37, Line 10: Please correct "(0" to read --(f)--

Column 38, Line 63: Please correct "(0" to read --(f)--

Column 39, Line 28: Please correct "of about" to read --of about 0.16;--

Column 39, Line 30: Please correct "0.12, 0.14," to read --0.12, 0.13, 0.14,--

Column 41, Line 32: Please correct "(0" to read --(f)--

Column 43, Line 41: Please correct "(0" to read --(f)--

Column 44, Line 40: Please correct "(0" to read --(f)--

Column 45, Line 1: Please correct "(0" to read --(f)--

Column 45, Line 34: Please correct "(0" to read --(f)--

Column 45, Line 63: Please correct "(0" to read --(f)--

Column 54, Line 20: Please correct "4, 6," to read --4, 5, 6,--

Column 54, Line 20: Please correct "15, 6, 17," to read --15, 16, 17,--

Column 56, Line 61: Please correct "14, 16," to read --14, 15, 16,--

Column 56, Line 63: Please correct "39, 41," to read --39, 40, 41,--

Column 57, Lines 1-2: Please correct "about 15 to about about" to read --about 15 to about 50, about--

Column 57, Line 8: Please correct "24, 26," to read --24, 25, 26,--

Column 58, Line 13: Please correct "4, 6," to read --4, 5, 6,--

CERTIFICATE OF CORRECTION (continued)
U.S. Pat. No. 11,959,072 B2

Column 59, Line 4: Please delete SEQ ID NO: 198 and replace with the following:
5'-NNNNNNNNNNNNNNNNNNNN-3' RNA Spacer (SEQ ID NO:198)
   ||||||||||||||||||||

Column 59, Line 9: Please delete SEQ ID NO: 199 and replace with the following:
3'AAANNNNNNNNNNNNNNNNNNNN-5' Target strand (SEQ ID NO:199)
   ||||

Column 60, Line 24: Please correct "A,ISV-G" to read --VSV-G--

Column 62, Line 40: Please correct "(0" to read --(f)--

Column 66, Line 21: Please insert a paragraph break between "*B. nigra*)." and "In"

Column 66, Line 59: Please correct "Cry1Ab, Cry1A," to read --CryIAb, CryIAC,--

Column 72, Line 49: Please correct "400 Ξmol" to read --400 µmol--